US011845975B2

(12) United States Patent
Yasui et al.

(10) Patent No.: US 11,845,975 B2
(45) Date of Patent: Dec. 19, 2023

(54) EXTRACT FROM A BODY FLUID COMPRISING A MICRO RNA

(71) Applicant: Craif Inc., Tokyo (JP)

(72) Inventors: Takao Yasui, Aichi (JP); Daiki Takeshita, Aichi (JP); Yoshinobu Baba, Aichi (JP)

(73) Assignee: Craif Inc., Tokyo (JP)

( * ) Notice: Subject to any disclaimer, the term of this patent is extended or adjusted under 35 U.S.C. 154(b) by 402 days.

(21) Appl. No.: 16/709,780

(22) Filed: Dec. 10, 2019

(65) Prior Publication Data

US 2020/0255906 A1    Aug. 13, 2020

(30) Foreign Application Priority Data

Dec. 12, 2018    (JP) ................................. 2018-248924

(51) Int. Cl.
*C12Q 1/6886* (2018.01)
*G01N 33/493* (2006.01)

(52) U.S. Cl.
CPC ......... *C12Q 1/6886* (2013.01); *G01N 33/493* (2013.01); *C12Q 2600/178* (2013.01); *G01N 2800/60* (2013.01)

(58) Field of Classification Search
None
See application file for complete search history.

(56) References Cited

U.S. PATENT DOCUMENTS

2008/0306017 A1* 12/2008 Croce .................. C12Q 1/6886
435/6.14
2018/0258483 A1    9/2018 Van Keuren-Jensen et al.

FOREIGN PATENT DOCUMENTS

| JP | 2020092688 A | 6/2020 |
|---|---|---|
| JP | 2020150930 A | 9/2020 |
| WO | WO-2017154951 A1 | 9/2017 |
| WO | WO-2020090860 A1 | 5/2020 |
| WO | WO-2020158832 A1 | 8/2020 |

OTHER PUBLICATIONS

Yasui (Sci Adv 2017; 3 e1701133).*
Zhou (Regulatory Toxicology and Pharmacology 78 (2016) pp. 78-84).*
Takeshita (MicroTAS 2015—19th International Conference on Miniaturized Systems for Chemistry and Life Sciences. Chemical and Biological Microsystems Society, Oct. 2015. p. 1516-1518).*
Bryzgunova (PLOS One 2016 11(6) e0157566).*
Ghorai (Frontiers in Genetics Apr. 2014 vol. 5 article 100).*
Raposo, Graca et al., "Extracellular vesicles: exosomes, microvesicles and friends," J Cell Biol, vol. 200, No. 4, (Feb. 18, 2013), pp. 373-383.
Szatanek, Rafal et al., "Isolation of extracellular vesicles: Determining the correct approach (Review)," Int J Mol Med, vol. 36, No. 1, (Apr. 22, 2015), pp. 11-17.
Jeppesen, Dennis K. et al., "Comparative analysis of discrete exosome fractions obtained by differential centrifugation," J Extracell Vesicles, vol. 3, No. 1, (Nov. 6, 2014), p. 25011.
Weber, Jessica A. et al., "The MicroRNA Spectrum in 12 Body Fluids," Clin Chem, vol. 56, No. 11. (Sep. 16, 2010), pp. 1733-1741.
Lv, Lin-Li et al., "Isolation and Quantification of MicroRNAs from Urinary Exosomes/Microvesicles for Biomarker Discovery," Int J Biol Sci, vol. 9, No. 10, (Oct. 12, 2013), pp. 1021-1031.
Alvarez, M. Lucrecia et al., "Comparison of Protein, microRNA, and mRNA yields using different methods of urinary exosome isolation for the discovery of kidney disease," Kidney Int, vol. 82, No. 9, (Jul. 11, 2012), pp. 1024-1032.
Zhang, Jian et al., "Exosome and Exosomal MicroRNA: Trafficking, Sorting, and Function," Genomics Proteomics Bioinformatics, vol. 13, No. 1, (Feb. 24, 2015), pp. 17-24.
Kosaka, Nobuyoshi et al., Circulating microRNA in body fluid: a new potential biomarker for cancer diagnosis and prognosis, Cancer Sci., vol. 101, No. 10, (Jul. 7, 2010), pp. 2087-2092.
Iero, M. et al., "Tumour-released exosomes and their implications in cancer immunity," Cell Death Differ, vol. 15, No. 1, (Oct. 12, 2007), pp. 80-88.
Taylor, Douglas D. et al., "MicroRNA signatures of tumor-derived exosomes as diagnostic biomarkers of ovarian cancer," Gynecol Oncol., vol. 110, No. 1, (Jul. 2008), pp. 13-21.
Al-Nedawi, Khalid et al., "Intercellular transfer of the oncogenic receptor EGFRvIII by microvesibles derived from tumour cells," Nat Cell Biol, vol. 10, No. 5, (Apr. 20, 2008), pp. 619-624.
Yoshioka, Yusuke et al., "Ultra-sentive liquid biopsy of circulating extracellular vesicles using ExoScreen," Nat Commun, vol. 5, No. 3591, (Apr. 7, 2014), pp. 1-8.
Peinado, Hector et al., "Melanoma exosomes educate bone marrow progenitor cells toward a pro-metastic phenotype through MET," Nat Med, vol. 18, No. 6, (May 27, 2012), pp. 883-891.
Chen, Christopher Y. et al., "Purification of Exosomes-like Vesicles from Urine," Methods Enzymol, vol. 524, (Mar. 15, 2013), pp. 225-241.
Webber, Jason et al., "Cancer Exosomes Trigger Fibroblast to Myofibroblast Differentiation," Cancer Res, vol. 70, No. 23, (Nov. 23, 2010), pp. 9621-9630.
Skog, Johan et al., "Glioblastoma microvesicles transport RNA and proteins that promote tumour growth and provide diagnostic biomarkers," Nat Cell Biol, vol. 10, No. 12, (Nov. 16, 2008), pp. 1470-1476.
Vlassov, Alexander V. et al., "Exosomes: Current knowledge of their composition, biological functions, and diagnostic and therapeutic potentials," Biochim Biophys Acta, vol. 1820, No. 7. (Apr. 1, 2012), pp. 940-948.
Arnaud, Celia Henry, "Seeking Tiny Vesicles For Diagnostics: Researchers Mine Exosomes for Information on Disease States," American Chemical Society, vol. 93, No. 29, (Jul. 20, 2015), pp. 30-32.
Kirschner, Michaela B. et al., "The impact of hemolysis on cell-free microRNA biomarkers," Front Genet, vol. 4, No. 94, (May 24, 2013), pp. 1-13 [supplemental information included].

(Continued)

*Primary Examiner* — Amanda Haney
(74) *Attorney, Agent, or Firm* — Wilson Sonsini Goodrich & Rosati

(57) ABSTRACT

The present disclosure provides a body fluid extract comprising micro RNA.

19 Claims, 16 Drawing Sheets

(56) References Cited

OTHER PUBLICATIONS

Taylor, Douglas D. et al., "Exosome Isolation for Proteomic Analyses and RNA Profiling," Methods Mol Biol, vol. 728, (Feb. 23, 2011), pp. 235-246.

Jeong, Sangmoo et al., "Integrated Magneto-Electrochemical Sensor for Exosome Analysis," ACS Nano, vol. 10, No. 2, (Jan. 28, 2016), pp. 1802-1809 [supplemental information included].

Sunkara, Vijaya et al., "Emerging techniques in the isolation and characterization of extracellular vesicles and their roles in cancer diagnostics and prognostics," Analyst, vol. 141, No. 2, (Oct. 26, 2015), pp. 371-381.

Zhang, Peng et al., "Ultrasensitive microfluidic analysis of circulating exosomes using a nanostructured graphene oxide/polydopamine coating," Lab Chip, vol. 16, No. 16, (Aug. 2, 2016), pp. 3033-3042 [supplemental information included].

Wunsch, Benjamin H. et al., "Nanoscale lateral displacement arrays for the separation of exosomes and colloids down to 20 nm," Nat Nanotechnol, vol. 11, No. 11, (Aug. 1, 2016), pp. 936-940.

Woo, Hyun-Kyung et al., "Exodisc for Rapid, Size-Selective, and Efficient Isolation and Analysis of Nanoscale Extracellular Vesicles from Biological Samples," ACS Nano, vol. 11, No. 2, (Jan. 17, 2017), pp. 1360-1370 [supplemental information included].

Barutta, Federica et al., "Urinary Exosomal MicroRNAs in Incipient Diabetic Nephropathy," Plos One, vol. 8, No. 11, (Nov. 4, 2013), p. e73798 [supplemental information included].

Théry, Clotilde et al., "Isolation and Characterization of Exosomes from Cell Culture Supernatants and Biological Fluids," Curr Protoc Cell Biol, vol. 30, No. 1, (Apr. 1, 2006), pp. 1-29.

Petersen, Kevin E. et al., "A review of exosome separation techniques and characterization of B16-F10 mouse melanoma exosomes with AF4-UV-MALS-DLS-TEM," Anal Bioanal Chem, vol. 406, No. 30, (Aug. 2, 2014), pp. 7855-7866.

Evans-Osses, Ingrid et al., "Exosomes or microvesicles? Two kinds of extracellular vesicles with different routes to modify protozoan-host cell interaction," Parasitol Res, vol. 114, No. 10, (Aug. 15, 2015), pp. 3567-3575.

Ma, Pei et al., "Extracellular vesicles-mediated noncoding RNAs transfer in cancer," J Hematol Oncol, vol. 10, No. 57. (Feb. 23, 2017), pp. 1-11.

Ito, et al. Nanowire Devices for Exosomal MicroRNA Extraction. 17th International Conference on Miniaturized Systems for Chemistry and Life Sciences, MicroTAS. vol. 3, 2013, pp. 1887-1889.

Office action dated Oct. 27, 2022 for JP Application No. 2018-248924 (English Translation).

Yasui, et al. Nanowires for early cancer and diabetes diagnosis via micro-RNA detection in urine extracellular vesicles. 20th International Conference on Miniaturized Systems for Chemistry and Life Sciences, MicroTAS. 2016, pp. 108-109.

International search report with written opinion dated Jan. 28, 2020 for PCT/JP2019/042499.

International search report with written opinion dated Dec. 8, 2020 for PCT/JP2020/037487.

Yasui, et al. Nanobiodevice-based Single Cell Analysis and Single Biomolecule Analysis. Bunseki Kagaku, 2015, vol. 64, Issue 6, pp. 413-419, Released on J-STAGE Jul. 7, 2015, Print ISSN 0525-1931, https://doi.org/10.2116/bunsekikagaku.64.413 (English Abstract p. 7).

Yasui, et al. Urinary MicroRNA Analysis. Bunseki Jun. 5, 2020, No. 6, pp. 204-207 (Japanese).

Yasui, T. Cancer Diagnosis Using Nanowire Devices. Journal of the Japan Society for Precision Engineering. Sep. 5, 2019, vol. 85, No. 9, pp. 757-760 (Machine Translation).

Yukawa, et al. Special issue: The impact of exosome research on industry. Development of Exosome Diagnosis Device. Bio Industry, 2015, vol. 32, No. 11, pp. 15-19 (Japanese).

\* cited by examiner

EXTRACT FROM A BODY FLUID COMPRISING A MICRO RNA

CROSS-REFERENCE TO RELATED APPLICATIONS

This application claims priority to Japanese Patent Application No. 2018-248924, filed 12 Dec. 2018. The disclosure of the priority application is incorporated in its entirety herein by reference.

TECHNICAL FIELD

The present disclosure relates to body fluid extracts comprising microRNAs.

BACKGROUND OF THE INVENTION

The inclusion of microRNAs (miRNA) within extracellular vesicles (hereinafter sometimes simply referred to as "EV") such as exosomes, microvesicles, and apoptotic bodies (Non-Patent Documents 1-4) has been found in a variety of body fluids, including healthy individuals and diseased patients (Non-Patent Documents 6-20).

Differences in the EV-inclusion miRNA between two groups of humans can be a sign of warning of various diseases (Non-Patent Document 20).

The inclusion of miRNA in EV is believed to be advantageous in that it can reduce the effects of ribonucleases on RNA degradation (Non-Patent Document 21), and miRNA in EV is believed to be more stable than free floating miRNA.

Heretofore, three techniques have been used for EV collection: ultracentrifugation or differential centrifugation, immunoaffinity-based capture, and size exclusion chromatography (Non-Patent Document 4).

Possible alternatives have been reported, such as polymer precipitation (Non-Patent Document 22), microfluidic based platforms (Non-Patent Documents 23-26), and size based filtration (Non-Patent Document 27).

However, these existing methods of collecting EV-including miRNA have not been adequate for collecting EV from urines containing EV at very low concentrations (<0.01 vol %) (Non-Patent Document 28).

For example, although ultracentrifugation is the most commonly used method for the collection of EVs in urine, ultracentrifugation has identified between 200 and 300 species of miRNA in urine (Non-Patent Documents 29-31).

It was estimated that more than 2,000 species of human miRNAs were present, and it was not clear whether the remaining 90% were present or absent in urine.

PRIOR ART LITERATURE

Non-Patent Literature

[Non-Patent Literature 1] G. Raposo, W. Stoorvogel, J. Cell Biol. 200, 373-383 (2013).
[Non-Patent Literature 2] I. Evans-Osses, L. H. Reichembach, M. I., Parasitol. Res. 114, 3567-3575 (2015).
[Non-Patent Literature 3] P. Ma, Y. et al., J. Hematol. Oncol. 10, 57 (2017).
[Non-Patent Literature 4] R. Szatanek et al., Int. J. Mol. Med. 36, 11-17 (2015).
[Non-Patent Literature 5] D. K. Jeppesen et al., J. Extracell. Vesicles 3, 25011 (2014).
[Non-Patent Literature 6] J. A. Weber et al., Clin. Chem. 56, 1733-1741 (2010).
[Non-Patent Literature 7] L.-L. Lv et al., Int. J. Biol. Sci. 9, 1021-1031 (2013).
[Non-Patent Literature 8] M. L. Alvarez et al., Kidney Int. 82, 1024-1032 (2012).
[Non-Patent Literature 9] J. Zhang et al., Genomics Proteomics Bioinformatics 13, 17-24 (2015).
[Non-Patent Literature 10] N. Kosaka et al., Cancer Sci. 101, 2087-2092 (2010).
[Non-Patent Literature 11] M. Iero et al., Cell Death Differ. 15, 80-88 (2008).
[Non-Patent Literature 12] D. D. Taylor, C. Gercel-Taylor, Gynecol. Oncol. 110, 13-21 (2008).
[Non-Patent Literature 13] K. Al-Nedawi et al., Nat. Cell Biol. 10, 619-624 (2008).
[Non-Patent Literature 14] Y. Yoshioka et al., Nat. Commun. 5, 3591 (2014).
[Non-Patent Literature 15] H. Peinado et al., Nat. Med. 18, 883-891 (2012).
[Non-Patent Literature 16] C. Y Chen et al., Methods Enzymol. 524, 225-241 (2013).
[Non-Patent Literature 17] J. Webber et al., Cancer Res. 70, 9621-9630 (2010).
[Non-Patent Literature 18] J. Skog et al., Nat. Cell Biol. 10, 1470-1476 (2008).
[Non-Patent Literature 19] A. V. Vlassov et al., Biochim. Biophys. Acta 1820, 940-948 (2012).
[Non-Patent Literature 20] C. H. Arnaud, Chem. Eng. News 93, 30-32 (2015).
[Non-Patent Literature 21] M. B. Kirschner et al., Front. Genet. 4, 94 (2013).
[Non-Patent Literature 22] D. D. Taylor et al., Methods Mol. Biol. 728, 235-246 (2011).
[Non-Patent Literature 23] S. Jeong et al., ACS Nano 10, 1802-1809 (2016).
[Non-Patent Literature 24] V. Sunkara et al., Analyst 141, 371-381 (2016).
[Non-Patent Literature 25] P. Zhang, M. He, Y. Zeng, Lab Chip 16, 3033-3042 (2016).
[Non-Patent Literature 26] B. H. Wunsch et al., Nat. Nanotechnol. 11, 936-940 (2016).
[Non-Patent Literature 27] H.-K. Woo et al., ACS Nano 11, 1360-1370 (2017).
[Non-Patent Literature 28] F. Barutta et al., PLOS ONE 8, e73798 (2013).
[Non-Patent Literature 29] C. Théry et al., Cell Biol. Chapter 3, Unit 3.22 (2006).
[Non-Patent Literature 30] K. E. Petersen et al., Anal. Bioanal. Chem. 406,

SUMMARY OF THE INVENTION

The present disclosure provides a bodily fluid extract comprising microRNAs.

The present inventors have found that when a nanowire (nanorod) having a positive charge is contacted with a solution containing an extracellular vesicle (EV) in a solution (in particular, the pH of urine), the EV can be efficiently captured on the nanowire.

The inventors have found that by contacting the urine with a nanowire, it is possible to effectively capture EV and miRNA in the urine and thereby obtain a urine extract containing miRNA of species which could not be extracted by conventional methods. The present disclosure is based on such findings.

According to the present disclosure, the following industrially applicable inventions may be provided.

(1) A urine extract comprising any of the microRNAs of the data S1 or Table 2.

(2) The urine extract according to (1) above, comprising an extracellular vesicle, wherein said microRNA is contained in the extracellular vesicle, or wherein said microRNA is extracted from the extracellular vesicle.

(3) The urine extract according to (1) above, wherein said RNA is in the form of free microRNA.

(4) The urinary extract according to any one of (1) to (3) above, wherein the microRNA is at least one or all species of the microRNAs selected from the group consisting of miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166, miR-3167, miR-16-1-3p, miR-424-3p, miR-519c-5p, miR-525-5p, miR-551b-5p, miR-558, miR-921, miR-942-3p, miR-3126-3p, miR-3127-5p, miR-3129-5p, miR-3144-5p, miR-3150a-5p, miR-3152-5p, miR-3155a, miR-3157-3p, miR-3159, miR-3165, miR-3678-3p, miR-4321, miR-4521, miR-4800-3p, miR-4999-5p, miR-5096, miR-5187-5p, miR-6874-5p, miR-3127-3p, miR-3130-5p, miR-3131, miR-3141, miR-3150b-5p, miR-3151-3p, miR-3151-5p, miR-3154, miR-3160-3p, miR-3160-5p, miR-378a-5p, miR-520c-3p, miR-526b-3p, miR-3150a-3p, miR-3162-5p and miR-4254.

(5) The urinary extract according to any one of (1) to (4) above, wherein the microRNA is at least one species of microRNA or all species of microRNAs selected from the group consisting of miR-3163, miR-16-1-3p, miR-424-3p, miR-558, miR-3127-5p and miR-4521.

(6) The urinary extract according to any one of (1) to (4) above, wherein the microRNA is at least one species of microRNA or all species of microRNAs selected from the group consisting of miR-378a-5p, miR-520c-3p and miR-526b-3p.

(7) The urine extract according to any one of (1) to (6) above, wherein the urine is urine of a subject having lung cancer.

(8) The urine extract according to any one of (1) to (3) above, wherein the microRNA is at least one or all species of the microRNAs selected from the group consisting of let-7i-3p, miR-183-5p, miR-202-5p, miR-409-5p, miR-4661-5p, miR-4800-3p, miR-5587-5p, miR-372-3p, miR-378b, miR-520b, miR-1266-3p, miR-3605-5p, miR-3612, miR-4645-3p, miR-4694-3p, miR-4752, miR-6816-3p, miR-8087, let-7f-2-3p, miR-15a-3p, miR-20a-3p, miR-33b-3p, miR-34c-5p, miR-93-5p, miR-130a-5p, miR-135a-5p, miR-135b-5p, miR-185-5p, miR-203a-3p, miR-302d-5p, miR-337-3p, miR-378c, miR-422a, miR-449c-5p, miR-483-5p, miR-506-3p, miR-511-5p, miR-520c-3p, miR-654-3p, miR-668-5p, miR-670-5p, miR-671-3p, miR-744-3p, miR-1178-3p, miR-1254, miR-1284, miR-1323, miR-2116-5p, miR-2355-3p, miR-3132, miR-3138, miR-3164, miR-3186-3p, miR-3189-3p, miR-3198, miR-3200-5p, miR-3657, miR-3667-5p, miR-3680-5p, miR-3692-5p, miR-3713, miR-3921, miR-3936, miR-4273, miR-4299, miR-4306, miR-4316, miR-4319, miR-4421, miR-4429, miR-4435, miR-4441, miR-4473, miR-4506, miR-4633-5p, miR-4658, miR-4733-5p, miR-4733-3p, miR-5004-3p, miR-5194, miR-5197-5p, miR-5571-5p, miR-6083, miR-6717-5p, miR-6720-5p, miR-6767-3p, miR-6781-3p, miR-6811-3p, miR-6821-3p, miR-6828-5p, miR-6832-5p, miR-6837-3p, miR-6841-5p, miR-6853-5p, miR-6871-3p, miR-6875-5p, miR-6878-5p, miR-7112-3p, miR-7703, miR-7848-3p and miR-7856-5p.

(9) The urine extract of (8) above, wherein the microRNA is at least one or all species of the microRNAs selected from the group consisting of miR-183-5p, miR-202-5p and miR-409-5p.

(10) The urine extract of (8) above, wherein the microRNA is at least one or all species of the microRNAs selected from the group consisting of miR-372-3p, miR-520b, miR-15a-3p, miR-34c-5p, miR-135a-5p, miR-185-5p, miR-337-3p, miR-422a, miR-506-3p, miR-520c-3p, miR-1284, miR-1323 and miR-4273.

(11) The urine extract according to any one of (8) to (10) above, wherein the urine is urine of a subject having pancreatic cancer.

(12) The urine extract according to any one of (1) to (3) above, wherein the microRNA is at least one or all species of the microRNAs selected from the group consisting of miR-4521, let-7c-3p, let-7i-5p, miR-16-1-3p, miR-26a-1-3p, miR-28-5p, miR-105-5p, miR-195-3p, miR-200b-5p, miR-219a-2-3p, miR-297, miR-300, miR-330-3p, miR-374b-5p, miR-431-5p, miR-454-5p, miR-513c-5p, miR-548ax, miR-593-5p, miR-623, miR-664a-5p, miR-942-3p, miR-1205, miR-1276, miR-1288-3p, miR-1297, miR-3678-3p, miR-4283, miR-4295, miR-4439, miR-4524b-5p, miR-4703-3p, miR-4768-5p, miR-4800-3p, miR-5187-5p, miR-5696, miR-7161-5p, let-7i-2-3p and miR-520c-3p.

(13) The urine extract of (12) above, wherein the microRNA is at least one or all species of the microRNAs selected from the group consisting of miR-16-1-3p, miR-28-5p, miR-297, miR-300, miR-330-3p, miR-454-5p, miR-1297 and miR-4295.

(14) The urine extract of (12) above, wherein the microRNA is miR-520c-3p.

(15) The urine extract according to any one of (12) to (14) above, wherein the urine is urine of a subject having liver cancer.

(16) The urine extract according to any one of (1) to (3) above, wherein the microRNA is at least one or all species of the microRNAs selected from the group consisting of miR-16-1-3p, miR-23b-3p, miR-28-5p, miR-92a-2-5p, miR-142-3p, miR-195-3p, miR-196b-5p, miR-299-3p, miR-492, miR-513b-5p, miR-601, miR-619-5p, miR-1285-3p, miR-3155a, miR-3162-5p, miR-3678-3p, miR-4283, miR-4295, miR-4311, miR-4531, miR-5096, miR-5187-5p, let-7f-2-3p, miR-520c-3p and miR-4783-5p.

(17) The urine extract of (16) above, wherein the microRNA is at least one or all species of the microRNAs selected from the group consisting of miR-16-1-3p, miR-23b-3p, miR-28-5p, miR-142-3p, miR-195-3p, miR-299-3p and miR-4295.

(18) The urine extract according to (16) above, wherein the microRNA is miR-520c-3p.

(19) The urine extract according to any one of (16) to (18) above, wherein the urine is urine of a subject having bladder cancer.

(20) The urine extract according to any one of (1) to (3) above, wherein the microRNA is at least one or all species of the microRNAs selected from the group consisting of miR-4531, miR-28-5p, miR-103a-2-5p, miR-105-5p, miR-124-3p, miR-151a-5p, miR-151b, miR-200a-5p, miR-300, miR-424-3p, miR-519c-5p, miR-551b-5p, miR-617, miR-873-3p, miR-921, miR-1288-3p, miR-3124-5p, miR-3155a, miR-3917, miR-4283, miR-4727-3p, miR-5096, miR-5187-5p, miR-6074, miR-6874-5p, miR-6892-5p, miR-15a-3p, miR-135b-5p, miR-520c-3p, miR-4783-5p and miR-7849-3p.

(21) The urine extract according to (20) above, wherein the microRNA is at least one or all species of the microR- NAs selected from the group consisting of miR-28-5p, miR-105-5p, miR-124-3p, miR-151a-5p and miR-300.

(22) The urine extract according to (20) above, wherein the microRNA is at least one or all species of the microRNAs selected from the group consisting of miR-15a-3p and miR-520c-3p.

(23) The urine extract according to any one of (20) to (22) above, wherein the urine is urine of a subject having prostate cancer.

(24) The urine extract according to any one of (1) to (6), (8) to (10), (12) to (14), (16) to (18), and (20) to (22) above, wherein the urine is urine of a healthy person.

(25) A method of testing (also referred to as "examining") a risk (also referred to as "possibility", "probability", and "likelihood") that a subject has cancer, the method comprising one or more selected from the group consisting of (a) to (e) below:

(a) detecting at least one species of microRNA or all species of microRNAs selected from the group consisting of miR-3163, miR-16-1-3p, miR-424-3p, miR-558, miR-3127-5p and miR-4521 in a urine or a urine extract obtained from a subject, wherein if the amount of the microRNA is greater than a predetermined amount, it indicates a risk that the subject has lung cancer;

(b) detecting at least one or all microRNAs selected from the group consisting of miR-183-5p, miR-202-5p and miR-409-5p in a urine or a urine extract obtained from a subject, wherein the amount of microRNA is greater than a predetermined amount, it indicates a risk that the subject has pancreatic cancer;

(c) detecting at least one species or all species of microRNAs selected from the group consisting of miR-16-1-3p, miR-28-5p, miR-297, miR-300, miR-330-3p, miR-454-5p, miR-1297 and miR-4295 in a urine or a urine extract obtained from the subject, wherein if the amount of the microRNA is greater than a predetermined amount, it indicates a risk that the subject has liver cancer;

(d) detecting at least one species or all species of microRNAs selected from the group consisting of miR-16-1-3p, miR-23b-3p, miR-28-5p, miR-142-3p, miR-195-3p, miR-299-3p and miR-4295 in a urine or a urine extract obtained from a subject, wherein if the amount of the microRNA is greater than a predetermined amount, it indicates a risk that the subject has bladder cancer;

(e) detecting at least one species or all species of microRNAs selected from the group consisting of miR-28-5p, miR-105-5p, miR-124-3p, miR-151a-5p and miR-300 in a urine or a urine extract obtained from the subject, wherein if the amount of the microRNA is greater than a predetermined amount, it indicates a risk that the subject has prostatic cancer.

(26) The method according to (25) above,
the method comprising one or more selected from the group consisting of (A) to (E):

(A) further detecting at least one species of microRNA or all species of microRNAs selected from the group consisting of miR-378a-5p, miR-520c-3p and miR-526b-3p in the urine or the urine extract obtained from the subject in (a) above, wherein if the amount of the microRNA is smaller than a predetermined amount, it indicates a risk that the subject has lung cancer;

(B) further detecting at least one or all species of the microRNAs selected from the group consisting of miR-372-3p, miR-520b, miR-15a-3p, miR-34c-5p, miR-135a-5p, miR-185-5p, miR-337-3p, miR-422a, miR-506-3p, miR-520c-3p, miR-1284, miR-1323 and miR-4273 in the urine or the urine extract obtained from the subject in (b) above, wherein if the amount of the microRNA is smaller than a predetermined amount, it indicates a risk that the subject has pancreatic cancer;

(C) further detecting miR-520c-3p in the urine or the urine extract obtained from the subject in (c) above, wherein if the amount of the microRNA is smaller than a predetermined amount, it indicates a risk that the subject has liver cancer;

(D) further detecting miR-520c-3p in the urine or the urine extract obtained from the subject in (d) above, wherein if the amount of the microRNA is smaller than a predetermined amount, it indicates a risk that the subject has bladder cancer;

(E) further detecting at least one or all species of microRNAs selected from the group consisting of miR-15a-3p and miR-520c-3p in the urine or the urine extract obtained from the subject in (e) above, wherein if the amount of the microRNAs is smaller than a predetermined value, it indicates a risk that the subject has prostatic cancer.

(27) An urine extract obtained by contacting a nanowire with a urine and extracting a component bound to the nanowire.

(27a) The urine extract according to (27) above, wherein a pH of the urine contacted with the nanowire is in a numerical range with a lower limit of 2, 3, 4, or 5 and an upper limit of 11, 10, 9, 8, 7, 6, or 5.

(27b) The urine extract according to (27) or (27a) above, wherein the nanowire is a nanowire of a metal oxide or a nanowire whose surface is coated with a metal oxide.

(27c) The urine extract according to (27b) above, wherein the metal oxide is an oxide of a transition metal.

(27d) The urine extract according to (27), (27a), (27b) or (27c) above, wherein the nanowire is zinc oxide nanowire or a nanowire whose surface is coated with zinc oxide.

(27e) The urine extract according to (27), (27a), (27b), (27c), (27d) or (27e) above, wherein the nanowire and the urine are contacted under a neutral pH condition.

(28) The urine extract according to (27) above, comprising either microRNAs described in data S1 or Table 2.

(29) The urine extract according to (27), (27a), (27b), (27c), (27d) or (27e) above, comprising 20% or more of the extracellular vesicles contained in the urine.

(29') The urine extract according to (27), (27a), (27b), (27c), (27d) or (27e) above, comprising 25% or more of the extracellular vesicles contained in the urine.

(29a) The urine extract according to (27), (27a), (27b), (27c), (27d) or (27e) above, comprising 30% or more of the extracellular vesicles in the urine.

(29a') The urine extract according to (27), (27a), (27b), (27c), (27d) or (27e) above, comprising 35% or more of the extracellular vesicles contained in the urine.

(29b) The urine extract according to (27), (27a), (27b), (27c), (27d) or (27e) above, comprising 40% or more of the extracellular vesicles in the urine.

(29b') The urine extract according to (27), (27a), (27b), (27c), (27d) or (27e) above, comprising 45% or more of the extracellular vesicles contained in the urine.

(29c) The urine extract according to (27), (27a), (27b), (27c), (27d) or (27e) above, comprising 50% or more of the extracellular vesicles contained in the urine.

(29c') The urine extract according to (27), (27a), (27b), (27c), (27d) or (27e) above, comprising 55% or more of the extracellular vesicles contained in the urine.

(29d) The urine extract according to (27), (27a), (27b), (27c), (27d) or (27e) above, comprising 60% or more of the extracellular vesicles contained in the urine.

(29d') The urine extract according to (27), (27a), (27b), (27c), (27d) or (27e) above, comprising 65% or more of the extracellular vesicles contained in the urine.

(29e) The urine extract according to (27), (27a), (27b), (27c), (27d) or (27e) above, comprising 70% or more of the extracellular vesicles contained in the urine.

(29e') The urine extract according to (27), (27a), (27b), (27c), (27d) or (27e) above, comprising 75% or more of the extracellular vesicles contained in the urine.

(29f) The urine extract according to (27), (27a), (27b), (27c), (27d) or (27e) above, comprising 80% or more of the extracellular vesicles contained in the urine.

(29f') The urine extract according to (27), (27a), (27b), (27c), (27d) or (27e) above, comprising 85% or more of the extracellular vesicles contained in the urine.

(29g) The urine extract according to (27), (27a), (27b), (27c), (27d) or (27e) above, comprising 90% or more of the extracellular vesicles contained in the urine.

(29h) The urine extract according to (27), (27a), (27b), (27c), (27d) or (27e) above, comprising 95% or more of the extracellular vesicles contained in the urine.

(29i) The urine extract according to (27), (27a), (27b), (27c), (27d) or (27e) above, comprising 97% or more of the extracellular vesicles contained in the urine.

(29j) The urine extract according to (27), (27a), (27b), (27c), (27d) or (27e) above, comprising 99% or more of the extracellular vesicles contained in the urine.

(30) The urine extract according to (1) above, comprising the microRNA concentrated.

(31) The urine extract comprising at least 500 species of microRNAs present in a urine.

(31A) The urine extract according to the above (1) or (31), comprising 500 or more species of microRNAs present in the urine.

Yellow (bright in the grey scale) indicates nanowires, blue indicates PDMS, and white dotted line indicates the edge of the PDMS.

The scale bar indicates 1 μm.

Figure 1A:
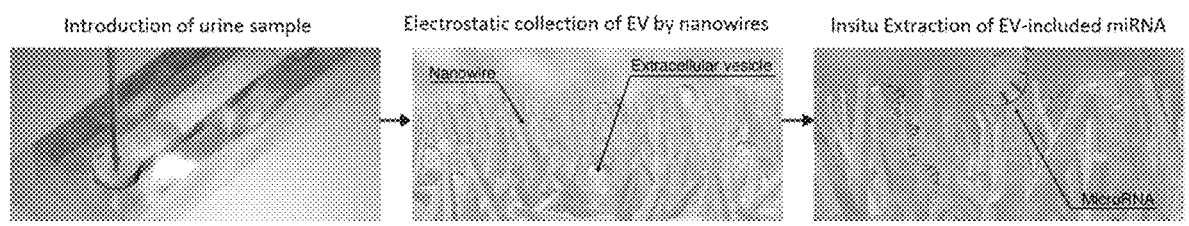
FIG. 1A is a schematic of the collection (capture) of EV in urine using a nanowire-incorporated microdevice and the in situ extraction of EV-included miRNA in urine.
Figure 1B:
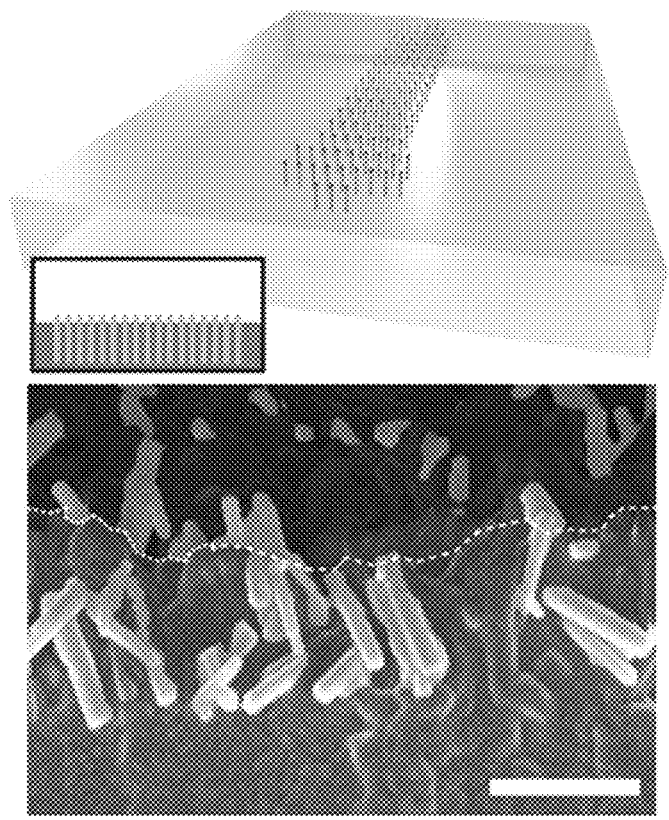
FIG. 1B shows a schematic representation of the embedded nanowires after pouring, curing and stripping of the PDMS, and the vertical cross-sectional FESEM image of the embedded nanowires (nanowires shown as rods, PDMS shown as clear areas) and the lower left schematic inset showing the cross-sectional image.
Figure 1C:
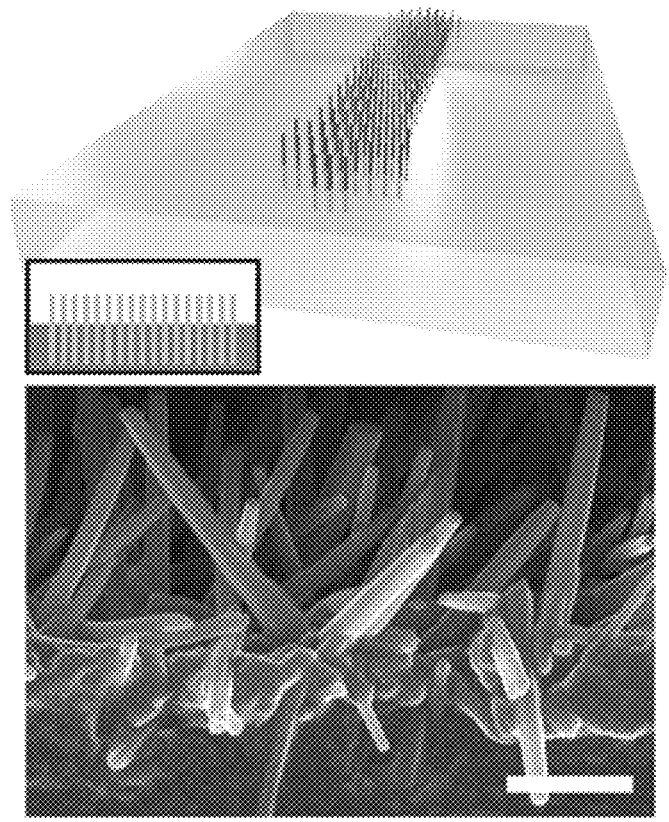
FIG. 1 relates to electrostatic collection of EV in urine by nanowires followed by in situ extraction of EV-included miRNA.

FIG. 1C is a schematic view showing a cross-sectional image of nanowires growth from embedded nanowires (nanowire-incorporated PDMS) with a schematic inset at the bottom left, and a vertical cross-sectional view of a nanowire-incorporated PDMS.

The scale bar indicates 1 μm.

Figure 1D:
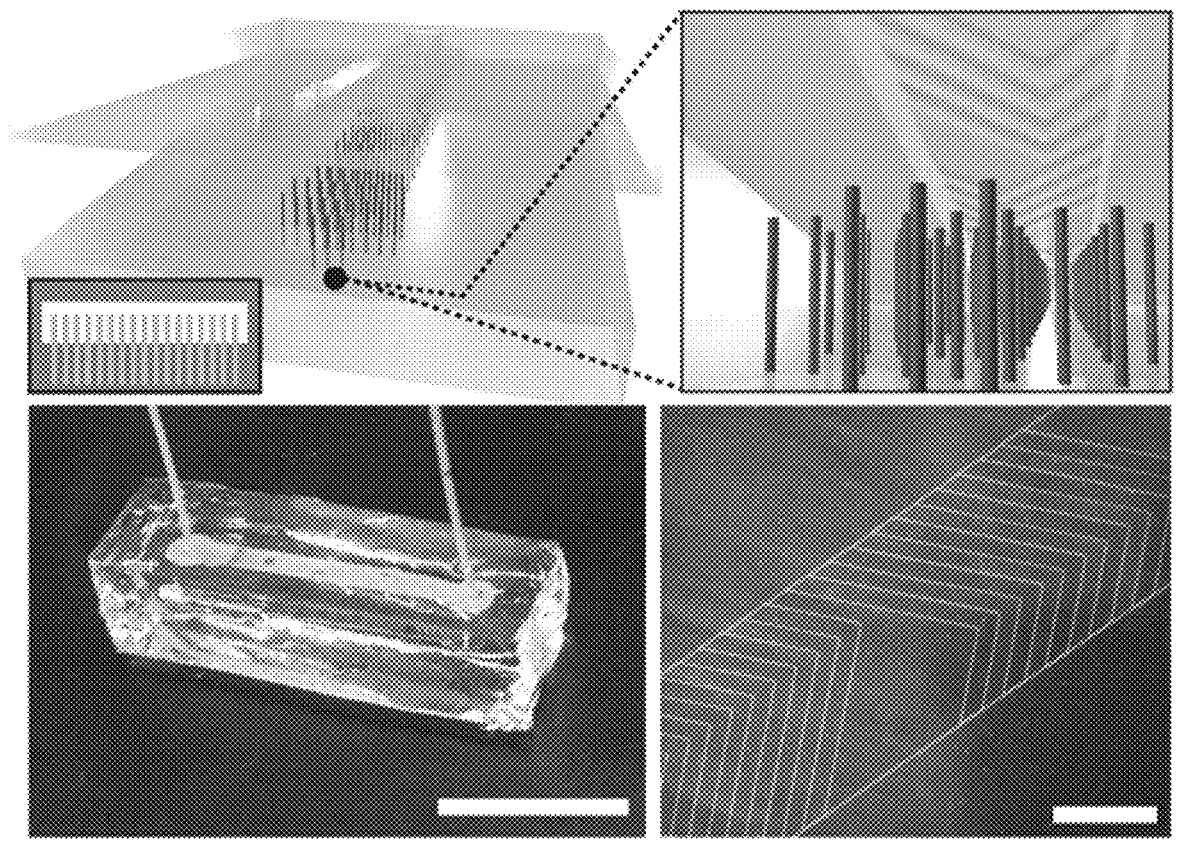

FIG. 1D shows: a schematic cross-sectional view of bonding the nanowire-incorporated PDMS to a PDMS substrate having a microfluidic herring-bone structure; a schematic inset at the bottom left; a photograph of a nanowire-incorporated microfluidic device having polyetheretherketone (PEEK) tubes for the inlet and the outlet (a nanowire-incorporated PDMS is adhered to a PDMS substrate having a microfluidic herring-bone structure); and a laser microscopic image of the microfluidic herring-bone structure on the PDMS substrate.

The scale bar indicates 1 μm.

Figure 1E:
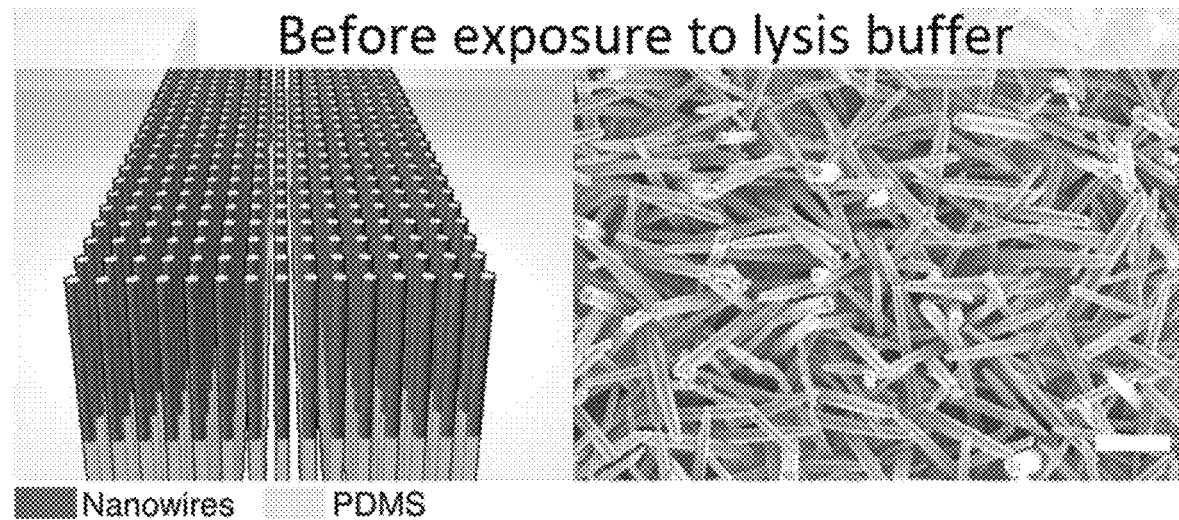

FIG. 1E shows a schematic of the nanowire-incorporated device and FESEM images from the top surface of the nanowire-incorporated PDMS before being exposed to the lysis buffer.

The scale bar indicates 1 μm.

Figure 1F:
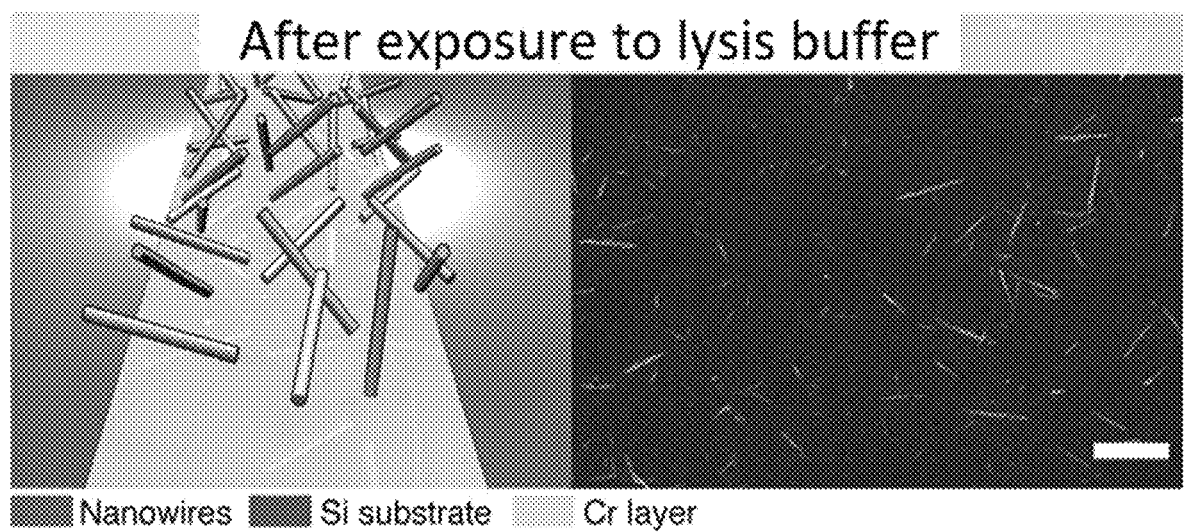

FIG. 1F shows a schematic of the nanowires on the Si substrate and a FESEM image from the top of the nanowires on the Si substrate after being exposed to the lysis buffer.

Figure 2:
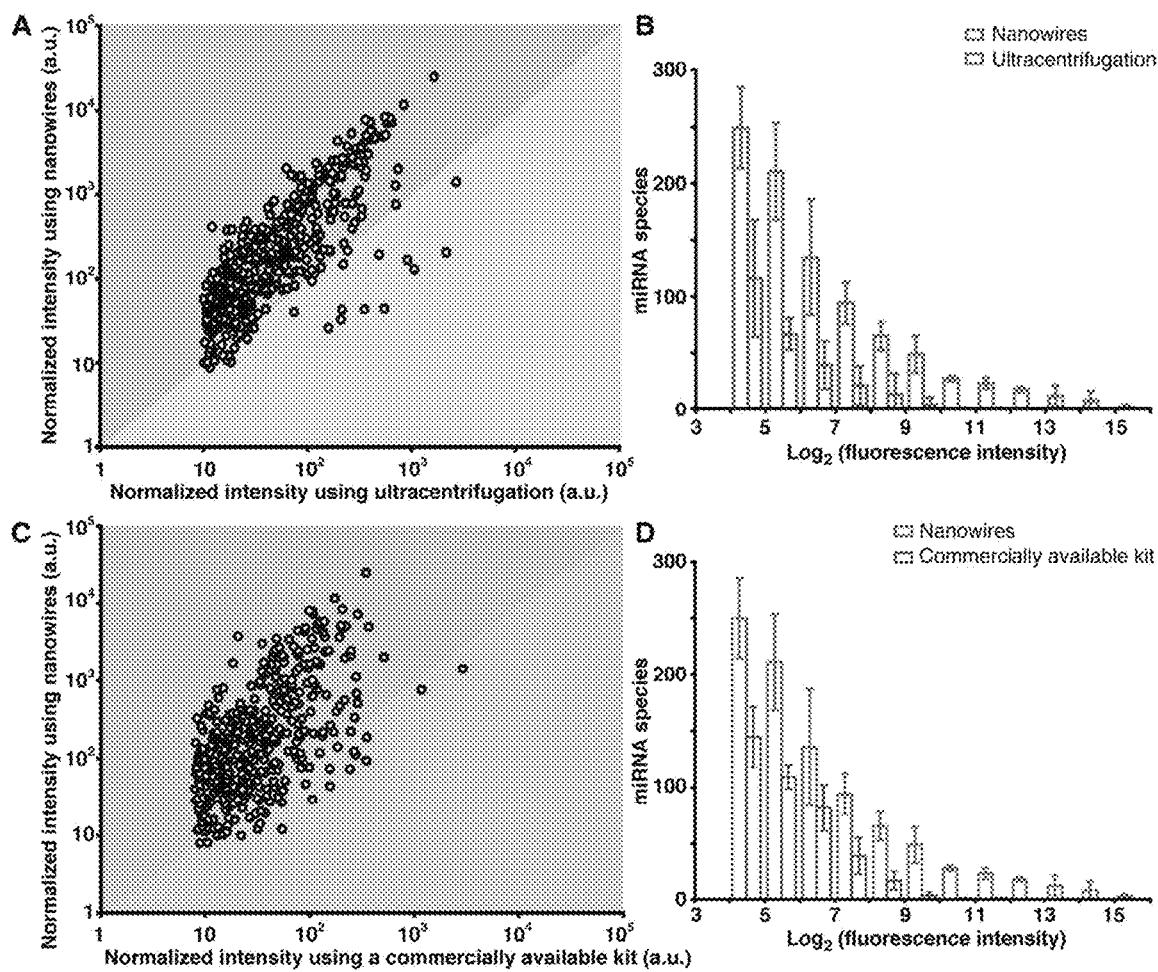

FIG. 2 relates to in situ extractions of miRNA using nanowire-incorporated microfluidic devices.

FIG. 2A shows a scatter plot of normalized intensities of miRNA extracted from EVs collected by the disclosed nanowire incorporated devices and by the ultracentrifugation method.

FIG. 2B shows histograms of miRNA species that were extracted by a method using the disclosed nanowire incorporated devices and by the ultracentrifugation (n=3).

FIG. 2C shows a scatter plot of normalized intensities of miRNA extracted from EVs collected by the disclosed nanowire incorporated devices and by using commercial kits.

FIG. 2D shows histograms of miRNA species that were extracted by a method using the disclosed nanowire incorporated devices and by the ultracentrifugation (n=3).

The error bars indicate the SD of the measurements (n=3). "a.u." denotes arbitrary unit.

Figure 3:
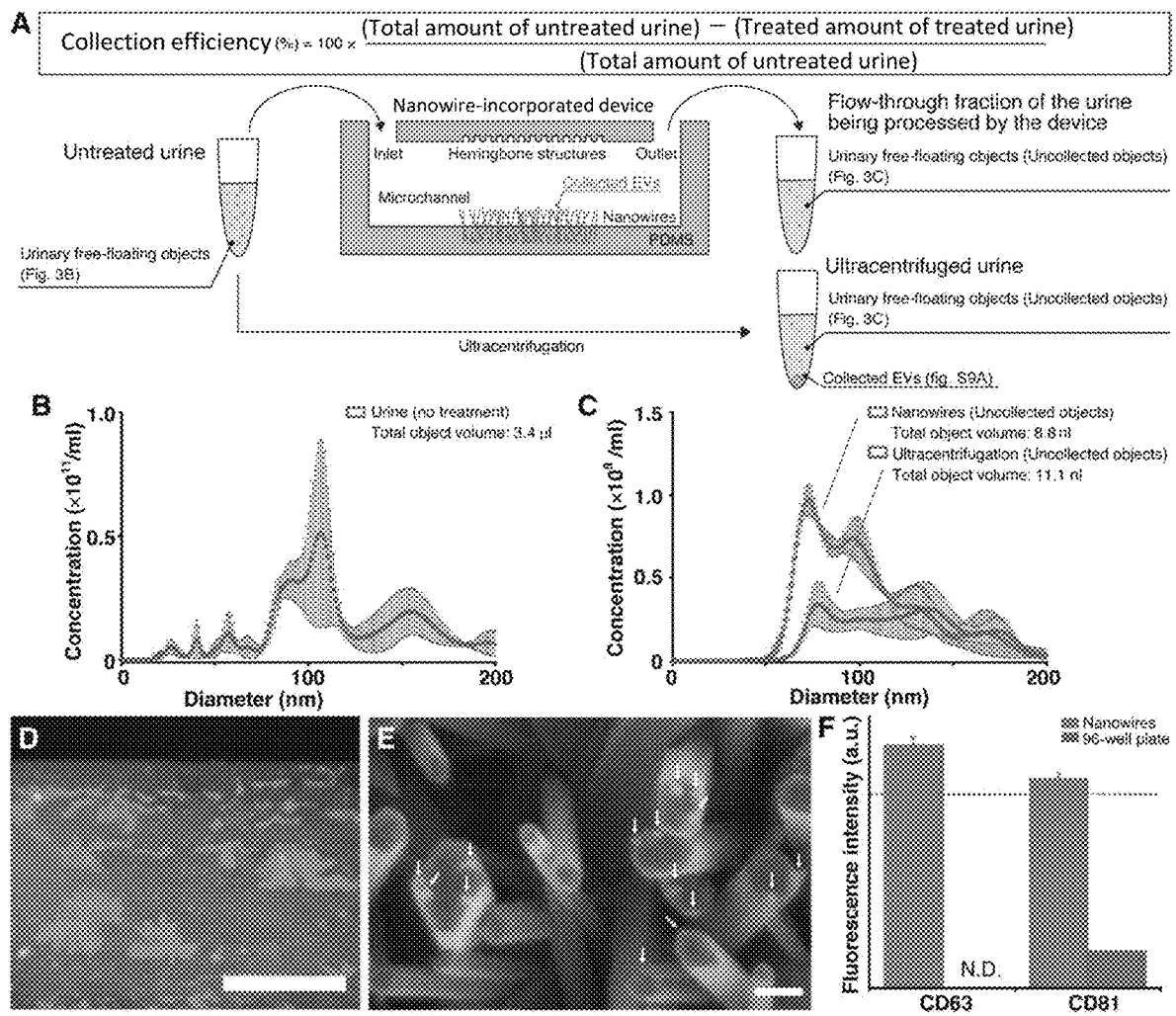

FIG. 3 relates to the collection of EVs on nanowires.

FIG. 3A is a schematic relating to experimental processes and calculation of the collection efficiencies.

FIG. 3B shows the size-distribution of the free suspensions of urine in untreated urine.

The error bars indicate SD for measurement (n=3).

FIG. 3C shows the flow-through fraction of urine treated by the disclosed nanowire-incorporated devices and the error bars showing the size-distribution of the free suspension of urine in ultracentrifuged urine. The error bars indicate the SDs for the measurements (n=3).

FIG. 3D shows EVs collected with nanowires and fluorescent-labeled (RKH26).

In the figure, PKH26 labeled EVs on nanowires are shown.

The scale bar indicates 500 μm.

FIG. 3E shows an FESEM image of the nanowires after introduction of PKH26 labeled EVs.

The white arrows indicate collected EVs

The scale bar indicates 200 nm.

FIG. 3F shows the results of detecting EVs on nanowires and 96-well plates using antibodies to CD63 or CD81.

The measured concentrations of free suspensions in urine were 1.4×108 ml-1.

"N.D." indicates that no fluorescence was observed.

The dotted line indicates the 3SD signal level above background.

The error bars indicate SD for measurements (n=24 for nanowires; n=3 for 96-well plates).

Figure 4:
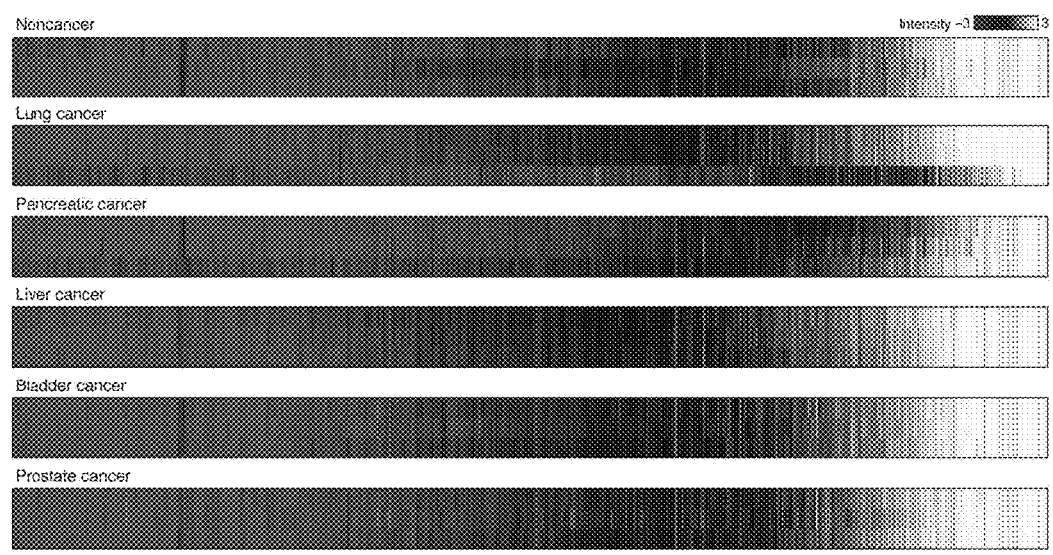

FIG. 4 shows the results of in situ extractions of cancer-related miRNA using nanowire-incorporated devices.

In FIG. 4, a heat map of the miRNA expression arrays is shown for each of the urine samples of non-cancerous donors, donors of lung cancers, donors of liver cancers, donors of bladder cancers and donors of prostate cancers.

Gradients of colors based on signal intensities are used to intuitively understand the expression of each miRNA and the comparisons between the groups.

If the logarithmic signal intensity is 5, it is black; blue for 2 or smaller; and yellow for 8 or greater.

Each column of the heat map represents the logarithmic signal intensities of the miRNA, with specific numerical values shown in S1.

Figure 5:
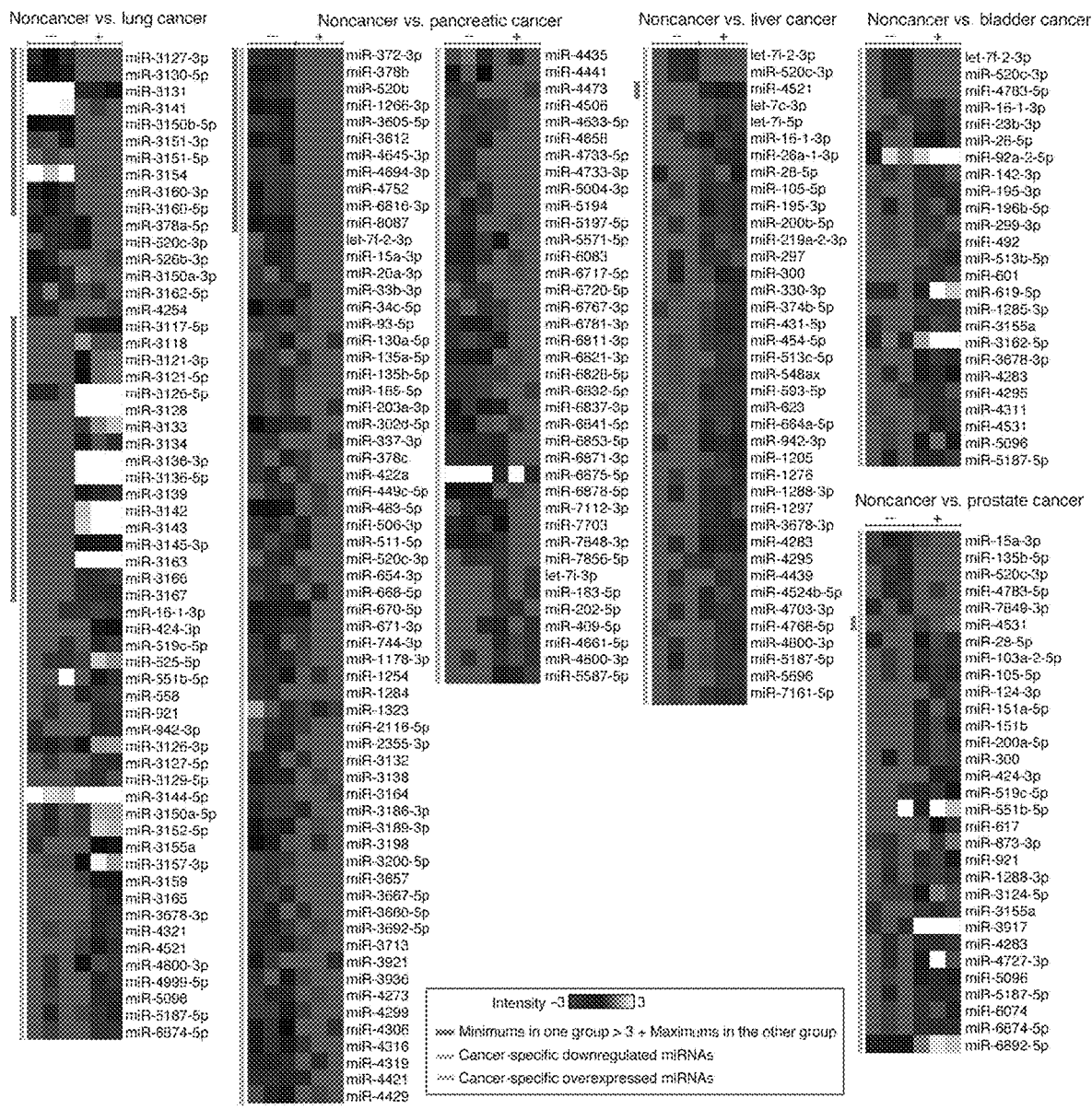

FIG. 5 shows the down-regulation and overexpression of miRNA extracted from FIG. 4 between non-cancer donors and donors with various cancers.

The extracted miRNA were those which showed the second smallest log signal intensity in one group larger than the second largest log signal intensity in the other group.

The symbols "−" and "+" indicate non-cancerous donors and cancerous donors, respectively.

The doubled portion of the left line indicates that one of the smallest logarithmic signal intensities was larger than the other of the largest logarithmic signal intensities.

In other cases, one logarithmic signal intensity is higher or lower than the other logarithmic signal intensity.

Figure 6:
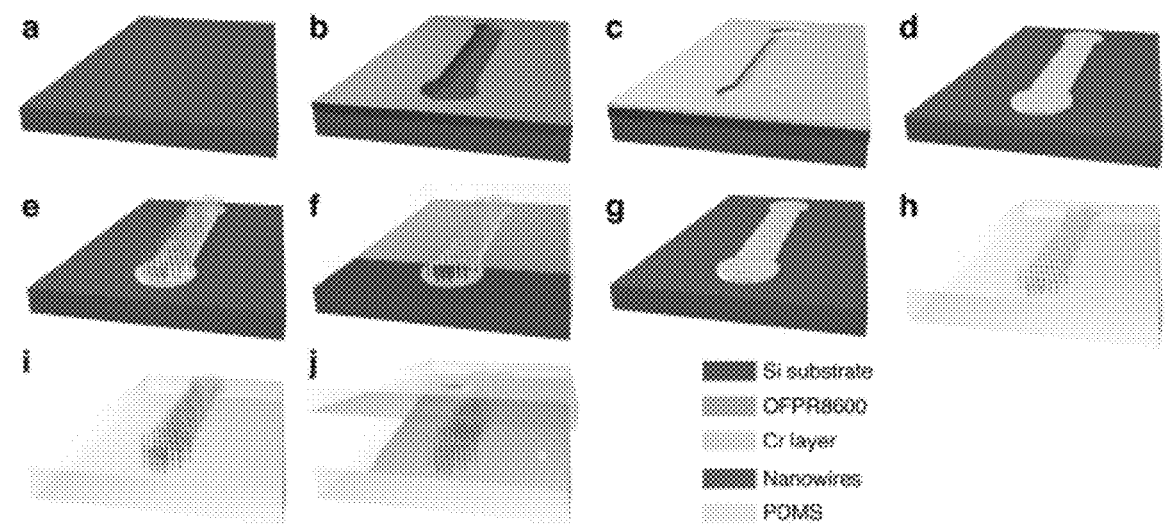

FIG. 6 shows a schematic of the processes for making nanowires incorporated into a PDMS.

In FIGS. 6a to 6g, nanowires are incorporated in the PDMS by lithographic and PDMS curing processes.

Components include a Si-substrate and an OFPR8600 photoresist, a Cr-layer, nanowires, and PDMS.

A Si-substrate is prepared in FIG. 6a, and a photoresist is laminated in FIG. 6b.

A Cr layer is further deposited in FIG. 6c, the photo-resist is removed in FIG. 6d, and nanowires are grown from the Cr layer in FIG. 6e.

In FIG. 6f PDMS is poured and cured.

In FIG. 6g the cured PDMS layer is stripped from the substrate.

FIG. 6h shows a schematic of the embedded nanowires after pouring, curing and stripping of the PDMS.

FIG. 6i shows a schematic of the process of growing nanowires from embedded nanowires.

FIG. 6j shows a schematic of the process of laminating a nanowire-incorporated PDMS substrate to a microfluidic herring-bone-structured PDMS substrate.

Figure 7:
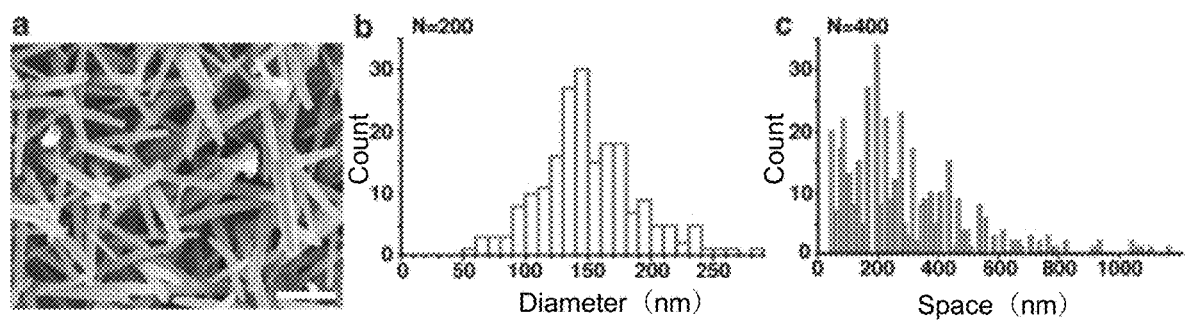

FIG. 7 relates to the incorporation of nanowires into a PDMS.

FIG. 7a is a FESEM image from the top of the nanowires.

The scale bar is 1 μm.

FIG. 7b shows the diametrical distribution of the nanowires.

The average diameter of the nanowires was 150 nm.

FIG. 7c shows the distribution of the spaces between the nanowires.

The space was defined as the shortest distance between two nanowires and was determined from cross-sectional SEM images.

The average space between the nanowires was 200 nm.

Figure 8:
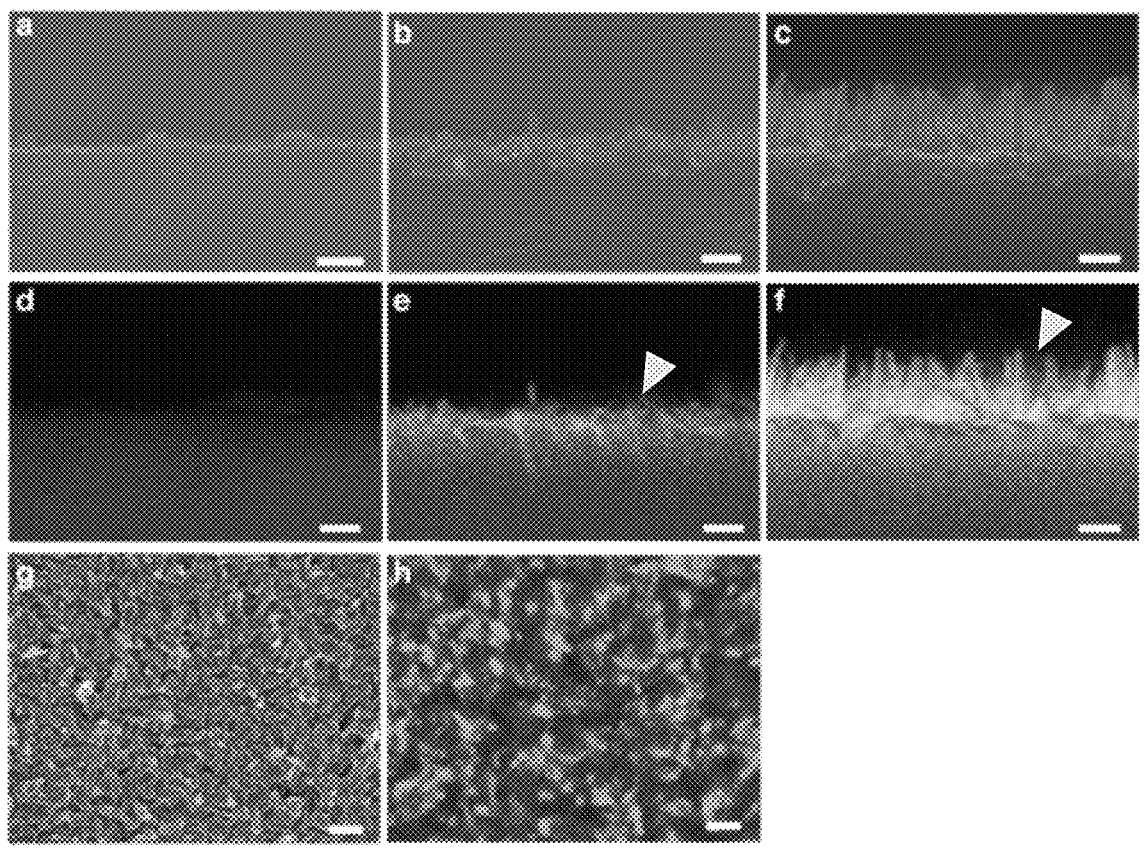

FIG. 8 relates to FESEM images and corresponding EDS-element mappings of PDMS substrates without nanowires, PDMS substrates with embedded nanowires, and a nanowire-incorporated PDMS substrate, respectively.

FIGS. 8a to 8c are FESEM images of vertical cross sections of a PDMS substrate without nanowires, a PDMS substrate with embedded nanowires, and a nanowire-incorporated PDMS substrate, respectively.

FIGS. 8d to 8f show the element mappings corresponding to the FESEM images of the cross sections of FIGS. 8a to 8c.

Si and Zn are represented by blue (dark) and green (parts indicated with arrowheads and bright), respectively.

In FIG. 8e, the nanowires (green) were slightly exposed on the surface of the PDMS substrate (blue).

In FIG. 8f, it was observed that the thickness of the nanowires increased.

FIG. 8g is a FESEM image from the top of a PDMS with embedded nanowires.

FIG. 8h shows an EDS-element mapping corresponding to the FESEM image from the top of FIG. 8g.

Si and Zn are represented by blue and green, respectively (scattered bright areas in gray scale).

Figure 9:
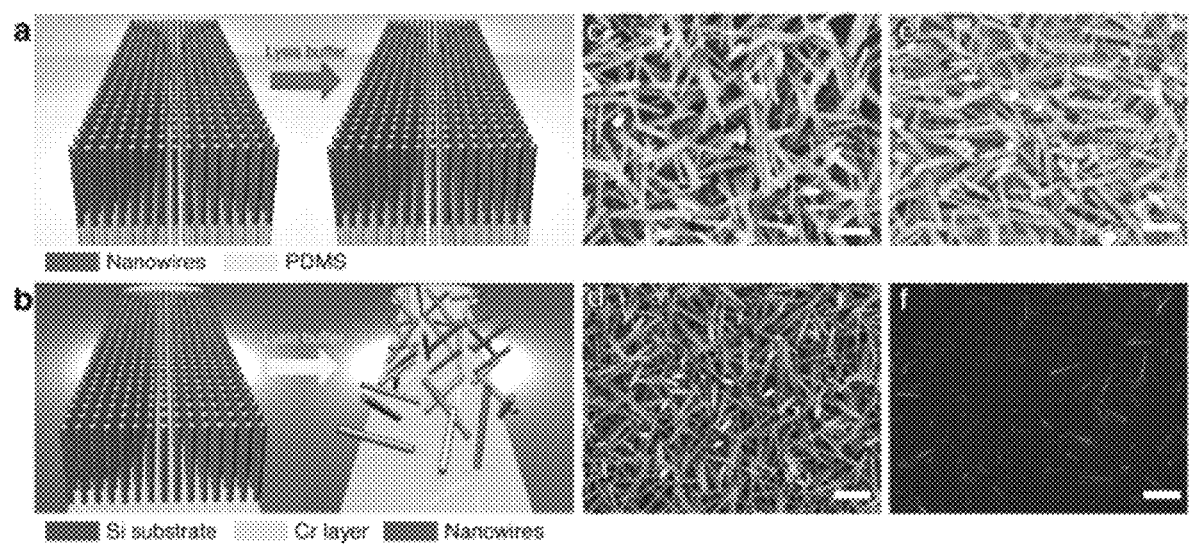

FIG. 9 relates to the mechanical stability of incorporated and unincorporated nanowires.

FIGS. 9a and b are schematic illustrations of nanowires incorporated in a PDMS prior to exposure to a lysis buffer and nanowires on a Si-substrate.

Components include nanowires, PDMS, a Si-substrate, and a Cr-layers.

The unincorporated nanowires were fabricated on a thermally oxidized chromium layer on a Si substrate.

FIGS. 9c and 9d are FESEM images from the top of the nanowires incorporated in the PDMS and the nanowires on the Si-substrate, respectively.

The scale bar indicates 1 μm.

FIGS. 9e and 9f are FESEM images from the nanowires incorporated in the PDMS and the nanowires on the Si-substrate, respectively, when exposed in the lysis buffer.

The scale bar indicates 1 μm.

After exposure to the lysis buffer, the nanowires on the Si-substrate peeled off, whereas the nanowires incorporated into the PDMS did not peel off.

Figure 10:
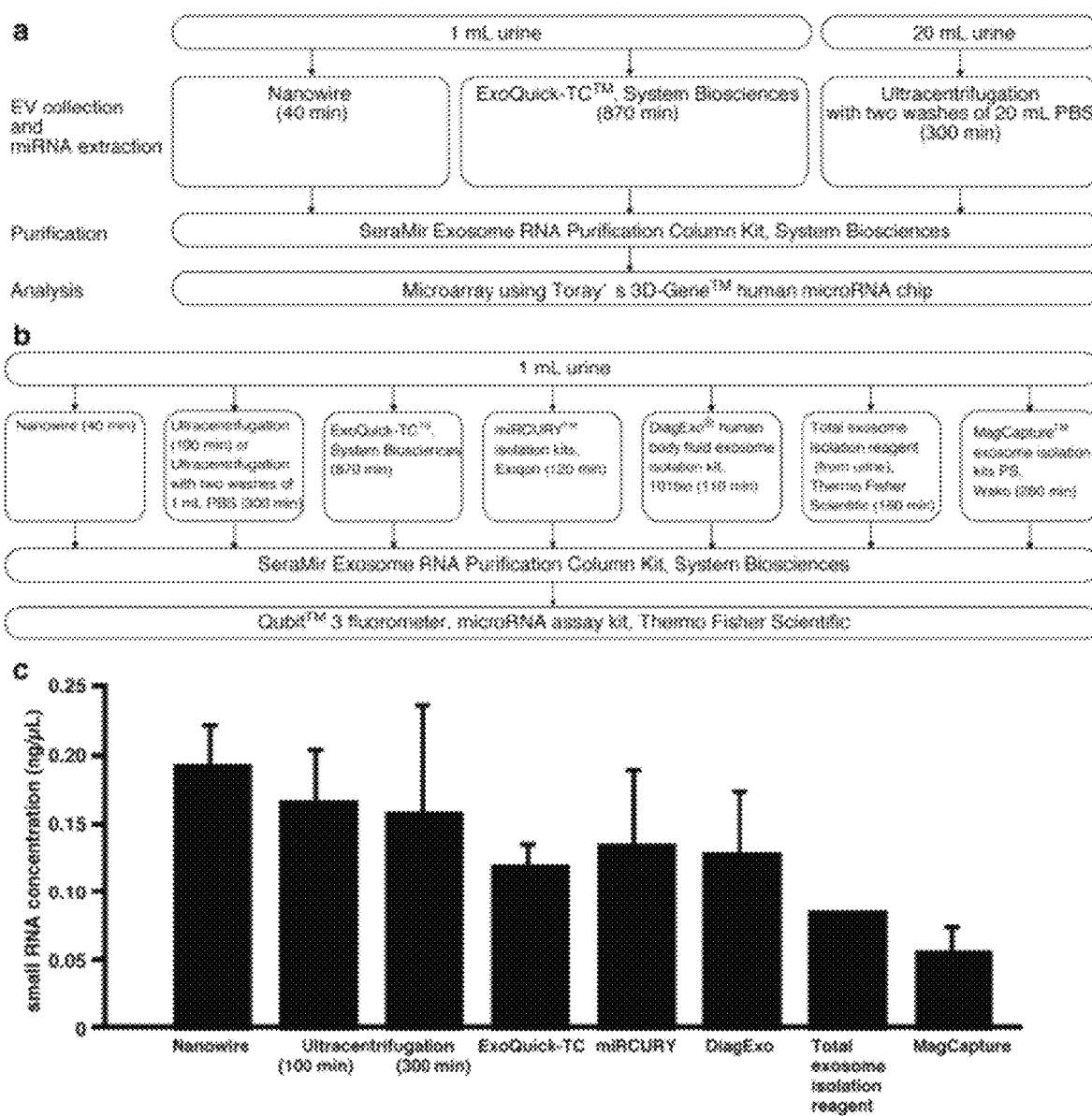

FIG. 10 shows an example of processes for extracting urinary miRNA using nanowire-incorporated devices, ultra-centrifugation, and commercially available kits.

FIG. 10a shows the experimental procedures for microarray analyses of miRNA expression.

FIG. 10b shows the experimental procedures for the quantitation of small RNAs using Qubit™ microRNA assay kit (Thermo Fisher Scientific).

After extracting the miRNA by various methods, RNA production and quantification of small-molecule RNA were carried out.

FIG. 10c shows the quantitation of small molecule RNA using various methods.

In the Qubit (trademark) microRNA assay kit (Thermo Fisher Scientific), since not only miRNA but also small-molecule RNA (~20 nucleotides or base pairs) can be quantified, the concentrations of small-molecule RNA were set on the Y-axis.

According to these data, the washing step did not affect the RNA collection efficiency. The error bars indicate SD for measurements (N≥3).

Figure 11:
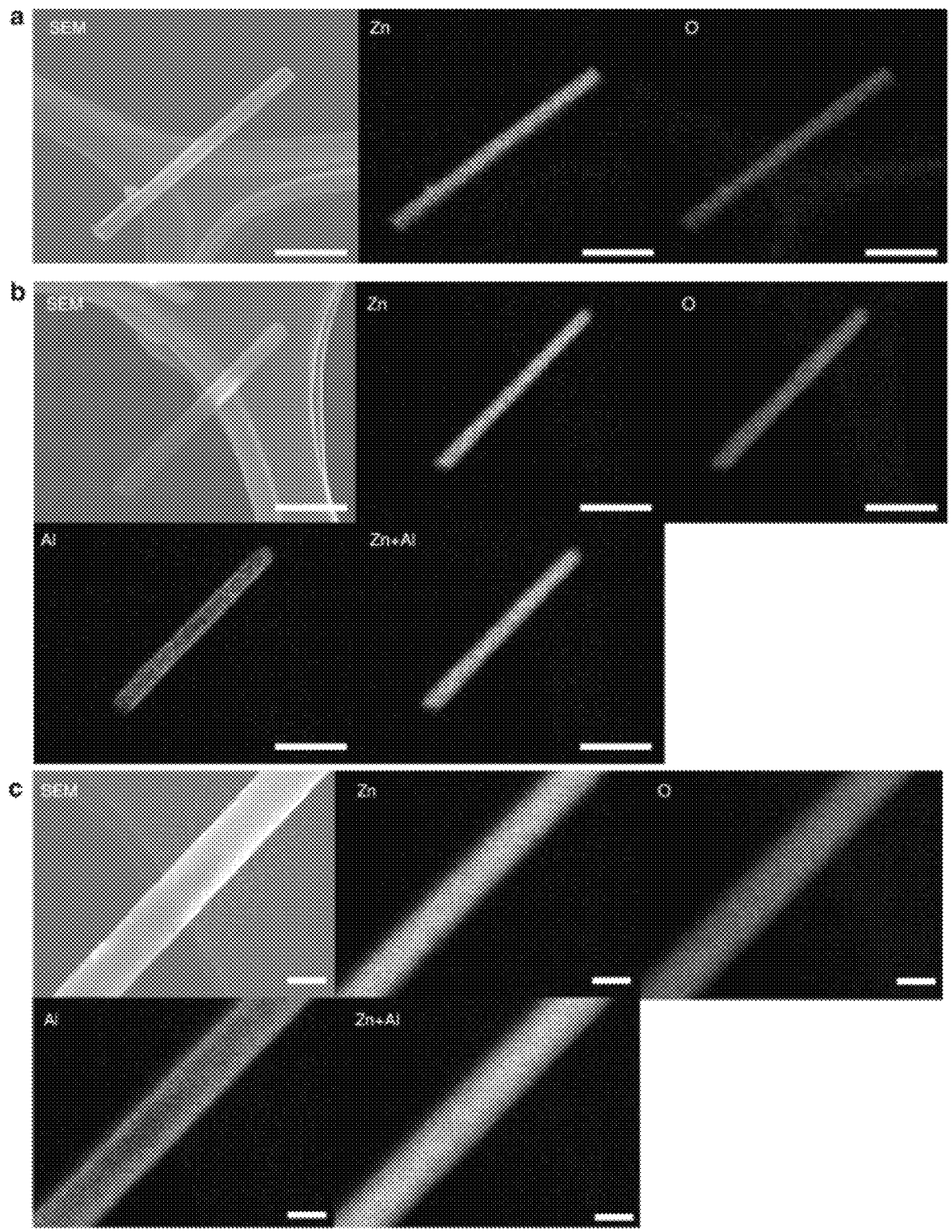

FIG. 11 shows EDS-element mappings of FESEM and STEM images of a single nanowire.

Zn, O, and Al are shown in green, red, and orange, respectively.

FIG. 11a shows nanowires of ZnO alone.

The scale bar indicates 500 nm.

FIG. 11b shows a ZnO/Al2O3 core-shell nanowire.

The scale bar indicates 500 nm.

In FIG. 11b, Al was seen to cover the Zn core.

FIG. 11c shows a ZnO/Al2O3 core-shell nanowire.

The scale bar indicates 100 nm.

In FIG. 11b, Al was seen to cover the core of Zn, and O was seen to overlap Al and Zn.

Figure 12:
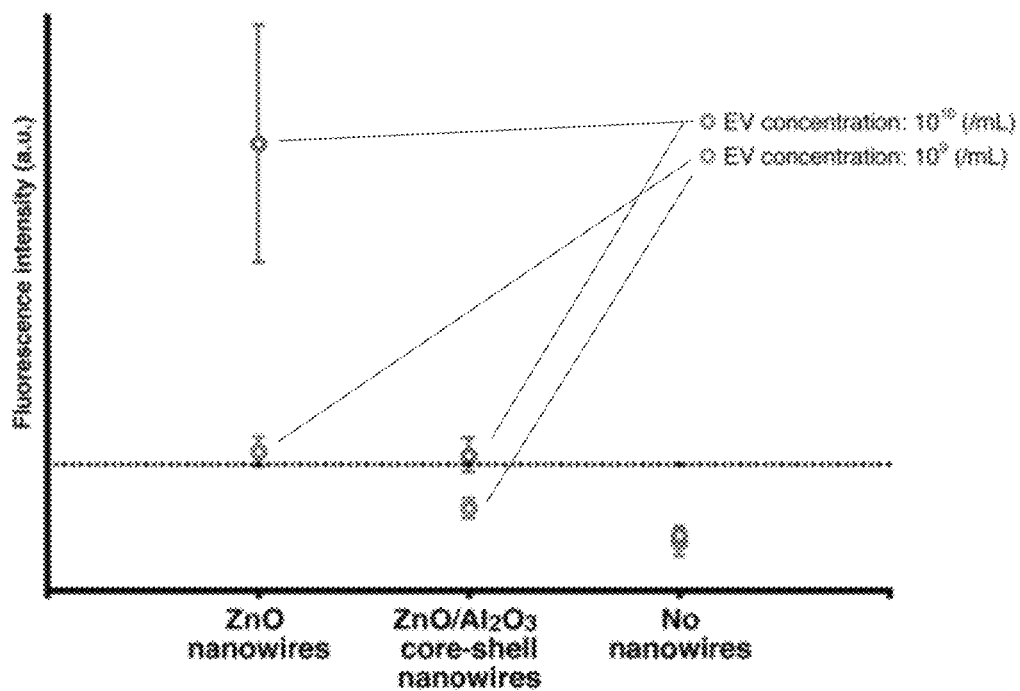

FIG. 12 relates to the detection of EVs by anti CD9 antibodies on Zn nanowires, ZnO/Al2O3 core-shell nanowires, and a surface without ZnO nanowires.

The dotted line indicates the signal strength of the 3SD above background.

The error bars are the standard deviations (SD) for measurements of ZnO nanowires, ZnO/Al2O3 core-shell nanowires, and a surface without ZnO nanowires (n=40, 24, and 24, respectively).

Points on the graph show signal intensities as the result of extracting miRNA on ZnO nanowires, ZnO/Al2O3 core-shell nanowires, and a surface without ZnO nanowires, for samples with EVs concentrations of 10 9/mL and 10 10/mL.

After introduction of EV, these three devices were perfused with PBS to remove EV that could not be collected.

The first device had ZnO nanowires, the second device had ZnO/Al2O3 core-shell nanowires, and the third device had no nanowires.

1% BSA solution was introduced into these devices and allowed to stand for 15 minutes.

After washing these devices with PBS, murine anti-human CD9 antibodies (10 µg/mL, Abcam, Plc.) were introduced into the respective devices, after which the devices were allowed to stand for 15 minutes.

CD9 is known as membrane proteins expressed on exosomes.

In addition, each device was washed with PBS, and each device was introduced with AlexaFluor488 labeled goat polyclonal anti-mouse IgG antibodies (5 µg/mL, Abcam, Plc.) before the device was allowed to stand for 15 minutes.

Finally, the devices were washed with PBS and fluorescence intensity was observed using a fluorescent microscopy (Olympus, Co. Ltd.).

ZnO nanowires effectively collected EV, whereas ZnO/Al2O3 core-shell nanowires collected only a small amount of EV.

This indicated the importance of the surface charge of the nanowires.

Figure 13:
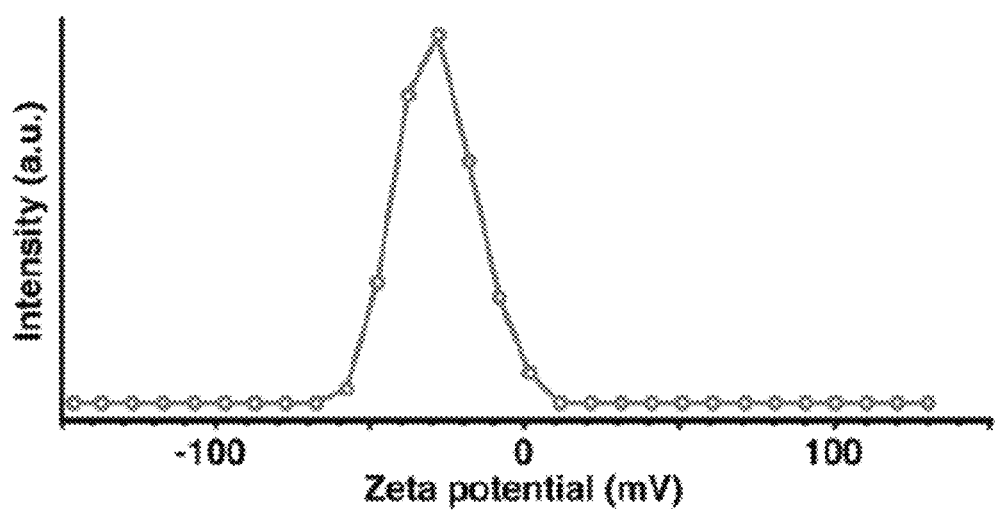

FIG. 13 shows the zeta potential of EV in urine.

The zeta-potential of the EVs was measured using a dynamic-light-scattering device (Zetasizer Nano-ZS, Malvern Instruments, Ltd.).

The average zeta potential of the EV was −28 mV.

Figure 14:
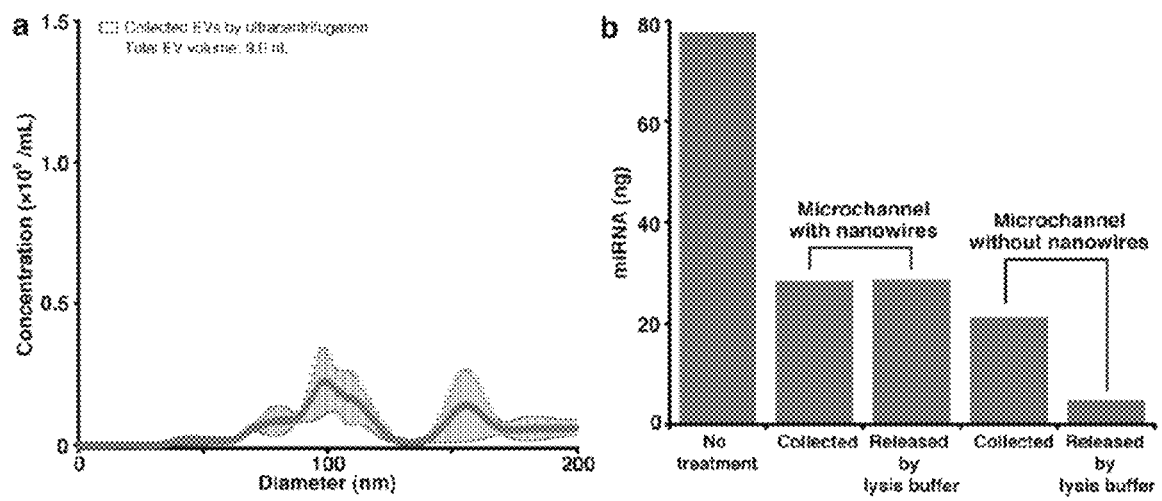

FIG. 14 shows the size distributions of EV collected by ultracentrifugation.

FIG. 14 also shows the presence of EV-free miRNA collected on the nanowires.

In FIG. 14a, the concentration of collected EVs were 1.6×109 mL-1.

Error bars indicate the standard deviation for the measurement (n=3).

FIG. 14b shows the amount of miRNA collected and miRNA released by quantitative reverse transcription-polymerase chain reaction (qRT-PCR).

As an EV-free miRNA, 100 nM miRNA (sequence: miRNA (sequence, uugcauagucacaaaagugauc) was used.

"Untreated" indicates a volume of 100 nM miRNA.

The collection of microchannels with or without nanowires was 100% and 23%, respectively.

Figure 15:
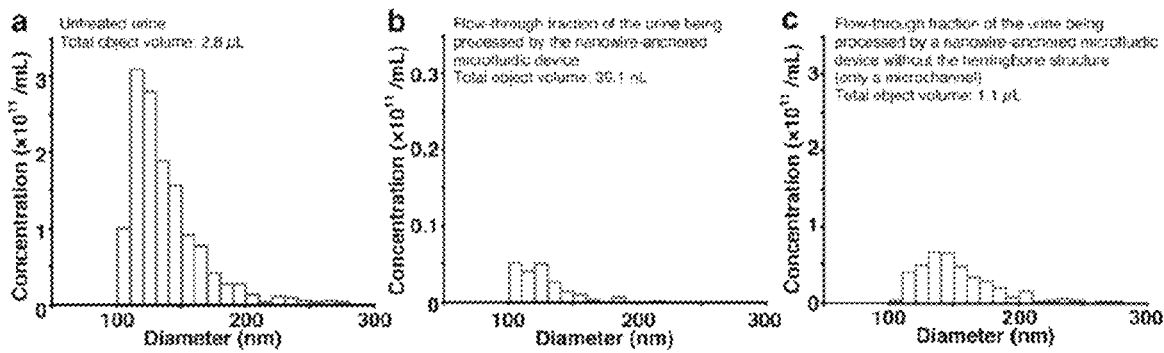

FIG. 15 shows the size distributions of free matter in the urine.

Size distributions and concentrations of urinary free suspensions were measured using nanoparticle detector (qNano, Meiwafosis Co., Ltd., with 100 nm nanopore membrane (NP100, Meiwafosis Co., Ltd.

FIG. 15a is for a free suspension of untreated urine and concentrations were 1.4×1012 mL-1.

FIG. 15b is data for free suspensions in the flow-through fraction of urine treated by nanowire-incorporated devices, the concentration was 2.4×1010 mL-1 (capture efficiency was 99%).

FIG. 15c is data for free suspensions in the flow-through fraction of urine treated with nanowire-incorporated devices without herringbone structures, concentrations were 4.3× 1011 mL-1 (capture efficiency was 61%).

DETAILED DESCRIPTION OF THE INVENTION

As used herein, "subject" means a subject for urinalysis.
The subject may be an animal.
The subject may be a reptile, a mammal, an amphibian.
Mammals may be dogs, cats, cows, horses, sheep, pigs, hamsters, mice, squirrels, and primates such as monkeys, gorillas, chimpanzees, bonovos, humans.
As used herein, "urine" means liquid waste produced by the kidneys.
Urine may be either of the one drained out through the urethra and the one accumulated in the bladder.
Urine may be extracted or collected from inside the body using an extractor such as a syringe.
In the present specification, the urine is not particularly limited, and may be, for example, the urine of a reptile, a mammal, or an amphibian.
Mammals may be dogs, cats, cows, horses, sheep, pigs, hamsters, mice, squirrels, and primates such as monkeys, gorillas, chimpanzees, bonovos, humans.
"Urine" may be urine of a healthy subject, urine of a subject with a particular disease (e.g., cancer selected from cancers such as lung cancer, liver cancer, pancreatic cancer, bladder cancer, and prostate cancer, etc.), or urine of a subject suspected of suffering from a particular disease.
"Urine" may be used as the stock solution, or it may be a liquid diluted or concentrated from the stock solution.
"Urine" may include an additive added to a urine sample.
The additive may be, for example, a stabilizer or a pH adjusting agent.
"Urine" may be urine in a frozen state.
As used herein, "microRNA" (also referred to as "miRNA") is a type of non-coding RNA (ncRNA) that is believed not to encode proteins.
MicroRNAs are processed from their precursors into mature bodies.
The mature microRNAs are known to have lengths on the order of 20 to 25 bases.
Human microRNAs are named hsa.
Precursors are given mir and matures are given miR.
The identified sequences are numbered in the order in which they are identified, and for similar sequences, the numbers are followed by a lower case alphabet.
If there is a precursor derived from the 5' end and a precursor derived from the 3' end, the microRNAs derived from the 5' end are labeled with 5p and those derived from the 3' end are labeled with 3p.
These symbols and numbers are connected by hyphens.
The mature microRNA may be double-stranded.
As used herein, "extracellular vesicles" (also referred to as "EV") are vesicles that are released from cells, including those released from cells during apoptosis, and those released from healthy cells.
Extracellular vesicles are broadly divided into exosomes (exosome), microvesicles (micro vesicle; MV), and apoptotic bodies (apoptosis body), depending on size and surface markers.
Exosomes usually have diameters of 40-120 nanometers and are capable of expressing one or more or all molecules selected from the group consisting of Alix, Tsg101, CD9, CD63, CD81 and flotillin.

Microvesicles usually have diameters of 50-1,000 nanometers and are capable of expressing one or more or all molecules selected from the group consisting of integrins, selectins, and CD40.

Apoptotic bodies usually have a diameter of 500-2,000 nm and are capable of expressing one or more molecules selected from the group consisting of annexin V and phosphatidylserine.

Exosomes can include proteins and nucleic acids, such as mRNA, miRNA, ncRNA.

Microvesicles can include proteins and nucleic acids, such as mRNA, miRNA, ncRNA. Apoptotic bodies are thought to contain fragmented nuclei and organelles.

As used herein, the term "extract" means an extracted product in which a particular component is more concentrated than before extraction.

As used herein, "urine extract" means a product extracted from urine in which certain components, particularly microRNAs, are more concentrated than in the urine prior to extraction.

The urine extract may be an aqueous solution (solution or suspension), or it may be a solid obtained by drying them.

In urine extracts, extracts from which components other than the extracellular vesicles and nucleic acids in the urine have been substantially removed may also be referred to as urine purifications.

The urine extract may comprise a surfactant, preferably a nonionic surfactant.

The urine extract may include detergents and debris of extracellular vesicles (e.g., exosomes and/or microvesicles).

The urine extract may be free or substantially free of one or more selected from the group consisting of detergents and debris of extracellular vesicles (e.g., exosomes and/or microvesicles).

The urine extract may further comprise a stabilizing agent (e.g., a nucleic acid stabilizing agent) and/or a pH adjusting agent (e.g., a buffering agent).

The urine extract may comprise salts.

The urine extract may comprise a urine component, e.g., one or more urine components selected from the group consisting of urea, creatinine, uric acid, ammonia, urobilin, riboflavin, urinary protein, sugar and urinary hormones (e.g., chorionic gonadotropin).

The pH of the urine extract may be equal to or greater than, or greater than, a value such as 2, 3, 4, or 5.

The pH of the urine extract may be equal to or less than, or less than, a value such as 10, 9, 8, 7, 6, or 5.

In the present disclosure, the urine extract comprises microRNAs.

In the present disclosure, the urine extract may comprise enriched/concentrated microRNAs or groups thereof.

In the present disclosure, the urine extract may comprise microRNAs extracted by the extraction methods described herein.

In this disclosure, the urine extract may include at least one or all of the microRNAs listed in data S1 (or Table 3 disclosing data S1).

In the present disclosure, the urine extract may be obtained by contacting urine with a nanowire having a positively charged surface (e.g., a nanowire having at least one surface selected from the group consisting of ZnO, $SiO_2$, $Li_2O$, MgO, $Al_2O_3$, CaO, $TiO_2$, $Mn_2O_3$, $Fe_2O_3$, CoO, NiO, CuO, $Ga_2O_3$, SrO, $In_2O_3$, $SnO_2$, $Sm_2O_3$, and EuO) in a pH-environment of urine, then washing if required, and then extracting the urine extract with a buffer containing a nonionic surfactant or the like (the urine extract thus obtained may be referred to as the "urine extract of the present disclosure").

Urine may also be pH adjusted such that the surface charge of the nanowires is positive when contacting the nanowires with urine, before, after, or during contact.

As used herein, "in situ extraction" means disrupting EV captured on nanowires using a nanowire-incorporated microfluidic device to extract small molecule RNAs (e.g., microRNAs) in situ, or extracting small molecule RNAs (e.g., microRNAs) captured on nanowires into solutions from nanowires.

As used herein, "free" when used in the context of a form of microRNA present in urine means that the microRNA is not encapsulated in an extracellular vesicle and is present in an unassociated state with the extracellular vesicle.

As used herein, "inclusion" when used in the context of a form of presence of microRNA in urine means that the microRNA is incorporated in an extracellular vesicle (either fully or partially inclusive).

As used herein, "nanowire" means a rod-like structure having a size (e.g., a diameter of 1 to several hundred nanometers) such as a cross-sectional shape or diameter on the order of nanometers.

The size of the nanowires is not particularly limited, but for example, 1 nm, 5 nm, 10 nm, 15 nm, 20 nm, 25 nm, 30 nm, 40 nm, 50 nm, 60 nm, 70 nm, 80 nm, 90 nm, 100 nm, 105 nm, 110 nm, 115 nm, 120 nm, 125 nm, 130 nm, 135 nm, 140 nm, 145 nm, 150 nm, 155 nm, 160 nm, 175 nm, 180 nm, 185 nm, 190 nm, 200 nm, 210 nm, 220 nm, 240 nm, 250 nm, 260 nm, 280 nm, 290 nm, 300 nm, 310 nm, 330 nm, 350 nm, 360 nm, 370 nm, 380 nm, 390 nm, 400 nm, 410 nm, 420 nm, 430 nm, 440 nm, 450 nm, 470 nm, 480 nm, or 490 nm, or may be larger than one lower limit value selected from the above group of numbers.

The size of the nanowires is also not particularly limited, but for example, 1000 nm, 990 nm, 980 nm, 970 nm, 960 nm, 930 nm, 920 nm, 910 nm, 900 nm, 890 nm, 880 nm, 870 nm, 860 nm, 850 nm, 840 nm, 820 nm, 810 nm, 800 nm, 790 nm, 780 nm, 770 nm, 760 nm, 750 nm, 740 nm, 730 nm, 720 nm, 710 nm, 700 nm, 690 nm, 680 nm, 670 nm, 660 nm, 650 nm, 640 nm, 560 nm, 550 nm, 550 nm, 540 nm, 530 nm, 520 nm, 510 nm or 500 nm, or may be smaller than one lower limit value selected from the above group of numbers.

The size of the nanowire is not particularly limited, and may be any size between the upper limit and the lower limit shown above, for example.

In the devices of the present disclosure, nanowires can be used to increase the surface area, which can increase the collection capacity of the EV.

The length of the nanowire is not particularly limited, and may be any length between two values selected from 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm, for example.

The length and diameter of the nanowires can affect the physical strength and surface area of the nanowires.

The length and diameter could be adjusted to suit the environment of use.

As used herein, "free" when used in combination with a component just before the term means substantially free or free of the component.

"Substantially free" does not exclude the inclusion of a level of the component in the extract that cannot be removed.

The present inventors have found that by contacting the urine of a subject with a nanowire having a positively charged surface (e.g., the surface of zinc oxide (ZnO)) in environments of pH 6 to 8, the extracellular vesicles (EV) (and free miRNA) in the urine adsorb to the nanowire efficiently and without being destroyed.

The inventors have also found that EV and miRNA adsorbed on the nanowires can be effectively collected by the surfactant.

According to the present disclosure, there is provided a urine extract comprising any one or more of the microRNAs described in data S1 (or Table 3).

According to the present disclosure, there is provided a urine extract comprising all the microRNAs described in data S1 (or Table 3).

According to the present disclosure, there is provided a urine extract comprising any one or more of the microRNAs described in Table 2.

According to the present disclosure, there is provided an extract of urine comprising all of the microRNAs described in Table 2.

In some aspects of the present disclosure, a urine extract comprising any one or more or all of the microRNAs described in data S1 (or Table 3) may comprise 500 or more, 600 or more, 700 or more, 800 or more, 900 or more, 1000 or more, or 1100 or more species of microRNAs (particularly microRNAs present in urine).

In some aspects, a urine extract comprising any one or more or all of the microRNAs described in data S1 (or Table 3) may comprise 749 or more, 822 or more, or 1111 or more species of microRNAs (particularly microRNAs present in urine).

In some aspects of the present disclosure, microRNAs present in urine may comprise 500 or more, 600 or more, 700 or more, 800 or more, 900 or more, 1000 or more, or 1100 or more species.

In some embodiments, the number of species of microRNAs contained in urine may be the number of species of microRNAs actually contained.

In some embodiments, the number of species of microRNAs contained in urine may be defined by microRNA detection methods or detection techniques.

For example, the number of species of microRNAs contained in urine may depend on the detection limits of the microRNA detection methods.

In some aspects of the present disclosure, it may preferably be prepared from urine using the nanowire-incorporated devices of the present disclosure.

In some aspects of the present disclosures, the microRNA may comprise at least one or all of the microRNAs selected from the group consisting of microRNAs exhibiting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, and 16 or more in the values described in data S1 (or Table 3) (values log 2 transformed after background intensities have been subtracted).

In some aspects of the present disclosures, the microRNA may comprise at least one or all of the microRNAs selected from the group consisting of microRNAs exhibiting at least 1 to less than 2, 2 to less than 3, 3 to less than 4, 4 to less than 5, 5 to less than 6, 6 to less than 7, 7 to less than 8, 8 to less than 9, 9 to less than 10, 10 to less than 11, 11 to less than 12, 12 to less than 13, 13 to less than 14, 14 to less than 15, and 16 or more in the values described in data S1 (or Table 3) (values log 2 converted after background intensities have been subtracted).

In this aspect, the numerical value above may be a numerical value in a non-cancerous donor, (e.g., a healthy person), a numerical value in a lung cancer patient, a numerical value in a pancreatic cancer patient, a numerical value in a liver cancer patient, a numerical value in a bladder cancer patient, and/or a numerical value in a prostate cancer patient.

According to the present disclosure there is provided a urinary extract comprising at least one or all species of microRNAs selected from the group consisting of miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166, miR-3167, miR-16-1-3p, miR-424-3p, miR-519c-5p, miR-525-5p, miR-551b-5p, miR-558, miR-921, miR-942-3p, miR-3126-3p, miR-3127-5p, miR-3129-5p, miR-3144-5p, miR-3150a-5p, miR-3152-5p, miR-3155a, miR-3157-3p, miR-3159, miR-3165, miR-3678-3p, miR-4321, miR-4521, miR-4800-3p, miR-4999-5p, miR-5096, miR-5187-5p, miR-6874-5p, miR-3127-3p, miR-3130-5p, miR-3131, miR-3141, miR-3150b-5p, miR-3151-3p, miR-3151-5p, miR-3154, miR-3160-3p, miR-3160-5p, miR-378a-5p, miR-520c-3p, miR-526b-3p, miR-3150a-3p, miR-3162-5p and miR-4254.

According to the present disclosure there is provided a urinary extract comprising at least one species of microRNA or all microRNAs selected from the group consisting of miR-3163, miR-16-1-3p, miR-424-3p, miR-558, miR-3127-5p and miR-4521.

According to the present disclosure there is provided a urinary extract comprising at least one species of microRNA or all microRNAs selected from the group consisting of miR-378a-5p, miR-520c-3p and miR-526b-3p.

These microRNAs can be detected in the urine of lung cancer patients.

Thus, according to the present disclosure, the urine may be a urine of a subject having lung cancer.

According to the present disclosure there is provided a urinary extract comprising at least one or all species of microRNAs selected from the group consisting of let-7i-3p, miR-183-5p, miR-202-5p, miR-409-5p, miR-4661-5p, miR-4800-3p, miR-5587-5p, miR-372-3p, miR-378b, miR-520b, miR-1266-3p, miR-3605-5p, miR-3612, miR-4645-3p, miR-4694-3p, miR-4752, miR-6816-3p, miR-8087, let-7f-2-3p, miR-15a-3p, miR-20a-3p, miR-33b-3p, miR-34c-5p, miR-93-5p, miR-130a-5p, miR-135a-5p, miR-135b-5p, miR-185-5p, miR-203a-3p, miR-302d-5p, miR-337-3p, miR-378c, miR-422a, miR-449c-5p, miR-483-5p, miR-506-3p, miR-511-5p, miR-520c-3p, miR-654-3p, miR-668-5p, miR-670-5p, miR-671-3p, miR-744-3p, miR-1178-3p, miR-1254, miR-1284, miR-1323, miR-2116-5p, miR-2355-3p, miR-3132, miR-3138, miR-3164, miR-3186-3p, miR-3189-3p, miR-3198, miR-3200-5p, miR-3657, miR-3667-5p, miR-3680-5p, miR-3692-5p, miR-3713, miR-3921, miR-3936, miR-4273, miR-4299, miR-4306, miR-4316, miR-4319, miR-4421, miR-4429, miR-4435, miR-4441, miR-4473, miR-4506, miR-4633-5p, miR-4658, miR-4733-5p, miR-4733-3p, miR-5004-3p, miR-5194, miR-5197-5p, miR-5571-5p, miR-6083, miR-6717-5p, miR-6720-5p, miR-6767-3p, miR-6781-3p, miR-6811-3p, miR-6821-3p, miR-6828-5p, miR-6832-5p, miR-6837-3p, miR-6841-5p, miR-6853-5p, miR-6871-3p, miR-6875-5p, miR-6878-5p, miR-7112-3p, miR-7703, miR-7848-3p and miR-7856-5p.

According to the present disclosures there is provided a urinary extract comprising at least one or all species of microRNAs selected from the group consisting of miR-183-5p, miR-202-5p and miR-409-5p.

According to the present disclosure there is provided a urinary extract comprising at least one or all species of microRNAs selected from the group consisting of miR-372-3p, miR-520b, miR-15a-3p, miR-34c-5p, miR-135a-5p, miR-185-5p, miR-337-3p, miR-422a, miR-506-3p, miR-520c-3p, miR-1284, miR-1323 and miR-4273.

These microRNAs can be detected in the urine of pancreatic cancer patients.

Thus, according to the present disclosure, the urine may be a urine of a subject having pancreatic cancer.

According to the present disclosure there is provided a urinary extract comprising at least one or all species of microRNAs selected from the group consisting of miR-4521, let-7c-3p, let-7i-5p, miR-16-1-3p, miR-26a-1-3p, miR-28-5p, miR-105-5p, miR-195-3p, miR-200b-5p, miR-219a-2-3p, miR-297, miR-300, miR-330-3p, miR-374b-5p, miR-431-5p, miR-454-5p, miR-513c-5p, miR-548ax, miR-593-5p, miR-623, miR-664a-5p, miR-942-3p, miR-1205, miR-1276, miR-1288-3p, miR-1297, miR-3678-3p, miR-4283, miR-4295, miR-4439, miR-4524b-5p, miR-4703-3p, miR-4768-5p, miR-4800-3p, miR-5187-5p, miR-5696, miR-7161-5p, let-7i-2-3p and miR-520c-3p.

According to the present disclosure there is provided a urinary extract comprising at least one or all species of microRNAs selected from the group consisting of miR-16-1-3p, miR-28-5p, miR-297, miR-300, miR-330-3p, miR-454-5p, miR-1297 and miR-4295.

According to the present disclosures, urinary extracts comprising miR-520c-3p are provided.

These microRNAs can be detected in the urine of subjects having liver cancer.

Thus, the urine may be a urine of a subject having liver cancer.

According to the present disclosure there is provided a urinary extract comprising at least one or all species of microRNAs selected from the group consisting of miR-16-1-3p, miR-23b-3p, miR-28-5p, miR-92a-2-5p, miR-142-3p, miR-195-3p, miR-196b-5p, miR-299-3p, miR-492, miR-513b-5p, miR-601, miR-619-5p, miR-1285-3p, miR-3155a, miR-3162-5p, miR-3678-3p, miR-4283, miR-4295, miR-4311, miR-4531, miR-5096, miR-5187-5p, let-7f-2-3p, miR-520c-3p and miR-4783-5p.

According to the present disclosure there is provided a urinary extract comprising at least one or all species of microRNAs selected from the group consisting of miR-16-1-3p, miR-23b-3p, miR-28-5p, miR-142-3p, miR-195-3p, miR-299-3p and miR-4295.

According to the present disclosures, there is provided a urinary extract comprising miR-520c-3p.

These microRNAs can be detected in aspects of having bladder cancer.

Thus, in the present disclosure, the urine may be a urine of a subject having bladder cancer.

According to the present disclosure there is provided a urinary extract comprising at least one or all species of microRNAs selected from the group consisting of miR-4531, miR-28-5p, miR-103a-2-5p, miR-105-5p, miR-124-3p, miR-151a-5p, miR-151b, miR-200a-5p, miR-300, miR-424-3p, miR-519c-5p, miR-551b-5p, miR-617, miR-873-3p, miR-921, miR-1288-3p, miR-3124-5p, miR-3155a, miR-3917, miR-4283, miR-4727-3p, miR-5096, miR-5187-5p, miR-6074, miR-6874-5p, miR-6892-5p, miR-15a-3p, miR-135b-5p, miR-520c-3p, miR-4783-5p and miR-7849-3p.

According to the present disclosures there is provided a urinary extract comprising at least one or all species of microRNAs selected from the group consisting of miR-28-5p, miR-105-5p, miR-124-3p, miR-151a-5p and miR-300.

According to the present disclosures there is provided a urinary extract comprising at least one or all species of microRNAs selected from the group consisting of miR-15a-3p and miR-520c-3p.

These microRNAs can be detected in aspects of having prostate cancer.

Thus, in the present disclosure, the urine may be a urine of a subject having prostate cancer.

In another aspect of the disclosure, a method of testing a subject for a risk of having cancer is provided.

Methods for testing the risk of being cancerous can be replaced by methods for diagnosing whether it is cancer, obtaining preliminary information to diagnose it is cancer, determining whether cancer cells are present in a subject, or determining the risk that a subject is cancerous.

In the present disclosure, a definitive diagnosis may be made by a physician or the like after a subject is determined to have a risk of having cancer by a method of testing the risk of the subject being cancerous.

In accordance with the methods of the present disclosure, there is provided a method comprising diagnosing cancer and administering an anti-cancer therapy to a patient diagnosed with cancer.

In this disclosure, the risk of a subject being cancerous can be determined by the level of expression of any of the microRNAs described in data S1 (or Table 3) in the body fluid sample, as indicator.

In some aspects of the present disclosure, a bodily fluid sample means a bodily fluid obtained from a subject or a sample derived from the bodily fluid.

The body fluid sample may be blood, serum, plasma, lymph fluid, tissue fluids such as interstitial fluid, intercellular fluid, interstitial fluid, and the like, and may be body cavity fluid, serosal fluid, pleural fluid, ascites fluid, capsular fluid, cerebrospinal fluid (CSF), joint fluid (synovial fluid), and aqueous humor of the eye (aqueous humor).

The body fluid may be digestive fluid such as saliva, gastric juice, bile, pancreatic juice, intestinal fluid, etc., and may be sweat, tears, runny nose, urine, semen, vaginal fluid, amniotic fluid, milk, etc.

The bodily fluid may be an animal bodily fluid or a human bodily fluid.

Preferably, urine or an extract thereof can be used as a body fluid sample in the present disclosure.

Preferably, in the present disclosure, the urine extract may be a urine extract of the present disclosure.

The cancer may be, for example, but not limited to, one or more cancers selected from solid cancers, hematopoietic tumors, and the like.

Cancers include, for example, one or more selected from the group consisting of lung cancer, pancreatic cancer, liver cancer, bladder cancer, and prostate cancer.

The risk that the subject is cancerous can be assessed by the microRNA level of the subject's body fluid sample, as indicator.

For example, in data S1 (or Table 3), for microRNAs that exhibit higher expression in a subject that is cancerous than in a subject that is non-cancerous, it can be determined that the risk of the subject being cancerous is higher, with an indicator that the microRNA level of the subject's fluid sample is higher than a predetermined value (hereinafter sometimes referred to as a "threshold").

In the above, in the data S1 (or Table 3), for example, for microRNAs exhibiting higher expression in three subjects who are cancerous than in any of three subjects who are non-cancerous, it can be determined that the risk of the subject being cancerous is higher, with an indicator that the microRNA level of the subject's body fluid sample is higher than a predetermined value (hereinafter, sometimes referred to as a "threshold").

Also, for example, in data S1 (or Table 3), for microRNAs (e.g., 2 times or more, 3 times or more, 4 times or more, 5 or more, 6 or more, 7 or more, 8 or more, 9 or more, or 10 or more) that exhibit higher expression in a subject that is cancerous than in a subject that is non-cancerous, it can be determined that the risk of the subject being cancerous is lower, with an indicator that the microRNA level of the subject's fluid sample is lower than a predetermined value (hereinafter sometimes referred to as a "threshold").

In the above, in data S1 (or Table 3), for example, for microRNAs (e.g., 2 times or more, 3 times or more, 4- or more, 5- or more, 6- or more, 7- or more, 8- or more, 9- or more, or 10- or more) that exhibit lower expression in three cancerous subjects than any of three non-cancerous subjects, it can be determined that the risk of the subject being cancerous is lower, with an indicator that the microRNA level of the subject's fluid sample is lower than a predetermined value (hereinafter sometimes referred to as a "threshold").

In these cases, the predetermined value may be, for example, but not limited to, any numerical value (statistical value or index value) between two values selected from the group consisting of a mean, a median, a third quartile, a first quartile, and a lowest values of the microRNA level in the group of subjects with cancer.

Also, for example, the predetermined value may be any numerical value between two values selected from the group consisting of, for example, but not limited to, a maximum value, a third quartile, an average value, a median value, and a first quantile value of the microRNA level in a non-cancerous subject group.

In the present disclosure, the number of species of the microRNA to be measured and/or the species of the microRNA serving as an indicator of the risk of cancer can be, for example, 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, 1000 or more, or 1100 or more.

Among the number of species of microRNAs of the subject fluid sample, the number of species of the microRNAs to be measured and/or the number of species of the microRNAs serving as an indicator of the risk of cancer may be, for example, 2000 or less, 1900 or less, 1800 or less, 1700 or less, 1600 or less, 1500 or less, 1400 or less, 1300 or less, 1200 or less, 1100 or less, 1000 or less, 900 or less, 800 or less, 700 or less, 600 or less, 500 or less, 400 or less, 300 or less, 200 or less, 100 or less, 90 or less, 80 or less, 70 or less, 60 or less, 50 or less, 40 or less, 30 or less, 20 or less, or 10 or less.

Methods in which to use microRNAs as an indicator of cancer risk are disclosed herein.

Also, for example, in data S1 (or Table 3), for microRNAs that exhibit lower expression in a subject who is cancerous than in a subject who is not cancerous, it can be determined that the risk of the subject being cancerous is lower, with an indicator that the microRNA level of the subject's body fluid sample is lower than a predetermined value.

In the above, in data S1 (or Table 3), for example, for microRNAs (e.g., 2 times or more, 3 times or more, 4 or more, 5 or more, 6 or more, 7 or more, 8 or more, 9 or more, or 10 or more) exhibiting lower expression in three cancerous subjects than any of three non-cancerous subjects, it can be determined that the risk of the subject being cancerous is lower, with an indicator that the microRNA level of the subject's body fluid sample is lower than a predetermined value (hereinafter sometimes referred to as a "threshold").

Also, for example, in data S1 (or Table 3), for microRNAs that exhibit lower expression in a subject who is cinereous than in a subject who is not cancerous, it can be determined that the risk of the subject being cancerous is lower, with an indicator that the microRNA level of the subject's body fluid sample is higher than a predetermined value.

In the above, in data S1 (or Table 3), for example, for a microRNA (e.g., 2 times or more, 3 times or more, 4 or more, 5 or more, 6 or more, 7 or more, 8 or more, 9 or more, or 10 or more) exhibiting lower expression in three cancerous subjects than any of three non-cancerous subjects, it can be determined that the risk of the subject being cancerous is lower, with an indicator the microRNA level of the subject's fluid sample is higher than a predetermined value (hereinafter sometimes referred to as a "threshold").

In these cases, the predetermined value is not limited, but for example, may be any numerical value between two values selected from the group consisting of a mean, a median, a third quartile, a first quartile, and a lowest value of the microRNA level in a cancerous subject group.

Also, for example, the predetermined value is not limited, but for example, may be any numerical value between two values selected from the group consisting of a maximum value, a third quartile, an average value, a median value, and a first quantile value of the microRNA level in a non-cancerous subject group.

According to the present disclosure, a method of testing a risk of a subject having lung cancer is provided.

According to the present disclosure, a method of testing a risk of a subject having lung cancer can test the risk that the subject has lung cancer, with the levels of any one or more microRNAs selected from data S1 (or Table 3) in a bodily fluid sample of the subject, as an indicator.

According to the present disclosure, the risk that a subject has lung cancer can be tested using with the levels of at least one or all species of microRNA selected from the group consisting of miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166, miR-3167, miR-16-1-3p, miR-424-3p, miR-519c-5p, miR-525-5p, miR-551b-5p, miR-558, miR-921, miR-942-3p, miR-3126-3p, miR-3127-5p, miR-3129-5p, miR-3144-5p, miR-3150a-5p, miR-3152-5p, miR-3155a, miR-3157-3p, miR-3159, miR-3165, miR-3678-3p, miR-4321, miR-4521, miR-4800-3p, miR-4999-5p, miR-5096, miR-5187-5p, miR-6874-5p, miR-3127-3p, miR-3130-5p, miR-3131, miR-3141, miR-3150b-5p, miR-3151-3p, miR-3151-5p, miR-3154, miR-3160-3p, miR-3160-5p, miR-378a-5p, miR-520c-3p, miR-526b-3p, miR-3150a-3p, miR-3162-5p and miR-4254 in a bodily fluid sample of the subject, as an indicator.

According to the present disclosures the risk that a subject has lung cancer can be tested with the levels of at least one species of microRNA or all microRNAs selected from the group consisting of miR-3163, miR-16-1-3p, miR-424-3p, miR-558, miR-3127-5p and miR-4521 in a body fluid sample of the subject, as an indicator.

If the levels of at least one microRNA or all of the microRNAs selected from the group consisting of miR-3163, miR-16-1-3p, miR-424-3p, miR-558, miR-3127-5p and miR-4521 in a body fluid sample are higher than a predetermined value, it can be determined that the subject has a risk of having lung cancer (and/or if the levels are lower than a predetermined value, it can be determined that the subject has a possibility of not having lung cancer).

According to the present disclosure the risk that a subject has lung cancer can be tested with the levels of at least one species of microRNA or all microRNAs selected from the group consisting of miR-378a-5p, miR-520c-3p and miR-526b-3p in a bodily fluid sample of the subject, as an indicator.

If at least one or all species of the microRNAs selected from the group consisting of miR-378a-5p, miR-520c-3p and miR-526b-3p in the bodily fluid sample are lower than a predetermined value, it can be determined that the subject has a risk of having lung cancer (and/or if higher than a predetermined value, it can be determined that the subject has a possibility of not having lung cancer).

Also according to the present disclosure, the microRNAs in the urine that can be indicators of lung cancer may be at least one or all species selected from the group consisting of miR-3127-3p, miR-3130-5p, miR-3131, miR-3141, miR-3150b-5p, miR-3151-3p, miR-3151-5p, miR-3154, miR-3160-3p and miR-3160-5p.

According to the present disclosure, the microRNAs in the urine that can be indicators of lung cancer may be at least one or all species selected from the group consisting of miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166 and miR-3167.

According to the present disclosure, there is provided a method of testing the risk of a subject having pancreatic cancer.

According to the present disclosure, a method of testing the risk of a subject having pancreatic cancer can test the risk that the subject has pancreatic cancer, with the levels of any one or more species of microRNAs selected from data S1 (or Table 3) in a bodily fluid sample of the subject, as indicator.

According to the present disclosure, the risk of a subject having pancreatic cancer can be tested with the levels of at least one or all species of microRNA selected from the group consisting of let-7i-3p, miR-183-5p, miR-202-5p, miR-409-5p, miR-4661-5p, miR-4800-3p, miR-5587-5p, miR-372-3p, miR-378b, miR-520b, miR-1266-3p, miR-3605-5p, miR-3612, miR-4645-3p, miR-4694-3p, miR-4752, miR-6816-3p, miR-8087, let-7f-2-3p, miR-15a-3p, miR-20a-3p, miR-33b-3p, miR-34c-5p, miR-93-5p, miR-130a-5p, miR-135a-5p, miR-135b-5p, miR-185-5p, miR-203a-3p, miR-302d-5p, miR-337-3p, miR-378c, miR-422a, miR-449c-5p, miR-483-5p, miR-506-3p, miR-511-5p, miR-520c-3p, miR-654-3p, miR-668-5p, miR-670-5p, miR-671-3p, miR-744-3p, miR-1178-3p, miR-1254, miR-1284, miR-1323, miR-2116-5p, miR-2355-3p, miR-3132, miR-3138, miR-3164, miR-3186-3p, miR-3189-3p, miR-3198, miR-3200-5p, miR-3657, miR-3667-5p, miR-3680-5p, miR-3692-5p, miR-3713, miR-3921, miR-3936, miR-4273, miR-4299, miR-4306, miR-4316, miR-4319, miR-4421, miR-4429, miR-4435, miR-4441, miR-4473, miR-4506, miR-4633-5p, miR-4658, miR-4733-5p, miR-4733-3p, miR-5004-3p, miR-5194, miR-5197-5p, miR-5571-5p, miR-6083, miR-6717-5p, miR-6720-5p, miR-6767-3p, miR-6781-3p, miR-6811-3p, miR-6821-3p, miR-6828-5p, miR-6832-5p, miR-6837-3p, miR-6841-5p, miR-6853-5p, miR-6871-3p, miR-6875-5p, miR-6878-5p, miR-7112-3p, miR-7703, miR-7848-3p and miR-7856-5p in a bodily fluid sample of the subject, as indicator.

Also, according to the present disclosure, the risk of a subject having pancreatic cancer can be tested with the levels of at least one or all species of microRNAs selected from the group consisting of miR-183-5p, miR-202-5p and miR-409-5p in a body fluid sample of the subject, as indicator.

If the levels of at least one or all species of the microRNAs selected from the group consisting of miR-183-5p, miR-202-5p and miR-409-5p in the bodily fluid sample are higher than a predetermined value, then it can be determined that the subject has a risk of having pancreatic cancer (and/or, if lower, it can be determined that the subject has a possibility of not having pancreatic cancer).

Also, according to the present disclosure, the risk of a subject having pancreatic cancer can be tested with the levels of at least one or all species of microRNA selected from the group consisting of miR-372-3p, miR-520b, miR-15a-3p, miR-34c-5p, miR-135a-5p, miR-185-5p, miR-337-3p, miR-422a, miR-506-3p, miR-520c-3p, miR-1284, miR-1323 and miR-4273, as an indicator.

If the levels of at least one or all species of the microRNAs selected from the group consisting of miR-372-3p, miR-520b, miR-15a-3p, miR-34c-5p, miR-135a-5p, miR-185-5p, miR-337-3p, miR-422a, miR-506-3p, miR-520c-3p, miR-1284, miR-1323 and miR-4273 in a body fluid sample are lower than a predetermined value, it can be determined that the subject has a risk of having pancreatic cancer (and/or, if higher, it can be determined that the subject has a possibility of not having pancreatic cancer).

Also according to the present disclosure, the microRNAs in the urine that can be indicator of pancreatic cancer may be at least one or all species selected from the group consisting of miR-372-3p, miR-378b, miR-520b, miR-1266-3p, miR-3605-5p, miR-3612, miR-4645-3p, miR-4694-3p, miR-4752, miR-6816-3p and miR-8087.

According to the present disclosure, there is provided a method of testing a risk of a subject having liver cancer.

According to the present disclosure, the method of testing the risk of a subject having liver cancer can test the risk of the subject having liver cancer, with the levels of one or more species of microRNAs selected from data S1 (or Table 3) in the bodily liquid sample of the subject, as indicator.

According to the present disclosure, the risk of a subject having liver cancer can be tested with the levels of at least one or all species of microRNAs selected from the group consisting of miR-4521, let-7c-3p, let-7i-5p, miR-16-1-3p, miR-26a-1-3p, miR-28-5p, miR-105-5p, miR-195-3p, miR-200b-5p, miR-219a-2-3p, miR-297, miR-300, miR-330-3p, miR-374b-5p, miR-431-5p, miR-454-5p, miR-513c-5p, miR-548ax, miR-593-5p, miR-623, miR-664a-5p, miR-942-3p, miR-1205, miR-1276, miR-1288-3p, miR-1297, miR-3678-3p, miR-4283, miR-4295, miR-4439, miR-4524b-5p, miR-4703-3p, miR-4768-5p, miR-4800-3p, miR-5187-5p, miR-5696, miR-7161-5p, let-7i-2-3p and miR-520c-3p, as indicator.

According to the present disclosure, the risk of a subject having liver cancer can be tested with the levels of at least one or all species of the microRNA selected from the group consisting of miR-4521, let-7c-3p, let-7i-5p, miR-16-1-3p, miR-26a-1-3p, miR-28-5p, miR-105-5p, miR-195-3p, miR-200b-5p, miR-219a-2-3p, miR-297, miR-300, miR-330-3p, miR-374b-5p, miR-431-5p, miR-454-5p, miR-513c-5p, miR-548ax, miR-593-5p, miR-623, miR-664a-5p, miR-942-3p, miR-1205, miR-1276, miR-1288-3p, miR-1297, miR-3678-3p, miR-4283, miR-4295, miR-4439, miR-4524b-5p, miR-4703-3p, miR-4768-5p, miR-4800-3p, miR-5187-5p, miR-5696, miR-7161-5p, let-7i-2-3p and miR-520c-3p, as indicator.

If the levels of at least one or all species of the microR-NAs selected from the group consisting of miR-16-1-3p, miR-28-5p, miR-297, miR-300, miR-330-3p, miR-454-5p, miR-1297 and miR-4295 in a body fluid sample are higher than a predetermined value, it can be determined that the subject has a risk of having liver cancer (and/or, if lower, it can be determined that the subject has a possibility of not having liver cancer).

In the present disclosure, levels of miR-520c-3p can be used as indicator to test the risk of a subject having liver cancer.

If the level of miR-520c-3p in a body fluid sample is lower than a predetermined value, it can be determined that the subject has a risk of having liver cancer (and/or if higher, it can be determined that the subject has a possibility of not having liver cancer).

Also according to the present disclosure, microRNA in urine that can be an indicator of liver cancer can be miR-4521.

According to the present disclosure, there is provided a method of testing a risk of a subject having bladder cancer.

According to the present disclosure, the method of testing the risk of a subject having bladder cancer can test the risk of the subject having bladder cancer, with the levels of one or more species of microRNAs selected from data S1 (or Table 3) in the body liquid sample of the subject, as indicator.

According to the present disclosures, the risk of the subject having bladder cancer can be tested with the levels of at least one or all species of microRNAs selected from the group consisting of miR-16-1-3p, miR-23b-3p, miR-28-5p, miR-92a-2-5p, miR-142-3p, miR-195-3p, miR-196b-5p, miR-299-3p, miR-492, miR-513b-5p, miR-601, miR-619-5p, miR-1285-3p, miR-3155a, miR-3162-5p, miR-3678-3p, miR-4283, miR-4295, miR-4311, miR-4531, miR-5096, miR-5187-5p, let-7f-2-3p, miR-520c-3p and miR-4783-5p as indicator.

According to the present disclosure, the risk of a subject having bladder cancer can be tested with the levels of at least one or all species of the microRNA selected from the group consisting of miR-16-1-3p, miR-23b-3p, miR-28-5p, miR-142-3p, miR-195-3p, miR-299-3p and miR-4295 as indicator.

If the levels of at least one or all species of the microR-NAs selected from the group consisting of miR-16-1-3p, miR-23b-3p, miR-28-5p, miR-142-3p, miR-195-3p, miR-299-3p and miR-4295 in a bodily fluid sample are higher than a predetermined value, it can be determined that the subject has a risk of having bladder cancer (and/or, if lower, it can be determined that the subject has a possibility of not having bladder cancer).

In the present disclosure, levels of miR-520c-3p can be used as indicator to test the risk of a subject having bladder cancer.

If the level of miR-520c-3p in a body fluid sample is lower than a predetermined value, it can be determined that the subject has a risk of having bladder cancer (and/or if higher, it can be determined that the subject has a possibility of not having bladder cancer).

According to the present disclosure, a method of testing a subject for a risk of prostate cancer is provided.

According to the present disclosure, the method of testing the risk of a subject having prostate cancer can test the risk of the subject having prostate cancer, with the levels of one or more species of microRNAs selected from data S1 (or Table 3) in the body liquid sample of the subject, as indicator.

According to the present disclosure, the risk of a subject having prostate cancer can be tested with the levels of at least one or all species of microRNAs selected from the group consisting of miR-4531, miR-28-5p, miR-103a-2-5p, miR-105-5p, miR-124-3p, miR-151a-5p, miR-151b, miR-200a-5p, miR-300, miR-424-3p, miR-519c-5p, miR-551b-5p, miR-617, miR-873-3p, miR-921, miR-1288-3p, miR-3124-5p, miR-3155a, miR-3917, miR-4283, miR-4727-3p, miR-5096, miR-5187-5p, miR-6074, miR-6874-5p, miR-6892-5p, miR-15a-3p, miR-135b-5p, miR-520c-3p, miR-4783-5p and miR-7849-3p, as indicator.

According to the present disclosures, the risk of a subject having prostate cancer can be tested with the levels of at least one or all species of microRNAs selected from the group consisting of miR-28-5p, miR-105-5p, miR-124-3p, miR-151a-5p and miR-300, as indicator.

If the levels of at least one or all species of the microR-NAs selected from the group consisting of miR-28-5p, miR-105-5p, miR-124-3p, miR-151a-5p and miR-300 in the bodily fluid sample are higher than a predetermined value, it can be determined that the subject has a risk of having prostate cancer (and/or, if lower, it can be determined that the subject has a possibility of not having prostate cancer).

In the present disclosure, levels of at least one or all species of the microRNAs selected from the group consisting of miR-15a-3p and miR-520c-3p can be used as indicator to test the risk of a subject having liver cancer.

If the level of at least one or all species of the microRNAs selected from the group consisting of miR-15a-3p and miR-520c-3p in the bodily fluid sample are lower than a predetermined value, it can be determined that the subject has a risk of having prostate cancer (and/or, if higher, it can be determined that the subject has a possibility of not having prostate cancer).

Also according to the present disclosure, microRNA in urine that can be indicators of prostatic cancer can be miR-4531.

In the present disclosure, when a plurality of microRNAs are used as indicators to test a subject's risk of having a cancer or a particular cancer, in some embodiments the plurality of microRNA levels may be compared to respective predetermined values, or in some embodiments the scores obtained by weighting the plurality of microRNA levels may be compared to predetermined values obtained by similarly weighting.

If multiple levels of microRNAs are compared to respective predetermined values, the number of microRNAs suggesting a risk of cancer and the number of microRNAs suggesting a possibility of non-cancer can be compared to determine whether the risk of cancer is high and/or whether the possibility of non-cancer is high.

Also in the present disclosure, if multiple microRNA levels are weighted to obtain scores (e.g., when scoring microRNA signatures), each microRNA level may be normalized and then scored (e.g., Z-scores may be obtained) by adding or multiplying the normalized values, with or without weighting.

The microRNA score thus obtained can be compared to a predetermined value obtained in a similar manner (i.e., a score obtained in a similar manner from a cancer patient or a non-cancer subject, etc.) to determine whether the risk of cancer is high or the possibility of non-cancer is high.

The weighting can be positive for larger amounts of body fluid samples in cancerous subjects and negative for smaller amounts (or vice versa), as compared to non-cancerous subject body fluid samples.

Weighting can also be done by multiplying larger numbers for those with large differences or correlations between cancerous and non-cancerous subjects.

In some embodiments, a machine-learned computer or artificial intelligence may be used to determine the presence or absence of a disease, to identify the disease, or to calculate the probability of developing the disease from multiple levels of microRNA levels.

In this case, in the machine learning or artificial intelligence, for example, a plurality of microRNA levels can be learned by judging the presence or absence of a disease, identifying a disease or learning in association with the probability of developing the disease, so that the machine (computer) or the artificial intelligence (AI) can be learned.

Here, machine learning or learning for artificial intelligence can be performed using:

(i) association data of the expression levels of at least one or all species of microRNAs selected from the group consisting of miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166, miR-3167, miR-16-1-3p, miR-424-3p, miR-519c-5p, miR-525-5p, miR-551b-5p, miR-558, miR-921, miR-942-3p, miR-3126-3p, miR-3127-5p, miR-3129-5p, miR-3144-5p, miR-3150a-5p, miR-3152-5p, miR-3155a, miR-3157-3p, miR-3159, miR-3165, miR-3678-3p, miR-4321, miR-4521, miR-4800-3p, miR-4999-5p, miR-5096, miR-5187-5p, miR-6874-5p, miR-3127-3p, miR-3130-5p, miR-3131, miR-3141, miR-3150b-5p, miR-3151-3p, miR-3151-5p, miR-3154, miR-3160-3p, miR-3160-5p, miR-378a-5p, miR-520c-3p, miR-526b-3p, miR-3150a-3p, miR-3162-5p and miR-4254, associated with cancer;

(ii) association data of the expression levels of at least one or all species of microRNAs selected from the group consisting of let-7i-3p, miR-183-5p, miR-202-5p, miR-409-5p, miR-4661-5p, miR-4800-3p, miR-5587-5p, miR-372-3p, miR-378b, miR-520b, miR-1266-3p, miR-3605-5p, miR-3612, miR-4645-3p, miR-4694-3p, miR-4752, miR-6816-3p, miR-8087, let-7f-2-3p, miR-15a-3p, miR-20a-3p, miR-33b-3p, miR-34c-5p, miR-93-5p, miR-130a-5p, miR-135a-5p, miR-135b-5p, miR-185-5p, miR-203a-3p, miR-302d-5p, miR-337-3p, miR-378c, miR-422a, miR-449c-5p, miR-483-5p, miR-506-3p, miR-511-5p, miR-520c-3p, miR-654-3p, miR-668-5p, miR-670-5p, miR-671-3p, miR-744-3p, miR-1178-3p, miR-1254, miR-1284, miR-1323, miR-2116-5p, miR-2355-3p, miR-3132, miR-3138, miR-3164, miR-3186-3p, miR-3189-3p, miR-3198, miR-3200-5p, miR-3657, miR-3667-5p, miR-3680-5p, miR-3692-5p, miR-3713, miR-3921, miR-3936, miR-4273, miR-4299, miR-4306, miR-4316, miR-4319, miR-4421, miR-4429, miR-4435, miR-4441, miR-4473, miR-4506, miR-4633-5p, miR-4658, miR-4733-5p, miR-4733-3p, miR-5004-3p, miR-5194, miR-5197-5p, miR-5571-5p, miR-6083, miR-6717-5p, miR-6720-5p, miR-6767-3p, miR-6781-3p, miR-6811-3p, miR-6821-3p, miR-6828-5p, miR-6832-5p, miR-6837-3p, miR-6841-5p, miR-6853-5p, miR-6871-3p, miR-6875-5p, miR-6878-5p, miR-7112-3p, miR-7703, miR-7848-3p and miR-7856-5p, associated with cancer;

(iii) association data of the expression levels of at least one or all species of microRNAs selected from the group consisting of miR-4521, let-7c-3p, let-7i-5p, miR-16-1-3p, miR-26a-1-3p, miR-28-5p, miR-105-5p, miR-195-3p, miR-200b-5p, miR-219a-2-3p, miR-297, miR-300, miR-330-3p, miR-374b-5p, miR-431-5p, miR-454-5p, miR-513c-5p, miR-548ax, miR-593-5p, miR-623, miR-664a-5p, miR-942-3p, miR-1205, miR-1276, miR-1288-3p, miR-1297, miR-3678-3p, miR-4283, miR-4295, miR-4439, miR-4524b-5p, miR-4703-3p, miR-4768-5p, miR-4800-3p, miR-5187-5p, miR-5696, miR-7161-5p, let-7i-2-3p and miR-520c-3p, associated with cancer;

(iv) association data of the expression levels of at least one or all species of microRNAs selected from the group consisting of miR-16-1-3p, miR-23b-3p, miR-28-5p, miR-92a-2-5p, miR-142-3p, miR-195-3p, miR-196b-5p, miR-299-3p, miR-492, miR-513b-5p, miR-601, miR-619-5p, miR-1285-3p, miR-3155a, miR-3162-5p, miR-3678-3p, miR-4283, miR-4295, miR-4311, miR-4531, miR-5096, miR-5187-5p, let-7f-2-3p, miR-520c-3p and miR-4783-5p, associated with cancer; or (v) association data of the expression levels of at least one or all species of microRNAs selected from the group consisting of miR-4531, miR-28-5p, miR-103a-2-5p, miR-105-5p, miR-124-3p, miR-151a-5p, miR-151b, miR-200a-5p, miR-300, miR-424-3p, miR-519c-5p, miR-551b-5p, miR-617, miR-873-3p, miR-921, miR-1288-3p, miR-3124-5p, miR-3155a, miR-3917, miR-4283, miR-4727-3p, miR-5096, miR-5187-5p, miR-6074, miR-6874-5p, miR-6892-5p, miR-15a-3p, miR-135b-5p, miR-520c-3p, miR-4783-5p and miR-7849-3p, associated with cancer.

The learned computer or artificial intelligence may comprise a memory (including a computer including a magnetic recording medium such as a ROM, RAM, hard disk, SSD and the like and a computer including the magnetic recording medium) storing one or more data selected from the group consisting of (i) to (v) above, or may be connected to the memory via an electronic communication circuit.

The learned computer or artificial intelligence may be further learned by one or more data selected from the group consisting of (i) to (v) above (in this case, the data used for learning may be further added to the memory).

The learned computer or artificial intelligence can determine the risk that the subject is cancerous based on the data of the expression levels of the at least one or all microRNAs, associated with cancer and the expression levels of the at least one or all microRNAs in the subject's bodily fluid sample.

The learning of computer or artificial intelligence by the association data above can be performed by using a plurality of the association data as teacher data to evaluate non-evaluation data and repeatedly learning different association data until, for example, the sensitivity and/or specificity of cancer detection exceeds a predetermined value.

The predetermined value may vary depending on the requirements for sensitivity and/or specificity, but may be, for example, 10%, 20%, 30%, 40%, 50%, 60%, 70%, 80%, or 90% or more.

Generally, increasing sensitivity increases false positives and decreasing sensitivity increases false negatives.

Therefore, the sensitivity is preferably set according to the purpose of the test.

In general, increasing specificity increases false negatives, and decreasing sensitivity increases false positives.

Therefore, it is desirable to set the specificity according to the purpose of the test.

In the present disclosure, after testing the risk of cancer, data indicating the risk of having cancer and/or the possibility of not having cancer may be output to a medium such as electronic media, paper or the like.

The output data may be presented to a physician and/or patient (or their family, relatives, etc.) and may be used to review subsequent treatment plans or to review subsequent detailed tests (e.g., to select tests).

After testing the risk of cancer, patients can be treated with anticancer therapies such as chemotherapy, radiation therapy, and surgery (e.g., anticancer therapy for certain cancers which it has been determined for the patients to have the risk of having).

In the present disclosure, there is provided a method of detecting microRNA in urine or urine extract of a subject, for example, the method of detecting one or more selected from a group of microRNAs that exhibit higher expression in three cancerous subjects than in any of three non-cancerous subjects, in data S1 (or Table 3).

The microRNAs detected in this aspect can be, for example, one or more from the group of microRNAs exhibiting higher expression in a subject that is cancerous than in a subject that is non-cancerous (e.g., 2 times or more, 3 times or more, 4 or more, 5 or more, 6 or more, 7 or more, 8 or more, 9 or more, or 10 or more).

Such microRNAs include, for example, miR-3117-5p, miR-3118, miR-3121-3p, miR-3121-5p, miR-3126-5p, miR-3128, miR-3133, miR-3134, miR-3136-3p, miR-3136-5p, miR-3139, miR-3142, miR-3143, miR-3145-3p, miR-3163, miR-3166, miR-3167, miR-0558, miR-3126-3p, miR-3129-5p, miR-3144-5p, miR-3150a-5p, miR-3152-5p, miR-3157-3p, miR-3159, miR-4521, miR-0029b-3p, miR-0030b-3p, miR-0106b-3p, miR-0320c, miR-0494-3p, miR-0566, miR-0572, miR-0645, miR-0939-3p, miR-0943, miR-1972, miR-3129-3p, miR-3132, miR-3140-3p, miR-3144-3p, miR-3199, miR-3613-3p, miR-4304, miR-4454, miR-4491, miR-4506, miR-4519, miR-5006-5p, miR-6068, miR-6084, miR-6726-5p, miR-6862-5p, miR-6871-5p, miR-6877-5p, miR-4661-5p, miR-5587-5p, miR-0150-3p, miR-0718, miR-0770-5p, miR-4515, miR-4520-3p, miR-4655-3p, miR-4684-5p, miR-6723-5p, miR-6762-5p, miR-8059, miR-8063, let-7c-3p, miR-0026a-1-3p, miR-0105-5p, miR-0195-3p, miR-0219a-2-3p, miR-0431-5p, miR-0454-5p, miR-0548ax, miR-0593-5p, miR-0623, miR-0664a-5p, miR-0942-3p, miR-1205, miR-1297, miR-3678-3p, miR-4283, miR-7161-5p, let-7b-3p, let-7b-5p, miR-0018a-3p, miR-0018b-3p, miR-0021-3p, miR-0024-2-5p, miR-0025-3p, miR-0025-5p, miR-0026b-3p, miR-0030b-5p, miR-0030d-5p, miR-0030e-3p, miR-0033a-3p, miR-0033b-3p, miR-0034b-5p, miR-0092a-3p, miR-0092b-3p, miR-0093-5p, miR-0098-3p, miR-0099b-5p, miR-0125a-3p, miR-0128-2-5p, miR-0129-2-3p, miR-0130b-5p, miR-0132-3p, miR-0133a-3p, miR-0133a-5p, miR-0133b, miR-0150-5p, miR-0181a-2-3p, miR-0188-5p, miR-0191-3p, miR-0192-5p, miR-0193b-3p, miR-0194-3p, miR-0197-3p, miR-0199a-5p, miR-0199b-5p, miR-0200a-5p, miR-0202-3p, miR-0203a-3p, miR-0204-5p, miR-0205-5p, miR-0210-5p, miR-0212-3p, miR-0216b-3p, miR-0223-3p, miR-0223-5p, miR-0224-3p, miR-0296-5p, miR-0299-5p, miR-0320a, miR-0320b, miR-0320e, miR-0326, miR-0328-3p, miR-0337-3p, miR-0338-3p, miR-0339-5p, miR-0340-3p, miR-0342-5p, miR-0346, miR-0361-3p, miR-0362-3p, miR-0365a-3p, miR-365b-3p, miR-0371a-3p, miR-0371b-3p, miR-0377-5p, miR-0378d, miR-0383-3p, miR-0409-3p, miR-0411-3p, miR-0422a, miR-0423-5p, miR-0431-3p, miR-0449c-3p, miR-0483-3p, miR-0484, miR-0485-3p, miR-0485-5p, miR-0486-5p, miR-0491-3p, miR-0501-5p, miR-0503-3p, miR-0504-5p, miR-0506-3p, miR-0508-5p, miR-0509-5p, miR-0510-5p, miR-0512-5p, miR-0514b-3p, miR-0516b-3p, miR-516a-3p, miR-0518b, miR-0518c-5p, miR-0519d-3p, miR-0519e-3p, miR-0520a-3p, miR-0520g-3p, miR-0550a-3p, miR-0550a-5p, miR-0552-5p, miR-0557, miR-0574-3p, miR-0574-5p, miR-0575, miR-0580-3p, miR-0584-5p, miR-0589-3p, miR-0589-5p, miR-0601, miR-0605-5p, miR-0610, miR-0612, miR-0615-3p, miR-0625-3p, miR-0628-3p, miR-0630, miR-0634, miR-0635, miR-0636, miR-0642a-5p, miR-0650, miR-0656-5p, miR-0657, miR-0659-5p, miR-0663b, miR-0664a-3p, miR-0664b-3p, miR-0671-3p, miR-0764, miR-0766-3p, miR-0874-3p, miR-0877-3p, miR-0877-5p, miR-0888-5p, miR-0935, miR-0937-3p, miR-0938, miR-0940, miR-1181, miR-1182, miR-1200, miR-1204, miR-1207-3p, miR-1224-3p, miR-1225-3p, miR-1228-3p, miR-1234-3p, miR-1238-3p, miR-1238-5p, miR-1247-5p, miR-1249-3p, miR-1250-3p, miR-1250-5p, miR-1255b-5p, miR-1260a, miR-1260b, miR-1266-5p, miR-1273h-3p, miR-1281, miR-1286, miR-1292-3p, miR-1295b-3p, miR-1296-3p, miR-1296-5p, miR-1304-3p, miR-1306-5p, miR-1343-3p, miR-1470, miR-1538, miR-1539, miR-1825, miR-1909-5p, miR-1910-5p, miR-1911-3p, miR-1911-5p, miR-1913, miR-1914-5p, miR-1976, miR-2110, miR-2355-5p, miR-2909, miR-3064-5p, miR-3074-3p, miR-3127-3p, miR-3130-5p, miR-3141, miR-3147, miR-3150a-3p, miR-3150b-5p, miR-3151-3p, miR-3160-3p, miR-3180-5p, miR-3184-3p, miR-3186-3p, miR-3189-5p, miR-3190-5p, miR-3191-3p, miR-3192-3p, miR-3194-5p, miR-3195, miR-3200-3p, miR-3200-5p, miR-3614-5p, miR-3615, miR-3619-5p, miR-3620-3p, miR-3622a-3p, miR-3622a-5p, miR-3622b-3p, miR-3646, miR-3659, miR-3670, miR-3675-3p, miR-3679-3p, miR-3689d, miR-3690, miR-3909, miR-3918, miR-3921, miR-3922-3p, miR-3940-3p, miR-3943, miR-4253, miR-4260, miR-4267, miR-4268, miR-4269, miR-4274, miR-4278, miR-4279, miR-4280, miR-4284, miR-4286, miR-4289, miR-4290, miR-4292, miR-4310, miR-4312, miR-4313, miR-4317, miR-4318, miR-4319, miR-4323, miR-4329, miR-4433a-5p, miR-4433b-5p, miR-4436b-5p, miR-4447, miR-4455, miR-4463, miR-4494, miR-4632-3p, miR-4638-3p, miR-4640-3p, miR-4642, miR-4646-5p, miR-4649-3p, miR-4649-5p, miR-4652-3p, miR-4652-5p, miR-4653-5p, miR-4664-3p, miR-4665-3p, miR-4667-3p, miR-4675, miR-4676-3p, miR-4685-3p, miR-4687-5p, miR-4690-5p, miR-4691-5p, miR-4697-3p, miR-4697-5p, miR-4700-3p, miR-4701-5p, miR-4706, miR-4707-3p, miR-4708-3p, miR-4712-3p, miR-4713-5p, miR-4714-5p, miR-4716-5p, miR-4717-5p, miR-4718, miR-4719, miR-4722-5p, miR-4723-3p, miR-4725-5p, miR-4726-3p, miR-4727-3p, miR-4728-3p, miR-4731-3p, miR-4733-3p, miR-4740-5p, miR-4749-5p, miR-4758-3p, miR-4761-3p, miR-4763-5p, miR-4769-3p, miR-4780, miR-4783-3p, miR-4787-3p, miR-4793-5p, miR-4794, miR-4804-3p, miR-5008-3p, miR-5008-5p, miR-5091, miR-5190, miR-5196-3p, miR-5587-3p, miR-5588-5p, miR-5693, miR-5699-5p, miR-5705, miR-6086, miR-6088, miR-6124, miR-6165, miR-6501-5p, miR-6505-5p, miR-6508-5p, miR-6513-3p, miR-6515-3p, miR-6722-5p, miR-6726-3p, miR-6727-3p, miR-6728-3p, miR-6729-3p, miR-6730-3p, miR-6731-3p, miR-6732-3p, miR-6735-3p, miR-6735-5p, miR-6737-3p, miR-6738-5p, miR-6743-3p, miR-6746-3p, miR-6749-3p, miR-6752-3p, miR-6753-5p, miR-6759-3p, miR-6760-3p, miR-6763-3p, miR-6765-3p, miR-6765-5p, miR-6768-5p, miR-6769a-3p, miR-6769b-3p, miR-6770-5p, miR-6775-3p, miR-6777-3p, miR-6784-3p, miR-6785-3p, miR-6785-5p, miR-6787-3p, miR-6788-3p, miR-6788-5p, miR-6790-3p, miR-6791-3p, miR-6792-3p, miR-6792-5p, miR-6793-3p, miR-6794-3p, miR-6795-3p, miR-6799-3p, miR-6800-3p, miR-6801-3p, miR-6802-3p, miR-6803-3p, miR-6806-5p, miR-6807-3p, miR-6808-5p, miR-6810-3p, miR-6811-3p, miR-6812-3p, miR-6813-3p, miR-6816-3p, miR-6819-3p, miR-6820-3p, miR-6823-3p, miR-6824-3p, miR-6825-3p, miR-6826-3p, miR-6828-3p, miR-6828-5p, miR-6829-3p, miR-6840-5p, miR-6845-3p, miR-6846-3p, miR-6848-3p, miR-6849-3p, miR-6851-3p, miR-6852-3p, miR-6857-3p, miR-6858-3p, miR-6859-3p, miR-6860, miR-6861-3p, miR-6865-3p, miR-6865-5p, miR-6867-3p, miR-6870-3p, miR-6871-3p, miR-6873-3p, miR-6874-3p, miR-6877-3p, miR-6879-3p, miR-6880-3p, miR-6884-3p, miR-6885-3p, miR-6887-3p, miR-6889-3p, miR-6890-3p, miR-6891-3p, miR-6895-3p, miR-7106-3p, miR-7109-3p, miR-7111-3p, miR-7113-3p, miR-7114-3p, miR-7853-5p, miR-8060, miR-8078, miR-8485, miR-0513b-5p, miR-0619-5p, miR-1285-3p, miR-3162-5p, miR-4311, miR-4531, miR-5096, miR-0016-2-3p, miR-0030c-1-3p, miR-0125a-5p, miR-0125b-5p, miR-0183-3p, miR-0184, miR-0193a-3p, miR-0211-3p, miR-0324-3p, miR-0432-5p, miR-0433-3p, miR-0483-5p, miR-0493-3p, miR-0505-5p, miR-0642a-3p, miR-0642b-3p, miR-0642b-5p, miR-0652-5p, miR-0658, miR-0663a, miR-0760, miR-0765, miR-0873-3p, miR-0885-3p, miR-0937-5p, miR-1202, miR-1224-5p, miR-1229-5p, miR-1249-5p, miR-1251-3p, miR-1273e, miR-1273g-3p, miR-1908-5p, miR-2392, miR-2467-3p, miR-3124-5p, miR-3138, miR-3156-3p, miR-3158-5p, miR-3175, miR-3190-3p, miR-3198, miR-3612, miR-3619-3p, miR-3649, miR-3653-3p, miR-3655, miR-3657, miR-3667-5p, miR-3679-5p, miR-3682-3p, miR-3917, miR-3945, miR-4255, miR-4294, miR-4307, miR-4321, miR-4419a, miR-4448, miR-4496, miR-4524a-5p, miR-4530, miR-4638-5p, miR-4725-3p, miR-4726-5p, miR-4748, miR-4754, miR-4769-5p, miR-4786-5p, miR-4800-5p, miR-5006-3p, miR-5088-3p, miR-5089-3p, miR-5093, miR-5196-5p, miR-5585-3p, miR-5698, miR-6077, miR-6716-5p, miR-6718-5p, miR-6740-5p, miR-6751-3p, miR-6756-3p, miR-6766-5p, miR-6769b-5p, miR-6778-5p, miR-6780a-5p, miR-6780b-5p, miR-6794-5p, miR-6799-5p, miR-6812-5p, miR-6824-5p, miR-6825-5p, miR-6830-3p, miR-6831-3p, miR-6831-5p, miR-6833-5p, miR-6839-5p, miR-6855-3p, miR-6861-5p, miR-6870-5p, miR-6879-5p, miR-6892-5p, miR-6894-5p, miR-7109-5p, miR-7150, miR-7154-3p, miR-8085, miR-8087, miR-0103a-2-5p, miR-0151b, miR-0519c-5p, miR-523-5p, miR-518e-5p, miR-522-5p, miR-519a-5p, miR-519b-5p, miR-0617, miR-0921, miR-6874-5p, miR-0030c-2-3p, miR-0034a-5p, miR-0092a-2-5p, miR-0129-1-3p, miR-0134-3p, miR-0181a-5p, miR-0185-5p, miR-0204-3p, miR-0302c-5p, miR-0324-5p, miR-0338-5p, miR-0370-3p, miR-0382-5p, miR-0421, miR-0450a-5p, miR-0491-5p, miR-0518f-3p, miR-0518f-5p, miR-0520b, miR-0520d-5p, miR-0520e, miR-0527, miR-0518a-5p, miR-0541-3p, miR-0550b-2-5p, miR-0622, miR-0668-5p, miR-0708-5p, miR-0766-5p, miR-0767-3p, miR-0920, miR-1184, miR-1185-1-3p, miR-1185-2-3p, miR-1227-3p, miR-1237-3p, miR-1265, miR-1267, miR-1273h-5p, miR-1301-3p, miR-2116-5p, miR-3116, miR-3137, miR-3151-5p, miR-3156-5p, miR-3157-5p, miR-3164, miR-3177-3p, miR-3189-3p, miR-3202, miR-3622b-5p, miR-3651, miR-3925-5p, miR-3928-3p, miR-3975, miR-4257, miR-4261, miR-4296, miR-4300, miR-4306, miR-4316, miR-4431, miR-4443, miR-4444, miR-4453, miR-4459, miR-4465, miR-4482-3p, miR-4489, miR-4499, miR-4514, miR-4657, miR-4664-5p, miR-4669, miR-4698, miR-4749-3p, miR-4750-3p, miR-4753-5p, miR-4756-3p, miR-5000-5p, miR-5001-5p, miR-5010-5p, miR-5571-3p, miR-6076, miR-6127, miR-6500-3p, miR-6503-5p, miR-6507-3p, miR-6507-5p, miR-6511b-5p, miR-6515-5p, miR-6516-5p, miR-6717-5p, miR-6728-5p, miR-6734-5p, miR-6741-5p, miR-6742-3p, miR-6742-5p, miR-6745, miR-6746-5p, miR-6747-5p, miR-6748-5p, miR-6756-5p, miR-6760-5p, miR-6766-3p, miR-6771-3p, miR-6776-5p, miR-6782-3p, miR-6795-5p, miR-6796-3p, miR-6815-5p, miR-6823-5p, miR-6827-5p, miR-6829-5p, miR-6830-5p, miR-6834-5p, miR-6841-3p, miR-6842-5p, miR-6849-5p, miR-6853-5p, miR-6872-5p, miR-6887-5p, miR-6891-5p, miR-7106-5p, miR-7107-5p, miR-7108-3p, miR-7111-5p, miR-7846-3p, miR-7855-5p, miR-8062, miR-8071 and miR-8082, and one or more microRNAs selected from the group consisting of these (preferably human microRNAs) can be detected.

Also in the present disclosure there is provided a method of detecting microRNA in urine or urine extract of a subject, for example, the method of detecting one or more selected from the group of microRNAs that exhibit lower expression in three cancerous subjects than in three non-cancerous subjects, in data S1 (or Table 3).

The microRNAs detected in this aspect can be, for example, one or more from the group of microRNAs (e.g., 2 times or more, 3 times or more, 4 times or more, 5 times or more, 6 times or more, 7 times or more, 8 times or more, 9 or more, or 10 or more) that exhibit lower expression in three cancerous subjects than in any of three non-cancerous subjects.

Such microRNAs include, for example, miR-3127-3p, miR-3130-5p, miR-3131, miR-3141, miR-3150b-5p, miR-3151-3p, miR-3151-5p, miR-3154, miR-3160-3p, miR-3160-5p, miR-3162-5p, miR-0015b-5p, miR-0034c-5p, miR-0093-5p, miR-0128-2-5p, miR-0135a-5p, miR-0149-3p, miR-0214-5p, miR-0320a, miR-0339-5p, miR-0365a-5p, miR-0372-3p, miR-0378b, miR-0424-5p, miR-0488-5p, miR-0498, miR-0512-3p, miR-0512-5p, miR-0580-3p, miR-0670-5p, miR-0671-5p, miR-0758-5p, miR-0933, miR-0937-3p, miR-0942-5p, miR-1178-3p, miR-1207-3p, miR-1224-3p, miR-1233-3p, miR-1233-5p, miR-1249-5p, miR-1266-3p, miR-2277-3p, miR-2277-5p, miR-3065-5p, miR-3122, miR-3135b, miR-3153, miR-3156-3p, miR-3158-5p, miR-3162-3p, miR-3174, miR-3180, miR-3529-5p, miR-3680-3p, miR-3689f, miR-4266, miR-4273, miR-4281, miR-4327, miR-4526, miR-4643, miR-4646-3p, miR-4675, miR-4698, miR-4706, miR-4718, miR-4728-3p, miR-4752, miR-4753-3p, miR-4801, miR-5192, miR-5195-5p, miR-5704, miR-6069, miR-6088, miR-6132, miR-6502-5p, miR-6505-3p, miR-6510-5p, miR-6511b-3p, miR-6516-5p, miR-6744-5p, miR-6749-3p, miR-6754-5p, miR-6757-3p, miR-6757-5p, miR-6765-5p, miR-6771-3p, miR-6775-5p, miR-6781-3p, miR-6800-5p, miR-6807-5p, miR-6811-3p, miR-6813-5p, miR-6822-5p, miR-6829-5p, miR-6832-3p, miR-6841-3p, miR-6845-3p, miR-6864-3p, miR-6865-5p, miR-6873-5p, miR-6877-3p, miR-6878-5p, miR-6881-5p, miR-6885-5p, miR-6886-5p, miR-7106-5p, miR-7111-5p, miR-7153-3p, miR-7848-3p, miR-7978, miR-8059, miR-0520b, miR-3605-5p, miR-3612, miR-4645-3p, miR-4694-3p, miR-6816-3p, miR-8087, miR-0015a-3p, miR-0135b-5p, miR-0185-5p, miR-0302d-5p, miR-0483-5p, miR-0671-3p, miR-1254, miR-1284, miR-1323, miR-3138, miR-3164, miR-3189-3p, miR-3200-5p, miR-3657, miR-3667-5p, miR-3692-5p, miR-3713, miR-4299, miR-4306, miR-4316, miR-4319, miR-4441, miR-4658, miR-5004-3p, miR-5194, miR-6083, miR-6720-5p, miR-6821-3p, miR-6832-5p, miR-6875-5p, miR-0001-5p, miR-0007-2-3p, miR-0025-5p, miR-0030c-1-3p, miR-0030c-2-3p, miR-0125a-3p, miR-0134-5p, miR-0146a-5p, miR-0183-3p, miR-0193a-5p, miR-0193b-3p, miR-0197-5p, miR-0198, miR-0212-5p, miR-0221-3p, miR-0299-5p, miR-0326, miR-0328-5p, miR-0374c-3p, miR-0423-5p, miR-0432-5p, miR-0433-5p, miR-0483-3p, miR-0505-5p, miR-0513a-5p, miR-0521, miR-0532-3p, miR-0550a-3-5p, miR-0550a-5p, miR-0550b-3p, miR-0551b-3p, miR-0589-3p, miR-0591, miR-0615-3p, miR-0642a-3p, miR-0642b-3p, miR-0650, miR-0652-5p, miR-0664b-3p, miR-0668-3p, miR-0675-5p, miR-0711, miR-0744-5p, miR-0764, miR-0939-3p, miR-1180-3p, miR-1185-1-3p, miR-1185-2-3p, miR-1193, miR-1199-

3p, miR-1202, miR-1207-5p, miR-1228-5p, miR-1229-5p, miR-1238-5p, miR-1273h-5p, miR-1275, miR-1911-3p, miR-2276-3p, miR-2278, miR-2355-5p, miR-2861, miR-3074-5p, miR-3137, miR-3144-5p, miR-3147, miR-3184-5p, miR-3188, miR-3190-3p, miR-3202, miR-3610, miR-3622b-5p, miR-3666, miR-3679-5p, miR-3689d, miR-3911, miR-3918, miR-3919, miR-3927-5p, miR-3928-3p, miR-4251, miR-4259, miR-4265, miR-4271, miR-4279, miR-4288, miR-4290, miR-4294, miR-4298, miR-4301, miR-4322, miR-4329, miR-4419a, miR-4419b, miR-4447, miR-4462, miR-4472, miR-4476, miR-4483, miR-4484, miR-4492, miR-4496, miR-4499, miR-4513, miR-4523, miR-4632-5p, miR-4646-5p, miR-4655-5p, miR-4656, miR-4667-5p, miR-4685-5p, miR-4687-3p, miR-4697-5p, miR-4709-3p, miR-4722-3p, miR-4723-5p, miR-4726-3p, miR-4726-5p, miR-4728-5p, miR-4732-5p, miR-4739, miR-4743-5p, miR-4747-5p, miR-4748, miR-4751, miR-4756-5p, miR-4783-3p, miR-4788, miR-4800-5p, miR-5088-3p, miR-5698, miR-5702, miR-5739, miR-6085, miR-6086, miR-6087, miR-6124, miR-6133, miR-6501-5p, miR-6504-5p, miR-6513-3p, miR-6716-5p, miR-6727-3p, miR-6730-5p, miR-6733-3p, miR-6734-5p, miR-6735-3p, miR-6735-5p, miR-6741-5p, miR-6744-3p, miR-6745, miR-6746-5p, miR-6749-5p, miR-6750-5p, miR-6760-5p, miR-6769a-5p, miR-6769b-5p, miR-6774-5p, miR-6776-3p, miR-6779-5p, miR-6787-5p, miR-6788-3p, miR-6790-5p, miR-6792-5p, miR-6794-5p, miR-6797-5p, miR-6799-5p, miR-6803-5p, miR-6806-5p, miR-6812-5p, miR-6814-5p, miR-6815-5p, miR-6819-5p, miR-6822-3p, miR-6823-5p, miR-6824-5p, miR-6827-5p, miR-6830-5p, miR-6831-3p, miR-6831-5p, miR-6833-5p, miR-6842-5p, miR-6851-5p, miR-6858-5p, miR-6862-5p, miR-6866-3p, miR-6870-5p, miR-6872-5p, miR-6879-5p, miR-6883-5p, miR-6884-3p, miR-6891-5p, miR-6894-5p, miR-7107-5p, miR-7109-5p, miR-7110-3p, miR-7111-5p, miR-7112-5p, miR-7150, miR-7152-3p, miR-7154-3p, miR-7155-3p, miR-7706, miR-7843-5p, miR-7845-5p, miR-7846-3p, miR-7847-3p, miR-7973, miR-8052, miR-8058, miR-8074, miR-8089, miR-0378a-5p, miR-4489, miR-6511b-5p, miR-0187-5p, miR-0208a-5p, miR-0486-3p, miR-0511-5p, miR-0585-5p, miR-0643, miR-0663b, miR-1231, miR-3187-5p, miR-3665, miR-4446-3p, miR-4466, miR-4525, miR-4634, miR-4674, miR-4734, miR-4785, miR-4787-5p, miR-4794, miR-5008-5p, miR-6499-5p, miR-6510-3p, miR-6727-5p, miR-6814-3p, miR-6836-3p, miR-7704, miR-8069, miR-7849-3p, miR-0025-3p, miR-0092a-3p, miR-0092b-3p, miR-0099b-5p, miR-0128-1-5p, miR-0139-3p, miR-0149-5p, miR-0192-5p, miR-0205-5p, miR-0216b-3p, miR-0223-5p, miR-0346, miR-0371a-3p, miR-0378c, miR-0425-3p, miR-0503-3p, miR-0520a-3p, miR-0520h, miR-0548ay-3p, miR-0548q, miR-0557, miR-0631, miR-0636, miR-0638, miR-0659-3p, miR-0762, miR-0935, miR-1203, miR-1225-5p, miR-1237-5p, miR-1268a, miR-1469, miR-1539, miR-1909-3p, miR-1910-5p, miR-1914-5p, miR-2682-3p, miR-3064-5p, miR-3065-3p, miR-3130-3p, miR-3173-3p, miR-3178, miR-3180-3p, miR-3196, miR-3935, miR-3937, miR-3940-5p, miR-3960, miR-4270, miR-4276, miR-4442, miR-4485-5p, miR-4488, miR-4505, miR-4508, miR-4632-3p, miR-4649-5p, miR-4676-3p, miR-4688, miR-4707-5p, miR-4708-5p, miR-4722-5p, miR-4730, miR-4738-3p, miR-4747-3p, miR-4761-3p, miR-4763-3p, miR-4773, miR-5196-3p, miR-5584-3p, miR-5787, miR-6089, miR-6090, miR-6508-5p, miR-6721-5p, miR-6722-5p, miR-6726-3p, miR-6729-5p, miR-6737-5p, miR-6738-5p, miR-6746-3p, miR-6767-3p, miR-6771-5p, miR-6784-5p, miR-6785-5p, miR-6786-5p, miR-6789-3p, miR-6789-5p, miR-6805-5p, miR-6816-5p, miR-6825-3p, miR-6833-3p, miR-6837-3p, miR-6847-3p, miR-6848-5p, miR-6850-5p, miR-6869-5p, miR-6871-3p, miR-6895-3p, miR-7155-5p, miR-7844-5p, miR-8072, miR-8485 and miR-9500, and one or more microRNAs selected from the group consisting of these (preferably human microRNAs) can be detected.

In these aspects, the species of microRNA to be detected and the species of microRNA used as indicator can each independently be, for example, 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, 1000 or more, or 1100 or more.

In these aspects, the species of microRNAs to be detected and the species of microRNAs used as indicators may be independently, for example, 2000 or less, 1900 or less, 1800 or less, 1700 or less, 1600 or less, 1500 or less, 1400 or less, 1300 or less, 1200 or less, 1100 or less, 1000 or less, 900 or less, 800 or less, 700 or less, 600 or less, 500 or less, 400 or less, 300 or less, 200 or less, 100 or less, 90 or less, 80 or less, 70 or less, 60 or less, 50 or less, 40 or less, 30 or less, 20 or less, or 10 or less.

The species of microRNA to be detected and the species of microRNA used as indicator may be completely identical, or a portion of the microRNAs to be detected may be used as indicator.

After detection, cancer diagnosis can be performed as described in the present disclosure using the expression level or the presence or absence of the microRNA as indicator.

Patients diagnosed as having a risk of having cancerous may be treated by e.g., cancer therapies such as chemotherapy, anticancer drug therapy, surgery, immunotherapy, and radiation therapy.

The microRNAs may be present in the body fluid in free and/or EV-included form. Thus, according to the present disclosure, microRNAs may be present in urine and urine extracts in a free form and/or in EV (particularly exosomal and/or microvesicular) inclusive forms.

MicroRNA collection can be performed by contacting bodily fluids with nanowires of the nanowire-incorporated devices of the present disclosure.

The collection of microRNAs can be performed under conditions in which the nanowires have a positive surface charge.

For example, by contacting the nanowires with bodily fluids under pH conditions where the nanowires have a positive surface charge, free and EV-included forms of microRNA can be captured on the nanowires.

Thus, the body fluid may be pH adjusted such that the nanowires have a positive surface charge.

Alternatively, the nanowires may be made of a material having a positive surface charge in the bodily fluid to match the pH of the bodily fluid.

Some aspects of the present disclosure include adjusting the pH of a bodily fluid and contacting the bodily fluid with nanowires of a nanowire-incorporated device of the present disclosure.

The pH of the bodily fluid can be adjusted before, after, or during contact with the nanowires.

In some embodiments of the present disclosure, the pH of the bodily fluid may be adjusted to be greater than or greater than a value, such as 2, 3, 4, or 5.

The pH of the bodily fluid may be adjusted to be less than or equal to a value such as 10, 9, 8, 7, 6, or 5.

In some embodiments of the present disclosure, the pH of the urine may be adjusted to between 6 and 8.

In some embodiments, the bodily fluid is urine, the pH of which is between 6 and 8, or the pH of which is urine adjusted to a pH of between pH 6 and 8.

In some embodiments of the present disclosure, the nanowires may be zinc oxide nanowires or zinc oxide coated nanowires.

In certain aspects/embodiments of the present disclosure, substantially nanowires may be grown directly on the substrate (i.e., may not be incorporated) and may be partially incorporated within the substrate.

The material of the substrate is not particularly limited to, and may be, a material selected from polyethylene, polypropylene, polyvinyl chloride, polyvinylidene chloride, polystyrene, polyvinyl acetate, polytetrafluoroethylene, ABS (acrylonitrile butadiene styrene) resin, AS (acrylonitrile styrene) resin, thermoplastic resin such as acrylic resin (PMMA), phenolic resin, epoxy resin, melamine resin, urea resin, unsaturated polyester resin, alkyd resin, polyurethane, polyimide, silicone rubber, polymethylmethacrylate (PMMA), and polycarbonate (PC).

In some aspects/embodiments of the present disclosure, metal and metal oxides, such as platinum, aluminum, copper, iron, cobalt, silver, tin, indium, zinc, gallium, chromium, and oxides thereof, can be used as the seed layer (catalyst layer) of the nanowires.

Nanowires can be grown from the seed layer and then the substrate material (in liquid form) can be poured onto the nanowires and cured to incorporate the nanowires into the substrate material.

Thereafter, nanowires incorporated in the substrate can be prepared by further growing the nanowires from the nanowires exposed from the substrate.

If the nanowires are not exposed from the substrate, they may be exposed by cutting and/or polishing as appropriate.

The nanowire incorporated substrate so obtained can be used as a substrate on which nanowires are immobilized in the device of the present disclosure, and can be highly physicochemical resistant and useful.

By contacting the nanowires with the body fluid sample, EV and small molecular RNAs in free form are captured on the nanowires.

The small-molecule RNA contained in the captured EV and the captured small-molecule RNA in the free form can be obtained by dissociating from the nanowires by a buffer solution.

In obtaining small molecule RNA from a nanowire, for example, a buffer containing a nonionic surfactant can be used.

The buffer may include an inhibitor of RNase.

According to the present disclosure, the urine extract containing any one or more or all of microRNAs of data S1 (or Table 3) and Table 2 may be a solution substituted with a test solution or may have a solution composition of the test solution.

The microRNA test solution may have a solution composition suitable for tests to confirm the presence or abundance of ncRNA such as microRNA.

The test solution may include, for example, one or more selected from the group consisting of a surfactant (e.g., a non-ionic surfactant), a salt (e.g., natrium, and potassium, etc.), a nucleic acid stabilizer (e.g., an inhibitor of RNA decomposition enzymes, etc.), a pH regulator (e.g., a buffer) and water.

Detection of microRNAs can be performed using miRNA detection methods known to those skilled in the art, such as quantitative PCR, microarrays for miRNA detection, RNA-Seq, and multiplex miRNA profiling, and the like.

In the present disclosure, the urinary extract obtained by extracting microRNAs with the devices of the present disclosure may comprise, for example, 500 or more species of miRNA.

Therefore, in order to confirm the expression of all of these miRNA, for example, a microarray for detecting miRNA, a RNA-Seq method, a multiplex miRNA profiling method, and the like can be used.

Quantitative PCR-based methods, multiplex miRNA profiling methods, and the like can also be used to detect one or more of particular miRNAs in a urinary extract.

Detection and analysis of the miRNA by the microarray can include labeling the miRNA (e.g., using a fluorescent label as the label), preparing a solution for hybridization, hybridizing the miRNA in the sample with miRNA detection reagents such as nucleic acids on the microarray, washing the microarray, and then measuring the amount of label (e.g., amount of fluorescence).

Quality of the extracted RNA samples can be confirmed by using, for example, methods well known to those skilled in the art or commercially available equipment and kits (e.g., Agilent 2100 Bioanalyzer and RNA LabChip from Agilent Technologies, Inc.), with the appearance of peaks between 20 and 30 nucleotides in sizes, as indicator.

Labeling of the miRNA can be done, for example, using methods well known to those skilled in the art and commercially available kits (e.g., 3D-Gene™ miRNA labeling kit (manufactured by Toray Corporation)).

Also, for example, miRNA analyses by microarrays can be performed using the 3D-Gene™ Human/Mouse/Rat/4animal miRNA Olico chip—4 plex manufactured by Toray Corporation in accordance with the manufacturer's instructions for the products.

Microarray for detecting microRNAs can be:

a microarray comprising probes for one or more selected from the group of microRNAs that exhibit higher expression in the three cancerous subjects than any of the three non-cancerous subjects, for example, in data S1 (or Table 3);

a microarray comprising probes for one or more of the groups of microRNAs (e.g., 2 times or more, 3 times or more, 4 or more, 5 or more, 6 or more, 7 or more, 8 times or more, 9 or more, or 10 or more) that exhibit higher expression in a cancerous subject than in a non-cancerous subject, for example, in data S1 (or Table 3);

a microarray comprising probes for one or more selected from the group of microRNAs that exhibit higher expression in a cancerous subject than in a non-cancerous subject, for example, in data S1 (or Table 3);

a microarray is raised that includes probes for one or more of a group of microRNAs (e.g., 2 times or more, 3 times or more, 4 or more, 5 or more, 6 or more, 7 or more, 8 or more, 9-fold or more, or 10 or more) that exhibit higher expression in a cancerous subject than in a non-cancerous subject, for example, in data S1 (or Table 3).

In this aspect, the species of the microRNA to be detected (i.e., the kinds of the probes mounted on the microarray) can be, for example, 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, 1000 or more, or 1100 or more.

In these aspect, the species of microRNA to be detected (i.e., the kinds of probes mounted on the microarray) can be, for example, 2000 or less, 1900 or less, 1800 or less, 1700 or less, 1600 or less, 1500 or less, 1400 or less, 1300 or less, 1200 or less, 1100 or less, 1000 or less, 900 or less, 800 or less, 700 or less, 600 or less, 500 or less, 400 or less, 300 or less, 200 or less, 100 or less, 90 or less, 80 or less, 70 or less, 60 or less, 50 or less, 40 or less, 30 or less, 20 or less, or 10 or less.

Probes for microRNAs in microarrays can be nucleic acids and derivatives thereof capable of hybridizing to the microRNAs, and can be appropriately designed by those skilled in the art.

EXAMPLES

Example 1

Fabrication of Nanowires Immobilized on Polydimethylsiloxane (PDMS)

After a Si(100) substrate (Advantech Co. Ltd.) was cleaned (see FIG. 6a), the Si substrate was coated with the positive photoresist (OFPR8600, Tokyo Ohka Kogyo Co), and then channel patterns were formed by photolithography (see FIG. 6b).

A 140-nm-thick Cr layer (catalytic layer) was deposited on the substrate by sputtering (see FIG. 6b).

After the photoresist was removed (see FIG. 6d), the Cr layer was thermally oxidized at 400° C. for 2 hours.

The Cr layer was used as a seed layer for growth of ZnO nanowires.

ZnO nanowires were grown by immersing the obtained substrates in a mixed solution of 15 mM hexamethylenetetramine (HMTA; Wako Pure Chemical Industries Ltd.) and 15 mM zinc nitrate hexahydrate (Thermo Fisher Scientific Inc.) at 95° C. for 3 hours (see FIG. 6e).

The nanowires grown on the substrate were washed with Millipore water and air-dried overnight in a vacuum desiccator.

Thereafter, PDMS (Silpot 184, Dow Corning Corp.) was poured onto the substrates on which the nanowires were grown, and cured (see FIG. 6f).

Upon stripping the PDMS from the substrate, the nanowires were transferred from the substrate to the PDMS.

The transferred nanowires were uniformly deeply embedded in the PDMS with a slight exposure of the head (see FIG. 6h) (this embedded condition may be referred to herein as "incorporated"), which provided a growing point for the secondary nanowires.

The secondary nanowires were grown by immersing the resulting PDMS in a mixed solution of 15 mM HMTA and 15 mM zinc nitrate hexahydrate at 95° C. for 3 hours (see FIG. 6i).

The nanowire-embedded PDMS substrate was cleaned with Millipore water, then air-dried in a vacuum desiccator, and the diameters of the nanowires and the distances between the nanowires were measured using a field emission scanning electron microscope (FESEM) (SUPRA 40VP, Carl Zeiss).

Nanowire-Incorporated Microfluidic Devices Capable of In-Situ Extracting Urinary Extracellular Vesicle (EV)-Included miRNA Nanowire-incorporated microfluidic devices for in situ extractions of urinary EV-inclusion-type miRNA were fabricated by bonding a nanowire-incorporated PDMS substrate with a herringbone-structured PDMS substrate.

The PDMS substrates of the herringbone structure had microchannels (widths of 2 mm; lengths of 2 cm; and heights of 50 μm) with a herringbone structure height of 12 μm.

Nanowire-incorporated PDMS substrates and the surface of PDMS substrate with herringbone structures were treated by a plasma-etching equipment (Meiwafosis Co. Ltd.) and adhered.

The bonding devices were heated at 180° C. for 3 minutes to achieve strong bonding, (see FIG. 6J).

Next, the PDMS of the herringbone structure was connected to polyetheretherketone (PEEK) tubes [0.5 mm (outer diameter)×0.26 mm (inner diameter); length of 10 cm; Institute of Microchemical Technology Co. LTD.] at the inlet and the outlet.

In this manner, a nanowire-incorporated microfluidic device (hereinafter also referred to simply as a "nanowire-incorporated device" or "device of the present disclosure") of the title, capable of in-situ extraction, was obtained.

The microfluidic herringbone structure contributed to improvement of collection efficiency, see FIG. 15.

EDS-Element Mapping of Cross-Sectional FESEM Images

Elemental mappings of the nanowire-free PDMS, the nanowire-buried PDMS (i.e., the PDMS where the nanowires were not exposed), and the ZnO-nanowire-incorporated PDMS were obtained by FESEM (JSM-7610F, Jeol with EDS-function).

For the top view image and the cross-sectional image, acceleration voltages of 5 keV and 30 keV were used, respectively.

The image had 512×384 pixels and the delay time for each pixel was 0.1 second. Images were integrated for 100 cycles.

The peaks of Si Kα (1.739 keV) and Zn Lα (1.012 keV) were selected to construct elemental mapping images.

Elemental mappings of ZnO—Al2O3 core-shell nanowires were performed by an EDS-equipped FESEM at the acceleration voltage of 30 keV.

For preparation of Scanning Transmission Electron Microscopy (STEM) samples, the nanowires were cut from the substrates using a conventional cutting blade, collected and replaced on a TEM-grid (Cu-mesh with carbon microgrid, JEOL) by the adhesion method.

The STEM image had 512×384 pixels, and the delay time of each pixel was 0.1 ms.

The image was integrated for 100 cycles.

The peaks of Zn Kα (8.630 keV), O Kα (0.525 keV), and Al Kα (1.486 keV) were selected to construct elemental mapping images.

In Situ Extraction of Urinary EV-Included miRNA Using Nanowire-Incorporated Microfluidic Devices Commercial urine (single-donor human urine, Innovative Research Inc.) was centrifuged (15 min, 4° C., 3000 g) prior to use to remove apoptotic bodies (see Document 5).

Thereafter, 1 ml urine samples were introduced into the nanowire incorporated devices using a syringe pump (KDS-200, KD Scientific Inc.) at a flow rate of 50 μL/min.

Extractions of miRNA from EVs collected on nanowires were performed by introducing cytolysis buffer M [20 mM tris-HCl (pH 7.4), 200 mM sodium chloride, 2.5 mM magnesium chloride, and 0.05 w/v % NP-40; (Wako Pure Chemical Industries Ltd.) into nanowire incorporated devices using a syringe pump at a flow rate of 50 μL/min.

The same lysis buffer was used at a flow rate of 50 μL/min in experiments studying the detachment of the nanowires (FIGS. 1I to K and FIG. 9).

EV Collection and Urinary miRNA Extractions Using Ultracentrifuge (Ultracentrifuge)

Commercial urine (single donor human urine) was centrifuged (15 min, 4° C., 3000 g) prior to use to remove apoptotic bodies (see Document 5).

The urine was then centrifuged (15 min, 4° C., 12000 g) to remove cellular debris (see Document 29).

Next, 20 mL urine samples were ultracentrifuged (2 hours, 4° C., 110,000 g) (see Document 29).

The supernatant was removed, and 20 ml of phosphate buffered saline (PBS; Thermo Fisher Scientific Inc.) filtered through a 0.22-μm filter was added to the collected EVs and further ultracentrifuged (70 min, 4° C., 110,000 g).

The supernatant was removed and 20 ml of phosphate buffered saline (PBS; Thermo Fisher Scientific Inc.) filtered through a 0.22-μm filter was added to the collected EVs and ultracentrifuged (70 min, 4° C., 110,000 g) for the third time.

Finally, the supernatant was removed, and lysis buffer was added to extract the miRNA.

EV Collection and Extraction of miRNA with Commercial Kits (Polymer Precipitation Method)

Commercial urine (single donor human urine) was centrifuged (15 min, 4° C., 3000 g) prior to use, to remove apoptotic bodies.

EVs were collected from 1 ml urine samples according to the manufacturer's instructions for ExoQuick-TC, System Biosciences Inc.

Finally, lysis buffer was added to extract the miRNA.

Microarray Analyses of miRNA Expression miRNA expression profiles were obtained using Toray 3D-Gene (Toray Industries) human miRNA chips.

The miRNA extracted with lysis buffer was purified using SeraMir Exosome RNA Purification Column Kit (System Biosciences Inc.) according to the manufacturer's instructions.

15 μl of purified miRNA was analyzed for miRNA profiling using 3D-Gene Human miRNA Oligo chip ver. 21 (Toray Industries).

In microarray analyses of miRNA expression, each of the signal intensities corresponds to one species of miRNA.

The expression level of each miRNA is expressed as the signal intensities of all miRNA in each microarray, subtracted by the background.

Signal intensities were normalized throughout in contrast of expression levels of miRNA over the extractions using nanowire incorporated devices and extraction using centrifugation or commercial kits, in miRNA samples of the same urine.

Scatter plots were generated for intensities standardized throughout and are shown for intensity equal to or greater than 10 (intensity by extraction with nanowire incorporated devices/intensity by ultracentrifugation or extraction with commercial kits).

Thus, each point on the scatter plot is a standardized intensity.

Signal intensities were log 2 transformed for comparison of expression levels of miRNAs over the extractions using nanowire incorporated devices and extraction using centrifugation or commercial kits, in miRNA samples of the same urine.

For comparisons of miRNA between cancerous donor and non-cancerous donor urine samples, normalized intensities were log 2 transformed throughout the samples. The normalized intensities were shown on the heat map as black (intensity=5), blue (intensity≤2) and yellow (intensity≥8).

Zeta Potential of EV

After the ultracentrifugation step, the zeta-potential of the EVs was measured using a Dynamic Light-Scattering Device (Zetasizer Nano ZS, Malvern Instruments Ltd.).

Size Distribution and Concentration of Free Urine Suspensions

Size distributions and concentrations of free urinary suspensions were determined using a nanoparticle analyzing system (NanoSight, Malvern Instruments Ltd.).

Concentrations of urine free suspensions in untreated urine, in the flow-through fraction of urine treated with nanowire incorporated devices, and in urine after ultracentrifugation were $2.6 \times 10^{12}$ ml-1, $5.8 \times 10^{9}$ ml-1 and $3.5 \times 10^{9}$ ml-1, respectively.

Size-distribution and concentrations of urinary free suspensions were measured using a nanoparticle detector (qNano, Meiwafosis Co. with Ltd.) attached with a 100-nm nanopore membrane (NP100, Meiwafosis Co. Ltd.)

Concentrations of urine free suspensions in untreated urine, in the flow-through fraction of urine treated with nanowire incorporated devices, and in urine after ultracentrifugation were $1.4 \times 10^{12}$ ml-1, $2.4 \times 10^{10}$ ml-1, and $2.5 \times 10^{10}$ ml-1, respectively.

Fluorescent Molecular Labeling of EV

EV was labeled by using PKH26, a fluorescent molecule that can penetrate the lipidic bilayer of EVs (excited light/fluorescence=551/567 nm; Sigma-Aldrich Co. LLC).

5 mg of PKH26 was added to $1.5 \times 10^{8}$ ml-1 EVs in Millipore water (240 μL) filtered by a 0.22-μm filter.

The PKH26 labeled EV was introduced into the nanowire incorporated device using a syringe pump at a flow rate of 10 μl/min, and then Millipore water was introduced into the nanowire incorporated device at the same flow rate to remove uncollected EV (EV not bound to the nanowires).

Finally, fluorescence of EVs was observed using a fluorescence microscope (AZ100, Nikon Corp.).

The nanowire incorporated devices were then peeled off and the nanowires which collected EVs were observed using FESEM (SUPRA 40VP, Carl Zeiss).

Detection of Membrane Proteins

After EV was introduced into the nanowire incorporated device, PBS was introduced to remove uncollected EV.

Thereafter, 1% bovine serum albumin (BSA) solution (Kirkegaard & Perry Laboratories Inc.) was introduced into the devices, and the devices were allowed to stand for 15 minutes.

The devices were washed with PBS and Alexa Fluor 488 labeled mouse anti-human CD63 monoclonal antibody (10 μg/ml; Santa Cruz Biotechnology Inc.) or mouse anti-human CD81 monoclonal antibody (10 μg/ml; Abcam PLC) was introduced into the devices, and allowed to stand for 15 minutes.

For detecting CD81, the devices were washed and then a Alexa Fluor 488 labeled goat-anti-mouse IgG polyclonal antibody was introduced into the devices as a secondary antibody, and then allowed to stand for 15 minutes.

Finally, the devices were washed with PBS and the fluorescence intensity was observed under a fluorescent microscope (Olympus Co. Ltd.).

PBS was used instead of EV samples to obtain background values.

For detection using 96-well plates (Nunc Co. Ltd.), EV samples were injected into the holes of the plate and allowed to stand for 6 hours, after which the holes were washed with PBS.

1% BSA solution was introduced into the holes of the plate and allowed to stand for 90 minutes.

The wells were then washed with PBS and Alexa Fluor 488 labeled mouse anti-human CD63 monoclonal antibody (10 μg/ml) or mouse anti-human CD81 antibody (10 μg/ml) was introduced into the wells of the plates and allowed to stand for 45 minutes.

For the CD81 detection, in addition to this, the holes of the plate were washed with PBS, and then a goat-anti-mouse IgG polyclonal antibody (5 μg/ml) labeled with Alexa Fluor 488 was introduced as a secondary antibody into the holes of the plate, and then allowed to stand for 45 minutes.

Finally, the holes of the plate were washed with PBS, and the fluorescent intensities were observed using a plate reader (POLARstar OPTIMA, BMG Labtech Japan Ltd.). PBS was used instead of EV samples to obtain background values.

Fabrication of ZnO—Al2O3 Core-Shell Nanowires

After fabrication of the ZnO nanowires, the wires were coated using an atomic-layer depositor (Savannah G2, Ultratech Inc.).

Al2O3 deposition was performed by repeating 100 cycles of flowing trimethylaluminum and H2O precursors into a chamber containing nanowires in an atomic layer deposition system and reacting at 150° C.

In Situ Extractions of EV-Included miRNA Using Urinary Samples and Nanowire-Incorporated Devices The following urine samples (BioreclamationIVT) were used: non-cancer patients (53 years old, 60 years old, and 50 years old), lung cancer patients (68 years old, stage 2b; 54 years old, stage 3a; 50 years old, stage 3b), pancreatic cancer patients (56 years old, stage 2a; 61 years old, stage 2a; 74 years old, stage 3), liver cancer patients (49 years old, stage 3; 64 years old, stage 3a; 18 years old, stage 3c), bladder cancer patients (63 years old, stage 1; 65 years old, stage 1; 67 years old, 0a), and prostate cancer (58 years old, stage 4; 57 years old, stage 2a; 54 years old, stage 2b).

These urine samples were centrifuged (15 min, 4° C., 3000 g) prior to use to remove apoptotic bodies.

1 ml urine sample was introduced into the nanowire incorporated devices using a syringe pump at a flow rate of 50 μl/min.

Extractions of miRNA from EVs collected on nanowires were performed in-situ by introducing lysis buffer into the devices using a syringe pump at a flow rate of 50 ml/min.

Identification of Urinary miRNA as Biomarker of Cancer

The 95% confidence interval was calculated using (mean) ±1.96×(mean×CV/100) according to a Z-score of 1.96 (95% confidence level and 5% significance level) and the relation of variability (CVs) (without specific values) to log 2 (strength) provided by Toray.

Using X % for CVs in relation to log 2 (strength)=3, the upper limit of the confidence interval was 8+0.16X.

The CV values at log 2 (strength)=5 or 6 were 0.7X % and 0.5X % according to the relation.

Considering the 5% significance level, CVs for each case were less than 40 and 71%. In FIG. 5, CV values greater than 70% were not considered reasonable, and three log intensity differences were determined for statistically significant thresholds.

Results

To establish a methodology for collecting EV-included miRNA, we developed nanowires incorporated in microfluidic substrates.

These nanowires serve a significant function as a solid phase for electrostatic collection of EV, and subsequently as an in-situ extraction of the EV-included miRNA (see FIG. 1A).

Nanowire Incorporated PDMS Substrates

Nanowire incorporated PDMS substrates were fabricated by four steps (see Document 40 and FIG. 6).

In the first step, nanowires were grown from a thermally oxidized chrome layer on a Si-substrate; in the second step, uncured PDMS was poured onto the grown nanowires; in the third step, the PDMS with the nanowires was cured and stripped to obtain a PDMS with embedded nanowires (see FIG. 1B); and in the fourth step, nanowires were grown from the embedded nanowires (see FIG. 1C).

The substrate is referred to as a nanowire incorporated PDMS substrate obtained here.

Field emission scanning electron microscopy (FESEM) images in vertical cross-sections of the incorporated nanowires showed that the nanowires were uniformly and deeply embedded in the PDMS with only a small exposure of their heads (see FIG. 1B), and the heads provided a growth point for the secondary nanowire growth (see FIG. 1C and FIG. 7).

Elemental mappings by energy-dispersive X-ray spectroscopy (EDS) of cross-sectional FESEM images of PDMS without nanowires were compared with the nanowire incorporated PDMS (see FIG. 8), and it was confirmed that ZnO nanowires were embedded in PDMS in the nanowire incorporated PDMS.

In addition, the ESD-element mappings of the vertical cross-section and the whole FESEM image and the cross-sectional FESEM image showed that the secondary nanowire growths occurred on the embedded nanowires.

In this way, nanowire incorporated PDMS substrates were successfully fabricated.

In order to promote the contact of the nanowires with the EVs and to prevent pressure-drops, a PDMS substrate having a microfluidic herringbone structure with a channel height (50 μm) greater than the nanowire length (2 μm) was used as a cover of the nanowire-incorporated PDMS substrate (the herringbone structure ensures good convection and dispersion of the solutions) (see Document 41) (see FIG. 1D).

Nanowire embedded devices for extracting EV-incorporated miRNA in urine were completed by adhering a nanowire incorporated PDMS substrate to a PDMS substrate with ring-bone structures to microfluidics and connecting polyetheretherketone (PEEK) tubes for introducing and collecting urine samples (see FIG. 1D).

The nanowires incorporated in the PDMS substrate were mechanically stable in exposure to the dissolution buffer and prevented delamination of the nanowires from the substrate as would occur for nanowires not incorporated into the PDMS (see FIGS. 1E and F, and FIG. 9).

Microarray Analyses of miRNA Expression

Microarray analyses of miRNA expression (2565 species) revealed that the extraction with nanowire incorporated devices allowed extraction of miRNA species (about 1,000 species) with greater diversity compared to extractions by conventional ultracentrifugation or polymeric precipitation methods using commercial kits (see FIGS. 2 and 10A).

The completion of the EV-included miRNA in urine within 40 minutes (20 minutes for adsorption and 20 minutes for extractions) was demonstrated by introducing urine samples (1 ml) into the devices and then introducing lysis buffer (1 ml).

In contrast, extraction of miRNA from EVs by ultracentrifugation required 20 ml of urine and required more than 5 hours for adsorption and extraction.

Since the commercial kit used in this study has been reported to be superior to other EV isolation methods in terms of yield of small-molecule RNAs (see FIGS. 10B and 10C) (see Document 22), extraction of miRNA by suspending 1 ml of EV collected from urine with 1 ml of lysis buffer using the kit revealed that this operation required more than 14 hours to collect and extract.

Scatter plots and histograms revealed that the expression levels of miRNA extracted with the disclosed nanowire-incorporated devices were much higher than the miRNA obtained by ultracentrifugation (see FIGS. 2A and B), despite consuming less than a twentieth in quantity of urine than for miRNA extraction by ultracentrifugation.

Usually, the amount of miRNA obtained by ultracentrifugation should be higher than the amount of miRNA obtained by the disclosed devices, since more than 20 times the amount of urine was used, but the results were reversed.

Compared to the ultracentrifugation method, the device of the present disclosure provided a 5-time larger miRNA volume (see FIG. 2A) and the species of the extractable miRNA were also diverse (miRNA extraction volume by the device of the present disclosure: 749,822, species: 1,111 species; miRNA extraction volume by the centrifugation method: 171 261, species: 352 species) (see FIG. 2B).

In addition, scatter plots and histograms show that the amount of miRNA extracted using the disclosed devices was much larger than the amount of miRNA obtained with the kits described above, even though the volume of urine samples consumed was the same (see FIGS. 2C and D).

Compared to the kits described above, the devices of the present disclosure provided four times larger miRNA volumes (see FIG. 2C) and the species of extractable miRNA were also diverse (miRNA extraction volume by the devices of the present disclosure: 749,822, species: 1,111 species; miRNA extraction volume by centrifugation: 337,355, species: 491 species) (see FIG. 2D).

Thus, it was concluded that the disclosed devices are superior in terms of miRNA extraction efficiency (see FIG. 2), extraction time (see FIGS. 10A and B), and extraction efficiency of small molecular RNAs (see FIG. 10C) as compared to conventional methods (ultracentrifugation or polymeric precipitation).

EV Collection Ability

The ability of the device of the present disclosure to collect EVs was verified, and it has been found that the device of the present disclosure can efficiently collect EVs (see FIG. 3).

Specifically, considering that the total amount of free suspension of urine was 3.4 µl, 8.8 nl, and 11.1 nl, respectively, in untreated urine, in the flow-through fraction (input: 1 ml) of urine treated with the device of the present disclosure and in urine treated with the ultracentrifugation method (input: 20 ml), the efficiency of collection of the suspension by the device of the present disclosure was estimated to be 99% or higher, and a volume larger than the dose obtained by the ultracentrifugation method could be collected (see FIG. 3A~3C) (the volume of EV collected was calculated by subtracting the volume of urine treated from the volume of untreated urine).

After observing the fluorescently labeled EVs, the nanowire-incorporated PDMS was peeled off from the PDMS substrates having the microfluidic herringbone structures, and the FESEM images were obtained.

This revealed that the free suspensions collected by the nanowires contained EVs (see FIGS. 3C and 3D).

CD63 and CD81, which are membrane proteins expressed on EV and known to be expressed on exosomal membranes, were detected, to further confirm that the free suspensions collected by the nanowires contain EV (see Documents 2 and 42-44).

Fluorescent intensities of EVs in urine collected on nanowires (or wells of 96-well plates) (concentrations: 1.4× 108 ml-1) showed that only nanowires were able to collect these membrane proteins (see FIG. 3E).

This indicates that EVs can be efficiently collected on nanowires in the devices of the present disclosure.

Next, instead of ZnO nanowires, ZnO—Al2O3 core-shell nanowires were prepared in which the core of ZnO was completely covered with a 10 nm-thick Al2O3 layer (see FIG. 11).

ZnO—Al2O3 core-shell nanowires have surfaces that are almost neutral in charge (which may be slightly positive or slightly negative) at pH 6~8 because the Al2O3 has an isoelectric point of about 7.5 (see Documents 45 and 46).

Therefore, it was confirmed whether the charge states on the surfaces of the nanowires had a dominant effect on the collection of the EVs by using ZnO—Al2O3 core-shell nanowires (see FIG. 12).

It can be seen that ZnO nanowires allow for efficient EV collection, since ZnO nanowires have a positively charged surface at pH 6~8 because of their isoelectric point of about 9.5, whereas EV in urine has a negatively charged surface at pH 6~8 (see Documents 47 and 48).

These results further demonstrate that ZnO nanowires can collect urine free suspensions with diameters up to 200 nm, such as EV, with collection efficiencies of 99% or higher.

Benefits of EV Collection Using Nanowires

The amount of material collected by ultracentrifugation (i.e., exosomes (9.0 nl; see FIG. 14A)) added to the amount of material not collected (11.1 nl; FIG. 3C) does not correspond to the volume of suspended matter in untreated urine of 3.4 µl (FIG. 3B). Although it is not yet easy to completely distinguish between exosomes and microvesicles, this suggests that the ultracentrifugation method primarily collects exosomes (see Documents 4, 5, and 29).

Also, when the EV is collected by the ultracentrifugal method, many of the EV may be fused and collapsed by being pressed against the inner wall of the ultracentrifugal tube, and the miRNA included in the microvesicles may be released to the periphery in this process.

The mechanism of EV collection by ultracentrifugation is based on a balance between the force applied and the density of the objects collected.

Thus, the experimental condition of ultracentrifugation is considered unsuitable for collection of the released miRNA.

On the other hand, it is considered that the mechanism of EV collection by nanowires is based on the electrostatic interaction of positively charged nanowires with negatively charged objects, which allows the nanowires to collect exosomes and microvesicles.

In addition, since nucleic acids such as miRNA have negatively charged surface properties at pH 6~8, it is considered that EV-free miRNA (free miRNA) can be collected by nanowires.

However, the collection of free miRNA is not considered possible by ultracentrifugation or polymer-precipitation methods.

Also, the collection of miRNA from the nanowires by introducing the lysis buffer was nearly 100% (see FIG. 14).

Nanowires with positively charged surfaces will provide significant benefits in collecting negatively charged materials in urine, such as exosomes, microvesicles, and free miRNA.

Given the properties such as collection efficiency, selectivity of the objects to be obtained, and the ability to collect urinary miRNA (see Table 1), the ultracentrifugation method has high collection efficiency, high selectivity of the objects to be obtained (only exosomes can be collected), and low collection capacity, whereas the disclosed devices have high collection efficiency, low selectivity (extensive collection of exosomes, microvesicles, and free miRNA), and high collection capacity.

Also, kits using polymer precipitation methods are halfway in these properties. Furthermore, the protamine precipitation method of EV is achieved by overnight incubation with protamine/polyethylene glycol at 4° C. (similar to ExoQuick). When compared to such an EV charge-based isolation procedure (see Document 49), the extraction of the EV-included miRNA by the disclosed devices only requires 40 minutes at room temperature (20 minutes for collection or adsorption and 20 minutes for extraction).

In addition, as compared to the charge-based isolation technique for free nucleic acids using chitosan polymers with amine groups yielding positively charged surfaces below pH 6.3 (see Document 50), the extraction of the EV-included miRNA by the disclosed devices has the benefit of ensuring that the nanowires are positively charged in pH 6~8 urines.

Based on these findings, the collection of EVs (and free miRNA) to ZnO nanowires by electrostatic interaction and the mechanical stability of nanowires incorporated into PDMS in the application of lysis buffer are expected to be significant mechanisms, enabling early diagnosis of diseases and timely health checkups based on analyses of urinary miRNA.

Table 1
TABLE 1 Comparisons of Three miRNA Extraction Methods
★see attached Table 1.docx★

Identification of miRNA from Urine Samples from Different Cancer Donors

Next it was examined whether miRNAs which have not yet been discovered in the urines of various cancer donors could be identified. (see FIG. 4).

In this study, miRNA were extracted from urine samples from cancerous donors and healthy individuals (non-cancerous donors) with the disclosed devices and compared on a heat map.

As shown in FIG. 4, it was possible to observe the presence of various miRNAs whose expression levels vary in relation to cancer.

The comparisons of cancerous donors with non-cancerous donors revealed decreasing miRNAs and increasing miRNsA associated with cancers in the urine (see FIG. 5 and Table 2).

The heat map suggests that decreasing miRNAs and increasing miRNAs will each be new indicators of cancer, and that combinations of these can be new indicators of cancer.

Table 2
TABLE 2 Cancer-Related Human miRNA Shown in FIG. 5
★see attached Table 2.docx★

An attempt was made to clarify the statistically significantly reduced miRNA and increased miRNA based on comparisons with published results (see Documents 52-95).

As a result, the miRNA extracted with the disclosed devices included two miRNA groups: a group of miRNA with an unknown physiological function and a group of miRNA with a reported physiological function.

The group of miRNA whose physiological function is unknown can be further divided into two subgroups: the group of miRNA associated with cancer and the group of artifacts derived from free miRNA.

The miRNA group with reported physiological functions was also broadly divided into two subgroups: a group of miRNA positively correlated with the outcome of diseases such as miR-520c-3p (a tumor suppressor, miRNA decreased in urine from all cancer patients) (see Documents 53-57) and a group of miRNA showing anti-intuitive correlations between functions of miR-16-1-3p (miRNA that suppresses invasion and metastases of gastric cancer cells, miRNA overexpressed in urine from patients with liver and bladder cancer) and the like, and diseases (see Document 60). In the counter-intuitive case, the following three possibilities were considered: the first possibility is that patients have corresponding risks; the second possibility is that this study does not cover the relations between miRNA and type of cancer; and the third possibility is that miRNA is attributed to artifacts.

When comparing the previously reported urine miRNA (shown as the top 25 of the increased miRNA from cell-free and exosome-derived) extracted with commercial kits from 4 ml urine from patients with bladder cancer (see Document 96) with the over-expressed miRNA obtained with the disclosed devices, 20 species of miRNAs containing miR-4454 were found by this study (see Data S1 or Table 3).

However, the miRNA disclosed in Document 96 is not identified in the present disclosure as candidates for an indicator of cancer.

The reason is that, in the present disclosure, the miRNA disclosed in Document 96 was also found in the urine of the non-cancer donor, and there were no significant differences in log fluorescent intensities between the non-cancer donor and the urine of the bladder cancer patients.

Relevant Literature List (Hereinafter Shown with Document Number)

1. G. Raposo, W. Stoorvogel, Extracellular vesicles: Exosomes, microvesicles, and friends. J. Cell Biol. 200, 373-383 (2013).

2. I. Evans-Osses, L. H. Reichembach, M. I. Ramirez, Exosomes or microvesicles? Two kinds of extracellular vesicles with different routes to modify protozoan-host cell interaction. Parasitol. Res. 114, 3567-3575 (2015).

3. P. Ma, Y. Pan, W. Li, C. Sun, J. Liu, T. Xu, Y Shu, Extracellular vesicles-mediated noncoding RNAs transfer in cancer. J. Hematol. Oncol. 10, 57 (2017).

4. R. Szatanek, J. Baran, M. Siedlar, M. Baj-Krzyworzeka, Isolation of extracellular vesicles: Determining the correct approach (Review). Int. J. Mol. Med. 36, 11-17 (2015).

5. D. K. Jeppesen, M. L. Hvam, B. Primdahl-Bengtson, A. T. Boysen, B. Whitehead, L. Dyrskjot, T. F. Orntoft, K. A. Howard, M. S. Ostenfeld, Comparative analysis of discrete exosome fractions obtained by differential centrifugation. J. Extracell. Vesicles 3, 25011 (2014).

6. J. A. Weber, D. H. Baxter, S. Zhang, D. Y. Huang, K. H. Huang, M. J. Lee, D. J. Galas, K. Wang, The microRNA spectrum in 12 body fluids. Clin. Chem. 56, 1733-1741 (2010).

7. L.-L. Lv, Y. Cao, D. Liu, M. Xu, H. Liu, R.-N. Tang, K.-L. Ma, B.-C. Liu, Isolation and quantification of microRNAs from urinary exosomes/microvesicles for biomarker discovery. Int. J. Biol. Sci. 9, 1021-1031 (2013).

8. M. L. Alvarez, M. Khosroheidari, R. K. Ravi, J. K. DiStefano, Comparison of protein, microRNA, and mRNA yields using different methods of urinary exosome isolation for the discovery of kidney disease biomarkers. Kidney Int. 82, 1024-1032 (2012).

9. J. Zhang, S. Li, L. Li, M. Li, C. Guo, J. Yao, S. Mi, Exosome and exosomal microRNA: Trafficking, sorting, and function. Genomics Proteomics Bioinformatics 13, 17-24 (2015).

10. N. Kosaka, H. Iguchi, T. Ochiya, Circulating microRNA in body fluid: A new potential biomarker for cancer diagnosis and prognosis. Cancer Sci. 101, 2087-2092 (2010).

11. M. Iero, R. Valenti, V Huber, P. Filipazzi, G. Parmiani, S. Fais, L. Rivoltini, Tumour-released exosomes and their implications in cancer immunity. Cell Death Differ. 15, 80-88 (2008).

12. D. D. Taylor, C. Gercel-Taylor, MicroRNA signatures of tumor-derived exosomes as diagnostic biomarkers of ovarian cancer. Gynecol. Oncol. 110, 13-21 (2008).

13. K. Al-Nedawi, B. Meehan, J. Micallef, V. Lhotak, L. May, A. Guha, J. Rak, Intercellular transfer of the oncogenic receptor EGFRvIII by microvesicles derived from tumour cells. Nat. Cell Biol. 10, 619-624 (2008).

14. Y Yoshioka, N. Kosaka, Y. Konishi, H. Ohta, H. Okamoto, H. Sonoda, R. Nonaka, H. Yamamoto, H. Ishii, M. Mori, K. Furuta, T. Nakajima, H. Hayashi, H. Sugisaki, H. Higashimoto, T. Kato, F. Takeshita, T. Ochiya, Ultra-sensitive liquid biopsy of circulating extracellular vesicles using ExoScreen. Nat. Commun. 5, 3591 (2014).

15. H. Peinado, M. Aleekovie, S. Lavotshkin, I. Matei, B. Costa-Silva, G. Moreno-Bueno, M. Hergueta-Redondo, C. Williams, G. Garcia-Santos, C. M. Ghajar, A. Nitadori-Hoshino, C. Hoffman, K. Badal, B. A. Garcia, M. K. Callahan, J. Yuan, V R. Martins, J. Skog, R. N. Kaplan, M. S. Brady, J. D. Wolchok, P. B. Chapman, Y. Kang, J. Bromberg, D. Lyden, Melanoma exosomes educate bone marrow progenitor cells toward a pro-metastatic phenotype through MET. Nat. Med. 18, 883-891 (2012).

16. C. Y. Chen, M. C. Hogan, C. J. Ward, Purification of exosome-like vesicles from urine. Methods Enzymol. 524, 225-241 (2013).

17. J. Webber, R. Steadman, M. D. Mason, Z. Tabi, A. Clayton, Cancer exosomes trigger fibroblast to myofibroblast differentiation. Cancer Res. 70, 9621-9630 (2010).

18. J. Skog, T. Wiirdinger, S. van Rijn, D. H. Meijer, L. Gainche, W. T. Curry Jr., B. S. Carter, A. M. Krichevsky, X. 0. Breakefield, Glioblastoma microvesicles transport RNA and proteins that promote tumour growth and provide diagnostic biomarkers. Nat. Cell Biol. 10, 1470-1476 (2008).

19. A. V. Vlassov, S. Magdaleno, R. Setterquist, R. Conrad, Exosomes: Current knowledge of their composition, biological functions, and diagnostic and therapeutic potentials. Biochim. Biophys. Acta 1820, 940-948 (2012).

20. C. H. Arnaud, Seeking tiny vesicles for diagnostics. Chem. Eng. News 93, 30-32 (2015).

21. M. B. Kirschner, J. J. B. Edelman, S. C.-H. Kao, M. P. Vallely, N. van Zandwijk, G. Reid, The impact of hemolysis on cell-free microRNA biomarkers. Front. Genet. 4, 94 (2013).

22. D. D. Taylor, W. Zacharias, C. Gercel-Taylor, Exosome isolation for proteomic analyses and RNA profiling. Methods Mol. Biol. 728, 235-246 (2011).

23. S. Jeong, J. Park, D. Pathania, C. M. Castro, R. Weissleder, H. Lee, Integrated magneto-electrochemical sensor for exosome analysis. ACS Nano 10, 1802-1809 (2016).

24. V Sunkara, H.-K. Woo, Y.-K. Cho, Emerging techniques in the isolation and characterization of extracellular vesicles and their roles in cancer diagnostics and prognostics. Analyst 141, 371-381 (2016).

25. P. Zhang, M. He, Y Zeng, Ultrasensitive microfluidic analysis of circulating exosomes using a nanostructured graphene oxide/polydopamine coating. Lab Chip 16, 3033-3042 (2016).

26. B. H. Wunsch, J. T. Smith, S. M. Gifford, C. Wang, M. Brink, R. L. Bruce, R. H. Austin, G. Stolovitzky, Y. Astier, Nanoscale lateral displacement arrays for the separation of exosomes and colloids down to 20 nm. Nat. Nanotechnol. 11, 936-940 (2016).

27. H.-K. Woo, V. Sunkara, J. Park, T.-H. Kim, J.-R. Han, C.-J. Kim, H.-I. Choi, Y.-K. Kim, Y.-K. Cho, Exodisc for rapid, size-selective, and efficient isolation and analysis of nanoscale extracellular vesicles from biological samples. ACS Nano 11, 1360-1370 (2017).

28. F. Barutta, M. Tricarico, A. Corbelli, L. Annaratone, S. Pinach, S. Grimaldi, G. Bruno, D. Cimino, D. Taverna, M. C. Deregibus, M. P. Rastaldi, P. C. Perin, G. Gruden, Urinary exosomal microRNAs in incipient diabetic nephropathy. PLOS ONE 8, e73798 (2013).

29. C. Thery, S. Amigorena, G. Raposo, A. Clayton, Isolation and characterization of exosomes from cell culture supernatants and biological fluids. Curr. Protoc. Cell Biol. Chapter 3, Unit 3.22 (2006).

30. K. E. Petersen, E. Manangon, J. L. Hood, S. A. Wickline, D. P. Fernandez, W. P. Johnson, B. K. Gale, A review of exosome separation techniques and characterization of B16-F10 mouse melanoma exosomes with AF4-UV-MALS-DLS-TEM. Anal. Bioanal. Chem. 406, 7855-7866 (2014).

31. L. Cheng, X. Sun, B. J. Scicluna, B. M. Coleman, A. F. Hill, Characterization and deep sequencing analysis of exosomal and non-exosomal miRNA in human urine. Kidney Int. 86, 433-444 (2014).

32. X. Duan, R. Gao, P. Xie, T. Cohen-Karni, Q. Qing, H. S. Choe, B. Tian, X. Jiang, C. M. Lieber, Intracellular recordings of action potentials by an extracellular nanoscale field-effect transistor. Nat. Nanotechnol. 7, 174-179 (2012).

33. R. Yan, J.-H. Park, Y. Choi, C.-J. Heo, S.-M. Yang, L. P. Lee, P. Yang, Nanowire-based single-cell endoscopy. Nat. Nanotechnol. 7, 191-196 (2012).

34. T. Yasui, S. Rahong, K. Motoyama, T. Yanagida, Q. Wu, N. Kaji, M. Kanai, K. Doi, K. Nagashima, M. Tokeshi, M. Taniguchi, S. Kawano, T. Kawai, Y. Baba, DNA manipulation and separation in sublithographic-scale nanowire array. ACS Nano 7, 3029-3035 (2013).

35. H. So, K. Lee, N. Murthy, A. P. Pisano, All-in-one nanowire-decorated multifunctional membrane for rapid cell lysis and direct DNA isolation. ACS Appl. Mater. Interfaces 6, 20693-20699 (2014).

36. J. Liu, T.-M. Fu, Z. Cheng, G. Hong, T. Zhou, L. Jin, M. Duvvuri, Z. Jiang, P. Kruskal, C. Xie, Z. Suo, Y. Fang, C. M. Lieber, Syringe-injectable electronics. Nat. Nanotechnol. 10, 629-636 (2015).

37. Q. Shen, L. Xu, L. Zhao, D. Wu, Y. Fan, Y. Zhou, W.-H. OuYang, X. Xu, Z. Zhang, M. Song, T. Lee, M. A. Garcia, B. Xiong, S. Hou, H.-R. Tseng, X. Fang, Specific capture and release of circulating tumor cells using aptamer-modified nanosubstrates. Adv. Mater. 25, 2368-2373 (2013).

38. J. Kim, J. W. Hong, D. P. Kim, J. H. Shin, I. Park, Nanowire-integrated microfluidic devices for facile and reagent-free mechanical cell lysis. Lab Chip 12, 2914-2921 (2012).

39. S. Rahong, T. Yasui, N. Kaji, Y. Baba, Recent developments in nanowires for bio-applications from molecular to cellular levels. Lab Chip 16, 1126-1138 (2016).

40. S. Zhang, Y. Shen, H. Fang, S. Xu, J. Song, Z. L. Wang, Growth and replication of ordered ZnO nanowire arrays on general flexible substrates. J. Mater. Chem. 20, 10606-10610 (2010).

41. A. D. Stroock, S. K. W. Dertinger, A. Ajdari, I. Mezić, H. A. Stone, G. M. Whitesides, Chaotic mixer for microchannels. Science 295, 647-651 (2002).

42. D. Xiao, J. Ohlendorf, Y. Chen, D. D. Taylor, S. N. Rai, S. Waigel, W. Zacharias, H. Hao, K. M. McMasters, Identifying mRNA, microRNA and protein profiles of melanoma exosomes. PLOS ONE 7, e46874 (2012).

43. D.-S. Choi, D.-Y Choi, B. S. Hong, S. C. Jang, D.-K. Kim, J. Lee, Y.-K. Kim, K. P. Kim, Y. S. Gho, Quantitative proteomics of extracellular vesicles derived from human primary and metastatic colorectal cancer cells. J. Extracell. Vesicles 1, 18704 (2012).

44. J. R. Edgar, Q&A: What are exosomes, exactly? BMC Biol. 14, 46 (2016).

45. J. W. Elam, S. M. George, Growth of ZnO/Al2O3 alloy films using atomic layer deposition techniques. Chem. Mater. 15, 1020-1028 (2003).

46. B. Liu, R. Hu, J. Deng, Studies on a potentiometric urea biosensor based on an ammonia electrode and urease: Immobilized on a g-aluminum oxide matrix. Anal. Chim. Acta 341, 161-169 (1997).

47. S. Xu, Z. L. Wang, One-dimensional ZnO nanostructures: Solution growth and functional properties. Nano Res. 4, 1013-1098 (2011).

48. J. Zang, C. M. Li, X. Cui, J. Wang, X. Sun, H. Dong, C. Q. Sun, Tailoring zinc oxide nanowires for high performance amperometric glucose sensor. Electroanalysis 19, 1008-1014 (2007).

49. M. C. Deregibus, F. Figliolini, S. D'Antico, P. M. Manzini, C. Pasquino, M. De Lena, C. Tetta, M. F. Brizzi, G. Camussi, Charge-based precipitation of extracellular vesicles. Int. J. Mol. Med. 38, 1359-1366 (2016).

50. T. S. Schlappi, S. E. McCalla, N. G. Schoepp, R. F. Ismagilov, Flow-through capture and in situ amplification can enable rapid detection of a few single molecules of nucleic acids from several milliliters of solution. Anal. Chem. 88, 7647-7653 (2016).

51. J. A. Hanley, B. J. McNeil, The meaning and use of the area under a receiver operating characteristic (ROC) curve. Radiology 143, 29-36 (1982).

52. Z. Wang, B. Ma, X. Ji, Y Deng, T. Zhang, X. Zhang, H. Gao, H. Sun, H. Wu, X. Chen, R. Zhao, MicroRNA-378-5p suppresses cell proliferation and induces apoptosis in colorectal cancer cells by targeting BRAF. Cancer Cell Int. 15, 40 (2015).

53. H.-L. Miao, C.-J. Lei, Z.-D. Qiu, Z.-K. Liu, R. Li, S.-T. Bao, M.-Y. Li, MicroRNA-520c-3p inhibits hepatocellular carcinoma cell proliferation and invasion through induction of cell apoptosis by targeting glypican-3. Hepatol. Res. 44, 338-348 (2014).

54. S. Lu, Q. Zhu, Y Zhang, W. Song, M. J. Wilson, P. Liu, Dual-functions of miR-373 and miR-520c by differently regulating the activities of MMP2 and MMP9. J. Cell. Physiol. 230, 1862-1870 (2015).

55. K. Mazan-Mamczarz, X. F. Zhao, B. Dai, J. J. Steinhardt, R. J. Peroutka, K. L. Berk, A. L. Landon, M. Sadowska, Y. Zhang, E. Lehrmann, K. G. Becker, R. Shaknovich, Z. Liu, R. B. Gartenhaus, Down-regulation of eIF4GII by miR-520c-3p represses diffuse large B cell lymphoma development. PLOS Genet. 10, e1004105 (2014).

56. C.-J. Lei, C. Yao, D.-K. Li, Z.-X. Long, Y. Li, D. Tao, Y.-P. Liou, J.-Z. Zhang, N. Liu, Effect of co-transfection of miR-520c-3p and miR-132 on proliferation and apoptosis of hepatocellular carcinoma Huh7. Asian Pac. J. Trop. Med. 9, 898-902 (2016).

57. G. Mudduluru, K. Ilm, S. Fuchs, U. Stein, Epigenetic silencing of miR-520c leads to induced S100A4 expression and its mediated colorectal cancer progression. Oncotarget 8, 21081-21094 (2017).

58. R. Zhang, J. Zhao, J. Xu, J. Wang, J. Jia, miR-526b-3p functions as a tumor suppressor in colon cancer by regulating HIF-1a. Am. J. Transl. Res. 8, 2783-2789 (2016).

59. L. Su, D. Han, J. Wu, X. Huo, Skp2 regulates non-small cell lung cancer cell growth by Meg3 and miR-3163. Tumour Biol. 37, 3925-3931 (2016).

60. T. Wang, J. Hou, Z. Li, Z. Zheng, J. Wei, D. Song, T. Hu, Q. Wu, J. Y. Yang, J.-c. Cai, miR-15a-3p and miR-16-1-3p negatively regulate Twistl to repress gastric cancer cell invasion and metastasis. Int. J. Biol. Sci. 13, 122-134 (2017).

61. Q.-y. Chen, D.-m. Jiao, L. Yan, Y-q. Wu, H.-z. Hu, J. Song, J. Yan, L.-j. Wu, L.-q. Xu, J.-g. Shi, Comprehensive gene and microRNA expression profiling reveals miR-206 inhibits MET in lung cancer metastasis. Mol. Biosyst. 11, 2290-2302 (2015).

62. L. Zheng, W. Jiao, H. Song, H. Qu, D. Li, H. Mei, Y Chen, F. Yang, H. Li, K. Huang, Q. Tong, miRNA-558 promotes gastric cancer progression through attenuating Smad4-mediated repression of heparanase expression. Cell Death Dis. 7, e2382 (2016).

63. Y Sun, C. Chen, P. Zhang, H. Xie, L. Hou, Z. Hui, Y Xu, Q. Du, X. Zhou, B. Su, W. Gao, Reduced miR-3127-5p expression promotes NSCLC proliferation/invasion and contributes to dasatinib sensitivity via the c-Abl/Ras/ERK pathway. Sci. Rep. 4, 6527 (2014).

64. Y Fang, J. Xiang, Z. Chen, X. Gu, Z. Li, F. Tang, Z. Zhou, miRNA expression profile of colon cancer stem cells compared to non-stem cells using the SW1116 cell line. Oncol. Rep. 28, 2115-2124 (2012).

65. X. Huang, M. Huang, L. Kong, Y Li, miR-372 suppresses tumour proliferation and invasion by targeting IGF2BP1 in renal cell carcinoma. Cell Prolif. 48, 593-599 (2015).

66. Y.-C. Lu, A.-J. Cheng, L.-Y. Lee, G.-R. You, Y.-L. Li, H.-Y. Chen, J. T. Chang, MiR-520b as a novel molecular target for suppressing stemness phenotype of head-neck cancer by inhibiting CD44. Sci. Rep. 7, 2042 (2017).

67. A. Druz, Y.-C. Chen, R. Guha, M. Betenbaugh, S. E. Martin, J. Shiloach, Large-scale screening identifies a novel microRNA, miR-15a-3p, which induces apoptosis in human cancer cell lines. RNA Biol. 10, 287-300 (2013).

68. Z. Wu, Y Wu, Y. Tian, X. Sun, J. Liu, H. Ren, C. Liang, L. Song, H. Hu, L. Wang, B. Jiao, Differential effects of miR-34c-3p and miR-34c-5p on the proliferation, apoptosis and invasion of glioma cells. Oncol. Lett. 6, 1447-1452 (2013).

69. Z. Cheng, F. Liu, H. Zhang, X. Li, Y Li, J. Li, F. Liu, Y Cao, L. Cao, F. Li, miR-135a inhibits tumor metastasis and angiogenesis by targeting FAK pathway. Oncotarget 8, 31153-31168 (2017).

70. C. Liu, G. Li, S. Ren, Z. Su, Y Wang, Y Tian, Y. Liu, Y Qiu, miR-185-3p regulates the invasion and metastasis of nasopharyngeal carcinoma by targeting WNT2B in vitro. Oncol. Lett. 13, 2631-2636 (2017).

71. R. Zhang, H. Leng, J. Huang, Y Du, Y. Wang, W. Zang, X. Chen, G. Zhao, miR-337 regulates the proliferation and invasion in pancreatic ductal adenocarcinoma by targeting HOXB7. Diagn. Pathol. 9, 171 (2014).

72. M. Lu, X. Zhou, C.-G. Zheng, F.-J. Liu, Expression profiling of miR-96, miR-584 and miR-422a in colon cancer and their potential involvement in colon cancer pathogenesis. Trop. J. Pharm. Res. 15, 2535-2542 (2016).

73. Z. Zhao, X. Ma, T.-H. Hsiao, G. Lin, A. Kosti, X. Yu, U. Suresh, Y. Chen, G. E. Tomlinson, A. Pertsemlidis, L. Du, A high-content morphological screen identifies novel microRNAs that regulate neuroblastoma cell differentiation. Oncotarget 5, 2499-2512 (2014).

74. W. Chen, Z. Tang, Y. Sun, Y Zhang, X. Wang, Z. Shen, F. Liu, X. Qin, miRNA expression profile in primary gastric cancers and paired lymph node metastases indicates that miR-10a plays a role in metastasis from primary gastric cancer to lymph nodes. Exp. Ther. Med. 3, 351-356 (2012).

75. Y Li, W. Han, T.-T. Ni, L. Lu, M. Huang, Y. Zhang, H. Cao, H.-Q. Zhang, W. Luo, H. Li, Knockdown of microRNA-1323 restores sensitivity to radiation by suppression of PRKDC activity in radiation-resistant lung cancer cells. Oncol. Rep. 33, 2821-2828 (2015).

76. A. R. Lee, J. Park, K. J. Jung, S. H. Jee, S J Kim-Yoon, Genetic variation rs7930 in the miR-4273-5p target site is associated with a risk of colorectal cancer. Oncotargets Ther. 9, 6885-6895 (2016).

77. F. Miao, J. Zhu, Y Chen, N. Tang, X. Wang, X. Li, MicroRNA-183-5p promotes the proliferation, invasion and metastasis of human pancreatic adenocarcinoma cells. Oncol. Lett. 11, 134-140 (2016).

78. H. R. Mody, S. W. Hung, R. K. Pathak, J. Griffin, Z. Cruz-Monserrate, R. Govindarajan, miR-202 diminishes TGFb receptors and attenuates TGFb1-induced EMT in pancreatic cancer. Mol. Cancer Res. 15, 1029-1039 (2017).

79. S. Josson, M. Gururajan, P. Hu, C. Shao, G. C.-Y. Chu, H. E. Zhau, C. Liu, K. Lao, C.-L. Lu, Y-T. Lu, J. Lichterman, S. Nandana, Q. Li, A. Rogatko, D. Berel, E. M. Posadas, L. Fazli, D. Sareen, L. W. K. Chung, miR-409-3p/-5p promotes tumorigenesis, epithelial-to-mesenchymal transition, and bone metastasis of human prostate cancer. Clin. Cancer Res. 20, 4636-4646 (2014).

80. X. Shi, F. Teng, Down-regulated miR-28-5p in human hepatocellular carcinoma correlated with tumor proliferation and migration by targeting insulin-like growth factor-1 (IGF-1). Mol. Cell. Biochem. 408, 283-293 (2015).

81. Y. Sun, J. Zhao, X. Yin, X. Yuan, J. Guo, J. Bi, miR-297 acts as an oncogene by targeting GPC5 in lung adenocarcinoma. Cell Prolif. 49, 636-643 (2016).

82. H.-q. Liang, R.-j. Wang, C.-f. Diao, J.-w. Li, J.-l. Su, S. Zhang, The PTTG1-targeting miRNAs miR-329, miR-300, miR-381, and miR-655 inhibit pituitary tumor cell tumorigenesis and are involved in a p53/PTTG1 regulation feedback loop. Oncotarget 6, 29413-29427 (2015).

83. A. Mesci, X. Huang, S. Taeb, S. Jahangiri, Y Kim, E. Fokas, J. Bruce, H. S. Leong, S. K. Liu, Targeting of CCBE1 by miR-330-3p in human breast cancer promotes metastasis. Br. J. Cancer 116, 1350-1357 (2017).

84. L. Yu, X. Gong, L. Sun, H. Yao, B. Lu, L. Zhu, miR-454 functions as an oncogene by inhibiting CHD5 in hepatocellular carcinoma. Oncotarget 6, 39225-39234 (2015).

85. C. Liu, C. Wang, J. Wang, H. Huang, miR-1297 promotes cell proliferation by inhibiting RB1 in liver cancer. Oncol. Lett. 12, 5177-5182 (2016).

86. M. Shao, Y. Geng, P. Lu, Y. Xi, S. Wei, L. Wang, Q. Fan, W. Ma, miR-4295 promotes cell proliferation and invasion in anaplastic thyroid carcinoma via CDKN1A. Biochem. Biophys. Res. Commun. 464, 1309-1313 (2015).

87. Y An, Z. Zhang, Y. Shang, X. Jiang, J. Dong, P. Yu, Y Nie, Q. Zhao, miR-23b-3p regulates the chemoresistance of gastric cancer cells by targeting ATG12 and HMGB2. Cell Death Dis. 6, e1766 (2015).

88. C. T. D. Dickman, J. Lawson, J. Jabalee, S. A. MacLellan, N. E. LePard, K. L. Bennewith, C. Garnis, Selective extracellular vesicle exclusion of miR-142-3p by oral cancer cells promotes both internal and extracellular malignant phenotypes. Oncotarget 8, 15252-15266 (2017).

89. L. Jin, X. Li, Y. Li, Z. Zhang, T. He, J. Hu, J. Liu, M. Chen, M. Shi, Z. Jiang, Y. Gui, S. Yang, X. Mao, Y. Lai, Identification of miR-195-3p as an oncogene in RCC. Mol. Med. Rep. 15, 1916-1924 (2017).

90. A. R. Göhring, S. Reuter, J. H. Clement, X. Cheng, J. Theobald, S. Wölfl, R. Mrowka, Human microRNA-299-3p decreases invasive behavior of cancer cells by downregulation of Oct4 expression and causes apoptosis. PLOS ONE 12, e0174912 (2017).

91. Y.-H. Nan, J. Wang, Y. Wang, P.-H. Sun, Y.-P. Han, L. Fan, K.-C. Wang, F.-J. Shen, W.-H. Wang, MiR-4295 promotes cell growth in bladder cancer by targeting BTG1. Am. J. Transl. Res. 9, 1960 (2017).

92. N. Nabavi, N. R. N. Saidy, E. Venalainen, A. Haegert, A. Parolia, H. Xue, Y Wang, R. Wu, X. Dong, C. Collins, F. Crea, Y. Wang, miR-100-5p inhibition induces apoptosis in dormant prostate cancer cells and prevents the emergence of castration-resistant prostate cancer. Sci. Rep. 7, 4079 (2017).

93. D. Deng, L. Wang, Y Chen, B. Li, L. Xue, N. Shao, Q. Wang, X. Xia, Y. Yang, F. Zhi, MicroRNA-124-3p regulates cell proliferation, invasion, apoptosis, and bioenergetics by targeting PIM1 in astrocytoma. Cancer Sci. 107, 899-907 (2016).

94. T. Chiyomaru, S. Yamamura, M. S. Zaman, S. Majid, G. Deng, V. Shahryari, S. Saini, H. Hirata, K. Ueno, I. Chang, Y. Tanaka, Z. L. Tabatabai, H. Enokida, M. Nakagawa, R. Dahiya, Genistein suppresses prostate cancer growth through inhibition of oncogenic microRNA-151. PLOS ONE 7, e43812 (2012).

95. Z. Xue, J. Zhao, L. Niu, G. An, Y. Guo, L. Ni, Up-regulation of MiR-300 promotes proliferation and invasion of osteosarcoma by targeting BRD7. PLOS ONE 10, e0127682 (2015).

96. D. A. Armstrong, B. B. Green, J. D. Seigne, A. R. Schned, C. J. Marsit, MicroRNA molecular profiling from matched tumor and bio-fluids in bladder cancer. Mol. Cancer 14, 194 (2015).

Table 3
TABLE 3 Data S1
★see attached Table 3 Data S1-1, S1-2.docx★

TABLE 1

| | TABLE 1 Comparisons of Three miRNA Extraction Methods | | |
|---|---|---|---|
| | Device of Present Disclosure | ExoQuick ™ | Ultracentrifugation method |
| Substances to be Collection | Exosomes Microvesicles EV free miRNA | Exosomes Microvesicles | Exosomes |

TABLE 1-continued

TABLE 1 Comparisons of Three miRNA Extraction Methods

| | Device of Present Disclosure | ExoQuick ™ | Ultracentrifugation method |
|---|---|---|---|
| Collection mechanism | Electrostatic interaction between nanowire surface charge and substances to be collected | Capture of substances with a diameter of 60 to 180 nm by polymer, according to manufacturer's instructions | Balance between applied force and density of substances collected |
| Required volume of sample | 1 ml | 1 ml | 1 ml for quantitation of small molecule RNAs; 20 ml for urinary miRNA profiling |
| Treating time | 40 minutes | 870 minutes | 300 minutes |
| Collection efficiency (Yield of small-molecule RNAs) | 0.194 ± 0.028 ng/μl | 0.120 ± 0.015 ng/μl | 0.159 ± 0.077 ng/μl |
| Identified Urinary miRNA extract species | 749 species, 822 species, 1111 species (n = 3) | 337 species, 355 species, 491 species (n = 3) | 171 species, 261 species, 352 species (n = 3) 200 species~300 species* |

*By Chang et al. (31)

TABLE 2

TABLE 2 Cancer-Related Human miRNA Shown in FIG. 5

| Type of cancer (down-regulation/overexpression) | miRNA | Physiological function |
|---|---|---|
| Lung cancer (down-regulation) | miR-3127-3p* | |
| | miR-3130-5p* | |
| | miR-3131* | |
| | miR-3141* | |
| | miR-3150b-5p* | |
| | miR-3151-3p* | |
| | miR-3151-5p* | |
| | miR-3154* | |
| | miR-3160-3p* | |
| | miR-3160-5p* | |
| | miR-378a-5p | cell proliferation suppression and induces apoptosis (Document 52) |
| | miR-520c-3p | tumor suppressor (Documents 53-57) |
| | miR-526b-3p | tumor suppressor (Documents 58) |
| | miR-3150a-3p | |
| | miR-3162-5p | |
| | miR-4254 | |
| Lung cancer (overexpression) | miR-3117-5p* | |
| | miR-3118* | |
| | miR-3121-3p* | |
| | miR-3121-5p* | |
| | miR-3126-5p* | |
| | miR-3128* | |
| | miR-3133* | |
| | miR-3134* | |
| | miR-3136-3p* | |
| | miR-3136-5p* | |
| | miR-3139* | |
| | miR-3142* | |
| | miR-3143* | |
| | miR-3145-3p* | |
| | miR-3163* | Suppression of non small cell lung cancer cell proliferation (Document 59) |
| | miR-3166* | |
| | miR-3167* | |
| | miR-16-1-3p | Suppression of infiltration and metastases of gastric cancer cells (Document 60) |
| | miR-424-3p | miRNAs in relation to metastasis (Document 61) |
| | miR-519c-5p | |
| | miR-525-5p | |
| | miR-551b-5p | |

TABLE 2-continued

TABLE 2 Cancer-Related Human miRNA Shown in FIG. 5

| Type of cancer (down-regulation/overexpression) | miRNA | Physiological function |
|---|---|---|
| | miR-558 | Enhancement of tumorigenicity (Document 62) |
| | miR-921 | |
| | miR-942-3p | |
| | miR-3126-3p | |
| | miR-3127-5p | Suppression of non small cell lung cancer cell proliferation (Document 63) |
| | miR-3129-5p | |
| | miR-3144-5p | |
| | miR-3150a-5p | |
| | miR-3152-5p | |
| | miR-3155a | |
| | miR-3157-3p | |
| | miR-3159 | |
| | miR-3165 | |
| | miR-3678-3p | |
| | miR-4321 | miRNAs significantly increased in cancer stem cells (Document 64) |
| | miR-4521 | |
| | miR-4800-3p | |
| | miR-4999-5p | |
| | miR-5096 | |
| | miR-5187-5p | |
| | miR-6874-5p | |
| Pancreatic cancer (down-regulation) | miR-372-3p* | Tumor suppressor (Document 65) |
| | miR-378b* | |
| | miR-520b* | Suppression of migration and infiltration of cells (Document 66) |
| | miR-1266-3p* | |
| | miR-3605-5p* | |
| | miR-3612* | |
| | miR-4645-3p* | |
| | miR-4694-3p* | |
| | miR-4752* | |
| | miR-6816-3p* | |
| | miR-8087* | |
| | let-7f-2-3p | |
| | miR-15a-3p | Apoptosis induction in human cancer cell lines (Document 67) |
| | miR-20a-3p | |
| | miR-33b-3p | |
| | miR-34c-5p | Tumor suppressor (Document 68) |
| | miR-93-5p | |
| | miR-130a-5p | |
| | miR-135a-5p | Suppression of tumor metastasis (Document 69) |
| | miR-135b-5p | |
| | miR-185-5p | Tumor suppressor (Document 70) |
| | miR-203a-3p | |
| | miR-302d-5p | |
| | miR-337-3p | Tumor suppressor (Document 71) |
| | miR-378c | |
| | miR-422a | Down regulation in colon cancer (Document 72) |
| | miR-449c-5p | |
| | miR-483-5p | |
| | miR-506-3p | Induction of differentiation (Document 73) |
| | miR-511-5p | |
| | miR-520c-3p | Tumor suppressor (Documents 53-57) |
| | miR-654-3p | |
| | miR-668-5p | |
| | miR-670-5p | |
| | miR-671-3p | |
| | miR-744-3p | |
| | miR-1178-3p | |
| | miR-1254 | |
| | miR-1284 | Down regulation in lymph node metastases (Document 74) |
| | miR-1323 | Adjustment of radiation resistance (Document 75) |
| | miR-2116-5p | |
| | miR-2355-3p | |
| | miR-3132 | |
| | miR-3138 | |
| | miR-3164 | |
| | miR-3186-3p | |
| | miR-3189-3p | |
| | miR-3198 | |
| | miR-3200-5p | |

TABLE 2-continued

TABLE 2 Cancer-Related Human miRNA Shown in FIG. 5

| Type of cancer (down-regulation/overexpression) | miRNA | Physiological function |
|---|---|---|
| | miR-3657 | |
| | miR-3667-5p | |
| | miR-3680-5p | |
| | miR-3692-5p | |
| | miR-3713 | |
| | miR-3921 | |
| | miR-3936 | |
| | miR-4273 | Increase of colorectal cancer risk (Document 76) |
| | miR-4299 | |
| | miR-4306 | |
| | miR-4316 | |
| | miR-4319 | |
| | miR-4421 | |
| | miR-4429 | |
| | miR-4435 | |
| | miR-4441 | |
| | miR-4473 | |
| | miR-4506 | |
| | miR-4633-5p | |
| | miR-4658 | |
| | miR-4733-5p | |
| | miR-4733-3p | |
| | miR-5004-3p | |
| | miR-5194 | |
| | miR-5197-5p | |
| | miR-5571-5p | |
| | miR-6083 | |
| | miR-6717-5p | |
| | miR-6720-5p | |
| | miR-6767-3p | |
| | miR-6781-3p | |
| | miR-6811-3p | |
| | miR-6821-3p | |
| | miR-6828-5p | |
| | miR-6832-5p | |
| | miR-6837-3p | |
| | miR-6841-5p | |
| | miR-6853-5p | |
| | miR-6871-3p | |
| | miR-6875-5p | |
| | miR-6878-5p | |
| | miR-7112-3p | |
| | miR-7703 | |
| | miR-7848-3p | |
| | miR-7856-5p | |
| Pancreatic cancer (overexpression) | let-7i-3p | |
| | miR-183-5p | Promotion of proliferation, infiltration, and metastasis of cancer (Document 77) |
| | miR-202-5p | Increase of protein expression of TGFBR1 and TGFBR2 (Document 78) |
| | miR-409-5p | Promotion of cancer formation (Document 79) |
| | miR-4661-5p | |
| | miR-4800-3p | |
| | miR-5587-5p | |
| Liver cancer (down-regulation) | let-7i-2-3p | |
| | miR-520c-3p | Tumor suppressor (Documents 53-57) |
| Liver cancer (overexpression) | miR-4521* | |
| | let-7c-3p | |
| | let-7i-5p | |
| | miR-61-1-3p | Suppression of infiltration and metastases of gastric cancer cells (Document 60) |
| | miR-26a-1-3p | |
| | miR-28-5p | Suppression of expression of insulin like growth factor (Document 80) |
| | miR-105-5p | |
| | miR-195-3p | |
| | miR-200b-5p | |
| | miR-219a-2-3p | |
| | miR-297 | Promotion of cell proliferation and infiltration (Document 81) |

TABLE 2-continued

TABLE 2 Cancer-Related Human miRNA Shown in FIG. 5

| Type of cancer (down-regulation/overexpression) | miRNA | Physiological function |
|---|---|---|
| | miR-300 | Suppresion of pituitary gland transforming gene expression (Document 82) |
| | | Promotion of infiltration and metastasis (Document 83) |
| | miR-330-3p | |
| | miR-374b-5p | |
| | miR-431-5p | Promotion cancer formation (Document 84) |
| | miR-454-5p | |
| | miR-513c-5p | |
| | miR-548ax | |
| | miR-593-5p | |
| | miR-623 | |
| | miR-664a-5p | |
| | miR-942-3p | |
| | miR-1205 | |
| | miR-1276 | |
| | miR-1288-3p | Promotion of cell proliferation (Document 85) |
| | miR-1297 | |
| | miR-3678-3p | |
| | miR-4283 | Promotion of cell proliferation and infiltration (Document 86) |
| | miR-4295 | |
| | miR-4439 | |
| | miR-4524b-5p | |
| | miR-4703-3p | |
| | miR-4768-5p | |
| | miR-4800-3p | |
| | miR-5187-5p | |
| | miR-5696 | |
| | miR-7161-5p | |
| Bladder cancer (down-regulation) | let-7f-2-3p | |
| | miR-520c-3p | Tumor suppressor (Documents 53-57) |
| | miR-4783-5p | |
| Bladder cancer (overexpression) | miR-16-1-3p | Suppression of infiltration and metastases of gastric cancer cells (Document 60) |
| | miR-23b-3p | Control of chemical resistance of gastric cancer cells (Document 87) |
| | miR-28-5p | Suppression of expression of insulin like growth factor (Document 80) |
| | miR-92a-2-5p | |
| | miR-142-3p | Promotion of malignant phenotypes (Document 88) |
| | miR-195-3p | Promotion of tumor formation and suppression of apoptosis (Document 89) |
| | miR-196b-5p | |
| | miR-299-3p | |
| | miR-492 | Decrease of Oct4 gene expression (Document 90) |
| | miR-513b-5p | |
| | miR-601 | |
| | miR-619-5p | |
| | miR-1285-3p | |
| | miR-3155a | |
| | miR-3162-5p | |
| | miR-3678-3p | |
| | miR-4283 | |
| | miR-4295 | |
| | miR-4311 | Promotion of bladder cancer cell proliferation (Document 91) |
| | miR-4531 | |
| | miR-5096 | |
| | miR-5187-5p | |
| Prostate cancer (down-regulation) | miR-15a-3p | Induction of apoptosis in human cancer cell lines (Document 67) |
| | miR-135b-5p | |
| | miR-520c-3p | Tumor suppressor (Documents 53-57) |
| | miR-4783-5p | |
| | miR-7849-3p | |
| Prostate cancer (overexpression) | miR-4531* | |
| | miR-28-5p | Suppression of expression of insulin like growth factor (Document 80) |
| | miR-103a-2-5p | |
| | miR-105-5p | Suppression of tumor suppressor gene expression (Document 92) |
| | miR-124-3p | Control of cell proliferation, infiltration, and apoptosis (Document 93) |

TABLE 2-continued

TABLE 2 Cancer-Related Human miRNA Shown in FIG. 5

| Type of cancer (down-regulation/overexpression) | miRNA | Physiological function |
|---|---|---|
| | miR-151a-5p | Migration and infiltration of cancer cells (Document 94) |
| | miR-151b | |
| | miR-200a-5p | |
| | miR-300 | Promotion of proliferation and infiltration of cancer (Document 95) |
| | miR-424-3p | |
| | miR-519c-5p | |
| | miR-551b-5p | |
| | miR-617 | |
| | miR-873-3p | |
| | miR-921 | |
| | miR-1288-3p | |
| | miR-3124-5p | |
| | miR-3155a | |
| | miR-3917 | |
| | miR-4283 | |
| | miR-4727-3p | |
| | miR-5096 | |
| | miR-5187-5p | |
| | miR-6074 | |
| | miR-6874-5p | |
| | miR-6892-5p | |

TABLE 3

Data S1-1

| miRNA species | Non-cancerous | | | | Lung cancer | | | Pancreatic cancer | |
|---|---|---|---|---|---|---|---|---|---|
| hsa-let-7a-5p | 0.0 | 0.0 | 0.0 | 0.0 | 0.0 | 0.0 | 0.0 | 2.4 | 0.0 |
| hsa-let-7c-5p | 0.0 | 2.0 | 0.0 | 0.0 | 0.0 | 0.0 | 0.0 | 0.0 | 0.0 |
| hsa-let-7d-5p | 0.0 | 0.0 | 0.0 | 0.0 | 0.0 | 0.0 | 0.0 | 0.0 | 0.0 |
| hsa-let-7e-3p | 0.0 | 0.0 | 2.5 | 0.0 | 0.0 | 0.0 | 0.0 | 0.0 | 0.0 |
| hsa-let-7f-2-3p | 0.0 | 3.5 | 3.8 | 2.5 | 0.0 | 1.8 | 0.0 | 0.0 | 0.0 |
| hsa-let-7f-5p | 0.0 | 0.0 | 0.0 | 0.0 | 0.0 | 0.0 | 0.0 | 0.0 | 0.0 |
| hsa-let-7g-3p | 0.0 | 0.0 | 2.1 | 2.4 | 0.0 | 0.0 | 4.0 | 0.0 | 0.0 |
| hsa-let-7i-3p | 0.0 | 1.9 | 0.0 | 2.8 | 0.0 | 0.0 | 3.3 | 0.0 | 3.0 |
| hsa-miR-0001-3p | 0.0 | 0.0 | 0.0 | 6.2 | 0.0 | 0.0 | 0.0 | 0.0 | 0.0 |
| hsa-miR-0001-5p | 2.6 | 3.4 | 2.1 | 0.0 | 0.0 | 2.2 | 0.0 | 0.0 | 0.0 |
| hsa-miR-0009-5p | 0.0 | 1.9 | 0.0 | 0.0 | 0.0 | 0.0 | 0.0 | 0.0 | 0.0 |
| hsa-miR-0015a-3p | 2.6 | 4.0 | 3.6 | 2.7 | 0.0 | 2.3 | 0.0 | 0.0 | 0.0 |
| hsa-miR-0015a-5p | 0.0 | 0.0 | 0.0 | 0.0 | 0.0 | 2.0 | 3.7 | 0.0 | 0.0 |
| hsa-miR-0015b-3p | 0.0 | 0.0 | 0.0 | 0.0 | 0.0 | 0.0 | 0.0 | 0.0 | 0.0 |
| hsa-miR-0016-2-3p | 2.4 | 1.9 | 0.0 | 0.0 | 2.1 | 2.2 | 0.0 | 0.0 | 0.0 |
| hsa-miR-0016-5p | 0.0 | 0.0 | 0.0 | 0.0 | 0.0 | 0.0 | 3.4 | 0.0 | 0.0 |
| hsa-miR-0017-5p | 0.0 | 0.0 | 0.0 | 0.0 | 0.0 | 0.0 | 0.0 | 0.0 | 0.0 |
| hsa-miR-0018b-5p | 0.0 | 0.0 | 3.4 | 3.9 | 1.6 | 0.0 | 0.0 | 0.0 | 0.0 |
| hsa-miR-0019a-3p | 0.0 | 0.0 | 0.0 | 0.0 | 0.0 | 0.0 | 0.0 | 0.0 | 2.9 |
| hsa-miR-0019a-5p | 0.0 | 0.0 | 0.0 | 0.0 | 0.0 | 0.0 | 0.0 | 0.0 | 0.0 |
| hsa-miR-0019b-1-5p | 0.0 | 0.0 | 0.0 | 2.4 | 0.0 | 0.0 | 0.0 | 0.0 | 0.0 |
| hsa-miR-0019b-2-5p | 0.0 | 0.0 | 0.0 | 0.0 | 0.0 | 0.0 | 3.1 | 0.0 | 0.0 |
| hsa-miR-0020b-5p | 0.0 | 2.0 | 0.0 | 0.0 | 1.8 | 0.0 | 0.0 | 3.1 | 0.0 |
| hsa-miR-0021-5p | 0.0 | 0.0 | 0.0 | 0.0 | 0.0 | 0.0 | 0.0 | 0.0 | 0.0 |
| hsa-miR-0022-5p | 0.0 | 0.0 | 0.0 | 0.0 | 0.0 | 0.0 | 3.0 | 0.0 | 0.0 |
| hsa-miR-0023b-5p | 0.0 | 0.0 | 0.0 | 0.0 | 0.0 | 0.0 | 0.0 | 0.0 | 0.0 |
| hsa-miR-0023c | 0.0 | 0.0 | 0.0 | 0.0 | 0.0 | 0.0 | 0.0 | 0.0 | 0.0 |
| hsa-miR-0024-1-5p | 0.0 | 0.0 | 2.6 | 0.0 | 0.0 | 0.0 | 2.7 | 3.1 | 0.0 |
| hsa-miR-0024-2-5p | 0.0 | 0.0 | 0.0 | 0.0 | 2.3 | 2.0 | 0.0 | 0.0 | 0.0 |
| hsa-miR-0024-3p | 2.1 | 2.6 | 2.6 | 0.0 | 2.9 | 2.9 | 0.0 | 2.8 | 0.0 |
| hsa-miR-0026a-2-3p | 0.0 | 0.0 | 0.0 | 0.0 | 0.0 | 0.0 | 3.4 | 0.0 | 0.0 |
| hsa-miR-0026a-5p | 0.0 | 0.0 | 2.5 | 2.5 | 0.0 | 0.0 | 3.1 | 0.0 | 0.0 |
| hsa-miR-0027a-5p | 0.0 | 0.0 | 3.4 | 0.0 | 0.0 | 0.0 | 0.0 | 0.0 | 0.0 |
| hsa-miR-0028-3p | 0.0 | 2.1 | 3.9 | 0.0 | 2.2 | 0.0 | 0.0 | 0.0 | 3.7 |
| hsa-miR-0029a-5p | 0.0 | 2.2 | 3.7 | 5.1 | 0.0 | 0.0 | 2.6 | 0.0 | 0.0 |
| hsa-miR-0029b-1-5p | 0.0 | 0.0 | 0.0 | 0.0 | 1.7 | 0.0 | 2.6 | 0.0 | 0.0 |
| hsa-miR-0029c-3p | 0.0 | 0.0 | 2.2 | 0.0 | 0.0 | 0.0 | 0.0 | 0.0 | 0.0 |
| hsa-miR-0030a-5p | 0.0 | 0.0 | 0.0 | 0.0 | 0.0 | 0.0 | 0.0 | 0.0 | 0.0 |
| hsa-miR-0031-3p | 0.0 | 0.0 | 3.3 | 5.5 | 0.0 | 0.0 | 4.0 | 0.0 | 0.0 |
| hsa-miR-0031-5p | 0.0 | 0.0 | 0.0 | 0.0 | 0.0 | 0.0 | 3.8 | 0.0 | 0.0 |
| hsa-miR-0032-3p | 1.7 | 2.6 | 3.2 | 0.0 | 1.9 | 2.3 | 0.0 | 2.9 | 0.0 |
| hsa-miR-0032-5p | 0.0 | 2.6 | 0.0 | 0.0 | 2.5 | 0.0 | 0.0 | 0.0 | 0.0 |

TABLE 3-continued

| | | | | | | | | | |
|---|---|---|---|---|---|---|---|---|---|
| hsa-miR-0033a-3p | 0.0 | 0.0 | 0.0 | 0.0 | 0.0 | 1.5 | 0.0 | 0.0 | 0.0 |
| hsa-miR-0033a-5p | 0.0 | 0.0 | 0.0 | 0.0 | 0.0 | 0.0 | 0.0 | 0.0 | 3.6 |
| hsa-miR-0033b-5p | 0.0 | 0.0 | 0.0 | 0.0 | 0.0 | 0.0 | 0.0 | 0.0 | 0.0 |
| hsa-miR-0034a-3p | 0.0 | 0.0 | 0.0 | 2.4 | 0.0 | 0.0 | 0.0 | 0.0 | 0.0 |
| hsa-miR-0095-5p | 0.0 | 0.0 | 4.1 | 3.8 | 0.0 | 0.0 | 0.0 | 0.0 | 0.0 |
| hsa-miR-0096-5p | 0.0 | 0.0 | 0.0 | 0.0 | 0.0 | 0.0 | 0.0 | 0.0 | 3.0 |
| hsa-miR-0099a-5p | 0.0 | 0.0 | 0.0 | 0.0 | 0.0 | 0.0 | 3.3 | 2.7 | 0.0 |
| hsa-miR-0100-3p | 0.0 | 0.0 | 0.0 | 2.5 | 0.0 | 0.0 | 0.0 | 0.0 | 0.0 |
| hsa-miR-0100-5p | 0.0 | 2.1 | 0.0 | 2.8 | 0.0 | 0.0 | 0.0 | 2.7 | 0.0 |
| hsa-miR-0101-3p | 0.0 | 0.0 | 0.0 | 2.4 | 0.0 | 0.0 | 0.0 | 0.0 | 0.0 |
| hsa-miR-0101-5p | 0.0 | 0.0 | 0.0 | 0.0 | 0.0 | 0.0 | 0.0 | 0.0 | 0.0 |
| hsa-miR-0103a-3p | 0.0 | 2.4 | 0.0 | 0.0 | 0.0 | 2.4 | 0.0 | 0.0 | 2.5 |
| hsa-miR-0103b | 0.0 | 0.0 | 0.0 | 0.0 | 0.0 | 0.0 | 3.5 | 0.0 | 0.0 |
| hsa-miR-0105-3p | 0.0 | 0.0 | 0.0 | 2.5 | 0.0 | 0.0 | 0.0 | 0.0 | 0.0 |
| hsa-miR-0106a-3p | 0.0 | 0.0 | 0.0 | 0.0 | 0.0 | 0.0 | 0.0 | 0.0 | 2.6 |
| hsa-miR-0106a-5p | 0.0 | 0.0 | 0.0 | 0.0 | 1.4 | 0.0 | 0.0 | 0.0 | 0.0 |
| hsa-miR-0106b-5p | 0.0 | 0.0 | 0.0 | 0.0 | 6.3 | 1.7 | 0.0 | 0.0 | 0.0 |
| hsa-miR-0107 | 0.0 | 2.0 | 0.0 | 0.0 | 0.0 | 0.0 | 0.0 | 0.0 | 0.0 |
| hsa-miR-0122-3p | 0.0 | 2.4 | 1.9 | 0.0 | 2.5 | 1.4 | 0.0 | 0.0 | 0.0 |
| hsa-miR-0124-3p | 0.0 | 0.0 | 0.0 | 0.0 | 0.0 | 0.0 | 3.3 | 0.0 | 0.0 |
| hsa-miR-0125b-1-3p | 0.0 | 2.1 | 4.4 | 3.1 | 0.0 | 2.0 | 2.7 | 0.0 | 0.0 |
| hsa-miR-0126-5p | 0.0 | 0.0 | 1.7 | 0.0 | 0.0 | 0.0 | 2.6 | 0.0 | 0.0 |
| hsa-miR-0127-3p | 0.0 | 0.0 | 1.6 | 0.0 | 0.0 | 0.0 | 0.0 | 0.0 | 0.0 |
| hsa-miR-0130a-3p | 0.0 | 0.0 | 0.0 | 0.0 | 1.3 | 0.0 | 0.0 | 0.0 | 0.0 |
| hsa-miR-0130b-3p | 0.0 | 0.0 | 0.0 | 0.0 | 2.8 | 0.0 | 0.0 | 0.0 | 3.1 |
| hsa-miR-0132-3p | 0.0 | 0.0 | 0.0 | 0.0 | 2.0 | 1.6 | 0.0 | 0.0 | 0.0 |
| hsa-miR-0132-5p | 0.0 | 2.2 | 0.0 | 0.0 | 0.0 | 0.0 | 0.0 | 0.0 | 0.0 |
| hsa-miR-0133a-5p | 0.0 | 0.0 | 0.0 | 0.0 | 1.7 | 0.0 | 2.5 | 0.0 | 3.1 |
| hsa-miR-0135b-3p | 0.0 | 0.0 | 0.0 | 2.5 | 0.0 | 0.0 | 0.0 | 0.0 | 0.0 |
| hsa-miR-0136-5p | 0.0 | 0.0 | 0.0 | 6.0 | 0.0 | 0.0 | 0.0 | 0.0 | 0.0 |
| hsa-miR-0139-5p | 0.0 | 0.0 | 0.0 | 5.0 | 0.0 | 0.0 | 0.0 | 0.0 | 0.0 |
| hsa-miR-0140-3p | 0.0 | 0.0 | 0.0 | 0.0 | 0.0 | 0.0 | 0.0 | 0.0 | 0.0 |
| hsa-miR-0140-5p | 0.0 | 0.0 | 0.0 | 6.3 | 0.0 | 0.0 | 0.0 | 0.0 | 0.0 |
| hsa-miR-0141-3p | 0.0 | 0.0 | 0.0 | 0.0 | 0.0 | 0.0 | 0.0 | 0.0 | 0.0 |
| hsa-miR-0142-5p | 0.0 | 0.0 | 0.0 | 6.4 | 0.0 | 0.0 | 0.0 | 0.0 | 0.0 |
| hsa-miR-0144-3p | 0.0 | 0.0 | 0.0 | 0.0 | 0.0 | 0.0 | 0.0 | 0.0 | 2.9 |
| hsa-miR-0145-3p | 0.0 | 0.0 | 0.0 | 2.9 | 0.0 | 0.0 | 0.0 | 0.0 | 2.7 |
| hsa-miR-0146a-3p | 0.0 | 0.0 | 0.0 | 0.0 | 0.0 | 0.0 | 3.2 | 0.0 | 0.0 |
| hsa-miR-0146b-5p | 0.0 | 0.0 | 3.8 | 4.1 | 0.0 | 0.0 | 3.7 | 0.0 | 0.0 |
| hsa-miR-0148a-5p | 0.0 | 0.0 | 0.0 | 0.0 | 0.0 | 0.0 | 0.0 | 0.0 | 0.0 |
| hsa-miR-0148b-3p | 2.1 | 0.0 | 0.0 | 4.7 | 0.0 | 0.0 | 3.0 | 0.0 | 0.0 |
| hsa-miR-0148b-5p | 0.0 | 2.8 | 0.0 | 0.0 | 2.2 | 0.0 | 3.3 | 0.0 | 0.0 |
| hsa-miR-0151a-3p | 0.0 | 0.0 | 3.8 | 0.0 | 0.0 | 2.2 | 3.6 | 0.0 | 0.0 |
| hsa-miR-0151a-5p | 0.0 | 2.1 | 0.0 | 0.0 | 0.0 | 1.7 | 0.0 | 0.0 | 0.0 |
| hsa-miR-0152-3p | 0.0 | 0.0 | 0.0 | 0.0 | 0.0 | 0.0 | 0.0 | 0.0 | 0.0 |
| hsa-miR-0153-3p | 0.0 | 0.0 | 0.0 | 0.0 | 0.0 | 0.0 | 2.7 | 0.0 | 0.0 |
| hsa-miR-0154-3p | 0.0 | 2.6 | 0.0 | 0.0 | 0.0 | 1.3 | 0.0 | 0.0 | 0.0 |
| hsa-miR-0155-3p | 0.0 | 2.5 | 0.0 | 2.5 | 2.7 | 1.4 | 0.0 | 0.0 | 3.3 |
| hsa-miR-0155-5p | 0.0 | 0.0 | 0.0 | 5.8 | 0.0 | 0.0 | 0.0 | 0.0 | 0.0 |
| hsa-miR-0181a-3p | 0.0 | 0.0 | 4.4 | 0.0 | 0.0 | 0.0 | 0.0 | 0.0 | 0.0 |
| hsa-miR-0181b-2-3p | 0.0 | 0.0 | 0.0 | 3.0 | 0.0 | 0.0 | 3.0 | 0.0 | 0.0 |
| hsa-miR-0181c-3p | 0.0 | 0.0 | 0.0 | 0.0 | 0.0 | 0.0 | 0.0 | 0.0 | 0.0 |
| hsa-miR-0181c-5p | 0.0 | 0.0 | 0.0 | 0.0 | 0.0 | 0.0 | 2.7 | 0.0 | 0.0 |
| hsa-miR-0181d-5p | 0.0 | 0.0 | 0.0 | 2.8 | 0.0 | 0.0 | 0.0 | 0.0 | 0.0 |
| hsa-miR-0182-3p | 0.0 | 0.0 | 0.0 | 0.0 | 1.3 | 0.0 | 3.1 | 0.0 | 0.0 |
| hsa-miR-0182-5p | 0.0 | 0.0 | 2.8 | 2.4 | 1.8 | 0.0 | 3.3 | 0.0 | 0.0 |
| hsa-miR-0186-3p | 0.0 | 0.0 | 0.0 | 0.0 | 0.0 | 0.0 | 2.9 | 0.0 | 0.0 |
| hsa-miR-0186-5p | 0.0 | 0.0 | 0.0 | 0.0 | 1.9 | 0.0 | 0.0 | 0.0 | 0.0 |
| hsa-miR-0188-3p | 0.0 | 0.0 | 1.8 | 0.0 | 2.2 | 2.1 | 2.9 | 2.3 | 0.0 |
| hsa-miR-0190a-3p | 0.0 | 2.7 | 0.0 | 2.3 | 0.0 | 0.0 | 4.0 | 0.0 | 0.0 |
| hsa-miR-0190b | 0.0 | 2.5 | 0.0 | 4.6 | 0.0 | 0.0 | 0.0 | 0.0 | 0.0 |
| hsa-miR-0191-5p | 0.0 | 0.0 | 0.0 | 3.0 | 0.0 | 0.0 | 2.6 | 0.0 | 0.0 |
| hsa-miR-0192-3p | 0.0 | 0.0 | 3.9 | 4.1 | 1.3 | 0.0 | 0.0 | 0.0 | 2.6 |
| hsa-miR-0193a-3p | 0.0 | 0.0 | 0.0 | 0.0 | 1.7 | 0.0 | 0.0 | 0.0 | 0.0 |
| hsa-miR-0200a-3p | 0.0 | 0.0 | 0.0 | 0.0 | 0.0 | 0.0 | 0.0 | 0.0 | 0.0 |
| hsa-miR-0200c-3p | 0.0 | 0.0 | 0.0 | 0.0 | 0.0 | 0.0 | 0.0 | 0.0 | 0.0 |
| hsa-miR-0202-5p | 0.0 | 0.0 | 0.0 | 0.0 | 0.0 | 0.0 | 3.2 | 3.4 | 0.0 |
| hsa-miR-0203a-5p | 0.0 | 3.4 | 1.7 | 4.2 | 0.0 | 1.3 | 0.0 | 0.0 | 0.0 |
| hsa-miR-0208a-3p | 0.0 | 0.0 | 0.0 | 6.3 | 0.0 | 0.0 | 0.0 | 0.0 | 0.0 |
| hsa-miR-0208b-3p | 0.0 | 2.5 | 2.4 | 3.2 | 0.0 | 0.0 | 0.0 | 0.0 | 0.0 |
| hsa-miR-0216a-5p | 0.0 | 0.0 | 1.9 | 3.0 | 1.7 | 1.4 | 0.0 | 0.0 | 0.0 |
| hsa-miR-0216b-5p | 0.0 | 2.6 | 4.2 | 0.0 | 0.0 | 0.0 | 0.0 | 0.0 | 0.0 |
| hsa-miR-0218-1-3p | 0.0 | 0.0 | 3.8 | 4.0 | 0.0 | 0.0 | 3.2 | 0.0 | 0.0 |
| hsa-miR-0218-2-3p | 0.0 | 2.1 | 0.0 | 0.0 | 0.0 | 0.0 | 0.0 | 0.0 | 0.0 |
| hsa-miR-0218-5p | 0.0 | 3.0 | 0.0 | 0.0 | 0.0 | 0.0 | 2.7 | 0.0 | 0.0 |
| hsa-miR-0219a-2-3p | 0.0 | 0.0 | 0.0 | 0.0 | 0.0 | 0.0 | 0.0 | 0.0 | 0.0 |
| hsa-miR-0219a-5p | 0.0 | 0.0 | 0.0 | 4.3 | 0.0 | 0.0 | 0.0 | 0.0 | 0.0 |
| hsa-miR-0224-5p | 0.0 | 2.5 | 0.0 | 0.0 | 0.0 | 0.0 | 0.0 | 0.0 | 0.0 |
| hsa-miR-0298 | 0.0 | 0.0 | 0.0 | 0.0 | 2.9 | 0.0 | 3.2 | 0.0 | 0.0 |
| hsa-miR-0299-3p | 0.0 | 2.5 | 0.0 | 0.0 | 2.1 | 2.2 | 0.0 | 0.0 | 0.0 |

TABLE 3-continued

| | | | | | | | | | |
|---|---|---|---|---|---|---|---|---|---|
| hsa-miR-0301a-3p | 0.0 | 2.3 | 0.0 | 0.0 | 0.0 | 0.0 | 0.0 | 0.0 | 0.0 |
| hsa-miR-0301a-5p | 0.0 | 3.2 | 0.0 | 0.0 | 2.0 | 1.5 | 0.0 | 0.0 | 3.0 |
| hsa-miR-0301b-3p | 0.0 | 0.0 | 3.3 | 0.0 | 0.0 | 0.0 | 0.0 | 0.0 | 0.0 |
| hsa-miR-0301b-5p | 0.0 | 0.0 | 0.0 | 0.0 | 0.0 | 3.3 | 0.0 | 0.0 | 0.0 |
| hsa-miR-0302a-5p | 0.0 | 0.0 | 2.2 | 0.0 | 0.0 | 0.0 | 3.1 | 0.0 | 0.0 |
| hsa-miR-0302b-3p | 0.0 | 0.0 | 0.0 | 0.0 | 0.0 | 0.0 | 3.2 | 0.0 | 0.0 |
| hsa-miR-0302b-5p | 0.0 | 0.0 | 0.0 | 4.8 | 1.9 | 0.0 | 3.9 | 0.0 | 0.0 |
| hsa-miR-0302c-3p | 0.0 | 0.0 | 0.0 | 0.0 | 0.0 | 2.4 | 0.0 | 0.0 | 0.0 |
| hsa-miR-0302d-3p | 0.0 | 1.9 | 2.9 | 0.0 | 2.0 | 1.6 | 0.0 | 0.0 | 0.0 |
| hsa-miR-0302f | 0.0 | 0.0 | 0.0 | 0.0 | 1.9 | 0.0 | 3.2 | 0.0 | 0.0 |
| hsa-miR-0320d | 0.0 | 0.0 | 0.0 | 0.0 | 0.0 | 0.0 | 0.0 | 0.0 | 0.0 |
| hsa-miR-0320e | 0.0 | 0.0 | 0.0 | 0.0 | 0.0 | 0.0 | 0.0 | 0.0 | 0.0 |
| hsa-miR-0323b-3p | 0.0 | 0.0 | 0.0 | 5.5 | 0.0 | 1.3 | 0.0 | 0.0 | 0.0 |
| hsa-miR-0329-3p | 0.0 | 0.0 | 0.0 | 0.0 | 0.0 | 0.0 | 3.0 | 0.0 | 0.0 |
| hsa-miR-0331-5p | 0.0 | 0.0 | 0.0 | 0.0 | 0.0 | 0.0 | 3.1 | 0.0 | 0.0 |
| hsa-miR-0335-3p | 0.0 | 3.0 | 0.0 | 0.0 | 2.8 | 2.1 | 0.0 | 0.0 | 0.0 |
| hsa-miR-0337-5p | 0.0 | 0.0 | 0.0 | 0.0 | 0.0 | 0.0 | 0.0 | 0.0 | 0.0 |
| hsa-miR-0340-5p | 0.0 | 0.0 | 0.0 | 2.5 | 0.0 | 0.0 | 0.0 | 0.0 | 0.0 |
| hsa-miR-0361-5p | 0.0 | 0.0 | 0.0 | 6.2 | 0.0 | 0.0 | 2.7 | 0.0 | 0.0 |
| hsa-miR-0362-5p | 0.0 | 0.0 | 2.4 | 0.0 | 0.0 | 0.0 | 0.0 | 0.0 | 0.0 |
| hsa-miR-0363-3p | 0.0 | 0.0 | 2.5 | 0.0 | 0.0 | 0.0 | 0.0 | 0.0 | 0.0 |
| hsa-miR-0367-5p | 0.0 | 0.0 | 0.0 | 0.0 | 0.0 | 0.0 | 2.5 | 0.0 | 0.0 |
| hsa-miR-0372-5p | 1.6 | 0.0 | 0.0 | 0.0 | 0.0 | 0.0 | 0.0 | 0.0 | 0.0 |
| hsa-miR-0374a-3p | 0.0 | 0.0 | 0.0 | 0.0 | 0.0 | 0.0 | 0.0 | 0.0 | 3.3 |
| hsa-miR-0374a-5p | 0.0 | 0.0 | 0.0 | 6.4 | 0.0 | 0.0 | 0.0 | 0.0 | 0.0 |
| hsa-miR-0374c-5p | 1.7 | 2.0 | 0.0 | 0.0 | 0.0 | 0.0 | 0.0 | 0.0 | 0.0 |
| hsa-miR-0375 | 0.0 | 0.0 | 4.1 | 0.0 | 0.0 | 2.6 | 0.0 | 0.0 | 0.0 |
| hsa-miR-0376a-2-5p | 0.0 | 2.0 | 0.0 | 0.0 | 0.0 | 0.0 | 0.0 | 0.0 | 0.0 |
| hsa-miR-0376a-3p | 0.0 | 0.0 | 2.9 | 0.0 | 0.0 | 0.0 | 0.0 | 0.0 | 0.0 |
| hsa-miR-0376a-5p | 0.0 | 0.0 | 0.0 | 0.0 | 0.0 | 0.0 | 2.8 | 0.0 | 0.0 |
| hsa-miR-0376b-3p | 0.0 | 0.0 | 0.0 | 3.4 | 0.0 | 0.0 | 0.0 | 0.0 | 0.0 |
| hsa-miR-0376b-5p | 0.0 | 0.0 | 0.0 | 0.0 | 0.0 | 0.0 | 2.8 | 0.0 | 0.0 |
| hsa-miR-0376c-5p | 0.0 | 0.0 | 0.0 | 0.0 | 0.0 | 0.0 | 3.6 | 0.0 | 0.0 |
| hsa-miR-0377-3p | 3.3 | 0.0 | 0.0 | 5.5 | 0.0 | 0.0 | 3.7 | 0.0 | 0.0 |
| hsa-miR-0377-5p | 0.0 | 0.0 | 2.1 | 0.0 | 1.2 | 2.0 | 0.0 | 0.0 | 0.0 |
| hsa-miR-0378j | 0.0 | 0.0 | 0.0 | 6.4 | 0.0 | 0.0 | 0.0 | 0.0 | 0.0 |
| hsa-miR-0379-5p | 0.0 | 0.0 | 0.0 | 0.0 | 0.0 | 0.0 | 2.9 | 0.0 | 0.0 |
| hsa-miR-0380-3p | 0.0 | 0.0 | 3.8 | 0.0 | 2.7 | 2.7 | 0.0 | 0.0 | 0.0 |
| hsa-miR-0381-3p | 0.0 | 0.0 | 0.0 | 0.0 | 0.0 | 0.0 | 0.0 | 0.0 | 3.0 |
| hsa-miR-0384 | 0.0 | 0.0 | 6.2 | 0.0 | 0.0 | 0.0 | 0.0 | 0.0 | 0.0 |
| hsa-miR-0409-5p | 0.0 | 0.0 | 3.6 | 3.8 | 0.0 | 0.0 | 3.9 | 0.0 | 3.3 |
| hsa-miR-0410-3p | 0.0 | 0.0 | 0.0 | 0.0 | 2.0 | 0.0 | 2.7 | 0.0 | 0.0 |
| hsa-miR-0411-5p | 0.0 | 0.0 | 3.5 | 0.0 | 0.0 | 0.0 | 0.0 | 0.0 | 0.0 |
| hsa-miR-0412-5p | 0.0 | 0.0 | 3.1 | 5.1 | 0.0 | 0.0 | 0.0 | 0.0 | 0.0 |
| hsa-miR-0424-3p | 0.0 | 0.0 | 1.6 | 0.0 | 5.2 | 5.1 | 0.0 | 3.1 | 0.0 |
| hsa-miR-0424-5p | 1.9 | 2.7 | 3.2 | 0.0 | 0.0 | 0.0 | 0.0 | 0.0 | 0.0 |
| hsa-miR-0429 | 0.0 | 0.0 | 0.0 | 0.0 | 0.0 | 0.0 | 0.0 | 0.0 | 0.0 |
| hsa-miR-0433-3p | 0.0 | 0.0 | 0.0 | 0.0 | 0.0 | 0.0 | 0.0 | 0.0 | 0.0 |
| hsa-miR-0433-5p | 2.7 | 3.6 | 2.4 | 0.0 | 2.4 | 3.6 | 0.0 | 0.0 | 0.0 |
| hsa-miR-0448 | 0.0 | 2.2 | 0.0 | 0.0 | 0.0 | 2.3 | 2.6 | 3.3 | 0.0 |
| hsa-miR-0450a-2-3p | 2.0 | 0.0 | 2.4 | 4.5 | 0.0 | 0.0 | 0.0 | 0.0 | 0.0 |
| hsa-miR-0451a | 0.0 | 0.0 | 3.6 | 0.0 | 0.0 | 0.0 | 0.0 | 0.0 | 0.0 |
| hsa-miR-0451b | 0.0 | 0.0 | 2.5 | 4.7 | 0.0 | 0.0 | 3.5 | 0.0 | 0.0 |
| hsa-miR-0454-3p | 0.0 | 0.0 | 0.0 | 0.0 | 0.0 | 0.0 | 3.6 | 0.0 | 0.0 |
| hsa-miR-0455-3p | 0.0 | 2.4 | 0.0 | 6.0 | 2.2 | 0.0 | 0.0 | 0.0 | 0.0 |
| hsa-miR-0487a-3p | 0.0 | 0.0 | 0.0 | 0.0 | 2.1 | 0.0 | 0.0 | 0.0 | 0.0 |
| hsa-miR-0489-3p | 2.3 | 3.0 | 0.0 | 0.0 | 0.0 | 0.0 | 0.0 | 0.0 | 0.0 |
| hsa-miR-0490-3p | 1.9 | 0.0 | 0.0 | 0.0 | 1.8 | 0.0 | 0.0 | 0.0 | 0.0 |
| hsa-miR-0490-5p | 0.0 | 1.9 | 0.0 | 0.0 | 0.0 | 0.0 | 0.0 | 0.0 | 0.0 |
| hsa-miR-0492 | 0.0 | 2.5 | 0.0 | 0.0 | 2.0 | 2.1 | 0.0 | 0.0 | 0.0 |
| hsa-miR-0493-5p | 3.3 | 0.0 | 0.0 | 4.3 | 0.0 | 0.0 | 0.0 | 0.0 | 0.0 |
| hsa-miR-0495-3p | 0.0 | 2.0 | 0.0 | 2.4 | 1.9 | 0.0 | 3.7 | 0.0 | 2.9 |
| hsa-miR-0496 | 0.0 | 0.0 | 2.5 | 0.0 | 2.3 | 0.0 | 0.0 | 0.0 | 0.0 |
| hsa-miR-0497-5p | 1.9 | 0.0 | 0.0 | 0.0 | 0.0 | 0.0 | 3.1 | 0.0 | 0.0 |
| hsa-miR-0499a-3p | 0.0 | 0.0 | 0.0 | 0.0 | 0.0 | 0.0 | 3.7 | 0.0 | 0.0 |
| hsa-miR-0499a-5p | 0.0 | 0.0 | 0.0 | 0.0 | 0.0 | 0.0 | 3.0 | 0.0 | 0.0 |
| hsa-miR-0500a-3p | 0.0 | 1.8 | 0.0 | 0.0 | 2.3 | 1.7 | 0.0 | 0.0 | 0.0 |
| hsa-miR-0501-3p | 0.0 | 0.0 | 0.0 | 0.0 | 1.2 | 0.0 | 0.0 | 0.0 | 0.0 |
| hsa-miR-0503-5p | 0.0 | 0.0 | 0.0 | 2.5 | 1.8 | 0.0 | 0.0 | 0.0 | 0.0 |
| hsa-miR-0504-5p | 0.0 | 0.0 | 0.0 | 3.2 | 0.0 | 0.0 | 3.6 | 0.0 | 0.0 |
| hsa-miR-0506-5p | 0.0 | 0.0 | 2.2 | 0.0 | 0.0 | 0.0 | 0.0 | 0.0 | 0.0 |
| hsa-miR-0509-5p | 0.0 | 0.0 | 0.0 | 0.0 | 0.0 | 0.0 | 4.1 | 0.0 | 0.0 |
| hsa-miR-0513b-3p | 0.0 | 0.0 | 0.0 | 4.8 | 1.2 | 0.0 | 0.0 | 0.0 | 0.0 |
| hsa-miR-0513c-5p | 0.0 | 2.3 | 0.0 | 0.0 | 0.0 | 0.0 | 0.0 | 0.0 | 0.0 |
| hsa-miR-0514a-5p | 0.0 | 0.0 | 0.0 | 0.0 | 2.6 | 0.0 | 0.0 | 0.0 | 0.0 |
| hsa-miR-0515-5p | 1.6 | 0.0 | 0.0 | 5.3 | 2.0 | 0.0 | 0.0 | 0.0 | 0.0 |
| hsa-miR-0516a-5p | 1.5 | 0.0 | 0.0 | 3.1 | 0.0 | 0.0 | 3.9 | 0.0 | 0.0 |
| hsa-miR-0516b-3p, hsa-miR-516a-3p | 0.0 | 0.0 | 0.0 | 0.0 | 0.0 | 0.0 | 0.0 | 0.0 | 0.0 |
| hsa-miR-0517c-3p | 0.0 | 2.1 | 0.0 | 0.0 | 1.7 | 2.3 | 0.0 | 0.0 | 0.0 |

TABLE 3-continued

| | | | | | | | | | |
|---|---|---|---|---|---|---|---|---|---|
| hsa-miR-0518a-3p | 0.0 | 0.0 | 0.0 | 0.0 | 1.6 | 0.0 | 0.0 | 0.0 | 0.0 |
| hsa-miR-0518c-3p | 0.0 | 0.0 | 0.0 | 0.0 | 0.0 | 0.0 | 0.0 | 3.3 | 0.0 |
| hsa-miR-0518d-3p | 1.9 | 0.0 | 2.1 | 0.0 | 0.0 | 0.0 | 2.6 | 4.9 | 0.0 |
| hsa-miR-0519c-3p | 0.0 | 0.0 | 0.0 | 2.6 | 0.0 | 0.0 | 0.0 | 0.0 | 0.0 |
| hsa-miR-0520a-5p | 0.0 | 0.0 | 2.5 | 0.0 | 2.9 | 0.0 | 0.0 | 0.0 | 0.0 |
| hsa-miR-0520c-3p | 0.0 | 3.5 | 3.7 | 5.2 | 0.0 | 0.0 | 0.0 | 0.0 | 0.0 |
| hsa-miR-0520d-3p | 0.0 | 0.0 | 0.0 | 0.0 | 2.6 | 0.0 | 0.0 | 0.0 | 3.2 |
| hsa-miR-0520f-3p | 0.0 | 0.0 | 0.0 | 0.0 | 1.8 | 1.6 | 0.0 | 0.0 | 0.0 |
| hsa-miR-0520f-5p | 0.0 | 0.0 | 0.0 | 0.0 | 0.0 | 0.0 | 2.3 | 2.5 | 0.0 |
| hsa-miR-0520g-5p | 0.0 | 0.0 | 0.0 | 0.0 | 1.7 | 0.0 | 2.8 | 0.0 | 0.0 |
| hsa-miR-0521 | 2.2 | 2.3 | 2.3 | 0.0 | 3.1 | 2.6 | 0.0 | 0.0 | 0.0 |
| hsa-miR-0522-3p | 0.0 | 0.0 | 0.0 | 0.0 | 0.0 | 0.0 | 0.0 | 0.0 | 0.0 |
| hsa-miR-0523-3p | 0.0 | 0.0 | 0.0 | 0.0 | 1.9 | 0.0 | 0.0 | 0.0 | 0.0 |
| hsa-miR-0524-3p | 0.0 | 0.0 | 0.0 | 0.0 | 0.0 | 0.0 | 3.1 | 0.0 | 0.0 |
| hsa-miR-0539-5p | 0.0 | 0.0 | 0.0 | 0.0 | 0.0 | 1.6 | 0.0 | 0.0 | 0.0 |
| hsa-miR-0542-5p | 0.0 | 2.6 | 0.0 | 0.0 | 2.3 | 0.0 | 2.5 | 0.0 | 0.0 |
| hsa-miR-0544b | 0.0 | 0.0 | 0.0 | 0.0 | 1.8 | 0.0 | 0.0 | 0.0 | 0.0 |
| hsa-miR-0545-3p | 0.0 | 0.0 | 0.0 | 0.0 | 0.0 | 0.0 | 2.5 | 0.0 | 0.0 |
| hsa-miR-0545-5p | 0.0 | 0.0 | 0.0 | 5.5 | 0.0 | 0.0 | 0.0 | 0.0 | 0.0 |
| hsa-miR-0548a-3p | 0.0 | 0.0 | 0.0 | 6.3 | 0.0 | 0.0 | 0.0 | 0.0 | 0.0 |
| hsa-miR-0548a-5p | 0.0 | 0.0 | 0.0 | 3.8 | 0.0 | 0.0 | 0.0 | 0.0 | 0.0 |
| hsa-miR-0548aa, hsa-miR-548t-3p | 0.0 | 0.0 | 0.0 | 0.0 | 0.0 | 0.0 | 0.0 | 0.0 | 2.7 |
| hsa-miR-0548ab | 0.0 | 0.0 | 0.0 | 0.0 | 0.0 | 0.0 | 0.0 | 0.0 | 0.0 |
| hsa-miR-0548ac | 0.0 | 0.0 | 2.1 | 0.0 | 0.0 | 0.0 | 0.0 | 0.0 | 0.0 |
| hsa-miR-0548ag | 0.0 | 0.0 | 0.0 | 6.1 | 0.0 | 0.0 | 0.0 | 0.0 | 0.0 |
| hsa-miR-0548ah-3p | 0.0 | 0.0 | 0.0 | 4.5 | 0.0 | 0.0 | 3.2 | 0.0 | 0.0 |
| hsa-miR-0548ai, hsa-miR-570-5p | 0.0 | 0.0 | 0.0 | 6.1 | 0.0 | 0.0 | 0.0 | 0.0 | 0.0 |
| hsa-miR-0548al | 0.0 | 0.0 | 0.0 | 0.0 | 0.0 | 0.0 | 3.7 | 0.0 | 0.0 |
| hsa-miR-0548am-3p | 0.0 | 0.0 | 0.0 | 0.0 | 0.0 | 0.0 | 3.3 | 0.0 | 0.0 |
| hsa-miR-0548an | 0.0 | 3.1 | 0.0 | 3.2 | 0.0 | 0.0 | 2.6 | 0.0 | 0.0 |
| hsa-miR-0548ao-3p | 0.0 | 0.0 | 0.0 | 5.1 | 0.0 | 0.0 | 3.9 | 0.0 | 0.0 |
| hsa-miR-0548ao-5p | 0.0 | 0.0 | 2.3 | 0.0 | 0.0 | 0.0 | 0.0 | 0.0 | 0.0 |
| hsa-miR-0548ap-3p | 0.0 | 0.0 | 0.0 | 0.0 | 3.5 | 0.0 | 0.0 | 0.0 | 0.0 |
| hsa-miR-0548aq-5p | 0.0 | 2.1 | 0.0 | 0.0 | 0.0 | 0.0 | 0.0 | 0.0 | 0.0 |
| hsa-miR-0548as-3p | 0.0 | 0.0 | 3.6 | 4.8 | 0.0 | 0.0 | 0.0 | 0.0 | 0.0 |
| hsa-miR-0548as-5p | 1.7 | 0.0 | 2.8 | 5.0 | 0.0 | 0.0 | 0.0 | 0.0 | 0.0 |
| hsa-miR-0548at-5p | 0.0 | 0.0 | 0.0 | 0.0 | 0.0 | 0.0 | 2.7 | 0.0 | 3.3 |
| hsa-miR-0548au-3p | 0.0 | 2.1 | 0.0 | 0.0 | 0.0 | 0.0 | 3.1 | 0.0 | 0.0 |
| hsa-miR-0548av-3p | 0.0 | 0.0 | 0.0 | 0.0 | 0.0 | 0.0 | 3.7 | 0.0 | 2.6 |
| hsa-miR-0548ay-5p | 0.0 | 0.0 | 0.0 | 0.0 | 0.0 | 0.0 | 0.0 | 0.0 | 0.0 |
| hsa-miR-0548az-3p | 0.0 | 0.0 | 0.0 | 0.0 | 0.0 | 0.0 | 3.3 | 0.0 | 0.0 |
| hsa-miR-0548b-3p | 0.0 | 0.0 | 2.8 | 0.0 | 0.0 | 0.0 | 3.5 | 0.0 | 0.0 |
| hsa-miR-0548c-3p | 0.0 | 0.0 | 0.0 | 0.0 | 0.0 | 0.0 | 3.4 | 0.0 | 0.0 |
| hsa-miR-0548c-5p, hsa-miR-548o-5p, hsa-miR-548am-5p | 0.0 | 0.0 | 0.0 | 5.8 | 0.0 | 0.0 | 0.0 | 0.0 | 0.0 |
| hsa-miR-0548e-3p | 0.0 | 0.0 | 0.0 | 4.9 | 0.0 | 0.0 | 0.0 | 0.0 | 0.0 |
| hsa-miR-0548e-5p | 0.0 | 0.0 | 0.0 | 0.0 | 0.0 | 0.0 | 3.9 | 0.0 | 0.0 |
| hsa-miR-0548f-3p | 0.0 | 0.0 | 0.0 | 0.0 | 0.0 | 0.0 | 3.3 | 0.0 | 0.0 |
| hsa-miR-0548h-5p | 0.0 | 0.0 | 0.0 | 0.0 | 0.0 | 0.0 | 0.0 | 0.0 | 0.0 |
| hsa-miR-0548j-5p | 0.0 | 2.4 | 4.4 | 5.2 | 0.0 | 0.0 | 0.0 | 0.0 | 0.0 |
| hsa-miR-0548k | 0.0 | 0.0 | 0.0 | 0.0 | 2.1 | 0.0 | 0.0 | 0.0 | 0.0 |
| hsa-miR-0548l | 0.0 | 0.0 | 1.8 | 0.0 | 0.0 | 0.0 | 0.0 | 0.0 | 0.0 |
| hsa-miR-0548m | 0.0 | 0.0 | 0.0 | 0.0 | 0.0 | 0.0 | 0.0 | 0.0 | 3.3 |
| hsa-miR-0548p | 0.0 | 0.0 | 0.0 | 0.0 | 0.0 | 0.0 | 3.2 | 0.0 | 0.0 |
| hsa-miR-0548s | 0.0 | 0.0 | 0.0 | 0.0 | 0.0 | 0.0 | 3.8 | 0.0 | 0.0 |
| hsa-miR-0548t-5p | 0.0 | 0.0 | 0.0 | 0.0 | 0.0 | 0.0 | 3.0 | 0.0 | 0.0 |
| hsa-miR-0548w | 0.0 | 0.0 | 0.0 | 0.0 | 0.0 | 0.0 | 0.0 | 0.0 | 0.0 |
| hsa-miR-0551b-3p | 2.1 | 3.7 | 2.8 | 0.0 | 3.2 | 2.8 | 0.0 | 0.0 | 0.0 |
| hsa-miR-0551b-5p | 0.0 | 0.0 | 8.1 | 0.0 | 5.2 | 5.6 | 0.0 | 0.0 | 0.0 |
| hsa-miR-0552-3p | 0.0 | 1.8 | 0.0 | 0.0 | 0.0 | 0.0 | 0.0 | 0.0 | 0.0 |
| hsa-miR-0554 | 0.0 | 0.0 | 2.5 | 0.0 | 0.0 | 0.0 | 2.7 | 0.0 | 0.0 |
| hsa-miR-0555 | 0.0 | 0.0 | 0.0 | 0.0 | 0.0 | 0.0 | 0.0 | 0.0 | 0.0 |
| hsa-miR-0556-5p | 0.0 | 0.0 | 0.0 | 0.0 | 0.0 | 0.0 | 2.6 | 0.0 | 0.0 |
| hsa-miR-0559 | 0.0 | 0.0 | 0.0 | 0.0 | 0.0 | 0.0 | 2.9 | 0.0 | 0.0 |
| hsa-miR-0563 | 0.0 | 0.0 | 0.0 | 0.0 | 0.0 | 2.1 | 0.0 | 0.0 | 0.0 |
| hsa-miR-0567 | 0.0 | 0.0 | 0.0 | 2.9 | 0.0 | 0.0 | 0.0 | 0.0 | 0.0 |
| hsa-miR-0570-3p | 0.0 | 0.0 | 0.0 | 0.0 | 0.0 | 2.1 | 0.0 | 0.0 | 0.0 |
| hsa-miR-0571 | 0.0 | 0.0 | 0.0 | 0.0 | 0.0 | 0.0 | 0.0 | 0.0 | 0.0 |
| hsa-miR-0573 | 0.0 | 2.0 | 0.0 | 0.0 | 0.0 | 0.0 | 0.0 | 0.0 | 0.0 |
| hsa-miR-0582-3p | 0.0 | 0.0 | 0.0 | 0.0 | 2.0 | 0.0 | 0.0 | 0.0 | 0.0 |
| hsa-miR-0582-5p | 0.0 | 1.8 | 0.0 | 0.0 | 0.0 | 0.0 | 2.9 | 0.0 | 0.0 |
| hsa-miR-0586 | 0.0 | 0.0 | 0.0 | 0.0 | 0.0 | 0.0 | 0.0 | 3.2 | 0.0 |
| hsa-miR-0587 | 0.0 | 0.0 | 2.9 | 0.0 | 0.0 | 0.0 | 2.7 | 0.0 | 0.0 |
| hsa-miR-0588 | 0.0 | 0.0 | 0.0 | 0.0 | 0.0 | 0.0 | 2.7 | 0.0 | 0.0 |
| hsa-miR-0592 | 0.0 | 0.0 | 0.0 | 0.0 | 0.0 | 0.0 | 0.0 | 0.0 | 0.0 |
| hsa-miR-0597-3p | 0.0 | 2.1 | 2.6 | 4.2 | 0.0 | 0.0 | 0.0 | 0.0 | 0.0 |
| hsa-miR-0597-5p | 0.0 | 0.0 | 0.0 | 0.0 | 0.0 | 0.0 | 0.0 | 0.0 | 3.1 |

TABLE 3-continued

| | | | | | | | | | |
|---|---|---|---|---|---|---|---|---|---|
| hsa-miR-0598-3p | 2.0 | 2.9 | 0.0 | 0.0 | 0.0 | 0.0 | 0.0 | 0.0 | 0.0 |
| hsa-miR-0599 | 0.0 | 0.0 | 0.0 | 6.3 | 0.0 | 0.0 | 0.0 | 0.0 | 0.0 |
| hsa-miR-0600 | 0.0 | 0.0 | 0.0 | 6.4 | 0.0 | 0.0 | 2.5 | 0.0 | 0.0 |
| hsa-miR-0601 | 0.0 | 0.0 | 0.0 | 0.0 | 2.9 | 2.5 | 0.0 | 0.0 | 0.0 |
| hsa-miR-0616-3p | 0.0 | 0.0 | 0.0 | 0.0 | 0.0 | 0.0 | 0.0 | 0.0 | 0.0 |
| hsa-miR-0616-5p | 0.0 | 2.0 | 0.0 | 5.8 | 0.0 | 0.0 | 0.0 | 0.0 | 0.0 |
| hsa-miR-0619-3p | 0.0 | 0.0 | 0.0 | 0.0 | 0.0 | 0.0 | 3.4 | 0.0 | 0.0 |
| hsa-miR-0623 | 2.6 | 0.0 | 0.0 | 0.0 | 0.0 | 0.0 | 2.2 | 0.0 | 0.0 |
| hsa-miR-0624-3p | 0.0 | 2.3 | 2.5 | 6.1 | 0.0 | 0.0 | 4.1 | 0.0 | 0.0 |
| hsa-miR-0627-3p | 0.0 | 0.0 | 0.0 | 0.0 | 0.0 | 0.0 | 3.3 | 0.0 | 0.0 |
| hsa-miR-0629-5p | 0.0 | 0.0 | 0.0 | 0.0 | 1.3 | 0.0 | 3.0 | 0.0 | 0.0 |
| hsa-miR-0631 | 2.4 | 3.4 | 2.9 | 6.0 | 0.0 | 2.9 | 2.8 | 0.0 | 0.0 |
| hsa-miR-0633 | 0.0 | 0.0 | 0.0 | 0.0 | 0.0 | 0.0 | 3.4 | 0.0 | 0.0 |
| hsa-miR-0639 | 0.0 | 0.0 | 0.0 | 0.0 | 0.0 | 0.0 | 0.0 | 0.0 | 0.0 |
| hsa-miR-0640 | 0.0 | 0.0 | 0.0 | 0.0 | 1.6 | 0.0 | 0.0 | 0.0 | 0.0 |
| hsa-miR-0641 | 0.0 | 0.0 | 0.0 | 6.8 | 0.0 | 0.0 | 0.0 | 0.0 | 0.0 |
| hsa-miR-0643 | 1.7 | 1.9 | 3.6 | 2.6 | 2.6 | 0.0 | 2.9 | 0.0 | 0.0 |
| hsa-miR-0644a | 2.8 | 0.0 | 4.4 | 3.1 | 0.0 | 2.4 | 0.0 | 0.0 | 3.5 |
| hsa-miR-0646 | 0.0 | 0.0 | 3.3 | 5.4 | 0.0 | 0.0 | 2.6 | 0.0 | 0.0 |
| hsa-miR-0647 | 0.0 | 0.0 | 0.0 | 0.0 | 0.0 | 0.0 | 3.5 | 0.0 | 0.0 |
| hsa-miR-0653-3p | 0.0 | 0.0 | 0.0 | 0.0 | 0.0 | 0.0 | 2.8 | 0.0 | 0.0 |
| hsa-miR-0653-5p | 0.0 | 0.0 | 0.0 | 6.6 | 0.0 | 0.0 | 0.0 | 0.0 | 0.0 |
| hsa-miR-0655-3p | 2.6 | 0.0 | 0.0 | 5.1 | 0.0 | 0.0 | 0.0 | 0.0 | 0.0 |
| hsa-miR-0655-5p | 0.0 | 2.2 | 0.0 | 0.0 | 0.0 | 0.0 | 2.5 | 0.0 | 0.0 |
| hsa-miR-0656-3p | 2.0 | 0.0 | 1.9 | 4.9 | 1.2 | 0.0 | 3.7 | 0.0 | 0.0 |
| hsa-miR-0659-5p | 2.5 | 2.1 | 0.0 | 0.0 | 1.2 | 0.0 | 3.5 | 0.0 | 0.0 |
| hsa-miR-0660-5p | 0.0 | 0.0 | 0.0 | 0.0 | 1.3 | 1.3 | 0.0 | 0.0 | 0.0 |
| hsa-miR-0758-3p | 0.0 | 0.0 | 0.0 | 6.2 | 0.0 | 0.0 | 0.0 | 0.0 | 0.0 |
| hsa-miR-0759 | 0.0 | 0.0 | 0.0 | 0.0 | 0.0 | 0.0 | 3.2 | 0.0 | 0.0 |
| hsa-miR-0761 | 0.0 | 2.1 | 0.0 | 3.8 | 0.0 | 2.1 | 0.0 | 0.0 | 0.0 |
| hsa-miR-0769-5p | 2.1 | 3.0 | 0.0 | 2.4 | 0.0 | 1.2 | 3.0 | 0.0 | 0.0 |
| hsa-miR-0802 | 0.0 | 0.0 | 0.0 | 2.6 | 2.0 | 0.0 | 3.8 | 0.0 | 0.0 |
| hsa-miR-0875-5p | 0.0 | 0.0 | 0.0 | 2.4 | 0.0 | 0.0 | 0.0 | 0.0 | 0.0 |
| hsa-miR-0876-3p | 0.0 | 0.0 | 0.0 | 0.0 | 0.0 | 0.0 | 0.0 | 0.0 | 0.0 |
| hsa-miR-0890 | 0.0 | 0.0 | 0.0 | 5.8 | 0.0 | 0.0 | 0.0 | 0.0 | 0.0 |
| hsa-miR-0892c-3p | 0.0 | 2.7 | 0.0 | 0.0 | 0.0 | 1.9 | 0.0 | 0.0 | 0.0 |
| hsa-miR-0924 | 0.0 | 2.9 | 0.0 | 0.0 | 0.0 | 0.0 | 0.0 | 0.0 | 0.0 |
| hsa-miR-0934 | 0.0 | 0.0 | 0.0 | 0.0 | 1.2 | 0.0 | 0.0 | 0.0 | 3.5 |
| hsa-miR-0941 | 2.5 | 0.0 | 3.4 | 0.0 | 0.0 | 0.0 | 0.0 | 0.0 | 0.0 |
| hsa-miR-0944 | 0.0 | 0.0 | 0.0 | 3.5 | 1.5 | 0.0 | 0.0 | 0.0 | 0.0 |
| hsa-miR-1178-5p | 0.0 | 0.0 | 1.6 | 8.0 | 0.0 | 0.0 | 0.0 | 0.0 | 3.8 |
| hsa-miR-1179 | 0.0 | 0.0 | 0.0 | 4.7 | 0.0 | 0.0 | 3.9 | 0.0 | 0.0 |
| hsa-miR-1180-3p | 1.9 | 2.8 | 2.3 | 4.5 | 1.2 | 0.0 | 0.0 | 0.0 | 0.0 |
| hsa-miR-1180-5p | 0.0 | 0.0 | 0.0 | 0.0 | 0.0 | 0.0 | 4.2 | 0.0 | 0.0 |
| hsa-miR-1183 | 0.0 | 0.0 | 0.0 | 0.0 | 0.0 | 0.0 | 0.0 | 0.0 | 0.0 |
| hsa-miR-1185-5p | 0.0 | 0.0 | 0.0 | 6.6 | 0.0 | 0.0 | 2.5 | 0.0 | 0.0 |
| hsa-miR-1208 | 0.0 | 0.0 | 0.0 | 0.0 | 0.0 | 0.0 | 0.0 | 0.0 | 0.0 |
| hsa-miR-1226-5p | 0.0 | 3.3 | 1.9 | 0.0 | 3.7 | 3.9 | 2.6 | 0.0 | 0.0 |
| hsa-miR-1245b-3p | 0.0 | 0.0 | 0.0 | 0.0 | 0.0 | 0.0 | 3.6 | 0.0 | 0.0 |
| hsa-miR-1245b-5p | 0.0 | 0.0 | 0.0 | 0.0 | 0.0 | 0.0 | 3.7 | 0.0 | 0.0 |
| hsa-miR-1248 | 0.0 | 0.0 | 0.0 | 2.6 | 0.0 | 0.0 | 2.7 | 0.0 | 0.0 |
| hsa-miR-1251-5p | 0.0 | 0.0 | 0.0 | 0.0 | 1.6 | 0.0 | 0.0 | 0.0 | 0.0 |
| hsa-miR-1252-3p | 0.0 | 0.0 | 0.0 | 4.8 | 0.0 | 0.0 | 2.5 | 0.0 | 0.0 |
| hsa-miR-1253 | 0.0 | 0.0 | 0.0 | 0.0 | 0.0 | 0.0 | 0.0 | 0.0 | 0.0 |
| hsa-miR-1255b-5p | 0.0 | 0.0 | 0.0 | 0.0 | 0.0 | 0.0 | 0.0 | 0.0 | 0.0 |
| hsa-miR-1256 | 0.0 | 0.0 | 3.8 | 4.5 | 2.3 | 0.0 | 0.0 | 0.0 | 0.0 |
| hsa-miR-1257 | 0.0 | 0.0 | 2.7 | 3.4 | 0.0 | 0.0 | 0.0 | 0.0 | 0.0 |
| hsa-miR-1263 | 0.0 | 2.0 | 0.0 | 0.0 | 2.4 | 0.0 | 0.0 | 0.0 | 0.0 |
| hsa-miR-1264 | 0.0 | 1.8 | 0.0 | 0.0 | 0.0 | 0.0 | 0.0 | 0.0 | 0.0 |
| hsa-miR-1265 | 0.0 | 2.8 | 0.0 | 0.0 | 2.1 | 2.5 | 3.8 | 2.6 | 0.0 |
| hsa-miR-1269a | 0.0 | 0.0 | 0.0 | 0.0 | 0.0 | 1.5 | 0.0 | 0.0 | 0.0 |
| hsa-miR-1270 | 0.0 | 0.0 | 0.0 | 0.0 | 0.0 | 0.0 | 0.0 | 0.0 | 0.0 |
| hsa-miR-1272 | 0.0 | 0.0 | 0.0 | 3.6 | 0.0 | 0.0 | 0.0 | 0.0 | 0.0 |
| hsa-miR-1273a | 0.0 | 0.0 | 3.9 | 4.2 | 0.0 | 2.5 | 4.3 | 2.3 | 0.0 |
| hsa-miR-1273c | 0.0 | 0.0 | 2.1 | 0.0 | 2.4 | 1.5 | 0.0 | 0.0 | 0.0 |
| hsa-miR-1273d | 0.0 | 0.0 | 0.0 | 2.6 | 0.0 | 0.0 | 0.0 | 0.0 | 0.0 |
| hsa-miR-1277-5p | 0.0 | 0.0 | 0.0 | 5.6 | 0.0 | 0.0 | 2.6 | 0.0 | 0.0 |
| hsa-miR-1279 | 0.0 | 0.0 | 0.0 | 3.1 | 0.0 | 0.0 | 0.0 | 0.0 | 0.0 |
| hsa-miR-1282 | 0.0 | 0.0 | 0.0 | 0.0 | 2.8 | 0.0 | 0.0 | 0.0 | 0.0 |
| hsa-miR-1283 | 0.0 | 0.0 | 0.0 | 6.6 | 0.0 | 0.0 | 0.0 | 0.0 | 0.0 |
| hsa-miR-1285-3p | 0.0 | 0.0 | 0.0 | 0.0 | 2.4 | 3.1 | 0.0 | 2.7 | 0.0 |
| hsa-miR-1289 | 0.0 | 1.9 | 0.0 | 2.6 | 0.0 | 0.0 | 0.0 | 0.0 | 0.0 |
| hsa-miR-1290 | 0.0 | 0.0 | 0.0 | 0.0 | 0.0 | 0.0 | 0.0 | 0.0 | 0.0 |
| hsa-miR-1292-5p | 0.0 | 0.0 | 2.2 | 0.0 | 0.0 | 2.0 | 0.0 | 0.0 | 0.0 |
| hsa-miR-1294 | 0.0 | 0.0 | 0.0 | 0.0 | 2.4 | 0.0 | 0.0 | 0.0 | 0.0 |
| hsa-miR-1295a | 0.0 | 0.0 | 0.0 | 0.0 | 0.0 | 0.0 | 0.0 | 0.0 | 0.0 |
| hsa-miR-1295b-5p | 0.0 | 0.0 | 0.0 | 0.0 | 0.0 | 0.0 | 2.6 | 0.0 | 0.0 |
| hsa-miR-1302 | 0.0 | 0.0 | 2.1 | 0.0 | 0.0 | 0.0 | 3.0 | 0.0 | 0.0 |
| hsa-miR-1304-5p | 0.0 | 0.0 | 4.7 | 5.0 | 0.0 | 0.0 | 0.0 | 0.0 | 3.7 |
| hsa-miR-1305 | 0.0 | 0.0 | 0.0 | 0.0 | 0.0 | 0.0 | 0.0 | 2.7 | 0.0 |

TABLE 3-continued

| | | | | | | | | | |
|---|---|---|---|---|---|---|---|---|---|
| hsa-miR-1307-5p | 0.0 | 1.8 | 0.0 | 0.0 | 1.6 | 2.1 | 3.4 | 0.0 | 0.0 |
| hsa-miR-1321 | 2.4 | 0.0 | 0.0 | 0.0 | 1.9 | 2.5 | 0.0 | 0.0 | 0.0 |
| hsa-miR-1468-3p | 0.0 | 0.0 | 0.0 | 0.0 | 0.0 | 0.0 | 0.0 | 0.0 | 2.7 |
| hsa-miR-1537-3p | 0.0 | 0.0 | 0.0 | 2.8 | 0.0 | 0.0 | 2.8 | 0.0 | 2.7 |
| hsa-miR-1827 | 0.0 | 0.0 | 0.0 | 4.7 | 0.0 | 0.0 | 0.0 | 0.0 | 0.0 |
| hsa-miR-1911-5p | 0.0 | 0.0 | 0.0 | 2.6 | 0.0 | 0.0 | 0.0 | 0.0 | 0.0 |
| hsa-miR-1973 | 0.0 | 0.0 | 0.0 | 0.0 | 0.0 | 0.0 | 0.0 | 0.0 | 0.0 |
| hsa-miR-2052 | 0.0 | 0.0 | 0.0 | 3.8 | 0.0 | 0.0 | 0.0 | 0.0 | 0.0 |
| hsa-miR-2053 | 0.0 | 0.0 | 0.0 | 6.4 | 0.0 | 0.0 | 0.0 | 0.0 | 0.0 |
| hsa-miR-2054 | 0.0 | 0.0 | 0.0 | 6.3 | 0.0 | 0.0 | 0.0 | 0.0 | 0.0 |
| hsa-miR-2114-3p | 0.0 | 0.0 | 0.0 | 0.0 | 1.2 | 0.0 | 3.2 | 0.0 | 0.0 |
| hsa-miR-2114-5p | 0.0 | 0.0 | 0.0 | 0.0 | 0.0 | 0.0 | 0.0 | 0.0 | 0.0 |
| hsa-miR-2115-3p | 0.0 | 0.0 | 0.0 | 0.0 | 0.0 | 0.0 | 3.4 | 0.0 | 0.0 |
| hsa-miR-2115-5p | 0.0 | 2.5 | 0.0 | 0.0 | 0.0 | 0.0 | 3.0 | 0.0 | 0.0 |
| hsa-miR-2681-3p | 0.0 | 0.0 | 0.0 | 0.0 | 0.0 | 0.0 | 0.0 | 0.0 | 0.0 |
| hsa-miR-3065-5p | 2.6 | 2.3 | 3.2 | 0.0 | 0.0 | 0.0 | 0.0 | 0.0 | 0.0 |
| hsa-miR-3119 | 0.0 | 0.0 | 0.0 | 5.0 | 0.0 | 0.0 | 2.8 | 0.0 | 0.0 |
| hsa-miR-3120-3p | 0.0 | 2.9 | 0.0 | 0.0 | 0.0 | 0.0 | 3.4 | 0.0 | 0.0 |
| hsa-miR-3122 | 4.0 | 4.4 | 5.4 | 0.0 | 1.6 | 2.1 | 0.0 | 4.4 | 3.4 |
| hsa-miR-3123 | 0.0 | 0.0 | 0.0 | 0.0 | 1.9 | 2.5 | 0.0 | 0.0 | 0.0 |
| hsa-miR-3125 | 2.9 | 3.4 | 0.0 | 0.0 | 0.0 | 0.0 | 2.6 | 0.0 | 0.0 |
| hsa-miR-3127-3p | 5.4 | 5.0 | 5.4 | 0.0 | 0.0 | 0.0 | 5.9 | 3.6 | 4.1 |
| hsa-miR-3130-3p | 2.1 | 2.8 | 2.0 | 2.8 | 0.0 | 0.0 | 3.3 | 0.0 | 0.0 |
| hsa-miR-3130-5p | 4.4 | 4.8 | 4.2 | 0.0 | 0.0 | 0.0 | 4.4 | 4.8 | 4.0 |
| hsa-miR-3135a | 0.0 | 0.0 | 0.0 | 4.7 | 0.0 | 0.0 | 0.0 | 0.0 | 0.0 |
| hsa-miR-3140-5p | 0.0 | 0.0 | 3.0 | 2.6 | 0.0 | 0.0 | 0.0 | 0.0 | 0.0 |
| hsa-miR-3148 | 0.0 | 2.8 | 1.8 | 3.8 | 0.0 | 0.0 | 0.0 | 0.0 | 3.4 |
| hsa-miR-3149 | 2.5 | 4.1 | 0.0 | 6.4 | 0.0 | 0.0 | 4.1 | 0.0 | 2.8 |
| hsa-miR-3150a-3p | 5.2 | 4.3 | 5.5 | 6.3 | 0.0 | 0.0 | 5.0 | 3.8 | 4.3 |
| hsa-miR-3150b-5p | 4.9 | 5.1 | 5.1 | 0.0 | 1.2 | 0.0 | 6.0 | 4.4 | 4.6 |
| hsa-miR-3151-3p | 5.7 | 5.9 | 5.3 | 0.0 | 0.0 | 0.0 | 5.9 | 5.5 | 5.0 |
| hsa-miR-3151-5p | 6.2 | 5.9 | 6.1 | 0.0 | 0.0 | 0.0 | 6.0 | 5.7 | 5.4 |
| hsa-miR-3160-5p | 3.2 | 4.2 | 3.4 | 0.0 | 0.0 | 0.0 | 3.9 | 3.7 | 0.0 |
| hsa-miR-3181 | 0.0 | 0.0 | 3.0 | 6.0 | 0.0 | 1.2 | 4.6 | 0.0 | 0.0 |
| hsa-miR-3182 | 0.0 | 0.0 | 4.5 | 4.9 | 0.0 | 0.0 | 0.0 | 0.0 | 0.0 |
| hsa-miR-3183 | 0.0 | 0.0 | 0.0 | 0.0 | 2.1 | 0.0 | 3.2 | 0.0 | 0.0 |
| hsa-miR-3192-5p | 0.0 | 3.6 | 0.0 | 0.0 | 2.8 | 2.7 | 3.7 | 0.0 | 2.5 |
| hsa-miR-3194-3p | 0.0 | 0.0 | 0.0 | 0.0 | 0.0 | 0.0 | 0.0 | 0.0 | 0.0 |
| hsa-miR-3199 | 0.0 | 2.3 | 2.5 | 5.7 | 2.8 | 4.8 | 3.7 | 0.0 | 0.0 |
| hsa-miR-3591-5p | 0.0 | 2.2 | 0.0 | 4.3 | 0.0 | 0.0 | 0.0 | 0.0 | 0.0 |
| hsa-miR-3606-3p | 0.0 | 0.0 | 0.0 | 0.0 | 0.0 | 0.0 | 3.2 | 0.0 | 0.0 |
| hsa-miR-3607-3p | 0.0 | 0.0 | 0.0 | 0.0 | 0.0 | 0.0 | 3.2 | 0.0 | 0.0 |
| hsa-miR-3611 | 0.0 | 0.0 | 0.0 | 0.0 | 0.0 | 0.0 | 4.0 | 0.0 | 0.0 |
| hsa-miR-3613-3p | 0.0 | 0.0 | 0.0 | 2.4 | 1.7 | 2.4 | 3.2 | 0.0 | 0.0 |
| hsa-miR-3614-3p | 0.0 | 0.0 | 2.5 | 0.0 | 0.0 | 0.0 | 3.2 | 0.0 | 2.6 |
| hsa-miR-3617-5p | 0.0 | 0.0 | 0.0 | 0.0 | 0.0 | 0.0 | 2.7 | 0.0 | 0.0 |
| hsa-miR-3653-3p | 0.0 | 0.0 | 0.0 | 0.0 | 0.0 | 0.0 | 0.0 | 0.0 | 0.0 |
| hsa-miR-3660 | 2.3 | 0.0 | 0.0 | 0.0 | 0.0 | 2.0 | 2.9 | 0.0 | 0.0 |
| hsa-miR-3661 | 0.0 | 3.6 | 0.0 | 0.0 | 2.6 | 3.4 | 3.4 | 0.0 | 0.0 |
| hsa-miR-3664-5p | 0.0 | 0.0 | 0.0 | 0.0 | 0.0 | 0.0 | 0.0 | 0.0 | 3.3 |
| hsa-miR-3670 | 0.0 | 0.0 | 0.0 | 0.0 | 0.0 | 0.0 | 0.0 | 0.0 | 3.0 |
| hsa-miR-3671 | 0.0 | 0.0 | 0.0 | 0.0 | 0.0 | 0.0 | 2.9 | 0.0 | 0.0 |
| hsa-miR-3672 | 0.0 | 0.0 | 0.0 | 0.0 | 0.0 | 0.0 | 2.6 | 0.0 | 0.0 |
| hsa-miR-3674 | 0.0 | 0.0 | 0.0 | 0.0 | 0.0 | 0.0 | 2.6 | 0.0 | 0.0 |
| hsa-miR-3675-5p | 0.0 | 2.5 | 0.0 | 0.0 | 0.0 | 1.3 | 0.0 | 2.3 | 0.0 |
| hsa-miR-3680-5p | 3.1 | 3.9 | 0.0 | 0.0 | 2.9 | 2.9 | 3.3 | 0.0 | 0.0 |
| hsa-miR-3681-5p | 0.0 | 0.0 | 0.0 | 5.3 | 0.0 | 0.0 | 0.0 | 0.0 | 0.0 |
| hsa-miR-3683 | 0.0 | 0.0 | 0.0 | 0.0 | 1.4 | 0.0 | 0.0 | 0.0 | 0.0 |
| hsa-miR-3689a-5p, hsa-miR-3689b-5p, hsa-miR-3689e | 0.0 | 2.1 | 0.0 | 0.0 | 0.0 | 0.0 | 3.1 | 0.0 | 0.0 |
| hsa-miR-3907 | 0.0 | 0.0 | 0.0 | 0.0 | 0.0 | 0.0 | 3.0 | 0.0 | 0.0 |
| hsa-miR-3909 | 0.0 | 0.0 | 2.0 | 2.4 | 0.0 | 0.0 | 3.2 | 0.0 | 0.0 |
| hsa-miR-3910 | 2.3 | 0.0 | 0.0 | 0.0 | 1.6 | 1.9 | 2.9 | 0.0 | 0.0 |
| hsa-miR-3912-5p | 0.0 | 0.0 | 0.0 | 0.0 | 0.0 | 0.0 | 0.0 | 0.0 | 0.0 |
| hsa-miR-3913-5p | 2.2 | 2.3 | 0.0 | 0.0 | 0.0 | 1.6 | 3.5 | 0.0 | 0.0 |
| hsa-miR-3915 | 0.0 | 0.0 | 0.0 | 0.0 | 2.2 | 0.0 | 3.4 | 0.0 | 0.0 |
| hsa-miR-3919 | 2.8 | 1.9 | 3.2 | 0.0 | 2.4 | 0.0 | 0.0 | 0.0 | 0.0 |
| hsa-miR-3920 | 0.0 | 0.0 | 0.0 | 5.7 | 0.0 | 0.0 | 4.3 | 0.0 | 2.6 |
| hsa-miR-3924 | 0.0 | 2.9 | 0.0 | 0.0 | 1.3 | 0.0 | 0.0 | 0.0 | 0.0 |
| hsa-miR-3925-3p | 0.0 | 0.0 | 0.0 | 0.0 | 0.0 | 0.0 | 0.0 | 0.0 | 0.0 |
| hsa-miR-3926 | 0.0 | 1.8 | 0.0 | 0.0 | 2.7 | 1.3 | 3.4 | 0.0 | 0.0 |
| hsa-miR-3938 | 0.0 | 0.0 | 1.8 | 4.1 | 0.0 | 0.0 | 2.9 | 0.0 | 0.0 |
| hsa-miR-3939 | 0.0 | 0.0 | 0.0 | 0.0 | 0.0 | 0.0 | 0.0 | 0.0 | 0.0 |
| hsa-miR-3941 | 0.0 | 2.8 | 0.0 | 0.0 | 0.0 | 0.0 | 0.0 | 0.0 | 0.0 |
| hsa-miR-3942-3p | 0.0 | 0.0 | 0.0 | 0.0 | 0.0 | 0.0 | 0.0 | 0.0 | 0.0 |
| hsa-miR-3942-5p | 0.0 | 0.0 | 0.0 | 0.0 | 0.0 | 0.0 | 0.0 | 0.0 | 0.0 |
| hsa-miR-3974 | 0.0 | 0.0 | 3.7 | 0.0 | 0.0 | 0.0 | 0.0 | 0.0 | 0.0 |
| hsa-miR-3977 | 3.2 | 0.0 | 2.3 | 4.9 | 2.2 | 2.5 | 0.0 | 0.0 | 0.0 |
| hsa-miR-3978 | 0.0 | 0.0 | 3.4 | 4.8 | 0.0 | 0.0 | 0.0 | 0.0 | 0.0 |

TABLE 3-continued

| | | | | | | | | | |
|---|---|---|---|---|---|---|---|---|---|
| hsa-miR-4263 | 0.0 | 0.0 | 0.0 | 0.0 | 0.0 | 0.0 | 4.0 | 0.0 | 0.0 |
| hsa-miR-4267 | 0.0 | 2.7 | 1.8 | 0.0 | 2.1 | 3.6 | 4.1 | 0.0 | 0.0 |
| hsa-miR-4285 | 0.0 | 0.0 | 3.3 | 0.0 | 0.0 | 0.0 | 0.0 | 0.0 | 0.0 |
| hsa-miR-4289 | 0.0 | 0.0 | 0.0 | 0.0 | 2.1 | 0.0 | 0.0 | 0.0 | 0.0 |
| hsa-miR-4293 | 0.0 | 0.0 | 1.9 | 5.6 | 0.0 | 0.0 | 3.1 | 0.0 | 0.0 |
| hsa-miR-4309 | 0.0 | 0.0 | 0.0 | 3.0 | 0.0 | 0.0 | 2.9 | 0.0 | 0.0 |
| hsa-miR-4311 | 2.3 | 0.0 | 0.0 | 0.0 | 0.0 | 2.1 | 0.0 | 0.0 | 0.0 |
| hsa-miR-4315 | 0.0 | 2.0 | 0.0 | 0.0 | 1.2 | 1.9 | 3.5 | 0.0 | 0.0 |
| hsa-miR-4321 | 0.0 | 2.6 | 0.0 | 2.4 | 3.7 | 3.0 | 0.0 | 3.0 | 0.0 |
| hsa-miR-4418 | 0.0 | 0.0 | 0.0 | 0.0 | 0.0 | 0.0 | 0.0 | 0.0 | 0.0 |
| hsa-miR-4422 | 0.0 | 0.0 | 2.4 | 0.0 | 0.0 | 0.0 | 0.0 | 0.0 | 0.0 |
| hsa-miR-4423-3p | 0.0 | 2.3 | 0.0 | 0.0 | 0.0 | 0.0 | 2.7 | 0.0 | 0.0 |
| hsa-miR-4424 | 0.0 | 0.0 | 2.2 | 0.0 | 0.0 | 0.0 | 0.0 | 0.0 | 0.0 |
| hsa-miR-4427 | 0.0 | 0.0 | 0.0 | 0.0 | 0.0 | 2.2 | 0.0 | 0.0 | 0.0 |
| hsa-miR-4431 | 2.2 | 2.5 | 0.0 | 0.0 | 2.3 | 1.7 | 0.0 | 0.0 | 0.0 |
| hsa-miR-4432 | 0.0 | 0.0 | 1.7 | 2.5 | 0.0 | 0.0 | 0.0 | 0.0 | 0.0 |
| hsa-miR-4435 | 2.3 | 6.4 | 3.6 | 5.8 | 6.2 | 5.9 | 0.0 | 5.5 | 0.0 |
| hsa-miR-4439 | 0.0 | 3.3 | 0.0 | 0.0 | 3.3 | 2.0 | 2.7 | 0.0 | 0.0 |
| hsa-miR-4445-5p | 2.2 | 0.0 | 2.7 | 5.1 | 0.0 | 0.0 | 3.5 | 3.4 | 0.0 |
| hsa-miR-4452 | 0.0 | 0.0 | 0.0 | 0.0 | 0.0 | 0.0 | 2.7 | 0.0 | 0.0 |
| hsa-miR-4457 | 0.0 | 2.1 | 0.0 | 0.0 | 0.0 | 0.0 | 0.0 | 0.0 | 0.0 |
| hsa-miR-4458 | 0.0 | 2.6 | 0.0 | 0.0 | 2.5 | 2.2 | 3.3 | 0.0 | 0.0 |
| hsa-miR-4461 | 0.0 | 0.0 | 0.0 | 6.8 | 0.0 | 0.0 | 0.0 | 0.0 | 0.0 |
| hsa-miR-4464 | 0.0 | 0.0 | 0.0 | 0.0 | 0.0 | 0.0 | 0.0 | 0.0 | 0.0 |
| hsa-miR-4468 | 0.0 | 0.0 | 0.0 | 0.0 | 0.0 | 0.0 | 0.0 | 0.0 | 0.0 |
| hsa-miR-4469 | 0.0 | 0.0 | 0.0 | 2.4 | 0.0 | 0.0 | 0.0 | 0.0 | 0.0 |
| hsa-miR-4470 | 0.0 | 2.8 | 3.1 | 2.6 | 4.7 | 4.3 | 4.0 | 0.0 | 0.0 |
| hsa-miR-4471 | 0.0 | 3.3 | 0.0 | 0.0 | 0.0 | 2.5 | 0.0 | 0.0 | 0.0 |
| hsa-miR-4475 | 0.0 | 0.0 | 0.0 | 0.0 | 1.5 | 0.0 | 0.0 | 0.0 | 0.0 |
| hsa-miR-4480 | 0.0 | 0.0 | 0.0 | 0.0 | 0.0 | 0.0 | 2.7 | 0.0 | 0.0 |
| hsa-miR-4485-3p | 0.0 | 0.0 | 0.0 | 0.0 | 0.0 | 0.0 | 0.0 | 0.0 | 0.0 |
| hsa-miR-4490 | 0.0 | 0.0 | 2.1 | 0.0 | 0.0 | 0.0 | 0.0 | 0.0 | 0.0 |
| hsa-miR-4493 | 0.0 | 0.0 | 3.4 | 4.9 | 0.0 | 0.0 | 0.0 | 0.0 | 3.1 |
| hsa-miR-4500 | 0.0 | 0.0 | 0.0 | 0.0 | 2.5 | 0.0 | 0.0 | 0.0 | 0.0 |
| hsa-miR-4503 | 0.0 | 0.0 | 0.0 | 0.0 | 0.0 | 0.0 | 3.0 | 0.0 | 0.0 |
| hsa-miR-4504 | 0.0 | 0.0 | 0.0 | 6.3 | 0.0 | 0.0 | 0.0 | 0.0 | 0.0 |
| hsa-miR-4509 | 0.0 | 0.0 | 3.7 | 3.2 | 0.0 | 0.0 | 0.0 | 0.0 | 0.0 |
| hsa-miR-4510 | 0.0 | 2.2 | 0.0 | 0.0 | 2.4 | 2.3 | 0.0 | 0.0 | 0.0 |
| hsa-miR-4511 | 0.0 | 2.4 | 0.0 | 0.0 | 0.0 | 0.0 | 0.0 | 0.0 | 0.0 |
| hsa-miR-4512 | 0.0 | 0.0 | 0.0 | 0.0 | 0.0 | 0.0 | 3.1 | 0.0 | 0.0 |
| hsa-miR-4515 | 0.0 | 3.5 | 3.2 | 3.5 | 3.0 | 3.7 | 3.8 | 3.9 | 3.9 |
| hsa-miR-4517 | 0.0 | 3.7 | 0.0 | 2.6 | 0.0 | 0.0 | 0.0 | 0.0 | 0.0 |
| hsa-miR-4519 | 0.0 | 0.0 | 0.0 | 6.0 | 1.5 | 1.5 | 3.7 | 0.0 | 0.0 |
| hsa-miR-4520-2-3p | 0.0 | 0.0 | 0.0 | 0.0 | 2.3 | 0.0 | 0.0 | 0.0 | 0.0 |
| hsa-miR-4522 | 0.0 | 0.0 | 2.9 | 0.0 | 2.4 | 1.8 | 3.7 | 0.0 | 0.0 |
| hsa-miR-4524a-3p | 0.0 | 2.4 | 2.1 | 0.0 | 0.0 | 0.0 | 0.0 | 0.0 | 0.0 |
| hsa-miR-4536-3p | 0.0 | 0.0 | 0.0 | 0.0 | 0.0 | 0.0 | 3.0 | 0.0 | 0.0 |
| hsa-miR-4537 | 0.0 | 0.0 | 0.0 | 0.0 | 0.0 | 1.9 | 0.0 | 0.0 | 0.0 |
| hsa-miR-4633-3p | 0.0 | 0.0 | 2.2 | 4.1 | 0.0 | 0.0 | 0.0 | 0.0 | 0.0 |
| hsa-miR-4637 | 0.0 | 0.0 | 3.3 | 4.6 | 0.0 | 0.0 | 2.9 | 0.0 | 0.0 |
| hsa-miR-4643 | 2.5 | 2.3 | 3.8 | 0.0 | 2.1 | 1.8 | 0.0 | 0.0 | 0.0 |
| hsa-miR-4650-3p | 0.0 | 0.0 | 0.0 | 0.0 | 0.0 | 0.0 | 0.0 | 0.0 | 0.0 |
| hsa-miR-4653-3p | 0.0 | 2.6 | 1.7 | 5.1 | 0.0 | 0.0 | 0.0 | 0.0 | 0.0 |
| hsa-miR-4659a-3p | 0.0 | 0.0 | 1.8 | 0.0 | 0.0 | 0.0 | 0.0 | 0.0 | 0.0 |
| hsa-miR-4659a-5p | 0.0 | 0.0 | 4.9 | 0.0 | 2.0 | 0.0 | 2.6 | 0.0 | 0.0 |
| hsa-miR-4659b-5p | 0.0 | 2.3 | 2.4 | 0.0 | 0.0 | 0.0 | 0.0 | 0.0 | 0.0 |
| hsa-miR-4661-3p | 2.7 | 3.0 | 0.0 | 0.0 | 1.8 | 1.7 | 0.0 | 0.0 | 0.0 |
| hsa-miR-4662a-3p | 0.0 | 2.8 | 0.0 | 0.0 | 0.0 | 0.0 | 0.0 | 0.0 | 0.0 |
| hsa-miR-4662a-5p | 0.0 | 0.0 | 0.0 | 6.3 | 0.0 | 0.0 | 3.3 | 0.0 | 0.0 |
| hsa-miR-4666a-3p | 0.0 | 0.0 | 0.0 | 5.0 | 0.0 | 0.0 | 0.0 | 0.0 | 0.0 |
| hsa-miR-4666b | 0.0 | 0.0 | 0.0 | 0.0 | 0.0 | 1.4 | 0.0 | 0.0 | 0.0 |
| hsa-miR-4668-3p | 0.0 | 0.0 | 0.0 | 2.9 | 0.0 | 0.0 | 0.0 | 0.0 | 0.0 |
| hsa-miR-4670-3p | 0.0 | 0.0 | 0.0 | 0.0 | 0.0 | 0.0 | 0.0 | 0.0 | 0.0 |
| hsa-miR-4670-5p | 0.0 | 0.0 | 3.2 | 0.0 | 0.0 | 0.0 | 3.1 | 0.0 | 0.0 |
| hsa-miR-4671-3p | 0.0 | 0.0 | 0.0 | 0.0 | 0.0 | 0.0 | 0.0 | 0.0 | 0.0 |
| hsa-miR-4679 | 0.0 | 0.0 | 0.0 | 0.0 | 1.6 | 0.0 | 0.0 | 0.0 | 0.0 |
| hsa-miR-4683 | 0.0 | 0.0 | 0.0 | 0.0 | 0.0 | 0.0 | 0.0 | 0.0 | 0.0 |
| hsa-miR-4699-3p | 0.0 | 0.0 | 0.0 | 0.0 | 0.0 | 0.0 | 0.0 | 0.0 | 0.0 |
| hsa-miR-4699-5p | 0.0 | 0.0 | 4.5 | 4.8 | 0.0 | 0.0 | 0.0 | 0.0 | 0.0 |
| hsa-miR-4704-5p | 0.0 | 0.0 | 2.6 | 0.0 | 0.0 | 0.0 | 0.0 | 0.0 | 0.0 |
| hsa-miR-4705 | 0.0 | 0.0 | 0.0 | 0.0 | 0.0 | 0.0 | 0.0 | 0.0 | 0.0 |
| hsa-miR-4714-3p | 0.0 | 0.0 | 0.0 | 6.1 | 0.0 | 0.0 | 0.0 | 0.0 | 0.0 |
| hsa-miR-4715-3p | 0.0 | 0.0 | 3.1 | 0.0 | 0.0 | 0.0 | 0.0 | 0.0 | 0.0 |
| hsa-miR-4715-5p | 0.0 | 2.6 | 0.0 | 0.0 | 1.9 | 1.3 | 0.0 | 0.0 | 0.0 |
| hsa-miR-4719 | 0.0 | 0.0 | 0.0 | 0.0 | 0.0 | 0.0 | 3.3 | 0.0 | 0.0 |
| hsa-miR-4720-3p | 0.0 | 0.0 | 0.0 | 6.1 | 0.0 | 0.0 | 0.0 | 0.0 | 0.0 |
| hsa-miR-4724-5p | 1.7 | 2.9 | 0.0 | 6.9 | 0.0 | 2.0 | 0.0 | 0.0 | 0.0 |
| hsa-miR-4727-5p | 0.0 | 0.0 | 2.7 | 3.3 | 0.0 | 0.0 | 4.1 | 0.0 | 0.0 |
| hsa-miR-4735-3p | 0.0 | 0.0 | 2.4 | 0.0 | 0.0 | 0.0 | 0.0 | 0.0 | 0.0 |
| hsa-miR-4737 | 2.1 | 3.4 | 0.0 | 0.0 | 2.6 | 2.7 | 0.0 | 0.0 | 0.0 |

TABLE 3-continued

| | | | | | | | | | |
|---|---|---|---|---|---|---|---|---|---|
| hsa-miR-4743-3p | 0.0 | 3.1 | 0.0 | 0.0 | 1.6 | 0.0 | 0.0 | 0.0 | 0.0 |
| hsa-miR-4744 | 0.0 | 0.0 | 0.0 | 0.0 | 0.0 | 0.0 | 3.8 | 0.0 | 0.0 |
| hsa-miR-4753-3p | 3.2 | 3.3 | 2.3 | 0.0 | 1.8 | 2.0 | 0.0 | 0.0 | 0.0 |
| hsa-miR-4753-5p | 0.0 | 2.4 | 1.9 | 0.0 | 0.0 | 0.0 | 3.6 | 0.0 | 0.0 |
| hsa-miR-4757-5p | 0.0 | 0.0 | 2.2 | 0.0 | 0.0 | 0.0 | 3.2 | 0.0 | 2.7 |
| hsa-miR-4759 | 0.0 | 0.0 | 0.0 | 0.0 | 0.0 | 1.6 | 0.0 | 0.0 | 0.0 |
| hsa-miR-4760-5p | 0.0 | 0.0 | 0.0 | 3.8 | 0.0 | 0.0 | 0.0 | 0.0 | 0.0 |
| hsa-miR-4761-5p | 0.0 | 0.0 | 3.7 | 4.8 | 0.0 | 1.3 | 3.2 | 0.0 | 0.0 |
| hsa-miR-4762-5p | 0.0 | 2.0 | 0.0 | 6.4 | 0.0 | 0.0 | 2.7 | 0.0 | 0.0 |
| hsa-miR-4764-5p | 0.0 | 0.0 | 0.0 | 0.0 | 1.2 | 0.0 | 0.0 | 0.0 | 0.0 |
| hsa-miR-4768-5p | 2.5 | 0.0 | 0.0 | 0.0 | 0.0 | 2.1 | 0.0 | 0.0 | 0.0 |
| hsa-miR-4770 | 2.5 | 2.9 | 0.0 | 0.0 | 0.0 | 0.0 | 3.1 | 0.0 | 0.0 |
| hsa-miR-4772-3p | 0.0 | 0.0 | 0.0 | 5.9 | 0.0 | 0.0 | 0.0 | 0.0 | 0.0 |
| hsa-miR-4774-3p | 0.0 | 2.0 | 0.0 | 0.0 | 1.8 | 2.2 | 0.0 | 0.0 | 0.0 |
| hsa-miR-4774-5p | 0.0 | 0.0 | 0.0 | 0.0 | 0.0 | 0.0 | 2.8 | 0.0 | 0.0 |
| hsa-miR-4777-5p | 0.0 | 0.0 | 0.0 | 5.5 | 0.0 | 0.0 | 0.0 | 0.0 | 0.0 |
| hsa-miR-4778-3p | 0.0 | 1.8 | 0.0 | 0.0 | 0.0 | 0.0 | 0.0 | 0.0 | 0.0 |
| hsa-miR-4778-5p | 0.0 | 0.0 | 0.0 | 0.0 | 0.0 | 0.0 | 0.0 | 0.0 | 0.0 |
| hsa-miR-4779 | 0.0 | 0.0 | 0.0 | 0.0 | 0.0 | 0.0 | 0.0 | 0.0 | 0.0 |
| hsa-miR-4781-5p | 0.0 | 0.0 | 0.0 | 0.0 | 2.3 | 0.0 | 0.0 | 0.0 | 0.0 |
| hsa-miR-4782-5p | 5.7 | 0.0 | 0.0 | 0.0 | 0.0 | 0.0 | 0.0 | 0.0 | 0.0 |
| hsa-miR-4785 | 2.7 | 3.4 | 4.3 | 2.9 | 3.9 | 3.3 | 3.5 | 3.7 | 0.0 |
| hsa-miR-4789-3p | 0.0 | 0.0 | 0.0 | 0.0 | 0.0 | 0.0 | 2.7 | 0.0 | 0.0 |
| hsa-miR-4789-5p | 0.0 | 2.1 | 0.0 | 0.0 | 0.0 | 0.0 | 0.0 | 0.0 | 0.0 |
| hsa-miR-4791 | 0.0 | 0.0 | 0.0 | 5.0 | 0.0 | 0.0 | 0.0 | 0.0 | 0.0 |
| hsa-miR-4792 | 0.0 | 2.6 | 3.3 | 5.4 | 1.7 | 4.3 | 3.2 | 4.0 | 0.0 |
| hsa-miR-4795-3p | 0.0 | 0.0 | 0.0 | 0.0 | 0.0 | 0.0 | 0.0 | 0.0 | 0.0 |
| hsa-miR-4797-5p | 0.0 | 0.0 | 0.0 | 4.9 | 0.0 | 0.0 | 3.6 | 0.0 | 0.0 |
| hsa-miR-4798-5p | 0.0 | 0.0 | 0.0 | 5.4 | 0.0 | 0.0 | 0.0 | 0.0 | 0.0 |
| hsa-miR-4801 | 2.4 | 2.7 | 2.4 | 0.0 | 0.0 | 2.1 | 0.0 | 0.0 | 0.0 |
| hsa-miR-4803 | 0.0 | 2.0 | 0.0 | 0.0 | 0.0 | 2.3 | 2.8 | 0.0 | 0.0 |
| hsa-miR-4804-5p | 0.0 | 3.4 | 0.0 | 0.0 | 0.0 | 0.0 | 0.0 | 0.0 | 0.0 |
| hsa-miR-4999-3p | 2.0 | 2.7 | 0.0 | 0.0 | 2.6 | 2.1 | 2.6 | 0.0 | 0.0 |
| hsa-miR-5000-3p | 0.0 | 2.8 | 0.0 | 0.0 | 2.0 | 0.0 | 0.0 | 2.4 | 0.0 |
| hsa-miR-5004-3p | 3.1 | 2.2 | 3.4 | 0.0 | 2.2 | 2.5 | 0.0 | 0.0 | 0.0 |
| hsa-miR-5007-3p | 0.0 | 0.0 | 0.0 | 0.0 | 0.0 | 0.0 | 0.0 | 0.0 | 0.0 |
| hsa-miR-5009-5p | 0.0 | 0.0 | 0.0 | 0.0 | 0.0 | 0.0 | 0.0 | 0.0 | 2.6 |
| hsa-miR-5047 | 0.0 | 0.0 | 1.7 | 5.9 | 0.0 | 0.0 | 3.1 | 0.0 | 0.0 |
| hsa-miR-5089-5p | 0.0 | 2.4 | 3.4 | 3.6 | 0.0 | 0.0 | 0.0 | 0.0 | 0.0 |
| hsa-miR-5092 | 0.0 | 0.0 | 2.6 | 0.0 | 2.7 | 2.1 | 2.7 | 0.0 | 0.0 |
| hsa-miR-5579-5p | 0.0 | 0.0 | 0.0 | 0.0 | 0.0 | 0.0 | 0.0 | 0.0 | 0.0 |
| hsa-miR-5582-5p | 0.0 | 0.0 | 0.0 | 0.0 | 0.0 | 0.0 | 2.9 | 0.0 | 0.0 |
| hsa-miR-5584-5p | 0.0 | 0.0 | 0.0 | 3.2 | 0.0 | 0.0 | 0.0 | 0.0 | 0.0 |
| hsa-miR-5585-5p | 0.0 | 1.8 | 0.0 | 0.0 | 1.4 | 0.0 | 0.0 | 0.0 | 0.0 |
| hsa-miR-5586-3p | 0.0 | 2.2 | 0.0 | 0.0 | 0.0 | 0.0 | 0.0 | 0.0 | 0.0 |
| hsa-miR-5586-5p | 0.0 | 0.0 | 0.0 | 0.0 | 0.0 | 0.0 | 0.0 | 0.0 | 0.0 |
| hsa-miR-5587-5p | 0.0 | 0.0 | 0.0 | 0.0 | 2.8 | 2.9 | 4.2 | 3.8 | 2.8 |
| hsa-miR-5588-5p | 0.0 | 0.0 | 0.0 | 0.0 | 0.0 | 1.4 | 0.0 | 0.0 | 0.0 |
| hsa-miR-5590-3p | 0.0 | 0.0 | 0.0 | 2.7 | 0.0 | 0.0 | 0.0 | 0.0 | 0.0 |
| hsa-miR-5590-5p | 0.0 | 0.0 | 0.0 | 0.0 | 0.0 | 0.0 | 0.0 | 0.0 | 2.6 |
| hsa-miR-5684 | 0.0 | 1.8 | 0.0 | 0.0 | 0.0 | 0.0 | 0.0 | 0.0 | 0.0 |
| hsa-miR-5691 | 0.0 | 0.0 | 0.0 | 0.0 | 0.0 | 0.0 | 3.4 | 0.0 | 0.0 |
| hsa-miR-5692b | 0.0 | 0.0 | 0.0 | 0.0 | 0.0 | 0.0 | 0.0 | 3.8 | 2.6 |
| hsa-miR-5697 | 0.0 | 0.0 | 0.0 | 0.0 | 0.0 | 0.0 | 0.0 | 0.0 | 2.8 |
| hsa-miR-5707 | 0.0 | 0.0 | 0.0 | 0.0 | 0.0 | 1.6 | 0.0 | 0.0 | 3.0 |
| hsa-miR-6070 | 0.0 | 0.0 | 0.0 | 3.1 | 0.0 | 0.0 | 4.5 | 0.0 | 0.0 |
| hsa-miR-6071 | 0.0 | 2.2 | 0.0 | 0.0 | 0.0 | 1.2 | 0.0 | 0.0 | 0.0 |
| hsa-miR-6074 | 0.0 | 2.7 | 0.0 | 0.0 | 3.2 | 3.0 | 0.0 | 0.0 | 0.0 |
| hsa-miR-6078 | 0.0 | 0.0 | 0.0 | 0.0 | 0.0 | 0.0 | 3.0 | 0.0 | 0.0 |
| hsa-miR-6080 | 0.0 | 2.3 | 2.8 | 6.0 | 1.7 | 2.9 | 0.0 | 0.0 | 0.0 |
| hsa-miR-6084 | 0.0 | 0.0 | 0.0 | 5.3 | 2.3 | 1.9 | 3.6 | 0.0 | 0.0 |
| hsa-miR-6129 | 2.0 | 3.2 | 0.0 | 5.8 | 2.2 | 3.5 | 2.8 | 0.0 | 0.0 |
| hsa-miR-6130 | 0.0 | 2.9 | 2.0 | 0.0 | 2.6 | 3.0 | 0.0 | 0.0 | 0.0 |
| hsa-miR-6501-3p | 2.4 | 0.0 | 2.1 | 7.2 | 0.0 | 1.9 | 3.6 | 0.0 | 0.0 |
| hsa-miR-6502-3p | 0.0 | 0.0 | 3.8 | 2.8 | 0.0 | 0.0 | 0.0 | 0.0 | 0.0 |
| hsa-miR-6502-5p | 2.8 | 3.3 | 2.0 | 0.0 | 1.8 | 1.7 | 3.1 | 0.0 | 0.0 |
| hsa-miR-6506-3p | 0.0 | 0.0 | 0.0 | 0.0 | 0.0 | 0.0 | 3.5 | 0.0 | 0.0 |
| hsa-miR-6516-3p | 0.0 | 0.0 | 0.0 | 6.5 | 0.0 | 0.0 | 0.0 | 0.0 | 0.0 |
| hsa-miR-6715a-3p | 1.6 | 2.0 | 0.0 | 0.0 | 0.0 | 0.0 | 3.5 | 0.0 | 0.0 |
| hsa-miR-6715b-3p | 0.0 | 0.0 | 0.0 | 0.0 | 0.0 | 0.0 | 3.2 | 0.0 | 0.0 |
| hsa-miR-6719-3p | 0.0 | 0.0 | 0.0 | 0.0 | 0.0 | 0.0 | 0.0 | 0.0 | 0.0 |
| hsa-miR-6750-5p | 1.9 | 2.9 | 2.6 | 0.0 | 2.6 | 3.5 | 0.0 | 0.0 | 0.0 |
| hsa-miR-6755-5p | 0.0 | 0.0 | 0.0 | 0.0 | 0.0 | 1.5 | 0.0 | 0.0 | 0.0 |
| hsa-miR-6767-3p | 3.2 | 1.9 | 3.3 | 0.0 | 2.1 | 2.7 | 3.0 | 0.0 | 0.0 |
| hsa-miR-6773-5p | 0.0 | 2.3 | 0.0 | 6.4 | 0.0 | 0.0 | 0.0 | 0.0 | 0.0 |
| hsa-miR-6806-3p | 0.0 | 0.0 | 0.0 | 5.0 | 0.0 | 0.0 | 3.6 | 0.0 | 0.0 |
| hsa-miR-6808-3p | 0.0 | 2.2 | 0.0 | 0.0 | 0.0 | 1.4 | 0.0 | 0.0 | 0.0 |
| hsa-miR-6811-5p | 0.0 | 2.2 | 0.0 | 0.0 | 2.6 | 0.0 | 3.1 | 0.0 | 0.0 |
| hsa-miR-6814-5p | 2.7 | 3.7 | 2.7 | 0.0 | 2.2 | 3.4 | 0.0 | 0.0 | 0.0 |
| hsa-miR-6828-3p | 0.0 | 0.0 | 0.0 | 0.0 | 0.0 | 1.4 | 2.8 | 0.0 | 0.0 |

TABLE 3-continued

| | | | | | | | | | |
|---|---|---|---|---|---|---|---|---|---|
| hsa-miR-6835-3p | 0.0 | 0.0 | 0.0 | 2.9 | 1.9 | 0.0 | 0.0 | 0.0 | 0.0 |
| hsa-miR-6838-3p | 0.0 | 1.9 | 0.0 | 0.0 | 0.0 | 0.0 | 0.0 | 0.0 | 0.0 |
| hsa-miR-6842-3p | 0.0 | 2.2 | 0.0 | 2.7 | 0.0 | 1.9 | 0.0 | 0.0 | 0.0 |
| hsa-miR-6853-3p | 0.0 | 0.0 | 1.8 | 0.0 | 0.0 | 0.0 | 0.0 | 0.0 | 0.0 |
| hsa-miR-6854-5p | 0.0 | 2.1 | 0.0 | 0.0 | 0.0 | 0.0 | 0.0 | 0.0 | 0.0 |
| hsa-miR-6864-5p | 0.0 | 0.0 | 2.4 | 0.0 | 0.0 | 1.4 | 0.0 | 0.0 | 0.0 |
| hsa-miR-6866-5p | 0.0 | 0.0 | 0.0 | 0.0 | 0.0 | 0.0 | 0.0 | 0.0 | 0.0 |
| hsa-miR-6869-3p | 0.0 | 2.1 | 0.0 | 2.6 | 0.0 | 0.0 | 4.0 | 0.0 | 0.0 |
| hsa-miR-6882-5p | 0.0 | 2.0 | 0.0 | 0.0 | 2.3 | 1.5 | 0.0 | 0.0 | 0.0 |
| hsa-miR-6888-3p | 0.0 | 2.1 | 0.0 | 0.0 | 0.0 | 0.0 | 0.0 | 0.0 | 0.0 |
| hsa-miR-7153-5p | 0.0 | 2.1 | 0.0 | 0.0 | 0.0 | 0.0 | 0.0 | 0.0 | 0.0 |
| hsa-miR-7154-5p | 0.0 | 0.0 | 0.0 | 6.6 | 0.0 | 0.0 | 0.0 | 0.0 | 0.0 |
| hsa-miR-7156-3p | 0.0 | 3.3 | 2.8 | 5.1 | 0.0 | 1.4 | 4.7 | 0.0 | 0.0 |
| hsa-miR-7156-5p | 2.0 | 3.2 | 0.0 | 4.9 | 2.4 | 2.4 | 0.0 | 0.0 | 0.0 |
| hsa-miR-7158-3p | 0.0 | 2.2 | 0.0 | 0.0 | 0.0 | 0.0 | 0.0 | 0.0 | 0.0 |
| hsa-miR-7159-3p | 0.0 | 0.0 | 0.0 | 0.0 | 0.0 | 0.0 | 3.1 | 0.0 | 0.0 |
| hsa-miR-7160-3p | 0.0 | 0.0 | 0.0 | 2.4 | 0.0 | 2.5 | 0.0 | 0.0 | 0.0 |
| hsa-miR-7515 | 0.0 | 0.0 | 3.8 | 0.0 | 0.0 | 2.9 | 0.0 | 0.0 | 0.0 |
| hsa-miR-7705 | 0.0 | 0.0 | 1.6 | 0.0 | 0.0 | 0.0 | 2.9 | 0.0 | 0.0 |
| hsa-miR-7706 | 3.1 | 2.0 | 2.6 | 0.0 | 1.2 | 2.1 | 0.0 | 0.0 | 0.0 |
| hsa-miR-7978 | 2.2 | 2.0 | 1.9 | 0.0 | 0.0 | 1.8 | 0.0 | 0.0 | 0.0 |
| hsa-miR-8053 | 0.0 | 0.0 | 0.0 | 0.0 | 0.0 | 0.0 | 0.0 | 0.0 | 0.0 |
| hsa-miR-8054 | 0.0 | 2.3 | 0.0 | 0.0 | 0.0 | 0.0 | 0.0 | 0.0 | 0.0 |
| hsa-miR-8056 | 0.0 | 0.0 | 2.0 | 0.0 | 0.0 | 0.0 | 0.0 | 0.0 | 0.0 |
| hsa-miR-8058 | 3.3 | 1.8 | 2.1 | 4.8 | 0.0 | 0.0 | 0.0 | 0.0 | 0.0 |
| hsa-miR-8067 | 0.0 | 0.0 | 0.0 | 0.0 | 0.0 | 0.0 | 3.6 | 0.0 | 0.0 |
| hsa-miR-8068 | 0.0 | 0.0 | 0.0 | 0.0 | 0.0 | 1.4 | 0.0 | 0.0 | 0.0 |
| hsa-miR-8074 | 3.0 | 2.0 | 2.4 | 4.6 | 2.1 | 2.4 | 0.0 | 0.0 | 0.0 |
| hsa-miR-8079 | 0.0 | 2.6 | 0.0 | 0.0 | 0.0 | 1.8 | 0.0 | 2.4 | 0.0 |
| hsa-miR-8086 | 0.0 | 2.4 | 0.0 | 0.0 | 2.5 | 1.2 | 0.0 | 0.0 | 0.0 |
| hsa-miR-8088 | 0.0 | 0.0 | 3.2 | 0.0 | 1.3 | 0.0 | 0.0 | 0.0 | 0.0 |
| hsa-miR-4694-5p | 0.0 | 1.8 | 0.0 | 0.0 | 0.0 | 1.5 | 2.9 | 0.0 | 0.0 |
| hsa-miR-4746-5p | 0.0 | 0.0 | 0.0 | 0.0 | 0.0 | 0.0 | 0.0 | 0.0 | 0.0 |
| hsa-miR-0517-5p | 0.0 | 2.1 | 2.0 | 0.0 | 0.0 | 2.2 | 3.3 | 0.0 | 0.0 |
| hsa-miR-4302 | 0.0 | 0.0 | 0.0 | 0.0 | 0.0 | 0.0 | 0.0 | 0.0 | 0.0 |
| hsa-miR-3908 | 0.0 | 2.2 | 0.0 | 0.0 | 2.2 | 0.0 | 0.0 | 2.4 | 0.0 |
| hsa-miR-0611 | 0.0 | 1.9 | 0.0 | 0.0 | 1.7 | 0.0 | 3.3 | 0.0 | 0.0 |
| hsa-miR-0873-5p | 0.0 | 0.0 | 0.0 | 2.9 | 0.0 | 0.0 | 0.0 | 0.0 | 0.0 |
| hsa-miR-4423-5p | 0.0 | 3.2 | 1.6 | 0.0 | 2.7 | 3.2 | 0.0 | 0.0 | 0.0 |
| hsa-miR-0383-5p | 0.0 | 1.8 | 0.0 | 0.0 | 0.0 | 0.0 | 3.3 | 0.0 | 0.0 |
| hsa-miR-6500-5p | 1.7 | 3.1 | 0.0 | 0.0 | 2.2 | 2.1 | 3.3 | 2.4 | 0.0 |
| hsa-miR-4454 | 1.8 | 2.1 | 2.2 | 3.3 | 3.3 | 2.6 | 3.6 | 0.0 | 0.0 |
| hsa-miR-0203b-3p | 1.8 | 0.0 | 0.0 | 3.2 | 0.0 | 0.0 | 0.0 | 0.0 | 0.0 |
| hsa-miR-4711-5p | 0.0 | 0.0 | 0.0 | 0.0 | 0.0 | 0.0 | 0.0 | 0.0 | 0.0 |
| hsa-miR-0664a-5p | 0.0 | 2.2 | 0.0 | 0.0 | 2.0 | 1.2 | 2.8 | 0.0 | 0.0 |
| hsa-miR-0548v | 0.0 | 2.3 | 0.0 | 0.0 | 0.0 | 0.0 | 0.0 | 0.0 | 2.8 |
| hsa-miR-3916 | 0.0 | 0.0 | 0.0 | 5.6 | 0.0 | 0.0 | 0.0 | 0.0 | 0.0 |
| hsa-miR-4691-3p | 0.0 | 2.6 | 0.0 | 0.0 | 3.2 | 1.2 | 0.0 | 0.0 | 0.0 |
| hsa-miR-0548z, hsa-548h-3p | 0.0 | 0.0 | 0.0 | 6.5 | 0.0 | 0.0 | 3.3 | 0.0 | 0.0 |
| hsa-miR-0027b-5p | 0.0 | 0.0 | 0.0 | 0.0 | 0.0 | 0.0 | 0.0 | 0.0 | 0.0 |
| hsa-miR-2681-5p | 2.4 | 2.2 | 2.8 | 0.0 | 2.3 | 1.7 | 2.6 | 0.0 | 0.0 |
| hsa-miR-3161 | 2.4 | 1.9 | 3.0 | 0.0 | 2.3 | 1.7 | 3.2 | 3.1 | 0.0 |
| hsa-miR-0604 | 1.6 | 3.3 | 0.0 | 0.0 | 2.8 | 2.4 | 0.0 | 2.5 | 0.0 |
| hsa-miR-1269b | 0.0 | 2.1 | 0.0 | 4.5 | 0.0 | 0.0 | 0.0 | 0.0 | 0.0 |
| hsa-miR-4659b-3p | 0.0 | 2.4 | 0.0 | 0.0 | 0.0 | 0.0 | 0.0 | 0.0 | 0.0 |
| hsa-miR-0938 | 2.2 | 2.1 | 0.0 | 0.0 | 2.5 | 1.7 | 3.5 | 0.0 | 0.0 |
| hsa-miR-4733-3p | 2.3 | 2.3 | 0.0 | 0.0 | 2.0 | 3.1 | 3.7 | 2.7 | 0.0 |
| hsa-miR-0491-3p | 0.0 | 0.0 | 0.0 | 0.0 | 0.0 | 1.5 | 3.2 | 0.0 | 0.0 |
| hsa-miR-6505-5p | 0.0 | 0.0 | 1.8 | 0.0 | 1.3 | 0.0 | 3.0 | 0.0 | 0.0 |
| hsa-miR-0630 | 0.0 | 0.0 | 0.0 | 5.5 | 0.0 | 1.6 | 0.0 | 0.0 | 0.0 |
| hsa-miR-3688-3p | 0.0 | 0.0 | 0.0 | 0.0 | 0.0 | 0.0 | 0.0 | 0.0 | 0.0 |
| hsa-miR-3179 | 0.0 | 0.0 | 0.0 | 0.0 | 0.0 | 0.0 | 0.0 | 0.0 | 3.0 |
| hsa-miR-4755-3p | 0.0 | 0.0 | 0.0 | 0.0 | 1.6 | 0.0 | 0.0 | 0.0 | 0.0 |
| hsa-miR-6720-5p | 1.7 | 3.3 | 3.2 | 2.9 | 0.0 | 2.7 | 0.0 | 0.0 | 0.0 |
| hsa-miR-0452-3p | 3.0 | 0.0 | 4.0 | 3.5 | 0.0 | 0.0 | 0.0 | 0.0 | 0.0 |
| hsa-miR-0374b-3p | 0.0 | 0.0 | 0.0 | 6.0 | 0.0 | 0.0 | 0.0 | 0.0 | 0.0 |
| hsa-miR-0022-3p | 0.0 | 0.0 | 0.0 | 0.0 | 0.0 | 0.0 | 0.0 | 0.0 | 0.0 |
| hsa-miR-0222-3p | 1.6 | 0.0 | 0.0 | 0.0 | 1.9 | 0.0 | 0.0 | 0.0 | 0.0 |
| hsa-miR-0093-3p | 0.0 | 0.0 | 3.1 | 0.0 | 2.6 | 0.0 | 0.0 | 0.0 | 0.0 |
| hsa-miR-0200a-5p | 0.0 | 0.0 | 0.0 | 0.0 | 1.2 | 2.5 | 0.0 | 0.0 | 0.0 |
| hsa-miR-0362-3p | 0.0 | 0.0 | 0.0 | 0.0 | 2.1 | 1.9 | 0.0 | 2.3 | 0.0 |
| hsa-miR-0144-5p | 0.0 | 0.0 | 0.0 | 0.0 | 0.0 | 0.0 | 0.0 | 0.0 | 0.0 |
| hsa-miR-0628-3p | 0.0 | 0.0 | 0.0 | 0.0 | 1.6 | 1.7 | 0.0 | 0.0 | 0.0 |
| hsa-miR-0378c | 3.0 | 2.0 | 3.8 | 0.0 | 2.5 | 2.9 | 2.9 | 0.0 | 0.0 |
| hsa-miR-0335-5p | 0.0 | 0.0 | 0.0 | 0.0 | 0.0 | 0.0 | 0.0 | 0.0 | 0.0 |
| hsa-miR-7112-3p | 2.2 | 3.7 | 4.0 | 5.9 | 2.1 | 2.9 | 4.0 | 0.0 | 0.0 |
| hsa-miR-5009-3p | 0.0 | 0.0 | 0.0 | 0.0 | 0.0 | 0.0 | 0.0 | 0.0 | 0.0 |
| hsa-let-7g-5p | 0.0 | 0.0 | 0.0 | 0.0 | 0.0 | 0.0 | 0.0 | 0.0 | 0.0 |
| hsa-miR-0130a-5p | 2.2 | 3.1 | 4.2 | 3.3 | 0.0 | 2.2 | 0.0 | 0.0 | 3.2 |

TABLE 3-continued

| | | | | | | | | | |
|---|---|---|---|---|---|---|---|---|---|
| hsa-miR-0215-5p | 0.0 | 0.0 | 0.0 | 0.0 | 0.0 | 0.0 | 0.0 | 0.0 | 0.0 |
| hsa-miR-3186-3p | 3.9 | 3.1 | 3.1 | 0.0 | 4.5 | 5.5 | 3.6 | 0.0 | 0.0 |
| hsa-miR-4745-3p | 0.0 | 3.6 | 2.6 | 3.7 | 2.2 | 2.6 | 4.8 | 2.8 | 3.7 |
| hsa-miR-0449a | 0.0 | 3.0 | 0.0 | 2.5 | 2.2 | 3.0 | 0.0 | 0.0 | 0.0 |
| hsa-miR-0017-3p | 0.0 | 0.0 | 0.0 | 2.6 | 0.0 | 0.0 | 0.0 | 0.0 | 0.0 |
| hsa-miR-4786-5p | 2.7 | 3.5 | 3.0 | 0.0 | 3.0 | 3.6 | 3.6 | 3.3 | 0.0 |
| hsa-miR-5695 | 0.0 | 2.6 | 0.0 | 0.0 | 1.9 | 0.0 | 2.8 | 0.0 | 0.0 |
| hsa-miR-3927-3p | 0.0 | 0.0 | 0.0 | 0.0 | 0.0 | 0.0 | 2.7 | 0.0 | 0.0 |
| hsa-miR-0200b-5p | 0.0 | 3.1 | 0.0 | 0.0 | 3.3 | 2.6 | 0.0 | 0.0 | 0.0 |
| hsa-miR-0010a-5p | 0.0 | 0.0 | 0.0 | 5.7 | 2.5 | 0.0 | 3.5 | 0.0 | 0.0 |
| hsa-miR-0181d-3p | 0.0 | 2.3 | 3.3 | 0.0 | 2.6 | 2.4 | 0.0 | 0.0 | 0.0 |
| hsa-miR-0369-3p | 0.0 | 2.9 | 0.0 | 0.0 | 3.1 | 0.0 | 0.0 | 0.0 | 0.0 |
| hsa-miR-0578 | 0.0 | 3.1 | 0.0 | 0.0 | 2.9 | 3.7 | 0.0 | 0.0 | 2.8 |
| hsa-miR-3193 | 1.7 | 0.0 | 0.0 | 0.0 | 2.1 | 0.0 | 0.0 | 0.0 | 0.0 |
| hsa-miR-0302a-3p | 0.0 | 0.0 | 0.0 | 0.0 | 0.0 | 0.0 | 0.0 | 0.0 | 0.0 |
| hsa-miR-0549a | 0.0 | 0.0 | 0.0 | 0.0 | 0.0 | 0.0 | 0.0 | 0.0 | 0.0 |
| hsa-miR-1255b-2-3p | 0.0 | 3.3 | 0.0 | 4.9 | 0.0 | 1.4 | 0.0 | 0.0 | 0.0 |
| hsa-miR-6510-3p | 2.9 | 2.9 | 4.0 | 0.0 | 2.0 | 2.9 | 3.6 | 0.0 | 0.0 |
| hsa-miR-0363-5p | 0.0 | 2.4 | 0.0 | 0.0 | 1.6 | 1.9 | 0.0 | 0.0 | 3.4 |
| hsa-miR-0028-5p | 3.8 | 0.0 | 0.0 | 0.0 | 1.8 | 2.0 | 0.0 | 0.0 | 0.0 |
| hsa-miR-4720-5p | 0.0 | 1.8 | 0.0 | 0.0 | 0.0 | 0.0 | 3.2 | 0.0 | 0.0 |
| hsa-miR-0202-3p | 0.0 | 0.0 | 0.0 | 0.0 | 0.0 | 1.6 | 0.0 | 3.6 | 0.0 |
| hsa-miR-4255 | 1.8 | 2.3 | 0.0 | 0.0 | 2.1 | 2.8 | 0.0 | 0.0 | 0.0 |
| hsa-miR-0449c-5p | 1.9 | 3.3 | 3.6 | 0.0 | 2.9 | 2.8 | 0.0 | 2.8 | 0.0 |
| hsa-miR-0181b-3p | 0.0 | 2.4 | 0.0 | 0.0 | 0.0 | 0.0 | 0.0 | 0.0 | 0.0 |
| hsa-miR-4775 | 2.4 | 2.6 | 0.0 | 0.0 | 2.6 | 3.5 | 0.0 | 0.0 | 0.0 |
| hsa-miR-0378h | 0.0 | 3.4 | 2.5 | 0.0 | 2.3 | 1.8 | 3.1 | 2.5 | 2.9 |
| hsa-miR-0152-5p | 0.0 | 2.4 | 0.0 | 0.0 | 2.7 | 1.9 | 3.1 | 0.0 | 0.0 |
| hsa-miR-0513b-5p | 0.0 | 0.0 | 1.9 | 0.0 | 3.4 | 0.0 | 0.0 | 0.0 | 0.0 |
| hsa-miR-0029b-3p | 0.0 | 0.0 | 0.0 | 3.8 | 1.9 | 1.9 | 2.8 | 3.1 | 0.0 |
| hsa-miR-1297 | 0.0 | 0.0 | 1.9 | 0.0 | 0.0 | 2.2 | 0.0 | 0.0 | 2.7 |
| hsa-miR-0020b-3p | 0.0 | 1.8 | 1.8 | 2.8 | 1.3 | 1.8 | 0.0 | 0.0 | 0.0 |
| hsa-miR-0541-3p | 1.7 | 2.4 | 0.0 | 0.0 | 2.1 | 2.4 | 0.0 | 0.0 | 0.0 |
| hsa-miR-1301-3p | 2.5 | 0.0 | 0.0 | 0.0 | 2.8 | 2.2 | 3.1 | 0.0 | 0.0 |
| hsa-miR-3115 | 0.0 | 0.0 | 0.0 | 0.0 | 2.8 | 2.2 | 0.0 | 0.0 | 0.0 |
| hsa-miR-6807-3p | 0.0 | 0.0 | 0.0 | 0.0 | 0.0 | 0.0 | 3.1 | 0.0 | 0.0 |
| hsa-miR-0532-5p | 0.0 | 0.0 | 0.0 | 0.0 | 0.0 | 0.0 | 3.1 | 0.0 | 0.0 |
| hsa-miR-6864-3p | 3.0 | 2.8 | 3.1 | 2.3 | 2.1 | 0.0 | 0.0 | 0.0 | 2.6 |
| hsa-miR-0196a-5p | 0.0 | 0.0 | 2.5 | 0.0 | 3.1 | 1.8 | 0.0 | 0.0 | 0.0 |
| hsa-miR-4676-3p | 2.9 | 2.2 | 2.4 | 0.0 | 2.4 | 2.0 | 0.0 | 2.4 | 0.0 |
| hsa-miR-0096-3p | 0.0 | 0.0 | 0.0 | 0.0 | 0.0 | 0.0 | 0.0 | 0.0 | 0.0 |
| hsa-miR-0126-3p | 0.0 | 1.8 | 0.0 | 0.0 | 0.0 | 1.2 | 0.0 | 0.0 | 0.0 |
| hsa-miR-0550a-3-5p | 3.9 | 3.8 | 4.8 | 0.0 | 4.2 | 4.3 | 2.8 | 2.8 | 0.0 |
| hsa-miR-0378f | 0.0 | 2.2 | 0.0 | 0.0 | 2.4 | 2.4 | 0.0 | 0.0 | 0.0 |
| hsa-miR-5581-5p | 3.1 | 0.0 | 2.7 | 0.0 | 2.1 | 2.5 | 3.8 | 0.0 | 0.0 |
| hsa-miR-0627-5p | 0.0 | 0.0 | 4.1 | 0.0 | 4.7 | 0.0 | 0.0 | 0.0 | 0.0 |
| hsa-miR-0649 | 0.0 | 0.0 | 0.0 | 0.0 | 2.7 | 0.0 | 3.9 | 0.0 | 0.0 |
| hsa-miR-0626 | 0.0 | 0.0 | 0.0 | 0.0 | 0.0 | 0.0 | 3.9 | 0.0 | 0.0 |
| hsa-miR-5007-5p | 1.9 | 3.6 | 0.0 | 0.0 | 2.9 | 3.2 | 4.0 | 2.4 | 0.0 |
| hsa-miR-7107-3p | 2.0 | 2.7 | 0.0 | 3.0 | 2.5 | 3.2 | 2.5 | 0.0 | 0.0 |
| hsa-miR-0030e-3p | 2.0 | 0.0 | 2.1 | 5.8 | 1.5 | 0.0 | 0.0 | 0.0 | 0.0 |
| hsa-miR-5589-3p | 1.6 | 2.1 | 0.0 | 0.0 | 0.0 | 0.0 | 3.1 | 0.0 | 0.0 |
| hsa-miR-0128-3p | 0.0 | 0.0 | 0.0 | 0.0 | 0.0 | 0.0 | 0.0 | 0.0 | 0.0 |
| hsa-miR-0421 | 0.0 | 0.0 | 0.0 | 0.0 | 1.5 | 0.0 | 2.9 | 0.0 | 0.0 |
| hsa-miR-7856-5p | 1.8 | 3.4 | 3.1 | 0.0 | 3.1 | 1.7 | 3.2 | 0.0 | 0.0 |
| hsa-miR-0378e | 2.4 | 2.8 | 0.0 | 0.0 | 1.6 | 2.6 | 0.0 | 0.0 | 3.0 |
| hsa-miR-1205 | 0.0 | 0.0 | 0.0 | 0.0 | 1.6 | 2.3 | 0.0 | 0.0 | 0.0 |
| hsa-miR-0579-3p | 0.0 | 1.8 | 2.8 | 0.0 | 0.0 | 1.4 | 0.0 | 2.3 | 2.7 |
| hsa-miR-6839-3p | 0.0 | 1.8 | 0.0 | 0.0 | 0.0 | 0.0 | 0.0 | 0.0 | 0.0 |
| hsa-miR-0219b-3p | 0.0 | 0.0 | 0.0 | 0.0 | 0.0 | 0.0 | 0.0 | 0.0 | 0.0 |
| hsa-miR-0662 | 0.0 | 0.0 | 0.0 | 0.0 | 0.0 | 0.0 | 0.0 | 0.0 | 0.0 |
| hsa-miR-7153-3p | 2.1 | 2.4 | 2.6 | 0.0 | 0.0 | 0.0 | 0.0 | 0.0 | 0.0 |
| hsa-miR-4742-3p | 0.0 | 2.5 | 0.0 | 2.7 | 0.0 | 2.3 | 0.0 | 0.0 | 0.0 |
| hsa-miR-1303 | 1.8 | 3.9 | 5.1 | 5.4 | 4.5 | 4.4 | 0.0 | 3.8 | 2.7 |
| hsa-miR-3117-5p | 0.0 | 0.0 | 0.0 | 5.4 | 4.5 | 4.4 | 0.0 | 0.0 | 0.0 |
| hsa-miR-0576-5p | 0.0 | 2.5 | 0.0 | 2.4 | 3.2 | 1.9 | 0.0 | 0.0 | 0.0 |
| hsa-miR-0372-3p | 3.4 | 3.7 | 3.6 | 0.0 | 2.4 | 2.7 | 0.0 | 0.0 | 0.0 |
| hsa-let-7e-5p | 2.8 | 0.0 | 3.4 | 0.0 | 0.0 | 2.2 | 0.0 | 0.0 | 0.0 |
| hsa-miR-3677-5p | 0.0 | 0.0 | 0.0 | 2.4 | 0.0 | 0.0 | 2.7 | 0.0 | 0.0 |
| hsa-miR-0092a-1-5p | 0.0 | 0.0 | 3.6 | 0.0 | 0.0 | 0.0 | 0.0 | 0.0 | 0.0 |
| hsa-miR-0029a-3p | 0.0 | 0.0 | 0.0 | 0.0 | 0.0 | 2.1 | 0.0 | 0.0 | 0.0 |
| hsa-miR-0007-1-3p | 1.7 | 2.7 | 0.0 | 0.0 | 0.0 | 2.5 | 2.9 | 0.0 | 0.0 |
| hsa-miR-0450a-5p | 0.0 | 2.3 | 0.0 | 0.0 | 3.1 | 0.0 | 0.0 | 0.0 | 0.0 |
| hsa-miR-4330 | 2.2 | 3.4 | 0.0 | 0.0 | 2.4 | 2.7 | 3.6 | 3.0 | 0.0 |
| hsa-miR-0515-3p | 0.0 | 3.0 | 3.3 | 0.0 | 2.8 | 2.8 | 0.0 | 2.8 | 0.0 |
| hsa-miR-0323a-3p | 0.0 | 0.0 | 0.0 | 7.1 | 0.0 | 0.0 | 3.4 | 0.0 | 0.0 |
| hsa-miR-7159-5p | 0.0 | 3.3 | 0.0 | 2.6 | 1.8 | 3.0 | 3.4 | 0.0 | 2.8 |
| hsa-miR-4766-5p | 0.0 | 2.4 | 0.0 | 0.0 | 0.0 | 0.0 | 0.0 | 0.0 | 0.0 |
| hsa-miR-4524a-5p | 0.0 | 2.1 | 0.0 | 0.0 | 2.1 | 2.5 | 0.0 | 0.0 | 0.0 |
| hsa-miR-7843-3p | 0.0 | 2.3 | 0.0 | 2.7 | 0.0 | 2.3 | 3.0 | 0.0 | 0.0 |

TABLE 3-continued

| | | | | | | | | | |
|---|---|---|---|---|---|---|---|---|---|
| hsa-miR-6809-5p | 0.0 | 2.4 | 0.0 | 0.0 | 1.7 | 0.0 | 0.0 | 0.0 | 0.0 |
| hsa-miR-6888-5p | 2.4 | 3.1 | 0.0 | 0.0 | 2.2 | 2.9 | 2.6 | 2.9 | 0.0 |
| hsa-miR-2909 | 3.5 | 2.5 | 3.3 | 0.0 | 1.6 | 3.0 | 4.0 | 0.0 | 3.1 |
| hsa-miR-3164 | 3.5 | 3.0 | 2.9 | 0.0 | 1.6 | 3.0 | 0.0 | 0.0 | 2.6 |
| hsa-miR-4520-3p | 0.0 | 1.9 | 0.0 | 0.0 | 6.1 | 0.0 | 2.6 | 2.3 | 3.3 |
| hsa-miR-0510-5p | 0.0 | 2.6 | 2.6 | 0.0 | 2.8 | 5.2 | 3.7 | 0.0 | 3.5 |
| hsa-miR-4690-3p | 0.0 | 2.5 | 3.3 | 0.0 | 0.0 | 1.8 | 0.0 | 0.0 | 0.0 |
| hsa-miR-0026a-1-3p | 2.0 | 0.0 | 0.0 | 0.0 | 1.7 | 0.0 | 2.9 | 0.0 | 0.0 |
| hsa-miR-4793-5p | 0.0 | 0.0 | 0.0 | 0.0 | 3.8 | 1.8 | 3.1 | 0.0 | 0.0 |
| hsa-miR-0624-5p | 0.0 | 0.0 | 0.0 | 0.0 | 0.0 | 2.3 | 0.0 | 0.0 | 0.0 |
| hsa-miR-0617 | 0.0 | 0.0 | 0.0 | 0.0 | 0.0 | 2.7 | 0.0 | 0.0 | 0.0 |
| hsa-miR-0371a-3p | 2.4 | 2.8 | 2.2 | 0.0 | 3.2 | 2.6 | 0.0 | 2.8 | 3.2 |
| hsa-miR-0500a-5p | 2.5 | 2.6 | 0.0 | 0.0 | 0.0 | 3.1 | 0.0 | 0.0 | 0.0 |
| hsa-miR-3687 | 0.0 | 3.0 | 0.0 | 0.0 | 1.8 | 2.5 | 2.7 | 0.0 | 0.0 |
| hsa-miR-0378i | 3.0 | 1.8 | 0.0 | 0.0 | 0.0 | 2.7 | 0.0 | 0.0 | 3.1 |
| hsa-miR-3934-3p | 1.9 | 3.0 | 0.0 | 0.0 | 2.9 | 2.8 | 0.0 | 0.0 | 0.0 |
| hsa-miR-5688 | 1.7 | 3.2 | 0.0 | 4.3 | 0.0 | 0.0 | 0.0 | 0.0 | 0.0 |
| hsa-miR-6768-3p | 2.8 | 3.4 | 0.0 | 0.0 | 1.4 | 2.2 | 3.0 | 2.2 | 0.0 |
| hsa-miR-0010b-5p | 0.0 | 2.4 | 0.0 | 0.0 | 0.0 | 1.3 | 2.8 | 0.0 | 0.0 |
| hsa-miR-0023a-3p | 0.0 | 2.1 | 0.0 | 0.0 | 0.0 | 0.0 | 0.0 | 0.0 | 0.0 |
| hsa-miR-0373-3p | 0.0 | 0.0 | 2.2 | 6.1 | 0.0 | 0.0 | 0.0 | 0.0 | 0.0 |
| hsa-miR-0487b-3p | 0.0 | 2.8 | 0.0 | 0.0 | 1.4 | 1.4 | 0.0 | 0.0 | 2.6 |
| hsa-miR-4661-5p | 0.0 | 0.0 | 0.0 | 0.0 | 3.0 | 1.9 | 3.7 | 2.7 | 3.3 |
| hsa-miR-0767-5p | 2.8 | 3.4 | 0.0 | 4.4 | 0.0 | 2.4 | 0.0 | 0.0 | 0.0 |
| hsa-miR-0922 | 0.0 | 0.0 | 0.0 | 0.0 | 0.0 | 0.0 | 0.0 | 0.0 | 0.0 |
| hsa-miR-4677-5p | 0.0 | 2.2 | 0.0 | 0.0 | 0.0 | 0.0 | 3.5 | 0.0 | 0.0 |
| hsa-miR-0502-3p | 0.0 | 0.0 | 0.0 | 0.0 | 2.6 | 0.0 | 0.0 | 0.0 | 0.0 |
| hsa-miR-0598-5p | 2.3 | 0.0 | 2.8 | 0.0 | 2.4 | 3.4 | 3.6 | 2.2 | 0.0 |
| hsa-miR-4521 | 0.0 | 0.0 | 0.0 | 3.0 | 4.3 | 3.4 | 0.0 | 2.7 | 3.1 |
| hsa-miR-0215-3p | 0.0 | 1.8 | 0.0 | 0.0 | 0.0 | 0.0 | 2.7 | 0.0 | 0.0 |
| hsa-miR-4261 | 2.9 | 0.0 | 3.0 | 0.0 | 2.0 | 1.9 | 0.0 | 0.0 | 0.0 |
| hsa-miR-4280 | 0.0 | 1.9 | 0.0 | 0.0 | 3.0 | 1.3 | 3.2 | 0.0 | 0.0 |
| hsa-miR-0027a-3p | 0.0 | 0.0 | 0.0 | 2.4 | 0.0 | 0.0 | 0.0 | 0.0 | 0.0 |
| hsa-miR-6073 | 0.0 | 0.0 | 0.0 | 0.0 | 1.3 | 0.0 | 2.7 | 0.0 | 0.0 |
| hsa-miR-0029b-2-5p | 0.0 | 0.0 | 0.0 | 0.0 | 2.3 | 0.0 | 0.0 | 0.0 | 0.0 |
| hsa-miR-4794 | 3.3 | 3.5 | 3.3 | 5.6 | 2.6 | 3.3 | 3.2 | 0.0 | 3.5 |
| hsa-miR-4645-5p | 0.0 | 0.0 | 0.0 | 0.0 | 0.0 | 0.0 | 2.7 | 0.0 | 0.0 |
| hsa-miR-3529-3p | 0.0 | 0.0 | 0.0 | 0.0 | 0.0 | 0.0 | 3.3 | 0.0 | 0.0 |
| hsa-miR-4325 | 0.0 | 0.0 | 0.0 | 6.4 | 0.0 | 0.0 | 0.0 | 0.0 | 0.0 |
| hsa-miR-5702 | 3.0 | 2.5 | 1.7 | 5.7 | 2.9 | 2.0 | 0.0 | 0.0 | 0.0 |
| hsa-miR-4262 | 2.0 | 3.1 | 3.0 | 0.0 | 3.1 | 2.9 | 0.0 | 2.8 | 3.6 |
| hsa-miR-0891a-3p | 1.6 | 2.7 | 0.0 | 3.3 | 0.0 | 2.0 | 3.4 | 0.0 | 0.0 |
| hsa-miR-0205-5p | 2.0 | 3.1 | 2.1 | 3.1 | 2.7 | 2.5 | 0.0 | 2.6 | 0.0 |
| hsa-miR-8078 | 2.7 | 3.3 | 2.7 | 0.0 | 3.9 | 3.9 | 2.8 | 3.0 | 3.1 |
| hsa-miR-0181a-5p | 0.0 | 2.0 | 0.0 | 0.0 | 0.0 | 2.1 | 2.6 | 0.0 | 0.0 |
| hsa-miR-4314 | 0.0 | 2.5 | 1.7 | 0.0 | 2.4 | 2.1 | 2.9 | 0.0 | 3.1 |
| hsa-miR-4633-5p | 2.6 | 3.5 | 3.1 | 0.0 | 2.8 | 3.2 | 2.9 | 0.0 | 0.0 |
| hsa-miR-0502-5p | 0.0 | 0.0 | 0.0 | 0.0 | 2.0 | 0.0 | 0.0 | 0.0 | 0.0 |
| hsa-miR-0494-3p | 2.0 | 2.2 | 2.5 | 2.8 | 3.8 | 3.0 | 3.0 | 0.0 | 3.7 |
| hsa-miR-4317 | 0.0 | 0.0 | 0.0 | 0.0 | 0.0 | 1.4 | 0.0 | 0.0 | 0.0 |
| hsa-miR-5003-3p | 0.0 | 0.0 | 0.0 | 6.0 | 0.0 | 0.0 | 0.0 | 0.0 | 0.0 |
| hsa-miR-0203a-3p | 3.3 | 2.3 | 3.2 | 0.0 | 2.9 | 2.8 | 0.0 | 0.0 | 3.2 |
| hsa-miR-5693 | 2.3 | 0.0 | 0.0 | 0.0 | 2.6 | 2.6 | 3.0 | 0.0 | 0.0 |
| hsa-miR-0151b | 0.0 | 0.0 | 1.8 | 0.0 | 0.0 | 2.2 | 0.0 | 0.0 | 0.0 |
| hsa-miR-0135b-5p | 3.1 | 2.9 | 3.7 | 0.0 | 3.3 | 2.1 | 2.5 | 0.0 | 0.0 |
| hsa-miR-0614 | 0.0 | 3.7 | 4.1 | 3.7 | 3.5 | 3.3 | 4.2 | 3.1 | 0.0 |
| hsa-miR-5690 | 0.0 | 2.4 | 0.0 | 0.0 | 2.3 | 2.9 | 0.0 | 0.0 | 4.0 |
| hsa-miR-2467-5p | 0.0 | 0.0 | 0.0 | 0.0 | 0.0 | 0.0 | 0.0 | 0.0 | 0.0 |
| hsa-miR-3160-3p | 5.3 | 5.1 | 5.4 | 0.0 | 0.0 | 0.0 | 5.3 | 3.9 | 4.7 |
| hsa-miR-5011-3p | 0.0 | 0.0 | 0.0 | 0.0 | 0.0 | 0.0 | 0.0 | 0.0 | 0.0 |
| hsa-miR-0219b-5p | 0.0 | 2.7 | 5.0 | 4.8 | 1.4 | 2.2 | 3.0 | 2.6 | 0.0 |
| hsa-miR-4318 | 0.0 | 2.1 | 0.0 | 2.6 | 2.3 | 0.0 | 2.9 | 0.0 | 3.0 |
| hsa-miR-0593-5p | 0.0 | 2.1 | 0.0 | 0.0 | 3.1 | 2.2 | 3.2 | 0.0 | 0.0 |
| hsa-miR-0181b-5p | 0.0 | 3.2 | 0.0 | 0.0 | 2.2 | 3.0 | 0.0 | 0.0 | 3.0 |
| hsa-miR-0195-5p | 0.0 | 0.0 | 0.0 | 0.0 | 3.0 | 0.0 | 4.1 | 0.0 | 0.0 |
| hsa-miR-5003-5p | 0.0 | 0.0 | 0.0 | 0.0 | 0.0 | 0.0 | 0.0 | 0.0 | 0.0 |
| hsa-miR-6068 | 3.1 | 4.0 | 3.7 | 5.2 | 4.7 | 5.1 | 3.3 | 3.5 | 0.0 |
| hsa-miR-2682-5p | 0.0 | 3.0 | 2.0 | 2.4 | 3.3 | 1.8 | 2.8 | 0.0 | 0.0 |
| hsa-miR-3162-5p | 5.5 | 6.3 | 5.5 | 2.4 | 3.3 | 1.8 | 5.4 | 5.9 | 5.5 |
| hsa-miR-4494 | 1.8 | 2.3 | 0.0 | 0.0 | 1.9 | 3.2 | 0.0 | 0.0 | 3.5 |
| hsa-miR-0635 | 2.3 | 2.6 | 0.0 | 0.0 | 3.1 | 3.5 | 3.8 | 0.0 | 3.0 |
| hsa-miR-3677-3p | 0.0 | 2.1 | 3.1 | 0.0 | 2.2 | 2.5 | 0.0 | 2.5 | 0.0 |
| hsa-miR-4694-3p | 3.4 | 3.0 | 3.0 | 3.6 | 1.2 | 3.3 | 0.0 | 0.0 | 0.0 |
| hsa-miR-0676-3p | 0.0 | 0.0 | 0.0 | 0.0 | 0.0 | 1.6 | 0.0 | 0.0 | 0.0 |
| hsa-miR-0509-3-5p | 0.0 | 0.0 | 0.0 | 0.0 | 1.6 | 0.0 | 2.5 | 0.0 | 0.0 |
| hsa-miR-6832-5p | 3.3 | 3.2 | 2.9 | 0.0 | 4.0 | 3.3 | 0.0 | 0.0 | 2.8 |
| hsa-miR-3692-3p | 0.0 | 0.0 | 0.0 | 0.0 | 1.7 | 0.0 | 0.0 | 0.0 | 0.0 |
| hsa-miR-4672 | 2.3 | 2.8 | 0.0 | 0.0 | 2.5 | 2.8 | 2.7 | 0.0 | 0.0 |
| hsa-miR-0449b-5p | 0.0 | 3.4 | 2.1 | 6.8 | 0.0 | 2.2 | 0.0 | 0.0 | 0.0 |
| hsa-miR-4712-3p | 0.0 | 0.0 | 0.0 | 0.0 | 2.1 | 3.1 | 0.0 | 0.0 | 0.0 |

TABLE 3-continued

| | | | | | | | | | |
|---|---|---|---|---|---|---|---|---|---|
| hsa-miR-3622b-3p | 3.3 | 3.1 | 0.0 | 0.0 | 3.3 | 2.2 | 3.6 | 0.0 | 3.5 |
| hsa-miR-0489-5p | 2.5 | 3.3 | 0.0 | 0.0 | 3.3 | 2.8 | 0.0 | 0.0 | 0.0 |
| hsa-miR-0374b-5p | 2.8 | 0.0 | 0.0 | 0.0 | 0.0 | 0.0 | 0.0 | 0.0 | 0.0 |
| hsa-miR-4256 | 0.0 | 0.0 | 0.0 | 0.0 | 0.0 | 0.0 | 3.5 | 0.0 | 0.0 |
| hsa-miR-0411-3p | 2.0 | 2.2 | 0.0 | 0.0 | 2.9 | 3.0 | 2.5 | 0.0 | 0.0 |
| hsa-miR-2277-3p | 3.7 | 3.6 | 4.2 | 0.0 | 3.6 | 3.6 | 4.6 | 3.2 | 2.7 |
| hsa-miR-3156-3p | 5.1 | 5.6 | 4.5 | 0.0 | 3.6 | 3.6 | 4.9 | 4.2 | 4.5 |
| hsa-miR-6513-5p | 0.0 | 2.5 | 0.0 | 0.0 | 2.5 | 1.8 | 0.0 | 2.3 | 0.0 |
| hsa-miR-0023b-3p | 0.0 | 3.0 | 0.0 | 0.0 | 1.7 | 2.1 | 4.3 | 0.0 | 0.0 |
| hsa-miR-0194-5p | 2.0 | 2.5 | 0.0 | 0.0 | 1.3 | 1.5 | 0.0 | 2.2 | 3.3 |
| hsa-miR-0206 | 0.0 | 3.1 | 2.1 | 0.0 | 0.0 | 1.9 | 2.8 | 0.0 | 0.0 |
| hsa-miR-7157-3p | 1.9 | 2.3 | 0.0 | 0.0 | 2.0 | 2.0 | 0.0 | 0.0 | 0.0 |
| hsa-miR-6717-5p | 3.2 | 3.7 | 2.0 | 0.0 | 3.1 | 4.0 | 0.0 | 2.2 | 0.0 |
| hsa-miR-4295 | 0.0 | 0.0 | 3.1 | 3.6 | 1.2 | 1.9 | 3.2 | 0.0 | 0.0 |
| hsa-miR-1912 | 1.8 | 2.7 | 0.0 | 0.0 | 2.9 | 0.0 | 3.7 | 0.0 | 3.1 |
| hsa-miR-3141 | 8.1 | 8.1 | 7.9 | 0.0 | 2.9 | 0.0 | 7.0 | 7.6 | 7.0 |
| hsa-miR-0382-3p | 0.0 | 2.3 | 0.0 | 0.0 | 0.0 | 1.5 | 0.0 | 0.0 | 0.0 |
| hsa-miR-0499b-3p | 2.2 | 2.5 | 0.0 | 0.0 | 0.0 | 0.0 | 0.0 | 0.0 | 0.0 |
| hsa-miR-0098-5p | 0.0 | 0.0 | 0.0 | 0.0 | 0.0 | 0.0 | 0.0 | 3.1 | 0.0 |
| hsa-miR-0378a-5p | 4.2 | 3.3 | 3.5 | 4.4 | 0.0 | 0.0 | 4.4 | 0.0 | 2.6 |
| hsa-miR-4253 | 4.0 | 5.1 | 5.1 | 2.5 | 5.2 | 5.8 | 3.3 | 5.1 | 4.0 |
| hsa-miR-0550b-2-5p | 2.4 | 2.9 | 0.0 | 2.4 | 3.8 | 2.7 | 0.0 | 0.0 | 0.0 |
| hsa-miR-0025-5p | 2.4 | 3.0 | 3.3 | 3.4 | 3.4 | 2.5 | 0.0 | 2.3 | 0.0 |
| hsa-miR-4796-5p | 3.1 | 4.3 | 0.0 | 6.4 | 2.6 | 3.5 | 3.7 | 2.9 | 3.2 |
| hsa-miR-0015b-5p | 2.6 | 3.8 | 2.7 | 0.0 | 1.7 | 2.5 | 3.2 | 2.7 | 0.0 |
| hsa-miR-0378g | 2.1 | 3.2 | 2.8 | 0.0 | 2.3 | 3.2 | 0.0 | 0.0 | 0.0 |
| hsa-miR-5704 | 2.5 | 2.7 | 2.8 | 0.0 | 0.0 | 1.9 | 3.4 | 2.7 | 0.0 |
| hsa-miR-0512-3p | 2.5 | 2.9 | 3.3 | 0.0 | 1.3 | 1.4 | 3.3 | 0.0 | 0.0 |
| hsa-miR-0027b-3p | 0.0 | 2.6 | 3.1 | 2.5 | 2.7 | 2.8 | 3.0 | 3.4 | 0.0 |
| hsa-miR-0122-5p | 1.6 | 2.6 | 0.0 | 0.0 | 1.8 | 1.9 | 0.0 | 0.0 | 0.0 |
| hsa-miR-4729 | 0.0 | 0.0 | 0.0 | 0.0 | 0.0 | 0.0 | 0.0 | 0.0 | 3.0 |
| hsa-miR-0324-5p | 0.0 | 1.8 | 2.8 | 0.0 | 3.0 | 3.0 | 3.3 | 0.0 | 0.0 |
| hsa-miR-5681a | 3.6 | 2.3 | 0.0 | 0.0 | 2.8 | 3.0 | 3.5 | 0.0 | 0.0 |
| hsa-miR-4421 | 3.5 | 3.4 | 3.7 | 3.9 | 3.2 | 2.9 | 3.6 | 0.0 | 0.0 |
| hsa-miR-1299 | 0.0 | 0.0 | 0.0 | 2.4 | 0.0 | 0.0 | 0.0 | 0.0 | 0.0 |
| hsa-miR-0196b-5p | 0.0 | 3.7 | 0.0 | 6.7 | 2.8 | 1.3 | 2.9 | 0.0 | 0.0 |
| hsa-let-7c-3p | 0.0 | 0.0 | 0.0 | 0.0 | 1.5 | 2.4 | 0.0 | 0.0 | 0.0 |
| hsa-miR-0200b-3p | 0.0 | 2.9 | 0.0 | 0.0 | 1.7 | 0.0 | 0.0 | 0.0 | 0.0 |
| hsa-miR-0519c-5p, hsa-miR-523-5p, hsa-miR-518e-5p, hsa-miR-522-5p, hsa-miR-519a-5p, hsa-miR-519b-5p | 0.0 | 0.0 | 3.1 | 0.0 | 3.8 | 3.1 | 2.8 | 0.0 | 0.0 |
| hsa-miR-6839-5p | 2.9 | 3.2 | 2.8 | 0.0 | 2.5 | 4.0 | 3.3 | 2.5 | 2.8 |
| hsa-miR-6818-5p | 1.6 | 2.0 | 2.8 | 0.0 | 2.4 | 2.4 | 0.0 | 0.0 | 3.2 |
| hsa-miR-6837-3p | 4.4 | 3.2 | 4.2 | 4.6 | 1.5 | 2.0 | 4.0 | 0.0 | 0.0 |
| hsa-miR-3936 | 3.3 | 2.0 | 4.3 | 0.0 | 2.6 | 3.7 | 2.6 | 0.0 | 0.0 |
| hsa-miR-6783-5p | 0.0 | 3.1 | 0.0 | 3.9 | 1.8 | 0.0 | 2.8 | 0.0 | 0.0 |
| hsa-miR-1911-3p | 3.4 | 2.4 | 2.5 | 2.7 | 3.1 | 1.9 | 0.0 | 0.0 | 0.0 |
| hsa-miR-3140-3p | 0.0 | 0.0 | 0.0 | 2.7 | 3.1 | 1.9 | 0.0 | 0.0 | 0.0 |
| hsa-miR-6770-5p | 1.8 | 2.6 | 0.0 | 3.3 | 0.0 | 2.6 | 3.4 | 2.4 | 0.0 |
| hsa-miR-4527 | 3.2 | 2.6 | 1.7 | 0.0 | 0.0 | 2.4 | 2.7 | 0.0 | 3.0 |
| hsa-miR-8055 | 3.5 | 3.4 | 1.9 | 2.8 | 3.2 | 3.2 | 3.3 | 0.0 | 3.3 |
| hsa-miR-3678-5p | 1.6 | 3.0 | 0.0 | 0.0 | 1.5 | 2.1 | 0.0 | 0.0 | 0.0 |
| hsa-miR-4451 | 2.2 | 3.7 | 0.0 | 3.3 | 3.8 | 3.1 | 3.3 | 0.0 | 0.0 |
| hsa-miR-4783-5p | 0.0 | 3.6 | 3.3 | 3.7 | 2.9 | 3.1 | 3.5 | 4.2 | 3.1 |
| hsa-miR-0380-5p | 0.0 | 0.0 | 0.0 | 0.0 | 1.4 | 0.0 | 3.7 | 0.0 | 0.0 |
| hsa-miR-0610 | 0.0 | 0.0 | 0.0 | 0.0 | 2.5 | 2.4 | 2.5 | 0.0 | 0.0 |
| hsa-miR-4660 | 2.6 | 3.2 | 0.0 | 0.0 | 3.9 | 3.1 | 0.0 | 2.4 | 0.0 |
| hsa-miR-6715b-5p | 0.0 | 3.0 | 2.2 | 0.0 | 2.3 | 2.0 | 0.0 | 0.0 | 0.0 |
| hsa-let-7i-5p | 0.0 | 3.3 | 0.0 | 6.2 | 2.8 | 2.2 | 0.0 | 0.0 | 0.0 |
| hsa-miR-0153-5p | 1.5 | 2.5 | 2.1 | 0.0 | 1.5 | 2.9 | 3.6 | 0.0 | 0.0 |
| hsa-miR-1245a | 0.0 | 0.0 | 0.0 | 0.0 | 0.0 | 0.0 | 0.0 | 0.0 | 0.0 |
| hsa-miR-2276-5p | 2.6 | 3.4 | 0.0 | 0.0 | 3.0 | 3.5 | 3.6 | 3.1 | 3.4 |
| hsa-miR-3155b | 3.3 | 4.2 | 3.1 | 0.0 | 3.0 | 3.5 | 4.2 | 2.8 | 0.0 |
| hsa-miR-0425-5p | 0.0 | 2.3 | 0.0 | 6.9 | 1.3 | 0.0 | 0.0 | 0.0 | 0.0 |
| hsa-miR-0888-3p | 0.0 | 2.4 | 0.0 | 0.0 | 1.7 | 0.0 | 0.0 | 0.0 | 0.0 |
| hsa-miR-0369-5p | 1.9 | 2.3 | 0.0 | 0.0 | 1.6 | 2.2 | 3.6 | 0.0 | 0.0 |
| hsa-miR-0034c-5p | 4.8 | 3.7 | 4.4 | 0.0 | 2.8 | 2.4 | 2.6 | 0.0 | 0.0 |
| hsa-miR-0585-3p | 0.0 | 0.0 | 3.1 | 6.1 | 0.0 | 0.0 | 0.0 | 0.0 | 0.0 |
| hsa-miR-0378d | 0.0 | 0.0 | 0.0 | 0.0 | 0.0 | 2.4 | 0.0 | 0.0 | 0.0 |
| hsa-miR-0605-3p | 0.0 | 0.0 | 0.0 | 0.0 | 0.0 | 0.0 | 0.0 | 0.0 | 0.0 |
| hsa-miR-4491 | 0.0 | 0.0 | 0.0 | 2.9 | 1.5 | 2.1 | 0.0 | 0.0 | 0.0 |
| hsa-miR-0525-3p | 0.0 | 2.0 | 2.8 | 0.0 | 2.4 | 2.0 | 0.0 | 2.5 | 0.0 |
| hsa-miR-0548ay-3p | 2.0 | 2.6 | 2.6 | 2.9 | 0.0 | 0.0 | 4.1 | 2.3 | 3.4 |
| hsa-miR-7162-5p | 0.0 | 1.8 | 0.0 | 6.6 | 0.0 | 0.0 | 3.1 | 0.0 | 0.0 |
| hsa-miR-4800-3p | 0.0 | 3.2 | 0.0 | 5.1 | 2.5 | 3.1 | 3.3 | 2.5 | 3.3 |
| hsa-miR-1286 | 2.3 | 2.1 | 2.1 | 0.0 | 2.1 | 2.0 | 2.9 | 2.4 | 0.0 |
| hsa-miR-0942-3p | 3.3 | 0.0 | 0.0 | 0.0 | 3.6 | 3.3 | 3.9 | 0.0 | 0.0 |

TABLE 3-continued

| | | | | | | | | | |
|---|---|---|---|---|---|---|---|---|---|
| hsa-miR-4771 | 0.0 | 3.1 | 0.0 | 3.5 | 0.0 | 1.8 | 3.1 | 0.0 | 2.8 |
| hsa-miR-3682-3p | 2.7 | 3.5 | 0.0 | 0.0 | 3.3 | 4.5 | 3.5 | 3.1 | 0.0 |
| hsa-miR-8083 | 3.1 | 4.0 | 1.8 | 0.0 | 4.5 | 4.4 | 4.6 | 3.5 | 2.9 |
| hsa-miR-6513-3p | 2.2 | 3.2 | 2.6 | 0.0 | 2.9 | 2.7 | 0.0 | 0.0 | 0.0 |
| hsa-miR-3929 | 2.1 | 2.8 | 0.0 | 6.8 | 2.4 | 2.8 | 0.0 | 0.0 | 0.0 |
| hsa-miR-3200-3p | 2.8 | 2.3 | 0.0 | 3.1 | 0.0 | 2.2 | 0.0 | 2.2 | 2.8 |
| hsa-miR-4703-3p | 0.0 | 3.5 | 0.0 | 0.0 | 2.3 | 2.8 | 0.0 | 2.5 | 0.0 |
| hsa-miR-3918 | 3.6 | 3.3 | 3.5 | 0.0 | 2.9 | 3.7 | 2.6 | 2.5 | 0.0 |
| hsa-miR-0650 | 2.0 | 3.3 | 3.0 | 0.0 | 5.0 | 6.1 | 0.0 | 0.0 | 0.0 |
| hsa-miR-0034b-5p | 2.2 | 2.1 | 0.0 | 0.0 | 2.6 | 2.0 | 3.3 | 0.0 | 2.7 |
| hsa-miR-4524b-5p | 0.0 | 2.6 | 0.0 | 0.0 | 2.5 | 0.0 | 0.0 | 0.0 | 0.0 |
| hsa-miR-4644 | 3.4 | 4.1 | 0.0 | 0.0 | 2.7 | 3.0 | 3.1 | 2.4 | 0.0 |
| hsa-miR-4283 | 0.0 | 3.4 | 0.0 | 0.0 | 3.0 | 3.8 | 3.1 | 2.3 | 0.0 |
| hsa-miR-5696 | 0.0 | 2.7 | 0.0 | 0.0 | 0.0 | 2.9 | 0.0 | 0.0 | 0.0 |
| hsa-miR-0127-5p | 0.0 | 0.0 | 0.0 | 2.6 | 3.2 | 0.0 | 2.6 | 0.0 | 0.0 |
| hsa-miR-3666 | 3.9 | 4.8 | 4.8 | 0.0 | 5.0 | 4.1 | 2.6 | 3.4 | 3.2 |
| hsa-miR-4786-3p | 0.0 | 3.7 | 3.2 | 0.0 | 3.1 | 3.0 | 4.0 | 3.0 | 0.0 |
| hsa-miR-0138-2-3p | 0.0 | 4.0 | 0.0 | 0.0 | 3.2 | 2.2 | 2.7 | 2.2 | 0.0 |
| hsa-miR-1276 | 0.0 | 2.9 | 0.0 | 0.0 | 2.9 | 3.2 | 0.0 | 2.3 | 0.0 |
| hsa-miR-4709-5p | 1.7 | 3.6 | 2.3 | 0.0 | 0.0 | 2.2 | 3.5 | 0.0 | 0.0 |
| hsa-miR-4681 | 0.0 | 3.7 | 1.9 | 0.0 | 3.1 | 3.4 | 3.8 | 2.2 | 0.0 |
| hsa-miR-5094 | 1.9 | 3.2 | 2.2 | 0.0 | 3.2 | 3.3 | 0.0 | 2.4 | 0.0 |
| hsa-miR-0431-5p | 0.0 | 2.1 | 0.0 | 0.0 | 0.0 | 0.0 | 3.4 | 0.0 | 2.8 |
| hsa-miR-0383-3p | 3.4 | 3.5 | 3.0 | 3.1 | 2.6 | 2.7 | 3.2 | 0.0 | 3.1 |
| hsa-miR-0183-5p | 0.0 | 0.0 | 2.1 | 0.0 | 0.0 | 0.0 | 3.5 | 0.0 | 3.2 |
| hsa-miR-3678-3p | 2.2 | 0.0 | 0.0 | 0.0 | 3.6 | 3.3 | 0.0 | 2.4 | 3.3 |
| hsa-miR-0370-5p | 0.0 | 2.0 | 1.8 | 0.0 | 0.0 | 1.9 | 0.0 | 0.0 | 0.0 |
| hsa-miR-4755-5p | 3.1 | 2.2 | 0.0 | 0.0 | 2.1 | 2.6 | 3.9 | 0.0 | 0.0 |
| hsa-miR-3605-5p | 3.0 | 3.3 | 4.1 | 0.0 | 3.5 | 3.7 | 0.0 | 0.0 | 0.0 |
| hsa-miR-0654-5p | 3.3 | 3.1 | 4.2 | 0.0 | 4.1 | 4.4 | 3.2 | 3.5 | 0.0 |
| hsa-miR-0579-5p | 2.7 | 3.3 | 2.8 | 0.0 | 2.1 | 3.6 | 2.7 | 0.0 | 3.1 |
| hsa-miR-8080 | 1.7 | 2.7 | 0.0 | 0.0 | 3.1 | 3.3 | 0.0 | 2.4 | 2.7 |
| hsa-miR-4437 | 2.6 | 4.3 | 1.7 | 0.0 | 3.3 | 3.0 | 0.0 | 2.6 | 0.0 |
| hsa-miR-7853-5p | 3.7 | 3.0 | 2.6 | 0.0 | 2.4 | 2.7 | 3.3 | 2.3 | 0.0 |
| hsa-miR-6718-5p | 3.0 | 3.4 | 0.0 | 0.0 | 3.1 | 3.6 | 0.0 | 3.0 | 0.0 |
| hsa-miR-6501-5p | 2.6 | 2.1 | 1.7 | 6.6 | 0.0 | 2.9 | 0.0 | 0.0 | 0.0 |
| hsa-miR-7641 | 0.0 | 3.9 | 4.4 | 3.5 | 3.8 | 3.7 | 3.8 | 4.5 | 4.1 |
| hsa-miR-0495-5p | 3.7 | 4.1 | 0.0 | 2.7 | 3.7 | 3.0 | 3.9 | 2.2 | 3.4 |
| hsa-miR-0888-5p | 3.4 | 2.4 | 0.0 | 0.0 | 2.4 | 3.2 | 4.6 | 0.0 | 0.0 |
| hsa-miR-5188 | 3.1 | 3.5 | 2.2 | 0.0 | 1.9 | 2.5 | 4.2 | 2.9 | 2.6 |
| hsa-miR-3174 | 3.3 | 3.4 | 3.2 | 0.0 | 3.0 | 2.4 | 0.0 | 2.3 | 2.8 |
| hsa-miR-0548ax | 0.0 | 2.3 | 0.0 | 2.5 | 0.0 | 1.6 | 0.0 | 0.0 | 3.4 |
| hsa-miR-1284 | 3.0 | 3.6 | 1.7 | 0.0 | 2.3 | 3.4 | 0.0 | 0.0 | 0.0 |
| hsa-miR-4724-3p | 0.0 | 2.2 | 5.5 | 0.0 | 2.2 | 2.0 | 0.0 | 0.0 | 0.0 |
| hsa-miR-4275 | 1.7 | 0.0 | 1.6 | 0.0 | 0.0 | 0.0 | 0.0 | 0.0 | 0.0 |
| hsa-miR-0193b-5p | 2.4 | 3.8 | 1.9 | 0.0 | 0.0 | 3.4 | 3.6 | 2.6 | 0.0 |
| hsa-miR-5006-5p | 3.4 | 3.7 | 3.3 | 4.5 | 4.9 | 5.1 | 4.0 | 3.6 | 0.0 |
| hsa-miR-4650-5p | 2.0 | 2.7 | 0.0 | 0.0 | 1.5 | 2.7 | 0.0 | 0.0 | 0.0 |
| hsa-miR-4465 | 2.7 | 3.0 | 2.0 | 0.0 | 4.0 | 3.2 | 2.7 | 0.0 | 2.6 |
| hsa-miR-0320c | 0.0 | 0.0 | 0.0 | 2.9 | 1.7 | 2.0 | 0.0 | 0.0 | 0.0 |
| hsa-miR-0030a-3p | 2.1 | 3.7 | 0.0 | 0.0 | 3.5 | 2.1 | 2.6 | 2.3 | 0.0 |
| hsa-miR-0892a | 0.0 | 2.9 | 0.0 | 2.8 | 2.7 | 2.2 | 0.0 | 2.5 | 2.7 |
| hsa-miR-0668-5p | 2.8 | 3.5 | 3.8 | 2.4 | 4.2 | 4.3 | 0.0 | 3.6 | 0.0 |
| hsa-miR-8057 | 3.3 | 4.3 | 3.4 | 0.0 | 3.6 | 4.9 | 0.0 | 2.2 | 3.4 |
| hsa-miR-3200-5p | 2.9 | 3.2 | 3.1 | 0.0 | 2.3 | 3.0 | 0.0 | 0.0 | 0.0 |
| hsa-miR-6874-5p | 0.0 | 2.8 | 0.0 | 0.0 | 3.3 | 3.2 | 3.2 | 0.0 | 0.0 |
| hsa-miR-0338-3p | 3.2 | 3.3 | 0.0 | 2.5 | 4.3 | 1.8 | 3.4 | 2.8 | 3.3 |
| hsa-miR-0184 | 0.0 | 2.8 | 2.3 | 0.0 | 0.0 | 1.5 | 3.4 | 2.3 | 2.7 |
| hsa-miR-5096 | 0.0 | 2.7 | 0.0 | 0.0 | 3.6 | 3.6 | 0.0 | 2.4 | 0.0 |
| hsa-miR-7848-3p | 4.0 | 4.2 | 3.9 | 3.3 | 3.4 | 2.9 | 3.3 | 0.0 | 0.0 |
| hsa-miR-6081 | 0.0 | 4.2 | 3.9 | 6.1 | 3.2 | 4.3 | 4.2 | 4.3 | 0.0 |
| hsa-miR-0196b-3p | 2.9 | 4.0 | 3.8 | 0.0 | 3.4 | 3.6 | 3.2 | 2.9 | 0.0 |
| hsa-miR-0147a | 3.1 | 3.0 | 2.7 | 0.0 | 3.5 | 3.5 | 0.0 | 3.8 | 2.9 |
| hsa-let-7b-5p | 3.0 | 2.9 | 2.8 | 0.0 | 3.3 | 3.7 | 0.0 | 3.4 | 3.0 |
| hsa-miR-0143-3p | 2.0 | 2.6 | 0.0 | 0.0 | 0.0 | 1.7 | 3.1 | 2.5 | 0.0 |
| hsa-miR-1273e | 2.8 | 3.3 | 0.0 | 0.0 | 3.8 | 4.1 | 0.0 | 3.8 | 0.0 |
| hsa-miR-4712-5p | 3.3 | 4.0 | 0.0 | 0.0 | 3.0 | 3.4 | 2.9 | 0.0 | 3.2 |
| hsa-miR-5011-5p | 0.0 | 0.0 | 0.0 | 0.0 | 0.0 | 0.0 | 3.0 | 0.0 | 0.0 |
| hsa-miR-0514b-3p | 2.0 | 2.0 | 0.0 | 0.0 | 0.0 | 2.5 | 2.7 | 0.0 | 0.0 |
| hsa-miR-0325 | 2.1 | 3.8 | 2.8 | 0.0 | 1.9 | 2.3 | 3.7 | 2.2 | 3.2 |
| hsa-miR-4482-5p | 2.5 | 3.0 | 0.0 | 2.4 | 1.7 | 2.6 | 3.6 | 0.0 | 0.0 |
| hsa-miR-4303 | 2.2 | 3.9 | 0.0 | 3.8 | 3.7 | 3.9 | 2.9 | 2.8 | 0.0 |
| hsa-miR-5680 | 2.3 | 3.3 | 0.0 | 0.0 | 1.8 | 2.7 | 4.5 | 0.0 | 0.0 |
| hsa-miR-0664b-5p | 0.0 | 3.4 | 0.0 | 0.0 | 2.3 | 2.7 | 0.0 | 0.0 | 0.0 |
| hsa-miR-6853-5p | 3.2 | 3.5 | 3.5 | 0.0 | 2.9 | 3.9 | 3.7 | 0.0 | 0.0 |
| hsa-miR-4752 | 4.3 | 3.1 | 3.3 | 0.0 | 2.8 | 3.0 | 0.0 | 0.0 | 0.0 |
| hsa-miR-5002-5p | 2.2 | 2.4 | 0.0 | 0.0 | 0.0 | 0.0 | 0.0 | 0.0 | 0.0 |
| hsa-miR-4524b-3p | 2.8 | 4.0 | 0.0 | 0.0 | 1.7 | 4.0 | 2.6 | 0.0 | 2.7 |
| hsa-miR-0589-3p | 2.8 | 3.0 | 2.3 | 0.0 | 0.0 | 3.0 | 0.0 | 0.0 | 0.0 |
| hsa-miR-1271-5p | 1.6 | 3.3 | 0.0 | 0.0 | 2.8 | 3.2 | 2.9 | 2.2 | 3.2 |

TABLE 3-continued

| | | | | | | | | | |
|---|---|---|---|---|---|---|---|---|---|
| hsa-miR-6509-5p | 2.3 | 3.3 | 0.0 | 7.8 | 3.2 | 2.6 | 0.0 | 2.3 | 0.0 |
| hsa-miR-4638-3p | 0.0 | 3.2 | 3.0 | 3.0 | 2.4 | 3.3 | 4.2 | 3.9 | 2.6 |
| hsa-miR-5689 | 0.0 | 1.9 | 0.0 | 0.0 | 1.8 | 2.7 | 3.3 | 0.0 | 0.0 |
| hsa-miR-8084 | 0.0 | 2.7 | 0.0 | 0.0 | 0.0 | 3.4 | 0.0 | 0.0 | 0.0 |
| hsa-miR-1295b-3p | 2.9 | 2.9 | 2.5 | 0.0 | 1.6 | 3.1 | 4.2 | 2.7 | 3.2 |
| hsa-miR-7154-3p | 1.7 | 2.1 | 1.8 | 6.4 | 0.0 | 2.4 | 0.0 | 0.0 | 0.0 |
| hsa-miR-5095 | 2.5 | 3.6 | 2.2 | 0.0 | 3.6 | 3.6 | 0.0 | 2.5 | 0.0 |
| hsa-miR-4273 | 2.9 | 3.7 | 3.7 | 0.0 | 2.7 | 2.8 | 0.0 | 2.4 | 0.0 |
| hsa-miR-0145-5p | 1.7 | 0.0 | 2.5 | 0.0 | 2.3 | 1.3 | 3.5 | 0.0 | 3.0 |
| hsa-miR-0142-3p | 0.0 | 3.1 | 0.0 | 0.0 | 2.4 | 1.7 | 0.0 | 0.0 | 0.0 |
| hsa-miR-4657 | 0.0 | 3.9 | 1.6 | 0.0 | 4.0 | 4.3 | 2.7 | 3.5 | 0.0 |
| hsa-miR-0519a-3p | 0.0 | 1.9 | 3.0 | 0.0 | 0.0 | 0.0 | 3.1 | 2.4 | 0.0 |
| hsa-miR-3689f | 2.2 | 3.1 | 1.8 | 0.0 | 1.2 | 1.8 | 3.4 | 0.0 | 0.0 |
| hsa-miR-5571-3p | 2.8 | 3.2 | 2.1 | 0.0 | 2.9 | 3.0 | 2.7 | 0.0 | 0.0 |
| hsa-miR-0566 | 0.0 | 2.4 | 3.0 | 3.9 | 3.9 | 3.3 | 4.4 | 2.8 | 4.4 |
| hsa-miR-0138-5p | 2.2 | 3.3 | 3.5 | 0.0 | 4.3 | 3.9 | 3.3 | 0.0 | 3.0 |
| hsa-miR-0526b-3p | 4.3 | 3.6 | 1.7 | 0.0 | 0.0 | 2.6 | 3.6 | 0.0 | 2.9 |
| hsa-miR-4717-5p | 2.8 | 3.1 | 0.0 | 0.0 | 3.4 | 3.2 | 3.1 | 2.3 | 0.0 |
| hsa-miR-5591-3p | 0.0 | 3.4 | 0.0 | 0.0 | 2.6 | 3.0 | 0.0 | 0.0 | 0.0 |
| hsa-miR-4254 | 3.8 | 3.7 | 0.0 | 0.0 | 0.0 | 2.9 | 3.8 | 2.3 | 4.0 |
| hsa-miR-3682-5p | 0.0 | 2.7 | 2.7 | 2.5 | 2.8 | 2.4 | 0.0 | 0.0 | 0.0 |
| hsa-miR-6506-5p | 1.8 | 3.8 | 0.0 | 0.0 | 3.1 | 2.8 | 3.2 | 3.0 | 0.0 |
| hsa-miR-8082 | 2.5 | 3.5 | 0.0 | 0.0 | 3.4 | 3.5 | 0.0 | 3.0 | 0.0 |
| hsa-miR-7974 | 2.9 | 3.8 | 3.0 | 0.0 | 3.6 | 3.2 | 0.0 | 3.1 | 3.0 |
| hsa-miR-4999-5p | 0.0 | 3.3 | 0.0 | 0.0 | 3.8 | 3.2 | 3.2 | 0.0 | 0.0 |
| hsa-miR-4797-3p | 1.8 | 2.6 | 2.0 | 0.0 | 2.0 | 2.7 | 3.5 | 0.0 | 2.9 |
| hsa-miR-4264 | 0.0 | 2.5 | 2.1 | 0.0 | 0.0 | 0.0 | 2.9 | 0.0 | 0.0 |
| hsa-miR-0378b | 4.2 | 4.1 | 3.5 | 0.0 | 2.0 | 3.2 | 0.0 | 0.0 | 0.0 |
| hsa-miR-0323a-5p | 3.4 | 4.4 | 3.3 | 0.0 | 2.8 | 3.9 | 4.3 | 3.5 | 0.0 |
| hsa-miR-3713 | 3.9 | 3.4 | 3.8 | 0.0 | 2.0 | 3.8 | 2.7 | 0.0 | 0.0 |
| hsa-miR-4308 | 2.1 | 2.9 | 2.4 | 0.0 | 2.3 | 1.4 | 3.3 | 0.0 | 0.0 |
| hsa-miR-0942-5p | 2.4 | 2.6 | 3.5 | 0.0 | 1.9 | 1.6 | 0.0 | 0.0 | 0.0 |
| hsa-miR-4450 | 3.3 | 3.9 | 2.5 | 2.4 | 2.9 | 4.1 | 4.8 | 4.0 | 3.9 |
| hsa-miR-0146a-5p | 2.8 | 4.5 | 2.4 | 6.2 | 1.6 | 2.4 | 0.0 | 0.0 | 0.0 |
| hsa-miR-0329-5p | 2.8 | 4.0 | 2.0 | 0.0 | 3.8 | 3.0 | 3.6 | 0.0 | 0.0 |
| hsa-miR-1178-3p | 2.9 | 3.7 | 3.6 | 0.0 | 2.2 | 2.7 | 2.5 | 0.0 | 0.0 |
| hsa-miR-3922-5p | 3.8 | 4.1 | 2.7 | 3.6 | 3.1 | 3.2 | 3.6 | 2.6 | 3.0 |
| hsa-miR-6811-3p | 3.4 | 2.7 | 3.3 | 2.7 | 0.0 | 2.1 | 4.0 | 0.0 | 0.0 |
| hsa-miR-6781-3p | 3.5 | 4.1 | 4.1 | 0.0 | 3.4 | 3.3 | 3.0 | 0.0 | 0.0 |
| hsa-miR-3651 | 2.5 | 3.6 | 3.4 | 0.0 | 2.9 | 3.4 | 3.1 | 3.1 | 2.7 |
| hsa-miR-0021-3p | 2.4 | 2.8 | 2.5 | 0.0 | 3.6 | 3.3 | 3.5 | 0.0 | 2.6 |
| hsa-miR-6817-5p | 2.2 | 4.1 | 2.6 | 0.0 | 3.5 | 3.3 | 0.0 | 3.3 | 0.0 |
| hsa-miR-0195-3p | 2.5 | 0.0 | 0.0 | 0.0 | 3.0 | 2.5 | 4.1 | 2.5 | 0.0 |
| hsa-miR-3913-3p | 0.0 | 2.4 | 2.7 | 2.9 | 2.0 | 2.6 | 0.0 | 0.0 | 0.0 |
| hsa-miR-0339-5p | 3.1 | 3.1 | 3.5 | 0.0 | 2.8 | 2.9 | 3.6 | 3.3 | 3.2 |
| hsa-miR-4718 | 3.4 | 3.3 | 2.8 | 0.0 | 2.4 | 2.1 | 3.5 | 0.0 | 3.7 |
| hsa-miR-0584-5p | 3.8 | 3.5 | 1.9 | 0.0 | 4.0 | 3.3 | 3.3 | 2.7 | 0.0 |
| hsa-miR-0345-5p | 1.9 | 3.7 | 2.8 | 0.0 | 3.1 | 2.3 | 0.0 | 2.3 | 2.7 |
| hsa-miR-7155-3p | 3.9 | 4.3 | 4.6 | 0.0 | 3.7 | 4.0 | 3.3 | 2.8 | 0.0 |
| hsa-miR-6505-3p | 4.0 | 4.3 | 3.7 | 0.0 | 3.5 | 3.2 | 3.5 | 3.0 | 3.0 |
| hsa-miR-1251-3p | 2.5 | 3.2 | 2.6 | 0.0 | 1.8 | 3.0 | 0.0 | 2.4 | 3.1 |
| hsa-miR-3690 | 2.6 | 3.1 | 0.0 | 0.0 | 4.0 | 3.1 | 3.4 | 0.0 | 2.8 |
| hsa-miR-5000-5p | 2.5 | 2.5 | 0.0 | 0.0 | 1.4 | 2.8 | 0.0 | 0.0 | 2.9 |
| hsa-miR-0596 | 0.0 | 3.4 | 1.9 | 0.0 | 3.3 | 3.2 | 3.4 | 4.1 | 0.0 |
| hsa-miR-0591 | 2.6 | 3.8 | 2.0 | 0.0 | 3.0 | 3.4 | 0.0 | 0.0 | 0.0 |
| hsa-miR-4658 | 2.8 | 3.2 | 3.9 | 0.0 | 2.2 | 3.2 | 0.0 | 0.0 | 0.0 |
| hsa-miR-3680-3p | 3.8 | 3.8 | 3.9 | 0.0 | 3.5 | 3.4 | 2.5 | 2.6 | 0.0 |
| hsa-miR-0379-3p | 2.1 | 3.6 | 0.0 | 0.0 | 3.8 | 2.3 | 3.1 | 0.0 | 3.2 |
| hsa-miR-0020a-3p | 3.1 | 0.0 | 3.7 | 0.0 | 4.2 | 1.6 | 0.0 | 0.0 | 0.0 |
| hsa-miR-5093 | 2.5 | 3.4 | 0.0 | 0.0 | 3.9 | 3.7 | 4.1 | 3.2 | 3.4 |
| hsa-miR-0524-5p | 2.6 | 2.8 | 1.7 | 0.0 | 2.1 | 2.3 | 0.0 | 0.0 | 3.6 |
| hsa-miR-4733-5p | 3.1 | 3.5 | 0.0 | 3.2 | 3.2 | 3.4 | 0.0 | 0.0 | 0.0 |
| hsa-miR-0619-5p | 3.4 | 3.6 | 1.7 | 3.1 | 3.7 | 3.9 | 2.6 | 4.6 | 0.0 |
| hsa-miR-0214-5p | 6.9 | 4.4 | 4.3 | 3.5 | 3.5 | 2.7 | 0.0 | 2.7 | 3.2 |
| hsa-miR-0423-3p | 3.9 | 3.1 | 3.9 | 2.5 | 3.4 | 2.3 | 3.9 | 0.0 | 2.9 |
| hsa-miR-6838-5p | 2.3 | 3.3 | 2.5 | 4.1 | 0.0 | 2.2 | 5.0 | 2.5 | 0.0 |
| hsa-miR-3186-5p | 3.0 | 4.2 | 2.8 | 5.0 | 3.4 | 3.0 | 4.7 | 2.6 | 0.0 |
| hsa-miR-6083 | 3.9 | 4.0 | 3.4 | 0.0 | 3.1 | 3.5 | 0.0 | 2.7 | 0.0 |
| hsa-miR-6761-5p | 3.4 | 4.1 | 2.7 | 0.0 | 3.6 | 2.8 | 3.7 | 3.1 | 0.0 |
| hsa-miR-0103a-2-5p | 0.0 | 2.9 | 0.0 | 0.0 | 0.0 | 2.8 | 2.5 | 0.0 | 0.0 |
| hsa-miR-6895-5p | 3.5 | 4.3 | 3.6 | 6.1 | 3.7 | 4.2 | 4.4 | 4.0 | 0.0 |
| hsa-miR-4645-3p | 3.2 | 3.0 | 4.2 | 0.0 | 3.6 | 3.5 | 0.0 | 0.0 | 0.0 |
| hsa-miR-0300 | 0.0 | 3.9 | 0.0 | 0.0 | 3.7 | 2.7 | 3.8 | 0.0 | 2.6 |
| hsa-miR-5089-3p | 2.8 | 3.1 | 0.0 | 7.5 | 2.8 | 1.9 | 0.0 | 0.0 | 0.0 |
| hsa-miR-4740-3p | 3.7 | 4.1 | 3.4 | 4.7 | 3.5 | 3.7 | 4.9 | 3.6 | 3.0 |
| hsa-miR-0511-5p | 3.4 | 2.7 | 3.4 | 4.0 | 2.4 | 1.6 | 4.0 | 0.0 | 0.0 |
| hsa-miR-6514-5p | 2.3 | 3.2 | 3.7 | 2.4 | 4.0 | 4.1 | 3.2 | 2.4 | 0.0 |
| hsa-miR-1288-5p | 2.0 | 3.7 | 0.0 | 0.0 | 0.0 | 3.0 | 3.1 | 0.0 | 3.0 |
| hsa-miR-0454-5p | 0.0 | 2.7 | 0.0 | 0.0 | 1.6 | 1.9 | 3.2 | 0.0 | 0.0 |
| hsa-miR-0645 | 2.8 | 2.7 | 0.0 | 3.9 | 2.9 | 2.8 | 0.0 | 0.0 | 0.0 |

TABLE 3-continued

| | | | | | | | | | |
|---|---|---|---|---|---|---|---|---|---|
| hsa-miR-3190-3p | 3.8 | 3.8 | 3.5 | 0.0 | 4.2 | 4.1 | 3.0 | 3.1 | 0.0 |
| hsa-miR-4438 | 2.8 | 3.0 | 0.0 | 0.0 | 0.0 | 1.7 | 0.0 | 2.4 | 0.0 |
| hsa-miR-0519d-5p | 0.0 | 2.4 | 0.0 | 0.0 | 0.0 | 0.0 | 3.0 | 0.0 | 2.7 |
| hsa-miR-1199-3p | 3.3 | 3.6 | 3.7 | 0.0 | 4.0 | 4.2 | 2.9 | 3.2 | 0.0 |
| hsa-miR-0330-3p | 0.0 | 2.5 | 0.0 | 0.0 | 3.3 | 1.9 | 4.3 | 0.0 | 2.9 |
| hsa-miR-0030c-5p | 2.6 | 3.4 | 0.0 | 2.6 | 2.4 | 2.5 | 0.0 | 0.0 | 3.3 |
| hsa-miR-7973 | 2.3 | 3.5 | 2.3 | 0.0 | 2.5 | 3.2 | 0.0 | 0.0 | 0.0 |
| hsa-miR-0509-3p | 3.0 | 3.2 | 4.1 | 0.0 | 5.0 | 4.7 | 0.0 | 3.4 | 2.8 |
| hsa-miR-1298-3p | 3.5 | 4.3 | 3.2 | 0.0 | 2.9 | 3.8 | 4.5 | 2.9 | 3.4 |
| hsa-miR-3667-5p | 3.3 | 2.7 | 3.6 | 5.6 | 1.3 | 2.8 | 0.0 | 0.0 | 0.0 |
| hsa-miR-0519b-3p | 0.0 | 3.1 | 0.0 | 0.0 | 0.0 | 0.0 | 0.0 | 0.0 | 3.0 |
| hsa-miR-6499-5p | 3.7 | 4.3 | 4.3 | 3.4 | 2.9 | 3.8 | 4.4 | 3.4 | 0.0 |
| hsa-miR-6850-3p | 0.0 | 3.4 | 3.5 | 2.9 | 2.4 | 3.4 | 3.5 | 4.4 | 2.9 |
| hsa-miR-5194 | 2.5 | 4.0 | 3.1 | 0.0 | 3.0 | 3.2 | 0.0 | 0.0 | 0.0 |
| hsa-miR-7849-3p | 3.6 | 2.1 | 3.8 | 0.0 | 3.4 | 2.7 | 2.9 | 3.1 | 2.7 |
| hsa-miR-0410-5p | 1.6 | 3.1 | 2.8 | 5.0 | 3.0 | 3.0 | 3.5 | 0.0 | 0.0 |
| hsa-miR-3654 | 2.5 | 3.1 | 2.9 | 3.6 | 2.7 | 2.3 | 2.8 | 0.0 | 0.0 |
| hsa-miR-4446-5p | 2.1 | 3.6 | 2.1 | 2.5 | 2.8 | 2.4 | 3.0 | 0.0 | 3.2 |
| hsa-miR-4740-5p | 3.1 | 3.4 | 2.6 | 2.8 | 3.3 | 3.1 | 3.4 | 2.6 | 3.2 |
| hsa-miR-6503-3p | 4.2 | 4.5 | 3.7 | 4.2 | 4.4 | 4.1 | 4.4 | 3.3 | 0.0 |
| hsa-miR-0106b-3p | 2.8 | 3.0 | 2.7 | 3.2 | 3.2 | 3.4 | 0.0 | 3.9 | 0.0 |
| hsa-miR-3657 | 3.0 | 3.3 | 2.5 | 0.0 | 2.4 | 3.2 | 0.0 | 0.0 | 0.0 |
| hsa-miR-5192 | 2.2 | 2.8 | 2.7 | 0.0 | 2.1 | 2.1 | 3.5 | 2.3 | 3.0 |
| hsa-miR-6818-3p | 3.4 | 3.9 | 3.5 | 0.0 | 3.3 | 3.8 | 4.5 | 2.8 | 2.7 |
| hsa-miR-1915-5p | 3.7 | 4.3 | 4.8 | 4.4 | 4.3 | 4.3 | 4.3 | 4.9 | 4.6 |
| hsa-miR-3145-3p | 0.0 | 0.0 | 0.0 | 4.4 | 4.3 | 4.3 | 0.0 | 0.0 | 0.0 |
| hsa-miR-4684-3p | 3.6 | 3.5 | 3.7 | 0.0 | 3.1 | 3.7 | 3.6 | 3.3 | 0.0 |
| hsa-miR-5694 | 2.7 | 3.8 | 2.3 | 0.0 | 3.1 | 3.8 | 3.8 | 2.7 | 0.0 |
| hsa-miR-0654-3p | 3.3 | 3.3 | 2.4 | 0.0 | 3.1 | 3.6 | 2.9 | 0.0 | 0.0 |
| hsa-miR-4773 | 3.0 | 3.4 | 2.6 | 5.5 | 3.0 | 2.5 | 3.1 | 0.0 | 0.0 |
| hsa-miR-7161-5p | 0.0 | 2.6 | 0.0 | 0.0 | 0.0 | 2.4 | 0.0 | 0.0 | 0.0 |
| hsa-miR-5197-5p | 3.3 | 3.7 | 1.9 | 0.0 | 1.6 | 2.9 | 0.0 | 2.5 | 0.0 |
| hsa-miR-5703 | 3.0 | 4.1 | 3.5 | 5.5 | 3.7 | 3.5 | 3.8 | 2.6 | 3.7 |
| hsa-miR-0141-5p | 4.2 | 4.0 | 0.0 | 0.0 | 1.2 | 3.6 | 3.6 | 2.4 | 0.0 |
| hsa-miR-5008-3p | 2.7 | 3.3 | 2.1 | 3.3 | 3.8 | 3.2 | 4.3 | 3.5 | 3.1 |
| hsa-miR-5681b | 3.9 | 4.1 | 3.0 | 5.1 | 3.9 | 3.7 | 2.7 | 3.2 | 3.6 |
| hsa-miR-0200c-5p | 1.9 | 3.9 | 0.0 | 0.0 | 4.1 | 2.7 | 3.6 | 0.0 | 3.3 |
| hsa-miR-0125b-2-3p | 0.0 | 2.1 | 2.8 | 0.0 | 1.8 | 0.0 | 0.0 | 0.0 | 0.0 |
| hsa-miR-4754 | 3.3 | 4.0 | 3.2 | 0.0 | 3.9 | 4.6 | 4.0 | 3.5 | 2.9 |
| hsa-miR-1322 | 0.0 | 3.8 | 1.6 | 0.0 | 2.9 | 3.3 | 2.8 | 3.2 | 2.7 |
| hsa-miR-3124-3p | 0.0 | 0.0 | 1.8 | 0.0 | 2.9 | 3.3 | 0.0 | 0.0 | 0.0 |
| hsa-miR-0381-5p | 2.7 | 3.4 | 0.0 | 2.4 | 2.4 | 2.8 | 2.9 | 0.0 | 0.0 |
| hsa-miR-5699-3p | 0.0 | 3.3 | 2.3 | 0.0 | 0.0 | 1.7 | 2.7 | 0.0 | 0.0 |
| hsa-miR-5584-3p | 4.0 | 3.8 | 4.1 | 4.7 | 3.0 | 3.1 | 4.2 | 0.0 | 2.8 |
| hsa-miR-5190 | 3.5 | 3.8 | 3.6 | 3.1 | 4.1 | 4.1 | 3.9 | 2.6 | 2.6 |
| hsa-miR-0892c-5p | 2.3 | 0.0 | 0.0 | 0.0 | 1.9 | 0.0 | 0.0 | 0.0 | 0.0 |
| hsa-miR-4445-3p | 2.5 | 3.8 | 0.0 | 7.5 | 1.9 | 2.7 | 0.0 | 0.0 | 0.0 |
| hsa-miR-5004-5p | 2.8 | 3.8 | 2.8 | 6.5 | 2.3 | 3.6 | 0.0 | 3.6 | 3.0 |
| hsa-miR-0889-5p | 3.3 | 4.2 | 2.9 | 0.0 | 3.9 | 4.0 | 4.0 | 3.7 | 3.3 |
| hsa-miR-0338-5p | 0.0 | 0.0 | 0.0 | 0.0 | 2.9 | 2.6 | 3.3 | 0.0 | 0.0 |
| hsa-miR-0488-5p | 3.5 | 3.9 | 3.5 | 0.0 | 3.4 | 2.8 | 4.9 | 2.8 | 4.0 |
| hsa-miR-4653-5p | 3.0 | 3.5 | 2.3 | 0.0 | 3.4 | 3.5 | 5.0 | 2.9 | 2.7 |
| hsa-miR-0016-1-3p | 0.0 | 0.0 | 3.2 | 3.2 | 2.8 | 3.3 | 2.7 | 2.8 | 0.0 |
| hsa-miR-4310 | 3.4 | 2.6 | 2.1 | 0.0 | 2.3 | 2.8 | 4.5 | 0.0 | 2.7 |
| hsa-miR-4316 | 4.3 | 3.4 | 4.4 | 5.1 | 3.9 | 4.1 | 3.1 | 0.0 | 0.0 |
| hsa-miR-1288-3p | 0.0 | 3.6 | 0.0 | 0.0 | 2.7 | 2.7 | 3.8 | 0.0 | 0.0 |
| hsa-miR-6854-3p | 2.7 | 4.6 | 3.2 | 5.8 | 1.6 | 3.5 | 4.2 | 3.0 | 3.0 |
| hsa-miR-0221-3p | 2.3 | 3.6 | 1.9 | 0.0 | 3.7 | 2.3 | 0.0 | 0.0 | 0.0 |
| hsa-miR-4299 | 3.1 | 3.1 | 4.3 | 3.8 | 3.6 | 3.5 | 2.8 | 0.0 | 0.0 |
| hsa-miR-7703 | 3.6 | 4.1 | 3.1 | 4.2 | 3.4 | 3.0 | 4.8 | 0.0 | 0.0 |
| hsa-miR-4520-5p | 3.5 | 4.6 | 3.0 | 0.0 | 4.1 | 4.2 | 4.4 | 3.4 | 3.9 |
| hsa-miR-0212-5p | 3.5 | 4.4 | 3.3 | 0.0 | 3.5 | 3.3 | 3.0 | 3.2 | 3.0 |
| hsa-miR-0025-3p | 3.5 | 3.6 | 3.3 | 2.4 | 3.5 | 3.3 | 3.5 | 2.9 | 3.3 |
| hsa-miR-0708-5p | 2.3 | 2.2 | 0.0 | 0.0 | 3.1 | 1.2 | 0.0 | 0.0 | 0.0 |
| hsa-miR-6821-3p | 3.9 | 4.1 | 4.2 | 0.0 | 4.1 | 3.6 | 0.0 | 0.0 | 2.5 |
| hsa-miR-0146b-3p | 3.3 | 4.0 | 0.0 | 0.0 | 3.7 | 3.9 | 3.2 | 3.6 | 0.0 |
| hsa-miR-4514 | 2.9 | 3.2 | 0.0 | 0.0 | 3.6 | 3.0 | 2.8 | 3.1 | 3.8 |
| hsa-miR-4429 | 2.3 | 3.9 | 4.3 | 3.4 | 3.6 | 4.5 | 0.0 | 2.6 | 0.0 |
| hsa-miR-0216a-3p | 3.4 | 4.6 | 4.2 | 0.0 | 4.0 | 4.5 | 4.0 | 3.9 | 4.5 |
| hsa-miR-0432-5p | 3.7 | 3.9 | 3.7 | 3.6 | 3.8 | 4.0 | 0.0 | 2.3 | 3.0 |
| hsa-miR-0525-5p | 1.7 | 3.2 | 5.6 | 2.6 | 7.3 | 6.7 | 0.0 | 2.4 | 3.0 |
| hsa-miR-1250-5p | 2.4 | 3.0 | 2.1 | 0.0 | 3.9 | 3.4 | 0.0 | 2.4 | 0.0 |
| hsa-miR-5580-3p | 2.8 | 3.6 | 3.0 | 0.0 | 3.8 | 3.3 | 4.1 | 3.1 | 3.0 |
| hsa-miR-0622 | 3.4 | 4.0 | 2.3 | 0.0 | 3.5 | 4.2 | 4.0 | 2.5 | 0.0 |
| hsa-miR-0875-3p | 3.2 | 2.9 | 0.0 | 0.0 | 3.2 | 3.0 | 0.0 | 2.5 | 0.0 |
| hsa-miR-0099b-5p | 3.9 | 4.0 | 2.9 | 0.0 | 4.0 | 3.2 | 3.9 | 2.6 | 3.5 |
| hsa-miR-0660-3p | 3.4 | 3.7 | 3.0 | 0.0 | 3.4 | 3.6 | 3.7 | 0.0 | 3.3 |
| hsa-miR-0520h | 2.8 | 3.1 | 3.6 | 3.4 | 3.2 | 3.1 | 4.2 | 2.3 | 3.7 |
| hsa-miR-8062 | 1.9 | 3.1 | 2.3 | 0.0 | 2.2 | 2.3 | 2.5 | 0.0 | 0.0 |
| hsa-miR-6765-3p | 3.1 | 2.5 | 3.4 | 3.4 | 3.8 | 3.5 | 3.8 | 3.0 | 0.0 |

TABLE 3-continued

| | | | | | | | | | |
|---|---|---|---|---|---|---|---|---|---|
| hsa-miR-0508-5p | 2.8 | 3.6 | 0.0 | 0.0 | 3.6 | 2.8 | 3.7 | 2.8 | 3.4 |
| hsa-miR-0501-5p | 2.0 | 3.4 | 0.0 | 0.0 | 2.5 | 3.2 | 2.6 | 0.0 | 0.0 |
| hsa-miR-6868-5p | 3.1 | 4.7 | 3.2 | 0.0 | 4.0 | 4.2 | 3.5 | 3.9 | 0.0 |
| hsa-miR-5187-3p | 3.8 | 4.1 | 3.0 | 0.0 | 2.6 | 3.6 | 3.8 | 2.7 | 2.7 |
| hsa-miR-3074-5p | 3.7 | 3.9 | 3.5 | 2.8 | 3.3 | 3.9 | 2.5 | 3.2 | 3.3 |
| hsa-miR-3170 | 2.3 | 3.3 | 0.0 | 2.8 | 3.3 | 3.9 | 4.0 | 2.8 | 2.6 |
| hsa-miR-0224-3p | 2.2 | 3.3 | 2.1 | 0.0 | 3.0 | 2.8 | 3.6 | 0.0 | 0.0 |
| hsa-miR-2116-5p | 0.0 | 3.4 | 3.6 | 0.0 | 4.1 | 3.1 | 2.9 | 0.0 | 0.0 |
| hsa-miR-3153 | 5.0 | 4.2 | 5.3 | 0.0 | 4.1 | 3.1 | 4.8 | 3.8 | 3.5 |
| hsa-miR-6728-5p | 3.9 | 4.1 | 3.7 | 0.0 | 4.2 | 4.0 | 3.8 | 3.2 | 0.0 |
| hsa-miR-4328 | 2.9 | 4.0 | 3.4 | 6.5 | 1.9 | 2.7 | 3.2 | 2.3 | 0.0 |
| hsa-miR-6804-5p | 3.1 | 4.0 | 3.1 | 0.0 | 3.3 | 4.2 | 3.2 | 0.0 | 2.6 |
| hsa-miR-0204-5p | 3.4 | 3.9 | 2.5 | 3.8 | 3.7 | 4.8 | 0.0 | 4.3 | |
| hsa-miR-4764-3p | 2.6 | 3.3 | 0.0 | 2.7 | 2.7 | 3.0 | 3.5 | 2.2 | 0.0 |
| hsa-miR-7854-3p | 2.7 | 3.9 | 2.6 | 0.0 | 4.0 | 4.4 | 3.7 | 3.8 | 0.0 |
| hsa-miR-0382-5p | 2.0 | 2.9 | 0.0 | 0.0 | 2.1 | 1.6 | 2.7 | 0.0 | 0.0 |
| hsa-miR-3615 | 3.4 | 3.3 | 2.9 | 0.0 | 4.7 | 3.3 | 4.5 | 0.0 | 3.7 |
| hsa-miR-5585-3p | 3.8 | 4.1 | 3.9 | 0.0 | 3.9 | 4.8 | 3.4 | 4.3 | 3.7 |
| hsa-miR-0422a | 3.1 | 3.8 | 1.8 | 7.1 | 1.9 | 2.9 | 3.1 | 0.0 | 0.0 |
| hsa-miR-6871-3p | 3.3 | 3.5 | 3.6 | 0.0 | 3.8 | 3.1 | 3.8 | 0.0 | 0.0 |
| hsa-miR-4756-3p | 3.9 | 3.7 | 2.3 | 0.0 | 3.2 | 3.4 | 3.4 | 2.3 | 2.6 |
| hsa-miR-0485-5p | 3.7 | 3.9 | 3.4 | 2.8 | 3.9 | 4.1 | 3.8 | 3.7 | 3.8 |
| hsa-miR-0921 | 0.0 | 3.1 | 0.0 | 0.0 | 3.5 | 3.2 | 2.8 | 0.0 | 0.0 |
| hsa-miR-0340-3p | 2.9 | 2.9 | 0.0 | 0.0 | 2.4 | 3.3 | 3.0 | 2.8 | 3.3 |
| hsa-miR-3529-5p | 3.5 | 3.8 | 3.5 | 0.0 | 3.2 | 2.9 | 2.8 | 2.4 | 0.0 |
| hsa-miR-0758-5p | 3.4 | 3.5 | 3.5 | 0.0 | 3.1 | 2.8 | 3.7 | 2.6 | 0.0 |
| hsa-miR-3681-3p | 2.4 | 3.3 | 0.0 | 5.4 | 1.2 | 2.3 | 3.3 | 0.0 | 0.0 |
| hsa-miR-3074-3p | 3.1 | 2.5 | 2.1 | 0.0 | 2.6 | 2.5 | 2.7 | 2.4 | 0.0 |
| hsa-miR-3169 | 0.0 | 0.0 | 0.0 | 0.0 | 2.6 | 2.5 | 0.0 | 0.0 | 0.0 |
| hsa-miR-0030b-5p | 2.3 | 3.5 | 3.3 | 0.0 | 3.6 | 3.7 | 4.1 | 2.5 | 3.2 |
| hsa-miR-0506-3p | 3.4 | 3.9 | 2.8 | 0.0 | 4.0 | 3.5 | 3.7 | 0.0 | 0.0 |
| hsa-miR-2117 | 2.2 | 3.5 | 0.0 | 0.0 | 2.2 | 1.6 | 4.4 | 0.0 | 2.9 |
| hsa-miR-3154 | 9.2 | 7.3 | 8.7 | 0.0 | 2.2 | 1.6 | 7.1 | 6.0 | 5.8 |
| hsa-miR-0943 | 3.0 | 3.5 | 2.5 | 3.7 | 3.6 | 3.6 | 3.7 | 3.1 | 0.0 |
| hsa-miR-0603 | 2.9 | 3.8 | 2.4 | 0.0 | 3.2 | 2.8 | 2.8 | 2.8 | 3.7 |
| hsa-miR-4784 | 3.0 | 4.2 | 0.0 | 0.0 | 3.8 | 4.5 | 2.6 | 3.2 | 3.2 |
| hsa-miR-0296-3p | 4.3 | 5.5 | 4.5 | 3.8 | 4.9 | 5.6 | 4.8 | 5.5 | 3.5 |
| hsa-miR-4529-5p | 3.3 | 3.9 | 1.6 | 0.0 | 3.0 | 3.8 | 2.6 | 3.0 | 0.0 |
| hsa-miR-8081 | 2.1 | 4.2 | 0.0 | 0.0 | 3.6 | 4.0 | 4.5 | 3.4 | 3.2 |
| hsa-miR-0034b-3p | 1.8 | 3.9 | 2.0 | 0.0 | 3.0 | 3.9 | 3.2 | 0.0 | 0.0 |
| hsa-miR-4768-3p | 0.0 | 2.4 | 0.0 | 0.0 | 1.4 | 2.2 | 0.0 | 0.0 | 0.0 |
| hsa-miR-6134 | 3.6 | 4.6 | 3.2 | 0.0 | 3.5 | 4.2 | 4.0 | 3.4 | 3.1 |
| hsa-miR-0558 | 0.0 | 2.7 | 0.0 | 3.8 | 3.1 | 2.8 | 0.0 | 0.0 | 0.0 |
| hsa-miR-4635 | 3.2 | 4.2 | 2.1 | 3.1 | 4.2 | 3.6 | 3.9 | 3.2 | 0.0 |
| hsa-miR-5091 | 2.4 | 3.3 | 0.0 | 0.0 | 2.9 | 3.5 | 0.0 | 0.0 | 0.0 |
| hsa-miR-1254 | 3.4 | 3.5 | 4.5 | 0.0 | 6.4 | 7.0 | 0.0 | 3.2 | 0.0 |
| hsa-miR-4296 | 2.9 | 3.8 | 0.0 | 3.0 | 4.5 | 3.4 | 4.0 | 4.1 | 0.0 |
| hsa-miR-6504-3p | 4.3 | 4.6 | 3.3 | 0.0 | 4.0 | 4.3 | 4.2 | 3.5 | 2.9 |
| hsa-miR-3944-5p | 4.1 | 4.7 | 3.3 | 2.4 | 3.0 | 3.9 | 4.0 | 2.9 | 3.8 |
| hsa-miR-0541-5p | 2.8 | 3.5 | 0.0 | 0.0 | 3.1 | 3.4 | 3.3 | 2.8 | 2.8 |
| hsa-miR-5580-5p | 3.0 | 4.2 | 2.6 | 0.0 | 3.7 | 4.0 | 0.0 | 2.5 | 2.9 |
| hsa-miR-3655 | 3.5 | 4.2 | 2.3 | 0.0 | 3.6 | 4.3 | 4.8 | 3.0 | 2.9 |
| hsa-miR-0029c-5p | 2.6 | 3.4 | 2.4 | 2.9 | 2.8 | 2.9 | 0.0 | 0.0 | 3.2 |
| hsa-miR-1184 | 4.0 | 3.9 | 4.2 | 0.0 | 4.3 | 4.4 | 4.5 | 3.3 | 3.6 |
| hsa-miR-5571-5p | 3.7 | 4.1 | 3.0 | 2.6 | 3.3 | 3.5 | 4.4 | 0.0 | 0.0 |
| hsa-miR-0092b-3p | 3.9 | 4.1 | 4.2 | 4.0 | 3.8 | 4.3 | 3.8 | 3.9 | 4.0 |
| hsa-miR-5587-3p | 2.4 | 3.7 | 3.2 | 2.7 | 3.1 | 4.7 | 4.5 | 4.1 | 3.7 |
| hsa-miR-0769-3p | 2.4 | 4.0 | 5.0 | 0.0 | 4.0 | 4.3 | 3.4 | 4.8 | 3.0 |
| hsa-miR-0935 | 3.5 | 4.1 | 4.0 | 0.0 | 4.1 | 4.1 | 4.6 | 4.1 | 0.0 |
| hsa-miR-1199-5p | 2.0 | 5.0 | 4.7 | 3.9 | 5.0 | 5.0 | 4.0 | 5.8 | 3.5 |
| hsa-miR-0520a-3p | 3.4 | 2.8 | 2.9 | 0.0 | 3.3 | 3.1 | 3.6 | 2.3 | 3.1 |
| hsa-miR-0297 | 0.0 | 3.7 | 0.0 | 0.0 | 1.3 | 2.8 | 0.0 | 0.0 | 0.0 |
| hsa-miR-6841-5p | 4.1 | 4.3 | 2.3 | 0.0 | 2.9 | 4.0 | 0.0 | 3.0 | 0.0 |
| hsa-miR-7151-5p | 3.2 | 4.2 | 2.0 | 0.0 | 3.1 | 3.9 | 3.5 | 3.2 | 0.0 |
| hsa-miR-1277-3p | 0.0 | 0.0 | 0.0 | 0.0 | 0.0 | 0.0 | 3.4 | 0.0 | 0.0 |
| hsa-miR-0033b-3p | 3.1 | 3.2 | 2.9 | 3.0 | 3.5 | 3.2 | 3.7 | 0.0 | 0.0 |
| hsa-miR-4304 | 1.8 | 2.8 | 2.9 | 3.3 | 3.7 | 3.9 | 4.1 | 3.2 | 2.9 |
| hsa-miR-0873-3p | 2.8 | 3.2 | 0.0 | 2.7 | 2.4 | 3.3 | 2.9 | 0.0 | 0.0 |
| hsa-miR-4420 | 2.7 | 4.0 | 2.0 | 0.0 | 4.4 | 4.3 | 4.0 | 3.0 | 0.0 |
| hsa-miR-4479 | 2.5 | 5.2 | 4.7 | 4.4 | 5.1 | 5.1 | 4.2 | 4.7 | 4.7 |
| hsa-miR-0105-5p | 0.0 | 3.0 | 0.0 | 0.0 | 4.2 | 2.9 | 4.4 | 2.8 | 0.0 |
| hsa-miR-6855-5p | 2.3 | 4.5 | 3.1 | 4.9 | 4.2 | 4.6 | 3.5 | 3.6 | 2.5 |
| hsa-miR-3975 | 2.9 | 2.6 | 2.1 | 0.0 | 2.8 | 3.2 | 3.0 | 0.0 | 0.0 |
| hsa-miR-4453 | 2.5 | 3.7 | 0.0 | 0.0 | 4.6 | 4.2 | 3.4 | 3.4 | 2.9 |
| hsa-miR-1236-5p | 4.1 | 4.3 | 3.8 | 5.5 | 3.9 | 3.6 | 3.9 | 2.3 | 0.0 |
| hsa-miR-7162-3p | 2.9 | 4.2 | 1.7 | 6.6 | 3.3 | 3.8 | 3.5 | 0.0 | 0.0 |
| hsa-miR-0580-3p | 2.2 | 2.5 | 1.8 | 0.0 | 1.4 | 0.0 | 0.0 | 0.0 | 0.0 |
| hsa-miR-6852-5p | 2.9 | 3.9 | 0.0 | 0.0 | 3.4 | 3.9 | 4.7 | 2.7 | 2.7 |
| hsa-miR-0154-5p | 3.9 | 4.5 | 2.8 | 0.0 | 4.2 | 4.5 | 4.3 | 2.3 | 3.4 |
| hsa-miR-0412-3p | 3.4 | 3.8 | 3.6 | 0.0 | 4.2 | 4.4 | 4.5 | 3.8 | 3.2 |

TABLE 3-continued

| | | | | | | | | | |
|---|---|---|---|---|---|---|---|---|---|
| hsa-miR-6863 | 3.4 | 3.7 | 4.1 | 0.0 | 4.5 | 3.9 | 4.4 | 3.5 | 0.0 |
| hsa-miR-0676-5p | 3.0 | 4.1 | 2.0 | 0.0 | 3.4 | 3.1 | 3.9 | 2.2 | 0.0 |
| hsa-miR-6733-3p | 3.9 | 4.2 | 3.7 | 0.0 | 2.0 | 3.9 | 0.0 | 2.4 | 2.5 |
| hsa-miR-3972 | 4.3 | 3.9 | 5.1 | 0.0 | 3.0 | 4.0 | 4.7 | 2.6 | 3.0 |
| hsa-miR-0007-2-3p | 3.8 | 4.0 | 3.1 | 0.0 | 3.6 | 3.8 | 0.0 | 2.5 | 3.1 |
| hsa-miR-4441 | 4.4 | 2.0 | 5.0 | 0.0 | 5.3 | 4.3 | 0.0 | 0.0 | 0.0 |
| hsa-miR-4300 | 2.6 | 3.8 | 1.8 | 0.0 | 4.4 | 4.2 | 3.3 | 2.5 | 0.0 |
| hsa-miR-6874-3p | 3.7 | 4.1 | 2.2 | 0.0 | 4.2 | 4.0 | 4.1 | 3.2 | 0.0 |
| hsa-miR-3691-3p | 3.9 | 3.7 | 2.7 | 3.0 | 3.3 | 3.6 | 3.5 | 2.9 | 0.0 |
| hsa-miR-0034c-3p | 3.2 | 4.8 | 3.6 | 0.0 | 3.6 | 4.0 | 4.2 | 2.7 | 0.0 |
| hsa-miR-0519e-3p | 4.2 | 4.1 | 2.5 | 2.5 | 5.2 | 4.1 | 3.2 | 0.0 | 3.0 |
| hsa-miR-6774-3p | 3.9 | 3.8 | 3.4 | 5.2 | 3.0 | 3.9 | 4.1 | 2.7 | 0.0 |
| hsa-miR-1285-5p | 2.8 | 4.2 | 3.7 | 6.6 | 3.5 | 3.4 | 4.6 | 3.3 | 3.6 |
| hsa-miR-0518f-3p | 2.4 | 0.0 | 3.5 | 0.0 | 4.7 | 2.7 | 0.0 | 0.0 | 0.0 |
| hsa-miR-6791-3p | 3.9 | 4.3 | 3.1 | 2.5 | 3.6 | 4.1 | 4.1 | 3.5 | 2.8 |
| hsa-miR-4761-3p | 3.7 | 3.4 | 4.0 | 3.5 | 3.3 | 3.1 | 3.9 | 3.0 | 4.1 |
| hsa-miR-0548d-3p | 0.0 | 0.0 | 0.0 | 0.0 | 2.4 | 0.0 | 3.3 | 0.0 | 0.0 |
| hsa-miR-1266-3p | 4.5 | 4.2 | 4.3 | 2.5 | 3.3 | 4.0 | 0.0 | 0.0 | 0.0 |
| hsa-miR-0212-3p | 3.1 | 3.9 | 3.7 | 3.2 | 4.1 | 4.1 | 0.0 | 3.1 | 4.0 |
| hsa-miR-0744-3p | 3.3 | 4.2 | 2.1 | 2.5 | 3.8 | 2.7 | 3.0 | 0.0 | 0.0 |
| hsa-miR-9500 | 5.2 | 4.3 | 4.5 | 0.0 | 3.5 | 4.3 | 5.2 | 2.9 | 3.8 |
| hsa-miR-0670-5p | 4.4 | 4.1 | 4.2 | 0.0 | 3.8 | 4.1 | 4.3 | 0.0 | 0.0 |
| hsa-miR-2276-3p | 4.3 | 4.8 | 4.9 | 0.0 | 4.9 | 4.5 | 3.5 | 3.2 | 0.0 |
| hsa-miR-3155a | 3.3 | 0.0 | 0.0 | 0.0 | 4.9 | 4.5 | 0.0 | 0.0 | 0.0 |
| hsa-miR-0517a-3p, hsa-miR-517b-3p | 2.8 | 3.3 | 0.0 | 0.0 | 3.5 | 3.3 | 2.5 | 0.0 | 0.0 |
| hsa-miR-0493-3p | 2.1 | 3.5 | 3.0 | 0.0 | 3.6 | 3.9 | 3.7 | 2.4 | 0.0 |
| hsa-miR-0302d-5p | 4.9 | 3.9 | 3.7 | 2.6 | 3.4 | 3.9 | 3.6 | 0.0 | 0.0 |
| hsa-miR-4727-3p | 1.7 | 3.5 | 0.0 | 0.0 | 4.5 | 4.9 | 0.0 | 2.2 | 3.8 |
| hsa-miR-2355-3p | 0.0 | 3.9 | 3.8 | 0.0 | 2.6 | 2.3 | 0.0 | 0.0 | 0.0 |
| hsa-miR-3157-5p | 0.0 | 0.0 | 0.0 | 0.0 | 2.6 | 2.3 | 2.7 | 0.0 | 0.0 |
| hsa-miR-0766-5p | 3.0 | 4.0 | 0.0 | 0.0 | 4.0 | 4.1 | 4.3 | 2.9 | 3.0 |
| hsa-miR-0605-5p | 2.1 | 3.0 | 0.0 | 0.0 | 3.1 | 2.6 | 3.2 | 2.5 | 3.1 |
| hsa-miR-6758-3p | 3.7 | 4.1 | 3.1 | 5.7 | 3.3 | 3.9 | 4.6 | 2.7 | 3.0 |
| hsa-miR-6515-5p | 2.9 | 4.1 | 4.8 | 0.0 | 7.0 | 6.9 | 3.5 | 4.3 | 0.0 |
| hsa-miR-3692-5p | 3.7 | 3.8 | 3.1 | 4.1 | 3.4 | 3.7 | 0.0 | 2.5 | 0.0 |
| hsa-miR-5187-5p | 0.0 | 3.8 | 0.0 | 2.6 | 3.3 | 3.8 | 0.0 | 2.8 | 0.0 |
| hsa-miR-1287-5p | 3.1 | 4.4 | 1.8 | 0.0 | 3.6 | 4.2 | 3.4 | 3.0 | 3.3 |
| hsa-miR-0518f-5p | 2.1 | 0.0 | 2.0 | 0.0 | 0.0 | 0.0 | 4.1 | 0.0 | 0.0 |
| hsa-miR-4425 | 2.6 | 3.2 | 2.2 | 0.0 | 3.1 | 3.2 | 3.5 | 2.6 | 0.0 |
| hsa-miR-0181a-2-3p | 2.9 | 3.3 | 0.0 | 0.0 | 3.0 | 3.2 | 0.0 | 2.3 | 3.1 |
| hsa-miR-0222-5p | 3.8 | 4.1 | 2.4 | 0.0 | 3.7 | 4.1 | 3.8 | 3.4 | 3.4 |
| hsa-miR-0129-5p | 3.9 | 4.5 | 2.8 | 0.0 | 4.3 | 3.9 | 4.0 | 3.6 | 3.5 |
| hsa-miR-3659 | 4.0 | 3.8 | 3.1 | 2.4 | 4.2 | 3.8 | 4.3 | 0.0 | 3.3 |
| hsa-miR-7158-5p | 3.7 | 3.7 | 2.1 | 0.0 | 3.4 | 3.6 | 0.0 | 2.8 | 3.4 |
| hsa-miR-6516-5p | 2.8 | 2.5 | 3.4 | 0.0 | 1.8 | 1.6 | 3.7 | 0.0 | 0.0 |
| hsa-miR-0216b-3p | 4.6 | 4.7 | 4.2 | 0.0 | 3.6 | 4.6 | 4.5 | 3.4 | 3.8 |
| hsa-miR-6739-3p | 2.9 | 4.1 | 0.0 | 3.1 | 4.2 | 3.8 | 4.4 | 3.8 | 0.0 |
| hsa-miR-0609 | 2.7 | 3.2 | 0.0 | 0.0 | 3.5 | 3.7 | 3.4 | 0.0 | 2.6 |
| hsa-miR-0210-3p | 4.1 | 4.7 | 4.3 | 2.4 | 4.2 | 4.5 | 4.4 | 4.2 | 4.2 |
| hsa-miR-0323b-5p | 2.2 | 4.0 | 2.9 | 0.0 | 4.3 | 3.7 | 3.8 | 3.7 | 3.2 |
| hsa-miR-7844-5p | 4.2 | 3.6 | 3.4 | 6.9 | 2.6 | 3.0 | 4.1 | 2.5 | 3.1 |
| hsa-miR-4301 | 3.2 | 3.8 | 3.3 | 0.0 | 3.7 | 3.9 | 0.0 | 2.6 | 2.8 |
| hsa-miR-0134-3p | 3.8 | 4.4 | 3.9 | 2.5 | 4.0 | 4.4 | 4.5 | 3.6 | 3.1 |
| hsa-miR-3691-5p | 2.1 | 3.6 | 0.0 | 3.5 | 3.0 | 3.5 | 0.0 | 2.3 | 0.0 |
| hsa-miR-0425-3p | 3.8 | 4.6 | 3.4 | 4.1 | 3.5 | 3.9 | 4.0 | 3.0 | 0.0 |
| hsa-miR-0135a-3p | 3.8 | 5.0 | 4.3 | 2.7 | 4.9 | 6.5 | 0.0 | 6.1 | 3.0 |
| hsa-miR-1207-3p | 4.5 | 4.6 | 4.6 | 0.0 | 4.1 | 4.4 | 4.9 | 3.1 | 3.2 |
| hsa-miR-6856-3p | 4.0 | 4.2 | 2.2 | 0.0 | 3.8 | 3.7 | 3.4 | 3.6 | 3.4 |
| hsa-miR-4641 | 3.5 | 4.4 | 2.0 | 0.0 | 3.8 | 3.7 | 4.3 | 3.3 | 3.5 |
| hsa-miR-0520g-3p | 4.1 | 3.4 | 2.3 | 0.0 | 3.3 | 2.9 | 4.5 | 2.2 | 2.8 |
| hsa-miR-6843-3p | 3.5 | 4.2 | 0.0 | 0.0 | 3.6 | 4.3 | 3.0 | 2.7 | 2.5 |
| hsa-miR-0877-5p | 3.5 | 3.9 | 2.9 | 0.0 | 3.6 | 3.6 | 3.1 | 2.6 | 3.2 |
| hsa-miR-0584-3p | 4.0 | 4.6 | 3.2 | 2.7 | 4.6 | 3.9 | 4.9 | 3.8 | 3.7 |
| hsa-miR-4260 | 4.1 | 3.9 | 3.9 | 0.0 | 5.1 | 5.3 | 4.2 | 3.9 | 3.6 |
| hsa-miR-3619-5p | 3.6 | 4.5 | 3.8 | 3.6 | 4.2 | 4.7 | 4.5 | 4.4 | 3.7 |
| hsa-miR-7975 | 3.5 | 4.6 | 3.1 | 0.0 | 4.0 | 3.8 | 4.5 | 3.6 | 3.1 |
| hsa-miR-0512-5p | 4.4 | 4.1 | 4.4 | 3.5 | 3.6 | 3.8 | 4.3 | 3.2 | 4.0 |
| hsa-miR-4691-5p | 3.7 | 3.5 | 3.1 | 2.5 | 4.1 | 4.5 | 3.0 | 3.3 | 3.3 |
| hsa-miR-4713-3p | 4.2 | 4.1 | 0.0 | 2.7 | 3.6 | 3.8 | 3.1 | 2.3 | 3.2 |
| hsa-miR-6755-3p | 3.2 | 3.1 | 0.0 | 0.0 | 2.4 | 2.9 | 2.7 | 0.0 | 2.7 |
| hsa-miR-3945 | 4.2 | 5.0 | 2.4 | 2.9 | 3.5 | 4.0 | 4.5 | 2.4 | 0.0 |
| hsa-miR-0030b-3p | 2.6 | 2.8 | 2.9 | 3.2 | 3.9 | 4.1 | 3.6 | 2.7 | 3.3 |
| hsa-miR-0185-5p | 3.3 | 2.7 | 3.5 | 0.0 | 4.9 | 3.3 | 0.0 | 0.0 | 0.0 |
| hsa-miR-6878-5p | 4.5 | 4.4 | 4.4 | 0.0 | 3.8 | 3.8 | 0.0 | 0.0 | 0.0 |
| hsa-miR-0129-1-3p | 4.6 | 3.6 | 4.6 | 4.8 | 4.2 | 3.9 | 4.9 | 2.9 | 2.6 |
| hsa-miR-0548ba | 3.9 | 2.8 | 0.0 | 0.0 | 0.0 | 0.0 | 0.0 | 0.0 | 0.0 |
| hsa-miR-0150-5p | 3.7 | 4.0 | 3.7 | 3.2 | 4.0 | 3.8 | 4.3 | 3.5 | 3.7 |
| hsa-miR-1910-3p | 3.1 | 4.4 | 2.8 | 0.0 | 3.8 | 3.9 | 4.2 | 3.5 | 3.4 |
| hsa-miR-3138 | 4.3 | 3.8 | 3.8 | 0.0 | 3.8 | 3.9 | 0.0 | 2.7 | 0.0 |

TABLE 3-continued

| | | | | | | | | | |
|---|---|---|---|---|---|---|---|---|---|
| hsa-miR-6500-3p | 3.6 | 4.2 | 3.2 | 2.9 | 4.4 | 4.7 | 3.2 | 3.2 | 0.0 |
| hsa-miR-7157-5p | 3.8 | 4.3 | 2.8 | 0.0 | 3.9 | 4.1 | 3.3 | 3.1 | 3.0 |
| hsa-miR-0593-3p | 2.7 | 4.3 | 0.0 | 0.0 | 3.9 | 3.8 | 2.9 | 3.4 | 0.0 |
| hsa-miR-0018a-3p | 2.9 | 4.0 | 2.5 | 2.9 | 3.7 | 4.0 | 0.0 | 3.2 | 2.7 |
| hsa-miR-1972 | 3.6 | 4.0 | 2.7 | 7.5 | 4.0 | 4.0 | 4.7 | 3.5 | 3.6 |
| hsa-miR-3145-5p | 0.0 | 4.2 | 2.4 | 7.5 | 4.0 | 4.0 | 4.6 | 2.8 | 0.0 |
| hsa-miR-3922-3p | 3.9 | 3.9 | 2.4 | 0.0 | 3.8 | 3.8 | 3.4 | 3.5 | 2.9 |
| hsa-miR-6746-3p | 3.8 | 4.4 | 3.9 | 0.0 | 4.3 | 4.4 | 4.8 | 4.5 | 3.8 |
| hsa-miR-0093-5p | 3.2 | 3.1 | 2.5 | 0.0 | 2.3 | 1.8 | 2.8 | 0.0 | 0.0 |
| hsa-miR-1301-5p | 3.7 | 4.8 | 3.9 | 0.0 | 3.9 | 4.1 | 3.2 | 3.9 | 3.6 |
| hsa-miR-3116 | 4.4 | 3.7 | 4.1 | 0.0 | 3.9 | 4.1 | 3.9 | 0.0 | 2.9 |
| hsa-miR-0937-3p | 4.0 | 3.7 | 3.8 | 2.5 | 3.7 | 3.7 | 4.1 | 3.3 | 3.7 |
| hsa-miR-3187-3p | 4.3 | 5.5 | 5.5 | 7.2 | 4.6 | 5.9 | 4.7 | 5.3 | 2.7 |
| hsa-miR-0581 | 3.7 | 4.3 | 1.7 | 0.0 | 3.0 | 3.7 | 4.2 | 3.2 | 4.2 |
| hsa-miR-6816-3p | 4.0 | 3.2 | 3.6 | 0.0 | 4.1 | 3.1 | 0.0 | 0.0 | 0.0 |
| hsa-miR-1296-3p | 4.3 | 4.5 | 4.5 | 0.0 | 4.1 | 4.3 | 3.9 | 4.5 | 4.2 |
| hsa-miR-3921 | 4.4 | 3.1 | 0.0 | 0.0 | 1.4 | 3.7 | 0.0 | 0.0 | 3.4 |
| hsa-miR-1273g-5p | 3.0 | 4.2 | 1.9 | 0.0 | 4.3 | 4.3 | 2.6 | 2.7 | 3.2 |
| hsa-miR-0432-3p | 4.5 | 4.1 | 2.3 | 2.9 | 4.4 | 4.0 | 3.1 | 3.3 | 3.3 |
| hsa-miR-0656-5p | 3.1 | 4.0 | 0.0 | 0.0 | 4.1 | 3.9 | 4.7 | 3.9 | 0.0 |
| hsa-miR-4726-3p | 3.8 | 3.9 | 3.7 | 2.5 | 3.8 | 3.7 | 3.3 | 3.0 | 3.4 |
| hsa-miR-0092a-3p | 3.7 | 3.9 | 3.3 | 3.7 | 4.0 | 4.4 | 2.7 | 2.8 | 4.7 |
| hsa-miR-4265 | 4.9 | 4.8 | 5.6 | 5.1 | 4.4 | 4.6 | 4.8 | 3.9 | 2.8 |
| hsa-miR-0608 | 2.8 | 4.5 | 0.0 | 0.0 | 4.6 | 4.2 | 4.2 | 4.2 | 3.0 |
| hsa-miR-0135a-5p | 3.5 | 3.0 | 1.7 | 0.0 | 1.4 | 1.3 | 3.3 | 0.0 | 0.0 |
| hsa-miR-0500b-3p | 3.9 | 5.0 | 2.9 | 2.6 | 3.6 | 4.6 | 3.6 | 4.0 | 3.1 |
| hsa-miR-6823-5p | 2.6 | 3.3 | 2.7 | 3.5 | 3.2 | 3.8 | 0.0 | 0.0 | 0.0 |
| hsa-miR-4767 | 4.1 | 4.6 | 4.8 | 4.5 | 4.5 | 4.7 | 5.6 | 4.8 | 4.8 |
| hsa-miR-6499-3p | 3.8 | 4.7 | 3.5 | 0.0 | 4.3 | 3.3 | 4.4 | 3.8 | 0.0 |
| hsa-miR-6788-5p | 3.9 | 3.4 | 0.0 | 0.0 | 4.0 | 4.2 | 3.8 | 2.9 | 0.0 |
| hsa-miR-1200 | 4.0 | 4.0 | 0.0 | 0.0 | 4.0 | 4.2 | 0.0 | 3.7 | 3.4 |
| hsa-miR-4436a | 3.7 | 4.9 | 3.6 | 0.0 | 4.4 | 4.9 | 3.8 | 2.5 | 3.1 |
| hsa-miR-4700-5p | 4.4 | 4.8 | 4.1 | 0.0 | 4.9 | 5.0 | 4.8 | 3.8 | 3.3 |
| hsa-miR-3928-5p | 3.5 | 4.7 | 4.0 | 3.5 | 4.1 | 4.6 | 4.8 | 4.4 | 3.3 |
| hsa-miR-5006-3p | 3.4 | 3.6 | 2.8 | 0.0 | 3.8 | 3.8 | 0.0 | 2.9 | 3.2 |
| hsa-miR-7152-3p | 5.8 | 4.6 | 4.6 | 3.7 | 4.3 | 4.9 | 4.4 | 3.4 | 0.0 |
| hsa-miR-6504-5p | 4.1 | 4.7 | 3.9 | 2.7 | 4.6 | 4.3 | 3.8 | 3.1 | 3.3 |
| hsa-miR-0602 | 0.0 | 7.1 | 6.2 | 5.8 | 6.9 | 6.8 | 4.3 | 7.1 | 4.8 |
| hsa-miR-0330-5p | 2.9 | 4.1 | 2.8 | 0.0 | 2.9 | 3.5 | 2.9 | 2.4 | 0.0 |
| hsa-miR-0491-5p | 4.2 | 4.5 | 5.1 | 2.9 | 6.0 | 6.1 | 4.8 | 4.4 | 3.2 |
| hsa-miR-6747-5p | 3.7 | 4.3 | 4.0 | 0.0 | 4.8 | 5.0 | 3.4 | 4.4 | 0.0 |
| hsa-miR-6822-3p | 4.1 | 4.5 | 4.4 | 4.1 | 3.5 | 3.9 | 3.4 | 2.8 | 0.0 |
| hsa-miR-7850-5p | 3.7 | 4.8 | 3.2 | 0.0 | 4.2 | 4.3 | 4.7 | 4.3 | 3.8 |
| hsa-miR-0572 | 3.8 | 4.6 | 4.1 | 4.6 | 5.8 | 5.6 | 4.7 | 4.6 | 4.6 |
| hsa-miR-3065-3p | 3.6 | 4.3 | 4.9 | 3.4 | 3.5 | 3.7 | 0.0 | 3.0 | 3.8 |
| hsa-miR-3167 | 0.0 | 0.0 | 0.0 | 3.4 | 3.5 | 3.7 | 0.0 | 0.0 | 0.0 |
| hsa-miR-1273h-3p | 4.1 | 3.6 | 3.7 | 3.5 | 3.8 | 3.6 | 4.3 | 3.2 | 3.0 |
| hsa-miR-3198 | 4.9 | 4.2 | 2.2 | 0.0 | 4.1 | 4.5 | 0.0 | 3.4 | 0.0 |
| hsa-miR-6764-3p | 5.0 | 4.1 | 4.6 | 7.0 | 4.6 | 4.5 | 4.4 | 3.1 | 2.7 |
| hsa-miR-4538 | 3.1 | 5.1 | 2.9 | 0.0 | 4.1 | 3.2 | 4.5 | 4.0 | 2.7 |
| hsa-miR-0378a-3p | 4.5 | 3.9 | 4.9 | 0.0 | 4.1 | 4.3 | 4.5 | 3.1 | 3.1 |
| hsa-miR-3612 | 4.3 | 3.9 | 4.0 | 0.0 | 4.6 | 4.2 | 0.0 | 0.0 | 0.0 |
| hsa-miR-0552-5p | 4.3 | 3.7 | 3.3 | 0.0 | 3.4 | 3.7 | 4.1 | 0.0 | 2.8 |
| hsa-miR-8070 | 3.3 | 4.0 | 2.5 | 0.0 | 2.6 | 3.7 | 4.3 | 3.1 | 0.0 |
| hsa-miR-3689b-3p, hsa-miR-3689c | 3.9 | 4.8 | 4.0 | 3.4 | 4.3 | 4.9 | 4.1 | 4.3 | 3.9 |
| hsa-let-7a-2-3p | 4.3 | 4.4 | 3.5 | 6.3 | 2.3 | 3.9 | 3.9 | 3.3 | 3.2 |
| hsa-miR-0668-3p | 4.5 | 4.8 | 4.9 | 2.4 | 4.7 | 4.4 | 4.3 | 4.2 | 4.3 |
| hsa-miR-0023a-5p | 3.9 | 4.5 | 2.5 | 3.4 | 4.3 | 4.3 | 4.4 | 3.2 | 3.4 |
| hsa-miR-4288 | 5.1 | 5.1 | 4.2 | 0.0 | 3.8 | 4.8 | 3.8 | 2.9 | 0.0 |
| hsa-miR-6077 | 4.9 | 4.5 | 4.2 | 0.0 | 3.9 | 4.5 | 4.7 | 2.7 | 2.8 |
| hsa-miR-0770-5p | 3.7 | 4.0 | 0.0 | 2.6 | 3.6 | 3.5 | 4.1 | 4.1 | 4.2 |
| hsa-miR-1306-3p | 3.1 | 4.3 | 0.0 | 2.9 | 4.0 | 3.4 | 4.2 | 4.0 | 3.5 |
| hsa-miR-3120-5p | 3.5 | 4.4 | 0.0 | 2.9 | 4.0 | 3.4 | 4.0 | 3.9 | 2.7 |
| hsa-miR-0337-3p | 3.2 | 3.3 | 0.0 | 2.6 | 3.8 | 2.6 | 0.0 | 0.0 | 3.1 |
| hsa-miR-6512-3p | 4.3 | 5.1 | 3.8 | 0.0 | 4.6 | 4.7 | 3.7 | 4.0 | 4.3 |
| hsa-miR-1914-5p | 4.7 | 4.8 | 4.8 | 4.2 | 4.7 | 4.5 | 5.6 | 4.8 | 5.1 |
| hsa-miR-3144-3p | 2.6 | 0.0 | 2.0 | 4.2 | 4.7 | 4.5 | 3.0 | 0.0 | 0.0 |
| hsa-miR-0887-5p | 4.7 | 4.0 | 5.3 | 0.0 | 5.1 | 5.3 | 4.1 | 4.2 | 3.6 |
| hsa-miR-3927-5p | 3.7 | 3.9 | 2.9 | 0.0 | 3.9 | 3.7 | 2.9 | 2.7 | 0.0 |
| hsa-miR-3177-5p | 3.2 | 5.3 | 4.6 | 4.7 | 5.5 | 5.6 | 4.9 | 5.7 | 5.1 |
| hsa-miR-3176 | 4.1 | 4.4 | 4.1 | 0.0 | 3.2 | 4.2 | 4.6 | 3.7 | 2.7 |
| hsa-miR-1291 | 3.4 | 3.9 | 2.9 | 2.9 | 4.2 | 3.9 | 3.9 | 3.2 | 3.7 |
| hsa-miR-0891a-5p | 3.0 | 4.2 | 0.0 | 0.0 | 3.7 | 4.4 | 4.5 | 3.3 | 3.5 |
| hsa-miR-4708-3p | 3.7 | 5.0 | 4.6 | 0.0 | 4.7 | 5.3 | 4.2 | 4.4 | 3.2 |
| hsa-miR-5010-5p | 4.2 | 5.3 | 5.0 | 3.7 | 4.7 | 5.9 | 4.3 | 5.1 | 2.9 |
| hsa-miR-6773-3p | 4.4 | 5.4 | 4.5 | 0.0 | 4.7 | 4.4 | 4.9 | 4.1 | 3.8 |
| hsa-miR-5581-3p | 4.4 | 4.8 | 4.2 | 0.0 | 4.7 | 4.9 | 4.8 | 4.1 | 4.0 |
| hsa-miR-0365b-5p | 4.2 | 4.5 | 4.4 | 6.6 | 4.3 | 4.7 | 4.6 | 3.6 | 3.9 |
| hsa-miR-4652-5p | 4.3 | 4.1 | 4.1 | 2.7 | 4.6 | 4.7 | 5.3 | 3.0 | 4.2 |

TABLE 3-continued

| | | | | | | | | | |
|---|---|---|---|---|---|---|---|---|---|
| hsa-miR-0125b-5p | 5.0 | 4.6 | 4.3 | 0.0 | 4.3 | 4.3 | 4.7 | 3.0 | 0.0 |
| hsa-miR-4502 | 2.6 | 3.9 | 2.9 | 6.1 | 3.5 | 4.0 | 3.2 | 2.7 | 0.0 |
| hsa-miR-4673 | 4.6 | 5.3 | 4.9 | 2.9 | 4.2 | 5.5 | 4.0 | 5.5 | 4.2 |
| hsa-miR-5588-3p | 3.5 | 4.5 | 3.6 | 0.0 | 3.7 | 3.9 | 3.3 | 3.6 | 3.5 |
| hsa-miR-0671-3p | 4.0 | 3.8 | 3.4 | 0.0 | 3.5 | 4.1 | 3.1 | 0.0 | 0.0 |
| hsa-miR-5001-3p | 3.8 | 4.7 | 0.0 | 0.0 | 4.2 | 4.4 | 3.2 | 3.1 | 0.0 |
| hsa-miR-6828-5p | 3.2 | 3.2 | 2.8 | 0.0 | 4.2 | 3.4 | 2.8 | 0.0 | 0.0 |
| hsa-miR-4319 | 3.9 | 3.9 | 3.6 | 2.9 | 3.7 | 4.4 | 0.0 | 3.5 | 0.0 |
| hsa-miR-6814-3p | 4.6 | 5.2 | 4.2 | 4.8 | 4.1 | 4.2 | 4.6 | 3.0 | 4.4 |
| hsa-miR-1273f | 3.6 | 5.2 | 3.9 | 2.9 | 4.4 | 5.1 | 3.4 | 4.2 | 0.0 |
| hsa-miR-0099b-3p | 3.6 | 4.7 | 3.9 | 3.5 | 4.1 | 4.1 | 4.6 | 3.1 | 3.8 |
| hsa-miR-3622a-5p | 3.8 | 4.5 | 4.2 | 3.6 | 4.5 | 5.0 | 3.3 | 4.5 | 3.0 |
| hsa-miR-6833-5p | 4.7 | 4.6 | 4.3 | 0.0 | 5.1 | 4.1 | 3.8 | 3.7 | 3.0 |
| hsa-miR-2277-5p | 4.0 | 4.7 | 4.6 | 3.0 | 4.0 | 3.7 | 3.8 | 2.6 | 3.6 |
| hsa-miR-3156-5p | 5.3 | 3.9 | 5.0 | 3.0 | 4.0 | 3.7 | 5.1 | 3.0 | 3.9 |
| hsa-miR-3685 | 4.2 | 4.4 | 3.4 | 0.0 | 4.3 | 3.8 | 4.1 | 4.0 | 3.6 |
| hsa-miR-7976 | 4.1 | 4.8 | 4.2 | 0.0 | 4.4 | 4.3 | 4.8 | 4.0 | 3.7 |
| hsa-miR-3189-3p | 4.6 | 3.8 | 4.1 | 0.0 | 4.7 | 6.0 | 0.0 | 2.4 | 0.0 |
| hsa-miR-0138-1-3p | 3.3 | 4.6 | 3.0 | 0.0 | 3.7 | 4.4 | 4.3 | 3.9 | 2.8 |
| hsa-miR-6789-3p | 4.5 | 4.8 | 5.0 | 0.0 | 4.2 | 4.8 | 4.7 | 3.9 | 2.9 |
| hsa-miR-0661 | 3.9 | 4.7 | 3.6 | 0.0 | 4.4 | 4.4 | 4.6 | 4.0 | 3.7 |
| hsa-miR-4654 | 2.6 | 5.2 | 3.4 | 6.0 | 4.4 | 4.7 | 5.0 | 4.0 | 4.0 |
| hsa-miR-4692 | 2.4 | 4.5 | 0.0 | 0.0 | 4.0 | 3.6 | 4.1 | 3.4 | 2.9 |
| hsa-miR-1471 | 4.7 | 5.4 | 4.9 | 3.0 | 5.5 | 5.9 | 4.8 | 4.7 | 4.2 |
| hsa-miR-3129-5p | 0.0 | 0.0 | 0.0 | 3.0 | 5.5 | 5.9 | 0.0 | 0.0 | 0.0 |
| hsa-miR-6764-5p | 3.9 | 4.8 | 3.0 | 3.0 | 4.5 | 4.2 | 4.4 | 3.7 | 4.7 |
| hsa-miR-4529-3p | 3.8 | 4.2 | 3.1 | 0.0 | 3.9 | 4.3 | 4.1 | 3.7 | 3.2 |
| hsa-miR-0505-5p | 4.6 | 4.2 | 4.1 | 0.0 | 4.8 | 4.6 | 3.7 | 2.5 | 4.0 |
| hsa-miR-6511b-5p | 4.7 | 5.1 | 5.3 | 4.4 | 5.4 | 5.5 | 4.8 | 3.9 | 3.7 |
| hsa-miR-4686 | 3.2 | 4.7 | 3.3 | 0.0 | 3.5 | 3.3 | 4.3 | 3.8 | 2.8 |
| hsa-miR-0551a | 3.1 | 4.6 | 3.1 | 0.0 | 3.9 | 3.9 | 3.0 | 2.9 | 3.6 |
| hsa-miR-6892-5p | 4.0 | 4.3 | 4.4 | 3.6 | 3.9 | 4.2 | 4.5 | 3.9 | 0.0 |
| hsa-miR-3935 | 4.4 | 5.2 | 4.5 | 0.0 | 4.0 | 4.9 | 4.8 | 4.4 | 2.7 |
| hsa-miR-0193a-5p | 3.6 | 4.4 | 3.9 | 2.8 | 4.5 | 4.6 | 3.2 | 3.6 | 3.5 |
| hsa-miR-1293 | 1.7 | 4.6 | 2.2 | 2.4 | 4.1 | 4.1 | 4.7 | 3.8 | 3.6 |
| hsa-miR-4540 | 4.0 | 4.7 | 2.7 | 6.2 | 4.4 | 4.6 | 3.0 | 3.8 | 3.8 |
| hsa-miR-0331-3p | 4.9 | 4.2 | 4.5 | 5.2 | 4.0 | 4.3 | 4.7 | 3.1 | 3.6 |
| hsa-miR-6817-3p | 4.0 | 4.5 | 2.9 | 0.0 | 4.3 | 4.5 | 4.1 | 3.2 | 3.9 |
| hsa-miR-6884-5p | 3.8 | 4.6 | 3.1 | 0.0 | 4.7 | 4.4 | 4.1 | 3.9 | 3.6 |
| hsa-miR-6862-5p | 5.0 | 4.2 | 5.6 | 6.1 | 6.1 | 6.4 | 3.6 | 3.8 | 3.4 |
| hsa-miR-1266-5p | 3.9 | 4.0 | 3.5 | 2.8 | 3.8 | 3.7 | 3.4 | 2.6 | 3.6 |
| hsa-miR-1204 | 3.6 | 3.9 | 0.0 | 0.0 | 4.6 | 4.3 | 3.9 | 3.7 | 4.2 |
| hsa-miR-0030c-1-3p | 4.4 | 5.8 | 4.4 | 3.6 | 4.9 | 5.3 | 4.2 | 3.2 | 3.3 |
| hsa-miR-1468-5p | 2.5 | 4.5 | 3.3 | 0.0 | 3.3 | 3.5 | 3.7 | 2.2 | 0.0 |
| hsa-miR-3127-5p | 0.0 | 3.1 | 0.0 | 0.0 | 3.3 | 3.5 | 0.0 | 2.6 | 0.0 |
| hsa-miR-0527, hsa-miR-518a-5p | 4.4 | 3.5 | 4.6 | 0.0 | 5.3 | 4.0 | 3.3 | 0.0 | 4.0 |
| hsa-miR-4307 | 4.3 | 4.2 | 3.9 | 2.9 | 4.0 | 4.0 | 4.2 | 2.8 | 3.7 |
| hsa-miR-6722-5p | 4.3 | 4.5 | 4.5 | 3.5 | 4.6 | 4.7 | 4.7 | 4.5 | 4.3 |
| hsa-miR-0657 | 4.2 | 4.2 | 4.0 | 0.0 | 4.2 | 4.2 | 4.1 | 3.3 | 4.3 |
| hsa-miR-4684-5p | 3.4 | 4.6 | 3.8 | 7.0 | 4.0 | 3.4 | 5.2 | 4.6 | 5.1 |
| hsa-miR-6780a-3p | 4.4 | 5.0 | 4.3 | 5.8 | 3.9 | 4.6 | 4.5 | 3.9 | 0.0 |
| hsa-miR-0885-3p | 3.9 | 4.8 | 5.5 | 3.4 | 5.4 | 5.5 | 4.1 | 4.4 | 3.1 |
| hsa-miR-0034a-5p | 3.1 | 3.6 | 1.6 | 2.6 | 3.5 | 4.2 | 3.1 | 3.3 | 2.8 |
| hsa-miR-0194-3p | 3.7 | 4.1 | 3.7 | 2.9 | 5.3 | 5.1 | 4.0 | 4.0 | 4.2 |
| hsa-miR-4776-3p | 3.2 | 4.4 | 3.8 | 0.0 | 3.9 | 4.1 | 4.2 | 3.5 | 3.6 |
| hsa-miR-3064-3p | 3.5 | 5.3 | 3.7 | 0.0 | 3.3 | 4.2 | 4.3 | 3.0 | 0.0 |
| hsa-miR-3165 | 0.0 | 2.2 | 0.0 | 0.0 | 3.3 | 4.2 | 3.7 | 0.0 | 0.0 |
| hsa-miR-4473 | 3.5 | 3.2 | 0.0 | 0.0 | 3.4 | 3.7 | 0.0 | 0.0 | 2.9 |
| hsa-miR-0625-5p | 3.9 | 0.0 | 5.0 | 0.0 | 6.4 | 4.8 | 2.8 | 0.0 | 2.9 |
| hsa-miR-4252 | 3.6 | 4.5 | 1.9 | 3.2 | 4.3 | 4.5 | 4.3 | 4.0 | 3.3 |
| hsa-miR-6866-3p | 4.1 | 4.7 | 3.9 | 0.0 | 3.4 | 4.3 | 3.5 | 2.9 | 0.0 |
| hsa-miR-1203 | 4.7 | 5.2 | 4.9 | 3.4 | 5.0 | 4.7 | 4.8 | 3.8 | 3.9 |
| hsa-miR-3934-5p | 3.3 | 4.1 | 3.0 | 6.7 | 3.6 | 4.2 | 3.2 | 3.2 | 0.0 |
| hsa-miR-4647 | 2.9 | 4.4 | 0.0 | 6.6 | 3.2 | 4.3 | 3.8 | 3.0 | 0.0 |
| hsa-miR-4711-3p | 3.3 | 4.6 | 0.0 | 0.0 | 4.7 | 4.5 | 4.5 | 3.9 | 3.9 |
| hsa-miR-4436b-3p | 3.2 | 4.7 | 3.3 | 0.0 | 4.3 | 3.8 | 2.8 | 3.5 | 3.5 |
| hsa-miR-0299-5p | 3.8 | 3.8 | 3.9 | 0.0 | 4.1 | 4.2 | 3.6 | 3.6 | 3.8 |
| hsa-miR-0193b-3p | 4.6 | 4.4 | 4.3 | 3.4 | 4.0 | 4.3 | 3.9 | 3.7 | 4.2 |
| hsa-miR-3689d | 4.3 | 4.4 | 4.4 | 4.2 | 4.1 | 4.4 | 4.2 | 4.0 | 3.5 |
| hsa-miR-3617-3p | 4.6 | 5.3 | 3.2 | 3.1 | 5.0 | 4.7 | 5.0 | 4.3 | 4.1 |
| hsa-miR-6876-5p | 3.7 | 5.1 | 3.8 | 2.6 | 4.8 | 4.7 | 3.5 | 4.1 | 4.0 |
| hsa-miR-6847-5p | 3.6 | 4.9 | 3.6 | 5.2 | 3.8 | 3.7 | 4.0 | 3.6 | 2.9 |
| hsa-miR-0767-3p | 4.6 | 4.7 | 4.3 | 3.9 | 3.6 | 4.4 | 5.1 | 3.3 | 3.4 |
| hsa-miR-4748 | 5.0 | 5.3 | 4.5 | 0.0 | 5.0 | 4.9 | 4.5 | 4.2 | 2.6 |
| hsa-miR-3177-3p | 4.0 | 3.8 | 4.4 | 2.6 | 4.7 | 4.8 | 4.1 | 3.8 | 3.2 |
| hsa-miR-6886-5p | 4.8 | 4.8 | 4.8 | 0.0 | 4.1 | 4.6 | 4.0 | 3.7 | 3.2 |
| hsa-miR-4717-3p | 5.5 | 4.7 | 5.1 | 4.5 | 4.4 | 4.9 | 5.5 | 4.4 | 4.4 |
| hsa-miR-2113 | 4.1 | 4.3 | 3.0 | 0.0 | 4.1 | 4.3 | 4.3 | 3.4 | 3.1 |
| hsa-miR-3150b-3p | 3.8 | 4.6 | 3.4 | 0.0 | 4.1 | 4.3 | 4.1 | 3.2 | 2.6 |

TABLE 3-continued

| | | | | | | | | | |
|---|---|---|---|---|---|---|---|---|---|
| hsa-miR-4326 | 4.5 | 5.3 | 4.7 | 0.0 | 4.4 | 4.6 | 4.5 | 3.5 | 4.6 |
| hsa-miR-0892b | 4.0 | 4.8 | 3.7 | 0.0 | 4.3 | 4.1 | 3.6 | 3.8 | 3.9 |
| hsa-miR-6895-3p | 4.9 | 4.9 | 4.5 | 3.6 | 4.5 | 4.9 | 5.0 | 4.1 | 2.6 |
| hsa-miR-4708-5p | 4.5 | 5.2 | 4.9 | 3.8 | 4.8 | 4.9 | 4.9 | 4.7 | 4.9 |
| hsa-miR-6856-5p | 4.5 | 5.1 | 4.0 | 3.0 | 5.0 | 5.3 | 4.8 | 4.7 | 4.0 |
| hsa-miR-0550a-5p | 4.1 | 4.4 | 4.1 | 2.9 | 4.3 | 4.5 | 3.9 | 3.7 | 2.7 |
| hsa-miR-4324 | 4.7 | 4.8 | 3.6 | 2.8 | 4.6 | 4.0 | 4.5 | 3.8 | 3.3 |
| hsa-miR-4776-5p | 4.2 | 4.8 | 3.8 | 3.6 | 5.0 | 5.4 | 4.7 | 4.4 | 3.7 |
| hsa-miR-0629-3p | 4.7 | 4.7 | 3.8 | 0.0 | 3.6 | 4.2 | 4.7 | 3.6 | 3.9 |
| hsa-miR-1273h-5p | 5.0 | 4.8 | 5.0 | 3.9 | 4.9 | 5.1 | 4.0 | 3.6 | 3.5 |
| hsa-miR-1909-5p | 4.3 | 4.6 | 4.3 | 3.3 | 5.2 | 5.6 | 5.0 | 4.2 | 3.8 |
| hsa-miR-3137 | 3.5 | 3.9 | 3.3 | 3.3 | 5.2 | 5.6 | 2.5 | 3.1 | 2.7 |
| hsa-miR-4780 | 4.7 | 4.9 | 4.3 | 3.4 | 4.0 | 4.5 | 4.9 | 4.5 | 4.2 |
| hsa-miR-8064 | 4.6 | 5.2 | 4.5 | 3.3 | 4.8 | 5.2 | 4.4 | 4.9 | 4.2 |
| hsa-miR-7702 | 4.8 | 4.9 | 4.2 | 4.7 | 4.6 | 4.5 | 4.5 | 3.9 | 3.9 |
| hsa-miR-1181 | 4.5 | 4.9 | 5.3 | 4.4 | 5.2 | 5.5 | 5.1 | 5.4 | 4.5 |
| hsa-miR-4448 | 4.2 | 4.4 | 3.5 | 3.6 | 4.6 | 5.0 | 4.0 | 3.5 | 4.1 |
| hsa-miR-4800-5p | 4.1 | 4.5 | 4.5 | 0.0 | 4.8 | 5.0 | 3.6 | 2.5 | 0.0 |
| hsa-miR-8075 | 3.8 | 5.3 | 3.6 | 4.4 | 5.1 | 3.9 | 4.7 | 4.3 | 4.3 |
| hsa-miR-0494-5p | 3.8 | 5.0 | 3.1 | 0.0 | 4.8 | 4.2 | 5.0 | 4.3 | 4.5 |
| hsa-miR-4506 | 2.5 | 3.0 | 3.3 | 3.3 | 4.2 | 4.3 | 2.9 | 0.0 | 0.0 |
| hsa-miR-3591-3p | 3.4 | 4.9 | 2.9 | 3.1 | 4.3 | 4.7 | 4.7 | 3.8 | 2.6 |
| hsa-miR-0612 | 4.1 | 4.9 | 4.2 | 4.4 | 4.6 | 4.8 | 4.9 | 4.9 | 4.8 |
| hsa-miR-3714 | 4.9 | 4.4 | 4.8 | 5.5 | 4.1 | 4.4 | 5.1 | 2.9 | 3.7 |
| hsa-miR-3616-3p | 4.4 | 5.6 | 5.3 | 4.7 | 4.8 | 5.5 | 5.2 | 5.4 | 5.4 |
| hsa-miR-0211-5p | 4.3 | 4.9 | 4.2 | 3.9 | 4.9 | 5.1 | 5.2 | 4.3 | 4.5 |
| hsa-miR-1287-3p | 5.0 | 4.6 | 3.9 | 2.5 | 4.3 | 4.3 | 5.0 | 3.7 | 4.4 |
| hsa-miR-1538 | 4.4 | 5.3 | 5.1 | 3.6 | 5.4 | 5.1 | 5.1 | 5.0 | 4.7 |
| hsa-miR-3131 | 11.1 | 9.7 | 11.8 | 3.6 | 5.4 | 5.1 | 9.6 | 8.7 | 9.3 |
| hsa-miR-0526a, hsa-miR-520c-5p, hsa-miR-518d-5p | 3.8 | 3.4 | 4.9 | 4.2 | 2.6 | 2.6 | 3.6 | 0.0 | 2.7 |
| hsa-miR-0449c-3p | 4.1 | 4.9 | 4.0 | 3.0 | 4.4 | 4.4 | 4.1 | 3.8 | 4.8 |
| hsa-miR-0636 | 4.6 | 5.0 | 5.0 | 4.2 | 5.2 | 5.3 | 5.6 | 4.9 | 4.8 |
| hsa-miR-0589-5p | 4.5 | 4.9 | 3.8 | 2.8 | 4.3 | 4.4 | 4.8 | 3.9 | 3.9 |
| hsa-miR-6815-3p | 4.7 | 4.9 | 3.7 | 2.6 | 4.3 | 4.5 | 4.7 | 3.8 | 4.5 |
| hsa-miR-6507-3p | 4.8 | 4.5 | 3.8 | 3.4 | 4.2 | 4.4 | 4.9 | 3.6 | 2.8 |
| hsa-miR-6822-5p | 5.3 | 5.3 | 5.5 | 2.5 | 4.9 | 5.0 | 4.9 | 4.3 | 4.1 |
| hsa-miR-7855-5p | 4.5 | 4.5 | 4.3 | 3.2 | 4.3 | 4.3 | 4.5 | 3.7 | 4.1 |
| hsa-miR-4428 | 4.0 | 7.6 | 3.3 | 2.9 | 4.9 | 4.4 | 4.3 | 3.9 | 2.9 |
| hsa-miR-4476 | 4.9 | 4.3 | 5.7 | 0.0 | 5.9 | 5.9 | 3.7 | 3.9 | 2.7 |
| hsa-miR-0129-2-3p | 4.4 | 4.2 | 4.3 | 3.3 | 4.5 | 3.9 | 5.2 | 3.3 | 4.4 |
| hsa-miR-4278 | 5.3 | 4.8 | 5.1 | 3.5 | 5.0 | 5.1 | 5.8 | 4.3 | 4.8 |
| hsa-miR-5685 | 4.4 | 4.6 | 3.9 | 0.0 | 4.4 | 4.6 | 4.2 | 4.3 | 4.1 |
| hsa-miR-0192-5p | 4.3 | 4.4 | 4.2 | 0.0 | 4.7 | 4.6 | 4.0 | 4.2 | 4.3 |
| hsa-miR-4482-3p | 5.4 | 5.3 | 5.9 | 5.1 | 5.6 | 5.7 | 5.4 | 5.1 | 4.5 |
| hsa-miR-1296-5p | 4.1 | 4.7 | 4.2 | 3.6 | 4.4 | 4.5 | 4.1 | 4.0 | 3.8 |
| hsa-miR-0324-3p | 4.5 | 4.8 | 4.5 | 3.7 | 4.8 | 4.7 | 4.6 | 3.5 | 3.8 |
| hsa-miR-6873-5p | 5.2 | 4.8 | 5.0 | 2.6 | 4.3 | 4.5 | 4.8 | 3.1 | 4.6 |
| hsa-miR-6847-3p | 4.7 | 4.9 | 4.6 | 2.4 | 5.2 | 5.3 | 4.9 | 4.6 | 4.2 |
| hsa-miR-5708 | 4.0 | 4.9 | 3.1 | 2.6 | 4.5 | 5.2 | 3.6 | 4.5 | 3.7 |
| hsa-miR-4747-3p | 4.8 | 4.8 | 6.1 | 4.4 | 5.6 | 5.8 | 4.9 | 5.6 | 3.3 |
| hsa-miR-6801-5p | 3.9 | 5.0 | 4.0 | 2.6 | 4.8 | 3.9 | 4.6 | 4.6 | 4.2 |
| hsa-miR-0125a-5p | 4.8 | 4.8 | 4.0 | 3.5 | 4.9 | 4.7 | 4.5 | 4.2 | 4.1 |
| hsa-miR-4269 | 4.3 | 4.9 | 5.1 | 3.5 | 5.0 | 4.9 | 4.8 | 5.1 | 4.0 |
| hsa-miR-6881-3p | 4.7 | 5.1 | 3.9 | 2.4 | 4.8 | 5.2 | 4.8 | 4.5 | 5.0 |
| hsa-miR-4664-5p | 5.5 | 4.7 | 5.6 | 4.0 | 6.0 | 5.8 | 5.0 | 3.8 | 3.9 |
| hsa-miR-0431-3p | 4.0 | 4.7 | 4.3 | 2.9 | 4.2 | 4.8 | 5.3 | 3.5 | 4.4 |
| hsa-miR-6503-5p | 5.1 | 4.6 | 4.6 | 4.6 | 4.9 | 4.5 | 5.4 | 3.5 | 3.2 |
| hsa-miR-6723-5p | 4.4 | 5.0 | 5.3 | 4.2 | 4.7 | 4.4 | 5.7 | 5.9 | 5.6 |
| hsa-miR-7113-5p | 4.0 | 4.9 | 2.9 | 5.0 | 4.6 | 3.9 | 3.9 | 3.9 | 4.7 |
| hsa-miR-2467-3p | 4.2 | 5.1 | 4.2 | 2.8 | 5.2 | 4.4 | 4.8 | 4.5 | 4.3 |
| hsa-miR-3159 | 0.0 | 0.0 | 0.0 | 2.8 | 5.2 | 4.4 | 0.0 | 0.0 | 0.0 |
| hsa-miR-8077 | 4.2 | 4.8 | 3.9 | 2.7 | 4.6 | 5.1 | 4.3 | 4.7 | 0.0 |
| hsa-miR-2682-3p | 4.6 | 5.2 | 4.8 | 2.7 | 4.9 | 5.0 | 5.3 | 4.4 | 3.9 |
| hsa-miR-3162-3p | 6.6 | 6.2 | 6.5 | 2.7 | 4.9 | 5.0 | 6.7 | 5.2 | 5.7 |
| hsa-miR-4639-3p | 4.0 | 5.3 | 2.8 | 0.0 | 4.9 | 4.2 | 4.9 | 4.4 | 4.8 |
| hsa-miR-4725-5p | 4.8 | 4.6 | 4.3 | 3.7 | 5.1 | 4.8 | 4.9 | 4.2 | 4.6 |
| hsa-miR-7151-3p | 3.3 | 5.3 | 3.2 | 3.0 | 4.7 | 5.2 | 4.4 | 4.7 | 3.7 |
| hsa-miR-4306 | 4.3 | 3.3 | 5.0 | 0.0 | 5.6 | 4.6 | 0.0 | 0.0 | 3.3 |
| hsa-miR-0585-5p | 5.2 | 5.7 | 5.1 | 5.3 | 4.6 | 4.8 | 5.6 | 4.3 | 4.5 |
| hsa-miR-4804-3p | 4.6 | 5.0 | 4.2 | 3.2 | 4.6 | 4.9 | 4.3 | 4.3 | 4.1 |
| hsa-miR-4474-3p | 3.5 | 4.4 | 2.4 | 0.0 | 4.4 | 3.7 | 4.2 | 2.4 | 3.9 |
| hsa-miR-6876-3p | 4.3 | 5.1 | 4.1 | 7.3 | 4.6 | 5.0 | 4.5 | 4.5 | 4.0 |
| hsa-miR-1224-5p | 4.1 | 5.0 | 4.5 | 2.8 | 5.0 | 5.3 | 4.3 | 4.6 | 4.1 |
| hsa-miR-6832-3p | 5.3 | 5.2 | 5.1 | 2.8 | 4.7 | 4.9 | 4.4 | 3.6 | 4.5 |
| hsa-miR-0191-3p | 4.8 | 4.6 | 4.7 | 2.7 | 5.2 | 4.7 | 5.3 | 4.0 | 4.5 |
| hsa-miR-4638-5p | 3.8 | 5.3 | 4.4 | 3.1 | 5.2 | 5.0 | 5.0 | 5.5 | 4.6 |
| hsa-miR-4518 | 4.2 | 4.7 | 3.1 | 0.0 | 3.9 | 4.4 | 4.7 | 3.0 | 2.7 |
| hsa-miR-4487 | 4.2 | 5.0 | 4.8 | 3.4 | 5.1 | 5.2 | 4.7 | 4.7 | 3.3 |

TABLE 3-continued

| | | | | | | | | | |
|---|---|---|---|---|---|---|---|---|---|
| hsa-miR-0764 | 4.9 | 4.8 | 4.7 | 3.1 | 4.9 | 4.8 | 4.4 | 4.1 | 4.4 |
| hsa-miR-6767-5p | 4.0 | 5.4 | 3.6 | 6.1 | 4.9 | 4.2 | 5.4 | 4.1 | 4.6 |
| hsa-miR-3944-3p | 4.7 | 5.4 | 4.3 | 3.4 | 5.2 | 4.9 | 5.2 | 5.0 | 5.0 |
| hsa-miR-6829-3p | 5.2 | 5.1 | 5.3 | 3.1 | 4.9 | 5.2 | 5.1 | 4.4 | 4.0 |
| hsa-miR-4292 | 4.7 | 4.6 | 4.8 | 3.6 | 4.9 | 4.4 | 4.9 | 4.7 | 4.4 |
| hsa-miR-4525 | 5.3 | 6.4 | 5.8 | 5.0 | 5.6 | 7.1 | 3.2 | 5.8 | 3.3 |
| hsa-miR-4676-5p | 3.6 | 5.0 | 3.2 | 3.0 | 4.9 | 3.4 | 4.5 | 4.4 | 4.1 |
| hsa-miR-4489 | 4.9 | 5.4 | 5.3 | 3.3 | 5.4 | 5.7 | 4.9 | 5.0 | 4.8 |
| hsa-miR-0615-5p | 4.8 | 5.1 | 6.4 | 4.4 | 6.9 | 6.4 | 5.1 | 5.3 | 4.2 |
| hsa-miR-0342-3p | 4.1 | 4.6 | 3.2 | 3.2 | 4.5 | 4.3 | 4.6 | 4.1 | 3.9 |
| hsa-miR-0550a-3p | 4.6 | 4.2 | 3.8 | 2.7 | 4.8 | 4.8 | 3.6 | 4.1 | 3.7 |
| hsa-miR-4456 | 2.9 | 4.9 | 2.5 | 0.0 | 4.8 | 4.8 | 4.3 | 3.5 | 3.7 |
| hsa-miR-1908-3p | 4.1 | 5.6 | 5.9 | 5.5 | 6.7 | 6.6 | 5.6 | 7.5 | 5.2 |
| hsa-miR-3135b | 7.3 | 8.0 | 8.7 | 5.5 | 6.7 | 6.6 | 6.8 | 7.4 | 6.3 |
| hsa-miR-1539 | 5.3 | 5.3 | 5.0 | 4.1 | 5.1 | 5.3 | 5.3 | 4.9 | 4.9 |
| hsa-miR-3132 | 3.7 | 3.9 | 0.0 | 4.1 | 5.1 | 5.3 | 3.2 | 0.0 | 0.0 |
| hsa-miR-4709-3p | 5.2 | 4.7 | 4.9 | 0.0 | 5.1 | 4.8 | 4.6 | 3.6 | 3.2 |
| hsa-let-7f-1-3p | 5.4 | 4.6 | 5.3 | 0.0 | 5.1 | 4.9 | 5.4 | 3.6 | 4.0 |
| hsa-miR-4305 | 4.4 | 5.2 | 3.5 | 2.7 | 4.7 | 4.8 | 4.5 | 4.1 | 3.2 |
| hsa-miR-6770-3p | 4.1 | 5.3 | 5.6 | 3.4 | 5.1 | 5.4 | 4.3 | 5.4 | 3.2 |
| hsa-miR-4732-5p | 5.0 | 5.6 | 5.5 | 3.3 | 5.2 | 5.4 | 4.4 | 5.0 | 3.6 |
| hsa-miR-6716-3p | 4.1 | 5.5 | 4.1 | 0.0 | 4.1 | 5.2 | 5.2 | 3.2 | 4.1 |
| hsa-miR-0483-5p | 5.1 | 5.1 | 4.4 | 0.0 | 3.9 | 4.6 | 0.0 | 2.7 | 0.0 |
| hsa-miR-1226-3p | 4.8 | 5.1 | 4.4 | 2.6 | 4.9 | 5.1 | 5.1 | 4.3 | 4.3 |
| hsa-miR-6883-5p | 5.4 | 5.2 | 5.9 | 0.0 | 7.1 | 6.4 | 4.9 | 4.6 | 4.5 |
| hsa-miR-6834-5p | 3.9 | 5.0 | 3.8 | 0.0 | 4.9 | 4.8 | 3.9 | 4.1 | 3.4 |
| hsa-miR-6849-3p | 4.5 | 5.0 | 4.1 | 2.6 | 4.9 | 5.1 | 4.4 | 4.7 | 3.8 |
| hsa-miR-3667-3p | 4.3 | 4.8 | 3.7 | 4.9 | 4.7 | 4.5 | 4.9 | 3.3 | 0.0 |
| hsa-miR-4669 | 4.5 | 5.0 | 4.1 | 3.3 | 5.2 | 4.4 | 3.7 | 4.7 | 4.0 |
| hsa-miR-4646-5p | 5.3 | 4.6 | 4.7 | 3.0 | 5.2 | 5.0 | 4.2 | 3.9 | 3.8 |
| hsa-miR-4743-5p | 5.0 | 5.3 | 4.9 | 3.5 | 5.4 | 5.5 | 4.3 | 4.6 | 3.9 |
| hsa-let-7d-3p | 3.7 | 5.0 | 3.8 | 5.9 | 4.2 | 4.5 | 5.0 | 4.1 | 3.3 |
| hsa-miR-6872-3p | 5.3 | 5.4 | 5.8 | 3.2 | 5.3 | 5.4 | 5.6 | 5.0 | 4.9 |
| hsa-miR-0526b-5p | 4.8 | 4.6 | 3.6 | 2.5 | 4.5 | 4.5 | 5.2 | 2.8 | 3.0 |
| hsa-miR-0550b-3p | 4.6 | 4.9 | 4.7 | 6.3 | 4.1 | 4.5 | 4.6 | 3.7 | 3.0 |
| hsa-miR-4652-3p | 4.5 | 4.4 | 4.1 | 2.5 | 4.9 | 4.9 | 4.8 | 3.8 | 3.5 |
| hsa-miR-4682 | 3.7 | 5.0 | 3.5 | 2.4 | 4.1 | 5.2 | 3.5 | 4.2 | 2.9 |
| hsa-miR-7851-3p | 4.5 | 5.6 | 5.3 | 3.9 | 5.7 | 5.8 | 5.1 | 5.3 | 4.6 |
| hsa-miR-1323 | 6.9 | 6.0 | 5.5 | 0.0 | 3.8 | 5.7 | 2.6 | 3.8 | 2.8 |
| hsa-miR-3124-5p | 2.2 | 2.8 | 2.9 | 0.0 | 3.8 | 5.7 | 0.0 | 3.1 | 0.0 |
| hsa-miR-6852-3p | 4.7 | 4.7 | 4.3 | 2.5 | 4.4 | 4.9 | 5.2 | 3.7 | 4.5 |
| hsa-miR-4266 | 6.8 | 5.3 | 5.5 | 0.0 | 4.7 | 4.6 | 4.3 | 3.1 | 0.0 |
| hsa-miR-1247-5p | 4.7 | 4.9 | 4.2 | 3.3 | 4.8 | 4.8 | 5.4 | 4.2 | 4.5 |
| hsa-miR-6836-5p | 3.5 | 5.7 | 5.8 | 4.1 | 5.8 | 4.8 | 5.1 | 6.0 | 4.3 |
| hsa-miR-0520b | 3.8 | 3.4 | 5.6 | 4.4 | 5.7 | 3.9 | 0.0 | 0.0 | 0.0 |
| hsa-miR-3649 | 5.7 | 5.9 | 4.1 | 2.7 | 4.3 | 5.2 | 4.4 | 3.9 | 2.9 |
| hsa-miR-6782-5p | 5.1 | 5.9 | 5.6 | 3.5 | 5.3 | 5.5 | 4.9 | 5.4 | 3.2 |
| hsa-miR-6878-3p | 4.8 | 5.6 | 4.3 | 5.7 | 4.7 | 5.0 | 5.4 | 4.4 | 3.9 |
| hsa-miR-3646 | 5.0 | 5.1 | 4.7 | 3.7 | 5.3 | 5.2 | 4.7 | 4.7 | 3.8 |
| hsa-miR-0520d-5p | 4.4 | 3.7 | 5.0 | 0.0 | 5.5 | 5.2 | 0.0 | 2.5 | 3.9 |
| hsa-miR-1182 | 3.9 | 3.3 | 4.3 | 0.0 | 5.8 | 5.8 | 3.5 | 3.0 | 3.4 |
| hsa-miR-6837-5p | 4.9 | 5.1 | 4.6 | 0.0 | 4.6 | 5.0 | 4.9 | 4.6 | 4.4 |
| hsa-miR-0098-3p | 4.7 | 4.7 | 4.7 | 2.5 | 5.0 | 4.7 | 5.2 | 3.5 | 4.5 |
| hsa-miR-3650 | 4.7 | 5.4 | 3.5 | 3.4 | 5.0 | 4.3 | 5.4 | 4.5 | 4.7 |
| hsa-miR-0130b-5p | 4.2 | 5.0 | 4.8 | 3.7 | 5.3 | 5.5 | 5.7 | 4.6 | 5.4 |
| hsa-miR-4701-3p | 4.0 | 4.9 | 0.0 | 0.0 | 5.1 | 5.5 | 4.9 | 4.8 | 4.2 |
| hsa-miR-1273g-3p | 4.4 | 5.1 | 3.8 | 6.8 | 4.7 | 5.8 | 5.4 | 6.2 | 3.7 |
| hsa-miR-3689a-3p | 4.1 | 4.7 | 4.0 | 0.0 | 4.9 | 4.9 | 0.0 | 4.1 | 4.2 |
| hsa-miR-0187-3p | 3.7 | 5.4 | 3.4 | 3.4 | 4.9 | 3.9 | 4.7 | 4.3 | 4.9 |
| hsa-miR-5100 | 4.5 | 7.0 | 6.0 | 4.7 | 5.3 | 4.9 | 4.8 | 6.3 | 4.6 |
| hsa-miR-6514-3p | 3.8 | 4.9 | 3.4 | 3.0 | 4.8 | 4.9 | 4.8 | 4.2 | 4.4 |
| hsa-miR-0133a-3p | 4.4 | 4.7 | 4.6 | 3.4 | 4.9 | 4.2 | 5.5 | 3.0 | 4.4 |
| hsa-miR-0519d-3p | 5.2 | 5.0 | 4.5 | 4.0 | 5.2 | 5.1 | 4.9 | 4.1 | 4.9 |
| hsa-miR-0326 | 5.0 | 5.1 | 5.1 | 7.0 | 4.8 | 4.7 | 4.1 | 4.2 | 3.7 |
| hsa-miR-6766-5p | 5.0 | 5.7 | 5.2 | 3.9 | 5.3 | 5.6 | 5.6 | 6.1 | 5.5 |
| hsa-miR-4732-3p | 4.4 | 5.2 | 4.0 | 3.7 | 5.5 | 5.3 | 4.8 | 4.6 | 4.7 |
| hsa-miR-3189-5p | 5.0 | 4.9 | 4.1 | 3.3 | 5.0 | 4.8 | 5.2 | 3.8 | 3.9 |
| hsa-miR-5088-3p | 5.1 | 5.2 | 5.0 | 3.7 | 4.9 | 5.3 | 4.3 | 4.7 | 4.8 |
| hsa-miR-4648 | 4.9 | 5.5 | 6.3 | 6.7 | 5.9 | 6.0 | 4.6 | 6.4 | 3.5 |
| hsa-miR-0183-3p | 4.9 | 3.9 | 5.3 | 0.0 | 5.4 | 4.3 | 3.6 | 3.2 | 3.7 |
| hsa-miR-8073 | 5.1 | 5.7 | 6.3 | 4.0 | 5.7 | 6.1 | 5.4 | 5.6 | 4.8 |
| hsa-miR-6508-5p | 5.4 | 5.2 | 5.1 | 3.6 | 5.0 | 5.3 | 5.3 | 4.2 | 4.6 |
| hsa-miR-6830-3p | 4.9 | 4.6 | 4.7 | 5.2 | 4.4 | 4.7 | 5.1 | 4.0 | 4.4 |
| hsa-miR-0409-3p | 4.8 | 4.6 | 4.9 | 2.8 | 5.4 | 5.1 | 4.6 | 4.4 | 4.3 |
| hsa-miR-0564 | 3.6 | 5.1 | 3.0 | 3.7 | 4.9 | 5.5 | 4.5 | 4.4 | 4.5 |
| hsa-miR-4533 | 4.4 | 5.5 | 4.9 | 7.0 | 5.3 | 5.6 | 5.5 | 5.5 | 5.3 |
| hsa-miR-0134-5p | 6.2 | 5.3 | 5.7 | 3.6 | 5.4 | 5.8 | 5.1 | 3.8 | 5.0 |
| hsa-miR-4312 | 5.4 | 5.2 | 5.1 | 3.8 | 5.4 | 5.1 | 5.4 | 4.6 | 4.6 |
| hsa-miR-6509-3p | 4.5 | 5.2 | 3.7 | 6.6 | 4.4 | 4.9 | 5.0 | 4.4 | 4.0 |
| hsa-miR-7152-5p | 4.9 | 5.6 | 3.9 | 3.5 | 5.0 | 5.4 | 5.2 | 5.0 | 4.5 |

TABLE 3-continued

| | | | | | | | | | |
|---|---|---|---|---|---|---|---|---|---|
| hsa-miR-0346 | 4.8 | 5.2 | 4.6 | 4.3 | 5.3 | 5.4 | 4.5 | 4.6 | 4.7 |
| hsa-miR-3653-5p | 4.9 | 5.2 | 3.8 | 0.0 | 4.9 | 4.6 | 4.7 | 3.9 | 3.8 |
| hsa-miR-6775-3p | 5.3 | 5.1 | 5.1 | 3.8 | 5.3 | 5.1 | 5.4 | 4.6 | 4.1 |
| hsa-miR-0664a-3p | 5.3 | 4.9 | 4.8 | 2.5 | 4.9 | 5.0 | 5.5 | 4.4 | 4.7 |
| hsa-miR-6859-5p | 4.1 | 5.0 | 3.5 | 3.2 | 4.8 | 4.5 | 5.0 | 4.3 | 4.0 |
| hsa-miR-0632 | 5.1 | 5.4 | 3.7 | 3.9 | 5.1 | 5.1 | 4.8 | 3.8 | 4.3 |
| hsa-miR-6740-5p | 4.4 | 4.9 | 4.1 | 6.8 | 4.1 | 5.0 | 4.2 | 4.0 | 3.4 |
| hsa-miR-1227-3p | 4.9 | 4.4 | 4.4 | 4.1 | 4.6 | 4.7 | 5.5 | 4.3 | 3.3 |
| hsa-miR-5193 | 5.0 | 5.6 | 4.3 | 2.4 | 4.9 | 5.3 | 5.4 | 4.3 | 4.5 |
| hsa-miR-0214-3p | 4.7 | 5.1 | 4.8 | 3.6 | 4.9 | 4.6 | 5.0 | 4.1 | 4.9 |
| hsa-miR-6072 | 3.9 | 5.4 | 0.0 | 2.6 | 5.2 | 3.5 | 4.6 | 4.7 | 4.6 |
| hsa-miR-6133 | 5.7 | 4.9 | 6.0 | 3.3 | 6.5 | 5.7 | 4.1 | 3.7 | 0.0 |
| hsa-miR-4722-3p | 5.3 | 5.8 | 5.3 | 2.8 | 5.3 | 5.7 | 5.2 | 4.7 | 4.9 |
| hsa-miR-2392 | 4.9 | 5.4 | 5.3 | 4.0 | 5.8 | 6.0 | 4.6 | 5.2 | 4.0 |
| hsa-miR-3158-5p | 7.1 | 6.9 | 6.3 | 4.0 | 5.8 | 6.0 | 5.4 | 4.4 | 3.4 |
| hsa-miR-6788-3p | 5.1 | 5.1 | 5.2 | 6.3 | 4.5 | 5.3 | 4.7 | 4.4 | 4.0 |
| hsa-miR-4769-5p | 4.3 | 5.1 | 4.3 | 0.0 | 5.4 | 5.3 | 4.4 | 4.3 | 4.6 |
| hsa-miR-3190-5p | 5.1 | 4.4 | 4.7 | 3.4 | 4.6 | 4.5 | 5.1 | 4.0 | 4.1 |
| hsa-miR-6734-3p | 4.8 | 5.5 | 4.6 | 6.0 | 5.1 | 4.9 | 5.3 | 4.3 | 4.5 |
| hsa-miR-0466 | 3.8 | 5.4 | 2.1 | 3.2 | 4.9 | 5.3 | 4.9 | 4.5 | 4.0 |
| hsa-miR-3187-5p | 4.9 | 5.9 | 5.7 | 4.5 | 6.3 | 6.4 | 4.6 | 5.6 | 4.9 |
| hsa-miR-4297 | 4.6 | 5.4 | 4.8 | 0.0 | 5.6 | 4.6 | 5.5 | 4.7 | 4.2 |
| hsa-miR-6824-3p | 5.3 | 5.5 | 4.9 | 3.0 | 5.2 | 5.4 | 5.4 | 4.8 | 4.7 |
| hsa-miR-6734-5p | 4.9 | 4.8 | 5.8 | 5.5 | 6.4 | 5.4 | 4.6 | 3.7 | 0.0 |
| hsa-miR-0139-3p | 5.5 | 5.5 | 6.3 | 5.9 | 6.1 | 6.5 | 4.8 | 6.3 | 4.5 |
| hsa-miR-3192-3p | 4.8 | 5.2 | 4.4 | 3.8 | 4.8 | 5.3 | 4.8 | 4.7 | 4.3 |
| hsa-miR-6799-3p | 5.1 | 4.6 | 5.0 | 3.0 | 5.3 | 5.2 | 4.9 | 4.4 | 4.4 |
| hsa-miR-4329 | 5.5 | 5.4 | 5.0 | 3.9 | 5.1 | 5.5 | 4.9 | 4.6 | 4.0 |
| hsa-miR-0199b-5p | 4.4 | 4.6 | 4.5 | 2.8 | 5.0 | 4.3 | 4.5 | 3.0 | 4.2 |
| hsa-miR-0885-5p | 5.1 | 5.4 | 4.5 | 3.7 | 5.5 | 5.0 | 4.9 | 4.6 | 4.5 |
| hsa-miR-5589-5p | 4.1 | 5.6 | 4.5 | 3.3 | 5.7 | 5.7 | 5.2 | 4.7 | 4.4 |
| hsa-miR-4539 | 4.9 | 5.7 | 5.1 | 3.9 | 5.6 | 5.2 | 5.1 | 5.4 | 4.3 |
| hsa-miR-0223-3p | 5.0 | 5.2 | 4.6 | 3.2 | 5.1 | 4.8 | 5.4 | 3.9 | 4.4 |
| hsa-miR-6772-3p | 4.4 | 5.5 | 4.1 | 6.5 | 4.7 | 5.2 | 5.0 | 4.5 | 3.9 |
| hsa-miR-6841-3p | 5.3 | 5.1 | 5.1 | 0.0 | 5.0 | 5.0 | 5.4 | 4.3 | 3.9 |
| hsa-miR-4632-3p | 5.3 | 5.4 | 5.5 | 7.4 | 4.8 | 5.1 | 5.6 | 4.8 | 4.7 |
| hsa-miR-4523 | 6.5 | 5.6 | 6.3 | 5.4 | 4.6 | 5.9 | 5.2 | 3.6 | 4.5 |
| hsa-miR-6868-3p | 4.4 | 5.3 | 4.3 | 8.1 | 5.1 | 5.1 | 5.2 | 4.7 | 4.4 |
| hsa-miR-6810-5p | 4.7 | 5.6 | 4.6 | 3.4 | 5.2 | 5.5 | 5.0 | 5.2 | 4.2 |
| hsa-miR-3620-3p | 5.1 | 5.4 | 4.8 | 2.6 | 5.3 | 5.1 | 5.4 | 4.7 | 4.6 |
| hsa-miR-1250-3p | 5.4 | 5.3 | 4.7 | 0.0 | 5.1 | 5.0 | 4.6 | 4.9 | 4.9 |
| hsa-miR-0595 | 3.8 | 5.5 | 3.4 | 3.0 | 5.0 | 4.1 | 5.0 | 4.6 | 4.7 |
| hsa-miR-0513a-5p | 5.4 | 3.7 | 6.5 | 2.7 | 7.5 | 4.9 | 3.6 | 0.0 | 3.6 |
| hsa-miR-4787-3p | 5.1 | 5.3 | 5.3 | 7.0 | 4.7 | 5.4 | 5.8 | 4.9 | 4.2 |
| hsa-miR-0518b | 5.2 | 4.8 | 5.0 | 3.0 | 5.1 | 4.8 | 5.0 | 3.2 | 5.0 |
| hsa-miR-6849-5p | 3.9 | 5.1 | 5.1 | 3.7 | 5.8 | 5.2 | 5.2 | 4.4 | 3.7 |
| hsa-miR-0320b | 5.1 | 5.0 | 2.6 | 3.0 | 3.2 | 4.6 | 4.6 | 3.2 | 3.5 |
| hsa-miR-3064-5p | 5.5 | 5.3 | 5.3 | 3.4 | 5.5 | 5.8 | 6.0 | 5.1 | 5.1 |
| hsa-miR-3166 | 0.0 | 0.0 | 0.0 | 3.4 | 5.5 | 5.8 | 0.0 | 0.0 | 0.0 |
| hsa-miR-4481 | 4.9 | 5.6 | 4.8 | 3.6 | 5.8 | 5.3 | 4.8 | 5.4 | 4.3 |
| hsa-miR-3175 | 6.1 | 6.1 | 5.4 | 4.3 | 4.8 | 6.7 | 6.2 | 5.8 | 5.5 |
| hsa-miR-3180-5p | 5.3 | 5.2 | 5.5 | 4.4 | 5.5 | 5.6 | 5.6 | 5.1 | 5.0 |
| hsa-miR-0615-3p | 4.8 | 5.2 | 4.8 | 5.9 | 3.7 | 4.8 | 4.6 | 4.4 | 3.4 |
| hsa-miR-4449 | 4.9 | 6.3 | 6.5 | 6.3 | 6.4 | 7.4 | 5.7 | 6.6 | 4.7 |
| hsa-miR-4496 | 4.9 | 4.7 | 5.1 | 2.6 | 5.7 | 5.3 | 4.3 | 3.3 | 3.8 |
| hsa-miR-0198 | 4.7 | 4.3 | 5.7 | 0.0 | 6.7 | 4.5 | 0.0 | 2.5 | 3.5 |
| hsa-miR-0026b-3p | 4.7 | 5.0 | 4.4 | 3.6 | 4.7 | 4.7 | 5.2 | 4.3 | 4.7 |
| hsa-miR-0675-3p | 5.0 | 5.9 | 5.1 | 3.3 | 4.9 | 5.5 | 5.1 | 5.0 | 5.1 |
| hsa-miR-0765 | 5.5 | 5.2 | 4.7 | 2.4 | 5.5 | 5.1 | 5.0 | 3.8 | 3.1 |
| hsa-miR-0487a-5p | 4.5 | 5.1 | 4.4 | 3.0 | 5.2 | 5.2 | 4.9 | 4.6 | 4.3 |
| hsa-miR-5189-5p | 3.7 | 5.3 | 4.7 | 4.0 | 5.2 | 5.4 | 4.3 | 4.5 | 3.3 |
| hsa-miR-6871-5p | 4.2 | 5.5 | 4.7 | 6.0 | 5.5 | 6.3 | 4.8 | 4.8 | 4.2 |
| hsa-miR-0575 | 5.3 | 5.4 | 4.9 | 4.0 | 5.5 | 5.8 | 5.2 | 5.1 | 4.7 |
| hsa-miR-1910-5p | 5.0 | 5.3 | 5.4 | 4.3 | 5.4 | 5.6 | 5.6 | 4.8 | 4.7 |
| hsa-miR-3139 | 0.0 | 0.0 | 0.0 | 4.3 | 5.4 | 5.6 | 0.0 | 0.0 | 0.0 |
| hsa-miR-6762-3p | 4.8 | 5.8 | 4.6 | 3.9 | 5.7 | 5.0 | 5.2 | 5.1 | 4.5 |
| hsa-miR-4251 | 5.3 | 3.1 | 6.4 | 0.0 | 7.6 | 5.8 | 3.0 | 0.0 | 2.9 |
| hsa-miR-6790-3p | 5.5 | 5.6 | 5.4 | 4.7 | 5.6 | 5.4 | 6.2 | 5.0 | 4.8 |
| hsa-miR-6751-5p | 4.8 | 5.7 | 4.5 | 5.2 | 5.4 | 5.9 | 4.9 | 5.3 | 4.4 |
| hsa-miR-3173-3p | 5.3 | 3.8 | 5.6 | 3.7 | 4.5 | 4.3 | 3.4 | 4.1 | 4.0 |
| hsa-miR-6783-3p | 4.8 | 5.5 | 4.5 | 3.2 | 5.3 | 5.3 | 5.4 | 4.8 | 4.5 |
| hsa-miR-6793-5p | 4.1 | 5.4 | 3.4 | 3.2 | 5.5 | 4.6 | 4.9 | 4.7 | 4.8 |
| hsa-miR-1193 | 5.5 | 5.5 | 6.0 | 4.4 | 5.6 | 6.1 | 5.2 | 5.1 | 5.4 |
| hsa-miR-0637 | 5.0 | 5.8 | 5.3 | 3.7 | 5.5 | 5.7 | 5.5 | 5.2 | 4.7 |
| hsa-miR-6738-3p | 4.5 | 5.4 | 3.7 | 3.5 | 5.1 | 4.7 | 5.5 | 5.1 | 4.6 |
| hsa-miR-0223-5p | 5.6 | 5.1 | 4.5 | 3.1 | 4.8 | 5.0 | 5.9 | 3.9 | 5.4 |
| hsa-miR-3940-3p | 5.0 | 5.7 | 4.9 | 3.8 | 5.3 | 5.2 | 5.0 | 5.1 | 5.0 |
| hsa-miR-6893-3p | 5.1 | 5.6 | 5.2 | 4.2 | 5.5 | 5.1 | 5.4 | 5.1 | 4.5 |
| hsa-miR-0342-5p | 5.1 | 4.3 | 5.2 | 3.3 | 6.3 | 5.9 | 5.3 | 2.7 | 4.2 |
| hsa-miR-1307-3p | 4.4 | 5.7 | 5.6 | 4.8 | 6.3 | 6.5 | 5.5 | 5.5 | 4.8 |

TABLE 3-continued

| | | | | | | | | | |
|---|---|---|---|---|---|---|---|---|---|
| hsa-miR-3121-5p | 0.0 | 0.0 | 0.0 | 4.8 | 6.3 | 6.5 | 0.0 | 0.0 | 0.0 |
| hsa-miR-6131 | 5.0 | 6.2 | 6.3 | 4.9 | 6.2 | 7.2 | 4.7 | 6.4 | 4.3 |
| hsa-miR-0485-3p | 4.6 | 5.3 | 3.9 | 3.0 | 5.5 | 5.2 | 5.7 | 4.5 | 4.9 |
| hsa-miR-5088-5p | 5.4 | 5.8 | 5.0 | 4.4 | 5.4 | 5.5 | 5.6 | 5.3 | 4.5 |
| hsa-miR-0642a-5p | 5.5 | 5.3 | 4.9 | 6.6 | 4.9 | 5.1 | 5.1 | 4.3 | 3.7 |
| hsa-miR-1470 | 5.4 | 5.4 | 5.5 | 4.6 | 5.5 | 5.6 | 6.0 | 5.6 | 5.5 |
| hsa-miR-3129-3p | 2.7 | 3.3 | 0.0 | 4.6 | 5.5 | 5.6 | 3.8 | 2.3 | 0.0 |
| hsa-miR-5002-3p | 4.0 | 5.6 | 3.8 | 3.3 | 5.2 | 4.5 | 5.1 | 4.9 | 4.8 |
| hsa-miR-0664b-3p | 5.1 | 5.2 | 5.1 | 3.4 | 5.2 | 5.3 | 4.9 | 4.6 | 4.2 |
| hsa-miR-4322 | 6.0 | 6.1 | 6.6 | 4.7 | 5.9 | 6.0 | 5.8 | 5.9 | 5.3 |
| hsa-miR-4535 | 4.3 | 6.0 | 5.1 | 4.3 | 5.9 | 6.0 | 5.7 | 5.7 | 5.4 |
| hsa-miR-1233-3p | 5.6 | 5.6 | 6.1 | 3.8 | 5.6 | 5.6 | 5.6 | 4.9 | 5.1 |
| hsa-miR-6825-3p | 5.2 | 5.6 | 5.5 | 4.6 | 5.7 | 5.9 | 5.3 | 6.2 | 5.0 |
| hsa-miR-6769b-3p | 5.4 | 5.4 | 4.9 | 3.4 | 5.0 | 5.3 | 5.5 | 4.5 | 4.8 |
| hsa-miR-4290 | 5.1 | 5.4 | 5.2 | 2.4 | 5.3 | 5.5 | 4.6 | 4.3 | 4.5 |
| hsa-miR-0874-3p | 5.6 | 5.9 | 5.4 | 6.1 | 5.7 | 5.7 | 5.6 | 5.3 | 5.2 |
| hsa-miR-0532-3p | 5.6 | 5.8 | 5.2 | 3.5 | 5.5 | 5.5 | 5.1 | 5.1 | 4.7 |
| hsa-miR-6744-3p | 5.9 | 5.3 | 5.3 | 2.9 | 5.0 | 5.4 | 5.2 | 4.5 | 4.8 |
| hsa-miR-0030d-5p | 5.2 | 5.0 | 5.0 | 4.0 | 5.7 | 5.2 | 5.6 | 4.9 | 5.1 |
| hsa-miR-3652 | 4.6 | 5.8 | 5.5 | 4.1 | 7.4 | 7.2 | 5.3 | 5.6 | 4.4 |
| hsa-miR-4710 | 5.6 | 5.7 | 5.0 | 5.0 | 5.6 | 6.0 | 5.7 | 5.1 | 4.9 |
| hsa-miR-5195-5p | 5.5 | 5.5 | 5.8 | 5.2 | 5.3 | 5.1 | 6.0 | 3.9 | 4.5 |
| hsa-miR-6812-3p | 5.6 | 5.3 | 5.3 | 4.1 | 5.2 | 5.5 | 5.6 | 4.4 | 4.2 |
| hsa-let-7b-3p | 5.3 | 5.4 | 5.3 | 6.4 | 5.0 | 5.3 | 5.4 | 4.4 | 4.5 |
| hsa-miR-0483-3p | 5.3 | 5.5 | 5.2 | 4.5 | 5.7 | 5.8 | 5.2 | 5.0 | 4.9 |
| hsa-miR-7106-3p | 5.5 | 5.5 | 5.2 | 3.8 | 5.3 | 5.3 | 5.5 | 5.0 | 4.7 |
| hsa-miR-0199a-5p | 4.9 | 5.3 | 4.4 | 2.7 | 4.8 | 4.8 | 5.0 | 4.0 | 4.6 |
| hsa-miR-0188-5p | 5.8 | 5.8 | 5.7 | 3.6 | 5.7 | 5.8 | 5.9 | 4.6 | 5.6 |
| hsa-miR-6737-3p | 5.3 | 5.3 | 4.9 | 3.7 | 5.5 | 5.1 | 5.7 | 4.6 | 4.1 |
| hsa-miR-6796-5p | 4.9 | 6.0 | 5.4 | 3.7 | 5.7 | 5.8 | 5.0 | 5.5 | 4.9 |
| hsa-miR-7843-5p | 5.9 | 6.1 | 5.3 | 2.5 | 5.7 | 5.4 | 4.8 | 4.2 | 3.8 |
| hsa-miR-4498 | 4.8 | 6.2 | 5.2 | 5.6 | 5.7 | 5.7 | 5.1 | 5.6 | 4.6 |
| hsa-miR-5010-3p | 5.2 | 5.4 | 5.0 | 3.3 | 5.1 | 5.2 | 5.4 | 4.3 | 4.6 |
| hsa-miR-8060 | 4.8 | 4.7 | 4.1 | 0.0 | 4.2 | 4.9 | 4.3 | 4.0 | 3.6 |
| hsa-miR-0487b-5p | 4.9 | 5.3 | 4.8 | 3.7 | 5.1 | 5.1 | 4.9 | 4.6 | 4.4 |
| hsa-miR-6831-3p | 5.7 | 5.6 | 5.5 | 0.0 | 5.4 | 5.6 | 4.9 | 4.7 | 4.4 |
| hsa-miR-0320a | 5.9 | 5.2 | 5.3 | 3.2 | 5.0 | 5.2 | 5.6 | 3.9 | 5.1 |
| hsa-miR-6771-3p | 5.5 | 5.3 | 5.5 | 4.2 | 5.1 | 4.9 | 5.9 | 4.3 | 4.4 |
| hsa-miR-6511a-3p | 5.1 | 5.8 | 5.1 | 5.5 | 5.8 | 5.6 | 5.5 | 5.4 | 5.4 |
| hsa-miR-0374c-3p | 6.6 | 5.3 | 5.3 | 0.0 | 4.6 | 5.7 | 5.3 | 4.2 | 5.0 |
| hsa-miR-8052 | 6.0 | 6.0 | 5.9 | 3.9 | 5.8 | 6.1 | 5.7 | 5.6 | 5.0 |
| hsa-miR-4531 | 0.0 | 2.4 | 0.0 | 0.0 | 3.7 | 2.6 | 0.0 | 0.0 | 3.2 |
| hsa-miR-6790-5p | 5.8 | 5.9 | 6.2 | 4.1 | 5.7 | 6.5 | 5.0 | 5.8 | 4.5 |
| hsa-miR-6883-3p | 4.4 | 5.4 | 4.3 | 3.5 | 5.1 | 5.2 | 5.0 | 4.8 | 4.7 |
| hsa-miR-4655-3p | 4.8 | 5.9 | 5.9 | 5.1 | 6.0 | 4.7 | 7.9 | 5.9 | 7.2 |
| hsa-miR-5189-3p | 5.1 | 5.7 | 4.9 | 3.7 | 5.6 | 5.0 | 5.6 | 5.2 | 5.1 |
| hsa-miR-6753-3p | 4.7 | 5.8 | 4.4 | 3.8 | 5.4 | 5.8 | 5.5 | 5.1 | 4.4 |
| hsa-miR-4455 | 5.1 | 6.0 | 5.0 | 3.7 | 5.9 | 5.5 | 5.4 | 5.3 | 4.8 |
| hsa-miR-3605-3p | 5.2 | 5.9 | 5.0 | 3.3 | 5.4 | 5.2 | 5.8 | 5.0 | 4.6 |
| hsa-miR-4642 | 5.3 | 5.6 | 5.0 | 2.6 | 5.4 | 5.7 | 5.7 | 4.7 | 4.6 |
| hsa-miR-7160-5p | 4.9 | 6.0 | 5.1 | 4.5 | 5.9 | 6.2 | 6.0 | 5.8 | 5.3 |
| hsa-miR-5008-5p | 6.2 | 6.0 | 6.2 | 4.8 | 6.1 | 6.0 | 6.2 | 5.8 | 5.8 |
| hsa-miR-1292-3p | 5.4 | 5.8 | 5.7 | 4.8 | 5.9 | 5.7 | 6.3 | 5.6 | 6.1 |
| hsa-miR-6753-5p | 5.3 | 6.1 | 5.7 | 4.6 | 6.1 | 5.7 | 5.6 | 5.6 | 5.2 |
| hsa-miR-4649-3p | 5.6 | 5.6 | 5.2 | 3.8 | 5.5 | 5.4 | 5.7 | 4.7 | 5.0 |
| hsa-miR-7846-3p | 6.6 | 6.1 | 6.3 | 3.3 | 5.9 | 6.2 | 5.5 | 4.9 | 4.3 |
| hsa-miR-0936 | 5.9 | 5.8 | 6.8 | 3.6 | 7.0 | 4.9 | 6.0 | 3.3 | 5.1 |
| hsa-miR-0504-3p | 5.5 | 5.9 | 5.5 | 3.8 | 6.1 | 6.2 | 5.0 | 6.0 | 5.4 |
| hsa-miR-4746-3p | 5.7 | 6.5 | 6.3 | 5.6 | 6.3 | 7.2 | 6.0 | 6.8 | 5.5 |
| hsa-miR-6833-3p | 5.5 | 5.7 | 5.4 | 3.7 | 5.3 | 5.6 | 5.7 | 5.2 | 4.9 |
| hsa-miR-4279 | 5.8 | 6.1 | 6.0 | 3.7 | 6.1 | 6.4 | 5.7 | 5.5 | 4.8 |
| hsa-miR-6776-5p | 4.8 | 5.4 | 5.0 | 3.0 | 6.0 | 6.0 | 4.3 | 5.6 | 4.3 |
| hsa-miR-6748-3p | 5.0 | 5.8 | 4.8 | 7.0 | 5.3 | 5.6 | 5.5 | 4.8 | 4.9 |
| hsa-miR-4721 | 5.2 | 5.7 | 4.7 | 4.2 | 5.9 | 6.2 | 5.7 | 5.1 | 5.2 |
| hsa-miR-0185-3p | 4.9 | 5.8 | 5.7 | 4.7 | 6.1 | 6.7 | 5.5 | 5.8 | 5.5 |
| hsa-miR-6735-3p | 5.8 | 5.5 | 5.5 | 4.2 | 5.8 | 5.9 | 5.3 | 4.8 | 5.0 |
| hsa-miR-4287 | 6.5 | 6.0 | 5.3 | 3.5 | 5.1 | 5.9 | 5.3 | 3.9 | 3.4 |
| hsa-miR-3173-5p | 4.6 | 5.8 | 4.0 | 3.9 | 5.7 | 5.0 | 5.3 | 5.3 | 5.0 |
| hsa-miR-6782-3p | 5.8 | 5.7 | 5.6 | 5.1 | 5.8 | 5.6 | 6.0 | 5.0 | 4.9 |
| hsa-miR-7112-5p | 5.9 | 6.1 | 6.4 | 5.4 | 5.9 | 6.4 | 5.7 | 5.8 | 5.5 |
| hsa-miR-6794-3p | 5.8 | 5.8 | 5.4 | 4.0 | 5.6 | 5.6 | 5.8 | 5.0 | 5.2 |
| hsa-miR-6757-3p | 5.9 | 5.6 | 5.6 | 3.2 | 5.5 | 5.3 | 6.0 | 4.7 | 5.1 |
| hsa-miR-3622a-3p | 5.0 | 5.7 | 4.6 | 4.2 | 5.9 | 5.8 | 5.5 | 4.9 | 5.1 |
| hsa-miR-6726-3p | 5.7 | 6.1 | 5.8 | 6.0 | 5.7 | 5.8 | 5.9 | 5.3 | 5.1 |
| hsa-miR-0642b-5p | 5.5 | 5.7 | 4.5 | 0.0 | 5.1 | 5.1 | 5.2 | 4.6 | 4.3 |
| hsa-miR-6809-3p | 5.0 | 5.4 | 3.9 | 4.0 | 5.6 | 5.8 | 5.2 | 4.9 | 5.2 |
| hsa-miR-6857-5p | 5.5 | 7.1 | 6.9 | 5.7 | 6.6 | 7.1 | 5.4 | 7.6 | 4.6 |
| hsa-miR-0197-3p | 5.4 | 5.9 | 5.2 | 3.8 | 6.0 | 5.4 | 5.5 | 5.2 | 5.5 |
| hsa-miR-0149-5p | 5.4 | 5.8 | 5.5 | 4.2 | 5.8 | 5.7 | 5.5 | 5.0 | 5.2 |
| hsa-miR-4485-5p | 5.6 | 6.2 | 5.6 | 4.3 | 5.7 | 6.3 | 6.0 | 5.5 | 5.2 |

TABLE 3-continued

| | | | | | | | | | |
|---|---|---|---|---|---|---|---|---|---|
| hsa-miR-0939-3p | 5.6 | 5.7 | 5.5 | 7.4 | 5.7 | 5.7 | 5.4 | 5.1 | 4.9 |
| hsa-miR-6780b-3p | 5.3 | 6.0 | 4.9 | 3.4 | 5.6 | 5.3 | 5.8 | 5.4 | 4.3 |
| hsa-miR-6748-5p | 5.1 | 4.7 | 5.8 | 3.5 | 6.6 | 6.1 | 5.2 | 4.8 | 4.9 |
| hsa-miR-6751-3p | 5.7 | 5.9 | 5.1 | 4.0 | 5.4 | 5.8 | 5.7 | 5.0 | 5.2 |
| hsa-miR-4736 | 5.7 | 6.8 | 7.1 | 5.2 | 6.6 | 6.6 | 5.6 | 6.4 | 5.6 |
| hsa-miR-6778-3p | 5.1 | 5.9 | 4.5 | 4.7 | 5.5 | 6.0 | 5.7 | 5.4 | 4.9 |
| hsa-miR-6827-3p | 5.7 | 5.1 | 5.1 | 3.7 | 5.4 | 5.3 | 5.3 | 4.5 | 4.1 |
| hsa-miR-5698 | 6.3 | 6.5 | 6.3 | 4.0 | 6.7 | 6.7 | 5.4 | 4.9 | 5.0 |
| hsa-miR-0371b-5p | 5.4 | 5.9 | 6.4 | 4.6 | 6.4 | 6.9 | 5.2 | 6.0 | 5.4 |
| hsa-miR-4714-5p | 5.5 | 5.2 | 5.3 | 4.1 | 5.4 | 5.0 | 5.8 | 4.4 | 4.7 |
| hsa-miR-6772-5p | 5.0 | 6.0 | 5.4 | 4.3 | 5.6 | 5.3 | 5.9 | 5.4 | 4.9 |
| hsa-miR-4462 | 7.1 | 6.2 | 5.9 | 3.9 | 5.3 | 6.4 | 5.6 | 4.7 | 4.7 |
| hsa-miR-6793-3p | 5.8 | 5.5 | 5.9 | 4.0 | 5.9 | 5.3 | 6.3 | 5.0 | 5.3 |
| hsa-miR-0328-3p | 5.6 | 6.0 | 5.4 | 4.5 | 5.7 | 5.7 | 5.8 | 5.2 | 5.2 |
| hsa-miR-3202 | 5.3 | 5.6 | 4.7 | 0.0 | 4.8 | 5.0 | 3.4 | 4.1 | 0.0 |
| hsa-miR-6867-5p | 6.2 | 6.0 | 5.3 | 3.5 | 5.7 | 5.3 | 6.1 | 4.9 | 4.8 |
| hsa-miR-0302c-5p | 5.0 | 4.6 | 5.5 | 3.8 | 6.0 | 5.4 | 4.9 | 3.6 | 4.3 |
| hsa-miR-6881-5p | 5.7 | 6.1 | 5.6 | 0.0 | 5.6 | 5.5 | 4.8 | 3.5 | 4.7 |
| hsa-miR-0574-5p | 5.2 | 5.9 | 4.9 | 4.6 | 6.0 | 5.5 | 5.8 | 5.4 | 5.2 |
| hsa-miR-1260b | 5.4 | 5.9 | 5.2 | 4.4 | 5.9 | 6.0 | 5.4 | 5.4 | 5.3 |
| hsa-miR-6834-3p | 5.6 | 5.8 | 5.2 | 2.8 | 5.7 | 5.8 | 5.4 | 5.0 | 5.3 |
| hsa-miR-4763-5p | 5.5 | 5.9 | 5.6 | 4.6 | 5.6 | 5.8 | 5.8 | 5.6 | 5.1 |
| hsa-miR-7110-3p | 5.7 | 6.0 | 5.3 | 7.5 | 5.6 | 5.9 | 5.0 | 5.1 | 4.7 |
| hsa-miR-1825 | 5.4 | 5.8 | 5.7 | 4.1 | 6.0 | 5.5 | 5.7 | 5.0 | 5.2 |
| hsa-miR-3134 | 0.0 | 0.0 | 0.0 | 4.1 | 6.0 | 5.5 | 0.0 | 0.0 | 0.0 |
| hsa-miR-3679-5p | 5.6 | 5.2 | 6.2 | 4.1 | 6.3 | 6.0 | 4.6 | 4.5 | 4.5 |
| hsa-miR-0370-3p | 5.2 | 5.7 | 6.1 | 3.8 | 7.4 | 8.3 | 5.4 | 5.4 | 4.6 |
| hsa-miR-0092a-2-5p | 5.3 | 7.5 | 6.6 | 5.6 | 7.9 | 7.6 | 5.8 | 8.6 | 6.6 |
| hsa-miR-7111-3p | 6.2 | 6.1 | 6.0 | 3.7 | 6.0 | 5.8 | 6.0 | 5.2 | 5.2 |
| hsa-miR-3663-5p | 4.8 | 6.0 | 4.8 | 4.9 | 6.1 | 6.1 | 5.8 | 5.6 | 5.7 |
| hsa-miR-0503-3p | 6.0 | 6.1 | 5.6 | 4.2 | 5.5 | 5.8 | 6.3 | 5.2 | 5.1 |
| hsa-miR-6736-5p | 5.7 | 6.1 | 4.8 | 4.8 | 6.1 | 5.9 | 5.7 | 5.4 | 5.6 |
| hsa-miR-3191-5p | 4.9 | 5.8 | 4.7 | 3.4 | 5.4 | 5.7 | 5.5 | 4.9 | 4.9 |
| hsa-miR-5705 | 6.0 | 5.6 | 5.9 | 4.0 | 5.7 | 5.9 | 5.6 | 5.3 | 5.4 |
| hsa-miR-7977 | 5.4 | 6.0 | 5.1 | 4.4 | 5.8 | 5.2 | 5.6 | 5.6 | 5.5 |
| hsa-miR-6840-5p | 5.6 | 5.6 | 5.8 | 4.0 | 5.7 | 5.7 | 5.8 | 4.8 | 5.1 |
| hsa-miR-6865-3p | 5.7 | 5.9 | 5.5 | 4.4 | 5.8 | 5.9 | 5.7 | 5.3 | 5.1 |
| hsa-miR-6754-3p | 5.3 | 6.0 | 4.7 | 4.0 | 5.9 | 5.5 | 5.5 | 5.6 | 5.4 |
| hsa-miR-6830-5p | 5.7 | 5.5 | 5.4 | 0.0 | 6.6 | 6.2 | 4.7 | 4.4 | 3.2 |
| hsa-miR-6736-3p | 5.1 | 5.9 | 4.6 | 4.1 | 5.9 | 5.3 | 5.6 | 5.3 | 4.8 |
| hsa-miR-6842-5p | 6.4 | 6.2 | 6.1 | 4.4 | 6.5 | 7.1 | 5.4 | 5.9 | 4.3 |
| hsa-miR-6761-3p | 5.4 | 6.2 | 5.0 | 4.1 | 6.0 | 6.1 | 5.7 | 5.4 | 5.2 |
| hsa-miR-1236-3p | 6.1 | 6.0 | 5.9 | 4.2 | 6.1 | 5.8 | 6.0 | 5.4 | 4.8 |
| hsa-miR-5196-3p | 5.7 | 5.9 | 5.6 | 4.5 | 5.8 | 6.0 | 5.9 | 5.4 | 5.4 |
| hsa-miR-1234-3p | 6.3 | 5.7 | 6.3 | 4.2 | 5.5 | 6.0 | 6.2 | 5.3 | 4.9 |
| hsa-miR-3925-5p | 5.9 | 4.3 | 6.1 | 3.8 | 6.4 | 5.6 | 5.0 | 3.7 | 4.4 |
| hsa-miR-6872-5p | 4.4 | 4.8 | 5.6 | 2.5 | 6.2 | 4.9 | 4.3 | 3.3 | 4.2 |
| hsa-miR-4483 | 6.1 | 6.5 | 5.6 | 3.8 | 5.8 | 6.4 | 5.6 | 5.0 | 4.8 |
| hsa-miR-3917 | 5.6 | 5.9 | 5.5 | 6.6 | 5.8 | 6.2 | 5.9 | 6.1 | 5.6 |
| hsa-miR-6877-3p | 5.7 | 6.2 | 5.7 | 4.3 | 5.7 | 5.6 | 5.7 | 5.4 | 5.1 |
| hsa-miR-0520e | 4.2 | 2.0 | 5.9 | 4.7 | 5.9 | 4.2 | 4.1 | 0.0 | 3.6 |
| hsa-miR-4436b-5p | 5.7 | 6.1 | 5.5 | 5.1 | 6.2 | 6.2 | 5.8 | 5.6 | 5.4 |
| hsa-miR-4444 | 4.2 | 3.2 | 4.8 | 0.0 | 5.5 | 4.8 | 3.8 | 0.0 | 3.6 |
| hsa-miR-6759-5p | 5.1 | 6.6 | 6.2 | 5.9 | 6.4 | 6.6 | 5.1 | 7.5 | 5.2 |
| hsa-miR-6511a-5p | 6.0 | 6.5 | 6.4 | 5.2 | 6.6 | 6.6 | 6.3 | 5.9 | 5.3 |
| hsa-miR-4430 | 5.6 | 6.0 | 6.6 | 4.0 | 6.8 | 6.6 | 5.5 | 5.7 | 5.0 |
| hsa-miR-6127 | 5.1 | 6.0 | 5.6 | 4.7 | 6.1 | 6.2 | 5.4 | 5.7 | 4.6 |
| hsa-miR-6740-3p | 5.2 | 6.1 | 5.0 | 6.8 | 5.8 | 5.6 | 5.8 | 5.0 | 4.8 |
| hsa-miR-6747-3p | 5.4 | 6.0 | 5.1 | 4.3 | 5.7 | 5.4 | 5.7 | 5.4 | 5.4 |
| hsa-miR-0133b | 5.7 | 5.4 | 5.5 | 4.0 | 6.1 | 5.6 | 6.0 | 4.6 | 5.5 |
| hsa-miR-4440 | 4.8 | 6.1 | 4.8 | 4.7 | 6.2 | 6.1 | 5.8 | 5.8 | 5.4 |
| hsa-miR-0548q | 5.9 | 6.1 | 6.8 | 4.4 | 5.8 | 6.1 | 5.9 | 6.1 | 5.9 |
| hsa-miR-6741-3p | 5.7 | 6.2 | 5.5 | 4.2 | 5.7 | 5.5 | 6.0 | 5.2 | 5.1 |
| hsa-miR-6779-3p | 5.7 | 6.1 | 5.2 | 4.0 | 5.8 | 5.6 | 5.8 | 5.1 | 5.3 |
| hsa-miR-3622b-5p | 6.1 | 5.6 | 5.8 | 2.5 | 6.4 | 5.6 | 4.9 | 4.4 | 4.1 |
| hsa-miR-6787-3p | 5.5 | 5.9 | 5.1 | 4.3 | 5.4 | 5.4 | 5.7 | 5.2 | 5.1 |
| hsa-miR-6873-3p | 5.4 | 6.1 | 4.7 | 4.1 | 5.7 | 6.1 | 6.3 | 5.4 | 5.4 |
| hsa-miR-4713-5p | 5.8 | 6.2 | 5.3 | 4.3 | 6.0 | 6.2 | 5.9 | 5.3 | 5.3 |
| hsa-miR-6742-3p | 6.0 | 6.0 | 5.7 | 6.0 | 5.6 | 5.7 | 6.0 | 4.8 | 5.3 |
| hsa-miR-0423-5p | 6.8 | 6.9 | 6.9 | 5.4 | 6.6 | 7.3 | 5.5 | 6.5 | 5.0 |
| hsa-miR-0204-3p | 4.5 | 6.1 | 4.8 | 4.6 | 5.5 | 6.5 | 4.2 | 4.6 | 4.0 |
| hsa-miR-6823-3p | 5.7 | 5.8 | 5.4 | 3.1 | 5.8 | 5.9 | 5.6 | 5.5 | 5.2 |
| hsa-miR-6877-5p | 5.7 | 6.4 | 6.2 | 7.8 | 6.5 | 6.9 | 5.7 | 6.4 | 5.1 |
| hsa-miR-4695-3p | 5.3 | 6.4 | 5.0 | 4.5 | 6.0 | 5.5 | 6.1 | 5.7 | 5.4 |
| hsa-miR-0018b-3p | 5.7 | 5.6 | 5.8 | 4.5 | 5.7 | 5.7 | 6.2 | 5.1 | 5.5 |
| hsa-miR-1260a | 5.6 | 5.8 | 5.3 | 4.1 | 5.8 | 5.6 | 5.6 | 5.4 | 5.5 |
| hsa-miR-6803-3p | 5.7 | 6.0 | 5.6 | 4.0 | 5.9 | 6.0 | 5.8 | 5.6 | 5.7 |
| hsa-miR-0211-3p | 6.2 | 6.4 | 7.1 | 6.0 | 7.4 | 7.5 | 5.3 | 7.1 | 5.1 |
| hsa-miR-6875-3p | 5.4 | 6.1 | 5.4 | 4.4 | 5.9 | 5.6 | 5.9 | 5.6 | 5.4 |
| hsa-miR-6882-3p | 5.4 | 6.2 | 5.0 | 3.4 | 6.1 | 5.5 | 5.7 | 5.6 | 5.3 |

TABLE 3-continued

| | | | | | | | | | |
|---|---|---|---|---|---|---|---|---|---|
| hsa-miR-8085 | 5.8 | 5.8 | 5.3 | 2.8 | 6.1 | 6.3 | 5.6 | 5.3 | 5.1 |
| hsa-miR-6750-3p | 5.6 | 6.1 | 5.1 | 5.9 | 6.2 | 6.0 | 5.8 | 5.6 | 5.2 |
| hsa-miR-6879-3p | 5.8 | 6.1 | 6.2 | 5.0 | 6.5 | 6.7 | 6.3 | 6.1 | 5.6 |
| hsa-miR-6867-3p | 5.4 | 6.0 | 5.2 | 4.0 | 5.9 | 5.8 | 5.9 | 5.4 | 5.3 |
| hsa-miR-6890-5p | 6.4 | 6.6 | 5.6 | 4.4 | 5.8 | 6.5 | 6.2 | 6.1 | 5.7 |
| hsa-miR-6894-5p | 6.6 | 6.2 | 6.1 | 4.9 | 6.0 | 6.7 | 5.8 | 5.7 | 4.8 |
| hsa-miR-1306-5p | 6.1 | 6.2 | 5.9 | 4.5 | 6.2 | 6.4 | 6.2 | 5.6 | 5.6 |
| hsa-miR-3121-3p | 0.0 | 0.0 | 0.0 | 4.5 | 6.2 | 6.4 | 0.0 | 0.0 | 2.7 |
| hsa-miR-6886-3p | 5.5 | 6.2 | 5.5 | 6.2 | 5.9 | 6.3 | 5.7 | 5.6 | 5.3 |
| hsa-miR-1267 | 5.8 | 5.5 | 5.6 | 4.2 | 5.7 | 5.5 | 6.2 | 4.5 | 5.3 |
| hsa-miR-6862-3p | 5.8 | 6.3 | 5.3 | 6.4 | 5.9 | 5.8 | 5.5 | 5.5 | 5.3 |
| hsa-miR-4701-5p | 5.7 | 5.7 | 5.8 | 4.4 | 5.9 | 5.8 | 6.2 | 5.1 | 5.1 |
| hsa-miR-6792-5p | 6.3 | 6.2 | 6.3 | 5.3 | 6.3 | 6.4 | 6.2 | 6.0 | 5.8 |
| hsa-miR-4698 | 6.0 | 5.6 | 5.9 | 5.0 | 5.6 | 5.5 | 6.0 | 4.6 | 4.7 |
| hsa-miR-4738-3p | 5.4 | 6.2 | 6.0 | 5.4 | 5.8 | 5.7 | 6.0 | 6.2 | 6.1 |
| hsa-miR-4268 | 5.6 | 5.9 | 5.2 | 4.3 | 5.9 | 5.9 | 5.5 | 4.9 | 5.0 |
| hsa-miR-4664-3p | 5.8 | 6.0 | 5.7 | 4.3 | 6.1 | 6.0 | 6.3 | 5.4 | 5.3 |
| hsa-miR-0877-3p | 5.8 | 5.8 | 5.6 | 4.9 | 6.0 | 6.0 | 6.2 | 5.5 | 5.4 |
| hsa-miR-1304-3p | 6.0 | 5.9 | 5.5 | 6.7 | 5.9 | 5.9 | 6.2 | 5.2 | 5.2 |
| hsa-miR-3118 | 0.0 | 0.0 | 0.0 | 6.7 | 5.9 | 5.9 | 0.0 | 0.0 | 0.0 |
| hsa-miR-6870-3p | 6.0 | 6.0 | 5.7 | 6.8 | 6.0 | 5.8 | 6.2 | 5.0 | 5.1 |
| hsa-miR-0574-3p | 5.9 | 6.3 | 5.6 | 4.7 | 6.2 | 6.0 | 6.1 | 5.8 | 5.7 |
| hsa-miR-4646-3p | 6.0 | 6.2 | 5.9 | 3.8 | 5.8 | 5.7 | 5.9 | 5.5 | 5.4 |
| hsa-miR-6884-3p | 6.1 | 6.1 | 6.0 | 7.4 | 5.9 | 6.0 | 6.0 | 5.4 | 5.1 |
| hsa-miR-0658 | 5.8 | 6.4 | 6.3 | 4.6 | 6.5 | 6.5 | 5.3 | 6.0 | 4.8 |
| hsa-miR-3911 | 7.8 | 6.9 | 6.2 | 3.6 | 5.8 | 6.6 | 5.2 | 4.8 | 4.8 |
| hsa-miR-6743-3p | 5.9 | 6.4 | 5.9 | 4.4 | 6.1 | 6.4 | 6.3 | 5.8 | 5.6 |
| hsa-miR-6870-5p | 7.0 | 7.3 | 6.8 | 4.4 | 6.5 | 7.3 | 5.4 | 6.7 | 4.7 |
| hsa-miR-4685-3p | 5.5 | 6.1 | 5.0 | 4.0 | 6.2 | 5.7 | 6.1 | 5.8 | 5.2 |
| hsa-miR-3191-3p | 6.5 | 6.0 | 6.5 | 4.7 | 6.4 | 6.5 | 6.3 | 5.6 | 5.4 |
| hsa-miR-1281 | 6.2 | 6.1 | 6.0 | 4.7 | 6.2 | 6.1 | 6.3 | 5.6 | 5.8 |
| hsa-miR-4747-5p | 6.5 | 6.1 | 6.2 | 0.0 | 6.6 | 6.5 | 5.4 | 5.1 | 4.6 |
| hsa-miR-0887-3p | 5.4 | 7.6 | 7.8 | 6.7 | 7.7 | 7.8 | 6.3 | 7.9 | 6.2 |
| hsa-miR-4700-3p | 5.8 | 6.2 | 5.4 | 3.6 | 6.2 | 5.7 | 6.0 | 5.5 | 5.2 |
| hsa-miR-6727-3p | 6.0 | 6.3 | 6.1 | 4.6 | 6.2 | 6.2 | 5.8 | 5.9 | 5.6 |
| hsa-miR-5699-5p | 6.3 | 5.9 | 6.0 | 4.0 | 5.9 | 6.0 | 6.4 | 4.8 | 5.3 |
| hsa-miR-0498 | 6.9 | 6.8 | 7.2 | 5.3 | 6.8 | 6.6 | 6.8 | 5.9 | 6.4 |
| hsa-miR-0449b-3p | 5.7 | 6.3 | 5.3 | 4.3 | 5.9 | 6.2 | 6.0 | 5.7 | 5.6 |
| hsa-miR-6735-5p | 7.0 | 6.9 | 6.8 | 5.1 | 6.8 | 7.0 | 6.7 | 6.1 | 6.4 |
| hsa-miR-1343-3p | 5.8 | 6.2 | 6.3 | 4.6 | 6.8 | 6.9 | 6.1 | 5.8 | 6.4 |
| hsa-miR-3126-3p | 3.6 | 4.0 | 3.3 | 4.6 | 6.8 | 6.9 | 3.5 | 3.0 | 2.9 |
| hsa-miR-8071 | 4.8 | 6.4 | 5.4 | 4.9 | 6.2 | 6.6 | 5.9 | 6.3 | 4.9 |
| hsa-miR-1587 | 5.4 | 7.1 | 6.5 | 5.6 | 6.7 | 7.3 | 6.1 | 7.6 | 5.6 |
| hsa-miR-3133 | 0.0 | 0.0 | 0.0 | 5.6 | 6.7 | 7.3 | 0.0 | 0.0 | 0.0 |
| hsa-miR-4793-3p | 5.5 | 5.6 | 4.9 | 0.0 | 5.0 | 5.6 | 5.4 | 4.5 | 4.8 |
| hsa-miR-6730-5p | 6.2 | 5.6 | 6.8 | 3.3 | 7.2 | 6.2 | 5.4 | 4.5 | 4.1 |
| hsa-miR-6076 | 5.1 | 6.2 | 5.3 | 4.6 | 6.5 | 7.7 | 4.9 | 5.7 | 4.8 |
| hsa-miR-8089 | 7.0 | 7.0 | 7.0 | 5.0 | 6.7 | 7.1 | 6.5 | 6.4 | 5.7 |
| hsa-miR-6857-3p | 5.8 | 5.7 | 5.5 | 3.9 | 6.0 | 6.1 | 6.1 | 5.1 | 5.1 |
| hsa-miR-6749-3p | 6.5 | 6.2 | 6.3 | 4.4 | 5.9 | 6.1 | 6.1 | 5.5 | 5.2 |
| hsa-miR-6890-3p | 6.3 | 6.1 | 5.9 | 4.0 | 6.0 | 6.0 | 6.2 | 5.5 | 5.6 |
| hsa-miR-4751 | 6.4 | 5.2 | 6.9 | 3.0 | 6.7 | 6.1 | 4.5 | 4.2 | 3.6 |
| hsa-miR-6825-5p | 5.7 | 6.4 | 6.2 | 4.2 | 6.8 | 6.4 | 5.9 | 6.7 | 5.1 |
| hsa-miR-6810-3p | 6.3 | 6.1 | 6.0 | 4.1 | 6.1 | 6.0 | 6.7 | 5.5 | 5.1 |
| hsa-miR-0365a-3p, hsa-miR-365b-3p | 6.5 | 5.9 | 6.0 | 6.1 | 6.3 | 5.8 | 6.6 | 5.1 | 5.6 |
| hsa-miR-3943 | 6.2 | 6.0 | 6.0 | 3.7 | 6.0 | 5.9 | 6.4 | 5.2 | 5.3 |
| hsa-miR-6728-3p | 6.0 | 6.4 | 5.8 | 4.7 | 6.4 | 6.1 | 6.2 | 5.8 | 5.8 |
| hsa-miR-3185 | 5.9 | 8.1 | 7.7 | 6.5 | 8.3 | 8.5 | 5.8 | 7.8 | 5.5 |
| hsa-miR-6894-3p | 5.7 | 6.4 | 5.5 | 6.1 | 6.3 | 6.3 | 6.0 | 5.9 | 5.7 |
| hsa-miR-8485 | 6.1 | 6.4 | 6.0 | 4.5 | 6.2 | 6.6 | 6.1 | 6.0 | 5.9 |
| hsa-miR-6846-5p | 6.7 | 6.6 | 6.4 | 5.0 | 6.5 | 6.9 | 6.7 | 6.3 | 5.9 |
| hsa-miR-4286 | 6.3 | 6.0 | 6.1 | 4.1 | 6.1 | 5.9 | 6.5 | 5.3 | 5.3 |
| hsa-miR-4259 | 6.0 | 5.8 | 6.4 | 3.7 | 6.9 | 6.3 | 5.5 | 4.7 | 5.4 |
| hsa-miR-0208a-5p | 6.4 | 6.7 | 7.0 | 6.8 | 6.7 | 5.9 | 5.8 | 6.4 | 5.0 |
| hsa-miR-6851-3p | 6.3 | 5.9 | 5.9 | 4.4 | 6.3 | 6.1 | 6.2 | 5.3 | 5.7 |
| hsa-miR-4472 | 7.1 | 7.2 | 6.9 | 4.5 | 6.7 | 7.1 | 5.9 | 6.7 | 5.2 |
| hsa-miR-6820-5p | 5.8 | 6.7 | 7.3 | 5.6 | 7.1 | 7.0 | 5.9 | 6.6 | 5.6 |
| hsa-miR-6855-3p | 6.3 | 6.2 | 6.1 | 4.5 | 6.5 | 6.4 | 6.7 | 6.0 | 5.9 |
| hsa-miR-6801-3p | 6.3 | 6.2 | 6.2 | 4.6 | 6.4 | 6.3 | 6.4 | 5.6 | 5.8 |
| hsa-miR-0634 | 5.9 | 5.9 | 5.9 | 4.6 | 6.3 | 5.8 | 6.5 | 5.5 | 5.7 |
| hsa-miR-1229-3p | 6.0 | 6.3 | 5.6 | 7.7 | 6.1 | 6.4 | 5.9 | 5.7 | 5.8 |
| hsa-miR-7109-3p | 5.7 | 6.4 | 5.6 | 4.5 | 6.3 | 5.9 | 6.1 | 5.7 | 5.7 |
| hsa-miR-6804-3p | 6.1 | 6.3 | 5.8 | 5.4 | 6.0 | 5.8 | 6.1 | 5.8 | 5.6 |
| hsa-miR-4723-3p | 6.4 | 6.3 | 6.2 | 6.0 | 6.1 | 6.4 | 6.4 | 5.5 | 5.2 |
| hsa-miR-6742-5p | 5.9 | 6.5 | 6.3 | 6.4 | 6.3 | 6.8 | 5.5 | 6.6 | 5.4 |
| hsa-miR-6511b-3p | 6.2 | 6.4 | 6.1 | 5.1 | 5.7 | 5.9 | 6.2 | 5.5 | 5.5 |
| hsa-miR-6820-3p | 6.2 | 6.1 | 5.9 | 4.2 | 6.0 | 6.2 | 6.7 | 5.3 | 5.2 |
| hsa-miR-2278 | 7.6 | 6.1 | 8.0 | 4.9 | 7.9 | 6.9 | 5.7 | 4.1 | 5.3 |
| hsa-miR-3157-3p | 0.0 | 2.4 | 2.4 | 4.9 | 7.9 | 6.9 | 2.5 | 0.0 | 0.0 |

TABLE 3-continued

| | | | | | | | | | |
|---|---|---|---|---|---|---|---|---|---|
| hsa-miR-6776-3p | 5.9 | 6.4 | 5.9 | 4.6 | 6.5 | 6.0 | 5.9 | 5.8 | 5.4 |
| hsa-miR-6730-3p | 5.9 | 6.3 | 5.6 | 4.5 | 6.2 | 5.9 | 6.4 | 5.7 | 5.8 |
| hsa-miR-6797-3p | 6.9 | 6.3 | 6.8 | 4.7 | 6.5 | 6.4 | 6.5 | 5.6 | 5.8 |
| hsa-miR-0920 | 6.8 | 5.3 | 6.5 | 4.5 | 6.2 | 6.3 | 6.1 | 4.4 | 4.2 |
| hsa-miR-4443 | 5.3 | 6.5 | 5.9 | 6.4 | 7.2 | 6.6 | 6.0 | 6.3 | 5.5 |
| hsa-miR-6732-3p | 6.3 | 6.5 | 5.9 | 4.6 | 6.3 | 6.0 | 6.2 | 5.6 | 6.0 |
| hsa-miR-0365a-5p | 7.1 | 6.4 | 6.4 | 5.2 | 5.9 | 6.2 | 6.7 | 5.6 | 5.8 |
| hsa-miR-6780a-5p | 5.4 | 5.1 | 4.4 | 3.2 | 5.0 | 4.6 | 5.5 | 3.8 | 3.1 |
| hsa-miR-6510-5p | 7.1 | 7.2 | 7.0 | 4.3 | 6.6 | 7.0 | 6.1 | 5.5 | 5.0 |
| hsa-miR-6745 | 4.0 | 5.0 | 6.0 | 0.0 | 6.5 | 5.2 | 3.9 | 3.2 | 3.0 |
| hsa-miR-7114-3p | 6.5 | 6.2 | 6.1 | 4.4 | 6.5 | 6.2 | 6.5 | 5.5 | 5.6 |
| hsa-miR-7113-3p | 6.5 | 6.6 | 6.5 | 5.4 | 6.7 | 6.9 | 6.5 | 6.3 | 6.2 |
| hsa-miR-4276 | 6.1 | 6.7 | 6.9 | 7.7 | 6.5 | 7.1 | 6.4 | 7.1 | 6.4 |
| hsa-miR-6726-5p | 5.7 | 7.4 | 7.2 | 7.5 | 7.6 | 8.0 | 7.2 | 8.4 | 6.7 |
| hsa-miR-0125a-3p | 6.6 | 5.8 | 6.3 | 4.5 | 6.6 | 6.4 | 5.7 | 4.8 | 5.6 |
| hsa-miR-0486-5p | 6.0 | 6.2 | 6.0 | 4.7 | 6.6 | 6.3 | 6.5 | 5.6 | 5.9 |
| hsa-miR-4499 | 5.6 | 4.4 | 6.1 | 7.0 | 5.9 | 5.3 | 3.9 | 2.9 | 3.8 |
| hsa-miR-4697-3p | 6.0 | 6.3 | 5.6 | 4.6 | 6.2 | 6.0 | 6.3 | 5.5 | 5.5 |
| hsa-miR-6507-5p | 5.8 | 5.3 | 5.0 | 2.9 | 5.3 | 5.1 | 5.6 | 3.7 | 4.3 |
| hsa-miR-1976 | 6.1 | 6.5 | 6.1 | 4.8 | 6.2 | 6.6 | 6.5 | 5.9 | 5.9 |
| hsa-miR-3147 | 6.3 | 6.2 | 6.4 | 4.8 | 6.2 | 6.6 | 6.5 | 5.7 | 5.8 |
| hsa-miR-0519e-5p | 5.5 | 3.4 | 7.3 | 5.6 | 6.5 | 4.8 | 7.3 | 4.4 | 6.7 |
| hsa-miR-6815-5p | 4.9 | 4.9 | 6.9 | 5.4 | 7.0 | 6.9 | 4.5 | 4.3 | 4.3 |
| hsa-miR-4750-5p | 5.9 | 6.8 | 6.4 | 6.4 | 6.3 | 7.3 | 6.0 | 6.4 | 5.8 |
| hsa-miR-4687-5p | 6.6 | 6.6 | 6.6 | 5.3 | 6.6 | 6.8 | 6.7 | 6.3 | 6.2 |
| hsa-miR-6806-5p | 6.9 | 7.0 | 7.1 | 5.8 | 7.0 | 7.1 | 6.8 | 6.7 | 6.3 |
| hsa-miR-4783-3p | 6.9 | 6.7 | 7.3 | 6.5 | 6.5 | 7.1 | 6.6 | 6.3 | 6.1 |
| hsa-miR-6754-5p | 7.9 | 6.4 | 6.6 | 3.7 | 6.4 | 6.3 | 5.7 | 5.3 | 5.1 |
| hsa-miR-4419a | 6.8 | 6.2 | 6.4 | 3.6 | 7.0 | 6.8 | 5.7 | 5.0 | 5.2 |
| hsa-miR-6769a-3p | 6.3 | 6.4 | 6.1 | 4.7 | 6.4 | 6.4 | 6.5 | 5.8 | 5.7 |
| hsa-miR-6846-3p | 6.3 | 6.4 | 5.9 | 5.2 | 6.0 | 6.1 | 6.6 | 5.5 | 5.8 |
| hsa-miR-4769-3p | 6.5 | 6.5 | 6.3 | 5.3 | 6.3 | 6.4 | 6.5 | 5.5 | 5.8 |
| hsa-miR-0744-5p | 6.9 | 7.4 | 7.5 | 7.2 | 6.8 | 7.1 | 6.3 | 6.9 | 5.8 |
| hsa-miR-3184-3p | 6.4 | 6.6 | 6.4 | 4.8 | 6.8 | 6.2 | 6.8 | 6.1 | 6.0 |
| hsa-miR-6792-3p | 6.3 | 6.6 | 6.0 | 4.7 | 6.7 | 6.2 | 6.6 | 5.9 | 5.9 |
| hsa-miR-0150-3p | 5.9 | 6.1 | 6.1 | 4.7 | 6.5 | 6.1 | 6.9 | 6.5 | 6.6 |
| hsa-miR-7155-5p | 7.6 | 7.0 | 7.2 | 5.2 | 6.7 | 7.1 | 7.1 | 6.7 | 6.6 |
| hsa-miR-6858-3p | 6.6 | 6.4 | 6.3 | 4.7 | 6.4 | 6.9 | 6.9 | 5.8 | 5.5 |
| hsa-miR-4690-5p | 6.6 | 7.2 | 6.7 | 6.1 | 7.1 | 6.9 | 7.7 | 6.6 | 7.0 |
| hsa-miR-6861-3p | 6.6 | 6.4 | 6.2 | 3.8 | 6.2 | 6.4 | 6.6 | 5.5 | 5.4 |
| hsa-miR-6069 | 7.1 | 6.8 | 7.0 | 6.8 | 6.4 | 6.5 | 6.7 | 6.0 | 5.9 |
| hsa-miR-0766-3p | 5.9 | 6.3 | 5.8 | 4.8 | 6.4 | 6.4 | 6.6 | 6.0 | 6.0 |
| hsa-miR-4478 | 6.4 | 6.9 | 6.0 | 4.4 | 7.1 | 7.5 | 5.7 | 6.1 | 4.7 |
| hsa-miR-6827-5p | 6.2 | 6.1 | 6.3 | 3.9 | 6.5 | 6.0 | 5.9 | 5.3 | 5.3 |
| hsa-miR-4284 | 6.2 | 6.0 | 6.2 | 4.1 | 6.6 | 6.3 | 6.6 | 5.5 | 6.0 |
| hsa-miR-7108-3p | 6.7 | 6.4 | 6.8 | 5.3 | 6.6 | 6.5 | 6.8 | 5.9 | 5.6 |
| hsa-miR-6889-3p | 6.7 | 6.5 | 6.3 | 4.4 | 6.4 | 6.4 | 6.7 | 5.7 | 6.0 |
| hsa-miR-6860 | 6.6 | 6.9 | 6.5 | 5.4 | 6.6 | 6.7 | 6.7 | 6.9 | 6.4 |
| hsa-miR-3928-3p | 6.6 | 6.5 | 7.4 | 5.6 | 8.1 | 7.6 | 5.5 | 6.1 | 5.6 |
| hsa-miR-6760-5p | 5.3 | 5.7 | 6.9 | 3.6 | 7.5 | 6.4 | 4.7 | 4.2 | 4.6 |
| hsa-miR-4667-3p | 6.7 | 6.6 | 6.5 | 4.6 | 6.6 | 6.7 | 6.7 | 6.0 | 6.3 |
| hsa-miR-1247-3p | 6.6 | 6.3 | 6.9 | 6.1 | 6.8 | 6.9 | 6.8 | 6.1 | 5.9 |
| hsa-miR-6845-3p | 6.8 | 6.8 | 6.7 | 4.9 | 6.5 | 6.6 | 6.7 | 6.2 | 6.1 |
| hsa-miR-4486 | 7.0 | 8.1 | 8.1 | 6.7 | 7.9 | 8.4 | 7.2 | 7.9 | 6.7 |
| hsa-miR-5572 | 6.6 | 6.4 | 7.0 | 5.1 | 7.3 | 6.9 | 6.1 | 6.7 | 5.7 |
| hsa-miR-0484 | 6.7 | 6.5 | 6.4 | 4.9 | 6.7 | 6.5 | 6.7 | 5.7 | 6.2 |
| hsa-miR-6760-3p | 6.6 | 6.3 | 6.5 | 4.1 | 6.7 | 6.4 | 6.7 | 5.5 | 5.8 |
| hsa-miR-6885-3p | 6.6 | 6.3 | 6.3 | 4.6 | 6.4 | 6.6 | 6.4 | 5.6 | 5.8 |
| hsa-miR-6892-3p | 6.9 | 6.5 | 6.8 | 7.7 | 6.3 | 6.3 | 6.8 | 5.6 | 5.9 |
| hsa-miR-2355-5p | 6.3 | 6.0 | 6.1 | 4.4 | 6.1 | 6.0 | 6.0 | 5.3 | 5.3 |
| hsa-miR-3158-3p | 4.0 | 4.6 | 3.6 | 4.4 | 6.1 | 6.0 | 3.8 | 3.4 | 2.7 |
| hsa-miR-6759-3p | 6.4 | 6.5 | 6.2 | 4.8 | 6.8 | 6.7 | 6.6 | 6.0 | 6.2 |
| hsa-miR-0210-5p | 6.7 | 6.7 | 6.6 | 4.8 | 6.8 | 6.9 | 6.9 | 6.3 | 6.2 |
| hsa-miR-6778-5p | 6.4 | 6.8 | 6.3 | 5.5 | 6.7 | 7.4 | 6.4 | 6.6 | 5.9 |
| hsa-miR-2110 | 7.2 | 6.2 | 7.2 | 5.7 | 7.0 | 6.9 | 6.8 | 6.3 | 5.7 |
| hsa-miR-3150a-5p | 2.2 | 3.7 | 0.0 | 5.7 | 7.0 | 6.9 | 3.6 | 2.3 | 3.6 |
| hsa-miR-6731-5p | 7.3 | 5.7 | 7.9 | 4.1 | 8.0 | 7.5 | 5.8 | 5.1 | 5.1 |
| hsa-miR-6756-3p | 6.8 | 6.5 | 6.7 | 7.3 | 6.5 | 6.5 | 6.8 | 5.9 | 6.2 |
| hsa-miR-6786-3p | 6.5 | 6.8 | 6.4 | 5.4 | 6.7 | 6.6 | 7.0 | 6.2 | 6.2 |
| hsa-miR-6831-5p | 7.0 | 6.5 | 7.3 | 5.2 | 7.7 | 7.3 | 5.8 | 5.3 | 5.2 |
| hsa-miR-0652-5p | 8.3 | 7.6 | 7.5 | 5.4 | 8.4 | 8.8 | 6.4 | 5.9 | 5.5 |
| hsa-miR-4419b | 8.7 | 7.1 | 7.5 | 4.9 | 6.7 | 7.2 | 5.6 | 6.1 | 5.0 |
| hsa-miR-4685-5p | 7.5 | 7.0 | 6.7 | 4.9 | 6.4 | 7.1 | 6.6 | 6.5 | 6.5 |
| hsa-miR-0939-5p | 6.9 | 7.0 | 8.2 | 7.3 | 8.4 | 8.9 | 6.2 | 8.0 | 4.5 |
| hsa-miR-6819-3p | 6.7 | 6.1 | 6.4 | 4.2 | 6.3 | 6.6 | 6.5 | 5.4 | 5.8 |
| hsa-miR-6826-3p | 6.7 | 6.7 | 6.4 | 4.7 | 6.6 | 6.5 | 6.7 | 6.0 | 6.0 |
| hsa-miR-0030c-2-3p | 5.3 | 5.6 | 6.2 | 2.8 | 6.5 | 5.6 | 4.2 | 4.1 | 5.1 |
| hsa-miR-6132 | 7.6 | 8.1 | 8.7 | 6.6 | 7.1 | 7.3 | 6.2 | 6.9 | 5.0 |
| hsa-miR-6769b-5p | 7.3 | 7.3 | 6.7 | 4.7 | 6.7 | 7.2 | 6.5 | 6.6 | 5.7 |
| hsa-miR-6802-3p | 6.5 | 6.5 | 6.1 | 4.2 | 6.6 | 6.4 | 6.9 | 6.0 | 6.0 |

TABLE 3-continued

| | | | | | | | | | |
|---|---|---|---|---|---|---|---|---|---|
| hsa-miR-3194-5p | 7.0 | 6.7 | 6.6 | 5.4 | 6.6 | 6.6 | 6.8 | 5.9 | 6.2 |
| hsa-miR-0718 | 6.2 | 7.1 | 7.1 | 6.4 | 7.5 | 7.4 | 7.7 | 7.7 | 7.3 |
| hsa-miR-6861-5p | 7.1 | 7.2 | 7.3 | 6.3 | 7.4 | 7.8 | 7.3 | 7.5 | 6.7 |
| hsa-miR-4313 | 6.6 | 6.5 | 6.4 | 5.5 | 6.6 | 6.0 | 7.0 | 6.1 | 6.0 |
| hsa-miR-6777-5p | 5.9 | 6.7 | 7.7 | 5.2 | 8.4 | 7.4 | 5.8 | 6.7 | 5.6 |
| hsa-miR-6813-5p | 6.9 | 7.6 | 7.7 | 5.6 | 6.4 | 6.6 | 6.7 | 6.8 | 5.9 |
| hsa-miR-4707-3p | 6.6 | 6.5 | 7.0 | 5.4 | 6.8 | 6.8 | 6.9 | 6.5 | 6.0 |
| hsa-miR-7110-5p | 7.0 | 7.2 | 7.9 | 6.4 | 7.7 | 7.9 | 6.5 | 8.3 | 5.8 |
| hsa-miR-4258 | 7.1 | 7.0 | 7.9 | 7.1 | 7.7 | 7.8 | 7.0 | 7.9 | 6.2 |
| hsa-miR-4526 | 6.8 | 6.6 | 6.9 | 5.5 | 6.4 | 6.2 | 6.3 | 6.8 | 6.7 |
| hsa-miR-4758-3p | 6.6 | 6.9 | 6.3 | 4.8 | 6.6 | 6.7 | 6.8 | 6.2 | 6.0 |
| hsa-miR-6889-5p | 6.7 | 6.7 | 7.7 | 5.5 | 8.2 | 7.3 | 6.3 | 6.8 | 5.8 |
| hsa-miR-6752-3p | 6.9 | 6.7 | 6.7 | 4.8 | 6.9 | 6.7 | 7.1 | 6.0 | 6.2 |
| hsa-miR-0711 | 7.4 | 6.9 | 8.6 | 6.0 | 8.2 | 7.5 | 6.3 | 6.4 | 5.7 |
| hsa-miR-6879-5p | 6.9 | 7.0 | 7.4 | 6.6 | 7.6 | 7.9 | 6.5 | 6.3 | 5.4 |
| hsa-miR-8087 | 5.1 | 4.1 | 4.4 | 0.0 | 4.1 | 4.5 | 0.0 | 0.0 | 0.0 |
| hsa-miR-0933 | 8.2 | 6.3 | 6.7 | 3.6 | 5.9 | 5.1 | 5.8 | 3.7 | 4.6 |
| hsa-miR-4507 | 6.6 | 8.0 | 7.8 | 6.9 | 7.9 | 8.1 | 6.8 | 8.6 | 6.7 |
| hsa-miR-4756-5p | 8.2 | 6.8 | 7.3 | 4.9 | 7.3 | 7.2 | 6.4 | 5.7 | 5.7 |
| hsa-miR-1249-5p | 7.8 | 7.5 | 7.5 | 5.9 | 6.7 | 7.2 | 7.0 | 5.9 | 5.9 |
| hsa-miR-0197-5p | 8.2 | 7.8 | 7.7 | 6.1 | 7.1 | 8.0 | 6.6 | 7.4 | 5.9 |
| hsa-miR-4323 | 7.0 | 6.9 | 6.7 | 5.3 | 7.0 | 6.9 | 7.2 | 6.3 | 6.2 |
| hsa-miR-0092b-5p | 6.9 | 8.1 | 8.5 | 7.3 | 8.7 | 8.8 | 6.7 | 8.3 | 6.5 |
| hsa-miR-6887-3p | 7.0 | 6.8 | 6.9 | 4.9 | 7.0 | 7.0 | 7.2 | 6.1 | 6.2 |
| hsa-miR-6893-5p | 6.3 | 6.8 | 8.2 | 7.3 | 8.8 | 10.0 | 6.4 | 6.9 | 5.9 |
| hsa-miR-6813-3p | 7.3 | 6.8 | 7.2 | 4.7 | 7.1 | 6.8 | 7.5 | 6.2 | 6.4 |
| hsa-miR-6891-3p | 7.0 | 6.6 | 6.8 | 5.2 | 6.9 | 6.5 | 7.3 | 5.8 | 6.1 |
| hsa-miR-6731-3p | 6.6 | 6.4 | 6.8 | 4.9 | 6.8 | 6.6 | 7.2 | 5.8 | 6.1 |
| hsa-miR-0345-3p | 7.8 | 6.3 | 10.0 | 4.8 | 10.1 | 8.0 | 6.9 | 5.5 | 5.7 |
| hsa-miR-4640-3p | 7.2 | 6.8 | 6.9 | 5.4 | 7.0 | 6.7 | 7.2 | 5.8 | 6.5 |
| hsa-miR-4716-3p | 6.9 | 5.2 | 7.8 | 4.9 | 8.4 | 6.9 | 5.7 | 4.0 | 4.6 |
| hsa-miR-0371b-3p | 7.0 | 6.9 | 6.8 | 5.1 | 6.9 | 7.0 | 7.0 | 6.3 | 6.6 |
| hsa-miR-6812-5p | 8.2 | 7.2 | 7.0 | 4.8 | 7.1 | 7.8 | 6.7 | 6.2 | 6.5 |
| hsa-miR-6784-3p | 6.9 | 6.6 | 6.8 | 4.9 | 7.1 | 6.7 | 7.3 | 6.1 | 6.4 |
| hsa-miR-6716-5p | 8.1 | 7.6 | 7.8 | 5.5 | 7.2 | 8.6 | 6.9 | 6.8 | 6.4 |
| hsa-miR-4513 | 7.9 | 7.5 | 8.4 | 5.3 | 7.1 | 7.9 | 6.5 | 6.9 | 6.1 |
| hsa-miR-6848-3p | 7.1 | 7.1 | 6.9 | 5.4 | 7.1 | 7.1 | 7.3 | 6.3 | 6.7 |
| hsa-miR-1238-5p | 7.2 | 7.1 | 7.3 | 5.2 | 7.5 | 7.4 | 6.7 | 6.0 | 6.0 |
| hsa-miR-4530 | 7.0 | 8.2 | 8.3 | 6.9 | 8.2 | 8.9 | 6.9 | 8.2 | 6.5 |
| hsa-miR-4655-5p | 7.1 | 7.6 | 7.7 | 7.2 | 7.3 | 7.8 | 6.8 | 7.0 | 6.0 |
| hsa-miR-6785-3p | 7.2 | 6.8 | 7.1 | 5.4 | 7.1 | 6.9 | 7.5 | 6.2 | 6.4 |
| hsa-miR-4728-3p | 7.3 | 7.1 | 7.0 | 5.4 | 6.8 | 7.0 | 7.4 | 6.3 | 6.4 |
| hsa-miR-5090 | 7.2 | 7.9 | 8.6 | 7.3 | 7.8 | 7.6 | 7.5 | 8.4 | 7.9 |
| hsa-miR-6824-5p | 8.0 | 7.5 | 7.1 | 5.6 | 7.2 | 7.9 | 6.9 | 6.7 | 6.4 |
| hsa-miR-4667-5p | 7.8 | 7.2 | 7.7 | 5.0 | 7.3 | 7.0 | 6.7 | 6.1 | 5.3 |
| hsa-miR-0874-5p | 7.4 | 7.5 | 7.1 | 5.7 | 7.2 | 7.1 | 7.5 | 6.7 | 6.5 |
| hsa-miR-4749-5p | 7.7 | 7.6 | 7.7 | 6.3 | 7.8 | 8.2 | 7.3 | 7.9 | 6.7 |
| hsa-miR-6086 | 7.5 | 6.8 | 7.9 | 4.7 | 8.6 | 8.0 | 6.7 | 6.2 | 6.4 |
| hsa-miR-4257 | 7.1 | 6.8 | 6.4 | 5.9 | 6.3 | 7.1 | 7.8 | 6.9 | 6.4 |
| hsa-miR-1224-3p | 7.6 | 7.1 | 7.3 | 5.3 | 7.1 | 6.9 | 7.4 | 6.3 | 6.5 |
| hsa-miR-3610 | 7.6 | 6.4 | 9.2 | 5.4 | 10.2 | 9.1 | 6.0 | 5.7 | 5.5 |
| hsa-miR-6880-5p | 7.8 | 8.1 | 7.6 | 5.2 | 7.8 | 8.8 | 6.9 | 7.6 | 6.3 |
| hsa-miR-0663b | 7.5 | 8.0 | 8.0 | 6.5 | 8.1 | 8.0 | 7.9 | 7.7 | 7.4 |
| hsa-miR-1237-3p | 7.4 | 7.0 | 7.4 | 6.0 | 7.1 | 7.1 | 7.5 | 6.5 | 6.4 |
| hsa-miR-1225-3p | 7.3 | 7.2 | 7.3 | 6.2 | 7.4 | 7.4 | 7.5 | 6.8 | 6.5 |
| hsa-miR-6763-5p | 7.0 | 7.7 | 7.9 | 6.5 | 8.8 | 10.5 | 7.2 | 7.7 | 6.5 |
| hsa-miR-4707-5p | 7.5 | 8.4 | 8.6 | 7.6 | 8.0 | 8.8 | 7.4 | 8.4 | 6.8 |
| hsa-miR-3195 | 7.0 | 8.1 | 8.2 | 7.7 | 8.4 | 8.6 | 8.1 | 8.9 | 7.9 |
| hsa-miR-1231 | 6.9 | 8.2 | 8.1 | 8.2 | 7.4 | 8.1 | 7.3 | 8.2 | 6.1 |
| hsa-miR-4695-5p | 6.9 | 8.7 | 8.5 | 7.7 | 8.6 | 9.1 | 7.0 | 8.9 | 7.1 |
| hsa-miR-1225-5p | 7.6 | 8.5 | 8.2 | 7.1 | 8.3 | 8.7 | 6.8 | 8.9 | 6.7 |
| hsa-miR-6891-5p | 8.8 | 7.9 | 7.5 | 4.8 | 7.2 | 7.8 | 6.7 | 6.8 | 6.3 |
| hsa-miR-3188 | 8.8 | 8.0 | 9.6 | 5.3 | 10.1 | 9.5 | 6.9 | 6.8 | 6.3 |
| hsa-miR-1202 | 8.9 | 7.8 | 7.6 | 5.6 | 7.6 | 8.5 | 7.4 | 6.7 | 7.0 |
| hsa-miR-6807-5p | 9.2 | 7.9 | 7.5 | 5.1 | 6.7 | 7.3 | 6.8 | 5.9 | 5.6 |
| hsa-miR-6738-5p | 7.7 | 8.0 | 7.9 | 6.6 | 7.9 | 7.8 | 8.6 | 7.6 | 7.8 |
| hsa-miR-1238-3p | 7.2 | 7.3 | 7.2 | 5.7 | 7.7 | 7.3 | 7.6 | 6.6 | 7.1 |
| hsa-miR-6840-3p | 7.7 | 8.2 | 8.5 | 6.9 | 9.4 | 10.0 | 7.5 | 8.6 | 7.2 |
| hsa-miR-0583 | 6.4 | 4.2 | 8.5 | 0.0 | 9.6 | 7.3 | 4.0 | 0.0 | 4.4 |
| hsa-miR-4640-5p | 7.2 | 8.6 | 8.5 | 8.0 | 8.2 | 9.0 | 7.1 | 9.1 | 6.9 |
| hsa-miR-0518c-5p | 6.5 | 6.3 | 6.2 | 5.0 | 6.8 | 6.6 | 6.0 | 5.7 | 6.4 |
| hsa-miR-0671-5p | 10.5 | 9.0 | 8.9 | 5.5 | 7.7 | 8.6 | 7.7 | 6.6 | 6.4 |
| hsa-miR-6799-5p | 9.3 | 9.1 | 9.0 | 7.3 | 8.5 | 9.3 | 8.0 | 8.4 | 7.2 |
| hsa-miR-4298 | 8.9 | 8.3 | 8.1 | 5.9 | 8.2 | 8.3 | 7.7 | 6.8 | 7.2 |
| hsa-miR-6797-5p | 8.6 | 8.2 | 7.9 | 7.3 | 7.8 | 8.2 | 7.9 | 7.0 | 7.3 |
| hsa-miR-6829-5p | 7.5 | 7.6 | 7.7 | 6.1 | 7.3 | 7.4 | 7.6 | 7.2 | 6.8 |
| hsa-miR-1275 | 9.3 | 8.6 | 10.1 | 6.0 | 10.7 | 10.0 | 7.6 | 7.1 | 7.7 |
| hsa-miR-3614-5p | 7.9 | 7.6 | 7.5 | 5.6 | 8.0 | 7.8 | 8.2 | 6.9 | 7.4 |
| hsa-miR-4688 | 7.7 | 8.7 | 8.5 | 7.3 | 8.2 | 8.6 | 8.1 | 8.6 | 7.0 |
| hsa-miR-1207-5p | 8.6 | 8.1 | 8.8 | 6.7 | 9.6 | 9.5 | 7.7 | 7.4 | 7.0 |

TABLE 3-continued

| | | | | | | | | | |
|---|---|---|---|---|---|---|---|---|---|
| hsa-miR-6794-5p | 8.4 | 8.6 | 8.6 | 6.9 | 8.2 | 8.8 | 8.0 | 8.4 | 7.4 |
| hsa-miR-6721-5p | 8.3 | 9.0 | 9.2 | 7.5 | 8.6 | 8.8 | 7.8 | 9.5 | 7.7 |
| hsa-miR-0665 | 7.7 | 8.8 | 8.1 | 7.3 | 8.6 | 8.9 | 7.9 | 8.4 | 8.0 |
| hsa-miR-7845-5p | 8.8 | 8.7 | 8.3 | 6.3 | 8.0 | 8.4 | 8.0 | 7.0 | 7.2 |
| hsa-miR-7150 | 8.6 | 8.3 | 8.9 | 6.1 | 8.9 | 8.8 | 7.7 | 7.2 | 7.5 |
| hsa-miR-4433b-3p | 8.2 | 9.0 | 8.8 | 7.3 | 8.7 | 9.3 | 7.6 | 9.1 | 7.4 |
| hsa-miR-7114-5p | 8.9 | 8.5 | 9.2 | 7.3 | 9.8 | 10.0 | 8.6 | 8.1 | 7.8 |
| hsa-miR-4716-5p | 7.9 | 7.5 | 7.9 | 6.0 | 8.0 | 7.6 | 8.3 | 6.7 | 7.2 |
| hsa-miR-6795-3p | 8.0 | 7.6 | 7.8 | 5.9 | 7.9 | 7.6 | 8.3 | 6.9 | 7.2 |
| hsa-miR-4433a-5p | 8.1 | 7.7 | 8.2 | 6.2 | 7.9 | 7.8 | 8.5 | 7.0 | 7.3 |
| hsa-miR-6777-3p | 7.8 | 7.7 | 7.8 | 6.1 | 8.0 | 7.8 | 8.4 | 7.1 | 7.3 |
| hsa-miR-0557 | 8.9 | 8.9 | 8.9 | 7.3 | 8.6 | 9.1 | 8.6 | 9.8 | 8.3 |
| hsa-miR-1185-2-3p | 8.8 | 7.8 | 7.9 | 4.7 | 8.0 | 8.9 | 7.1 | 6.4 | 6.6 |
| hsa-miR-4731-3p | 7.8 | 7.7 | 7.7 | 6.1 | 8.1 | 7.8 | 8.3 | 7.0 | 7.6 |
| hsa-miR-4745-5p | 8.0 | 9.6 | 9.6 | 8.5 | 9.6 | 10.6 | 8.3 | 9.6 | 8.1 |
| hsa-miR-6763-3p | 8.1 | 7.6 | 8.0 | 6.1 | 7.8 | 7.6 | 8.6 | 7.1 | 7.4 |
| hsa-miR-3937 | 8.5 | 8.9 | 9.4 | 8.0 | 8.5 | 9.2 | 8.2 | 9.2 | 7.5 |
| hsa-miR-0625-3p | 8.1 | 7.9 | 8.1 | 6.3 | 8.3 | 7.9 | 8.6 | 7.3 | 7.7 |
| hsa-miR-6800-3p | 8.2 | 7.9 | 7.9 | 6.1 | 8.1 | 7.9 | 8.6 | 7.4 | 7.5 |
| hsa-miR-0940 | 8.4 | 7.8 | 8.0 | 8.0 | 7.8 | 7.9 | 8.4 | 7.2 | 7.3 |
| hsa-miR-6758-5p | 7.8 | 4.6 | 9.7 | 4.1 | 10.1 | 8.6 | 6.1 | 4.3 | 5.2 |
| hsa-miR-4274 | 8.4 | 7.7 | 8.2 | 6.2 | 8.1 | 7.9 | 8.4 | 7.1 | 7.5 |
| hsa-miR-4749-3p | 8.3 | 7.9 | 8.2 | 7.8 | 7.9 | 8.0 | 8.6 | 7.3 | 7.3 |
| hsa-miR-3675-3p | 8.2 | 7.8 | 7.9 | 6.2 | 8.3 | 8.1 | 8.5 | 7.3 | 7.5 |
| hsa-miR-0760 | 8.2 | 8.7 | 8.7 | 7.5 | 8.4 | 9.0 | 8.7 | 9.0 | 7.9 |
| hsa-miR-3620-5p | 8.0 | 9.4 | 9.2 | 8.1 | 9.2 | 9.5 | 8.2 | 9.8 | 8.2 |
| hsa-miR-4484 | 8.9 | 9.1 | 10.2 | 7.3 | 10.4 | 10.7 | 7.5 | 8.5 | 7.1 |
| hsa-miR-6774-5p | 9.0 | 8.3 | 8.8 | 6.5 | 8.3 | 9.4 | 7.4 | 7.4 | 6.9 |
| hsa-miR-0675-5p | 9.7 | 8.8 | 8.7 | 6.8 | 8.3 | 9.5 | 8.0 | 7.9 | 7.8 |
| hsa-miR-1229-5p | 10.1 | 8.6 | 9.6 | 6.5 | 9.4 | 10.0 | 8.0 | 7.7 | 8.3 |
| hsa-miR-4459 | 7.6 | 8.3 | 8.1 | 7.3 | 8.7 | 9.3 | 7.7 | 7.9 | 7.4 |
| hsa-miR-6787-5p | 9.1 | 9.0 | 9.1 | 7.4 | 8.8 | 9.5 | 8.2 | 8.9 | 7.7 |
| hsa-miR-4271 | 10.0 | 9.4 | 8.9 | 5.7 | 7.9 | 9.0 | 7.1 | 7.5 | 6.5 |
| hsa-miR-4417 | 8.7 | 9.4 | 9.2 | 8.1 | 9.3 | 9.8 | 8.5 | 9.6 | 8.4 |
| hsa-miR-4505 | 8.3 | 9.2 | 9.6 | 7.8 | 8.6 | 8.7 | 7.3 | 8.4 | 6.7 |
| hsa-miR-6875-5p | 9.0 | 8.2 | 10.5 | 8.1 | 9.7 | 10.1 | 5.5 | 8.0 | 5.5 |
| hsa-miR-4758-5p | 8.5 | 9.2 | 9.0 | 7.8 | 8.5 | 8.7 | 8.5 | 8.9 | 8.3 |
| hsa-miR-6741-5p | 9.2 | 8.3 | 8.7 | 6.3 | 8.3 | 8.5 | 8.0 | 7.3 | 7.0 |
| hsa-miR-0514b-5p | 10.1 | 8.2 | 9.4 | 6.2 | 9.2 | 8.5 | 8.7 | 7.1 | 8.0 |
| hsa-miR-4726-5p | 9.6 | 9.0 | 8.8 | 6.2 | 9.0 | 9.4 | 8.6 | 7.7 | 8.0 |
| hsa-miR-6791-5p | 8.8 | 10.3 | 10.2 | 8.9 | 10.0 | 10.4 | 8.6 | 10.5 | 8.2 |
| hsa-miR-6789-5p | 8.6 | 10.1 | 9.9 | 9.3 | 9.5 | 10.2 | 8.6 | 10.3 | 8.4 |
| hsa-miR-6762-5p | 8.4 | 8.8 | 8.9 | 8.0 | 9.0 | 8.5 | 9.4 | 9.3 | 9.0 |
| hsa-miR-6859-3p | 8.1 | 7.8 | 8.0 | 6.3 | 8.4 | 8.0 | 8.8 | 7.4 | 7.8 |
| hsa-miR-7109-5p | 9.7 | 9.0 | 8.9 | 6.9 | 8.7 | 10.0 | 8.1 | 8.2 | 7.8 |
| hsa-miR-0937-5p | 8.5 | 9.4 | 8.7 | 7.5 | 9.0 | 8.9 | 9.2 | 10.1 | 9.7 |
| hsa-miR-4722-5p | 8.4 | 8.4 | 8.2 | 7.4 | 8.6 | 8.7 | 8.5 | 7.6 | 8.4 |
| hsa-miR-6826-5p | 9.3 | 9.9 | 7.9 | 5.8 | 7.9 | 8.7 | 9.4 | 8.5 | 7.8 |
| hsa-miR-1228-3p | 8.5 | 8.3 | 8.5 | 6.9 | 8.7 | 8.5 | 8.9 | 7.9 | 8.1 |
| hsa-miR-6798-3p | 9.1 | 8.5 | 9.0 | 7.0 | 9.0 | 8.5 | 9.4 | 8.0 | 8.2 |
| hsa-miR-1268b | 8.7 | 10.3 | 10.7 | 9.3 | 10.3 | 10.8 | 8.3 | 10.5 | 8.1 |
| hsa-miR-1909-3p | 8.8 | 9.2 | 9.5 | 8.5 | 9.4 | 9.2 | 9.1 | 9.6 | 9.3 |
| hsa-miR-3136-5p | 0.0 | 0.0 | 0.0 | 8.5 | 9.4 | 9.2 | 0.0 | 0.0 | 0.0 |
| hsa-miR-7847-3p | 10.3 | 9.5 | 9.1 | 6.8 | 9.1 | 9.3 | 9.0 | 8.0 | 8.2 |
| hsa-miR-7107-5p | 7.8 | 8.1 | 8.3 | 5.9 | 8.6 | 8.2 | 6.9 | 7.2 | 6.7 |
| hsa-miR-6729-3p | 8.6 | 8.2 | 8.4 | 6.8 | 8.8 | 8.3 | 9.0 | 7.7 | 8.0 |
| hsa-miR-3648 | 8.7 | 9.6 | 9.8 | 8.7 | 9.9 | 10.7 | 8.7 | 9.1 | 8.7 |
| hsa-miR-6746-5p | 8.6 | 7.8 | 7.7 | 5.7 | 8.1 | 8.9 | 6.4 | 6.6 | 6.2 |
| hsa-miR-6821-5p | 9.4 | 9.4 | 9.6 | 8.0 | 9.0 | 9.9 | 8.7 | 9.4 | 8.1 |
| hsa-miR-6768-5p | 8.9 | 9.2 | 9.4 | 8.3 | 9.4 | 9.5 | 9.1 | 9.1 | 8.9 |
| hsa-miR-1185-1-3p | 9.8 | 8.8 | 8.7 | 5.4 | 8.6 | 9.3 | 7.9 | 6.8 | 7.4 |
| hsa-miR-6798-5p | 8.9 | 10.7 | 10.9 | 9.5 | 10.3 | 10.8 | 8.8 | 10.7 | 8.7 |
| hsa-miR-6743-5p | 8.8 | 9.7 | 9.7 | 8.4 | 9.8 | 10.0 | 8.9 | 9.4 | 8.9 |
| hsa-miR-7111-5p | 9.0 | 8.8 | 9.1 | 7.3 | 8.7 | 9.0 | 7.6 | 7.8 | 6.8 |
| hsa-miR-6769a-5p | 9.8 | 8.5 | 8.9 | 5.8 | 9.0 | 9.2 | 7.6 | 6.9 | 7.3 |
| hsa-miR-6845-5p | 9.0 | 9.7 | 10.2 | 8.9 | 9.8 | 10.1 | 9.4 | 10.2 | 8.9 |
| hsa-miR-3184-5p | 10.6 | 9.9 | 9.9 | 6.9 | 8.5 | 9.9 | 7.0 | 7.8 | 6.2 |
| hsa-miR-4656 | 10.3 | 9.2 | 10.0 | 7.0 | 9.2 | 9.2 | 8.1 | 8.3 | 7.5 |
| hsa-miR-4632-5p | 9.3 | 9.7 | 9.1 | 8.5 | 9.0 | 9.9 | 8.5 | 9.0 | 7.9 |
| hsa-miR-0642b-3p | 10.6 | 9.8 | 9.3 | 6.9 | 8.8 | 9.5 | 9.0 | 8.3 | 8.4 |
| hsa-miR-6724-5p | 8.4 | 10.4 | 10.0 | 9.5 | 10.1 | 10.7 | 9.1 | 10.5 | 8.6 |
| hsa-miR-4651 | 8.9 | 10.5 | 10.7 | 9.4 | 10.2 | 10.3 | 9.3 | 10.6 | 9.1 |
| hsa-miR-6805-3p | 9.1 | 8.7 | 9.3 | 7.7 | 9.3 | 9.1 | 9.4 | 8.5 | 8.3 |
| hsa-miR-4763-3p | 9.4 | 9.8 | 10.6 | 8.4 | 9.5 | 10.3 | 8.6 | 9.7 | 8.2 |
| hsa-miR-3619-3p | 8.8 | 8.1 | 7.7 | 5.8 | 7.7 | 8.7 | 8.2 | 7.2 | 7.7 |
| hsa-miR-6126 | 9.2 | 10.7 | 9.7 | 7.8 | 9.5 | 10.9 | 8.9 | 10.4 | 8.2 |
| hsa-miR-4706 | 9.2 | 8.8 | 8.8 | 7.3 | 8.5 | 8.6 | 8.8 | 8.0 | 8.2 |
| hsa-miR-4634 | 8.8 | 10.3 | 10.0 | 9.3 | 10.1 | 10.4 | 9.4 | 10.4 | 8.8 |
| hsa-miR-6722-3p | 9.1 | 9.7 | 9.6 | 8.6 | 9.8 | 9.9 | 9.6 | 10.3 | 9.3 |
| hsa-miR-6796-3p | 9.0 | 8.5 | 9.0 | 8.0 | 9.0 | 8.6 | 9.7 | 8.2 | 8.4 |

TABLE 3-continued

| | | | | | | | | | |
|---|---|---|---|---|---|---|---|---|---|
| hsa-miR-6165 | 8.6 | 7.8 | 8.6 | 6.4 | 9.0 | 8.4 | 8.5 | 7.4 | 7.7 |
| hsa-miR-4327 | 9.1 | 9.7 | 10.0 | 7.8 | 8.9 | 8.7 | 8.6 | 8.8 | 7.8 |
| hsa-miR-6781-5p | 9.2 | 10.5 | 10.5 | 9.5 | 10.0 | 10.6 | 9.2 | 10.7 | 8.5 |
| hsa-miR-1913 | 9.0 | 8.8 | 9.0 | 7.3 | 9.3 | 8.9 | 9.5 | 8.1 | 8.7 |
| hsa-miR-3142 | 0.0 | 0.0 | 0.0 | 7.3 | 9.3 | 8.9 | 3.2 | 0.0 | 0.0 |
| hsa-miR-0642a-3p | 11.0 | 10.0 | 9.3 | 6.3 | 8.5 | 9.5 | 8.7 | 7.7 | 7.5 |
| hsa-miR-6756-5p | 9.7 | 9.9 | 9.6 | 8.5 | 9.4 | 9.7 | 10.1 | 10.0 | 9.7 |
| hsa-miR-4731-5p | 10.2 | 9.3 | 9.2 | 7.1 | 8.8 | 9.4 | 9.4 | 7.9 | 8.6 |
| hsa-miR-5739 | 10.3 | 8.7 | 9.9 | 6.9 | 9.4 | 9.6 | 8.6 | 7.8 | 7.4 |
| hsa-miR-6766-3p | 9.4 | 9.0 | 9.2 | 7.6 | 9.2 | 8.9 | 9.7 | 8.3 | 8.5 |
| hsa-miR-4741 | 9.7 | 9.8 | 11.1 | 8.6 | 10.6 | 10.0 | 9.2 | 9.8 | 8.6 |
| hsa-miR-8063 | 9.8 | 10.2 | 10.1 | 9.3 | 10.3 | 9.6 | 10.9 | 11.0 | 10.8 |
| hsa-miR-1249-3p | 9.2 | 9.0 | 9.2 | 7.5 | 9.4 | 8.8 | 9.8 | 8.1 | 8.8 |
| hsa-miR-1914-3p | 9.7 | 8.6 | 10.4 | 7.4 | 11.2 | 10.2 | 9.0 | 7.9 | 8.4 |
| hsa-miR-3143 | 0.0 | 0.0 | 0.0 | 7.4 | 11.2 | 10.2 | 0.0 | 0.0 | 0.0 |
| hsa-miR-6858-5p | 10.9 | 10.1 | 9.9 | 8.1 | 9.3 | 10.4 | 9.8 | 9.3 | 8.9 |
| hsa-miR-3679-3p | 9.2 | 8.9 | 9.2 | 7.4 | 9.4 | 8.9 | 9.7 | 8.3 | 8.6 |
| hsa-miR-1227-5p | 9.8 | 10.7 | 10.7 | 9.4 | 10.3 | 10.4 | 10.0 | 10.7 | 9.5 |
| hsa-miR-6779-5p | 11.1 | 10.1 | 9.9 | 7.8 | 9.9 | 10.7 | 9.8 | 9.1 | 8.9 |
| hsa-miR-6836-3p | 9.0 | 9.6 | 9.9 | 9.1 | 10.3 | 9.6 | 10.1 | 9.9 | 9.5 |
| hsa-miR-5195-3p | 11.4 | 11.0 | 9.9 | 7.8 | 9.4 | 10.3 | 10.3 | 8.9 | 9.4 |
| hsa-miR-3180-3p | 9.9 | 10.3 | 10.4 | 9.2 | 10.2 | 10.3 | 9.6 | 10.1 | 9.5 |
| hsa-miR-4446-3p | 9.5 | 10.4 | 10.4 | 9.1 | 10.3 | 10.1 | 10.1 | 10.4 | 9.6 |
| hsa-miR-1915-3p | 9.2 | 11.5 | 11.1 | 10.3 | 11.4 | 11.5 | 10.1 | 11.5 | 9.7 |
| hsa-miR-3144-5p | 8.2 | 7.5 | 7.3 | 10.3 | 11.4 | 11.5 | 6.2 | 5.2 | 5.7 |
| hsa-miR-1908-5p | 10.0 | 11.1 | 11.3 | 9.9 | 11.1 | 11.8 | 9.7 | 11.2 | 9.3 |
| hsa-miR-3136-5p | 0.0 | 0.0 | 0.0 | 9.9 | 11.1 | 11.8 | 0.0 | 0.0 | 0.0 |
| hsa-miR-6800-5p | 10.6 | 10.6 | 10.9 | 9.3 | 10.4 | 10.3 | 10.2 | 10.4 | 10.1 |
| hsa-miR-0486-3p | 9.7 | 10.8 | 10.8 | 9.5 | 10.7 | 10.6 | 10.6 | 10.6 | 10.2 |
| hsa-miR-4294 | 10.4 | 10.3 | 9.9 | 8.0 | 10.1 | 10.0 | 9.5 | 8.8 | 8.5 |
| hsa-miR-4697-5p | 11.0 | 10.7 | 10.0 | 8.5 | 9.9 | 10.9 | 9.9 | 9.4 | 9.8 |
| hsa-miR-6515-3p | 10.0 | 9.7 | 10.0 | 7.9 | 10.0 | 9.8 | 10.6 | 9.2 | 9.3 |
| hsa-miR-3197 | 10.5 | 10.2 | 11.9 | 8.9 | 10.6 | 11.7 | 9.3 | 10.7 | 8.9 |
| hsa-miR-3180 | 10.5 | 10.6 | 10.7 | 9.6 | 10.1 | 10.4 | 10.3 | 10.4 | 9.8 |
| hsa-miR-6795-5p | 9.6 | 8.6 | 9.5 | 6.3 | 9.6 | 8.5 | 8.8 | 7.8 | 8.5 |
| hsa-miR-6819-5p | 11.5 | 10.9 | 10.5 | 8.1 | 10.6 | 11.2 | 10.2 | 9.7 | 9.5 |
| hsa-miR-1469 | 10.5 | 11.2 | 11.8 | 10.2 | 11.1 | 11.6 | 10.2 | 11.2 | 10.0 |
| hsa-miR-3128 | 0.0 | 0.0 | 0.0 | 10.2 | 11.1 | 11.6 | 0.0 | 0.0 | 0.0 |
| hsa-miR-7106-5p | 8.8 | 8.4 | 8.4 | 5.4 | 8.1 | 7.9 | 7.5 | 6.5 | 6.5 |
| hsa-miR-4728-5p | 10.0 | 9.2 | 11.0 | 7.1 | 11.3 | 10.4 | 8.9 | 7.7 | 8.3 |
| hsa-miR-6802-5p | 12.0 | 10.8 | 10.5 | 8.6 | 9.9 | 10.8 | 10.6 | 9.7 | 10.0 |
| hsa-miR-6749-5p | 11.4 | 10.5 | 10.5 | 8.6 | 10.2 | 10.7 | 9.9 | 9.7 | 8.9 |
| hsa-miR-0371a-5p | 11.2 | 10.4 | 10.1 | 7.9 | 9.6 | 10.6 | 10.2 | 9.1 | 9.4 |
| hsa-miR-4675 | 11.4 | 10.8 | 10.7 | 8.9 | 10.1 | 10.5 | 11.3 | 9.7 | 10.3 |
| hsa-miR-1343-5p | 10.2 | 10.5 | 11.1 | 9.4 | 10.9 | 11.4 | 9.9 | 10.9 | 9.5 |
| hsa-miR-3126-5p | 3.8 | 3.7 | 2.3 | 9.4 | 10.9 | 11.4 | 0.0 | 2.4 | 4.3 |
| hsa-miR-0149-3p | 11.1 | 10.9 | 10.9 | 9.5 | 10.4 | 10.8 | 10.6 | 10.6 | 10.2 |
| hsa-miR-1233-5p | 12.7 | 11.1 | 11.6 | 8.4 | 10.5 | 10.7 | 9.6 | 10.3 | 8.9 |
| hsa-miR-6125 | 10.6 | 12.8 | 12.5 | 11.6 | 12.5 | 13.0 | 10.5 | 13.0 | 10.3 |
| hsa-miR-6887-5p | 10.1 | 9.1 | 9.9 | 7.3 | 10.2 | 9.4 | 9.1 | 8.6 | 9.0 |
| hsa-miR-6775-5p | 11.3 | 10.3 | 10.4 | 8.3 | 9.7 | 10.1 | 10.3 | 9.3 | 9.3 |
| hsa-miR-6850-5p | 10.6 | 12.2 | 12.0 | 11.1 | 12.2 | 12.1 | 11.1 | 12.3 | 10.8 |
| hsa-miR-4534 | 11.1 | 9.7 | 11.9 | 7.4 | 12.2 | 10.3 | 10.0 | 8.2 | 9.5 |
| hsa-miR-0296-5p | 11.0 | 10.4 | 10.8 | 8.8 | 10.8 | 10.6 | 11.3 | 9.9 | 10.5 |
| hsa-miR-6803-5p | 12.2 | 11.9 | 11.9 | 10.3 | 11.3 | 12.1 | 11.3 | 11.8 | 10.5 |
| hsa-miR-0663a | 11.0 | 11.5 | 11.5 | 10.4 | 11.4 | 11.3 | 11.2 | 11.6 | 10.7 |
| hsa-miR-6752-5p | 11.2 | 12.0 | 12.3 | 10.7 | 11.9 | 12.1 | 11.1 | 11.8 | 10.9 |
| hsa-miR-4492 | 10.8 | 11.5 | 11.8 | 10.4 | 11.1 | 10.7 | 10.7 | 10.7 | 10.5 |
| hsa-miR-4270 | 12.5 | 11.5 | 11.2 | 9.4 | 10.4 | 11.6 | 11.6 | 10.0 | 10.8 |
| hsa-miR-6816-5p | 11.1 | 11.7 | 11.7 | 10.6 | 11.5 | 11.5 | 11.3 | 11.6 | 11.3 |
| hsa-miR-4687-3p | 13.0 | 12.2 | 11.5 | 9.1 | 10.8 | 12.2 | 10.7 | 10.8 | 10.2 |
| hsa-miR-6771-5p | 11.8 | 11.4 | 11.3 | 10.4 | 11.1 | 12.0 | 11.6 | 10.6 | 11.0 |
| hsa-miR-3656 | 11.2 | 12.4 | 12.3 | 11.3 | 12.4 | 12.4 | 11.4 | 12.5 | 11.3 |
| hsa-miR-4730 | 10.9 | 12.5 | 11.8 | 9.6 | 11.0 | 10.5 | 12.2 | 11.7 | 11.4 |
| hsa-miR-4463 | 11.8 | 12.0 | 11.8 | 10.6 | 11.8 | 11.8 | 11.7 | 11.9 | 11.6 |
| hsa-miR-6805-5p | 11.9 | 12.5 | 12.6 | 10.9 | 11.8 | 12.7 | 11.6 | 12.5 | 11.4 |
| hsa-miR-1268a | 11.8 | 12.3 | 12.6 | 11.0 | 11.9 | 12.3 | 11.4 | 12.3 | 11.4 |
| hsa-miR-8072 | 11.6 | 13.5 | 13.2 | 12.2 | 13.1 | 13.3 | 11.6 | 13.2 | 11.2 |
| hsa-miR-6757-5p | 13.7 | 11.5 | 12.4 | 8.1 | 11.1 | 11.0 | 10.0 | 9.7 | 8.9 |
| hsa-miR-4281 | 13.4 | 12.5 | 12.5 | 10.1 | 11.7 | 12.2 | 12.2 | 11.1 | 11.1 |
| hsa-miR-3663-3p | 11.0 | 12.8 | 12.3 | 11.4 | 12.5 | 12.6 | 12.8 | 12.8 | 12.3 |
| hsa-miR-6786-5p | 12.7 | 13.2 | 13.2 | 11.8 | 12.8 | 13.3 | 11.6 | 13.0 | 11.3 |
| hsa-miR-6765-5p | 12.1 | 12.2 | 12.3 | 11.2 | 11.9 | 12.1 | 12.3 | 12.0 | 11.9 |
| hsa-miR-6729-5p | 11.5 | 13.3 | 13.0 | 12.1 | 13.1 | 13.3 | 12.1 | 13.4 | 11.6 |
| hsa-miR-6087 | 13.3 | 13.0 | 13.2 | 11.3 | 11.9 | 13.0 | 13.2 | 12.7 | 11.8 |
| hsa-miR-6088 | 13.2 | 12.8 | 12.5 | 10.9 | 12.3 | 12.4 | 13.2 | 12.1 | 12.7 |
| hsa-miR-0638 | 11.9 | 13.2 | 13.0 | 12.1 | 13.2 | 13.3 | 11.9 | 13.3 | 11.6 |
| hsa-miR-4674 | 11.6 | 12.9 | 12.6 | 11.5 | 12.7 | 12.2 | 12.5 | 12.5 | 11.5 |
| hsa-miR-4734 | 11.9 | 13.4 | 13.2 | 12.2 | 12.9 | 13.1 | 12.6 | 13.3 | 11.6 |
| hsa-miR-4689 | 13.3 | 12.5 | 12.2 | 9.9 | 11.4 | 12.5 | 12.2 | 11.1 | 11.2 |

TABLE 3-continued

| | | | | | | | | | |
|---|---|---|---|---|---|---|---|---|---|
| hsa-miR-6784-5p | 12.7 | 12.9 | 13.5 | 12.1 | 13.1 | 13.1 | 12.6 | 13.0 | 12.4 |
| hsa-miR-6785-5p | 12.9 | 12.6 | 12.3 | 11.2 | 12.3 | 12.5 | 13.0 | 11.5 | 12.7 |
| hsa-miR-3621 | 11.9 | 13.1 | 12.8 | 12.2 | 13.1 | 12.8 | 13.1 | 13.4 | 12.8 |
| hsa-miR-0328-5p | 13.7 | 13.0 | 12.8 | 10.8 | 11.9 | 13.1 | 12.2 | 12.2 | 11.6 |
| hsa-miR-4739 | 14.5 | 13.3 | 13.3 | 10.7 | 12.2 | 13.4 | 12.1 | 11.9 | 11.3 |
| hsa-miR-6085 | 13.7 | 12.0 | 12.8 | 10.0 | 12.0 | 12.4 | 11.4 | 10.8 | 10.4 |
| hsa-miR-4442 | 14.0 | 12.9 | 12.6 | 10.4 | 12.2 | 13.4 | 13.2 | 11.6 | 12.6 |
| hsa-miR-4649-5p | 12.4 | 13.2 | 12.6 | 11.9 | 12.6 | 12.5 | 13.9 | 12.7 | 13.1 |
| hsa-miR-3196 | 12.8 | 13.4 | 13.4 | 12.2 | 13.3 | 13.1 | 12.6 | 13.0 | 12.1 |
| hsa-miR-4466 | 12.6 | 13.7 | 13.6 | 12.4 | 13.4 | 13.5 | 12.8 | 13.5 | 12.2 |
| hsa-miR-4508 | 12.5 | 13.7 | 13.7 | 12.4 | 13.4 | 13.4 | 12.5 | 13.4 | 12.2 |
| hsa-miR-1237-5p | 12.8 | 13.6 | 13.6 | 12.5 | 13.5 | 13.4 | 13.1 | 13.5 | 13.1 |
| hsa-miR-4532 | 12.2 | 13.6 | 13.5 | 11.9 | 13.5 | 12.9 | 12.6 | 13.2 | 10.9 |
| hsa-miR-6090 | 12.8 | 13.8 | 13.7 | 12.7 | 13.5 | 13.8 | 13.4 | 13.8 | 13.0 |
| hsa-miR-2861 | 14.2 | 13.5 | 13.6 | 12.0 | 13.2 | 13.9 | 13.1 | 13.3 | 12.7 |
| hsa-miR-3163 | 0.0 | 0.0 | 0.0 | 12.0 | 13.2 | 13.9 | 0.0 | 0.0 | 0.0 |
| hsa-miR-4723-5p | 13.6 | 11.9 | 12.7 | 9.7 | 12.9 | 12.7 | 11.7 | 10.1 | 10.9 |
| hsa-miR-3178 | 12.9 | 13.7 | 13.7 | 12.5 | 13.5 | 13.5 | 13.3 | 13.6 | 12.4 |
| hsa-miR-0128-2-5p | 13.9 | 13.9 | 13.3 | 12.0 | 12.9 | 13.3 | 14.1 | 12.7 | 13.3 |
| hsa-miR-1228-5p | 13.9 | 13.4 | 13.6 | 12.3 | 13.1 | 13.5 | 12.7 | 13.2 | 12.6 |
| hsa-miR-0762 | 13.3 | 14.1 | 14.4 | 13.2 | 14.2 | 13.8 | 14.0 | 14.2 | 13.1 |
| hsa-miR-4488 | 13.6 | 14.3 | 14.2 | 12.9 | 13.9 | 14.0 | 14.5 | 14.0 | 13.9 |
| hsa-miR-8069 | 13.7 | 14.5 | 14.3 | 13.1 | 14.1 | 14.2 | 13.7 | 14.3 | 12.9 |
| hsa-miR-3940-5p | 13.6 | 13.9 | 14.1 | 12.6 | 13.7 | 13.7 | 13.5 | 14.2 | 13.6 |
| hsa-miR-6869-5p | 13.0 | 14.5 | 14.3 | 13.0 | 14.1 | 13.8 | 13.8 | 14.1 | 13.0 |
| hsa-miR-6089 | 13.7 | 14.6 | 14.5 | 13.2 | 14.5 | 14.3 | 13.9 | 14.5 | 13.5 |
| hsa-miR-6727-5p | 13.8 | 14.7 | 14.4 | 13.2 | 14.5 | 14.2 | 14.3 | 14.5 | 13.5 |
| hsa-miR-6885-5p | 14.6 | 14.0 | 13.9 | 12.7 | 13.7 | 13.8 | 14.6 | 13.3 | 13.9 |
| hsa-miR-5787 | 13.5 | 14.8 | 14.8 | 13.5 | 14.4 | 13.7 | 14.7 | 14.4 | 14.2 |
| hsa-miR-4787-5p | 14.1 | 14.9 | 14.8 | 13.6 | 14.6 | 14.5 | 14.3 | 14.6 | 13.6 |
| hsa-miR-7704 | 14.2 | 15.2 | 15.0 | 13.8 | 14.9 | 14.7 | 14.8 | 14.9 | 13.9 |
| hsa-miR-4516 | 14.2 | 15.3 | 15.1 | 14.1 | 15.2 | 14.6 | 15.4 | 15.2 | 14.8 |
| hsa-miR-3665 | 14.7 | 15.8 | 15.5 | 14.3 | 15.6 | 15.1 | 15.4 | 15.4 | 14.6 |
| hsa-miR-3960 | 15.4 | 15.9 | 16.4 | 15.4 | 16.2 | 15.1 | 16.4 | 15.7 | 15.6 |

Data S1-2

| miRNA species | Liver cancer | | | Bladder cancer | | | Prostate cancer | | |
|---|---|---|---|---|---|---|---|---|---|
| hsa-let-7a-5p | 0.0 | 0.0 | 0.0 | 0.0 | 2.2 | 0.0 | 0.0 | 0.0 | 0.0 |
| hsa-let-7c-5p | 1.5 | 0.0 | 0.0 | 1.8 | 0.6 | 0.0 | 0.0 | 0.0 | 0.0 |
| hsa-let-7d-5p | 0.0 | 0.0 | 0.0 | 0.0 | 1.4 | 0.0 | 0.0 | 0.0 | 1.1 |
| hsa-let-7e-3p | 0.0 | 2.2 | 0.0 | 0.0 | 2.2 | 1.7 | 1.4 | 0.0 | 0.0 |
| hsa-let-7f-2-3p | 0.0 | 2.2 | 0.0 | 0.0 | 0.0 | 0.0 | 2.5 | 0.2 | 2.4 |
| hsa-let-7f-5p | 1.1 | 0.0 | 0.0 | 0.0 | 0.0 | 0.0 | 0.0 | 0.0 | 0.0 |
| hsa-let-7g-3p | 0.0 | 0.0 | 0.0 | 0.0 | 0.0 | 0.0 | 0.0 | 0.0 | 0.0 |
| hsa-let-7i-3p | 0.0 | 0.0 | 0.0 | 0.0 | 0.0 | 0.0 | 0.0 | 0.0 | 0.0 |
| hsa-miR-0001-3p | 0.0 | 0.0 | 0.0 | 0.0 | 0.0 | 0.0 | 0.0 | 0.0 | 0.0 |
| hsa-miR-0001-5p | 1.9 | 2.5 | 1.8 | 1.7 | 2.5 | 1.9 | 0.0 | 0.0 | 0.0 |
| hsa-miR-0009-5p | 1.1 | 0.0 | 0.0 | 0.0 | 0.0 | 0.0 | 0.0 | 0.0 | 0.0 |
| hsa-miR-0015a-3p | 0.0 | 3.0 | 3.0 | 1.7 | 0.0 | 1.8 | 2.5 | 0.0 | 0.0 |
| hsa-miR-0015a-5p | 0.0 | 0.0 | 1.3 | 0.0 | 0.0 | 0.0 | 0.0 | 0.0 | 0.0 |
| hsa-miR-0015b-3p | 0.0 | 1.2 | 0.0 | 0.0 | 0.0 | 0.0 | 0.0 | 0.0 | 0.0 |
| hsa-miR-0016-2-3p | 0.0 | 2.6 | 2.8 | 3.4 | 2.6 | 3.4 | 2.9 | 0.0 | 2.9 |
| hsa-miR-0016-5p | 0.0 | 0.0 | 0.0 | 0.0 | 2.0 | 0.0 | 0.0 | 0.0 | 0.0 |
| hsa-miR-0017-5p | 0.0 | 0.0 | 1.9 | 0.0 | 1.8 | 0.0 | 0.0 | 0.0 | 0.0 |
| hsa-miR-0018b-5p | 0.0 | 0.0 | 0.0 | 0.0 | 0.0 | 0.0 | 0.0 | 0.0 | 0.0 |
| hsa-miR-0019a-3p | 0.0 | 0.0 | 0.0 | 0.0 | 0.0 | 0.0 | 0.0 | 0.0 | 0.0 |
| hsa-miR-0019a-5p | 2.2 | 0.0 | 0.0 | 0.0 | 0.0 | 0.0 | 0.0 | 0.0 | 0.0 |
| hsa-miR-0019b-1-5p | 0.0 | 0.0 | 0.0 | 0.0 | 0.0 | 0.0 | 0.0 | 0.0 | 0.0 |
| hsa-miR-0019b-2-5p | 0.0 | 0.0 | 0.0 | 0.0 | 0.0 | 0.0 | 0.0 | 0.0 | 0.0 |
| hsa-miR-0020b-5p | 1.3 | 0.0 | 2.8 | 2.7 | 2.2 | 0.0 | 0.0 | 0.0 | 0.0 |
| hsa-miR-0021-5p | 0.0 | 0.0 | 0.0 | 0.0 | 1.1 | 0.0 | 0.0 | 0.0 | 0.0 |
| hsa-miR-0022-5p | 0.0 | 1.5 | 1.7 | 2.8 | 0.7 | 0.0 | 0.0 | 0.5 | 0.0 |
| hsa-miR-0023b-5p | 0.0 | 1.8 | 1.1 | 0.0 | 0.0 | 0.0 | 0.0 | 0.0 | 0.0 |
| hsa-miR-0023c | 0.0 | 0.0 | 2.1 | 0.0 | 1.6 | 0.0 | 0.0 | 0.0 | 1.8 |
| hsa-miR-0024-1-5p | 0.0 | 0.0 | 0.0 | 0.0 | 3.2 | 0.0 | 0.0 | 0.0 | 0.0 |
| hsa-miR-0024-2-5p | 2.2 | 1.5 | 3.2 | 2.1 | 0.0 | 1.1 | 0.0 | 0.0 | 0.0 |
| hsa-miR-0024-3p | 3.2 | 1.8 | 3.5 | 3.1 | 3.7 | 1.6 | 2.2 | 2.5 | 2.2 |
| hsa-miR-0026a-2-3p | 2.0 | 0.0 | 2.6 | 0.0 | 1.5 | 0.0 | 0.0 | 0.0 | 0.0 |
| hsa-miR-0026a-5p | 0.0 | 0.0 | 0.0 | 0.0 | 0.0 | 0.0 | 0.0 | 0.0 | 0.0 |
| hsa-miR-0027a-5p | 0.0 | 0.0 | 0.0 | 0.0 | 0.7 | 0.0 | 0.0 | 0.0 | 0.0 |
| hsa-miR-0028-3p | 0.0 | 2.3 | 0.0 | 0.0 | 2.0 | 0.0 | 0.0 | 0.0 | 0.0 |
| hsa-miR-0029a-5p | 0.0 | 0.0 | 0.0 | 0.0 | 2.2 | 0.0 | 0.0 | 0.0 | 0.0 |
| hsa-miR-0029b-1-5p | 0.0 | 0.0 | 0.0 | 0.0 | 0.0 | 0.0 | 0.0 | 0.0 | 0.0 |
| hsa-miR-0029c-3p | 0.0 | 0.0 | 0.0 | 0.0 | 0.0 | 0.0 | 0.0 | 1.1 | 0.0 |
| hsa-miR-0030a-5p | 0.0 | 0.0 | 0.0 | 0.0 | 1.5 | 0.0 | 0.0 | 0.0 | 0.0 |
| hsa-miR-0031-3p | 0.0 | 0.0 | 2.0 | 0.0 | 2.3 | 0.0 | 0.0 | 0.0 | 0.0 |
| hsa-miR-0031-5p | 0.0 | 0.0 | 2.1 | 0.0 | 0.0 | 0.0 | 0.0 | 0.0 | 0.0 |
| hsa-miR-0032-3p | 0.0 | 2.3 | 3.5 | 2.9 | 2.2 | 1.9 | 2.5 | 2.5 | 2.7 |

TABLE 3-continued

| | | | | | | | | | |
|---|---|---|---|---|---|---|---|---|---|
| hsa-miR-0032-5p | 0.0 | 0.0 | 0.0 | 0.0 | 0.0 | 0.0 | 0.0 | 0.0 | 0.0 |
| hsa-miR-0033a-3p | 3.3 | 1.8 | 2.7 | 3.2 | 0.0 | 2.0 | 0.0 | 1.9 | 1.9 |
| hsa-miR-0033a-5p | 0.0 | 1.0 | 0.0 | 0.0 | 0.0 | 0.0 | 0.0 | 0.0 | 0.0 |
| hsa-miR-0033b-5p | 2.4 | 0.0 | 0.0 | 0.0 | 0.0 | 0.0 | 0.0 | 0.0 | 0.0 |
| hsa-miR-0034a-3p | 0.0 | 0.0 | 0.0 | 0.0 | 0.0 | 0.0 | 0.0 | 0.0 | 0.0 |
| hsa-miR-0095-5p | 0.0 | 0.0 | 0.0 | 0.0 | 0.0 | 0.0 | 0.0 | 0.0 | 0.0 |
| hsa-miR-0096-5p | 1.7 | 0.0 | 2.9 | 0.0 | 0.0 | 0.0 | 0.0 | 0.0 | 0.0 |
| hsa-miR-0099a-5p | 0.0 | 0.0 | 0.0 | 0.0 | 0.0 | 0.0 | 0.0 | 0.0 | 0.0 |
| hsa-miR-0100-3p | 0.0 | 0.0 | 0.0 | 0.0 | 0.0 | 0.0 | 0.0 | 0.0 | 0.0 |
| hsa-miR-0100-5p | 0.0 | 0.0 | 0.0 | 0.0 | 0.6 | 0.0 | 0.0 | 0.0 | 0.0 |
| hsa-miR-0101-3p | 0.0 | 0.0 | 0.0 | 0.0 | 0.0 | 0.0 | 0.0 | 0.0 | 0.0 |
| hsa-miR-0101-5p | 0.0 | 0.0 | 1.6 | 0.0 | 0.0 | 0.0 | 0.0 | 0.0 | 0.0 |
| hsa-miR-0103a-3p | 2.5 | 0.0 | 3.3 | 3.2 | 0.5 | 1.2 | 2.0 | 1.3 | 1.9 |
| hsa-miR-0103b | 2.1 | 1.7 | 0.0 | 0.0 | 0.0 | 0.0 | 0.0 | 0.0 | 0.0 |
| hsa-miR-0105-3p | 0.0 | 0.0 | 0.0 | 0.0 | 0.0 | 0.0 | 0.0 | 0.0 | 0.0 |
| hsa-miR-0106a-3p | 0.0 | 0.0 | 1.2 | 0.0 | 0.0 | 0.0 | 0.0 | 0.0 | 0.0 |
| hsa-miR-0106a-5p | 0.0 | 0.0 | 0.0 | 0.0 | 0.0 | 0.0 | 0.0 | 0.0 | 0.0 |
| hsa-miR-0106b-5p | 0.0 | 1.8 | 0.0 | 0.0 | 1.3 | 0.0 | 0.0 | 0.0 | 0.0 |
| hsa-miR-0107 | 0.0 | 0.0 | 3.0 | 0.0 | 0.6 | 0.0 | 2.3 | 0.3 | 1.4 |
| hsa-miR-0122-3p | 0.0 | 2.1 | 2.3 | 1.9 | 0.0 | 0.0 | 0.0 | 0.0 | 0.0 |
| hsa-miR-0124-3p | 2.2 | 0.0 | 0.0 | 1.6 | 2.1 | 0.0 | 0.0 | 3.5 | 5.7 |
| hsa-miR-0125b-1-3p | 0.0 | 2.9 | 0.0 | 0.0 | 0.0 | 0.0 | 0.0 | 0.0 | 1.1 |
| hsa-miR-0126-5p | 0.0 | 0.0 | 0.0 | 0.0 | 0.0 | 0.0 | 0.0 | 0.0 | 0.0 |
| hsa-miR-0127-3p | 0.0 | 0.0 | 0.0 | 1.9 | 0.0 | 0.0 | 0.0 | 0.0 | 0.0 |
| hsa-miR-0130a-3p | 0.0 | 0.0 | 0.0 | 1.8 | 0.0 | 0.0 | 0.0 | 0.0 | 0.0 |
| hsa-miR-0130b-3p | 0.0 | 0.0 | 0.0 | 0.0 | 0.5 | 0.0 | 0.0 | 0.0 | 1.2 |
| hsa-miR-0132-3p | 2.5 | 1.5 | 2.2 | 0.0 | 2.6 | 0.0 | 1.4 | 0.0 | 0.0 |
| hsa-miR-0132-5p | 0.0 | 0.0 | 0.0 | 0.0 | 0.0 | 0.0 | 0.0 | 0.0 | 0.0 |
| hsa-miR-0133a-5p | 1.8 | 1.7 | 1.4 | 0.0 | 0.0 | 0.0 | 1.8 | 0.0 | 0.0 |
| hsa-miR-0135b-3p | 0.0 | 0.0 | 0.0 | 0.0 | 0.0 | 0.0 | 0.0 | 0.0 | 0.0 |
| hsa-miR-0136-5p | 0.0 | 0.0 | 0.0 | 0.0 | 0.0 | 0.0 | 0.0 | 0.0 | 0.0 |
| hsa-miR-0139-5p | 0.0 | 0.0 | 0.0 | 0.0 | 0.0 | 0.0 | 0.0 | 0.0 | 0.0 |
| hsa-miR-0140-3p | 0.0 | 0.0 | 0.0 | 1.5 | 0.0 | 0.0 | 0.0 | 0.0 | 0.0 |
| hsa-miR-0140-5p | 0.0 | 0.0 | 0.0 | 0.0 | 2.1 | 0.0 | 0.0 | 0.0 | 0.0 |
| hsa-miR-0141-3p | 0.0 | 0.0 | 0.0 | 0.0 | 0.0 | 0.0 | 0.0 | 1.0 | 0.0 |
| hsa-miR-0142-5p | 0.0 | 0.0 | 0.0 | 0.0 | 1.4 | 0.0 | 0.0 | 0.0 | 0.0 |
| hsa-miR-0144-3p | 0.0 | 0.0 | 0.0 | 0.0 | 0.0 | 0.0 | 0.0 | 0.0 | 0.0 |
| hsa-miR-0145-3p | 0.0 | 0.0 | 0.0 | 0.0 | 0.0 | 0.0 | 0.0 | 0.0 | 0.0 |
| hsa-miR-0146a-3p | 0.0 | 0.0 | 0.0 | 0.0 | 0.0 | 0.0 | 0.0 | 0.0 | 0.0 |
| hsa-miR-0146b-5p | 0.0 | 0.0 | 0.0 | 0.0 | 0.0 | 0.0 | 0.0 | 0.0 | 0.0 |
| hsa-miR-0148a-5p | 0.0 | 0.0 | 1.1 | 0.0 | 0.0 | 0.0 | 0.0 | 0.0 | 0.0 |
| hsa-miR-0148b-3p | 0.0 | 0.0 | 0.0 | 0.0 | 1.1 | 0.0 | 0.0 | 0.0 | 0.0 |
| hsa-miR-0148b-5p | 2.0 | 1.0 | 0.0 | 0.0 | 0.0 | 0.0 | 0.0 | 0.0 | 0.0 |
| hsa-miR-0151a-3p | 2.4 | 1.9 | 2.4 | 2.2 | 0.0 | 1.0 | 0.0 | 0.0 | 0.0 |
| hsa-miR-0151a-5p | 0.0 | 0.0 | 1.9 | 3.5 | 2.4 | 0.0 | 3.8 | 1.8 | 3.3 |
| hsa-miR-0152-3p | 1.6 | 0.0 | 1.1 | 0.0 | 1.7 | 0.0 | 0.0 | 0.0 | 0.0 |
| hsa-miR-0153-3p | 0.0 | 0.0 | 0.0 | 0.0 | 0.0 | 0.0 | 0.0 | 0.0 | 0.0 |
| hsa-miR-0154-3p | 0.0 | 3.0 | 2.6 | 0.0 | 0.0 | 1.6 | 2.2 | 0.0 | 1.9 |
| hsa-miR-0155-3p | 0.0 | 2.6 | 1.1 | 0.0 | 0.0 | 0.0 | 2.2 | 0.0 | 0.0 |
| hsa-miR-0155-5p | 0.0 | 0.0 | 0.0 | 0.0 | 0.0 | 0.0 | 0.0 | 0.0 | 0.0 |
| hsa-miR-0181a-3p | 2.2 | 0.0 | 0.0 | 0.0 | 0.0 | 0.0 | 0.0 | 0.0 | 0.0 |
| hsa-miR-0181b-2-3p | 0.0 | 0.0 | 0.0 | 0.0 | 0.0 | 0.0 | 0.0 | 0.0 | 0.0 |
| hsa-miR-0181c-3p | 0.0 | 1.4 | 0.0 | 0.0 | 0.0 | 0.0 | 0.0 | 1.5 | 0.0 |
| hsa-miR-0181c-5p | 0.0 | 0.0 | 0.0 | 0.0 | 0.0 | 0.0 | 0.0 | 0.0 | 0.0 |
| hsa-miR-0181d-5p | 0.0 | 2.6 | 1.9 | 1.5 | 0.0 | 1.6 | 0.0 | 0.0 | 0.0 |
| hsa-miR-0182-3p | 0.0 | 0.0 | 0.0 | 0.0 | 0.0 | 0.0 | 0.0 | 0.0 | 0.0 |
| hsa-miR-0182-5p | 0.0 | 0.0 | 2.3 | 0.0 | 0.0 | 0.0 | 0.0 | 0.0 | 0.0 |
| hsa-miR-0186-3p | 0.0 | 0.0 | 0.0 | 0.0 | 0.0 | 0.0 | 0.0 | 0.1 | 1.4 |
| hsa-miR-0186-5p | 0.0 | 0.0 | 0.0 | 0.0 | 0.0 | 0.0 | 0.0 | 0.0 | 0.0 |
| hsa-miR-0188-3p | 1.7 | 0.0 | 2.2 | 2.2 | 1.4 | 0.0 | 0.0 | 1.5 | 1.7 |
| hsa-miR-0190a-3p | 0.0 | 0.0 | 0.0 | 0.0 | 3.4 | 0.0 | 0.0 | 0.0 | 0.0 |
| hsa-miR-0190b | 0.0 | 0.0 | 0.0 | 0.0 | 0.0 | 0.0 | 0.0 | 0.0 | 0.0 |
| hsa-miR-0191-5p | 0.0 | 0.0 | 0.0 | 0.0 | 1.1 | 0.0 | 0.0 | 0.0 | 0.0 |
| hsa-miR-0192-3p | 0.0 | 0.0 | 1.1 | 0.0 | 2.9 | 0.0 | 0.0 | 0.0 | 0.0 |
| hsa-miR-0193a-3p | 1.9 | 0.0 | 2.9 | 2.2 | 1.2 | 1.2 | 0.0 | 0.0 | 0.0 |
| hsa-miR-0200a-3p | 2.7 | 0.0 | 0.0 | 0.0 | 0.0 | 0.0 | 0.0 | 0.0 | 0.0 |
| hsa-miR-0200c-3p | 2.7 | 0.0 | 0.0 | 2.2 | 0.0 | 1.8 | 0.0 | 0.0 | 0.0 |
| hsa-miR-0202-5p | 0.0 | 0.0 | 1.2 | 0.0 | 0.0 | 0.0 | 0.0 | 0.0 | 0.0 |
| hsa-miR-0203a-5p | 0.0 | 2.2 | 3.6 | 0.0 | 0.0 | 1.5 | 0.0 | 0.0 | 0.0 |
| hsa-miR-0208a-3p | 0.0 | 0.0 | 0.0 | 0.0 | 0.0 | 0.0 | 0.0 | 0.0 | 0.0 |
| hsa-miR-0208b-3p | 0.0 | 0.0 | 0.0 | 0.0 | 0.0 | 0.0 | 0.0 | 0.0 | 0.0 |
| hsa-miR-0216a-5p | 0.0 | 0.0 | 2.6 | 1.9 | 0.7 | 0.0 | 0.0 | 0.0 | 0.0 |
| hsa-miR-0216b-5p | 0.0 | 0.0 | 0.0 | 0.0 | 0.0 | 0.0 | 0.0 | 0.0 | 0.0 |
| hsa-miR-0218-1-3p | 0.0 | 0.0 | 0.0 | 0.0 | 0.0 | 0.0 | 0.0 | 0.0 | 3.4 |
| hsa-miR-0218-2-3p | 0.0 | 0.0 | 1.3 | 0.0 | 0.0 | 0.0 | 0.0 | 0.0 | 0.0 |
| hsa-miR-0218-5p | 0.0 | 0.0 | 0.0 | 0.0 | 1.5 | 0.0 | 0.0 | 0.0 | 0.0 |
| hsa-miR-0219a-2-3p | 3.5 | 2.4 | 3.1 | 1.8 | 0.0 | 0.0 | 0.0 | 0.6 | 1.2 |
| hsa-miR-0219a-5p | 0.0 | 0.0 | 0.0 | 0.0 | 0.0 | 0.0 | 0.0 | 0.0 | 0.0 |
| hsa-miR-0224-5p | 0.0 | 0.0 | 0.0 | 0.0 | 1.0 | 0.0 | 0.0 | 0.0 | 0.0 |
| hsa-miR-0298 | 0.0 | 1.1 | 0.0 | 1.7 | 0.0 | 0.0 | 0.0 | 0.0 | 0.0 |

TABLE 3-continued

| | | | | | | | | | |
|---|---|---|---|---|---|---|---|---|---|
| hsa-miR-0299-3p | 3.0 | 1.5 | 1.2 | 3.1 | 3.1 | 0.0 | 0.0 | 1.7 | 2.0 |
| hsa-miR-0301a-3p | 0.0 | 0.0 | 0.0 | 0.0 | 0.0 | 0.0 | 0.0 | 0.0 | 0.0 |
| hsa-miR-0301a-5p | 1.8 | 3.2 | 2.8 | 1.5 | 0.0 | 1.8 | 2.8 | 1.8 | 2.1 |
| hsa-miR-0301b-3p | 0.0 | 0.0 | 0.0 | 0.0 | 0.0 | 0.0 | 0.0 | 0.0 | 0.0 |
| hsa-miR-0301b-5p | 0.0 | 0.0 | 3.0 | 0.0 | 0.0 | 0.0 | 0.0 | 0.4 | 0.0 |
| hsa-miR-0302a-5p | 0.0 | 0.0 | 0.0 | 0.0 | 0.4 | 0.0 | 0.0 | 0.0 | 0.0 |
| hsa-miR-0302b-3p | 1.3 | 0.0 | 0.0 | 0.0 | 0.0 | 0.0 | 0.0 | 0.0 | 0.0 |
| hsa-miR-0302b-5p | 0.0 | 0.0 | 0.0 | 0.0 | 2.8 | 0.0 | 0.0 | 0.0 | 0.0 |
| hsa-miR-0302c-3p | 0.0 | 0.0 | 0.0 | 2.1 | 2.0 | 0.0 | 2.2 | 0.0 | 0.0 |
| hsa-miR-0302d-3p | 0.0 | 0.0 | 2.6 | 2.5 | 0.0 | 0.0 | 0.0 | 0.0 | 0.0 |
| hsa-miR-0302f | 0.0 | 0.0 | 2.5 | 0.0 | 0.0 | 0.0 | 3.0 | 0.0 | 0.0 |
| hsa-miR-0320d | 0.0 | 1.7 | 0.0 | 0.0 | 0.0 | 0.0 | 0.0 | 0.0 | 0.0 |
| hsa-miR-0320e | 1.8 | 1.7 | 1.5 | 1.9 | 0.0 | 0.0 | 0.0 | 1.0 | 1.2 |
| hsa-miR-0323b-3p | 0.0 | 1.5 | 0.0 | 0.0 | 0.0 | 0.0 | 0.0 | 0.0 | 0.0 |
| hsa-miR-0329-3p | 0.0 | 1.0 | 1.8 | 0.0 | 0.8 | 0.0 | 2.1 | 0.0 | 0.0 |
| hsa-miR-0331-5p | 0.0 | 0.0 | 0.0 | 0.0 | 0.0 | 0.0 | 0.0 | 0.0 | 0.0 |
| hsa-miR-0335-3p | 2.2 | 2.4 | 2.8 | 2.4 | 0.9 | 2.3 | 2.2 | 0.0 | 1.2 |
| hsa-miR-0337-5p | 0.0 | 1.1 | 0.0 | 0.0 | 0.0 | 2.2 | 1.5 | 0.0 | 0.0 |
| hsa-miR-0340-5p | 0.0 | 0.0 | 0.0 | 0.0 | 0.0 | 0.0 | 1.5 | 0.0 | 0.0 |
| hsa-miR-0361-5p | 0.0 | 0.0 | 2.2 | 2.0 | 0.0 | 1.2 | 2.4 | 0.0 | 0.0 |
| hsa-miR-0362-5p | 0.0 | 0.0 | 0.0 | 0.0 | 1.8 | 0.0 | 0.0 | 0.0 | 0.0 |
| hsa-miR-0363-3p | 0.0 | 0.0 | 1.8 | 2.8 | 1.1 | 2.0 | 1.5 | 0.0 | 0.0 |
| hsa-miR-0367-5p | 1.0 | 0.0 | 0.0 | 0.0 | 0.0 | 0.0 | 0.0 | 0.0 | 0.0 |
| hsa-miR-0372-5p | 0.0 | 0.0 | 1.9 | 0.0 | 0.0 | 0.0 | 0.0 | 0.0 | 1.2 |
| hsa-miR-0374a-3p | 0.0 | 0.0 | 0.0 | 0.0 | 0.0 | 0.0 | 0.0 | 0.0 | 0.0 |
| hsa-miR-0374a-5p | 0.0 | 0.0 | 2.0 | 0.0 | 0.0 | 0.0 | 0.0 | 0.0 | 0.0 |
| hsa-miR-0374c-5p | 3.4 | 2.5 | 1.4 | 2.6 | 1.2 | 1.4 | 2.0 | 0.0 | 0.0 |
| hsa-miR-0375 | 0.0 | 1.4 | 0.0 | 1.9 | 2.8 | 1.7 | 0.0 | 0.0 | 1.6 |
| hsa-miR-0376a-2-5p | 0.0 | 0.0 | 1.9 | 0.0 | 0.0 | 0.0 | 0.0 | 0.0 | 0.0 |
| hsa-miR-0376a-3p | 0.0 | 0.0 | 0.0 | 0.0 | 0.0 | 0.0 | 0.0 | 0.0 | 0.0 |
| hsa-miR-0376a-5p | 0.0 | 0.0 | 0.0 | 0.0 | 0.0 | 0.0 | 0.0 | 0.0 | 0.0 |
| hsa-miR-0376b-3p | 0.0 | 0.0 | 0.0 | 0.0 | 0.0 | 0.0 | 0.0 | 0.0 | 0.0 |
| hsa-miR-0376b-5p | 0.0 | 0.0 | 0.0 | 0.0 | 0.0 | 0.0 | 0.0 | 0.0 | 0.0 |
| hsa-miR-0376c-5p | 0.0 | 0.0 | 2.0 | 0.0 | 0.0 | 0.0 | 0.0 | 0.0 | 0.0 |
| hsa-miR-0377-3p | 0.0 | 0.0 | 0.0 | 2.4 | 2.9 | 0.0 | 0.0 | 0.0 | 0.0 |
| hsa-miR-0377-5p | 2.4 | 2.3 | 2.8 | 2.0 | 0.0 | 0.0 | 0.0 | 0.8 | 0.0 |
| hsa-miR-0378j | 0.0 | 0.0 | 1.5 | 0.0 | 0.0 | 0.0 | 0.0 | 0.2 | 0.0 |
| hsa-miR-0379-5p | 0.0 | 0.0 | 1.5 | 0.0 | 1.0 | 0.0 | 0.0 | 0.0 | 0.0 |
| hsa-miR-0380-3p | 2.2 | 1.9 | 1.3 | 0.0 | 1.1 | 1.9 | 1.7 | 1.6 | 0.0 |
| hsa-miR-0381-3p | 2.1 | 0.0 | 0.0 | 2.1 | 0.0 | 0.0 | 2.3 | 1.2 | 0.0 |
| hsa-miR-0384 | 0.0 | 0.0 | 0.0 | 0.0 | 0.0 | 0.0 | 0.0 | 0.0 | 0.0 |
| hsa-miR-0409-5p | 0.0 | 0.0 | 1.6 | 0.0 | 1.4 | 0.0 | 0.0 | 0.0 | 0.0 |
| hsa-miR-0410-3p | 1.7 | 0.0 | 0.0 | 0.0 | 0.0 | 0.0 | 0.0 | 0.0 | 0.0 |
| hsa-miR-0411-5p | 0.0 | 0.0 | 0.0 | 0.0 | 0.0 | 0.0 | 0.0 | 0.0 | 0.0 |
| hsa-miR-0412-5p | 0.0 | 0.0 | 0.0 | 0.0 | 0.0 | 0.0 | 0.0 | 0.0 | 0.0 |
| hsa-miR-0424-3p | 0.0 | 2.3 | 1.9 | 0.0 | 0.0 | 0.0 | 0.0 | 5.4 | 3.6 |
| hsa-miR-0424-5p | 0.0 | 0.0 | 2.1 | 0.0 | 0.0 | 0.0 | 0.0 | 0.0 | 0.0 |
| hsa-miR-0429 | 0.0 | 0.0 | 0.0 | 0.0 | 0.0 | 0.0 | 1.4 | 0.0 | 0.0 |
| hsa-miR-0433-3p | 0.0 | 1.6 | 2.4 | 2.5 | 2.2 | 1.2 | 0.0 | 0.0 | 0.0 |
| hsa-miR-0433-5p | 1.1 | 2.4 | 2.8 | 2.0 | 0.5 | 3.6 | 3.1 | 2.4 | 2.9 |
| hsa-miR-0448 | 2.6 | 1.9 | 3.6 | 2.8 | 2.8 | 0.0 | 2.6 | 1.9 | 0.0 |
| hsa-miR-0450a-2-3p | 0.0 | 0.0 | 0.0 | 0.0 | 0.0 | 0.0 | 0.0 | 0.0 | 1.8 |
| hsa-miR-0451a | 0.0 | 0.0 | 0.0 | 0.0 | 0.4 | 0.0 | 0.0 | 0.0 | 0.0 |
| hsa-miR-0451b | 0.0 | 0.0 | 0.0 | 0.0 | 0.0 | 0.0 | 0.0 | 0.0 | 0.0 |
| hsa-miR-0454-3p | 0.0 | 0.0 | 0.0 | 0.0 | 0.0 | 0.0 | 0.0 | 0.0 | 0.0 |
| hsa-miR-0455-3p | 0.0 | 1.6 | 1.8 | 0.0 | 0.0 | 1.2 | 0.0 | 0.0 | 0.0 |
| hsa-miR-0487a-3p | 0.0 | 0.0 | 2.7 | 2.4 | 1.5 | 0.0 | 0.0 | 0.9 | 0.0 |
| hsa-miR-0489-3p | 2.6 | 2.2 | 2.6 | 2.4 | 2.2 | 2.1 | 1.5 | 0.0 | 1.9 |
| hsa-miR-0490-3p | 0.0 | 0.0 | 2.2 | 0.0 | 1.8 | 0.0 | 0.0 | 0.0 | 0.0 |
| hsa-miR-0490-5p | 0.0 | 0.0 | 0.0 | 0.0 | 0.0 | 0.0 | 0.0 | 2.0 | 0.0 |
| hsa-miR-0492 | 2.0 | 2.2 | 2.7 | 3.0 | 2.5 | 3.1 | 2.2 | 1.4 | 2.2 |
| hsa-miR-0493-5p | 0.0 | 0.0 | 1.2 | 0.0 | 0.0 | 2.1 | 0.0 | 0.0 | 0.0 |
| hsa-miR-0495-3p | 0.0 | 0.0 | 0.0 | 0.0 | 0.0 | 0.0 | 0.0 | 0.0 | 0.0 |
| hsa-miR-0496 | 1.6 | 1.7 | 0.0 | 0.0 | 0.0 | 0.0 | 0.0 | 0.0 | 0.0 |
| hsa-miR-0497-5p | 0.0 | 0.0 | 3.4 | 2.1 | 1.3 | 2.3 | 2.1 | 1.5 | 0.0 |
| hsa-miR-0499a-3p | 2.6 | 2.2 | 0.0 | 0.0 | 0.0 | 0.0 | 0.0 | 0.0 | 0.0 |
| hsa-miR-0499a-5p | 0.0 | 0.0 | 0.0 | 0.0 | 0.0 | 0.0 | 0.0 | 0.0 | 0.0 |
| hsa-miR-0500a-3p | 2.3 | 0.0 | 0.0 | 2.1 | 0.0 | 0.0 | 0.0 | 1.4 | 0.0 |
| hsa-miR-0501-3p | 0.0 | 0.0 | 0.0 | 0.0 | 0.0 | 0.0 | 0.0 | 0.0 | 0.0 |
| hsa-miR-0503-5p | 0.0 | 0.0 | 1.5 | 2.4 | 0.0 | 0.0 | 0.0 | 0.9 | 0.0 |
| hsa-miR-0504-5p | 1.6 | 2.8 | 2.4 | 2.3 | 0.0 | 0.0 | 0.0 | 0.0 | 0.0 |
| hsa-miR-0506-5p | 1.2 | 0.0 | 1.8 | 0.0 | 0.0 | 0.0 | 0.0 | 0.0 | 0.0 |
| hsa-miR-0509-5p | 2.7 | 1.0 | 1.6 | 0.0 | 0.0 | 0.0 | 0.0 | 0.0 | 0.0 |
| hsa-miR-0513b-3p | 0.0 | 0.0 | 0.0 | 0.0 | 0.0 | 0.0 | 0.0 | 0.0 | 0.0 |
| hsa-miR-0513c-5p | 2.0 | 3.2 | 3.1 | 1.9 | 0.0 | 1.2 | 0.0 | 0.0 | 0.0 |
| hsa-miR-0514a-5p | 0.0 | 0.0 | 0.0 | 0.0 | 0.0 | 0.0 | 0.0 | 0.0 | 0.0 |
| hsa-miR-0515-5p | 0.0 | 0.0 | 2.5 | 0.0 | 2.5 | 0.0 | 0.0 | 0.0 | 0.0 |
| hsa-miR-0516a-5p | 0.0 | 0.0 | 0.0 | 0.0 | 0.0 | 0.0 | 0.0 | 0.0 | 0.0 |
| hsa-miR-0516b-3p, hsa-miR-516a-3p | 2.4 | 1.8 | 3.1 | 0.0 | 0.0 | 0.0 | 0.0 | 1.7 | 0.0 |

TABLE 3-continued

| | | | | | | | | | |
|---|---|---|---|---|---|---|---|---|---|
| hsa-miR-0517c-3p | 0.0 | 2.3 | 2.0 | 2.7 | 1.2 | 1.2 | 0.0 | 1.9 | 0.0 |
| hsa-miR-0518a-3p | 0.0 | 0.0 | 0.0 | 0.0 | 0.0 | 0.0 | 0.0 | 0.0 | 0.0 |
| hsa-miR-0518c-3p | 0.0 | 0.0 | 0.0 | 0.0 | 0.0 | 3.5 | 0.0 | 0.0 | 0.0 |
| hsa-miR-0518d-3p | 0.0 | 0.0 | 1.4 | 0.0 | 2.2 | 0.0 | 0.0 | 0.0 | 0.0 |
| hsa-miR-0519c-3p | 0.0 | 0.0 | 0.0 | 0.0 | 0.0 | 0.0 | 0.0 | 0.0 | 0.0 |
| hsa-miR-0520a-5p | 0.0 | 0.0 | 2.0 | 0.0 | 0.0 | 0.0 | 0.0 | 0.0 | 0.0 |
| hsa-miR-0520c-3p | 0.0 | 0.0 | 0.0 | 0.0 | 0.0 | 0.0 | 0.0 | 0.0 | 0.0 |
| hsa-miR-0520d-3p | 0.0 | 2.9 | 2.4 | 0.0 | 0.0 | 0.0 | 0.0 | 0.5 | 0.0 |
| hsa-miR-0520f-3p | 0.0 | 0.0 | 2.4 | 0.0 | 0.0 | 0.0 | 0.0 | 0.0 | 0.0 |
| hsa-miR-0520f-5p | 0.0 | 0.0 | 0.0 | 0.0 | 0.0 | 0.0 | 0.0 | 3.5 | 2.2 |
| hsa-miR-0520g-5p | 0.0 | 0.0 | 0.0 | 0.0 | 0.0 | 0.0 | 1.6 | 0.0 | 2.5 |
| hsa-miR-0521 | 3.0 | 1.8 | 3.6 | 2.8 | 2.8 | 2.1 | 2.7 | 1.6 | 2.6 |
| hsa-miR-0522-3p | 0.0 | 0.0 | 1.7 | 0.0 | 0.0 | 0.0 | 0.0 | 0.0 | 0.0 |
| hsa-miR-0523-3p | 1.2 | 1.6 | 0.0 | 0.0 | 0.0 | 0.0 | 0.0 | 0.0 | 0.0 |
| hsa-miR-0524-3p | 0.0 | 0.0 | 0.0 | 0.0 | 0.0 | 0.0 | 0.0 | 0.0 | 0.0 |
| hsa-miR-0539-5p | 0.0 | 0.0 | 2.5 | 1.9 | 0.0 | 2.1 | 0.0 | 0.0 | 1.2 |
| hsa-miR-0542-5p | 0.0 | 0.0 | 0.0 | 0.0 | 0.0 | 2.2 | 0.0 | 2.5 | 2.8 |
| hsa-miR-0544b | 0.0 | 0.0 | 0.0 | 0.0 | 0.0 | 0.0 | 0.0 | 0.0 | 0.0 |
| hsa-miR-0545-3p | 0.0 | 0.0 | 0.0 | 0.0 | 0.0 | 0.0 | 0.0 | 0.0 | 0.0 |
| hsa-miR-0545-5p | 0.0 | 0.0 | 0.0 | 0.0 | 0.0 | 0.0 | 0.0 | 0.0 | 0.0 |
| hsa-miR-0548a-3p | 0.0 | 0.0 | 0.0 | 0.0 | 1.2 | 0.0 | 0.0 | 0.0 | 0.0 |
| hsa-miR-0548a-5p | 0.0 | 0.0 | 0.0 | 0.0 | 0.0 | 0.0 | 0.0 | 0.0 | 0.0 |
| hsa-miR-0548aa, hsa-miR-548t-3p | 0.0 | 0.0 | 0.0 | 0.0 | 0.0 | 0.0 | 0.0 | 0.0 | 0.0 |
| hsa-miR-0548ab | 0.0 | 0.0 | 0.0 | 0.0 | 1.2 | 2.2 | 0.0 | 0.0 | 0.0 |
| hsa-miR-0548ac | 0.0 | 0.0 | 0.0 | 0.0 | 0.0 | 0.0 | 0.0 | 0.0 | 0.0 |
| hsa-miR-0548ag | 0.0 | 0.0 | 0.0 | 0.0 | 0.0 | 0.0 | 0.0 | 0.0 | 0.0 |
| hsa-miR-0548ah-3p | 0.0 | 0.0 | 0.0 | 0.0 | 2.6 | 0.0 | 0.0 | 0.0 | 0.0 |
| hsa-miR-0548ai, hsa-miR-570-5p | 0.0 | 0.0 | 0.0 | 0.0 | 0.0 | 0.0 | 0.0 | 0.0 | 0.0 |
| hsa-miR-0548al | 0.0 | 0.0 | 2.4 | 0.0 | 0.0 | 0.0 | 0.0 | 0.0 | 0.0 |
| hsa-miR-0548am-3p | 0.0 | 0.0 | 0.0 | 0.0 | 0.0 | 0.0 | 0.0 | 0.0 | 0.0 |
| hsa-miR-0548an | 0.0 | 0.0 | 0.0 | 0.0 | 0.0 | 0.0 | 0.0 | 0.0 | 0.0 |
| hsa-miR-0548ao-3p | 0.0 | 0.0 | 0.0 | 0.0 | 0.0 | 0.0 | 0.0 | 0.0 | 0.0 |
| hsa-miR-0548ao-5p | 0.0 | 0.0 | 0.0 | 0.0 | 0.0 | 0.0 | 0.0 | 0.0 | 0.0 |
| hsa-miR-0548ap-3p | 0.0 | 0.0 | 0.0 | 0.0 | 0.0 | 0.0 | 0.0 | 0.0 | 0.0 |
| hsa-miR-0548aq-5p | 0.0 | 0.0 | 0.0 | 0.0 | 0.0 | 0.0 | 0.0 | 0.0 | 0.0 |
| hsa-miR-0548as-3p | 0.0 | 0.0 | 0.0 | 0.0 | 0.0 | 0.0 | 0.0 | 0.0 | 0.0 |
| hsa-miR-0548as-5p | 0.0 | 0.0 | 2.6 | 0.0 | 0.0 | 1.8 | 0.0 | 0.0 | 0.0 |
| hsa-miR-0548at-5p | 0.0 | 2.8 | 1.9 | 0.0 | 0.0 | 0.0 | 0.0 | 0.0 | 0.0 |
| hsa-miR-0548au-3p | 0.0 | 1.8 | 1.2 | 0.0 | 0.0 | 0.0 | 0.0 | 0.6 | 0.0 |
| hsa-miR-0548av-3p | 0.0 | 0.0 | 0.0 | 0.0 | 0.0 | 0.0 | 0.0 | 0.0 | 0.0 |
| hsa-miR-0548ay-5p | 0.0 | 1.5 | 0.0 | 0.0 | 0.0 | 0.0 | 0.0 | 0.0 | 0.0 |
| hsa-miR-0548az-3p | 0.0 | 0.0 | 0.0 | 0.0 | 0.0 | 0.0 | 0.0 | 0.0 | 0.0 |
| hsa-miR-0548b-3p | 1.0 | 0.0 | 2.0 | 0.0 | 1.2 | 0.0 | 0.0 | 0.0 | 0.0 |
| hsa-miR-0548c-3p | 0.0 | 0.0 | 0.0 | 0.0 | 0.0 | 0.0 | 0.0 | 0.0 | 0.0 |
| hsa-miR-0548c-5p, hsa-miR-548o-5p, hsa-miR-548am-5p | 0.0 | 0.0 | 0.0 | 0.0 | 0.0 | 0.0 | 0.0 | 0.0 | 0.0 |
| hsa-miR-0548e-3p | 0.0 | 0.0 | 0.0 | 0.0 | 0.0 | 0.0 | 0.0 | 0.0 | 0.0 |
| hsa-miR-0548e-5p | 0.0 | 0.0 | 0.0 | 0.0 | 0.0 | 0.0 | 0.0 | 0.0 | 0.0 |
| hsa-miR-0548f-3p | 0.0 | 0.0 | 0.0 | 0.0 | 0.0 | 0.0 | 0.0 | 0.0 | 0.0 |
| hsa-miR-0548h-5p | 1.9 | 0.0 | 0.0 | 0.0 | 0.0 | 0.0 | 0.0 | 0.0 | 0.0 |
| hsa-miR-0548j-5p | 0.0 | 0.0 | 0.0 | 0.0 | 0.0 | 0.0 | 0.0 | 0.0 | 0.0 |
| hsa-miR-0548k | 0.0 | 0.0 | 0.0 | 0.0 | 0.0 | 0.0 | 0.0 | 0.0 | 0.0 |
| hsa-miR-0548l | 0.0 | 1.8 | 2.1 | 0.0 | 0.0 | 0.0 | 0.0 | 0.0 | 0.0 |
| hsa-miR-0548m | 0.0 | 0.0 | 0.0 | 0.0 | 0.0 | 0.0 | 0.0 | 0.0 | 0.0 |
| hsa-miR-0548p | 0.0 | 0.0 | 0.0 | 0.0 | 0.0 | 0.0 | 0.0 | 0.0 | 0.0 |
| hsa-miR-0548s | 3.1 | 0.0 | 0.0 | 0.0 | 0.0 | 0.0 | 0.0 | 0.0 | 0.0 |
| hsa-miR-0548t-5p | 0.0 | 0.0 | 0.0 | 0.0 | 0.0 | 0.0 | 0.0 | 0.0 | 0.0 |
| hsa-miR-0548w | 0.0 | 2.2 | 0.0 | 0.0 | 0.0 | 0.0 | 0.0 | 0.0 | 0.0 |
| hsa-miR-0551b-3p | 0.0 | 3.3 | 2.6 | 3.0 | 0.6 | 3.7 | 1.6 | 2.4 | 1.9 |
| hsa-miR-0551b-5p | 1.9 | 2.9 | 2.9 | 2.3 | 2.0 | 1.8 | 3.8 | 8.7 | 7.3 |
| hsa-miR-0552-3p | 0.0 | 1.2 | 2.6 | 0.0 | 0.0 | 0.0 | 0.0 | 0.7 | 1.9 |
| hsa-miR-0554 | 0.0 | 2.8 | 2.3 | 0.0 | 2.1 | 1.7 | 0.0 | 0.0 | 1.8 |
| hsa-miR-0555 | 1.2 | 0.0 | 3.4 | 2.8 | 0.0 | 0.0 | 0.0 | 1.3 | 0.0 |
| hsa-miR-0556-5p | 0.0 | 0.0 | 0.0 | 0.0 | 0.0 | 0.0 | 0.0 | 0.0 | 0.0 |
| hsa-miR-0559 | 0.0 | 0.0 | 0.0 | 0.0 | 0.0 | 0.0 | 0.0 | 0.0 | 0.0 |
| hsa-miR-0563 | 0.0 | 1.8 | 2.5 | 1.9 | 0.0 | 0.0 | 1.6 | 2.0 | 0.0 |
| hsa-miR-0567 | 0.0 | 0.0 | 0.0 | 0.0 | 0.0 | 0.0 | 0.0 | 0.0 | 0.0 |
| hsa-miR-0570-3p | 0.0 | 0.0 | 0.0 | 0.0 | 0.0 | 0.0 | 0.0 | 0.0 | 0.0 |
| hsa-miR-0571 | 3.0 | 0.0 | 2.4 | 0.0 | 2.7 | 0.0 | 0.0 | 0.0 | 1.3 |
| hsa-miR-0573 | 0.0 | 0.0 | 1.3 | 0.0 | 0.0 | 0.0 | 0.0 | 0.0 | 0.0 |
| hsa-miR-0582-3p | 2.7 | 0.0 | 0.0 | 0.0 | 0.0 | 0.0 | 0.0 | 0.0 | 0.0 |
| hsa-miR-0582-5p | 0.0 | 0.0 | 0.0 | 0.0 | 0.0 | 0.0 | 0.0 | 0.0 | 0.0 |
| hsa-miR-0586 | 0.0 | 0.0 | 0.0 | 0.0 | 2.6 | 0.0 | 0.0 | 0.0 | 0.0 |
| hsa-miR-0587 | 0.0 | 0.0 | 0.0 | 0.0 | 0.8 | 0.0 | 0.0 | 0.0 | 0.0 |
| hsa-miR-0588 | 0.0 | 1.8 | 2.5 | 0.0 | 0.0 | 0.0 | 0.0 | 0.0 | 0.0 |
| hsa-miR-0592 | 0.0 | 0.0 | 0.0 | 1.8 | 0.0 | 0.0 | 0.0 | 0.0 | 0.0 |
| hsa-miR-0597-3p | 0.0 | 0.0 | 0.0 | 0.0 | 0.0 | 0.0 | 0.0 | 0.0 | 0.0 |

TABLE 3-continued

| | | | | | | | | | |
|---|---|---|---|---|---|---|---|---|---|
| hsa-miR-0597-5p | 0.0 | 0.0 | 0.0 | 0.0 | 0.0 | 0.0 | 0.0 | 0.0 | 0.0 |
| hsa-miR-0598-3p | 2.3 | 1.2 | 1.5 | 1.7 | 0.0 | 1.1 | 0.0 | 0.0 | 1.3 |
| hsa-miR-0599 | 0.0 | 0.0 | 0.0 | 0.0 | 0.0 | 0.0 | 0.0 | 0.0 | 0.0 |
| hsa-miR-0600 | 0.0 | 0.0 | 0.0 | 0.0 | 0.0 | 0.0 | 0.0 | 0.0 | 0.0 |
| hsa-miR-0601 | 2.3 | 2.2 | 2.9 | 3.1 | 3.3 | 2.5 | 2.4 | 2.7 | 4.1 |
| hsa-miR-0616-3p | 0.0 | 0.0 | 0.0 | 0.0 | 2.0 | 1.1 | 1.4 | 1.2 | 0.0 |
| hsa-miR-0616-5p | 2.1 | 1.1 | 0.0 | 0.0 | 1.8 | 0.0 | 1.7 | 0.0 | 0.0 |
| hsa-miR-0619-3p | 0.0 | 1.0 | 0.0 | 0.0 | 0.9 | 0.0 | 0.0 | 0.0 | 0.0 |
| hsa-miR-0623 | 3.0 | 3.0 | 3.4 | 3.2 | 0.6 | 1.8 | 0.0 | 0.0 | 0.0 |
| hsa-miR-0624-3p | 0.0 | 0.0 | 0.0 | 0.0 | 2.9 | 2.8 | 0.0 | 0.0 | 0.0 |
| hsa-miR-0627-3p | 0.0 | 0.0 | 0.0 | 0.0 | 0.0 | 0.0 | 0.0 | 0.0 | 0.0 |
| hsa-miR-0629-5p | 0.0 | 0.0 | 0.0 | 2.5 | 2.3 | 0.0 | 2.6 | 2.1 | 0.0 |
| hsa-miR-0631 | 3.3 | 3.5 | 3.9 | 2.9 | 3.0 | 3.1 | 1.8 | 1.6 | 1.3 |
| hsa-miR-0633 | 0.0 | 0.0 | 1.7 | 0.0 | 0.0 | 0.0 | 0.0 | 0.0 | 0.0 |
| hsa-miR-0639 | 1.9 | 0.0 | 0.0 | 0.0 | 1.0 | 0.0 | 0.0 | 0.0 | 0.0 |
| hsa-miR-0640 | 1.8 | 1.3 | 0.0 | 0.0 | 0.0 | 0.0 | 0.0 | 0.0 | 0.0 |
| hsa-miR-0641 | 0.0 | 0.0 | 1.6 | 0.0 | 0.0 | 0.0 | 0.0 | 0.0 | 0.0 |
| hsa-miR-0643 | 0.0 | 1.8 | 2.3 | 0.0 | 0.6 | 0.0 | 0.0 | 0.0 | 0.0 |
| hsa-miR-0644a | 2.9 | 2.1 | 2.1 | 2.8 | 0.6 | 1.2 | 2.0 | 0.0 | 0.0 |
| hsa-miR-0646 | 0.0 | 0.0 | 0.0 | 0.0 | 3.2 | 0.0 | 0.0 | 0.0 | 0.0 |
| hsa-miR-0647 | 2.5 | 0.0 | 1.1 | 0.0 | 0.0 | 0.0 | 0.0 | 0.0 | 0.0 |
| hsa-miR-0653-3p | 0.0 | 0.0 | 0.0 | 0.0 | 0.0 | 0.0 | 0.0 | 0.0 | 0.0 |
| hsa-miR-0653-5p | 0.0 | 1.3 | 1.7 | 0.0 | 0.9 | 0.0 | 2.1 | 0.0 | 0.0 |
| hsa-miR-0655-3p | 0.0 | 0.0 | 0.0 | 0.0 | 1.4 | 0.0 | 0.0 | 0.0 | 0.0 |
| hsa-miR-0655-5p | 0.0 | 0.0 | 0.0 | 0.0 | 0.0 | 1.2 | 0.0 | 0.0 | 0.0 |
| hsa-miR-0656-3p | 0.0 | 1.5 | 1.3 | 0.0 | 0.0 | 0.0 | 0.0 | 0.0 | 1.8 |
| hsa-miR-0659-5p | 2.8 | 3.1 | 3.9 | 2.0 | 0.9 | 1.5 | 1.7 | 0.0 | 0.0 |
| hsa-miR-0660-5p | 1.5 | 0.0 | 1.8 | 0.0 | 0.0 | 0.0 | 0.0 | 0.0 | 0.0 |
| hsa-miR-0758-3p | 0.0 | 0.0 | 2.0 | 0.0 | 0.0 | 0.0 | 0.0 | 0.0 | 0.0 |
| hsa-miR-0759 | 0.0 | 0.0 | 0.0 | 0.0 | 0.0 | 0.0 | 0.0 | 0.0 | 0.0 |
| hsa-miR-0761 | 0.0 | 2.9 | 3.3 | 2.1 | 0.0 | 2.5 | 2.7 | 2.8 | 1.2 |
| hsa-miR-0769-5p | 1.2 | 2.0 | 2.9 | 2.9 | 1.7 | 2.3 | 2.5 | 1.8 | 2.8 |
| hsa-miR-0802 | 0.0 | 0.0 | 0.0 | 0.0 | 0.0 | 0.0 | 0.0 | 0.0 | 0.0 |
| hsa-miR-0875-5p | 0.0 | 0.0 | 0.0 | 0.0 | 0.0 | 0.0 | 0.0 | 0.0 | 0.0 |
| hsa-miR-0876-3p | 0.0 | 0.0 | 0.0 | 0.0 | 1.7 | 0.0 | 0.0 | 0.0 | 0.0 |
| hsa-miR-0890 | 0.0 | 0.0 | 0.0 | 0.0 | 0.0 | 0.0 | 0.0 | 1.7 | 0.0 |
| hsa-miR-0892c-3p | 1.9 | 2.5 | 3.5 | 2.2 | 0.0 | 2.7 | 1.9 | 1.0 | 0.0 |
| hsa-miR-0924 | 1.9 | 1.7 | 2.4 | 2.3 | 0.5 | 0.0 | 1.9 | 0.0 | 0.0 |
| hsa-miR-0934 | 0.0 | 0.0 | 0.0 | 0.0 | 0.0 | 0.0 | 0.0 | 0.0 | 0.0 |
| hsa-miR-0941 | 0.0 | 0.0 | 0.0 | 0.0 | 1.1 | 0.0 | 0.0 | 0.0 | 0.0 |
| hsa-miR-0944 | 0.0 | 0.0 | 0.0 | 0.0 | 2.6 | 0.0 | 0.0 | 0.0 | 2.1 |
| hsa-miR-1178-5p | 0.0 | 0.0 | 2.1 | 0.0 | 1.3 | 0.0 | 0.0 | 0.0 | 0.0 |
| hsa-miR-1179 | 0.0 | 0.0 | 0.0 | 0.0 | 0.0 | 0.0 | 0.0 | 0.0 | 0.0 |
| hsa-miR-1180-3p | 0.0 | 0.0 | 0.0 | 0.0 | 0.0 | 0.0 | 0.0 | 0.0 | 0.0 |
| hsa-miR-1180-5p | 2.8 | 1.9 | 0.0 | 0.0 | 0.0 | 0.0 | 0.0 | 0.2 | 1.3 |
| hsa-miR-1183 | 0.0 | 0.0 | 2.1 | 0.0 | 0.0 | 0.0 | 0.0 | 3.2 | 0.0 |
| hsa-miR-1185-5p | 0.0 | 0.0 | 1.9 | 0.0 | 0.0 | 0.0 | 0.0 | 0.0 | 0.0 |
| hsa-miR-1208 | 0.0 | 0.0 | 1.2 | 0.0 | 0.0 | 0.0 | 0.0 | 0.0 | 0.0 |
| hsa-miR-1226-5p | 3.7 | 3.5 | 2.4 | 2.6 | 0.0 | 2.6 | 0.0 | 3.9 | 2.7 |
| hsa-miR-1245b-3p | 0.0 | 0.0 | 0.0 | 0.0 | 0.0 | 0.0 | 0.0 | 0.0 | 0.0 |
| hsa-miR-1245b-5p | 0.0 | 0.0 | 1.4 | 0.0 | 0.0 | 0.0 | 0.0 | 0.0 | 0.0 |
| hsa-miR-1248 | 0.0 | 0.0 | 0.0 | 0.0 | 0.0 | 0.0 | 0.0 | 0.0 | 0.0 |
| hsa-miR-1251-5p | 0.0 | 0.0 | 0.0 | 0.0 | 0.0 | 0.0 | 0.0 | 0.0 | 0.0 |
| hsa-miR-1252-3p | 0.0 | 0.0 | 0.0 | 0.0 | 0.0 | 0.0 | 0.0 | 0.0 | 0.0 |
| hsa-miR-1253 | 0.0 | 0.0 | 0.0 | 0.0 | 0.4 | 0.0 | 0.0 | 0.0 | 0.0 |
| hsa-miR-1255b-5p | 1.7 | 1.8 | 2.3 | 0.0 | 0.0 | 0.0 | 0.0 | 0.0 | 0.0 |
| hsa-miR-1256 | 0.0 | 0.0 | 0.0 | 0.0 | 0.0 | 0.0 | 0.0 | 0.0 | 0.0 |
| hsa-miR-1257 | 0.0 | 0.0 | 0.0 | 0.0 | 0.0 | 0.0 | 0.0 | 0.0 | 2.3 |
| hsa-miR-1263 | 1.6 | 1.2 | 1.4 | 1.6 | 0.0 | 0.0 | 0.0 | 0.0 | 0.0 |
| hsa-miR-1264 | 1.4 | 0.0 | 1.5 | 0.0 | 0.0 | 0.0 | 0.0 | 0.0 | 0.0 |
| hsa-miR-1265 | 2.8 | 2.2 | 2.6 | 3.0 | 0.8 | 1.0 | 3.0 | 2.9 | 2.9 |
| hsa-miR-1269a | 0.0 | 0.0 | 0.0 | 0.0 | 0.0 | 1.0 | 0.0 | 0.0 | 0.0 |
| hsa-miR-1270 | 1.7 | 0.0 | 0.0 | 1.5 | 0.0 | 1.2 | 2.1 | 0.0 | 1.4 |
| hsa-miR-1272 | 0.0 | 0.0 | 0.0 | 0.0 | 0.0 | 0.0 | 0.0 | 0.0 | 0.0 |
| hsa-miR-1273a | 0.0 | 0.0 | 0.0 | 0.0 | 0.0 | 0.0 | 0.0 | 0.0 | 2.7 |
| hsa-miR-1273c | 2.8 | 1.5 | 2.6 | 0.0 | 0.0 | 0.0 | 0.0 | 0.0 | 1.3 |
| hsa-miR-1273d | 1.6 | 0.0 | 2.0 | 0.0 | 2.5 | 2.2 | 0.0 | 3.0 | 2.2 |
| hsa-miR-1277-5p | 0.0 | 0.0 | 0.0 | 0.0 | 0.0 | 0.0 | 0.0 | 0.0 | 0.0 |
| hsa-miR-1279 | 0.0 | 0.0 | 0.0 | 0.0 | 0.0 | 0.0 | 0.0 | 0.0 | 0.0 |
| hsa-miR-1282 | 1.8 | 1.3 | 0.0 | 0.0 | 0.0 | 0.0 | 0.0 | 0.0 | 0.0 |
| hsa-miR-1283 | 0.0 | 0.0 | 0.0 | 0.0 | 0.0 | 0.0 | 0.0 | 0.0 | 0.0 |
| hsa-miR-1285-3p | 2.1 | 0.0 | 1.9 | 2.8 | 3.2 | 3.1 | 1.6 | 2.7 | 3.9 |
| hsa-miR-1289 | 0.0 | 0.0 | 1.8 | 0.0 | 0.0 | 0.0 | 1.9 | 0.7 | 2.3 |
| hsa-miR-1290 | 0.0 | 1.8 | 0.0 | 0.0 | 0.0 | 0.0 | 0.0 | 0.0 | 0.0 |
| hsa-miR-1292-5p | 1.7 | 1.8 | 1.8 | 0.0 | 0.0 | 1.9 | 0.0 | 1.6 | 0.0 |
| hsa-miR-1294 | 0.0 | 0.0 | 2.0 | 2.1 | 0.0 | 0.0 | 0.0 | 0.0 | 0.0 |
| hsa-miR-1295a | 2.6 | 0.0 | 0.0 | 0.0 | 0.0 | 0.0 | 0.0 | 0.0 | 0.0 |
| hsa-miR-1295b-5p | 0.0 | 0.0 | 1.7 | 0.0 | 0.0 | 0.0 | 0.0 | 0.0 | 0.0 |
| hsa-miR-1302 | 0.0 | 0.0 | 0.0 | 0.0 | 0.0 | 0.0 | 0.0 | 0.0 | 0.0 |
| hsa-miR-1304-5p | 0.0 | 1.1 | 0.0 | 1.5 | 0.0 | 0.0 | 0.0 | 0.0 | 0.0 |

TABLE 3-continued

| | | | | | | | | | |
|---|---|---|---|---|---|---|---|---|---|
| hsa-miR-1305 | 0.0 | 0.0 | 0.0 | 0.0 | 0.0 | 0.0 | 0.0 | 0.0 | 0.0 |
| hsa-miR-1307-5p | 3.0 | 1.0 | 3.1 | 0.0 | 1.6 | 0.0 | 0.0 | 0.0 | 0.0 |
| hsa-miR-1321 | 1.7 | 1.7 | 2.8 | 3.2 | 0.0 | 2.4 | 0.0 | 3.3 | 1.4 |
| hsa-miR-1468-3p | 0.0 | 0.0 | 0.0 | 0.0 | 0.0 | 0.0 | 0.0 | 0.0 | 0.0 |
| hsa-miR-1537-3p | 0.0 | 0.0 | 1.3 | 0.0 | 0.0 | 0.0 | 0.0 | 0.0 | 0.0 |
| hsa-miR-1827 | 0.0 | 0.0 | 0.0 | 0.0 | 0.0 | 0.0 | 0.0 | 0.0 | 0.0 |
| hsa-miR-1911-5p | 1.3 | 2.1 | 1.9 | 0.0 | 0.0 | 0.0 | 0.0 | 1.9 | 1.9 |
| hsa-miR-1973 | 2.6 | 0.0 | 0.0 | 0.0 | 0.0 | 0.0 | 0.0 | 0.0 | 0.0 |
| hsa-miR-2052 | 0.0 | 0.0 | 0.0 | 0.0 | 0.0 | 0.0 | 0.0 | 0.0 | 0.0 |
| hsa-miR-2053 | 0.0 | 0.0 | 1.4 | 0.0 | 0.0 | 0.0 | 0.0 | 0.0 | 0.0 |
| hsa-miR-2054 | 0.0 | 0.0 | 0.0 | 0.0 | 0.0 | 0.0 | 0.0 | 0.0 | 0.0 |
| hsa-miR-2114-3p | 0.0 | 0.0 | 0.0 | 0.0 | 0.0 | 0.0 | 0.0 | 0.0 | 0.0 |
| hsa-miR-2114-5p | 0.0 | 0.0 | 2.6 | 0.0 | 1.1 | 0.0 | 0.0 | 0.0 | 0.0 |
| hsa-miR-2115-3p | 0.0 | 0.0 | 0.0 | 0.0 | 0.0 | 0.0 | 0.0 | 0.0 | 0.0 |
| hsa-miR-2115-5p | 0.0 | 0.0 | 1.4 | 0.0 | 0.0 | 0.0 | 0.0 | 0.0 | 0.0 |
| hsa-miR-2681-3p | 0.0 | 0.0 | 2.4 | 0.0 | 0.0 | 1.5 | 0.0 | 0.0 | 0.0 |
| hsa-miR-3065-5p | 2.6 | 3.6 | 2.1 | 1.8 | 1.0 | 2.0 | 0.0 | 0.0 | 0.0 |
| hsa-miR-3119 | 0.0 | 0.0 | 2.0 | 2.4 | 0.0 | 0.0 | 0.0 | 1.3 | 2.4 |
| hsa-miR-3120-3p | 1.0 | 2.6 | 2.9 | 2.6 | 0.0 | 1.7 | 2.9 | 1.7 | 1.9 |
| hsa-miR-3122 | 5.1 | 4.5 | 4.0 | 4.7 | 4.7 | 5.3 | 4.7 | 6.0 | 5.7 |
| hsa-miR-3123 | 0.0 | 0.0 | 1.9 | 0.0 | 0.0 | 0.0 | 0.0 | 0.0 | 0.0 |
| hsa-miR-3125 | 2.5 | 3.3 | 3.7 | 3.7 | 3.3 | 3.6 | 4.1 | 3.3 | 3.9 |
| hsa-miR-3127-3p | 5.6 | 5.6 | 6.0 | 5.4 | 5.1 | 5.0 | 6.3 | 5.8 | 6.1 |
| hsa-miR-3130-3p | 1.4 | 3.0 | 3.0 | 3.6 | 2.5 | 2.7 | 1.7 | 1.4 | 1.8 |
| hsa-miR-3130-5p | 5.3 | 5.0 | 5.4 | 5.1 | 4.7 | 4.9 | 4.6 | 5.0 | 4.8 |
| hsa-miR-3135a | 0.0 | 0.0 | 0.0 | 0.0 | 0.0 | 0.0 | 0.0 | 0.0 | 0.0 |
| hsa-miR-3140-5p | 0.0 | 0.0 | 0.0 | 0.0 | 0.0 | 0.0 | 0.0 | 0.0 | 0.0 |
| hsa-miR-3148 | 0.0 | 2.6 | 3.0 | 1.8 | 0.0 | 2.4 | 2.8 | 2.3 | 1.9 |
| hsa-miR-3149 | 3.5 | 3.9 | 4.1 | 4.0 | 3.2 | 2.7 | 3.8 | 3.1 | 3.6 |
| hsa-miR-3150a-3p | 5.9 | 5.7 | 5.6 | 5.4 | 5.6 | 5.0 | 5.5 | 5.7 | 5.7 |
| hsa-miR-3150b-5p | 5.6 | 5.5 | 5.9 | 5.3 | 5.2 | 4.9 | 6.0 | 5.6 | 5.8 |
| hsa-miR-3151-3p | 6.3 | 6.3 | 6.5 | 6.1 | 6.0 | 5.9 | 5.6 | 5.6 | 5.5 |
| hsa-miR-3151-5p | 6.0 | 6.1 | 6.2 | 6.5 | 5.9 | 6.1 | 6.9 | 7.7 | 7.3 |
| hsa-miR-3160-5p | 4.4 | 4.2 | 4.5 | 4.1 | 3.5 | 3.8 | 4.6 | 3.7 | 3.9 |
| hsa-miR-3181 | 0.0 | 2.7 | 0.0 | 0.0 | 3.0 | 0.0 | 0.0 | 0.0 | 0.0 |
| hsa-miR-3182 | 0.0 | 0.0 | 0.0 | 0.0 | 0.0 | 0.0 | 0.0 | 0.0 | 0.0 |
| hsa-miR-3183 | 0.0 | 1.1 | 0.0 | 0.0 | 0.0 | 0.0 | 0.0 | 0.0 | 0.0 |
| hsa-miR-3192-5p | 3.1 | 1.9 | 2.7 | 3.4 | 2.7 | 2.6 | 2.3 | 2.7 | 3.2 |
| hsa-miR-3194-3p | 0.0 | 0.0 | 2.2 | 0.0 | 0.0 | 0.0 | 0.0 | 0.0 | 0.0 |
| hsa-miR-3199 | 0.0 | 2.7 | 2.5 | 2.6 | 0.0 | 2.2 | 2.2 | 4.4 | 3.2 |
| hsa-miR-3591-5p | 0.0 | 1.4 | 1.8 | 1.9 | 0.5 | 0.0 | 2.0 | 0.3 | 0.0 |
| hsa-miR-3606-3p | 0.0 | 0.0 | 0.0 | 0.0 | 1.2 | 0.0 | 0.0 | 0.0 | 0.0 |
| hsa-miR-3607-3p | 0.0 | 0.0 | 0.0 | 0.0 | 0.0 | 0.0 | 0.0 | 0.0 | 0.0 |
| hsa-miR-3611 | 0.0 | 0.0 | 0.0 | 0.0 | 0.0 | 0.0 | 0.0 | 0.0 | 0.0 |
| hsa-miR-3613-3p | 2.9 | 3.0 | 2.4 | 1.6 | 0.0 | 0.0 | 0.0 | 0.0 | 2.2 |
| hsa-miR-3614-3p | 0.0 | 2.1 | 0.0 | 0.0 | 0.0 | 1.0 | 0.0 | 0.0 | 1.1 |
| hsa-miR-3617-5p | 0.0 | 0.0 | 0.0 | 0.0 | 0.0 | 0.0 | 0.0 | 0.0 | 0.0 |
| hsa-miR-3653-3p | 0.0 | 1.3 | 2.5 | 1.9 | 0.7 | 3.0 | 2.6 | 0.0 | 2.8 |
| hsa-miR-3660 | 1.8 | 2.3 | 2.8 | 2.2 | 2.6 | 2.6 | 2.7 | 3.0 | 1.8 |
| hsa-miR-3661 | 2.5 | 2.3 | 3.1 | 2.5 | 2.4 | 2.7 | 2.9 | 3.9 | 2.4 |
| hsa-miR-3664-5p | 0.0 | 0.0 | 2.3 | 0.0 | 0.0 | 0.0 | 0.0 | 0.0 | 0.0 |
| hsa-miR-3670 | 1.7 | 2.2 | 1.3 | 0.0 | 0.0 | 0.0 | 0.0 | 0.0 | 0.0 |
| hsa-miR-3671 | 0.0 | 0.0 | 0.0 | 0.0 | 0.0 | 0.0 | 0.0 | 0.0 | 0.0 |
| hsa-miR-3672 | 0.0 | 0.0 | 0.0 | 0.0 | 0.0 | 0.0 | 0.0 | 0.0 | 0.0 |
| hsa-miR-3674 | 0.0 | 0.0 | 0.0 | 0.0 | 0.0 | 0.0 | 0.0 | 0.0 | 0.0 |
| hsa-miR-3675-5p | 3.0 | 0.0 | 1.9 | 2.9 | 0.0 | 1.6 | 0.0 | 1.4 | 1.6 |
| hsa-miR-3680-5p | 3.0 | 2.8 | 0.0 | 2.4 | 0.0 | 2.2 | 2.6 | 1.8 | 2.2 |
| hsa-miR-3681-5p | 0.0 | 0.0 | 0.0 | 0.0 | 0.0 | 0.0 | 0.0 | 0.0 | 0.0 |
| hsa-miR-3683 | 0.0 | 0.0 | 0.0 | 0.0 | 0.0 | 0.0 | 0.0 | 0.0 | 0.0 |
| hsa-miR-3689a-5p, hsa-miR-3689b-5p, hsa-miR-3689e | 0.0 | 1.5 | 0.0 | 0.0 | 0.0 | 0.0 | 0.0 | 0.0 | 0.0 |
| hsa-miR-3907 | 2.3 | 0.0 | 0.0 | 0.0 | 0.0 | 0.0 | 0.0 | 0.7 | 0.0 |
| hsa-miR-3909 | 2.5 | 3.0 | 2.6 | 0.0 | 0.0 | 0.0 | 0.0 | 0.0 | 1.4 |
| hsa-miR-3910 | 3.2 | 2.2 | 2.4 | 2.2 | 0.0 | 0.0 | 1.6 | 0.0 | 0.0 |
| hsa-miR-3912-5p | 0.0 | 1.2 | 1.4 | 0.0 | 0.0 | 0.0 | 0.0 | 0.0 | 0.0 |
| hsa-miR-3913-5p | 0.0 | 2.6 | 3.9 | 2.9 | 0.0 | 2.1 | 2.4 | 0.0 | 1.1 |
| hsa-miR-3915 | 0.0 | 0.0 | 0.0 | 1.6 | 0.0 | 0.0 | 0.0 | 0.8 | 0.0 |
| hsa-miR-3919 | 1.1 | 2.1 | 2.7 | 2.7 | 0.0 | 2.1 | 0.0 | 0.0 | 1.9 |
| hsa-miR-3920 | 0.0 | 0.0 | 2.1 | 0.0 | 0.7 | 0.0 | 0.0 | 0.0 | 0.0 |
| hsa-miR-3924 | 0.0 | 0.0 | 0.0 | 0.0 | 0.0 | 0.0 | 0.0 | 0.0 | 0.0 |
| hsa-miR-3925-3p | 1.8 | 0.0 | 0.0 | 1.6 | 0.0 | 0.0 | 0.0 | 0.5 | 0.0 |
| hsa-miR-3926 | 1.2 | 0.0 | 1.5 | 2.0 | 0.0 | 0.0 | 0.0 | 0.7 | 2.0 |
| hsa-miR-3938 | 0.0 | 0.0 | 0.0 | 0.0 | 0.0 | 0.0 | 0.0 | 0.0 | 0.0 |
| hsa-miR-3939 | 1.7 | 0.0 | 0.0 | 0.0 | 0.0 | 0.0 | 0.0 | 0.0 | 0.0 |
| hsa-miR-3941 | 0.0 | 0.0 | 0.0 | 0.0 | 0.0 | 0.0 | 0.0 | 0.0 | 2.3 |
| hsa-miR-3942-3p | 0.0 | 0.0 | 1.2 | 0.0 | 0.0 | 0.0 | 0.0 | 0.0 | 0.0 |
| hsa-miR-3942-5p | 2.1 | 0.0 | 0.0 | 0.0 | 0.0 | 0.0 | 0.0 | 0.0 | 0.0 |
| hsa-miR-3974 | 0.0 | 0.0 | 0.0 | 0.0 | 0.0 | 0.0 | 0.0 | 0.0 | 0.0 |
| hsa-miR-3977 | 0.0 | 2.2 | 3.6 | 0.0 | 2.7 | 2.0 | 1.5 | 0.5 | 0.0 |

TABLE 3-continued

| | | | | | | | | | |
|---|---|---|---|---|---|---|---|---|---|
| hsa-miR-3978 | 0.0 | 1.2 | 2.7 | 0.0 | 0.0 | 0.0 | 1.6 | 3.7 | 1.7 |
| hsa-miR-4263 | 0.0 | 0.0 | 1.1 | 0.0 | 0.0 | 0.0 | 0.0 | 0.0 | 0.0 |
| hsa-miR-4267 | 3.8 | 3.6 | 3.4 | 3.3 | 3.1 | 2.6 | 2.9 | 3.3 | 3.2 |
| hsa-miR-4285 | 0.0 | 1.5 | 0.0 | 0.0 | 0.0 | 1.4 | 0.0 | 0.6 | 0.0 |
| hsa-miR-4289 | 2.2 | 2.2 | 2.7 | 2.3 | 2.4 | 0.0 | 0.0 | 0.0 | 2.1 |
| hsa-miR-4293 | 0.0 | 1.6 | 1.9 | 0.0 | 0.0 | 1.4 | 0.0 | 0.0 | 0.0 |
| hsa-miR-4309 | 1.5 | 0.0 | 0.0 | 0.0 | 0.0 | 0.0 | 0.0 | 0.0 | 0.0 |
| hsa-miR-4311 | 2.2 | 2.0 | 2.3 | 3.1 | 3.4 | 3.1 | 2.2 | 3.0 | 2.6 |
| hsa-miR-4315 | 0.0 | 0.0 | 1.9 | 1.5 | 0.0 | 0.0 | 0.0 | 0.1 | 0.0 |
| hsa-miR-4321 | 2.5 | 3.0 | 1.1 | 2.6 | 2.8 | 2.9 | 2.0 | 4.2 | 2.7 |
| hsa-miR-4418 | 0.0 | 0.0 | 1.4 | 0.0 | 0.0 | 0.0 | 0.0 | 0.0 | 0.0 |
| hsa-miR-4422 | 0.0 | 0.0 | 0.0 | 0.0 | 0.0 | 0.0 | 0.0 | 0.0 | 0.0 |
| hsa-miR-4423-3p | 1.3 | 1.5 | 2.0 | 2.0 | 2.6 | 0.0 | 2.3 | 0.1 | 1.6 |
| hsa-miR-4424 | 0.0 | 0.0 | 0.0 | 0.0 | 0.0 | 0.0 | 0.0 | 0.0 | 0.0 |
| hsa-miR-4427 | 0.0 | 0.0 | 0.0 | 0.0 | 0.0 | 0.0 | 0.0 | 0.0 | 0.0 |
| hsa-miR-4431 | 2.9 | 0.0 | 1.3 | 2.9 | 2.1 | 0.0 | 2.5 | 2.9 | 3.4 |
| hsa-miR-4432 | 0.0 | 0.0 | 0.0 | 0.0 | 0.0 | 0.0 | 0.0 | 0.0 | 0.0 |
| hsa-miR-4435 | 3.7 | 2.2 | 2.8 | 4.8 | 3.8 | 5.6 | 3.8 | 4.8 | 5.8 |
| hsa-miR-4439 | 1.8 | 3.4 | 3.0 | 2.9 | 2.0 | 3.3 | 3.4 | 1.5 | 2.8 |
| hsa-miR-4445-5p | 0.0 | 0.0 | 0.0 | 0.0 | 0.0 | 0.0 | 0.0 | 0.0 | 0.0 |
| hsa-miR-4452 | 0.0 | 0.0 | 0.0 | 0.0 | 0.0 | 0.0 | 0.0 | 0.0 | 0.0 |
| hsa-miR-4457 | 0.0 | 0.0 | 0.0 | 0.0 | 0.0 | 0.0 | 0.0 | 0.0 | 0.0 |
| hsa-miR-4458 | 2.8 | 2.0 | 3.8 | 2.5 | 1.3 | 2.6 | 2.1 | 3.6 | 2.1 |
| hsa-miR-4461 | 0.0 | 0.0 | 2.5 | 2.5 | 0.0 | 2.0 | 0.0 | 2.2 | 0.0 |
| hsa-miR-4464 | 0.0 | 0.0 | 1.3 | 0.0 | 0.0 | 0.0 | 0.0 | 0.0 | 0.0 |
| hsa-miR-4468 | 0.0 | 0.0 | 1.3 | 0.0 | 0.0 | 0.0 | 0.0 | 0.0 | 0.0 |
| hsa-miR-4469 | 0.0 | 0.0 | 1.3 | 0.0 | 0.0 | 0.0 | 0.0 | 0.0 | 0.0 |
| hsa-miR-4470 | 1.9 | 0.0 | 1.3 | 0.0 | 0.7 | 1.3 | 2.8 | 6.0 | 4.2 |
| hsa-miR-4471 | 0.0 | 1.8 | 2.7 | 0.0 | 1.6 | 1.4 | 3.0 | 0.0 | 2.0 |
| hsa-miR-4475 | 2.8 | 0.0 | 0.0 | 0.0 | 0.0 | 0.0 | 0.0 | 0.0 | 1.8 |
| hsa-miR-4480 | 0.0 | 0.0 | 0.0 | 0.0 | 0.0 | 0.0 | 0.0 | 0.0 | 0.0 |
| hsa-miR-4485-3p | 0.0 | 0.0 | 0.0 | 0.0 | 0.0 | 0.0 | 0.0 | 3.8 | 0.0 |
| hsa-miR-4490 | 0.0 | 0.0 | 2.3 | 0.0 | 0.0 | 0.0 | 0.0 | 0.0 | 0.0 |
| hsa-miR-4493 | 0.0 | 0.0 | 0.0 | 0.0 | 0.0 | 0.0 | 0.0 | 0.0 | 0.0 |
| hsa-miR-4500 | 0.0 | 0.0 | 0.0 | 0.0 | 0.0 | 0.0 | 0.0 | 0.0 | 0.0 |
| hsa-miR-4503 | 0.0 | 0.0 | 0.0 | 0.0 | 0.0 | 0.0 | 0.0 | 0.0 | 0.0 |
| hsa-miR-4504 | 0.0 | 0.0 | 0.0 | 0.0 | 0.0 | 0.0 | 0.0 | 0.0 | 0.0 |
| hsa-miR-4509 | 0.0 | 0.0 | 0.0 | 0.0 | 0.0 | 0.0 | 0.0 | 0.0 | 0.0 |
| hsa-miR-4510 | 1.8 | 0.0 | 0.0 | 0.0 | 0.0 | 1.4 | 1.8 | 0.2 | 2.1 |
| hsa-miR-4511 | 1.3 | 2.2 | 0.0 | 2.5 | 0.0 | 1.6 | 1.8 | 1.4 | 1.2 |
| hsa-miR-4512 | 0.0 | 1.2 | 3.1 | 0.0 | 0.8 | 0.0 | 0.0 | 0.0 | 0.0 |
| hsa-miR-4515 | 3.7 | 4.2 | 2.5 | 3.8 | 1.4 | 3.9 | 2.2 | 2.5 | 2.4 |
| hsa-miR-4517 | 0.0 | 0.0 | 0.0 | 0.0 | 0.0 | 0.0 | 0.0 | 0.0 | 0.0 |
| hsa-miR-4519 | 0.0 | 0.0 | 1.9 | 0.0 | 0.7 | 1.9 | 1.4 | 1.6 | 0.0 |
| hsa-miR-4520-2-3p | 0.0 | 0.0 | 2.4 | 0.0 | 0.0 | 0.0 | 0.0 | 0.0 | 0.0 |
| hsa-miR-4522 | 0.0 | 1.8 | 2.8 | 0.0 | 1.8 | 1.2 | 0.0 | 1.3 | 0.0 |
| hsa-miR-4524a-3p | 0.0 | 1.3 | 0.0 | 0.0 | 0.0 | 0.0 | 1.6 | 0.0 | 0.0 |
| hsa-miR-4536-3p | 0.0 | 0.0 | 0.0 | 0.0 | 0.0 | 0.0 | 0.0 | 0.0 | 0.0 |
| hsa-miR-4537 | 0.0 | 0.0 | 1.4 | 0.0 | 2.8 | 1.6 | 0.0 | 0.0 | 0.0 |
| hsa-miR-4633-3p | 0.0 | 0.0 | 0.0 | 0.0 | 0.0 | 0.0 | 0.0 | 0.0 | 0.0 |
| hsa-miR-4637 | 0.0 | 0.0 | 0.0 | 0.0 | 0.0 | 0.0 | 0.0 | 0.0 | 0.0 |
| hsa-miR-4643 | 0.0 | 1.8 | 0.0 | 0.0 | 3.6 | 1.1 | 0.0 | 0.0 | 0.0 |
| hsa-miR-4650-3p | 3.1 | 0.0 | 0.0 | 0.0 | 1.8 | 1.2 | 2.2 | 0.0 | 1.9 |
| hsa-miR-4653-3p | 0.0 | 0.0 | 0.0 | 0.0 | 0.0 | 2.0 | 2.0 | 0.0 | 2.1 |
| hsa-miR-4659a-3p | 0.0 | 1.3 | 2.5 | 0.0 | 0.0 | 0.0 | 0.0 | 0.0 | 0.0 |
| hsa-miR-4659a-5p | 2.6 | 0.0 | 1.5 | 0.0 | 0.7 | 1.0 | 2.0 | 0.3 | 0.0 |
| hsa-miR-4659b-5p | 0.0 | 0.0 | 0.0 | 0.0 | 0.0 | 0.0 | 0.0 | 0.0 | 0.0 |
| hsa-miR-4661-3p | 0.0 | 2.3 | 2.4 | 2.8 | 1.6 | 0.0 | 2.2 | 0.0 | 2.0 |
| hsa-miR-4662a-3p | 0.0 | 0.0 | 0.0 | 0.0 | 0.0 | 0.0 | 0.0 | 0.0 | 0.0 |
| hsa-miR-4662a-5p | 0.0 | 0.0 | 0.0 | 0.0 | 0.0 | 0.0 | 0.0 | 0.0 | 0.0 |
| hsa-miR-4666a-3p | 0.0 | 0.0 | 0.0 | 0.0 | 0.0 | 0.0 | 0.0 | 0.0 | 0.0 |
| hsa-miR-4666b | 0.0 | 0.0 | 1.7 | 0.0 | 0.0 | 0.0 | 0.0 | 0.0 | 0.0 |
| hsa-miR-4668-3p | 0.0 | 0.0 | 0.0 | 0.0 | 0.0 | 0.0 | 0.0 | 0.0 | 0.0 |
| hsa-miR-4670-3p | 0.0 | 0.0 | 1.8 | 0.0 | 0.0 | 0.0 | 0.0 | 0.0 | 1.2 |
| hsa-miR-4670-5p | 0.0 | 2.0 | 0.0 | 0.0 | 0.0 | 0.0 | 0.0 | 0.0 | 0.0 |
| hsa-miR-4671-3p | 0.0 | 0.0 | 0.0 | 0.0 | 0.0 | 0.0 | 0.0 | 1.1 | 0.0 |
| hsa-miR-4679 | 0.0 | 0.0 | 0.0 | 0.0 | 0.0 | 0.0 | 0.0 | 0.0 | 0.0 |
| hsa-miR-4683 | 0.0 | 0.0 | 2.1 | 0.0 | 0.0 | 0.0 | 0.0 | 0.0 | 0.0 |
| hsa-miR-4699-3p | 1.4 | 0.0 | 0.0 | 0.0 | 0.0 | 0.0 | 0.0 | 0.0 | 0.0 |
| hsa-miR-4699-5p | 0.0 | 0.0 | 0.0 | 0.0 | 0.0 | 0.0 | 0.0 | 0.0 | 0.0 |
| hsa-miR-4704-5p | 0.0 | 0.0 | 0.0 | 0.0 | 0.0 | 1.3 | 0.0 | 0.0 | 0.0 |
| hsa-miR-4705 | 0.0 | 0.0 | 1.1 | 0.0 | 0.0 | 0.0 | 0.0 | 0.0 | 0.0 |
| hsa-miR-4714-3p | 0.0 | 0.0 | 0.0 | 0.0 | 0.0 | 0.0 | 0.0 | 0.0 | 0.0 |
| hsa-miR-4715-3p | 0.0 | 0.0 | 0.0 | 0.0 | 0.0 | 0.0 | 0.0 | 0.0 | 0.0 |
| hsa-miR-4715-5p | 3.0 | 1.9 | 2.7 | 1.5 | 0.0 | 0.0 | 0.0 | 0.7 | 0.0 |
| hsa-miR-4719 | 1.7 | 1.3 | 2.6 | 0.0 | 0.0 | 0.0 | 0.0 | 0.0 | 0.0 |
| hsa-miR-4720-3p | 0.0 | 0.0 | 0.0 | 0.0 | 0.0 | 0.0 | 0.0 | 0.0 | 0.0 |
| hsa-miR-4724-5p | 1.9 | 1.5 | 3.0 | 2.5 | 0.7 | 2.5 | 0.0 | 0.7 | 1.1 |
| hsa-miR-4727-5p | 0.0 | 0.0 | 0.0 | 0.0 | 0.9 | 0.0 | 0.0 | 0.0 | 0.0 |
| hsa-miR-4735-3p | 0.0 | 0.0 | 0.0 | 0.0 | 0.0 | 0.0 | 0.0 | 0.0 | 0.0 |

TABLE 3-continued

| | | | | | | | | | |
|---|---|---|---|---|---|---|---|---|---|
| hsa-miR-4737 | 0.0 | 2.7 | 3.3 | 3.2 | 0.8 | 2.5 | 2.7 | 3.5 | 3.3 |
| hsa-miR-4743-3p | 0.0 | 2.0 | 2.7 | 3.2 | 0.0 | 2.3 | 2.1 | 0.9 | 2.7 |
| hsa-miR-4744 | 0.0 | 0.0 | 0.0 | 0.0 | 0.0 | 0.0 | 0.0 | 0.0 | 0.0 |
| hsa-miR-4753-3p | 2.5 | 3.1 | 2.9 | 2.7 | 0.5 | 2.8 | 2.6 | 2.1 | 2.6 |
| hsa-miR-4753-5p | 0.0 | 2.1 | 2.0 | 2.3 | 2.5 | 1.9 | 3.8 | 3.3 | 3.7 |
| hsa-miR-4757-5p | 0.0 | 0.0 | 3.2 | 0.0 | 0.0 | 0.0 | 0.0 | 0.0 | 0.0 |
| hsa-miR-4759 | 2.5 | 0.0 | 1.4 | 0.0 | 0.0 | 0.0 | 0.0 | 0.0 | 0.0 |
| hsa-miR-4760-5p | 0.0 | 0.0 | 0.0 | 0.0 | 0.0 | 0.0 | 0.0 | 0.0 | 0.0 |
| hsa-miR-4761-5p | 0.0 | 2.5 | 3.7 | 0.0 | 0.0 | 0.0 | 0.0 | 0.0 | 0.0 |
| hsa-miR-4762-5p | 2.2 | 2.7 | 0.0 | 2.5 | 2.2 | 2.0 | 1.9 | 0.0 | 1.1 |
| hsa-miR-4764-5p | 0.0 | 0.0 | 1.5 | 0.0 | 0.0 | 0.0 | 0.0 | 0.0 | 0.0 |
| hsa-miR-4768-5p | 2.2 | 3.4 | 3.5 | 2.8 | 1.5 | 3.1 | 2.0 | 0.0 | 1.1 |
| hsa-miR-4770 | 0.0 | 1.4 | 2.5 | 0.0 | 0.7 | 0.0 | 0.0 | 0.0 | 1.5 |
| hsa-miR-4772-3p | 0.0 | 0.0 | 0.0 | 0.0 | 0.0 | 0.0 | 0.0 | 0.0 | 0.0 |
| hsa-miR-4774-3p | 0.0 | 1.6 | 3.4 | 0.0 | 0.0 | 0.0 | 0.0 | 0.0 | 0.0 |
| hsa-miR-4774-5p | 0.0 | 0.0 | 0.0 | 0.0 | 0.0 | 0.0 | 0.0 | 0.0 | 0.0 |
| hsa-miR-4777-5p | 0.0 | 0.0 | 0.0 | 0.0 | 0.0 | 0.0 | 0.0 | 0.0 | 0.0 |
| hsa-miR-4778-3p | 0.0 | 0.0 | 0.0 | 0.0 | 0.0 | 0.0 | 0.0 | 0.0 | 0.0 |
| hsa-miR-4778-5p | 0.0 | 0.0 | 0.0 | 0.0 | 0.6 | 2.4 | 0.0 | 0.0 | 0.0 |
| hsa-miR-4779 | 1.3 | 0.0 | 2.0 | 0.0 | 0.0 | 0.0 | 0.0 | 0.0 | 0.0 |
| hsa-miR-4781-5p | 2.1 | 0.0 | 0.0 | 0.0 | 0.0 | 0.0 | 0.0 | 0.0 | 0.0 |
| hsa-miR-4782-5p | 0.0 | 0.0 | 0.0 | 0.0 | 0.0 | 0.0 | 0.0 | 0.0 | 0.0 |
| hsa-miR-4785 | 4.4 | 4.1 | 3.0 | 1.9 | 0.0 | 1.1 | 2.2 | 2.1 | 1.3 |
| hsa-miR-4789-3p | 0.0 | 0.0 | 0.0 | 0.0 | 0.0 | 0.0 | 0.0 | 0.0 | 0.0 |
| hsa-miR-4789-5p | 0.0 | 0.0 | 0.0 | 0.0 | 0.0 | 0.0 | 0.0 | 0.0 | 0.0 |
| hsa-miR-4791 | 0.0 | 0.0 | 0.0 | 0.0 | 0.0 | 0.0 | 0.0 | 0.0 | 0.0 |
| hsa-miR-4792 | 0.0 | 0.0 | 2.0 | 0.0 | 0.0 | 0.0 | 0.0 | 2.1 | 3.4 |
| hsa-miR-4795-3p | 0.0 | 0.0 | 2.8 | 0.0 | 0.0 | 0.0 | 0.0 | 0.0 | 0.0 |
| hsa-miR-4797-5p | 0.0 | 1.1 | 0.0 | 0.0 | 0.0 | 0.0 | 0.0 | 0.0 | 0.0 |
| hsa-miR-4798-5p | 0.0 | 0.0 | 0.0 | 0.0 | 0.0 | 0.0 | 0.0 | 0.0 | 0.0 |
| hsa-miR-4801 | 0.0 | 0.0 | 2.1 | 2.0 | 0.0 | 2.3 | 3.1 | 0.1 | 3.7 |
| hsa-miR-4803 | 0.0 | 0.0 | 2.7 | 0.0 | 0.8 | 0.0 | 0.0 | 0.0 | 0.0 |
| hsa-miR-4804-5p | 1.1 | 1.5 | 4.0 | 0.0 | 0.0 | 0.0 | 1.7 | 0.9 | 1.4 |
| hsa-miR-4999-3p | 2.0 | 1.5 | 3.3 | 2.3 | 2.7 | 1.7 | 2.6 | 2.3 | 2.9 |
| hsa-miR-5000-3p | 0.0 | 1.7 | 2.1 | 1.9 | 0.0 | 1.5 | 0.0 | 2.0 | 2.3 |
| hsa-miR-5004-3p | 2.9 | 2.9 | 2.7 | 2.8 | 2.3 | 2.4 | 2.1 | 3.1 | 2.3 |
| hsa-miR-5007-3p | 0.0 | 1.0 | 0.0 | 0.0 | 0.0 | 1.8 | 0.0 | 0.0 | 0.0 |
| hsa-miR-5009-5p | 0.0 | 0.0 | 0.0 | 0.0 | 0.0 | 0.0 | 0.0 | 0.0 | 0.0 |
| hsa-miR-5047 | 0.0 | 0.0 | 2.3 | 0.0 | 0.0 | 0.0 | 0.0 | 0.0 | 0.0 |
| hsa-miR-5089-5p | 0.0 | 0.0 | 2.1 | 0.0 | 0.0 | 0.0 | 0.0 | 0.0 | 0.0 |
| hsa-miR-5092 | 0.0 | 2.3 | 2.9 | 0.0 | 0.0 | 0.0 | 0.0 | 0.0 | 0.0 |
| hsa-miR-5579-5p | 0.0 | 0.0 | 1.7 | 0.0 | 0.0 | 0.0 | 0.0 | 0.0 | 0.0 |
| hsa-miR-5582-5p | 0.0 | 0.0 | 1.7 | 0.0 | 0.0 | 0.0 | 0.0 | 0.0 | 0.0 |
| hsa-miR-5584-5p | 0.0 | 0.0 | 0.0 | 0.0 | 0.0 | 0.0 | 0.0 | 1.6 | 1.7 |
| hsa-miR-5585-5p | 0.0 | 0.0 | 1.2 | 0.0 | 0.0 | 0.0 | 0.0 | 0.0 | 0.0 |
| hsa-miR-5586-3p | 0.0 | 0.0 | 0.0 | 0.0 | 0.0 | 0.0 | 0.0 | 0.4 | 0.0 |
| hsa-miR-5586-5p | 0.0 | 0.0 | 1.6 | 0.0 | 0.0 | 0.0 | 0.0 | 0.0 | 0.0 |
| hsa-miR-5587-5p | 3.9 | 1.9 | 0.0 | 1.5 | 0.0 | 0.0 | 0.0 | 1.8 | 2.6 |
| hsa-miR-5588-5p | 1.8 | 2.8 | 2.3 | 0.0 | 0.0 | 1.8 | 1.9 | 1.6 | 1.9 |
| hsa-miR-5590-3p | 0.0 | 0.0 | 0.0 | 0.0 | 0.0 | 0.0 | 0.0 | 0.0 | 0.0 |
| hsa-miR-5590-5p | 0.0 | 0.0 | 0.0 | 0.0 | 0.0 | 0.0 | 0.0 | 0.0 | 0.0 |
| hsa-miR-5684 | 0.0 | 1.8 | 2.3 | 1.9 | 0.0 | 2.3 | 1.8 | 0.3 | 1.9 |
| hsa-miR-5691 | 0.0 | 0.0 | 0.0 | 0.0 | 0.0 | 0.0 | 0.0 | 0.0 | 0.0 |
| hsa-miR-5692b | 0.0 | 0.0 | 0.0 | 0.0 | 0.0 | 0.0 | 0.0 | 0.0 | 0.0 |
| hsa-miR-5697 | 0.0 | 0.0 | 0.0 | 0.0 | 0.0 | 0.0 | 0.0 | 0.0 | 0.0 |
| hsa-miR-5707 | 0.0 | 0.0 | 2.4 | 2.3 | 0.0 | 0.0 | 0.0 | 0.0 | 1.3 |
| hsa-miR-6070 | 2.0 | 1.1 | 0.0 | 0.0 | 0.7 | 0.0 | 0.0 | 0.0 | 0.0 |
| hsa-miR-6071 | 3.6 | 2.2 | 1.9 | 0.0 | 4.2 | 2.6 | 0.0 | 1.5 | 0.0 |
| hsa-miR-6074 | 0.0 | 1.5 | 1.6 | 1.7 | 0.0 | 0.0 | 3.3 | 2.4 | 3.9 |
| hsa-miR-6078 | 0.0 | 0.0 | 1.4 | 0.0 | 0.0 | 0.0 | 0.0 | 0.0 | 0.0 |
| hsa-miR-6080 | 0.0 | 2.8 | 1.2 | 0.0 | 0.0 | 3.1 | 2.1 | 4.4 | 3.4 |
| hsa-miR-6084 | 1.0 | 2.8 | 1.8 | 0.0 | 2.7 | 2.4 | 0.0 | 2.5 | 1.5 |
| hsa-miR-6129 | 0.0 | 3.1 | 3.5 | 1.7 | 0.0 | 3.0 | 2.5 | 3.0 | 2.4 |
| hsa-miR-6130 | 0.0 | 2.4 | 0.0 | 0.0 | 0.0 | 2.3 | 2.3 | 3.3 | 1.2 |
| hsa-miR-6501-3p | 0.0 | 3.1 | 3.2 | 0.0 | 0.0 | 1.9 | 1.8 | 4.0 | 1.1 |
| hsa-miR-6502-3p | 0.0 | 0.0 | 0.0 | 0.0 | 0.0 | 0.0 | 0.0 | 0.0 | 0.0 |
| hsa-miR-6502-5p | 1.1 | 2.7 | 3.4 | 1.9 | 0.0 | 0.0 | 1.4 | 0.2 | 0.0 |
| hsa-miR-6506-3p | 0.0 | 0.0 | 2.8 | 0.0 | 0.0 | 0.0 | 0.0 | 0.0 | 0.0 |
| hsa-miR-6516-3p | 0.0 | 0.0 | 0.0 | 0.0 | 0.0 | 0.0 | 0.0 | 0.0 | 0.0 |
| hsa-miR-6715a-3p | 1.2 | 2.2 | 3.2 | 2.7 | 0.5 | 2.2 | 2.1 | 0.2 | 0.0 |
| hsa-miR-6715b-3p | 0.0 | 0.0 | 1.7 | 0.0 | 0.0 | 0.0 | 0.0 | 0.0 | 0.0 |
| hsa-miR-6719-3p | 0.0 | 0.0 | 1.7 | 0.0 | 0.0 | 0.0 | 0.0 | 0.0 | 0.0 |
| hsa-miR-6750-5p | 0.0 | 2.3 | 3.0 | 2.2 | 2.2 | 3.2 | 2.4 | 5.3 | 3.9 |
| hsa-miR-6755-5p | 0.0 | 0.0 | 0.0 | 0.0 | 0.0 | 0.0 | 0.0 | 0.0 | 0.0 |
| hsa-miR-6767-3p | 2.2 | 2.8 | 2.9 | 2.7 | 0.0 | 2.9 | 1.7 | 0.3 | 0.0 |
| hsa-miR-6773-5p | 0.0 | 0.0 | 2.4 | 0.0 | 0.0 | 1.8 | 0.0 | 0.0 | 0.0 |
| hsa-miR-6806-3p | 0.0 | 0.0 | 0.0 | 0.0 | 0.0 | 0.0 | 0.0 | 0.0 | 0.0 |
| hsa-miR-6808-3p | 2.0 | 0.0 | 2.8 | 0.0 | 0.0 | 2.2 | 1.8 | 0.0 | 0.0 |
| hsa-miR-6811-5p | 0.0 | 0.0 | 0.0 | 0.0 | 0.0 | 0.0 | 0.0 | 0.0 | 0.0 |
| hsa-miR-6814-5p | 2.3 | 3.2 | 3.2 | 3.6 | 0.0 | 3.4 | 2.4 | 3.2 | 2.7 |

TABLE 3-continued

| | | | | | | | | | |
|---|---|---|---|---|---|---|---|---|---|
| hsa-miR-6828-3p | 2.4 | 2.4 | 2.8 | 0.0 | 0.0 | 0.0 | 0.0 | 0.0 | 0.0 |
| hsa-miR-6835-3p | 1.6 | 0.0 | 1.4 | 0.0 | 0.0 | 0.0 | 0.0 | 0.0 | 0.0 |
| hsa-miR-6838-3p | 0.0 | 0.0 | 0.0 | 0.0 | 0.0 | 0.0 | 0.0 | 0.0 | 1.3 |
| hsa-miR-6842-3p | 0.0 | 2.1 | 1.5 | 0.0 | 0.0 | 1.8 | 0.0 | 2.9 | 2.6 |
| hsa-miR-6853-3p | 0.0 | 0.0 | 0.0 | 0.0 | 0.0 | 0.0 | 0.0 | 0.0 | 0.0 |
| hsa-miR-6854-5p | 1.7 | 0.0 | 2.1 | 0.0 | 0.0 | 0.0 | 0.0 | 0.0 | 0.0 |
| hsa-miR-6864-5p | 0.0 | 1.9 | 2.6 | 1.6 | 2.3 | 1.7 | 0.0 | 0.0 | 0.0 |
| hsa-miR-6866-5p | 2.0 | 0.0 | 2.8 | 0.0 | 0.0 | 0.0 | 1.7 | 0.0 | 0.0 |
| hsa-miR-6869-3p | 0.0 | 0.0 | 0.0 | 0.0 | 2.7 | 0.0 | 0.0 | 0.0 | 0.0 |
| hsa-miR-6882-5p | 2.4 | 1.2 | 0.0 | 1.6 | 2.2 | 0.0 | 1.5 | 1.7 | 2.5 |
| hsa-miR-6888-3p | 1.1 | 0.0 | 0.0 | 0.0 | 0.0 | 0.0 | 0.0 | 0.0 | 0.0 |
| hsa-miR-7153-5p | 0.0 | 0.0 | 0.0 | 1.6 | 0.0 | 0.0 | 0.0 | 0.0 | 1.4 |
| hsa-miR-7154-5p | 0.0 | 0.0 | 0.0 | 0.0 | 0.0 | 0.0 | 0.0 | 0.9 | 0.0 |
| hsa-miR-7156-3p | 0.0 | 1.6 | 2.2 | 2.5 | 1.4 | 3.1 | 3.0 | 3.4 | 3.3 |
| hsa-miR-7156-5p | 2.2 | 3.3 | 3.7 | 2.7 | 3.4 | 3.6 | 2.7 | 1.2 | 2.0 |
| hsa-miR-7158-3p | 2.3 | 0.0 | 3.6 | 1.7 | 3.3 | 2.1 | 2.2 | 0.0 | 0.0 |
| hsa-miR-7159-3p | 0.0 | 0.0 | 0.0 | 0.0 | 0.0 | 0.0 | 0.0 | 0.0 | 0.0 |
| hsa-miR-7160-3p | 1.8 | 0.0 | 0.0 | 0.0 | 0.0 | 0.0 | 0.0 | 0.0 | 0.0 |
| hsa-miR-7515 | 0.0 | 0.0 | 0.0 | 0.0 | 1.5 | 2.3 | 2.2 | 3.5 | 1.2 |
| hsa-miR-7705 | 2.7 | 0.0 | 0.0 | 0.0 | 0.0 | 0.0 | 0.0 | 0.0 | 0.0 |
| hsa-miR-7706 | 2.3 | 2.5 | 3.4 | 2.0 | 2.5 | 2.3 | 2.0 | 2.2 | 0.0 |
| hsa-miR-7978 | 2.3 | 2.1 | 2.9 | 0.0 | 0.0 | 0.0 | 0.0 | 0.0 | 0.0 |
| hsa-miR-8053 | 1.3 | 0.0 | 0.0 | 0.0 | 0.0 | 0.0 | 0.0 | 0.0 | 0.0 |
| hsa-miR-8054 | 0.0 | 0.0 | 1.6 | 0.0 | 0.0 | 0.0 | 0.0 | 0.0 | 0.0 |
| hsa-miR-8056 | 0.0 | 1.4 | 0.0 | 0.0 | 0.0 | 0.0 | 0.0 | 0.0 | 0.0 |
| hsa-miR-8058 | 0.0 | 0.0 | 2.1 | 0.0 | 1.5 | 1.8 | 0.0 | 0.0 | 0.0 |
| hsa-miR-8067 | 0.0 | 0.0 | 1.8 | 0.0 | 0.0 | 0.0 | 0.0 | 0.0 | 0.0 |
| hsa-miR-8068 | 0.0 | 0.0 | 0.0 | 0.0 | 2.2 | 1.6 | 1.5 | 0.0 | 0.0 |
| hsa-miR-8074 | 0.0 | 2.6 | 2.5 | 2.1 | 0.0 | 2.7 | 2.6 | 3.7 | 2.4 |
| hsa-miR-8079 | 2.3 | 2.0 | 3.6 | 0.0 | 2.6 | 1.7 | 1.4 | 0.0 | 1.7 |
| hsa-miR-8086 | 0.0 | 1.6 | 3.1 | 0.0 | 0.0 | 1.7 | 1.6 | 1.7 | 1.4 |
| hsa-miR-8088 | 0.0 | 0.0 | 0.0 | 0.0 | 0.0 | 0.0 | 0.0 | 0.0 | 0.0 |
| hsa-miR-4694-5p | 0.0 | 2.1 | 0.0 | 1.6 | 0.0 | 1.2 | 0.0 | 0.0 | 0.0 |
| hsa-miR-4746-5p | 0.0 | 0.0 | 0.0 | 0.0 | 0.0 | 0.0 | 0.0 | 0.0 | 0.0 |
| hsa-miR-0517-5p | 2.6 | 0.0 | 2.7 | 2.9 | 2.6 | 0.0 | 1.8 | 1.1 | 2.0 |
| hsa-miR-4302 | 0.0 | 0.0 | 0.0 | 0.0 | 0.0 | 0.0 | 0.0 | 0.0 | 0.0 |
| hsa-miR-3908 | 1.8 | 1.6 | 2.5 | 0.0 | 0.0 | 2.3 | 0.0 | 0.3 | 0.0 |
| hsa-miR-0611 | 1.9 | 2.0 | 0.0 | 0.0 | 2.3 | 0.0 | 0.0 | 0.0 | 1.3 |
| hsa-miR-0873-5p | 0.0 | 0.0 | 0.0 | 0.0 | 0.0 | 0.0 | 0.0 | 0.0 | 0.0 |
| hsa-miR-4423-5p | 0.0 | 1.4 | 3.1 | 2.8 | 0.8 | 2.4 | 2.7 | 2.7 | 2.3 |
| hsa-miR-0383-5p | 0.0 | 0.0 | 1.4 | 1.7 | 1.3 | 0.0 | 0.0 | 0.0 | 0.0 |
| hsa-miR-6500-5p | 1.6 | 1.9 | 3.0 | 2.9 | 1.9 | 2.0 | 1.9 | 1.4 | 2.1 |
| hsa-miR-4454 | 0.0 | 3.5 | 4.0 | 2.8 | 3.5 | 2.8 | 2.5 | 3.1 | 2.4 |
| hsa-miR-0203b-3p | 0.0 | 2.2 | 2.2 | 0.0 | 0.0 | 0.0 | 0.0 | 0.0 | 1.3 |
| hsa-miR-4711-5p | 0.0 | 0.0 | 0.0 | 0.0 | 0.0 | 0.0 | 0.0 | 0.0 | 0.0 |
| hsa-miR-0664a-5p | 3.5 | 2.7 | 3.7 | 2.8 | 0.9 | 0.0 | 0.0 | 0.0 | 0.0 |
| hsa-miR-0548v | 0.0 | 0.0 | 0.0 | 0.0 | 0.0 | 0.0 | 0.0 | 0.0 | 0.0 |
| hsa-miR-3916 | 0.0 | 1.8 | 2.6 | 0.0 | 0.0 | 2.0 | 1.8 | 0.0 | 0.0 |
| hsa-miR-4691-3p | 1.5 | 1.9 | 2.0 | 0.0 | 1.4 | 0.0 | 0.0 | 0.8 | 1.2 |
| hsa-miR-0548z, hsa-miR-548h-3p | 0.0 | 0.0 | 0.0 | 0.0 | 0.0 | 0.0 | 0.0 | 0.0 | 0.0 |
| hsa-miR-0027b-5p | 0.0 | 0.0 | 0.0 | 0.0 | 1.7 | 0.0 | 0.0 | 0.0 | 0.0 |
| hsa-miR-2681-5p | 2.7 | 3.5 | 3.4 | 2.2 | 2.7 | 2.6 | 2.5 | 2.8 | 1.6 |
| hsa-miR-3161 | 3.0 | 3.2 | 3.6 | 2.7 | 0.0 | 2.1 | 3.5 | 2.6 | 2.2 |
| hsa-miR-0604 | 2.7 | 2.9 | 3.3 | 3.4 | 3.0 | 2.6 | 0.0 | 2.3 | 2.7 |
| hsa-miR-1269b | 0.0 | 4.6 | 2.2 | 0.0 | 2.5 | 2.1 | 2.1 | 0.0 | 1.4 |
| hsa-miR-4659b-3p | 0.0 | 0.0 | 2.2 | 0.0 | 1.2 | 0.0 | 1.8 | 0.0 | 1.4 |
| hsa-miR-0938 | 3.6 | 2.3 | 2.8 | 3.5 | 1.7 | 2.4 | 1.8 | 0.5 | 0.0 |
| hsa-miR-4733-3p | 3.3 | 2.9 | 2.9 | 3.7 | 2.3 | 3.0 | 3.0 | 2.4 | 3.7 |
| hsa-miR-0491-3p | 3.2 | 2.7 | 2.6 | 2.4 | 1.9 | 1.5 | 2.5 | 1.0 | 2.4 |
| hsa-miR-6505-5p | 1.9 | 2.7 | 2.1 | 0.0 | 0.0 | 0.0 | 0.0 | 0.0 | 0.0 |
| hsa-miR-0630 | 1.7 | 3.2 | 2.7 | 1.9 | 0.4 | 2.6 | 0.0 | 0.0 | 0.0 |
| hsa-miR-3688-3p | 0.0 | 0.0 | 0.0 | 0.0 | 0.0 | 0.0 | 0.0 | 0.0 | 1.7 |
| hsa-miR-3179 | 0.0 | 1.5 | 1.3 | 0.0 | 1.5 | 1.0 | 0.0 | 2.9 | 0.0 |
| hsa-miR-4755-3p | 0.0 | 0.0 | 2.0 | 1.6 | 0.0 | 0.0 | 0.0 | 1.4 | 2.3 |
| hsa-miR-6720-5p | 2.1 | 3.9 | 2.1 | 2.7 | 0.0 | 3.0 | 0.0 | 1.4 | 2.0 |
| hsa-miR-0452-3p | 1.7 | 1.9 | 2.6 | 2.1 | 3.1 | 2.2 | 0.0 | 0.0 | 0.0 |
| hsa-miR-0374b-3p | 0.0 | 0.0 | 0.0 | 0.0 | 0.0 | 0.0 | 0.0 | 0.0 | 0.0 |
| hsa-miR-0022-3p | 0.0 | 0.0 | 0.0 | 0.0 | 0.9 | 0.0 | 0.0 | 0.0 | 0.0 |
| hsa-miR-0222-3p | 1.8 | 0.0 | 3.0 | 2.0 | 2.2 | 0.0 | 2.3 | 0.0 | 0.0 |
| hsa-miR-0093-3p | 1.3 | 2.0 | 3.0 | 2.1 | 0.0 | 0.0 | 0.0 | 0.0 | 0.0 |
| hsa-miR-0200a-5p | 2.1 | 2.5 | 3.5 | 3.7 | 2.9 | 2.0 | 3.5 | 2.5 | 3.2 |
| hsa-miR-0362-3p | 2.0 | 1.6 | 1.6 | 2.6 | 1.1 | 0.0 | 1.5 | 0.0 | 0.0 |
| hsa-miR-0144-5p | 0.0 | 1.3 | 2.2 | 0.0 | 0.0 | 0.0 | 0.0 | 0.0 | 0.0 |
| hsa-miR-0628-3p | 1.9 | 1.1 | 1.4 | 1.7 | 0.0 | 1.8 | 0.0 | 0.0 | 0.0 |
| hsa-miR-0378c | 0.0 | 3.2 | 3.8 | 2.7 | 1.9 | 2.8 | 1.8 | 0.4 | 1.5 |
| hsa-miR-0335-5p | 0.0 | 0.0 | 0.0 | 0.0 | 0.0 | 0.0 | 0.0 | 0.0 | 0.0 |
| hsa-miR-7112-3p | 0.0 | 3.6 | 4.1 | 1.5 | 3.4 | 4.3 | 2.0 | 1.7 | 3.0 |
| hsa-miR-5009-3p | 0.0 | 0.0 | 0.0 | 0.0 | 0.0 | 0.0 | 0.0 | 0.0 | 0.0 |
| hsa-let-7g-5p | 2.0 | 0.0 | 0.0 | 0.0 | 0.0 | 0.0 | 0.0 | 0.0 | 0.0 |

TABLE 3-continued

| | | | | | | | | | |
|---|---|---|---|---|---|---|---|---|---|
| hsa-miR-0130a-5p | 0.0 | 3.0 | 3.6 | 2.9 | 0.0 | 2.1 | 2.4 | 1.2 | 2.0 |
| hsa-miR-0215-5p | 1.5 | 0.0 | 1.9 | 2.9 | 1.1 | 0.0 | 0.0 | 0.0 | 0.0 |
| hsa-miR-3186-3p | 4.0 | 4.2 | 4.1 | 3.7 | 2.7 | 4.3 | 3.4 | 4.4 | 4.0 |
| hsa-miR-4745-3p | 3.9 | 4.2 | 3.3 | 3.4 | 2.0 | 1.7 | 0.0 | 0.0 | 0.0 |
| hsa-miR-0449a | 2.0 | 1.4 | 1.9 | 3.0 | 2.1 | 2.0 | 2.1 | 1.3 | 2.0 |
| hsa-miR-0017-3p | 1.1 | 0.0 | 2.7 | 1.5 | 2.2 | 0.0 | 0.0 | 0.0 | 0.0 |
| hsa-miR-4786-5p | 1.9 | 2.8 | 3.7 | 3.6 | 3.6 | 3.7 | 2.9 | 3.2 | 3.0 |
| hsa-miR-5695 | 0.0 | 1.7 | 2.4 | 0.0 | 0.0 | 0.0 | 0.0 | 0.0 | 0.0 |
| hsa-miR-3927-3p | 0.0 | 0.0 | 1.6 | 0.0 | 0.0 | 0.0 | 0.0 | 0.0 | 0.0 |
| hsa-miR-0200b-5p | 3.1 | 3.0 | 3.6 | 3.0 | 1.2 | 1.6 | 2.9 | 2.8 | 2.0 |
| hsa-miR-0010a-5p | 0.0 | 1.5 | 2.6 | 0.0 | 0.0 | 1.0 | 0.0 | 0.0 | 0.0 |
| hsa-miR-0181d-3p | 2.3 | 1.9 | 3.2 | 3.6 | 3.6 | 3.0 | 0.0 | 3.8 | 2.9 |
| hsa-miR-0369-3p | 0.0 | 0.0 | 0.0 | 0.0 | 0.0 | 0.0 | 0.0 | 0.0 | 0.0 |
| hsa-miR-0578 | 0.0 | 2.5 | 2.5 | 2.3 | 0.0 | 1.9 | 2.1 | 1.3 | 2.1 |
| hsa-miR-3193 | 2.0 | 3.0 | 0.0 | 2.8 | 0.0 | 1.1 | 0.0 | 1.0 | 2.2 |
| hsa-miR-0302a-3p | 1.8 | 0.0 | 1.4 | 2.4 | 2.3 | 0.0 | 0.0 | 0.0 | 1.1 |
| hsa-miR-0549a | 0.0 | 0.0 | 0.0 | 0.0 | 0.0 | 0.0 | 0.0 | 0.0 | 0.0 |
| hsa-miR-1255b-2-3p | 0.0 | 1.5 | 2.6 | 0.0 | 0.0 | 1.9 | 0.0 | 2.0 | 3.2 |
| hsa-miR-6510-3p | 3.0 | 3.6 | 3.1 | 2.3 | 0.8 | 2.5 | 1.5 | 0.7 | 1.6 |
| hsa-miR-0363-5p | 0.0 | 1.3 | 1.4 | 1.6 | 0.0 | 0.0 | 0.0 | 1.9 | 0.0 |
| hsa-miR-0028-5p | 3.1 | 0.0 | 4.2 | 4.1 | 4.3 | 3.1 | 4.3 | 2.6 | 3.5 |
| hsa-miR-4720-5p | 0.0 | 2.9 | 3.3 | 2.3 | 0.0 | 2.8 | 0.0 | 1.9 | 1.9 |
| hsa-miR-0202-3p | 3.1 | 1.6 | 2.9 | 2.5 | 3.1 | 1.9 | 0.0 | 0.0 | 0.0 |
| hsa-miR-4255 | 2.4 | 0.0 | 0.0 | 2.9 | 2.8 | 2.5 | 1.6 | 2.4 | 1.6 |
| hsa-miR-0449c-5p | 3.8 | 4.3 | 3.0 | 3.3 | 0.0 | 2.8 | 2.5 | 2.0 | 2.2 |
| hsa-miR-0181b-3p | 0.0 | 0.0 | 1.7 | 0.0 | 0.0 | 0.0 | 0.0 | 0.4 | 0.0 |
| hsa-miR-4775 | 1.8 | 2.9 | 3.4 | 2.3 | 0.5 | 0.0 | 2.0 | 0.0 | 0.0 |
| hsa-miR-0378h | 1.7 | 2.4 | 2.8 | 2.7 | 1.6 | 1.7 | 2.5 | 2.2 | 2.4 |
| hsa-miR-0152-5p | 1.2 | 2.6 | 1.8 | 2.4 | 0.0 | 0.0 | 2.8 | 1.4 | 2.6 |
| hsa-miR-0513b-5p | 3.2 | 1.6 | 0.0 | 2.2 | 3.2 | 3.8 | 2.0 | 0.8 | 3.3 |
| hsa-miR-0029b-3p | 3.1 | 1.3 | 1.1 | 2.2 | 2.4 | 0.0 | 0.0 | 0.8 | 0.0 |
| hsa-miR-1297 | 3.3 | 3.6 | 2.7 | 3.4 | 0.0 | 1.8 | 2.5 | 0.0 | 1.9 |
| hsa-miR-0020b-3p | 0.0 | 1.4 | 2.6 | 0.0 | 0.0 | 0.0 | 2.1 | 2.1 | 0.0 |
| hsa-miR-0541-3p | 1.4 | 2.2 | 2.7 | 2.8 | 0.4 | 2.0 | 3.4 | 4.0 | 3.3 |
| hsa-miR-1301-3p | 2.4 | 1.6 | 0.0 | 1.6 | 0.0 | 0.0 | 2.7 | 4.3 | 2.6 |
| hsa-miR-3115 | 0.0 | 0.0 | 0.0 | 0.0 | 0.0 | 0.0 | 0.0 | 0.0 | 0.0 |
| hsa-miR-6807-3p | 2.2 | 1.4 | 2.7 | 0.0 | 0.0 | 0.0 | 0.0 | 0.0 | 0.0 |
| hsa-miR-0532-5p | 1.9 | 0.0 | 0.0 | 0.0 | 0.7 | 0.0 | 0.0 | 0.0 | 2.0 |
| hsa-miR-6864-3p | 1.5 | 2.5 | 2.9 | 2.0 | 2.6 | 1.7 | 1.5 | 1.5 | 1.3 |
| hsa-miR-0196a-5p | 1.8 | 1.5 | 2.5 | 2.3 | 0.0 | 2.7 | 0.0 | 0.0 | 2.1 |
| hsa-miR-4676-3p | 3.4 | 3.4 | 3.4 | 2.6 | 2.9 | 2.7 | 2.0 | 2.1 | 1.8 |
| hsa-miR-0096-3p | 0.0 | 1.9 | 2.0 | 1.6 | 0.0 | 0.0 | 0.0 | 0.0 | 0.0 |
| hsa-miR-0126-3p | 0.0 | 0.0 | 2.8 | 0.0 | 0.0 | 0.0 | 0.0 | 0.0 | 0.0 |
| hsa-miR-0550a-3-5p | 3.0 | 3.7 | 3.7 | 3.0 | 3.0 | 4.1 | 3.6 | 4.3 | 4.9 |
| hsa-miR-0378f | 1.7 | 0.0 | 1.4 | 0.0 | 0.0 | 2.3 | 1.7 | 0.3 | 0.0 |
| hsa-miR-5581-5p | 0.0 | 1.3 | 2.8 | 0.0 | 0.6 | 4.4 | 1.9 | 0.0 | 0.0 |
| hsa-miR-0627-5p | 1.7 | 2.5 | 2.8 | 2.9 | 3.2 | 1.3 | 0.0 | 0.0 | 3.4 |
| hsa-miR-0649 | 1.6 | 0.0 | 1.8 | 2.3 | 0.0 | 1.2 | 0.0 | 0.0 | 2.2 |
| hsa-miR-0626 | 0.0 | 0.0 | 2.1 | 0.0 | 0.0 | 0.0 | 0.0 | 0.0 | 2.9 |
| hsa-miR-5007-5p | 1.5 | 2.4 | 4.0 | 3.5 | 2.9 | 2.5 | 3.1 | 3.0 | 2.8 |
| hsa-miR-7107-3p | 2.9 | 1.8 | 2.7 | 2.6 | 2.5 | 2.5 | 3.9 | 1.9 | 2.6 |
| hsa-miR-0030e-3p | 2.7 | 3.8 | 3.2 | 2.9 | 0.0 | 1.6 | 2.2 | 0.6 | 1.4 |
| hsa-miR-5589-3p | 1.1 | 2.5 | 0.0 | 0.0 | 0.0 | 0.0 | 0.0 | 0.0 | 0.0 |
| hsa-miR-0128-3p | 0.0 | 0.0 | 2.1 | 0.0 | 0.0 | 0.0 | 0.0 | 0.0 | 0.0 |
| hsa-miR-0421 | 1.2 | 1.6 | 0.0 | 0.0 | 0.0 | 0.0 | 1.5 | 0.5 | 1.7 |
| hsa-miR-7856-5p | 1.6 | 2.7 | 3.3 | 2.4 | 3.6 | 3.2 | 3.9 | 2.7 | 4.0 |
| hsa-miR-0378e | 2.2 | 2.5 | 2.5 | 0.0 | 1.6 | 2.9 | 1.6 | 1.9 | 1.6 |
| hsa-miR-1205 | 2.5 | 3.2 | 3.9 | 3.3 | 0.0 | 2.9 | 1.5 | 0.0 | 0.0 |
| hsa-miR-0579-3p | 1.4 | 3.4 | 3.1 | 3.0 | 3.2 | 2.6 | 0.0 | 0.8 | 0.0 |
| hsa-miR-6839-3p | 0.0 | 2.7 | 2.1 | 0.0 | 0.0 | 0.0 | 0.0 | 0.3 | 0.0 |
| hsa-miR-0219b-3p | 0.0 | 0.0 | 1.5 | 0.0 | 0.0 | 0.0 | 0.0 | 0.0 | 0.0 |
| hsa-miR-0662 | 1.4 | 0.0 | 0.0 | 0.0 | 1.8 | 0.0 | 0.0 | 0.0 | 0.0 |
| hsa-miR-7153-3p | 1.6 | 0.0 | 3.3 | 1.6 | 0.0 | 2.6 | 0.0 | 0.0 | 0.0 |
| hsa-miR-4742-3p | 2.0 | 0.0 | 1.7 | 0.0 | 0.0 | 0.0 | 2.2 | 1.9 | 1.1 |
| hsa-miR-1303 | 4.0 | 3.8 | 2.9 | 3.7 | 4.7 | 3.7 | 3.7 | 4.4 | 4.7 |
| hsa-miR-3117-5p | 0.0 | 0.0 | 0.0 | 0.0 | 0.0 | 0.0 | 0.0 | 0.0 | 0.0 |
| hsa-miR-0576-5p | 2.2 | 2.4 | 2.5 | 2.1 | 2.2 | 0.0 | 0.0 | 1.7 | 2.1 |
| hsa-miR-0372-3p | 2.4 | 2.9 | 4.4 | 3.4 | 0.0 | 2.0 | 3.3 | 0.0 | 2.2 |
| hsa-let-7e-5p | 1.6 | 2.1 | 3.6 | 3.4 | 3.2 | 1.8 | 2.3 | 1.3 | 0.0 |
| hsa-miR-3677-5p | 0.0 | 1.7 | 0.0 | 0.0 | 0.0 | 0.0 | 0.0 | 0.0 | 0.0 |
| hsa-miR-0092a-1-5p | 0.0 | 0.0 | 0.0 | 0.0 | 0.0 | 0.0 | 0.0 | 0.0 | 0.0 |
| hsa-miR-0029a-3p | 1.7 | 0.0 | 1.7 | 2.3 | 0.0 | 0.0 | 0.0 | 0.7 | 0.0 |
| hsa-miR-0007-1-3p | 1.5 | 1.2 | 2.0 | 2.6 | 0.0 | 2.1 | 2.9 | 2.5 | 2.0 |
| hsa-miR-0450a-5p | 0.0 | 3.0 | 2.5 | 3.0 | 2.3 | 2.1 | 2.9 | 2.8 | 2.6 |
| hsa-miR-4330 | 2.1 | 3.1 | 2.8 | 2.4 | 1.8 | 1.7 | 2.1 | 2.0 | 2.5 |
| hsa-miR-0515-3p | 1.3 | 1.9 | 3.0 | 3.1 | 2.9 | 1.0 | 1.5 | 2.8 | 1.8 |
| hsa-miR-0323a-3p | 0.0 | 0.0 | 0.0 | 1.8 | 0.8 | 0.0 | 0.0 | 0.0 | 0.0 |
| hsa-miR-7159-5p | 1.2 | 1.8 | 1.8 | 1.9 | 2.2 | 2.0 | 1.8 | 2.1 | 2.2 |
| hsa-miR-4766-5p | 0.0 | 0.0 | 2.8 | 1.9 | 0.0 | 1.5 | 0.0 | 1.6 | 1.3 |
| hsa-miR-4524a-5p | 1.9 | 0.0 | 3.1 | 2.9 | 2.4 | 2.3 | 2.8 | 1.8 | 2.0 |

TABLE 3-continued

| | | | | | | | | | |
|---|---|---|---|---|---|---|---|---|---|
| hsa-miR-7843-3p | 2.8 | 1.8 | 3.4 | 0.0 | 1.7 | 1.2 | 0.0 | 0.0 | 2.1 |
| hsa-miR-6809-5p | 1.9 | 1.5 | 2.1 | 0.0 | 2.6 | 3.4 | 0.0 | 0.2 | 0.0 |
| hsa-miR-6888-5p | 2.3 | 2.9 | 3.0 | 3.1 | 3.4 | 3.3 | 3.2 | 2.5 | 2.7 |
| hsa-miR-2909 | 4.0 | 3.7 | 4.6 | 3.5 | 2.3 | 3.1 | 2.8 | 2.5 | 2.3 |
| hsa-miR-3164 | 3.5 | 3.1 | 2.6 | 3.7 | 2.8 | 3.0 | 4.5 | 4.8 | 5.0 |
| hsa-miR-4520-3p | 0.0 | 0.0 | 2.5 | 2.7 | 0.0 | 1.2 | 2.8 | 2.0 | 2.3 |
| hsa-miR-0510-5p | 3.5 | 3.3 | 3.5 | 2.8 | 1.6 | 2.0 | 2.5 | 4.1 | 0.0 |
| hsa-miR-4690-3p | 1.1 | 0.0 | 0.0 | 0.0 | 0.0 | 0.0 | 0.0 | 0.0 | 0.0 |
| hsa-miR-0026a-1-3p | 2.8 | 3.6 | 3.7 | 2.6 | 0.0 | 0.0 | 0.0 | 0.0 | 0.0 |
| hsa-miR-4793-5p | 2.7 | 2.8 | 2.1 | 3.2 | 0.8 | 0.0 | 0.0 | 0.1 | 1.3 |
| hsa-miR-0624-5p | 1.9 | 1.1 | 0.0 | 2.1 | 0.0 | 0.0 | 0.0 | 0.0 | 0.0 |
| hsa-miR-0617 | 0.0 | 0.0 | 0.0 | 0.0 | 2.1 | 0.0 | 2.4 | 4.7 | 3.1 |
| hsa-miR-0371a-3p | 3.9 | 3.8 | 3.5 | 3.1 | 2.8 | 2.6 | 1.6 | 0.9 | 0.0 |
| hsa-miR-0500a-5p | 2.4 | 2.6 | 3.5 | 2.9 | 1.2 | 3.1 | 2.4 | 1.3 | 0.0 |
| hsa-miR-3687 | 2.5 | 1.9 | 0.0 | 1.7 | 0.0 | 2.1 | 2.5 | 1.3 | 1.7 |
| hsa-miR-0378i | 2.0 | 2.1 | 3.8 | 2.1 | 0.5 | 2.1 | 3.0 | 1.8 | 2.1 |
| hsa-miR-3934-3p | 0.0 | 2.0 | 2.8 | 2.5 | 2.8 | 2.5 | 2.8 | 2.1 | 1.6 |
| hsa-miR-5688 | 0.0 | 1.3 | 3.0 | 0.0 | 0.0 | 0.0 | 0.0 | 0.0 | 0.0 |
| hsa-miR-6768-3p | 2.5 | 3.2 | 3.6 | 2.3 | 1.3 | 2.4 | 2.2 | 2.2 | 1.5 |
| hsa-miR-0010b-5p | 0.0 | 1.2 | 2.3 | 2.3 | 1.7 | 0.0 | 0.0 | 0.0 | 1.1 |
| hsa-miR-0023a-3p | 1.9 | 1.8 | 1.8 | 2.8 | 0.8 | 2.6 | 0.0 | 1.5 | 1.5 |
| hsa-miR-0373-3p | 2.7 | 2.2 | 2.5 | 0.0 | 0.0 | 2.7 | 1.9 | 0.0 | 0.0 |
| hsa-miR-0487b-3p | 0.0 | 2.1 | 2.9 | 2.3 | 0.0 | 1.6 | 2.2 | 2.3 | 2.1 |
| hsa-miR-4661-5p | 2.8 | 2.6 | 2.4 | 2.5 | 2.4 | 1.7 | 2.2 | 1.3 | 2.9 |
| hsa-miR-0767-5p | 1.4 | 2.4 | 3.6 | 2.6 | 0.0 | 2.8 | 3.2 | 1.9 | 2.6 |
| hsa-miR-0922 | 0.0 | 0.0 | 0.0 | 0.0 | 0.8 | 0.0 | 0.0 | 0.0 | 0.0 |
| hsa-miR-4677-5p | 0.0 | 2.4 | 2.7 | 0.0 | 1.3 | 1.5 | 1.6 | 0.0 | 1.3 |
| hsa-miR-0502-3p | 0.0 | 0.0 | 0.0 | 0.0 | 0.0 | 0.0 | 0.0 | 0.0 | 0.0 |
| hsa-miR-0598-5p | 3.2 | 2.7 | 3.3 | 3.8 | 2.5 | 3.4 | 3.6 | 3.0 | 2.3 |
| hsa-miR-4521 | 3.6 | 4.1 | 3.8 | 0.0 | 1.4 | 1.9 | 2.1 | 0.0 | 1.6 |
| hsa-miR-0215-3p | 1.2 | 0.0 | 3.1 | 0.0 | 1.9 | 0.0 | 0.0 | 0.0 | 0.0 |
| hsa-miR-4261 | 3.1 | 2.8 | 2.4 | 2.7 | 2.7 | 4.1 | 3.9 | 4.9 | 4.3 |
| hsa-miR-4280 | 3.0 | 2.3 | 2.5 | 3.0 | 0.0 | 2.9 | 2.7 | 2.5 | 3.2 |
| hsa-miR-0027a-3p | 3.2 | 0.0 | 1.9 | 2.0 | 1.2 | 0.0 | 0.0 | 0.0 | 0.0 |
| hsa-miR-6073 | 0.0 | 1.8 | 2.7 | 0.0 | 0.0 | 0.0 | 0.0 | 0.0 | 0.0 |
| hsa-miR-0029b-2-5p | 0.0 | 0.0 | 0.0 | 0.0 | 0.0 | 1.7 | 2.3 | 0.0 | 0.0 |
| hsa-miR-4794 | 3.7 | 3.7 | 3.6 | 3.2 | 2.3 | 3.3 | 3.0 | 2.6 | 2.3 |
| hsa-miR-4645-5p | 0.0 | 0.0 | 1.6 | 0.0 | 0.0 | 1.2 | 0.0 | 0.0 | 1.2 |
| hsa-miR-3529-3p | 0.0 | 0.0 | 0.0 | 0.0 | 0.0 | 0.0 | 0.0 | 0.0 | 0.0 |
| hsa-miR-4325 | 0.0 | 0.0 | 1.1 | 0.0 | 0.0 | 0.0 | 0.0 | 0.3 | 0.0 |
| hsa-miR-5702 | 0.0 | 2.9 | 3.2 | 3.2 | 3.1 | 2.4 | 0.0 | 2.1 | 0.0 |
| hsa-miR-4262 | 3.4 | 2.1 | 3.0 | 3.5 | 1.1 | 3.6 | 3.0 | 2.5 | 3.2 |
| hsa-miR-0891a-3p | 1.8 | 2.3 | 4.2 | 2.3 | 0.0 | 2.5 | 2.0 | 0.5 | 0.0 |
| hsa-miR-0205-5p | 3.2 | 3.2 | 3.3 | 3.0 | 2.5 | 2.9 | 1.7 | 1.7 | 1.9 |
| hsa-miR-8078 | 4.1 | 3.9 | 3.5 | 4.2 | 4.1 | 4.8 | 3.5 | 4.7 | 4.1 |
| hsa-miR-0181a-5p | 2.0 | 0.0 | 4.3 | 3.1 | 2.3 | 0.0 | 2.2 | 2.0 | 2.2 |
| hsa-miR-4314 | 2.9 | 3.4 | 1.9 | 2.0 | 0.0 | 2.0 | 2.5 | 2.2 | 2.5 |
| hsa-miR-4633-5p | 3.5 | 3.2 | 4.8 | 3.4 | 2.8 | 2.6 | 3.6 | 2.3 | 3.1 |
| hsa-miR-0502-5p | 2.1 | 0.0 | 2.9 | 2.7 | 0.0 | 0.0 | 1.5 | 1.0 | 0.0 |
| hsa-miR-0494-3p | 1.8 | 1.3 | 2.7 | 3.3 | 2.7 | 3.1 | 4.0 | 4.4 | 4.1 |
| hsa-miR-4317 | 2.7 | 2.6 | 2.1 | 2.8 | 0.0 | 2.2 | 2.6 | 1.2 | 1.6 |
| hsa-miR-5003-3p | 0.0 | 0.0 | 2.5 | 0.0 | 0.0 | 0.0 | 2.2 | 0.0 | 0.0 |
| hsa-miR-0203a-3p | 3.9 | 4.1 | 4.3 | 4.3 | 3.1 | 3.2 | 3.1 | 0.0 | 2.0 |
| hsa-miR-5693 | 2.9 | 2.4 | 3.6 | 2.8 | 0.0 | 2.0 | 0.0 | 1.0 | 2.3 |
| hsa-miR-0151b | 0.0 | 0.0 | 2.7 | 0.0 | 1.5 | 1.7 | 3.7 | 2.6 | 4.1 |
| hsa-miR-0135b-5p | 1.5 | 2.0 | 3.5 | 2.5 | 1.9 | 1.9 | 0.0 | 0.0 | 0.0 |
| hsa-miR-0614 | 4.2 | 4.2 | 2.6 | 2.5 | 2.3 | 2.9 | 2.9 | 4.6 | 4.0 |
| hsa-miR-5690 | 0.0 | 1.5 | 3.4 | 2.6 | 0.0 | 0.0 | 0.0 | 1.6 | 0.0 |
| hsa-miR-2467-5p | 0.0 | 0.0 | 2.1 | 0.0 | 0.0 | 1.0 | 1.8 | 0.0 | 1.2 |
| hsa-miR-3160-3p | 5.5 | 5.7 | 6.3 | 5.9 | 5.6 | 5.2 | 6.0 | 5.6 | 5.9 |
| hsa-miR-5011-3p | 0.0 | 1.1 | 2.5 | 0.0 | 0.0 | 0.0 | 1.7 | 0.0 | 0.0 |
| hsa-miR-0219b-5p | 1.1 | 3.7 | 3.1 | 2.4 | 2.1 | 2.2 | 2.6 | 2.4 | 0.0 |
| hsa-miR-4318 | 3.4 | 2.5 | 3.0 | 2.7 | 0.0 | 1.6 | 0.0 | 0.4 | 0.0 |
| hsa-miR-0593-5p | 3.6 | 3.1 | 3.3 | 3.3 | 1.7 | 2.3 | 2.5 | 2.2 | 2.5 |
| hsa-miR-0181b-5p | 2.9 | 2.0 | 2.4 | 3.2 | 2.3 | 2.3 | 3.1 | 2.2 | 2.8 |
| hsa-miR-0195-5p | 1.2 | 0.0 | 2.2 | 1.6 | 0.7 | 0.0 | 1.5 | 0.0 | 0.0 |
| hsa-miR-5003-5p | 0.0 | 0.0 | 0.0 | 0.0 | 0.0 | 0.0 | 0.0 | 0.0 | 0.0 |
| hsa-miR-6068 | 3.5 | 3.7 | 3.7 | 1.7 | 2.7 | 5.4 | 3.8 | 6.2 | 5.5 |
| hsa-miR-2682-5p | 3.3 | 2.9 | 3.1 | 3.2 | 2.5 | 2.0 | 3.4 | 1.6 | 3.0 |
| hsa-miR-3162-5p | 6.3 | 6.2 | 5.6 | 6.9 | 8.7 | 8.6 | 7.2 | 7.8 | 7.6 |
| hsa-miR-4494 | 3.0 | 3.0 | 3.5 | 2.8 | 2.8 | 2.6 | 0.0 | 1.7 | 2.3 |
| hsa-miR-0635 | 3.1 | 3.1 | 3.3 | 2.7 | 3.4 | 1.1 | 2.0 | 2.3 | 2.4 |
| hsa-miR-3677-3p | 2.8 | 1.7 | 2.4 | 0.0 | 0.0 | 0.0 | 0.0 | 0.0 | 0.0 |
| hsa-miR-4694-3p | 0.0 | 2.4 | 3.5 | 2.6 | 3.2 | 2.9 | 3.3 | 1.6 | 2.4 |
| hsa-miR-0676-3p | 0.0 | 1.4 | 0.0 | 0.0 | 0.0 | 0.0 | 0.0 | 0.0 | 0.0 |
| hsa-miR-0509-3-5p | 0.0 | 1.3 | 1.1 | 0.0 | 0.0 | 0.0 | 1.6 | 0.0 | 0.0 |
| hsa-miR-6832-5p | 2.9 | 3.0 | 3.0 | 3.6 | 3.5 | 3.1 | 3.3 | 2.6 | 3.5 |
| hsa-miR-3692-3p | 0.0 | 2.2 | 0.0 | 0.0 | 0.0 | 1.5 | 0.0 | 0.2 | 0.0 |
| hsa-miR-4672 | 0.0 | 2.4 | 2.5 | 2.7 | 2.1 | 2.5 | 3.0 | 2.7 | 2.7 |
| hsa-miR-0449b-5p | 1.7 | 2.8 | 0.0 | 2.1 | 1.4 | 2.1 | 3.0 | 1.5 | 0.0 |

TABLE 3-continued

| | | | | | | | | | |
|---|---|---|---|---|---|---|---|---|---|
| hsa-miR-4712-3p | 2.2 | 1.9 | 2.6 | 2.1 | 0.0 | 1.7 | 2.4 | 1.8 | 1.9 |
| hsa-miR-3622b-3p | 3.7 | 3.6 | 3.7 | 2.9 | 3.7 | 2.5 | 2.3 | 0.9 | 1.7 |
| hsa-miR-0489-5p | 3.3 | 3.1 | 4.3 | 3.9 | 2.3 | 3.2 | 3.1 | 4.6 | 2.9 |
| hsa-miR-0374b-5p | 2.8 | 3.5 | 3.6 | 2.3 | 0.0 | 0.0 | 0.0 | 0.0 | 0.0 |
| hsa-miR-4256 | 2.8 | 0.0 | 2.1 | 0.0 | 2.2 | 1.5 | 0.0 | 0.0 | 0.0 |
| hsa-miR-0411-3p | 3.4 | 2.8 | 3.1 | 2.9 | 1.0 | 2.1 | 3.2 | 2.4 | 2.2 |
| hsa-miR-2277-3p | 4.2 | 4.4 | 4.5 | 3.7 | 3.5 | 3.8 | 3.5 | 2.6 | 3.2 |
| hsa-miR-3156-3p | 5.4 | 5.8 | 5.7 | 5.9 | 5.7 | 5.7 | 5.5 | 4.9 | 5.1 |
| hsa-miR-6513-5p | 1.1 | 1.7 | 2.5 | 0.0 | 0.0 | 2.0 | 1.6 | 1.1 | 1.4 |
| hsa-miR-0023b-3p | 2.9 | 2.5 | 2.9 | 3.2 | 3.6 | 3.0 | 2.4 | 1.9 | 2.4 |
| hsa-miR-0194-5p | 2.7 | 2.4 | 2.1 | 3.1 | 2.4 | 2.5 | 2.7 | 1.4 | 0.0 |
| hsa-miR-0206 | 2.7 | 3.3 | 3.9 | 3.4 | 3.1 | 2.7 | 3.0 | 2.5 | 1.7 |
| hsa-miR-7157-3p | 0.0 | 0.0 | 3.0 | 2.7 | 2.8 | 1.5 | 2.7 | 1.8 | 2.9 |
| hsa-miR-6717-5p | 2.2 | 3.4 | 3.2 | 2.8 | 3.2 | 4.4 | 5.0 | 7.5 | 6.0 |
| hsa-miR-4295 | 3.4 | 2.7 | 3.1 | 3.2 | 3.4 | 2.2 | 2.9 | 3.0 | 2.7 |
| hsa-miR-1912 | 1.9 | 3.5 | 2.1 | 2.9 | 1.3 | 2.7 | 2.3 | 0.5 | 1.8 |
| hsa-miR-3141 | 8.5 | 8.6 | 8.5 | 8.9 | 9.1 | 9.2 | 7.6 | 7.6 | 7.6 |
| hsa-miR-0382-3p | 2.5 | 1.7 | 0.0 | 1.7 | 1.2 | 2.4 | 0.0 | 0.0 | 1.8 |
| hsa-miR-0499b-3p | 2.6 | 0.0 | 1.8 | 1.9 | 0.0 | 2.2 | 3.3 | 0.0 | 1.3 |
| hsa-miR-0098-5p | 0.0 | 0.0 | 0.0 | 0.0 | 0.0 | 0.0 | 0.0 | 0.0 | 0.0 |
| hsa-miR-0378a-5p | 2.5 | 3.0 | 3.3 | 2.9 | 3.7 | 3.0 | 2.1 | 1.9 | 2.1 |
| hsa-miR-4253 | 5.7 | 5.8 | 5.3 | 4.9 | 4.9 | 4.7 | 3.7 | 4.2 | 4.0 |
| hsa-miR-0550b-2-5p | 0.0 | 3.1 | 3.9 | 2.6 | 1.4 | 3.3 | 3.1 | 3.8 | 3.5 |
| hsa-miR-0025-5p | 4.4 | 5.2 | 4.3 | 4.2 | 4.0 | 4.3 | 1.9 | 3.1 | 4.8 |
| hsa-miR-4796-5p | 0.0 | 3.5 | 3.6 | 2.6 | 0.0 | 2.5 | 3.9 | 2.9 | 3.1 |
| hsa-miR-0015b-5p | 3.6 | 3.5 | 3.4 | 3.7 | 2.9 | 2.1 | 3.7 | 3.0 | 3.0 |
| hsa-miR-0378g | 1.6 | 3.2 | 3.8 | 2.7 | 0.0 | 3.0 | 3.2 | 3.0 | 1.9 |
| hsa-miR-5704 | 2.9 | 3.1 | 1.7 | 3.4 | 1.9 | 2.8 | 2.9 | 2.0 | 2.0 |
| hsa-miR-0512-3p | 3.2 | 3.3 | 3.2 | 3.0 | 2.4 | 3.3 | 2.1 | 0.0 | 1.7 |
| hsa-miR-0027b-3p | 2.7 | 3.0 | 3.1 | 2.8 | 3.2 | 0.0 | 2.2 | 1.3 | 2.0 |
| hsa-miR-0122-5p | 3.1 | 1.6 | 1.7 | 2.2 | 2.6 | 0.0 | 2.4 | 1.8 | 2.3 |
| hsa-miR-4729 | 0.0 | 0.0 | 0.0 | 0.0 | 0.0 | 0.0 | 0.0 | 0.8 | 0.0 |
| hsa-miR-0324-5p | 4.0 | 2.5 | 4.0 | 3.1 | 3.8 | 2.4 | 3.8 | 3.3 | 3.4 |
| hsa-miR-5681a | 3.8 | 3.4 | 4.3 | 3.3 | 0.0 | 1.8 | 3.6 | 3.0 | 2.4 |
| hsa-miR-4421 | 2.4 | 3.8 | 3.7 | 3.5 | 3.7 | 3.1 | 3.9 | 3.4 | 3.9 |
| hsa-miR-1299 | 0.0 | 1.4 | 0.0 | 0.0 | 0.0 | 0.0 | 0.0 | 0.0 | 0.0 |
| hsa-miR-0196b-5p | 2.1 | 2.6 | 3.9 | 3.2 | 2.3 | 3.6 | 2.8 | 2.2 | 1.2 |
| hsa-let-7c-3p | 2.6 | 3.0 | 3.1 | 2.3 | 2.0 | 2.2 | 2.7 | 1.0 | 2.1 |
| hsa-miR-0200b-3p | 0.0 | 1.6 | 2.3 | 2.2 | 2.2 | 2.6 | 1.9 | 1.1 | 1.9 |
| hsa-miR-0519c-5p, hsa-miR-523-5p, hsa-miR-518e-5p, hsa-miR-522-5p, hsa-miR-519a-5p, hsa-miR-519b-5p | 2.9 | 2.6 | 1.2 | 0.0 | 0.0 | 0.0 | 3.7 | 5.6 | 4.5 |
| hsa-miR-6839-5p | 3.0 | 2.4 | 3.1 | 3.8 | 3.4 | 3.7 | 3.6 | 4.0 | 3.2 |
| hsa-miR-6818-5p | 0.0 | 1.6 | 0.0 | 2.2 | 0.0 | 1.2 | 2.8 | 1.3 | 2.5 |
| hsa-miR-6837-3p | 3.5 | 3.9 | 4.4 | 4.3 | 3.7 | 3.7 | 2.8 | 0.0 | 2.4 |
| hsa-miR-3936 | 2.6 | 4.1 | 3.5 | 3.0 | 1.3 | 2.9 | 3.7 | 4.5 | 3.5 |
| hsa-miR-6783-5p | 0.0 | 1.6 | 2.2 | 0.0 | 0.0 | 1.7 | 2.6 | 3.0 | 2.2 |
| hsa-miR-1911-3p | 4.3 | 3.9 | 4.3 | 3.8 | 2.1 | 3.2 | 2.8 | 2.1 | 1.9 |
| hsa-miR-3140-3p | 0.0 | 0.0 | 0.0 | 0.0 | 0.0 | 0.0 | 0.0 | 0.0 | 0.0 |
| hsa-miR-6770-5p | 2.8 | 3.3 | 3.4 | 1.8 | 0.6 | 2.1 | 0.0 | 0.5 | 1.8 |
| hsa-miR-4527 | 3.4 | 2.3 | 3.6 | 3.4 | 3.2 | 2.4 | 2.1 | 1.6 | 0.0 |
| hsa-miR-8055 | 1.8 | 3.9 | 4.6 | 3.8 | 2.8 | 3.5 | 3.9 | 2.8 | 2.8 |
| hsa-miR-3678-5p | 2.2 | 2.4 | 3.3 | 1.9 | 0.0 | 1.2 | 2.2 | 0.4 | 1.8 |
| hsa-miR-4451 | 3.3 | 2.8 | 3.4 | 4.1 | 3.6 | 2.7 | 3.7 | 3.4 | 3.6 |
| hsa-miR-4783-5p | 2.6 | 2.7 | 2.3 | 0.0 | 0.0 | 1.8 | 0.0 | 2.9 | 0.0 |
| hsa-miR-0380-5p | 2.7 | 0.0 | 0.0 | 0.0 | 0.0 | 0.0 | 1.4 | 0.0 | 0.0 |
| hsa-miR-0610 | 2.1 | 2.4 | 1.8 | 3.0 | 0.6 | 2.5 | 1.6 | 3.4 | 2.3 |
| hsa-miR-4660 | 2.3 | 2.5 | 3.7 | 2.6 | 2.2 | 2.6 | 2.6 | 3.1 | 3.4 |
| hsa-miR-6715b-5p | 2.9 | 2.8 | 1.3 | 2.4 | 3.2 | 3.1 | 1.9 | 0.8 | 1.8 |
| hsa-let-7i-5p | 2.8 | 3.6 | 3.1 | 2.8 | 2.5 | 3.4 | 1.4 | 0.0 | 2.0 |
| hsa-miR-0153-5p | 2.2 | 2.5 | 3.0 | 2.4 | 0.5 | 1.6 | 2.8 | 0.9 | 2.8 |
| hsa-miR-1245a | 0.0 | 0.0 | 0.0 | 0.0 | 0.0 | 0.0 | 0.0 | 0.0 | 0.0 |
| hsa-miR-2276-5p | 2.7 | 3.8 | 4.1 | 3.3 | 3.7 | 3.2 | 2.9 | 2.8 | 3.3 |
| hsa-miR-3155b | 3.9 | 3.5 | 4.7 | 4.5 | 4.2 | 4.4 | 4.5 | 4.2 | 3.7 |
| hsa-miR-0425-5p | 0.0 | 2.8 | 3.3 | 0.0 | 0.0 | 1.5 | 1.9 | 0.0 | 0.0 |
| hsa-miR-0888-3p | 0.0 | 1.3 | 1.3 | 0.0 | 2.0 | 0.0 | 2.7 | 1.9 | 2.6 |
| hsa-miR-0369-5p | 2.3 | 2.6 | 3.2 | 3.2 | 2.3 | 2.1 | 2.1 | 1.5 | 2.9 |
| hsa-miR-0034c-5p | 2.3 | 2.1 | 2.7 | 2.7 | 0.8 | 4.5 | 2.3 | 2.0 | 2.2 |
| hsa-miR-0585-3p | 0.0 | 1.9 | 2.1 | 0.0 | 0.0 | 1.5 | 0.0 | 0.0 | 0.0 |
| hsa-miR-0378d | 2.8 | 2.9 | 2.7 | 0.0 | 0.0 | 1.2 | 1.6 | 0.0 | 2.3 |
| hsa-miR-0605-3p | 0.0 | 0.0 | 0.0 | 0.0 | 0.0 | 0.0 | 0.0 | 0.0 | 3.2 |
| hsa-miR-4491 | 0.0 | 2.4 | 3.4 | 2.0 | 0.0 | 2.8 | 1.9 | 2.0 | 0.0 |
| hsa-miR-0525-3p | 3.5 | 3.1 | 2.6 | 0.0 | 2.1 | 0.0 | 0.0 | 1.7 | 1.7 |
| hsa-miR-0548ay-3p | 2.8 | 2.5 | 2.2 | 0.0 | 2.9 | 1.6 | 0.0 | 1.2 | 0.0 |
| hsa-miR-7162-5p | 0.0 | 1.7 | 2.2 | 0.0 | 1.5 | 0.0 | 1.5 | 0.0 | 0.0 |
| hsa-miR-4800-3p | 2.3 | 3.1 | 3.7 | 2.3 | 2.9 | 2.2 | 1.6 | 0.9 | 1.6 |
| hsa-miR-1286 | 3.5 | 2.9 | 4.4 | 3.2 | 2.8 | 3.6 | 2.1 | 1.5 | 1.9 |

TABLE 3-continued

| | | | | | | | | | |
|---|---|---|---|---|---|---|---|---|---|
| hsa-miR-0942-3p | 3.9 | 3.6 | 3.9 | 3.5 | 2.5 | 2.4 | 3.1 | 2.0 | 1.2 |
| hsa-miR-4771 | 0.0 | 1.6 | 2.5 | 2.7 | 0.9 | 0.0 | 0.0 | 0.0 | 0.0 |
| hsa-miR-3682-3p | 3.7 | 3.2 | 3.4 | 4.0 | 4.5 | 5.5 | 4.1 | 4.0 | 3.5 |
| hsa-miR-8083 | 3.4 | 3.4 | 4.2 | 3.8 | 3.3 | 3.5 | 4.4 | 3.9 | 3.5 |
| hsa-miR-6513-3p | 3.6 | 3.8 | 3.5 | 3.0 | 2.3 | 2.9 | 3.1 | 2.0 | 2.9 |
| hsa-miR-3929 | 0.0 | 2.7 | 3.4 | 3.4 | 2.5 | 2.9 | 3.4 | 2.2 | 2.8 |
| hsa-miR-3200-3p | 3.6 | 3.2 | 3.5 | 3.1 | 2.9 | 3.1 | 2.8 | 1.4 | 1.9 |
| hsa-miR-4703-3p | 3.6 | 3.2 | 3.1 | 3.2 | 0.0 | 0.0 | 2.2 | 2.4 | 1.1 |
| hsa-miR-3918 | 4.3 | 4.4 | 3.8 | 3.7 | 3.3 | 4.4 | 3.4 | 3.4 | 3.5 |
| hsa-miR-0650 | 3.6 | 3.5 | 4.0 | 3.3 | 3.0 | 3.3 | 2.5 | 6.0 | 4.6 |
| hsa-miR-0034b-5p | 3.7 | 2.8 | 3.0 | 3.7 | 3.6 | 2.7 | 3.1 | 2.4 | 2.3 |
| hsa-miR-4524b-5p | 3.6 | 2.6 | 3.3 | 2.4 | 0.0 | 0.0 | 1.5 | 0.3 | 0.0 |
| hsa-miR-4644 | 2.3 | 3.7 | 3.0 | 3.7 | 3.8 | 4.4 | 3.0 | 2.9 | 3.4 |
| hsa-miR-4283 | 4.0 | 3.6 | 3.8 | 4.1 | 3.6 | 4.5 | 3.4 | 3.4 | 3.0 |
| hsa-miR-5696 | 2.0 | 3.0 | 3.2 | 2.9 | 2.0 | 3.1 | 2.2 | 1.7 | 1.7 |
| hsa-miR-0127-5p | 1.9 | 1.9 | 0.0 | 0.0 | 1.6 | 0.0 | 0.0 | 1.9 | 1.1 |
| hsa-miR-3666 | 4.7 | 4.6 | 4.7 | 3.0 | 2.9 | 3.1 | 5.0 | 2.2 | 1.3 |
| hsa-miR-4786-3p | 3.9 | 3.3 | 3.7 | 3.3 | 2.6 | 3.0 | 3.7 | 2.8 | 2.8 |
| hsa-miR-0138-2-3p | 2.7 | 2.8 | 1.6 | 3.1 | 2.9 | 1.5 | 2.2 | 2.9 | 2.8 |
| hsa-miR-1276 | 3.3 | 2.9 | 3.6 | 3.2 | 2.5 | 3.0 | 1.7 | 2.2 | 2.9 |
| hsa-miR-4709-5p | 0.0 | 3.0 | 3.4 | 2.4 | 0.7 | 2.6 | 3.0 | 2.0 | 2.9 |
| hsa-miR-4681 | 2.9 | 2.9 | 2.5 | 3.1 | 0.0 | 2.3 | 2.7 | 3.2 | 3.1 |
| hsa-miR-5094 | 2.8 | 3.4 | 3.3 | 3.7 | 2.2 | 2.9 | 2.9 | 2.8 | 1.9 |
| hsa-miR-0431-5p | 3.0 | 3.7 | 3.6 | 2.7 | 2.7 | 0.0 | 1.6 | 0.0 | 0.0 |
| hsa-miR-0383-3p | 3.9 | 4.5 | 4.5 | 3.9 | 3.2 | 3.2 | 3.4 | 1.9 | 1.9 |
| hsa-miR-0183-5p | 2.4 | 2.2 | 1.5 | 2.1 | 0.0 | 0.0 | 0.0 | 0.0 | 0.0 |
| hsa-miR-3678-3p | 3.6 | 3.6 | 3.9 | 4.0 | 3.2 | 3.6 | 2.2 | 2.2 | 2.2 |
| hsa-miR-0370-5p | 0.0 | 3.1 | 2.6 | 2.5 | 0.0 | 2.7 | 2.5 | 0.1 | 1.2 |
| hsa-miR-4755-5p | 3.3 | 2.8 | 3.4 | 2.8 | 3.1 | 3.2 | 2.1 | 1.2 | 1.8 |
| hsa-miR-3605-5p | 0.0 | 3.1 | 3.1 | 2.9 | 3.5 | 3.0 | 3.2 | 3.2 | 3.2 |
| hsa-miR-0654-5p | 3.9 | 4.0 | 3.0 | 3.4 | 2.4 | 3.5 | 3.7 | 4.7 | 4.2 |
| hsa-miR-0579-5p | 3.2 | 3.1 | 3.7 | 3.2 | 1.4 | 2.4 | 3.8 | 2.1 | 3.5 |
| hsa-miR-8080 | 2.3 | 2.7 | 3.3 | 3.1 | 2.5 | 2.9 | 3.1 | 2.5 | 2.5 |
| hsa-miR-4437 | 1.5 | 2.1 | 1.8 | 3.0 | 0.0 | 3.1 | 2.7 | 3.5 | 3.3 |
| hsa-miR-7853-5p | 3.8 | 3.8 | 4.0 | 4.0 | 3.4 | 3.4 | 2.9 | 1.5 | 3.1 |
| hsa-miR-6718-5p | 3.2 | 3.7 | 4.1 | 4.2 | 3.9 | 3.6 | 3.6 | 3.5 | 3.6 |
| hsa-miR-6501-5p | 3.5 | 3.4 | 3.6 | 3.2 | 1.9 | 4.1 | 3.2 | 4.3 | 3.7 |
| hsa-miR-7641 | 4.1 | 4.8 | 3.6 | 3.5 | 3.3 | 2.6 | 2.7 | 3.3 | 1.6 |
| hsa-miR-0495-5p | 3.4 | 3.8 | 3.9 | 4.2 | 3.8 | 3.4 | 3.7 | 3.2 | 2.7 |
| hsa-miR-0888-5p | 3.4 | 3.8 | 4.7 | 4.0 | 3.6 | 3.9 | 3.1 | 1.8 | 2.1 |
| hsa-miR-5188 | 2.6 | 3.2 | 3.3 | 2.8 | 2.2 | 2.6 | 3.3 | 2.6 | 3.2 |
| hsa-miR-3174 | 2.8 | 4.4 | 3.8 | 2.6 | 2.6 | 3.4 | 3.3 | 1.3 | 2.3 |
| hsa-miR-0548ax | 2.9 | 3.3 | 3.6 | 0.0 | 0.0 | 0.0 | 0.0 | 0.0 | 0.0 |
| hsa-miR-1284 | 3.6 | 4.0 | 3.6 | 3.4 | 0.8 | 3.5 | 3.4 | 2.4 | 3.6 |
| hsa-miR-4724-3p | 2.1 | 2.1 | 3.1 | 2.3 | 0.0 | 0.0 | 2.1 | 0.7 | 1.8 |
| hsa-miR-4275 | 0.0 | 0.0 | 2.9 | 0.0 | 0.0 | 0.0 | 0.0 | 0.0 | 1.6 |
| hsa-miR-0193b-5p | 3.9 | 3.1 | 3.6 | 5.0 | 3.1 | 4.5 | 2.7 | 4.9 | 4.1 |
| hsa-miR-5006-5p | 2.8 | 4.2 | 4.5 | 3.8 | 3.8 | 5.1 | 4.1 | 6.6 | 4.4 |
| hsa-miR-4650-5p | 1.9 | 2.8 | 3.2 | 1.5 | 2.6 | 2.4 | 2.7 | 1.0 | 2.8 |
| hsa-miR-4465 | 3.6 | 3.1 | 2.9 | 4.0 | 0.0 | 3.1 | 3.2 | 3.9 | 4.1 |
| hsa-miR-0320c | 2.2 | 1.7 | 0.0 | 2.5 | 0.0 | 2.9 | 2.8 | 2.6 | 2.6 |
| hsa-miR-0030a-3p | 3.0 | 3.6 | 3.8 | 3.3 | 0.0 | 2.3 | 2.1 | 1.9 | 2.4 |
| hsa-miR-0892a | 2.2 | 3.4 | 2.8 | 2.2 | 0.0 | 2.0 | 2.2 | 2.1 | 2.3 |
| hsa-miR-0668-5p | 3.5 | 3.4 | 3.8 | 3.6 | 4.0 | 4.2 | 4.9 | 6.1 | 5.9 |
| hsa-miR-8057 | 3.8 | 3.5 | 4.3 | 2.7 | 0.6 | 3.8 | 2.9 | 4.3 | 3.3 |
| hsa-miR-3200-5p | 4.3 | 4.7 | 4.1 | 2.3 | 0.8 | 1.8 | 0.0 | 2.1 | 2.4 |
| hsa-miR-6874-5p | 2.4 | 2.4 | 2.3 | 2.7 | 2.8 | 2.0 | 3.4 | 3.5 | 3.4 |
| hsa-miR-0338-3p | 3.8 | 3.4 | 4.4 | 3.5 | 2.9 | 2.1 | 3.2 | 2.5 | 2.4 |
| hsa-miR-0184 | 1.6 | 2.7 | 2.5 | 4.8 | 3.6 | 4.0 | 2.9 | 5.9 | 3.7 |
| hsa-miR-5096 | 2.5 | 3.7 | 0.0 | 4.2 | 6.2 | 5.2 | 4.0 | 3.6 | 5.3 |
| hsa-miR-7848-3p | 3.1 | 3.8 | 4.8 | 3.3 | 4.7 | 3.9 | 3.7 | 2.3 | 2.6 |
| hsa-miR-6081 | 4.3 | 4.7 | 3.1 | 3.3 | 2.8 | 3.4 | 2.4 | 2.9 | 2.3 |
| hsa-miR-0196b-3p | 5.4 | 4.8 | 3.5 | 3.3 | 1.6 | 2.5 | 3.2 | 2.4 | 2.2 |
| hsa-miR-0147a | 3.4 | 2.6 | 3.8 | 3.5 | 3.0 | 2.5 | 2.8 | 3.4 | 2.1 |
| hsa-let-7b-5p | 3.6 | 3.6 | 3.7 | 4.1 | 3.8 | 3.1 | 3.2 | 3.1 | 0.0 |
| hsa-miR-0143-3p | 3.3 | 2.9 | 2.3 | 2.7 | 3.6 | 0.0 | 1.6 | 0.0 | 0.0 |
| hsa-miR-1273e | 3.6 | 3.1 | 1.2 | 4.2 | 5.0 | 3.9 | 3.1 | 3.1 | 4.7 |
| hsa-miR-4712-5p | 3.6 | 4.0 | 3.8 | 3.5 | 2.9 | 4.0 | 3.7 | 2.8 | 3.5 |
| hsa-miR-5011-5p | 0.0 | 0.0 | 1.6 | 0.0 | 0.0 | 0.0 | 0.0 | 0.0 | 0.0 |
| hsa-miR-0514b-3p | 4.0 | 3.2 | 3.2 | 2.4 | 0.0 | 2.0 | 1.6 | 1.4 | 1.1 |
| hsa-miR-0325 | 0.0 | 3.2 | 2.9 | 3.0 | 1.4 | 1.9 | 2.0 | 2.4 | 3.0 |
| hsa-miR-4482-5p | 0.0 | 3.2 | 3.4 | 2.8 | 0.5 | 1.6 | 3.5 | 1.8 | 2.1 |
| hsa-miR-4303 | 2.9 | 3.1 | 3.7 | 3.8 | 3.7 | 2.7 | 3.5 | 3.6 | 3.5 |
| hsa-miR-5680 | 3.5 | 2.8 | 3.4 | 2.5 | 0.5 | 0.0 | 2.1 | 1.7 | 0.0 |
| hsa-miR-0664b-5p | 0.0 | 0.0 | 3.0 | 2.5 | 1.9 | 2.0 | 2.8 | 1.1 | 0.0 |
| hsa-miR-6853-5p | 3.0 | 3.7 | 4.4 | 3.3 | 3.3 | 3.5 | 4.1 | 3.7 | 4.0 |
| hsa-miR-4752 | 0.0 | 2.8 | 4.3 | 2.2 | 2.4 | 2.7 | 3.4 | 2.2 | 3.2 |
| hsa-miR-5002-5p | 0.0 | 1.5 | 2.5 | 1.8 | 0.0 | 1.5 | 2.8 | 0.9 | 2.2 |
| hsa-miR-4524b-3p | 3.2 | 3.2 | 4.1 | 4.4 | 0.0 | 2.9 | 3.6 | 3.0 | 3.1 |
| hsa-miR-0589-3p | 3.2 | 3.4 | 3.4 | 3.2 | 1.2 | 2.9 | 3.3 | 2.6 | 3.1 |

TABLE 3-continued

| | | | | | | | | | |
|---|---|---|---|---|---|---|---|---|---|
| hsa-miR-1271-5p | 3.1 | 3.5 | 3.6 | 3.3 | 1.6 | 3.5 | 1.9 | 2.5 | 3.0 |
| hsa-miR-6509-5p | 1.1 | 3.4 | 3.6 | 2.1 | 2.9 | 2.8 | 1.9 | 2.4 | 2.8 |
| hsa-miR-4638-3p | 4.4 | 4.0 | 3.5 | 2.3 | 2.8 | 0.0 | 1.4 | 2.3 | 1.1 |
| hsa-miR-5689 | 0.0 | 1.8 | 1.9 | 2.4 | 0.0 | 2.2 | 3.1 | 0.9 | 2.7 |
| hsa-miR-8084 | 2.2 | 4.8 | 0.0 | 0.0 | 0.0 | 0.0 | 0.0 | 0.0 | 0.0 |
| hsa-miR-1295b-3p | 3.3 | 3.5 | 4.0 | 3.4 | 0.0 | 3.5 | 3.1 | 2.2 | 1.9 |
| hsa-miR-7154-3p | 0.0 | 2.4 | 3.2 | 2.2 | 2.9 | 2.8 | 2.8 | 2.2 | 3.0 |
| hsa-miR-5095 | 2.5 | 2.5 | 3.1 | 2.6 | 2.2 | 3.3 | 2.6 | 2.7 | 4.0 |
| hsa-miR-4273 | 3.5 | 2.8 | 3.6 | 3.4 | 2.5 | 3.3 | 3.1 | 2.7 | 2.4 |
| hsa-miR-0145-5p | 2.3 | 3.2 | 2.7 | 2.9 | 3.6 | 1.3 | 0.0 | 0.9 | 4.0 |
| hsa-miR-0142-3p | 1.8 | 2.7 | 2.6 | 3.4 | 3.2 | 1.4 | 2.7 | 1.0 | 2.9 |
| hsa-miR-4657 | 1.1 | 2.8 | 4.1 | 2.7 | 1.7 | 2.7 | 3.9 | 5.1 | 3.9 |
| hsa-miR-0519a-3p | 2.4 | 2.6 | 1.4 | 2.9 | 0.0 | 0.0 | 0.0 | 0.0 | 0.0 |
| hsa-miR-3689f | 0.0 | 2.4 | 0.0 | 1.8 | 0.0 | 1.4 | 2.1 | 2.0 | 0.0 |
| hsa-miR-5571-3p | 0.0 | 2.9 | 3.9 | 3.1 | 2.5 | 2.8 | 3.9 | 4.2 | 4.2 |
| hsa-miR-0566 | 4.3 | 4.1 | 3.5 | 4.8 | 2.7 | 3.9 | 2.4 | 2.5 | 3.3 |
| hsa-miR-0138-5p | 3.9 | 3.2 | 3.2 | 4.0 | 3.1 | 4.8 | 3.0 | 2.8 | 3.3 |
| hsa-miR-0526b-3p | 4.2 | 4.3 | 4.9 | 4.1 | 3.2 | 2.0 | 2.6 | 1.3 | 0.0 |
| hsa-miR-4717-5p | 3.1 | 3.8 | 3.9 | 3.6 | 2.5 | 3.2 | 3.0 | 2.5 | 2.3 |
| hsa-miR-5591-3p | 2.4 | 3.3 | 2.8 | 3.2 | 1.6 | 2.4 | 3.4 | 2.1 | 2.6 |
| hsa-miR-4254 | 3.4 | 4.1 | 3.9 | 3.7 | 2.9 | 3.8 | 2.5 | 2.1 | 2.9 |
| hsa-miR-3682-5p | 2.3 | 1.4 | 2.9 | 2.0 | 2.3 | 0.0 | 3.1 | 1.1 | 1.7 |
| hsa-miR-6506-5p | 2.3 | 3.6 | 4.0 | 3.2 | 2.0 | 2.3 | 2.8 | 2.6 | 2.1 |
| hsa-miR-8082 | 3.6 | 3.1 | 3.6 | 2.8 | 3.1 | 3.1 | 3.9 | 4.0 | 3.9 |
| hsa-miR-7974 | 3.6 | 3.7 | 4.0 | 3.4 | 1.9 | 3.4 | 3.3 | 2.4 | 3.8 |
| hsa-miR-4999-5p | 1.4 | 1.8 | 2.3 | 2.9 | 1.8 | 2.5 | 3.3 | 3.0 | 3.0 |
| hsa-miR-4797-3p | 1.4 | 2.5 | 4.1 | 2.7 | 0.0 | 1.4 | 2.9 | 1.8 | 1.7 |
| hsa-miR-4264 | 0.0 | 1.6 | 0.0 | 0.0 | 1.3 | 2.0 | 2.1 | 0.0 | 2.8 |
| hsa-miR-0378b | 2.7 | 3.5 | 3.8 | 3.5 | 3.1 | 3.9 | 2.9 | 2.1 | 3.0 |
| hsa-miR-0323a-5p | 4.2 | 4.2 | 3.6 | 3.7 | 3.1 | 3.7 | 3.1 | 3.9 | 3.0 |
| hsa-miR-3713 | 3.2 | 4.4 | 3.5 | 3.8 | 3.4 | 4.8 | 3.5 | 3.3 | 3.3 |
| hsa-miR-4308 | 3.0 | 3.2 | 2.6 | 3.0 | 4.2 | 2.9 | 2.2 | 2.6 | 1.5 |
| hsa-miR-0942-5p | 0.0 | 1.7 | 2.3 | 2.3 | 0.0 | 1.6 | 2.0 | 0.0 | 1.7 |
| hsa-miR-4450 | 2.5 | 3.3 | 3.5 | 4.0 | 3.8 | 4.5 | 3.6 | 3.4 | 3.9 |
| hsa-miR-0146a-5p | 3.5 | 3.2 | 3.7 | 3.1 | 0.0 | 3.1 | 2.7 | 1.1 | 2.2 |
| hsa-miR-0329-5p | 0.0 | 0.0 | 2.6 | 0.0 | 0.4 | 3.0 | 3.2 | 2.5 | 2.7 |
| hsa-miR-1178-3p | 3.4 | 4.2 | 3.3 | 3.1 | 2.0 | 2.7 | 3.1 | 2.6 | 2.9 |
| hsa-miR-3922-5p | 3.6 | 4.0 | 4.2 | 3.6 | 3.6 | 3.9 | 4.1 | 4.2 | 3.9 |
| hsa-miR-6811-3p | 3.5 | 4.1 | 4.2 | 3.3 | 1.7 | 3.4 | 3.4 | 2.0 | 2.7 |
| hsa-miR-6781-3p | 3.5 | 4.1 | 4.2 | 3.5 | 3.3 | 3.6 | 2.5 | 2.2 | 2.8 |
| hsa-miR-3651 | 3.6 | 4.3 | 3.2 | 3.2 | 2.8 | 2.8 | 3.7 | 4.4 | 4.0 |
| hsa-miR-0021-3p | 3.1 | 3.4 | 3.9 | 3.2 | 2.7 | 2.0 | 2.4 | 2.4 | 2.9 |
| hsa-miR-6817-5p | 2.9 | 3.2 | 2.5 | 3.9 | 3.4 | 3.3 | 3.7 | 3.6 | 3.4 |
| hsa-miR-0195-3p | 3.9 | 3.1 | 3.6 | 3.2 | 3.6 | 3.2 | 2.8 | 1.7 | 1.1 |
| hsa-miR-3913-3p | 3.0 | 2.2 | 2.7 | 2.8 | 0.0 | 2.3 | 2.8 | 0.9 | 2.1 |
| hsa-miR-0339-5p | 4.3 | 4.2 | 4.7 | 4.1 | 3.6 | 3.3 | 3.1 | 2.2 | 1.7 |
| hsa-miR-4718 | 3.7 | 4.4 | 4.2 | 3.4 | 2.9 | 3.1 | 3.0 | 2.1 | 2.1 |
| hsa-miR-0584-5p | 4.4 | 4.0 | 4.0 | 4.2 | 2.9 | 3.8 | 3.3 | 4.5 | 3.6 |
| hsa-miR-0345-5p | 3.1 | 3.2 | 3.3 | 3.8 | 3.2 | 3.8 | 3.2 | 1.9 | 2.8 |
| hsa-miR-7155-3p | 4.5 | 4.7 | 4.6 | 4.1 | 3.5 | 4.2 | 3.5 | 3.2 | 3.4 |
| hsa-miR-6505-3p | 4.1 | 4.5 | 4.6 | 4.4 | 4.5 | 4.0 | 4.0 | 3.6 | 3.8 |
| hsa-miR-1251-3p | 3.0 | 3.8 | 3.9 | 3.2 | 3.2 | 3.6 | 3.3 | 2.7 | 3.1 |
| hsa-miR-3690 | 3.7 | 3.7 | 3.7 | 3.5 | 1.1 | 3.0 | 3.2 | 1.8 | 2.0 |
| hsa-miR-5000-5p | 2.1 | 2.2 | 3.2 | 2.9 | 1.2 | 2.5 | 3.4 | 2.6 | 2.9 |
| hsa-miR-0596 | 4.0 | 3.7 | 3.4 | 1.7 | 0.0 | 0.0 | 3.0 | 3.5 | 3.3 |
| hsa-miR-0591 | 2.3 | 3.6 | 4.3 | 4.1 | 3.5 | 4.0 | 4.0 | 2.8 | 2.6 |
| hsa-miR-4658 | 3.4 | 3.4 | 4.2 | 2.9 | 3.3 | 3.6 | 2.9 | 3.8 | 3.5 |
| hsa-miR-3680-3p | 3.1 | 3.9 | 0.0 | 3.1 | 1.5 | 3.3 | 3.1 | 2.8 | 2.9 |
| hsa-miR-0379-3p | 2.9 | 3.7 | 2.9 | 2.9 | 0.0 | 2.3 | 2.9 | 1.4 | 1.9 |
| hsa-miR-0020a-3p | 3.2 | 3.1 | 4.2 | 3.1 | 2.9 | 0.0 | 1.8 | 0.0 | 3.0 |
| hsa-miR-5093 | 3.6 | 2.5 | 3.6 | 3.9 | 3.8 | 3.6 | 4.2 | 4.1 | 4.0 |
| hsa-miR-0524-5p | 0.0 | 2.3 | 3.4 | 2.4 | 2.8 | 0.0 | 1.9 | 2.0 | 3.2 |
| hsa-miR-4733-5p | 3.7 | 3.6 | 3.3 | 3.6 | 2.2 | 2.7 | 2.8 | 1.2 | 2.6 |
| hsa-miR-0619-5p | 4.3 | 4.0 | 3.0 | 5.4 | 8.0 | 7.4 | 4.7 | 4.5 | 6.3 |
| hsa-miR-0214-5p | 2.0 | 3.8 | 2.7 | 3.8 | 2.3 | 3.0 | 3.2 | 2.9 | 3.7 |
| hsa-miR-0423-3p | 3.3 | 3.3 | 3.5 | 3.3 | 2.6 | 2.8 | 3.6 | 2.3 | 2.8 |
| hsa-miR-6838-5p | 2.6 | 3.1 | 3.4 | 2.7 | 1.7 | 3.0 | 2.6 | 2.8 | 2.4 |
| hsa-miR-3186-5p | 2.5 | 3.9 | 4.0 | 3.4 | 3.2 | 3.3 | 3.8 | 3.3 | 3.7 |
| hsa-miR-6083 | 3.4 | 4.2 | 4.1 | 3.8 | 1.4 | 4.1 | 3.2 | 2.9 | 3.1 |
| hsa-miR-6761-5p | 3.8 | 3.7 | 4.1 | 4.0 | 4.0 | 3.3 | 3.8 | 3.7 | 3.4 |
| hsa-miR-0103a-2-5p | 1.9 | 3.1 | 2.6 | 3.3 | 2.8 | 2.8 | 3.5 | 2.9 | 3.2 |
| hsa-miR-6895-5p | 3.5 | 4.4 | 4.9 | 3.8 | 3.7 | 4.3 | 3.7 | 4.0 | 4.2 |
| hsa-miR-4645-3p | 3.7 | 3.6 | 3.8 | 3.5 | 3.5 | 3.2 | 3.6 | 2.7 | 2.5 |
| hsa-miR-0300 | 2.6 | 3.9 | 3.7 | 2.8 | 2.5 | 4.5 | 3.5 | 2.7 | 3.1 |
| hsa-miR-5089-3p | 0.0 | 2.6 | 3.9 | 3.2 | 3.4 | 3.5 | 3.3 | 2.7 | 2.9 |
| hsa-miR-4740-3p | 3.5 | 4.6 | 4.5 | 3.8 | 4.5 | 4.6 | 3.7 | 3.6 | 3.7 |
| hsa-miR-0511-5p | 2.9 | 3.4 | 3.3 | 2.5 | 2.2 | 2.1 | 2.5 | 0.5 | 2.3 |
| hsa-miR-6514-5p | 3.0 | 2.6 | 3.4 | 2.7 | 2.6 | 3.2 | 3.4 | 4.6 | 3.2 |
| hsa-miR-1288-5p | 3.1 | 3.4 | 2.6 | 2.3 | 0.0 | 2.8 | 2.8 | 1.4 | 1.5 |
| hsa-miR-0454-5p | 3.0 | 3.3 | 3.3 | 3.0 | 2.1 | 2.6 | 3.2 | 2.7 | 2.6 |

TABLE 3-continued

| | | | | | | | | | |
|---|---|---|---|---|---|---|---|---|---|
| hsa-miR-0645 | 3.1 | 3.5 | 3.5 | 3.2 | 3.2 | 3.4 | 3.3 | 1.5 | 2.6 |
| hsa-miR-3190-3p | 3.7 | 4.6 | 4.4 | 4.7 | 4.0 | 5.0 | 3.2 | 3.6 | 3.8 |
| hsa-miR-4438 | 0.0 | 2.7 | 3.3 | 3.4 | 2.3 | 2.7 | 2.6 | 2.0 | 2.1 |
| hsa-miR-0519d-5p | 1.7 | 0.0 | 2.3 | 0.0 | 0.0 | 0.0 | 0.0 | 2.1 | 1.8 |
| hsa-miR-1199-3p | 4.5 | 3.5 | 3.9 | 3.4 | 3.8 | 3.6 | 3.2 | 3.7 | 3.5 |
| hsa-miR-0330-3p | 1.9 | 3.1 | 3.6 | 3.8 | 2.4 | 2.8 | 2.8 | 2.1 | 2.6 |
| hsa-miR-0030c-5p | 3.4 | 2.9 | 3.9 | 3.3 | 2.6 | 2.0 | 2.6 | 1.3 | 1.6 |
| hsa-miR-7973 | 3.1 | 3.1 | 3.7 | 2.2 | 3.2 | 3.0 | 3.1 | 2.6 | 2.2 |
| hsa-miR-0509-3p | 3.7 | 3.8 | 4.5 | 4.7 | 4.3 | 3.6 | 3.4 | 3.5 | 3.1 |
| hsa-miR-1298-3p | 3.5 | 3.9 | 4.0 | 3.9 | 3.0 | 3.3 | 2.9 | 3.5 | 3.4 |
| hsa-miR-3667-5p | 3.0 | 3.7 | 4.1 | 3.7 | 4.8 | 4.4 | 3.9 | 3.4 | 4.1 |
| hsa-miR-0519b-3p | 3.6 | 2.9 | 2.7 | 3.0 | 0.0 | 1.2 | 0.0 | 0.0 | 0.0 |
| hsa-miR-6499-5p | 4.4 | 5.9 | 3.9 | 3.6 | 3.1 | 3.4 | 3.3 | 2.1 | 2.6 |
| hsa-miR-6850-3p | 4.4 | 4.2 | 3.3 | 2.7 | 2.9 | 3.1 | 3.2 | 2.0 | 1.5 |
| hsa-miR-5194 | 3.0 | 2.5 | 3.2 | 2.6 | 1.9 | 3.5 | 4.0 | 2.0 | 3.4 |
| hsa-miR-7849-3p | 3.4 | 3.8 | 4.1 | 3.6 | 2.6 | 2.7 | 0.0 | 1.1 | 0.0 |
| hsa-miR-0410-5p | 2.3 | 3.0 | 3.2 | 1.9 | 2.3 | 3.1 | 3.2 | 2.6 | 2.7 |
| hsa-miR-3654 | 3.2 | 3.2 | 2.9 | 2.3 | 0.0 | 2.7 | 1.4 | 3.9 | 2.7 |
| hsa-miR-4446-5p | 2.4 | 2.9 | 3.6 | 2.5 | 2.9 | 2.5 | 3.0 | 2.1 | 2.9 |
| hsa-miR-4740-5p | 3.8 | 4.4 | 4.3 | 4.3 | 2.8 | 4.0 | 2.7 | 2.5 | 3.9 |
| hsa-miR-6503-3p | 3.7 | 3.9 | 4.6 | 3.6 | 4.1 | 4.1 | 4.9 | 3.9 | 4.8 |
| hsa-miR-0106b-3p | 4.2 | 4.5 | 4.3 | 4.2 | 2.9 | 3.5 | 2.9 | 2.6 | 1.9 |
| hsa-miR-3657 | 3.2 | 4.0 | 4.4 | 3.5 | 3.7 | 3.4 | 3.3 | 2.9 | 2.7 |
| hsa-miR-5192 | 2.5 | 2.8 | 3.9 | 3.2 | 2.5 | 3.7 | 3.6 | 2.4 | 2.5 |
| hsa-miR-6818-3p | 3.3 | 3.9 | 4.0 | 3.8 | 3.3 | 3.7 | 4.0 | 3.1 | 3.5 |
| hsa-miR-1915-5p | 4.7 | 5.1 | 4.3 | 3.4 | 3.4 | 3.8 | 3.0 | 3.8 | 2.0 |
| hsa-miR-3145-3p | 0.0 | 0.0 | 0.0 | 0.0 | 0.0 | 0.0 | 0.0 | 0.0 | 0.0 |
| hsa-miR-4684-3p | 3.4 | 4.6 | 4.7 | 4.2 | 3.8 | 3.6 | 3.7 | 4.6 | 3.8 |
| hsa-miR-5694 | 2.5 | 3.4 | 4.0 | 3.4 | 2.2 | 3.4 | 4.2 | 3.4 | 3.8 |
| hsa-miR-0654-3p | 2.0 | 3.1 | 4.6 | 3.6 | 3.0 | 3.4 | 4.0 | 2.8 | 3.5 |
| hsa-miR-4773 | 3.0 | 4.0 | 3.8 | 3.1 | 2.5 | 3.2 | 2.1 | 1.1 | 0.0 |
| hsa-miR-7161-5p | 3.2 | 3.6 | 3.3 | 2.6 | 0.0 | 2.0 | 1.9 | 1.7 | 0.0 |
| hsa-miR-5197-5p | 3.6 | 3.5 | 3.7 | 3.9 | 3.2 | 4.1 | 2.5 | 2.7 | 2.4 |
| hsa-miR-5703 | 3.6 | 3.8 | 4.0 | 3.9 | 3.8 | 4.4 | 4.0 | 4.1 | 3.9 |
| hsa-miR-0141-5p | 4.3 | 3.7 | 5.0 | 4.3 | 2.4 | 3.6 | 3.1 | 2.2 | 2.4 |
| hsa-miR-5008-3p | 3.6 | 4.2 | 3.6 | 2.4 | 1.9 | 2.3 | 2.2 | 1.9 | 2.9 |
| hsa-miR-5681b | 3.8 | 4.4 | 4.1 | 3.9 | 3.7 | 3.3 | 1.9 | 3.6 | 2.7 |
| hsa-miR-0200c-5p | 0.0 | 3.1 | 3.2 | 3.2 | 1.2 | 2.2 | 2.6 | 2.6 | 3.2 |
| hsa-miR-0125b-2-3p | 2.1 | 0.0 | 2.3 | 2.7 | 0.0 | 1.9 | 2.3 | 2.2 | 2.0 |
| hsa-miR-4754 | 2.6 | 3.3 | 3.6 | 4.3 | 4.0 | 4.1 | 3.6 | 4.3 | 4.4 |
| hsa-miR-1322 | 3.2 | 2.9 | 2.6 | 4.1 | 1.5 | 3.0 | 3.1 | 2.3 | 3.5 |
| hsa-miR-3124-3p | 0.0 | 0.0 | 0.0 | 0.0 | 0.0 | 0.0 | 0.0 | 0.0 | 0.0 |
| hsa-miR-0381-5p | 1.8 | 3.4 | 3.4 | 3.1 | 2.8 | 2.7 | 2.6 | 3.2 | 2.9 |
| hsa-miR-5699-3p | 0.0 | 3.3 | 3.3 | 0.0 | 0.0 | 2.5 | 2.6 | 1.8 | 0.0 |
| hsa-miR-5584-3p | 3.6 | 4.4 | 3.7 | 3.8 | 3.9 | 4.0 | 3.4 | 3.5 | 3.4 |
| hsa-miR-5190 | 4.5 | 4.3 | 4.4 | 3.9 | 4.0 | 4.2 | 3.4 | 4.7 | 3.9 |
| hsa-miR-0892c-5p | 2.0 | 2.4 | 2.6 | 2.5 | 1.5 | 2.7 | 1.5 | 2.0 | 2.1 |
| hsa-miR-4445-3p | 1.9 | 2.8 | 3.6 | 3.1 | 3.4 | 2.8 | 2.7 | 1.5 | 2.1 |
| hsa-miR-5004-5p | 2.9 | 4.2 | 4.3 | 3.8 | 3.5 | 3.8 | 3.7 | 3.9 | 3.7 |
| hsa-miR-0889-5p | 3.1 | 3.7 | 3.9 | 4.1 | 4.2 | 3.7 | 3.3 | 3.9 | 3.6 |
| hsa-miR-0338-5p | 0.0 | 2.3 | 3.6 | 3.1 | 0.0 | 2.1 | 2.9 | 2.5 | 3.1 |
| hsa-miR-0488-5p | 3.6 | 4.2 | 4.3 | 4.3 | 3.7 | 4.1 | 3.8 | 2.4 | 3.4 |
| hsa-miR-4653-5p | 3.7 | 3.8 | 4.1 | 3.4 | 3.5 | 3.3 | 2.7 | 2.9 | 3.0 |
| hsa-miR-0016-1-3p | 4.2 | 3.0 | 3.6 | 3.1 | 3.6 | 2.6 | 2.9 | 2.2 | 2.9 |
| hsa-miR-4310 | 4.3 | 4.0 | 4.1 | 4.2 | 2.9 | 3.3 | 3.9 | 3.1 | 3.4 |
| hsa-miR-4316 | 1.7 | 4.2 | 4.5 | 4.5 | 3.8 | 4.4 | 4.5 | 4.9 | 4.5 |
| hsa-miR-1288-3p | 3.5 | 3.5 | 3.3 | 2.7 | 0.0 | 3.5 | 3.1 | 2.8 | 3.3 |
| hsa-miR-6854-3p | 3.8 | 4.4 | 4.5 | 3.6 | 3.7 | 3.3 | 3.7 | 3.4 | 3.3 |
| hsa-miR-0221-3p | 2.9 | 2.7 | 4.1 | 2.9 | 1.0 | 2.3 | 2.3 | 2.6 | 2.1 |
| hsa-miR-4299 | 3.1 | 3.6 | 3.6 | 3.6 | 2.5 | 3.6 | 3.1 | 2.9 | 2.8 |
| hsa-miR-7703 | 0.0 | 3.7 | 4.2 | 3.2 | 4.3 | 3.9 | 4.0 | 2.8 | 3.6 |
| hsa-miR-4520-5p | 2.8 | 3.8 | 4.0 | 4.5 | 3.6 | 3.9 | 3.7 | 4.0 | 4.1 |
| hsa-miR-0212-5p | 3.7 | 3.4 | 4.2 | 3.7 | 3.5 | 3.4 | 3.9 | 3.4 | 3.4 |
| hsa-miR-0025-3p | 4.0 | 4.6 | 4.3 | 3.8 | 3.1 | 3.3 | 3.2 | 2.6 | 3.0 |
| hsa-miR-0708-5p | 0.0 | 1.6 | 2.3 | 0.0 | 0.8 | 0.0 | 5.0 | 2.8 | 4.4 |
| hsa-miR-6821-3p | 3.8 | 4.6 | 4.4 | 4.0 | 3.4 | 4.2 | 3.3 | 2.1 | 2.9 |
| hsa-miR-0146b-3p | 4.3 | 3.7 | 4.2 | 4.0 | 3.6 | 3.9 | 4.0 | 3.2 | 3.6 |
| hsa-miR-4514 | 3.1 | 3.3 | 3.3 | 3.9 | 3.3 | 2.7 | 3.9 | 3.8 | 3.2 |
| hsa-miR-4429 | 2.3 | 3.8 | 3.6 | 3.0 | 2.3 | 3.5 | 4.1 | 4.2 | 4.3 |
| hsa-miR-0216a-3p | 4.7 | 4.6 | 4.5 | 4.4 | 4.1 | 3.5 | 3.4 | 4.0 | 3.8 |
| hsa-miR-0432-5p | 3.4 | 3.7 | 4.5 | 3.9 | 4.0 | 4.2 | 3.8 | 3.6 | 3.4 |
| hsa-miR-0525-5p | 4.3 | 3.6 | 3.3 | 3.3 | 3.9 | 3.3 | 2.8 | 4.4 | 3.8 |
| hsa-miR-1250-5p | 3.8 | 3.6 | 3.6 | 3.7 | 2.4 | 3.7 | 3.1 | 4.2 | 3.3 |
| hsa-miR-5580-3p | 3.9 | 3.9 | 3.6 | 3.7 | 2.1 | 3.0 | 3.4 | 3.0 | 3.5 |
| hsa-miR-0622 | 3.5 | 3.4 | 4.6 | 4.3 | 3.5 | 3.6 | 4.6 | 4.4 | 4.1 |
| hsa-miR-0875-3p | 2.8 | 3.1 | 3.8 | 3.2 | 1.5 | 3.6 | 3.7 | 2.5 | 2.0 |
| hsa-miR-0099b-5p | 4.5 | 4.6 | 4.7 | 4.3 | 4.0 | 3.6 | 2.8 | 2.4 | 2.4 |
| hsa-miR-0660-3p | 3.9 | 3.4 | 4.5 | 4.2 | 3.6 | 3.5 | 3.9 | 3.1 | 3.7 |
| hsa-miR-0520h | 3.4 | 4.2 | 4.4 | 3.0 | 3.3 | 2.2 | 2.3 | 2.8 | 2.4 |
| hsa-miR-8062 | 2.3 | 3.0 | 2.8 | 2.9 | 3.5 | 2.7 | 4.7 | 3.6 | 4.1 |

TABLE 3-continued

| | | | | | | | | | |
|---|---|---|---|---|---|---|---|---|---|
| hsa-miR-6765-3p | 3.9 | 4.1 | 3.9 | 2.6 | 3.5 | 3.4 | 2.3 | 2.8 | 3.1 |
| hsa-miR-0508-5p | 4.3 | 4.5 | 3.8 | 3.6 | 2.7 | 4.3 | 2.4 | 3.1 | 3.0 |
| hsa-miR-0501-5p | 3.4 | 4.0 | 3.5 | 4.0 | 1.8 | 3.1 | 3.3 | 3.4 | 3.3 |
| hsa-miR-6868-5p | 3.3 | 2.9 | 3.8 | 3.6 | 2.8 | 3.0 | 4.3 | 3.6 | 3.9 |
| hsa-miR-5187-3p | 3.4 | 4.0 | 4.3 | 3.9 | 3.3 | 3.9 | 4.5 | 3.0 | 4.2 |
| hsa-miR-3074-5p | 4.8 | 5.6 | 3.8 | 3.7 | 3.6 | 3.4 | 3.4 | 2.4 | 2.1 |
| hsa-miR-3170 | 3.0 | 3.3 | 4.2 | 3.7 | 3.4 | 2.8 | 3.1 | 2.8 | 3.2 |
| hsa-miR-0224-3p | 4.4 | 4.2 | 4.0 | 2.9 | 2.6 | 2.7 | 2.6 | 0.6 | 1.7 |
| hsa-miR-2116-5p | 3.5 | 3.0 | 3.5 | 2.9 | 4.6 | 3.6 | 3.8 | 3.8 | 4.4 |
| hsa-miR-3153 | 4.7 | 5.5 | 5.3 | 5.1 | 5.2 | 5.3 | 4.8 | 5.8 | 5.1 |
| hsa-miR-6728-5p | 3.7 | 4.1 | 4.4 | 4.0 | 4.0 | 3.8 | 4.5 | 4.2 | 4.2 |
| hsa-miR-4328 | 2.9 | 4.1 | 3.9 | 4.3 | 2.5 | 3.2 | 3.2 | 2.0 | 3.4 |
| hsa-miR-6804-5p | 3.0 | 3.3 | 3.4 | 3.5 | 3.2 | 4.2 | 3.9 | 4.8 | 4.0 |
| hsa-miR-0204-5p | 3.9 | 4.1 | 4.1 | 3.9 | 4.3 | 3.8 | 3.5 | 3.1 | 3.8 |
| hsa-miR-4764-3p | 3.3 | 3.5 | 3.2 | 3.1 | 2.8 | 3.0 | 3.0 | 2.7 | 2.4 |
| hsa-miR-7854-3p | 3.0 | 3.1 | 3.5 | 4.4 | 2.5 | 4.9 | 2.8 | 4.8 | 4.3 |
| hsa-miR-0382-5p | 2.7 | 2.5 | 3.7 | 3.7 | 3.1 | 2.4 | 3.2 | 3.5 | 3.1 |
| hsa-miR-3615 | 4.2 | 4.8 | 4.3 | 3.1 | 3.2 | 4.1 | 3.4 | 2.4 | 3.1 |
| hsa-miR-5585-3p | 4.0 | 4.5 | 4.5 | 4.6 | 4.4 | 4.2 | 3.8 | 3.9 | 4.3 |
| hsa-miR-0422a | 4.0 | 4.3 | 4.4 | 3.7 | 2.3 | 2.9 | 1.8 | 2.3 | 2.0 |
| hsa-miR-6871-3p | 3.7 | 4.2 | 4.1 | 3.6 | 4.0 | 3.6 | 3.0 | 2.7 | 3.2 |
| hsa-miR-4756-3p | 3.3 | 3.8 | 4.2 | 3.9 | 4.1 | 3.4 | 4.0 | 3.9 | 4.0 |
| hsa-miR-0485-5p | 5.0 | 4.6 | 4.7 | 4.5 | 4.2 | 3.8 | 3.6 | 3.9 | 3.7 |
| hsa-miR-0921 | 3.5 | 1.7 | 2.6 | 3.5 | 2.3 | 2.9 | 3.5 | 5.7 | 4.4 |
| hsa-miR-0340-3p | 3.7 | 3.4 | 3.7 | 3.5 | 3.9 | 3.3 | 2.7 | 2.9 | 2.9 |
| hsa-miR-3529-5p | 4.3 | 3.4 | 3.7 | 2.5 | 1.7 | 3.2 | 2.6 | 2.8 | 1.9 |
| hsa-miR-0758-5p | 2.0 | 3.1 | 3.9 | 3.7 | 2.9 | 3.2 | 3.4 | 3.4 | 3.5 |
| hsa-miR-3681-3p | 0.0 | 3.6 | 3.8 | 2.4 | 2.0 | 2.9 | 3.0 | 2.4 | 3.5 |
| hsa-miR-3074-3p | 3.9 | 3.9 | 3.6 | 3.5 | 1.1 | 3.4 | 3.2 | 2.5 | 2.3 |
| hsa-miR-3169 | 0.0 | 1.8 | 2.6 | 0.0 | 0.0 | 0.0 | 0.0 | 0.0 | 0.0 |
| hsa-miR-0030b-5p | 3.5 | 4.0 | 4.2 | 4.2 | 4.0 | 2.9 | 3.1 | 2.8 | 3.3 |
| hsa-miR-0506-3p | 4.6 | 4.3 | 4.4 | 3.9 | 3.9 | 3.7 | 3.3 | 3.7 | 3.1 |
| hsa-miR-2117 | 3.6 | 3.4 | 2.3 | 2.1 | 0.0 | 0.0 | 0.0 | 1.3 | 1.3 |
| hsa-miR-3154 | 8.1 | 8.1 | 8.8 | 8.6 | 8.9 | 8.6 | 9.0 | 8.6 | 8.8 |
| hsa-miR-0943 | 3.3 | 4.5 | 3.9 | 3.8 | 3.6 | 3.7 | 3.2 | 3.1 | 2.9 |
| hsa-miR-0603 | 3.8 | 3.3 | 3.7 | 4.0 | 4.1 | 3.4 | 3.6 | 3.5 | 3.4 |
| hsa-miR-4784 | 3.8 | 3.3 | 3.6 | 4.2 | 4.1 | 3.4 | 3.5 | 4.8 | 4.4 |
| hsa-miR-0296-3p | 5.1 | 4.4 | 4.5 | 5.4 | 5.8 | 5.2 | 5.3 | 6.1 | 5.9 |
| hsa-miR-4529-5p | 2.6 | 2.6 | 3.8 | 3.9 | 2.8 | 3.4 | 3.9 | 3.5 | 3.9 |
| hsa-miR-8081 | 3.8 | 3.6 | 3.4 | 3.7 | 3.8 | 3.3 | 2.7 | 3.5 | 3.4 |
| hsa-miR-0034b-3p | 3.1 | 3.5 | 3.5 | 2.9 | 3.0 | 3.3 | 2.4 | 2.6 | 2.7 |
| hsa-miR-4768-3p | 0.0 | 2.4 | 2.2 | 3.1 | 2.5 | 2.3 | 3.2 | 1.6 | 2.9 |
| hsa-miR-6134 | 4.1 | 5.3 | 3.9 | 4.1 | 3.5 | 4.3 | 4.0 | 2.9 | 3.5 |
| hsa-miR-0558 | 2.8 | 2.9 | 3.0 | 2.9 | 0.0 | 1.3 | 2.0 | 2.4 | 2.6 |
| hsa-miR-4635 | 4.0 | 3.8 | 3.9 | 4.0 | 3.7 | 3.6 | 3.3 | 2.9 | 2.7 |
| hsa-miR-5091 | 3.5 | 3.4 | 3.4 | 3.9 | 2.9 | 3.3 | 3.0 | 3.8 | 3.0 |
| hsa-miR-1254 | 3.8 | 3.7 | 3.5 | 3.1 | 3.8 | 4.3 | 3.9 | 7.5 | 4.9 |
| hsa-miR-4296 | 3.9 | 3.9 | 3.8 | 4.0 | 3.7 | 3.3 | 4.1 | 4.3 | 4.0 |
| hsa-miR-6504-3p | 3.8 | 4.0 | 4.3 | 4.5 | 4.3 | 4.0 | 4.2 | 3.9 | 4.3 |
| hsa-miR-3944-5p | 3.9 | 4.1 | 4.4 | 4.3 | 3.2 | 3.4 | 3.4 | 3.9 | 3.8 |
| hsa-miR-0541-5p | 3.5 | 3.6 | 3.7 | 3.8 | 3.4 | 2.8 | 3.8 | 3.7 | 3.0 |
| hsa-miR-5580-5p | 3.3 | 3.3 | 4.1 | 4.2 | 3.0 | 3.6 | 3.8 | 3.8 | 3.1 |
| hsa-miR-3655 | 4.0 | 3.9 | 4.3 | 4.4 | 4.3 | 4.2 | 3.3 | 4.1 | 4.0 |
| hsa-miR-0029c-5p | 2.9 | 3.5 | 3.7 | 3.5 | 1.8 | 3.5 | 3.3 | 2.7 | 3.2 |
| hsa-miR-1184 | 4.1 | 4.7 | 5.2 | 4.4 | 4.1 | 4.2 | 4.6 | 4.4 | 4.2 |
| hsa-miR-5571-5p | 3.9 | 4.1 | 4.2 | 3.5 | 2.8 | 3.5 | 4.0 | 3.5 | 3.7 |
| hsa-miR-0092b-3p | 4.9 | 5.2 | 5.0 | 4.4 | 4.0 | 4.0 | 3.3 | 3.2 | 3.2 |
| hsa-miR-5587-3p | 4.5 | 4.6 | 3.8 | 3.8 | 1.3 | 3.4 | 3.2 | 3.0 | 3.2 |
| hsa-miR-0769-3p | 4.7 | 3.4 | 3.4 | 3.7 | 5.0 | 4.4 | 4.0 | 4.9 | 4.9 |
| hsa-miR-0935 | 4.8 | 4.6 | 4.2 | 4.2 | 3.9 | 3.9 | 3.4 | 3.4 | 2.8 |
| hsa-miR-1199-5p | 5.4 | 5.2 | 4.2 | 3.6 | 3.5 | 3.3 | 3.3 | 4.7 | 2.9 |
| hsa-miR-0520a-3p | 3.9 | 3.9 | 4.4 | 3.2 | 1.7 | 2.2 | 2.7 | 2.2 | 2.5 |
| hsa-miR-0297 | 3.2 | 3.2 | 2.3 | 3.3 | 1.1 | 2.4 | 0.0 | 2.2 | 2.8 |
| hsa-miR-6841-5p | 4.3 | 4.1 | 5.0 | 5.0 | 4.1 | 4.7 | 4.0 | 2.7 | 2.8 |
| hsa-miR-7151-5p | 3.1 | 3.5 | 4.1 | 4.0 | 3.7 | 3.6 | 3.9 | 3.4 | 4.2 |
| hsa-miR-1277-3p | 0.0 | 0.0 | 0.0 | 0.0 | 0.0 | 0.0 | 0.0 | 0.0 | 0.0 |
| hsa-miR-0033b-3p | 4.6 | 4.6 | 4.6 | 3.4 | 4.1 | 2.8 | 3.7 | 3.1 | 3.8 |
| hsa-miR-4304 | 4.2 | 4.5 | 3.2 | 4.0 | 2.7 | 4.5 | 3.1 | 3.6 | 3.7 |
| hsa-miR-0873-3p | 2.1 | 3.2 | 3.9 | 4.5 | 3.8 | 3.5 | 6.2 | 5.6 | 6.3 |
| hsa-miR-4420 | 3.1 | 3.6 | 4.8 | 4.2 | 3.8 | 4.1 | 4.6 | 3.8 | 4.7 |
| hsa-miR-4479 | 5.0 | 5.2 | 4.4 | 3.4 | 2.8 | 3.9 | 2.7 | 2.7 | 2.8 |
| hsa-miR-0105-5p | 3.4 | 3.1 | 3.3 | 4.0 | 2.8 | 2.7 | 3.9 | 3.1 | 3.6 |
| hsa-miR-6855-5p | 1.4 | 3.0 | 3.6 | 2.9 | 3.8 | 4.4 | 3.8 | 4.8 | 4.2 |
| hsa-miR-3975 | 3.8 | 2.3 | 3.5 | 3.3 | 0.0 | 2.5 | 4.6 | 3.7 | 4.5 |
| hsa-miR-4453 | 2.4 | 3.6 | 3.2 | 3.8 | 3.3 | 2.8 | 4.1 | 4.0 | 3.9 |
| hsa-miR-1236-5p | 3.2 | 3.4 | 4.0 | 4.7 | 4.1 | 5.5 | 3.8 | 4.5 | 4.0 |
| hsa-miR-7162-3p | 2.7 | 3.7 | 4.4 | 3.9 | 3.0 | 3.4 | 3.5 | 4.6 | 3.7 |
| hsa-miR-0580-3p | 3.6 | 3.4 | 3.5 | 4.8 | 2.4 | 3.2 | 3.4 | 1.6 | 3.4 |
| hsa-miR-6852-5p | 3.6 | 3.3 | 3.7 | 4.1 | 3.5 | 4.2 | 3.4 | 3.4 | 3.7 |
| hsa-miR-0154-5p | 4.3 | 4.7 | 5.0 | 4.8 | 4.5 | 4.1 | 3.7 | 4.1 | 3.7 |

TABLE 3-continued

| | | | | | | | | | |
|---|---|---|---|---|---|---|---|---|---|
| hsa-miR-0412-3p | 3.4 | 4.0 | 4.4 | 4.4 | 4.1 | 3.4 | 3.8 | 3.7 | 3.8 |
| hsa-miR-6863 | 3.7 | 3.1 | 3.9 | 3.5 | 4.2 | 3.9 | 3.8 | 3.1 | 3.5 |
| hsa-miR-0676-5p | 2.4 | 3.5 | 3.3 | 2.4 | 1.4 | 2.8 | 3.9 | 2.5 | 3.4 |
| hsa-miR-6733-3p | 4.1 | 4.3 | 4.5 | 3.2 | 2.8 | 5.9 | 3.0 | 2.1 | 3.6 |
| hsa-miR-3972 | 4.0 | 4.8 | 5.0 | 4.4 | 3.5 | 4.1 | 4.4 | 3.3 | 3.7 |
| hsa-miR-0007-2-3p | 3.8 | 4.1 | 4.6 | 4.1 | 1.8 | 3.8 | 2.9 | 3.8 | 2.2 |
| hsa-miR-4441 | 5.2 | 4.5 | 5.1 | 5.3 | 5.2 | 4.5 | 3.4 | 3.7 | 3.1 |
| hsa-miR-4300 | 3.0 | 3.2 | 3.4 | 3.4 | 1.7 | 3.3 | 4.1 | 7.9 | 5.4 |
| hsa-miR-6874-3p | 4.1 | 4.5 | 4.8 | 4.2 | 3.5 | 4.0 | 3.6 | 3.2 | 3.3 |
| hsa-miR-3691-3p | 3.9 | 3.8 | 4.5 | 3.8 | 3.5 | 3.4 | 3.8 | 3.1 | 3.5 |
| hsa-miR-0034c-3p | 3.9 | 4.5 | 3.9 | 4.0 | 3.4 | 3.9 | 3.3 | 3.0 | 2.9 |
| hsa-miR-0519e-3p | 4.7 | 4.5 | 5.0 | 4.3 | 3.6 | 3.9 | 3.1 | 2.9 | 2.6 |
| hsa-miR-6774-3p | 3.5 | 4.7 | 5.1 | 3.9 | 3.8 | 4.0 | 4.0 | 3.4 | 3.4 |
| hsa-miR-1285-5p | 4.0 | 4.5 | 4.5 | 4.0 | 4.6 | 3.7 | 3.9 | 3.5 | 3.9 |
| hsa-miR-0518f-3p | 3.8 | 3.1 | 2.6 | 3.1 | 3.5 | 0.0 | 4.8 | 4.9 | 4.6 |
| hsa-miR-6791-3p | 4.7 | 4.9 | 4.6 | 3.7 | 3.7 | 3.9 | 4.0 | 3.5 | 3.0 |
| hsa-miR-4761-3p | 5.1 | 5.2 | 4.1 | 3.8 | 0.0 | 2.4 | 1.8 | 3.1 | 0.0 |
| hsa-miR-0548d-3p | 1.8 | 1.3 | 0.0 | 0.0 | 0.0 | 0.0 | 0.0 | 0.0 | 0.0 |
| hsa-miR-1266-3p | 4.5 | 4.7 | 4.1 | 4.1 | 4.8 | 5.3 | 4.1 | 3.7 | 4.5 |
| hsa-miR-0212-3p | 4.0 | 4.4 | 4.6 | 4.2 | 4.6 | 3.6 | 3.9 | 3.4 | 3.4 |
| hsa-miR-0744-3p | 4.3 | 4.2 | 4.0 | 4.0 | 3.2 | 3.5 | 3.9 | 3.6 | 3.4 |
| hsa-miR-9500 | 5.4 | 4.7 | 5.7 | 4.6 | 4.6 | 4.1 | 4.1 | 3.4 | 2.6 |
| hsa-miR-0670-5p | 3.5 | 4.5 | 5.2 | 4.4 | 3.8 | 4.7 | 4.9 | 4.1 | 4.6 |
| hsa-miR-2276-3p | 4.2 | 4.7 | 4.4 | 4.4 | 4.8 | 5.2 | 4.3 | 4.8 | 4.5 |
| hsa-miR-3155a | 2.8 | 3.0 | 3.2 | 3.5 | 2.5 | 3.0 | 3.1 | 3.5 | 2.7 |
| hsa-miR-0517a-3p, hsa-miR-517b-3p | 3.3 | 3.2 | 4.0 | 3.7 | 3.0 | 3.2 | 3.1 | 2.7 | 2.9 |
| hsa-miR-0493-3p | 3.0 | 3.8 | 3.5 | 4.5 | 4.4 | 4.9 | 3.8 | 3.7 | 3.7 |
| hsa-miR-0302d-5p | 4.8 | 3.6 | 5.3 | 3.7 | 2.8 | 2.9 | 4.3 | 3.8 | 4.2 |
| hsa-miR-4727-3p | 3.6 | 4.0 | 4.3 | 3.1 | 2.6 | 3.3 | 4.2 | 8.0 | 5.9 |
| hsa-miR-2355-3p | 3.5 | 4.0 | 3.6 | 2.8 | 0.0 | 2.9 | 1.8 | 1.9 | 1.6 |
| hsa-miR-3157-5p | 0.0 | 0.0 | 2.8 | 0.0 | 0.0 | 0.0 | 2.2 | 0.1 | 1.4 |
| hsa-miR-0766-5p | 0.0 | 3.3 | 3.9 | 3.1 | 1.5 | 3.4 | 4.4 | 4.4 | 4.1 |
| hsa-miR-0605-5p | 4.1 | 3.7 | 3.6 | 3.5 | 2.5 | 3.7 | 3.5 | 3.0 | 1.7 |
| hsa-miR-6758-3p | 3.5 | 4.9 | 4.8 | 3.6 | 4.0 | 3.8 | 3.3 | 3.4 | 3.5 |
| hsa-miR-6515-5p | 3.4 | 4.0 | 3.9 | 3.6 | 4.0 | 4.6 | 6.4 | 9.9 | 7.0 |
| hsa-miR-3692-5p | 3.1 | 3.8 | 4.4 | 2.9 | 3.2 | 3.3 | 3.9 | 3.1 | 3.4 |
| hsa-miR-5187-5p | 2.6 | 3.2 | 3.2 | 3.6 | 3.7 | 2.9 | 3.3 | 3.6 | 3.5 |
| hsa-miR-1287-5p | 3.6 | 3.5 | 4.8 | 4.2 | 3.2 | 3.0 | 4.4 | 3.8 | 3.6 |
| hsa-miR-0518f-5p | 1.8 | 2.2 | 2.4 | 2.1 | 3.0 | 0.0 | 3.4 | 2.9 | 3.1 |
| hsa-miR-4425 | 3.5 | 3.2 | 3.4 | 4.1 | 3.6 | 3.0 | 4.0 | 3.0 | 3.4 |
| hsa-miR-0181a-2-3p | 3.4 | 3.8 | 3.9 | 4.0 | 3.2 | 3.4 | 3.0 | 2.5 | 1.8 |
| hsa-miR-0222-5p | 3.9 | 4.1 | 4.6 | 4.6 | 3.9 | 3.8 | 3.8 | 3.8 | 3.5 |
| hsa-miR-0129-5p | 4.7 | 4.5 | 4.3 | 3.9 | 3.6 | 3.5 | 3.8 | 3.4 | 3.9 |
| hsa-miR-3659 | 4.5 | 4.1 | 4.6 | 4.8 | 4.1 | 3.6 | 4.0 | 4.2 | 3.9 |
| hsa-miR-7158-5p | 3.6 | 3.8 | 4.5 | 3.8 | 3.1 | 3.7 | 3.5 | 3.0 | 2.9 |
| hsa-miR-6516-5p | 1.7 | 2.9 | 3.5 | 3.6 | 1.7 | 3.5 | 4.6 | 3.4 | 4.4 |
| hsa-miR-0216b-3p | 5.2 | 5.5 | 5.6 | 5.2 | 5.0 | 5.0 | 3.4 | 3.0 | 2.9 |
| hsa-miR-6739-3p | 3.5 | 4.1 | 4.3 | 3.9 | 3.9 | 4.3 | 4.5 | 3.5 | 4.0 |
| hsa-miR-0609 | 2.7 | 3.5 | 3.0 | 3.1 | 2.2 | 2.9 | 3.6 | 2.9 | 3.1 |
| hsa-miR-0210-3p | 4.2 | 4.4 | 4.4 | 4.4 | 4.9 | 4.2 | 4.3 | 4.2 | 4.1 |
| hsa-miR-0323b-5p | 3.6 | 4.3 | 4.0 | 4.1 | 3.7 | 3.7 | 4.1 | 3.2 | 3.4 |
| hsa-miR-7844-5p | 4.2 | 4.0 | 5.1 | 3.7 | 3.8 | 3.8 | 3.3 | 2.8 | 2.4 |
| hsa-miR-4301 | 4.0 | 3.6 | 4.4 | 4.4 | 3.0 | 3.2 | 4.0 | 3.0 | 3.5 |
| hsa-miR-0134-3p | 3.7 | 4.2 | 4.5 | 4.0 | 4.4 | 4.3 | 4.8 | 5.0 | 4.6 |
| hsa-miR-3691-5p | 1.2 | 3.3 | 3.3 | 2.1 | 0.0 | 2.8 | 3.3 | 3.6 | 3.7 |
| hsa-miR-0425-3p | 3.7 | 4.5 | 3.8 | 3.6 | 4.1 | 3.9 | 3.2 | 2.2 | 2.2 |
| hsa-miR-0135a-3p | 6.0 | 4.4 | 4.8 | 4.7 | 5.7 | 5.6 | 4.9 | 5.5 | 5.4 |
| hsa-miR-1207-3p | 5.0 | 5.5 | 5.4 | 4.9 | 4.5 | 4.7 | 4.4 | 3.0 | 3.5 |
| hsa-miR-6856-3p | 4.1 | 4.3 | 4.6 | 4.2 | 4.0 | 3.7 | 3.6 | 3.3 | 3.7 |
| hsa-miR-4641 | 4.1 | 4.1 | 4.7 | 4.3 | 4.0 | 3.8 | 3.8 | 3.6 | 3.6 |
| hsa-miR-0520g-3p | 4.4 | 5.0 | 5.1 | 4.2 | 3.9 | 3.6 | 4.1 | 2.9 | 3.6 |
| hsa-miR-6843-3p | 4.2 | 4.5 | 4.4 | 3.6 | 2.9 | 3.9 | 4.0 | 3.0 | 3.9 |
| hsa-miR-0877-5p | 4.7 | 4.3 | 4.0 | 4.6 | 4.1 | 4.8 | 3.2 | 4.4 | 3.8 |
| hsa-miR-0584-3p | 3.7 | 4.3 | 4.6 | 4.7 | 4.5 | 3.7 | 4.1 | 4.1 | 4.1 |
| hsa-miR-4260 | 4.9 | 4.6 | 5.3 | 4.6 | 4.7 | 4.6 | 5.1 | 8.4 | 5.8 |
| hsa-miR-3619-5p | 4.8 | 4.6 | 4.7 | 4.3 | 4.5 | 4.9 | 4.1 | 4.1 | 3.6 |
| hsa-miR-7975 | 4.2 | 4.0 | 4.1 | 4.0 | 3.9 | 3.8 | 3.5 | 3.3 | 3.8 |
| hsa-miR-0512-5p | 4.9 | 4.9 | 5.1 | 4.9 | 4.4 | 4.1 | 4.1 | 3.8 | 3.5 |
| hsa-miR-4691-5p | 3.9 | 4.7 | 4.1 | 4.3 | 3.9 | 4.5 | 4.1 | 4.7 | 3.9 |
| hsa-miR-4713-3p | 4.0 | 4.4 | 5.2 | 4.0 | 4.5 | 4.5 | 3.8 | 3.8 | 5.4 |
| hsa-miR-6755-3p | 0.0 | 3.7 | 4.0 | 3.5 | 1.8 | 3.1 | 3.2 | 3.0 | 2.7 |
| hsa-miR-3945 | 4.6 | 4.4 | 5.0 | 5.4 | 5.6 | 6.3 | 4.5 | 3.5 | 4.1 |
| hsa-miR-0030b-3p | 4.2 | 4.3 | 3.7 | 3.9 | 3.7 | 5.2 | 3.7 | 6.3 | 4.3 |
| hsa-miR-0185-5p | 4.2 | 3.0 | 3.3 | 3.7 | 4.4 | 2.9 | 5.0 | 5.2 | 5.3 |
| hsa-miR-6878-5p | 3.8 | 4.4 | 4.9 | 3.5 | 4.5 | 4.0 | 3.8 | 4.7 | 4.3 |
| hsa-miR-0129-1-3p | 4.3 | 4.7 | 4.4 | 4.4 | 4.1 | 4.0 | 5.3 | 4.6 | 4.9 |
| hsa-miR-0548ba | 0.0 | 2.1 | 4.3 | 0.0 | 2.7 | 2.4 | 2.1 | 0.0 | 2.0 |
| hsa-miR-0150-5p | 4.6 | 4.7 | 4.5 | 4.5 | 4.3 | 3.8 | 3.4 | 3.2 | 3.8 |
| hsa-miR-1910-3p | 3.4 | 3.2 | 3.4 | 4.0 | 4.5 | 3.7 | 4.3 | 4.0 | 4.4 |

TABLE 3-continued

| | | | | | | | | | |
|---|---|---|---|---|---|---|---|---|---|
| hsa-miR-3138 | 3.6 | 4.0 | 4.9 | 4.6 | 4.8 | 5.0 | 4.2 | 5.2 | 3.8 |
| hsa-miR-6500-3p | 2.3 | 3.4 | 4.1 | 3.4 | 3.0 | 3.5 | 4.4 | 5.5 | 4.6 |
| hsa-miR-7157-5p | 4.2 | 3.5 | 4.7 | 4.1 | 4.4 | 3.3 | 4.4 | 4.3 | 4.1 |
| hsa-miR-0593-3p | 3.7 | 3.8 | 3.8 | 3.7 | 3.2 | 3.6 | 4.3 | 3.5 | 3.8 |
| hsa-miR-0018a-3p | 4.3 | 4.1 | 4.6 | 4.3 | 3.1 | 3.8 | 4.2 | 3.7 | 3.7 |
| hsa-miR-1972 | 4.9 | 4.7 | 4.9 | 4.1 | 5.2 | 4.7 | 3.7 | 4.0 | 4.6 |
| hsa-miR-3145-5p | 3.2 | 4.5 | 4.0 | 3.7 | 1.8 | 2.8 | 4.3 | 3.2 | 3.6 |
| hsa-miR-3922-3p | 4.6 | 4.6 | 4.6 | 4.5 | 4.0 | 3.9 | 3.3 | 3.0 | 3.2 |
| hsa-miR-6746-3p | 5.0 | 5.1 | 5.2 | 4.3 | 4.6 | 4.2 | 3.5 | 3.5 | 2.6 |
| hsa-miR-0093-5p | 3.3 | 3.6 | 3.9 | 3.4 | 3.4 | 2.6 | 4.5 | 2.8 | 3.9 |
| hsa-miR-1301-5p | 4.4 | 4.3 | 4.7 | 4.4 | 4.3 | 4.4 | 3.8 | 3.8 | 3.8 |
| hsa-miR-3116 | 4.1 | 4.8 | 4.8 | 5.0 | 4.3 | 4.2 | 4.8 | 4.7 | 4.9 |
| hsa-miR-0937-3p | 4.9 | 5.0 | 4.7 | 4.6 | 4.0 | 4.4 | 3.6 | 3.2 | 2.7 |
| hsa-miR-3187-3p | 4.7 | 4.8 | 4.7 | 4.5 | 4.7 | 5.0 | 3.9 | 5.9 | 5.2 |
| hsa-miR-0581 | 4.3 | 4.8 | 4.7 | 4.2 | 3.7 | 2.5 | 3.6 | 3.0 | 2.6 |
| hsa-miR-6816-3p | 4.1 | 4.2 | 4.3 | 4.0 | 5.1 | 4.8 | 4.1 | 3.7 | 4.7 |
| hsa-miR-1296-3p | 5.1 | 4.8 | 4.8 | 4.8 | 4.5 | 4.4 | 4.4 | 4.7 | 5.0 |
| hsa-miR-3921 | 4.6 | 5.3 | 5.5 | 4.3 | 3.5 | 3.7 | 3.5 | 2.2 | 2.0 |
| hsa-miR-1273g-5p | 3.5 | 3.9 | 3.9 | 4.0 | 4.0 | 3.6 | 3.8 | 4.3 | 3.8 |
| hsa-miR-0432-3p | 4.5 | 4.2 | 5.1 | 5.0 | 4.7 | 4.5 | 4.6 | 3.8 | 4.2 |
| hsa-miR-0656-5p | 4.2 | 4.1 | 4.0 | 4.3 | 3.1 | 3.7 | 4.3 | 4.2 | 3.6 |
| hsa-miR-4726-3p | 4.7 | 4.7 | 4.6 | 4.2 | 3.4 | 4.8 | 3.8 | 3.4 | 3.3 |
| hsa-miR-0092a-3p | 4.6 | 4.8 | 4.8 | 4.2 | 4.6 | 3.6 | 3.1 | 2.6 | 2.8 |
| hsa-miR-4265 | 4.4 | 5.1 | 5.0 | 4.0 | 4.3 | 5.1 | 4.2 | 4.0 | 3.7 |
| hsa-miR-0608 | 3.1 | 3.8 | 4.5 | 4.6 | 4.3 | 4.0 | 4.7 | 4.6 | 4.2 |
| hsa-miR-0135a-5p | 3.0 | 2.8 | 4.3 | 2.9 | 2.6 | 1.7 | 1.9 | 0.0 | 1.7 |
| hsa-miR-0500b-3p | 4.1 | 4.4 | 4.8 | 4.5 | 4.1 | 4.2 | 4.8 | 4.5 | 4.6 |
| hsa-miR-6823-5p | 1.8 | 3.6 | 3.1 | 2.8 | 2.9 | 3.3 | 3.7 | 4.8 | 3.8 |
| hsa-miR-4767 | 5.5 | 5.3 | 4.7 | 4.5 | 4.2 | 4.2 | 4.0 | 4.3 | 3.7 |
| hsa-miR-6499-3p | 3.6 | 4.7 | 4.4 | 4.4 | 4.4 | 3.9 | 4.3 | 3.2 | 3.8 |
| hsa-miR-6788-5p | 4.0 | 4.2 | 4.4 | 4.3 | 4.0 | 4.6 | 3.8 | 4.1 | 4.1 |
| hsa-miR-1200 | 4.9 | 4.8 | 4.9 | 4.4 | 4.0 | 4.2 | 4.0 | 2.9 | 3.4 |
| hsa-miR-4436a | 3.2 | 4.2 | 4.2 | 3.8 | 3.7 | 3.9 | 3.8 | 3.6 | 4.4 |
| hsa-miR-4700-5p | 3.7 | 4.4 | 4.5 | 5.1 | 4.5 | 4.9 | 3.9 | 5.8 | 4.7 |
| hsa-miR-3928-5p | 4.9 | 5.0 | 4.6 | 4.0 | 3.5 | 4.5 | 3.7 | 3.4 | 3.6 |
| hsa-miR-5006-3p | 3.9 | 3.5 | 3.9 | 4.4 | 4.0 | 4.3 | 4.2 | 4.1 | 4.2 |
| hsa-miR-7152-3p | 4.4 | 4.2 | 5.7 | 4.1 | 4.9 | 4.6 | 5.1 | 5.0 | 5.3 |
| hsa-miR-6504-5p | 4.3 | 3.9 | 4.2 | 4.5 | 4.1 | 4.1 | 4.4 | 4.0 | 4.0 |
| hsa-miR-0602 | 5.4 | 4.3 | 1.8 | 0.0 | 5.6 | 5.0 | 4.2 | 4.8 | 4.7 |
| hsa-miR-0330-5p | 4.4 | 4.1 | 3.8 | 3.5 | 3.6 | 3.8 | 3.0 | 3.3 | 2.9 |
| hsa-miR-0491-5p | 4.7 | 4.6 | 5.0 | 5.1 | 4.9 | 5.8 | 5.6 | 7.4 | 6.2 |
| hsa-miR-6747-5p | 2.8 | 4.1 | 3.7 | 4.3 | 4.8 | 4.7 | 4.8 | 6.8 | 4.9 |
| hsa-miR-6822-3p | 4.2 | 4.5 | 4.6 | 4.4 | 4.2 | 4.5 | 4.7 | 4.0 | 4.6 |
| hsa-miR-7850-5p | 4.0 | 4.1 | 4.1 | 4.7 | 4.1 | 4.2 | 4.0 | 4.6 | 4.6 |
| hsa-miR-0572 | 5.4 | 5.2 | 4.7 | 4.3 | 5.0 | 6.0 | 4.1 | 5.7 | 4.8 |
| hsa-miR-3065-3p | 3.3 | 4.6 | 3.9 | 3.7 | 2.6 | 3.4 | 3.3 | 3.1 | 3.3 |
| hsa-miR-3167 | 0.0 | 0.0 | 0.0 | 0.0 | 0.0 | 0.0 | 0.0 | 0.0 | 0.0 |
| hsa-miR-1273h-3p | 4.6 | 4.7 | 4.9 | 4.1 | 4.6 | 4.4 | 4.2 | 3.7 | 3.7 |
| hsa-miR-3198 | 4.6 | 4.0 | 5.3 | 5.6 | 5.8 | 6.0 | 3.9 | 4.5 | 3.7 |
| hsa-miR-6764-3p | 4.5 | 4.7 | 5.8 | 4.4 | 4.4 | 4.3 | 4.6 | 4.2 | 3.7 |
| hsa-miR-4538 | 3.2 | 3.5 | 4.3 | 4.4 | 4.2 | 3.8 | 4.3 | 5.8 | 4.5 |
| hsa-miR-0378a-3p | 4.4 | 4.9 | 5.4 | 4.1 | 4.6 | 4.2 | 4.5 | 3.8 | 4.2 |
| hsa-miR-3612 | 4.0 | 4.6 | 4.6 | 4.5 | 5.2 | 4.3 | 4.0 | 3.8 | 3.5 |
| hsa-miR-0552-5p | 4.8 | 4.7 | 4.9 | 4.0 | 3.8 | 3.7 | 3.9 | 2.2 | 2.7 |
| hsa-miR-8070 | 3.2 | 3.6 | 4.0 | 3.7 | 3.8 | 4.0 | 4.1 | 3.4 | 3.3 |
| hsa-miR-3689b-3p, hsa-miR-3689c | 4.4 | 4.3 | 4.9 | 4.6 | 4.7 | 4.3 | 4.2 | 4.8 | 4.8 |
| hsa-let-7a-2-3p | 4.2 | 4.8 | 5.0 | 4.4 | 3.5 | 4.0 | 4.0 | 3.6 | 3.4 |
| hsa-miR-0668-3p | 4.8 | 5.2 | 5.0 | 4.8 | 4.3 | 4.7 | 3.9 | 3.7 | 4.0 |
| hsa-miR-0023a-5p | 4.4 | 5.0 | 5.0 | 4.6 | 4.8 | 4.2 | 4.5 | 4.4 | 4.6 |
| hsa-miR-4288 | 4.4 | 4.7 | 6.0 | 4.7 | 3.9 | 4.5 | 5.1 | 3.8 | 4.1 |
| hsa-miR-6077 | 4.5 | 4.9 | 5.7 | 5.7 | 6.6 | 7.4 | 4.7 | 4.1 | 4.3 |
| hsa-miR-0770-5p | 4.9 | 4.9 | 4.4 | 4.3 | 3.5 | 3.4 | 3.9 | 3.7 | 3.3 |
| hsa-miR-1306-3p | 3.9 | 4.0 | 4.2 | 4.5 | 4.3 | 4.0 | 4.5 | 4.0 | 4.2 |
| hsa-miR-3120-5p | 4.2 | 4.2 | 4.6 | 4.1 | 4.3 | 3.9 | 3.9 | 3.8 | 4.1 |
| hsa-miR-0337-3p | 3.8 | 3.9 | 4.0 | 3.5 | 4.0 | 3.9 | 4.0 | 3.3 | 3.5 |
| hsa-miR-6512-3p | 4.6 | 4.7 | 4.9 | 5.0 | 4.6 | 4.5 | 4.4 | 4.7 | 4.3 |
| hsa-miR-1914-5p | 6.1 | 6.1 | 5.7 | 5.0 | 5.0 | 4.6 | 4.4 | 3.9 | 3.6 |
| hsa-miR-3144-3p | 0.0 | 3.5 | 3.9 | 2.8 | 2.1 | 2.9 | 2.9 | 2.5 | 2.8 |
| hsa-miR-0887-5p | 4.9 | 4.3 | 5.3 | 4.7 | 4.8 | 5.2 | 5.3 | 5.2 | 5.2 |
| hsa-miR-3927-5p | 2.5 | 3.5 | 4.3 | 3.8 | 3.9 | 3.7 | 4.0 | 3.8 | 3.7 |
| hsa-miR-3177-5p | 6.1 | 4.9 | 4.1 | 2.9 | 3.8 | 2.8 | 3.8 | 3.6 | 3.6 |
| hsa-miR-3176 | 4.3 | 4.4 | 4.1 | 4.4 | 4.1 | 4.3 | 4.0 | 4.8 | 4.0 |
| hsa-miR-1291 | 3.8 | 4.6 | 4.6 | 4.2 | 3.7 | 3.9 | 3.8 | 3.1 | 3.8 |
| hsa-miR-0891a-5p | 3.5 | 4.3 | 4.0 | 4.2 | 3.6 | 3.6 | 3.6 | 3.9 | 3.5 |
| hsa-miR-4708-3p | 5.2 | 5.0 | 5.1 | 4.8 | 4.6 | 4.7 | 4.2 | 4.4 | 4.3 |
| hsa-miR-5010-5p | 5.0 | 4.8 | 4.9 | 6.0 | 5.0 | 6.3 | 6.5 | 9.5 | 8.0 |
| hsa-miR-6773-3p | 4.5 | 5.0 | 4.9 | 4.6 | 4.0 | 4.8 | 4.6 | 4.2 | 4.9 |
| hsa-miR-5581-3p | 4.7 | 5.3 | 5.6 | 5.0 | 4.7 | 4.8 | 4.7 | 4.4 | 4.4 |
| hsa-miR-0365b-5p | 4.4 | 5.1 | 4.9 | 4.2 | 4.1 | 4.4 | 4.3 | 4.8 | 4.4 |

TABLE 3-continued

| | | | | | | | | | |
|---|---|---|---|---|---|---|---|---|---|
| hsa-miR-4652-5p | 5.2 | 5.1 | 4.9 | 4.6 | 3.6 | 3.3 | 3.7 | 4.1 | 3.4 |
| hsa-miR-0125b-5p | 4.9 | 4.6 | 5.7 | 5.4 | 5.3 | 5.3 | 4.7 | 3.9 | 3.6 |
| hsa-miR-4502 | 1.8 | 3.2 | 4.4 | 3.8 | 1.9 | 3.8 | 3.1 | 4.1 | 3.9 |
| hsa-miR-4673 | 5.2 | 5.4 | 4.2 | 4.7 | 4.8 | 5.8 | 4.3 | 4.6 | 4.3 |
| hsa-miR-5588-3p | 3.2 | 4.1 | 4.4 | 4.1 | 4.2 | 4.1 | 4.2 | 4.2 | 4.2 |
| hsa-miR-0671-3p | 4.4 | 4.6 | 4.9 | 4.1 | 4.1 | 4.9 | 4.0 | 3.9 | 3.8 |
| hsa-miR-5001-3p | 4.1 | 4.2 | 5.0 | 4.3 | 4.2 | 4.1 | 4.3 | 3.8 | 3.8 |
| hsa-miR-6828-5p | 3.3 | 3.6 | 3.9 | 4.0 | 4.2 | 4.8 | 5.2 | 5.2 | 5.1 |
| hsa-miR-4319 | 4.3 | 4.8 | 4.8 | 4.4 | 4.0 | 4.1 | 4.2 | 4.1 | 3.9 |
| hsa-miR-6814-3p | 4.3 | 5.0 | 5.2 | 4.1 | 3.7 | 4.2 | 4.1 | 4.1 | 4.3 |
| hsa-miR-1273f | 3.7 | 4.6 | 4.2 | 4.6 | 5.6 | 4.9 | 4.8 | 4.3 | 5.5 |
| hsa-miR-0099b-3p | 3.9 | 4.2 | 4.6 | 4.3 | 3.5 | 4.0 | 4.2 | 3.6 | 3.7 |
| hsa-miR-3622a-5p | 5.1 | 4.7 | 4.7 | 5.1 | 4.4 | 5.7 | 4.0 | 4.5 | 4.4 |
| hsa-miR-6833-5p | 4.5 | 4.5 | 4.7 | 5.3 | 5.6 | 5.7 | 4.4 | 6.3 | 4.8 |
| hsa-miR-2277-5p | 4.4 | 4.5 | 4.0 | 3.5 | 3.9 | 4.3 | 2.7 | 3.2 | 3.1 |
| hsa-miR-3156-5p | 4.3 | 4.8 | 5.6 | 5.3 | 5.3 | 4.6 | 5.9 | 7.2 | 6.8 |
| hsa-miR-3685 | 4.3 | 4.6 | 5.0 | 4.7 | 4.5 | 4.3 | 4.2 | 3.7 | 3.9 |
| hsa-miR-7976 | 4.1 | 4.7 | 4.7 | 4.3 | 4.4 | 4.4 | 4.3 | 4.2 | 4.1 |
| hsa-miR-3189-3p | 4.4 | 4.3 | 4.5 | 4.5 | 3.6 | 4.1 | 4.6 | 6.6 | 4.8 |
| hsa-miR-0138-1-3p | 4.6 | 4.7 | 4.3 | 4.0 | 3.4 | 3.8 | 3.2 | 3.5 | 3.7 |
| hsa-miR-6789-3p | 4.8 | 5.4 | 5.0 | 4.8 | 4.7 | 5.0 | 4.3 | 4.0 | 4.0 |
| hsa-miR-0661 | 4.6 | 4.8 | 4.8 | 4.5 | 4.5 | 4.0 | 4.5 | 4.1 | 4.3 |
| hsa-miR-4654 | 3.8 | 3.8 | 4.1 | 3.6 | 3.9 | 4.6 | 3.3 | 4.6 | 4.5 |
| hsa-miR-4692 | 2.9 | 3.5 | 4.3 | 3.5 | 2.3 | 3.6 | 4.3 | 4.1 | 4.1 |
| hsa-miR-1471 | 5.1 | 5.0 | 5.3 | 5.2 | 5.3 | 5.4 | 4.8 | 6.5 | 5.4 |
| hsa-miR-3129-5p | 0.0 | 0.0 | 0.0 | 0.0 | 0.0 | 0.0 | 0.0 | 0.0 | 0.0 |
| hsa-miR-6764-5p | 4.3 | 4.5 | 5.0 | 4.2 | 4.0 | 4.2 | 4.7 | 4.0 | 4.1 |
| hsa-miR-4529-3p | 3.9 | 4.5 | 4.5 | 3.8 | 3.0 | 4.0 | 3.0 | 3.4 | 3.7 |
| hsa-miR-0505-5p | 4.8 | 4.5 | 4.8 | 5.3 | 4.8 | 4.7 | 5.3 | 4.9 | 5.5 |
| hsa-miR-6511b-5p | 4.5 | 4.6 | 4.6 | 4.5 | 4.0 | 4.1 | 5.3 | 7.1 | 5.9 |
| hsa-miR-4686 | 3.3 | 4.1 | 4.2 | 3.9 | 2.9 | 3.7 | 4.6 | 4.1 | 4.4 |
| hsa-miR-0551a | 4.7 | 4.7 | 4.1 | 4.4 | 3.7 | 4.0 | 3.5 | 3.2 | 3.9 |
| hsa-miR-6892-5p | 3.7 | 3.9 | 4.5 | 4.7 | 5.3 | 5.7 | 6.5 | 7.6 | 7.3 |
| hsa-miR-3935 | 4.5 | 4.6 | 4.3 | 4.5 | 4.1 | 4.1 | 3.7 | 3.7 | 4.3 |
| hsa-miR-0193a-5p | 4.2 | 3.8 | 4.5 | 5.0 | 4.7 | 4.4 | 4.1 | 5.0 | 4.5 |
| hsa-miR-1293 | 3.5 | 3.8 | 4.3 | 4.0 | 2.8 | 4.0 | 5.0 | 4.2 | 4.8 |
| hsa-miR-4540 | 3.1 | 4.3 | 4.7 | 4.1 | 3.4 | 4.2 | 4.7 | 4.1 | 4.4 |
| hsa-miR-0331-3p | 4.6 | 4.8 | 5.2 | 4.5 | 4.1 | 4.1 | 5.0 | 4.2 | 4.8 |
| hsa-miR-6817-3p | 4.4 | 4.8 | 5.0 | 4.6 | 4.4 | 4.3 | 4.4 | 3.8 | 4.0 |
| hsa-miR-6884-5p | 3.9 | 4.6 | 4.7 | 4.1 | 3.6 | 3.8 | 4.6 | 4.1 | 4.2 |
| hsa-miR-6862-5p | 4.7 | 5.1 | 5.2 | 5.4 | 5.1 | 4.7 | 4.7 | 5.5 | 5.2 |
| hsa-miR-1266-5p | 4.6 | 4.8 | 4.4 | 4.2 | 3.9 | 4.7 | 4.0 | 3.2 | 3.9 |
| hsa-miR-1204 | 4.2 | 4.4 | 4.8 | 4.2 | 4.4 | 4.2 | 4.0 | 4.1 | 3.6 |
| hsa-miR-0030c-1-3p | 6.1 | 5.4 | 6.3 | 6.1 | 6.8 | 7.5 | 5.4 | 4.4 | 4.3 |
| hsa-miR-1468-5p | 3.4 | 3.5 | 3.4 | 3.8 | 3.1 | 2.7 | 2.9 | 2.7 | 3.8 |
| hsa-miR-3127-5p | 1.9 | 2.5 | 2.4 | 2.9 | 2.4 | 4.3 | 2.8 | 2.6 | 2.3 |
| hsa-miR-0527, hsa-miR-518a-5p | 4.4 | 4.0 | 4.2 | 3.5 | 4.4 | 2.3 | 4.7 | 5.1 | 4.9 |
| hsa-miR-4307 | 4.1 | 4.0 | 4.5 | 4.6 | 4.4 | 4.5 | 5.4 | 4.4 | 5.1 |
| hsa-miR-6722-5p | 5.1 | 5.3 | 4.8 | 4.6 | 4.6 | 4.4 | 4.2 | 4.2 | 4.1 |
| hsa-miR-0657 | 5.0 | 4.9 | 5.0 | 5.1 | 4.8 | 5.1 | 4.7 | 4.5 | 4.5 |
| hsa-miR-4684-5p | 4.7 | 5.4 | 4.7 | 4.0 | 4.1 | 3.0 | 3.6 | 4.4 | 2.5 |
| hsa-miR-6780a-3p | 3.3 | 4.5 | 4.9 | 4.8 | 4.6 | 4.9 | 4.6 | 4.4 | 4.6 |
| hsa-miR-0885-3p | 5.2 | 5.6 | 4.6 | 6.2 | 5.7 | 6.9 | 4.5 | 5.0 | 5.2 |
| hsa-miR-0034a-5p | 4.0 | 2.7 | 4.2 | 4.3 | 3.8 | 3.1 | 3.7 | 3.7 | 3.7 |
| hsa-miR-0194-3p | 4.5 | 4.7 | 4.6 | 4.8 | 4.2 | 4.5 | 4.3 | 5.7 | 5.2 |
| hsa-miR-4776-3p | 2.8 | 4.0 | 4.6 | 3.8 | 4.1 | 3.7 | 4.5 | 4.0 | 4.0 |
| hsa-miR-3064-3p | 3.9 | 4.4 | 4.3 | 3.9 | 3.3 | 3.8 | 4.4 | 3.3 | 3.9 |
| hsa-miR-3165 | 0.0 | 2.0 | 2.1 | 1.8 | 0.0 | 0.0 | 1.5 | 3.1 | 2.7 |
| hsa-miR-4473 | 3.4 | 4.1 | 4.9 | 3.3 | 2.4 | 3.1 | 4.1 | 3.3 | 3.9 |
| hsa-miR-0625-5p | 4.8 | 4.3 | 4.1 | 4.2 | 4.2 | 1.7 | 3.1 | 5.5 | 2.8 |
| hsa-miR-4252 | 3.9 | 4.4 | 4.5 | 4.5 | 4.5 | 4.2 | 3.7 | 4.0 | 4.2 |
| hsa-miR-6866-3p | 4.1 | 4.1 | 4.7 | 4.1 | 4.2 | 4.3 | 4.3 | 3.8 | 3.5 |
| hsa-miR-1203 | 5.7 | 5.4 | 5.1 | 5.0 | 5.8 | 6.2 | 4.6 | 3.8 | 3.8 |
| hsa-miR-3934-5p | 2.4 | 4.0 | 4.1 | 3.9 | 3.7 | 4.0 | 3.8 | 4.3 | 4.4 |
| hsa-miR-4647 | 1.8 | 4.0 | 4.7 | 4.4 | 3.9 | 4.1 | 4.1 | 4.4 | 4.2 |
| hsa-miR-4711-3p | 4.0 | 4.1 | 4.7 | 4.1 | 3.8 | 3.3 | 3.6 | 4.2 | 4.6 |
| hsa-miR-4436b-3p | 3.3 | 3.7 | 4.4 | 4.6 | 4.5 | 4.0 | 4.3 | 4.4 | 4.2 |
| hsa-miR-0299-5p | 5.0 | 4.8 | 5.2 | 5.1 | 4.4 | 4.3 | 3.8 | 4.0 | 3.6 |
| hsa-miR-0193b-3p | 5.1 | 5.3 | 5.6 | 5.2 | 5.1 | 4.8 | 4.2 | 3.5 | 3.4 |
| hsa-miR-3689d | 6.6 | 6.5 | 5.9 | 4.4 | 5.3 | 5.9 | 4.3 | 3.4 | 3.4 |
| hsa-miR-3617-3p | 5.0 | 4.7 | 5.3 | 5.1 | 4.9 | 4.6 | 5.1 | 4.6 | 4.6 |
| hsa-miR-6876-5p | 4.3 | 4.2 | 4.7 | 4.3 | 4.6 | 5.5 | 5.0 | 4.5 | 4.8 |
| hsa-miR-6847-5p | 3.3 | 3.9 | 4.7 | 4.2 | 3.9 | 4.1 | 4.7 | 4.5 | 4.2 |
| hsa-miR-0767-3p | 4.4 | 4.8 | 4.9 | 4.4 | 4.5 | 4.7 | 5.4 | 5.1 | 5.0 |
| hsa-miR-4748 | 4.8 | 5.0 | 5.1 | 6.0 | 6.4 | 6.9 | 5.1 | 4.1 | 5.4 |
| hsa-miR-3177-3p | 4.6 | 5.1 | 3.9 | 5.2 | 4.3 | 4.6 | 5.2 | 6.4 | 6.5 |
| hsa-miR-6886-5p | 4.8 | 4.8 | 5.1 | 4.5 | 4.6 | 4.7 | 4.5 | 5.0 | 4.7 |
| hsa-miR-4717-3p | 5.4 | 5.7 | 5.5 | 5.4 | 5.0 | 5.0 | 4.8 | 5.3 | 4.7 |
| hsa-miR-2113 | 3.9 | 4.3 | 5.0 | 4.3 | 4.6 | 4.0 | 4.7 | 3.3 | 4.3 |

TABLE 3-continued

| | | | | | | | | | |
|---|---|---|---|---|---|---|---|---|---|
| hsa-miR-3150b-3p | 3.6 | 4.5 | 4.5 | 4.1 | 3.5 | 4.2 | 4.0 | 3.9 | 4.2 |
| hsa-miR-4326 | 4.6 | 5.4 | 4.9 | 5.0 | 4.3 | 4.7 | 5.2 | 4.3 | 4.7 |
| hsa-miR-0892b | 4.3 | 4.6 | 5.0 | 4.8 | 4.8 | 4.6 | 4.7 | 4.4 | 4.8 |
| hsa-miR-6895-3p | 5.5 | 5.5 | 5.4 | 5.0 | 4.8 | 5.1 | 4.2 | 3.6 | 3.8 |
| hsa-miR-4708-5p | 5.4 | 5.5 | 4.9 | 4.8 | 4.8 | 4.9 | 4.2 | 3.7 | 4.2 |
| hsa-miR-6856-5p | 4.3 | 4.3 | 4.8 | 5.0 | 6.3 | 5.9 | 4.3 | 4.7 | 5.2 |
| hsa-miR-0550a-5p | 4.9 | 5.0 | 4.8 | 4.7 | 4.6 | 5.0 | 4.1 | 4.5 | 4.3 |
| hsa-miR-4324 | 5.1 | 4.5 | 5.2 | 5.1 | 4.7 | 4.6 | 4.4 | 3.8 | 4.0 |
| hsa-miR-4776-5p | 4.6 | 4.5 | 5.0 | 5.1 | 5.0 | 4.6 | 4.2 | 5.7 | 4.7 |
| hsa-miR-0629-3p | 4.7 | 5.1 | 4.9 | 4.7 | 3.6 | 4.6 | 3.9 | 3.5 | 3.8 |
| hsa-miR-1273h-5p | 4.5 | 4.9 | 5.3 | 4.9 | 6.2 | 6.1 | 5.1 | 6.1 | 5.8 |
| hsa-miR-1909-5p | 4.8 | 5.2 | 5.1 | 4.9 | 4.8 | 4.7 | 4.5 | 4.6 | 4.5 |
| hsa-miR-3137 | 3.6 | 3.3 | 4.0 | 4.0 | 3.2 | 4.1 | 4.0 | 5.1 | 4.6 |
| hsa-miR-4780 | 5.1 | 5.4 | 5.2 | 5.0 | 4.7 | 5.0 | 4.7 | 4.0 | 3.4 |
| hsa-miR-8064 | 5.0 | 5.1 | 4.7 | 5.2 | 5.2 | 5.5 | 4.2 | 5.2 | 4.9 |
| hsa-miR-7702 | 4.5 | 5.1 | 5.7 | 4.8 | 4.8 | 4.7 | 4.9 | 4.2 | 4.0 |
| hsa-miR-1181 | 5.8 | 5.7 | 5.4 | 4.9 | 5.2 | 5.3 | 4.4 | 4.2 | 4.6 |
| hsa-miR-4448 | 4.7 | 4.3 | 4.8 | 5.1 | 4.6 | 4.7 | 4.6 | 4.5 | 4.9 |
| hsa-miR-4800-5p | 4.4 | 4.3 | 4.5 | 4.7 | 5.6 | 5.8 | 5.0 | 5.9 | 5.3 |
| hsa-miR-8075 | 3.7 | 4.5 | 4.7 | 4.2 | 4.1 | 4.4 | 4.3 | 4.7 | 5.1 |
| hsa-miR-0494-5p | 4.6 | 4.9 | 5.2 | 4.9 | 4.7 | 4.9 | 4.5 | 4.5 | 4.3 |
| hsa-miR-4506 | 2.1 | 5.1 | 3.9 | 3.0 | 2.6 | 3.6 | 3.8 | 3.7 | 3.7 |
| hsa-miR-3591-3p | 3.9 | 3.8 | 4.3 | 3.6 | 2.4 | 3.7 | 3.7 | 4.3 | 4.8 |
| hsa-miR-0612 | 5.7 | 5.6 | 5.3 | 5.3 | 4.7 | 5.5 | 4.2 | 4.8 | 5.3 |
| hsa-miR-3714 | 3.8 | 5.4 | 5.0 | 4.7 | 4.3 | 5.3 | 4.5 | 4.5 | 5.0 |
| hsa-miR-3616-3p | 6.8 | 7.2 | 5.3 | 6.9 | 5.5 | 6.0 | 4.3 | 4.0 | 4.8 |
| hsa-miR-0211-5p | 4.5 | 4.5 | 4.5 | 4.6 | 5.1 | 4.4 | 4.8 | 4.6 | 4.3 |
| hsa-miR-1287-3p | 4.9 | 5.2 | 5.5 | 4.7 | 4.1 | 4.3 | 4.0 | 3.2 | 3.5 |
| hsa-miR-1538 | 5.6 | 5.6 | 5.3 | 5.3 | 4.5 | 5.0 | 4.8 | 4.7 | 4.6 |
| hsa-miR-3131 | 11.3 | 11.2 | 11.7 | 11.7 | 12.4 | 12.1 | 11.7 | 11.8 | 12.5 |
| hsa-miR-0526a, hsa-miR-520c-5p, hsa-miR-518d-5p | 3.9 | 2.7 | 3.7 | 3.0 | 4.3 | 2.4 | 3.9 | 4.0 | 3.9 |
| hsa-miR-0449c-3p | 5.2 | 5.2 | 5.2 | 4.8 | 4.7 | 4.5 | 4.4 | 4.6 | 4.1 |
| hsa-miR-0636 | 5.6 | 6.0 | 5.4 | 5.1 | 5.2 | 4.9 | 4.5 | 3.9 | 4.0 |
| hsa-miR-0589-5p | 5.1 | 5.4 | 5.5 | 4.8 | 4.4 | 3.6 | 4.4 | 4.0 | 3.4 |
| hsa-miR-6815-3p | 4.8 | 4.6 | 5.3 | 5.1 | 5.3 | 4.9 | 4.8 | 4.6 | 4.8 |
| hsa-miR-6507-3p | 4.5 | 4.6 | 5.3 | 4.6 | 4.6 | 4.5 | 5.5 | 5.1 | 5.4 |
| hsa-miR-6822-5p | 5.3 | 5.4 | 5.4 | 5.2 | 4.7 | 5.3 | 5.2 | 4.7 | 4.6 |
| hsa-miR-7855-5p | 4.5 | 4.2 | 4.7 | 4.4 | 3.9 | 4.6 | 5.7 | 5.3 | 5.5 |
| hsa-miR-4428 | 4.4 | 4.8 | 4.5 | 5.3 | 5.0 | 5.0 | 4.7 | 5.1 | 5.0 |
| hsa-miR-4476 | 5.2 | 5.8 | 5.0 | 5.9 | 5.3 | 7.1 | 4.7 | 4.9 | 5.1 |
| hsa-miR-0129-2-3p | 4.9 | 4.9 | 5.0 | 4.8 | 4.5 | 4.3 | 5.5 | 4.7 | 5.2 |
| hsa-miR-4278 | 5.7 | 5.5 | 5.4 | 5.2 | 5.2 | 4.8 | 5.1 | 4.8 | 4.6 |
| hsa-miR-5685 | 3.9 | 4.4 | 4.8 | 4.1 | 4.0 | 4.5 | 4.4 | 4.5 | 4.4 |
| hsa-miR-0192-5p | 4.6 | 4.5 | 5.1 | 4.5 | 4.4 | 4.4 | 4.0 | 4.1 | 4.1 |
| hsa-miR-4482-3p | 5.1 | 5.5 | 5.4 | 5.1 | 5.4 | 5.5 | 6.3 | 8.1 | 7.3 |
| hsa-miR-1296-5p | 5.4 | 5.3 | 5.2 | 4.5 | 4.7 | 4.5 | 4.5 | 4.0 | 4.3 |
| hsa-miR-0324-3p | 5.2 | 4.6 | 5.6 | 5.1 | 4.9 | 4.8 | 5.1 | 5.3 | 5.2 |
| hsa-miR-6873-5p | 4.6 | 5.3 | 5.8 | 5.2 | 5.4 | 4.6 | 4.4 | 4.4 | 4.5 |
| hsa-miR-6847-3p | 4.1 | 4.7 | 4.8 | 4.7 | 5.0 | 4.7 | 3.9 | 4.5 | 4.6 |
| hsa-miR-5708 | 4.7 | 4.2 | 4.6 | 4.7 | 4.4 | 4.2 | 3.9 | 4.6 | 4.4 |
| hsa-miR-4747-3p | 5.2 | 4.7 | 4.8 | 4.5 | 3.5 | 4.9 | 4.2 | 3.5 | 4.1 |
| hsa-miR-6801-5p | 4.6 | 4.5 | 4.8 | 4.4 | 4.0 | 4.0 | 5.1 | 4.6 | 4.5 |
| hsa-miR-0125a-5p | 4.8 | 5.1 | 5.4 | 5.3 | 5.0 | 4.9 | 4.6 | 3.9 | 3.9 |
| hsa-miR-4269 | 5.5 | 5.8 | 5.4 | 5.2 | 5.4 | 4.5 | 5.2 | 4.2 | 5.0 |
| hsa-miR-6881-3p | 5.1 | 5.4 | 5.6 | 5.4 | 5.3 | 4.8 | 5.3 | 4.7 | 4.9 |
| hsa-miR-4664-5p | 5.5 | 5.4 | 6.6 | 5.2 | 5.8 | 5.4 | 6.2 | 7.3 | 6.8 |
| hsa-miR-0431-3p | 5.1 | 5.4 | 5.3 | 4.5 | 3.8 | 3.8 | 4.6 | 3.9 | 3.7 |
| hsa-miR-6503-5p | 3.3 | 4.6 | 5.6 | 4.5 | 4.4 | 4.9 | 6.1 | 5.2 | 5.6 |
| hsa-miR-6723-5p | 6.1 | 6.4 | 5.4 | 4.8 | 5.0 | 3.9 | 4.5 | 5.5 | 3.5 |
| hsa-miR-7113-5p | 2.9 | 4.4 | 4.8 | 4.5 | 4.1 | 4.4 | 5.2 | 4.4 | 4.6 |
| hsa-miR-2467-3p | 5.0 | 5.1 | 5.0 | 5.2 | 5.2 | 5.2 | 5.0 | 4.8 | 4.9 |
| hsa-miR-3159 | 0.0 | 0.0 | 0.0 | 0.0 | 0.0 | 0.0 | 0.0 | 1.0 | 0.0 |
| hsa-miR-8077 | 4.4 | 4.2 | 4.7 | 4.8 | 5.3 | 4.9 | 4.0 | 5.5 | 5.0 |
| hsa-miR-2682-3p | 5.3 | 5.6 | 5.1 | 4.8 | 5.1 | 4.1 | 4.6 | 4.3 | 4.2 |
| hsa-miR-3162-3p | 6.6 | 6.7 | 6.9 | 6.6 | 6.4 | 6.2 | 7.2 | 6.5 | 7.0 |
| hsa-miR-4639-3p | 4.6 | 4.6 | 4.9 | 4.8 | 5.0 | 4.4 | 5.2 | 4.7 | 4.8 |
| hsa-miR-4725-5p | 5.4 | 5.5 | 5.4 | 5.2 | 5.2 | 5.2 | 4.7 | 4.2 | 4.4 |
| hsa-miR-7151-3p | 4.0 | 4.3 | 4.1 | 4.1 | 3.8 | 4.6 | 4.9 | 5.6 | 4.8 |
| hsa-miR-4306 | 4.4 | 5.0 | 5.2 | 4.6 | 5.2 | 4.0 | 5.8 | 6.4 | 6.4 |
| hsa-miR-0585-5p | 5.1 | 5.7 | 5.4 | 5.1 | 4.7 | 4.9 | 5.5 | 4.2 | 4.7 |
| hsa-miR-4804-3p | 5.0 | 5.2 | 5.5 | 4.6 | 4.6 | 4.5 | 4.5 | 4.2 | 4.1 |
| hsa-miR-4474-3p | 4.0 | 4.5 | 4.4 | 3.8 | 3.7 | 3.8 | 4.3 | 4.3 | 4.6 |
| hsa-miR-6876-3p | 3.7 | 4.8 | 5.5 | 4.6 | 4.2 | 4.4 | 5.0 | 4.5 | 4.5 |
| hsa-miR-1224-5p | 5.1 | 4.8 | 4.9 | 5.3 | 5.1 | 5.1 | 4.7 | 6.7 | 5.5 |
| hsa-miR-6832-3p | 4.9 | 5.4 | 5.6 | 5.2 | 5.5 | 5.4 | 5.1 | 4.4 | 5.0 |
| hsa-miR-0191-3p | 5.5 | 5.0 | 5.6 | 5.2 | 5.1 | 4.5 | 5.6 | 5.2 | 5.5 |
| hsa-miR-4638-5p | 5.4 | 5.4 | 5.2 | 5.8 | 5.7 | 5.7 | 4.9 | 6.2 | 5.3 |
| hsa-miR-4518 | 3.6 | 4.1 | 5.1 | 4.0 | 4.1 | 4.2 | 4.3 | 4.0 | 4.3 |

TABLE 3-continued

| | | | | | | | | | |
|---|---|---|---|---|---|---|---|---|---|
| hsa-miR-4487 | 5.3 | 5.2 | 4.7 | 4.9 | 5.0 | 5.1 | 4.4 | 4.9 | 4.8 |
| hsa-miR-0764 | 5.5 | 5.2 | 5.7 | 5.4 | 4.9 | 5.2 | 5.5 | 4.9 | 5.2 |
| hsa-miR-6767-5p | 4.0 | 4.8 | 5.0 | 4.5 | 5.0 | 4.5 | 4.8 | 4.7 | 4.9 |
| hsa-miR-3944-3p | 5.0 | 5.4 | 5.3 | 4.9 | 5.0 | 5.0 | 5.2 | 5.0 | 4.8 |
| hsa-miR-6829-3p | 5.5 | 5.5 | 5.8 | 5.2 | 5.2 | 5.4 | 5.2 | 4.4 | 4.7 |
| hsa-miR-4292 | 5.9 | 5.4 | 5.2 | 5.0 | 5.0 | 4.9 | 4.9 | 4.8 | 4.7 |
| hsa-miR-4525 | 5.4 | 4.8 | 6.3 | 4.5 | 5.0 | 4.9 | 6.0 | 5.3 | 5.3 |
| hsa-miR-4676-5p | 4.2 | 4.3 | 4.7 | 4.9 | 3.5 | 4.4 | 5.0 | 4.8 | 4.7 |
| hsa-miR-4489 | 4.8 | 4.7 | 4.9 | 5.7 | 5.4 | 5.5 | 5.8 | 7.3 | 6.2 |
| hsa-miR-0615-5p | 6.0 | 5.5 | 4.5 | 5.0 | 4.8 | 5.7 | 5.6 | 6.3 | 6.1 |
| hsa-miR-0342-3p | 4.9 | 4.6 | 4.2 | 4.7 | 4.5 | 4.3 | 3.8 | 3.7 | 4.2 |
| hsa-miR-0550a-3p | 5.4 | 5.2 | 5.2 | 5.2 | 4.6 | 4.4 | 4.7 | 4.6 | 4.7 |
| hsa-miR-4456 | 4.4 | 3.9 | 4.5 | 4.4 | 3.7 | 4.4 | 5.0 | 4.4 | 4.7 |
| hsa-miR-1908-3p | 6.2 | 5.6 | 5.1 | 4.8 | 4.9 | 4.9 | 5.2 | 5.7 | 5.3 |
| hsa-miR-3135b | 7.8 | 7.4 | 7.6 | 6.1 | 7.4 | 7.7 | 7.0 | 7.7 | 6.9 |
| hsa-miR-1539 | 5.9 | 6.0 | 6.0 | 5.6 | 5.3 | 5.3 | 4.9 | 4.8 | 4.6 |
| hsa-miR-3132 | 3.5 | 4.2 | 4.8 | 4.5 | 4.7 | 5.2 | 4.3 | 3.9 | 4.2 |
| hsa-miR-4709-3p | 5.1 | 5.7 | 5.8 | 5.0 | 5.0 | 5.3 | 4.9 | 5.1 | 5.3 |
| hsa-let-7f-1-3p | 5.2 | 5.5 | 5.4 | 5.1 | 4.8 | 5.1 | 5.9 | 5.1 | 5.5 |
| hsa-miR-4305 | 4.5 | 4.6 | 4.9 | 5.0 | 4.9 | 4.8 | 5.1 | 4.8 | 4.6 |
| hsa-miR-6770-3p | 5.3 | 5.0 | 4.9 | 2.7 | 4.6 | 4.7 | 3.6 | 5.5 | 4.1 |
| hsa-miR-4732-5p | 5.2 | 5.1 | 5.9 | 5.3 | 5.7 | 6.0 | 5.4 | 5.0 | 5.1 |
| hsa-miR-6716-3p | 4.6 | 4.8 | 4.9 | 4.4 | 4.0 | 4.7 | 4.9 | 3.6 | 5.1 |
| hsa-miR-0483-5p | 4.6 | 4.8 | 4.8 | 5.2 | 5.9 | 6.5 | 4.8 | 4.4 | 4.6 |
| hsa-miR-1226-3p | 5.1 | 5.4 | 5.7 | 5.1 | 4.9 | 4.9 | 4.9 | 4.3 | 4.7 |
| hsa-miR-6883-5p | 5.3 | 5.4 | 6.0 | 5.4 | 6.1 | 5.8 | 5.9 | 6.0 | 5.5 |
| hsa-miR-6834-5p | 4.2 | 4.4 | 4.4 | 5.0 | 4.9 | 4.6 | 5.1 | 6.3 | 5.9 |
| hsa-miR-6849-3p | 5.1 | 5.0 | 5.1 | 5.3 | 5.1 | 4.8 | 4.5 | 4.9 | 4.5 |
| hsa-miR-3667-3p | 4.1 | 5.1 | 5.3 | 4.7 | 4.8 | 5.0 | 4.7 | 4.7 | 4.9 |
| hsa-miR-4669 | 4.2 | 5.0 | 5.2 | 5.0 | 5.4 | 4.8 | 5.1 | 5.0 | 5.3 |
| hsa-miR-4646-5p | 5.3 | 5.5 | 5.5 | 5.7 | 6.0 | 5.3 | 5.8 | 5.4 | 5.9 |
| hsa-miR-4743-5p | 5.2 | 4.6 | 5.2 | 5.3 | 5.3 | 5.1 | 4.8 | 5.6 | 5.9 |
| hsa-let-7d-3p | 4.4 | 4.4 | 4.6 | 4.3 | 3.5 | 3.9 | 4.6 | 4.2 | 4.5 |
| hsa-miR-6872-3p | 5.5 | 6.2 | 6.0 | 5.5 | 6.0 | 5.6 | 5.3 | 5.7 | 5.7 |
| hsa-miR-0526b-5p | 4.5 | 4.6 | 5.3 | 4.5 | 4.7 | 4.4 | 4.7 | 4.5 | 4.5 |
| hsa-miR-0550b-3p | 4.4 | 5.2 | 5.2 | 4.5 | 4.3 | 4.7 | 4.8 | 4.2 | 4.0 |
| hsa-miR-4652-3p | 5.0 | 5.1 | 5.4 | 5.0 | 4.5 | 4.7 | 5.4 | 5.1 | 5.3 |
| hsa-miR-4682 | 3.5 | 4.5 | 4.4 | 4.0 | 3.1 | 4.5 | 4.0 | 4.5 | 4.8 |
| hsa-miR-7851-3p | 5.6 | 5.4 | 4.6 | 4.7 | 5.6 | 4.8 | 5.4 | 5.2 | 6.1 |
| hsa-miR-1323 | 5.7 | 5.5 | 7.0 | 5.6 | 5.6 | 6.4 | 5.9 | 6.4 | 5.9 |
| hsa-miR-3124-5p | 1.9 | 3.7 | 2.0 | 3.0 | 4.1 | 5.1 | 4.4 | 6.4 | 5.9 |
| hsa-miR-6852-3p | 5.1 | 5.1 | 5.8 | 4.8 | 4.5 | 4.6 | 4.8 | 4.4 | 4.5 |
| hsa-miR-4266 | 5.4 | 4.7 | 6.9 | 3.9 | 5.3 | 4.5 | 5.9 | 4.1 | 5.1 |
| hsa-miR-1247-5p | 5.2 | 5.4 | 5.3 | 5.1 | 4.9 | 4.9 | 5.4 | 4.9 | 5.2 |
| hsa-miR-6836-5p | 6.5 | 5.9 | 4.5 | 3.2 | 4.3 | 3.3 | 4.1 | 3.8 | 4.5 |
| hsa-miR-0520b | 3.7 | 3.0 | 4.5 | 3.4 | 4.3 | 3.2 | 5.0 | 5.7 | 6.2 |
| hsa-miR-3649 | 6.1 | 5.4 | 6.3 | 7.0 | 8.5 | 9.0 | 6.4 | 5.2 | 6.1 |
| hsa-miR-6782-5p | 5.2 | 5.9 | 4.7 | 5.4 | 6.5 | 6.8 | 5.3 | 6.2 | 5.8 |
| hsa-miR-6878-3p | 4.5 | 5.3 | 5.4 | 4.7 | 5.2 | 4.9 | 4.8 | 4.9 | 5.0 |
| hsa-miR-3646 | 5.4 | 5.8 | 5.8 | 5.6 | 4.8 | 5.4 | 4.8 | 4.8 | 4.6 |
| hsa-miR-0520d-5p | 4.7 | 4.3 | 4.6 | 4.2 | 4.8 | 2.9 | 5.2 | 6.0 | 5.7 |
| hsa-miR-1182 | 4.8 | 4.5 | 4.9 | 4.4 | 4.1 | 3.8 | 5.6 | 5.4 | 5.3 |
| hsa-miR-6837-5p | 5.1 | 5.2 | 4.9 | 4.9 | 4.8 | 5.6 | 4.7 | 4.5 | 4.8 |
| hsa-miR-0098-3p | 5.4 | 5.0 | 5.8 | 5.1 | 4.7 | 4.9 | 5.9 | 5.4 | 5.8 |
| hsa-miR-3650 | 5.3 | 5.5 | 5.4 | 4.9 | 3.8 | 4.7 | 5.2 | 4.6 | 4.5 |
| hsa-miR-0130b-5p | 5.7 | 6.0 | 5.8 | 5.1 | 4.9 | 4.5 | 4.7 | 5.0 | 4.5 |
| hsa-miR-4701-3p | 4.9 | 4.4 | 5.0 | 4.5 | 3.9 | 4.6 | 4.4 | 5.0 | 4.7 |
| hsa-miR-1273g-3p | 5.0 | 5.2 | 5.3 | 5.2 | 6.8 | 6.1 | 5.3 | 6.2 | 6.7 |
| hsa-miR-3689a-3p | 4.0 | 4.4 | 4.6 | 4.4 | 3.8 | 4.2 | 4.3 | 4.8 | 4.5 |
| hsa-miR-0187-3p | 4.7 | 4.8 | 4.8 | 4.3 | 3.9 | 4.2 | 5.1 | 4.4 | 4.7 |
| hsa-miR-5100 | 5.6 | 5.3 | 5.2 | 4.7 | 6.4 | 5.5 | 4.7 | 5.5 | 5.1 |
| hsa-miR-6514-3p | 4.4 | 4.8 | 4.8 | 4.7 | 4.3 | 4.6 | 4.4 | 4.5 | 4.5 |
| hsa-miR-0133a-3p | 5.3 | 5.2 | 5.6 | 5.2 | 4.9 | 4.3 | 5.6 | 4.7 | 5.0 |
| hsa-miR-0519d-3p | 5.4 | 5.6 | 5.9 | 5.2 | 5.0 | 5.1 | 5.2 | 4.4 | 4.7 |
| hsa-miR-0326 | 5.7 | 5.8 | 5.8 | 5.4 | 5.0 | 5.3 | 4.8 | 4.2 | 4.4 |
| hsa-miR-6766-5p | 6.2 | 6.4 | 5.1 | 7.2 | 6.6 | 6.6 | 5.9 | 6.7 | 7.1 |
| hsa-miR-4732-3p | 5.4 | 5.0 | 5.6 | 5.2 | 5.2 | 4.7 | 4.8 | 4.6 | 4.8 |
| hsa-miR-3189-5p | 5.6 | 5.3 | 5.8 | 5.4 | 5.0 | 5.0 | 5.6 | 5.1 | 5.4 |
| hsa-miR-5088-3p | 5.1 | 5.6 | 5.7 | 5.3 | 5.4 | 5.6 | 5.2 | 5.2 | 5.2 |
| hsa-miR-4648 | 5.6 | 5.8 | 5.1 | 4.1 | 5.2 | 6.0 | 4.6 | 5.3 | 5.1 |
| hsa-miR-0183-3p | 5.1 | 5.3 | 5.2 | 6.5 | 7.4 | 7.8 | 5.6 | 4.9 | 6.4 |
| hsa-miR-8073 | 5.7 | 6.2 | 5.7 | 5.4 | 5.6 | 6.2 | 5.4 | 6.8 | 6.0 |
| hsa-miR-6508-5p | 5.6 | 6.1 | 6.2 | 5.5 | 5.2 | 5.2 | 5.0 | 4.6 | 4.6 |
| hsa-miR-6830-3p | 4.6 | 5.2 | 5.5 | 5.1 | 5.2 | 5.3 | 5.4 | 4.6 | 5.2 |
| hsa-miR-0409-3p | 5.3 | 5.0 | 5.9 | 5.4 | 5.4 | 4.8 | 6.1 | 5.6 | 5.9 |
| hsa-miR-0564 | 4.6 | 4.7 | 4.8 | 4.2 | 3.7 | 4.6 | 3.9 | 4.6 | 4.7 |
| hsa-miR-4533 | 5.9 | 5.5 | 5.3 | 5.5 | 5.0 | 5.1 | 4.8 | 5.6 | 5.3 |
| hsa-miR-0134-5p | 6.1 | 6.1 | 5.6 | 6.4 | 5.9 | 5.9 | 5.5 | 5.2 | 5.2 |
| hsa-miR-4312 | 5.9 | 5.8 | 6.1 | 5.5 | 5.6 | 5.4 | 5.7 | 5.5 | 5.5 |
| hsa-miR-6509-3p | 4.1 | 5.1 | 5.0 | 4.7 | 4.7 | 4.8 | 4.3 | 4.6 | 4.5 |

TABLE 3-continued

| | | | | | | | | | |
|---|---|---|---|---|---|---|---|---|---|
| hsa-miR-7152-5p | 4.7 | 5.2 | 5.8 | 5.4 | 5.0 | 5.1 | 5.4 | 5.2 | 5.3 |
| hsa-miR-0346 | 5.3 | 5.7 | 5.8 | 5.3 | 5.4 | 5.1 | 4.4 | 4.6 | 4.4 |
| hsa-miR-3653-5p | 5.0 | 5.2 | 5.4 | 5.1 | 5.3 | 5.2 | 5.6 | 5.1 | 5.5 |
| hsa-miR-6775-3p | 5.9 | 5.8 | 5.9 | 5.3 | 5.2 | 5.1 | 5.5 | 5.2 | 5.2 |
| hsa-miR-0664a-3p | 5.6 | 5.9 | 6.3 | 5.4 | 5.2 | 5.0 | 5.7 | 5.3 | 5.6 |
| hsa-miR-6859-5p | 4.5 | 4.4 | 5.1 | 4.6 | 4.3 | 4.7 | 5.3 | 5.5 | 5.0 |
| hsa-miR-0632 | 5.2 | 4.8 | 5.9 | 5.8 | 5.0 | 4.8 | 5.2 | 5.0 | 4.9 |
| hsa-miR-6740-5p | 3.8 | 4.8 | 5.0 | 5.0 | 5.1 | 5.3 | 5.2 | 5.0 | 5.2 |
| hsa-miR-1227-3p | 4.6 | 5.3 | 5.6 | 5.0 | 5.2 | 4.9 | 5.6 | 5.0 | 5.4 |
| hsa-miR-5193 | 4.9 | 5.6 | 5.4 | 5.1 | 4.8 | 5.1 | 5.4 | 4.4 | 5.1 |
| hsa-miR-0214-3p | 4.6 | 5.1 | 5.1 | 5.5 | 5.4 | 4.9 | 5.0 | 4.3 | 4.6 |
| hsa-miR-6072 | 4.4 | 4.5 | 4.6 | 4.9 | 3.8 | 4.2 | 5.0 | 5.0 | 4.9 |
| hsa-miR-6133 | 5.2 | 5.8 | 5.9 | 5.7 | 6.0 | 6.1 | 5.7 | 5.7 | 5.5 |
| hsa-miR-4722-3p | 5.8 | 6.0 | 5.7 | 5.4 | 5.5 | 5.6 | 5.3 | 4.7 | 4.8 |
| hsa-miR-2392 | 5.4 | 5.3 | 5.1 | 5.8 | 6.0 | 6.7 | 5.3 | 6.2 | 5.6 |
| hsa-miR-3158-5p | 6.6 | 6.3 | 8.0 | 7.4 | 8.3 | 8.3 | 7.6 | 6.9 | 7.5 |
| hsa-miR-6788-3p | 5.2 | 5.8 | 6.0 | 5.2 | 5.3 | 5.4 | 5.2 | 4.9 | 4.8 |
| hsa-miR-4769-5p | 4.5 | 5.2 | 4.9 | 5.3 | 5.2 | 5.3 | 5.1 | 5.4 | 5.2 |
| hsa-miR-3190-5p | 5.3 | 5.3 | 5.5 | 5.3 | 4.6 | 4.7 | 6.2 | 5.4 | 5.6 |
| hsa-miR-6734-3p | 5.5 | 5.8 | 5.7 | 5.1 | 4.9 | 5.4 | 5.0 | 4.5 | 4.9 |
| hsa-miR-0466 | 4.9 | 4.1 | 4.7 | 4.0 | 3.0 | 4.1 | 4.2 | 4.8 | 4.7 |
| hsa-miR-3187-5p | 6.0 | 5.7 | 5.8 | 4.8 | 4.8 | 4.8 | 4.7 | 5.7 | 5.2 |
| hsa-miR-4297 | 5.0 | 5.5 | 5.7 | 5.5 | 5.5 | 4.7 | 5.3 | 5.0 | 5.1 |
| hsa-miR-6824-3p | 5.7 | 6.2 | 6.2 | 5.4 | 5.3 | 5.3 | 5.5 | 5.3 | 5.0 |
| hsa-miR-6734-5p | 4.9 | 5.1 | 5.2 | 5.2 | 5.4 | 5.8 | 6.0 | 5.9 | 6.2 |
| hsa-miR-0139-3p | 6.5 | 6.5 | 6.2 | 6.1 | 5.8 | 6.4 | 4.9 | 5.1 | 5.4 |
| hsa-miR-3192-3p | 5.6 | 5.7 | 5.9 | 5.4 | 5.1 | 5.4 | 4.9 | 4.6 | 4.7 |
| hsa-miR-6799-3p | 5.7 | 5.6 | 5.8 | 5.3 | 4.9 | 5.3 | 5.7 | 5.4 | 5.5 |
| hsa-miR-4329 | 5.5 | 5.8 | 6.0 | 5.7 | 5.5 | 5.5 | 5.7 | 5.4 | 5.1 |
| hsa-miR-0199b-5p | 5.1 | 5.2 | 5.5 | 5.4 | 4.9 | 4.6 | 5.7 | 4.9 | 5.3 |
| hsa-miR-0885-5p | 5.1 | 5.3 | 5.1 | 5.5 | 5.2 | 5.1 | 4.7 | 4.9 | 5.1 |
| hsa-miR-5589-5p | 4.9 | 5.0 | 4.5 | 4.1 | 4.2 | 4.6 | 4.6 | 6.0 | 5.5 |
| hsa-miR-4539 | 5.3 | 5.6 | 4.9 | 5.0 | 4.9 | 5.4 | 4.8 | 5.9 | 5.3 |
| hsa-miR-0223-3p | 5.2 | 5.5 | 5.8 | 5.3 | 4.9 | 5.2 | 6.3 | 5.4 | 5.8 |
| hsa-miR-6772-3p | 4.7 | 5.4 | 5.7 | 5.1 | 4.9 | 5.0 | 4.7 | 4.9 | 4.6 |
| hsa-miR-6841-3p | 5.5 | 5.2 | 6.1 | 5.3 | 5.4 | 5.3 | 6.1 | 5.7 | 5.7 |
| hsa-miR-4632-3p | 5.8 | 6.4 | 6.0 | 5.1 | 5.2 | 5.4 | 4.5 | 4.0 | 3.9 |
| hsa-miR-4523 | 5.4 | 6.6 | 7.1 | 5.4 | 5.6 | 6.1 | 5.5 | 4.8 | 4.9 |
| hsa-miR-6868-3p | 4.7 | 5.0 | 5.2 | 4.5 | 4.4 | 4.3 | 5.3 | 4.8 | 5.1 |
| hsa-miR-6810-5p | 4.7 | 5.5 | 4.9 | 5.0 | 5.0 | 4.6 | 4.7 | 5.2 | 5.4 |
| hsa-miR-3620-3p | 5.7 | 5.8 | 5.7 | 5.7 | 5.7 | 5.4 | 5.5 | 5.0 | 5.1 |
| hsa-miR-1250-3p | 5.5 | 5.5 | 6.0 | 5.4 | 5.0 | 5.4 | 5.4 | 5.2 | 4.7 |
| hsa-miR-0595 | 4.7 | 5.1 | 5.2 | 4.6 | 4.0 | 4.6 | 5.2 | 5.1 | 5.0 |
| hsa-miR-0513a-5p | 6.6 | 5.7 | 6.1 | 5.6 | 6.2 | 5.3 | 4.8 | 5.0 | 4.6 |
| hsa-miR-4787-3p | 5.6 | 5.8 | 5.9 | 5.3 | 5.4 | 5.6 | 5.2 | 4.8 | 5.1 |
| hsa-miR-0518b | 5.5 | 5.2 | 5.9 | 5.3 | 5.4 | 4.9 | 5.9 | 4.9 | 5.5 |
| hsa-miR-6849-5p | 4.6 | 4.6 | 4.9 | 4.9 | 5.4 | 5.3 | 5.7 | 6.8 | 5.7 |
| hsa-miR-0320b | 5.6 | 6.2 | 5.9 | 6.0 | 5.1 | 5.5 | 6.1 | 5.5 | 5.8 |
| hsa-miR-3064-5p | 5.7 | 5.8 | 5.7 | 5.7 | 5.8 | 5.4 | 4.7 | 5.0 | 4.9 |
| hsa-miR-3166 | 2.2 | 1.3 | 1.3 | 0.0 | 2.7 | 0.0 | 0.0 | 0.0 | 0.0 |
| hsa-miR-4481 | 4.7 | 5.5 | 5.8 | 4.8 | 5.0 | 5.9 | 5.6 | 5.8 | 5.3 |
| hsa-miR-3175 | 5.7 | 7.3 | 6.0 | 7.0 | 6.7 | 7.4 | 5.5 | 5.4 | 6.1 |
| hsa-miR-3180-5p | 6.0 | 6.2 | 6.1 | 5.7 | 5.6 | 5.3 | 5.8 | 5.4 | 5.5 |
| hsa-miR-0615-3p | 5.3 | 5.5 | 5.5 | 5.1 | 4.8 | 4.9 | 4.7 | 5.0 | 4.8 |
| hsa-miR-4449 | 6.3 | 6.5 | 5.6 | 5.2 | 5.9 | 6.5 | 4.6 | 5.6 | 5.4 |
| hsa-miR-4496 | 4.9 | 4.9 | 4.8 | 5.7 | 5.8 | 5.5 | 6.0 | 6.2 | 6.4 |
| hsa-miR-0198 | 5.1 | 4.9 | 5.2 | 5.1 | 5.5 | 5.2 | 6.0 | 5.1 | 5.9 |
| hsa-miR-0026b-3p | 5.5 | 5.3 | 5.4 | 5.3 | 4.8 | 4.9 | 5.3 | 4.5 | 4.9 |
| hsa-miR-0675-3p | 5.7 | 6.0 | 5.8 | 5.6 | 5.3 | 5.5 | 4.7 | 4.7 | 5.2 |
| hsa-miR-0765 | 5.5 | 5.3 | 5.3 | 7.2 | 8.2 | 9.0 | 5.5 | 5.1 | 5.2 |
| hsa-miR-0487a-5p | 4.8 | 4.8 | 5.0 | 5.3 | 5.0 | 4.9 | 4.5 | 4.8 | 5.0 |
| hsa-miR-5189-5p | 4.5 | 4.8 | 4.5 | 4.4 | 3.9 | 4.7 | 4.2 | 5.5 | 5.3 |
| hsa-miR-6871-5p | 4.2 | 4.9 | 5.3 | 4.8 | 4.8 | 4.8 | 4.6 | 6.9 | 5.5 |
| hsa-miR-0575 | 6.2 | 5.8 | 5.6 | 6.3 | 6.8 | 8.5 | 5.3 | 4.9 | 5.9 |
| hsa-miR-1910-5p | 6.0 | 6.1 | 5.8 | 5.6 | 5.2 | 5.4 | 4.8 | 4.6 | 4.6 |
| hsa-miR-3139 | 0.0 | 0.0 | 0.0 | 0.0 | 0.0 | 0.0 | 0.0 | 0.0 | 0.0 |
| hsa-miR-6762-3p | 5.2 | 5.4 | 5.9 | 4.9 | 5.2 | 5.5 | 5.0 | 5.2 | 5.2 |
| hsa-miR-4251 | 6.1 | 5.4 | 5.5 | 5.9 | 6.1 | 6.2 | 4.6 | 4.9 | 4.7 |
| hsa-miR-6790-3p | 5.8 | 6.0 | 6.3 | 5.2 | 5.5 | 5.5 | 6.0 | 5.7 | 5.8 |
| hsa-miR-6751-5p | 4.2 | 5.3 | 5.1 | 4.8 | 5.2 | 5.9 | 5.0 | 6.0 | 5.6 |
| hsa-miR-3173-3p | 5.5 | 5.9 | 5.4 | 5.4 | 5.5 | 5.6 | 3.4 | 3.4 | 3.5 |
| hsa-miR-6783-3p | 5.1 | 5.2 | 5.6 | 5.3 | 5.2 | 5.3 | 5.7 | 5.2 | 5.0 |
| hsa-miR-6793-5p | 5.0 | 5.1 | 5.6 | 4.6 | 4.9 | 5.0 | 5.4 | 5.2 | 5.1 |
| hsa-miR-1193 | 6.4 | 6.0 | 6.0 | 6.2 | 5.9 | 6.0 | 5.1 | 5.7 | 6.2 |
| hsa-miR-0637 | 5.4 | 5.8 | 5.4 | 5.8 | 5.3 | 5.8 | 5.5 | 5.5 | 5.2 |
| hsa-miR-6738-3p | 4.7 | 5.0 | 5.4 | 4.6 | 4.2 | 4.8 | 6.1 | 5.3 | 5.0 |
| hsa-miR-0223-5p | 5.8 | 6.3 | 6.3 | 5.2 | 4.5 | 3.8 | 4.2 | 3.6 | 3.1 |
| hsa-miR-3940-3p | 5.7 | 5.8 | 5.8 | 5.6 | 5.5 | 5.4 | 5.1 | 5.0 | 5.0 |
| hsa-miR-6893-3p | 5.4 | 5.7 | 5.6 | 5.2 | 5.3 | 5.5 | 5.0 | 5.2 | 5.3 |
| hsa-miR-0342-5p | 5.3 | 5.4 | 5.2 | 5.1 | 4.4 | 4.5 | 5.9 | 6.1 | 6.4 |

TABLE 3-continued

| | | | | | | | | | |
|---|---|---|---|---|---|---|---|---|---|
| hsa-miR-1307-3p | 5.9 | 5.4 | 5.5 | 5.2 | 5.5 | 5.4 | 5.2 | 5.6 | 5.6 |
| hsa-miR-3121-5p | 0.0 | 0.0 | 1.8 | 0.0 | 0.0 | 0.0 | 0.0 | 0.0 | 0.0 |
| hsa-miR-6131 | 5.4 | 5.9 | 4.9 | 4.9 | 5.5 | 5.9 | 6.1 | 9.4 | 6.5 |
| hsa-miR-0485-3p | 5.4 | 5.3 | 5.6 | 5.5 | 5.4 | 5.2 | 5.4 | 4.8 | 5.1 |
| hsa-miR-5088-5p | 5.6 | 5.8 | 5.7 | 5.9 | 5.7 | 6.0 | 5.4 | 4.9 | 5.0 |
| hsa-miR-0642a-5p | 5.7 | 6.0 | 6.1 | 5.7 | 5.6 | 6.1 | 5.3 | 4.5 | 4.9 |
| hsa-miR-1470 | 5.9 | 6.4 | 6.0 | 5.6 | 5.6 | 5.4 | 5.8 | 5.4 | 5.8 |
| hsa-miR-3129-3p | 3.4 | 2.9 | 2.5 | 2.8 | 1.8 | 2.5 | 2.0 | 2.1 | 2.9 |
| hsa-miR-5002-3p | 4.7 | 5.2 | 4.9 | 4.5 | 4.0 | 4.5 | 4.5 | 5.0 | 4.8 |
| hsa-miR-0664b-3p | 6.0 | 5.6 | 6.1 | 5.7 | 5.4 | 5.4 | 5.4 | 5.0 | 5.3 |
| hsa-miR-4322 | 6.3 | 6.0 | 6.0 | 5.6 | 5.7 | 6.0 | 5.2 | 6.1 | 5.4 |
| hsa-miR-4535 | 5.9 | 5.9 | 5.4 | 5.3 | 5.5 | 5.3 | 4.6 | 6.2 | 5.4 |
| hsa-miR-1233-3p | 6.1 | 6.4 | 6.2 | 5.7 | 5.6 | 5.5 | 4.8 | 4.5 | 4.8 |
| hsa-miR-6825-3p | 6.0 | 6.1 | 5.8 | 5.6 | 5.7 | 5.8 | 4.9 | 4.9 | 4.8 |
| hsa-miR-6769b-3p | 5.6 | 5.9 | 6.1 | 5.5 | 5.5 | 5.7 | 5.5 | 4.9 | 5.1 |
| hsa-miR-4290 | 5.5 | 5.9 | 5.6 | 5.5 | 5.4 | 5.6 | 5.0 | 4.9 | 5.1 |
| hsa-miR-0874-3p | 6.5 | 6.1 | 5.9 | 8.0 | 7.3 | 7.1 | 5.4 | 5.4 | 7.0 |
| hsa-miR-0532-3p | 5.8 | 6.2 | 5.7 | 6.0 | 5.4 | 5.8 | 5.1 | 5.0 | 5.0 |
| hsa-miR-6744-3p | 5.7 | 6.0 | 6.5 | 5.8 | 6.0 | 5.7 | 5.5 | 5.1 | 5.7 |
| hsa-miR-0030d-5p | 5.9 | 5.7 | 6.3 | 5.4 | 5.4 | 4.9 | 6.2 | 5.8 | 6.0 |
| hsa-miR-3652 | 5.9 | 5.7 | 5.3 | 5.4 | 5.9 | 6.4 | 5.0 | 6.6 | 6.2 |
| hsa-miR-4710 | 5.5 | 6.1 | 6.0 | 5.7 | 5.2 | 5.5 | 5.6 | 6.2 | 5.4 |
| hsa-miR-5195-5p | 5.0 | 5.7 | 5.9 | 5.4 | 5.3 | 5.2 | 6.7 | 5.7 | 6.2 |
| hsa-miR-6812-3p | 6.0 | 6.5 | 6.4 | 5.7 | 5.5 | 5.4 | 6.3 | 5.7 | 5.9 |
| hsa-let-7b-3p | 5.6 | 5.7 | 5.9 | 5.5 | 5.2 | 5.4 | 6.1 | 5.3 | 5.6 |
| hsa-miR-0483-3p | 6.0 | 5.8 | 6.1 | 5.8 | 5.8 | 5.7 | 5.4 | 5.0 | 5.2 |
| hsa-miR-7106-3p | 5.6 | 6.0 | 6.2 | 5.6 | 5.5 | 5.4 | 5.6 | 5.2 | 5.1 |
| hsa-miR-0199a-5p | 5.6 | 5.6 | 5.7 | 5.4 | 5.1 | 4.8 | 5.5 | 4.9 | 5.0 |
| hsa-miR-0188-5p | 6.6 | 6.9 | 7.0 | 6.1 | 6.1 | 6.0 | 5.9 | 6.8 | 6.3 |
| hsa-miR-6737-3p | 5.7 | 5.6 | 6.0 | 5.7 | 5.4 | 5.4 | 6.1 | 5.6 | 5.9 |
| hsa-miR-6796-5p | 5.3 | 5.6 | 5.5 | 5.4 | 5.1 | 5.5 | 5.3 | 8.4 | 6.6 |
| hsa-miR-7843-5p | 5.8 | 5.8 | 6.6 | 5.7 | 6.0 | 6.2 | 6.0 | 6.2 | 5.9 |
| hsa-miR-4498 | 4.9 | 5.7 | 5.8 | 5.3 | 5.1 | 5.6 | 5.0 | 5.5 | 5.7 |
| hsa-miR-5010-3p | 5.3 | 5.7 | 5.7 | 5.4 | 5.3 | 5.3 | 6.2 | 5.3 | 5.7 |
| hsa-miR-8060 | 5.2 | 5.3 | 5.9 | 5.7 | 5.9 | 5.6 | 5.7 | 6.2 | 6.2 |
| hsa-miR-0487b-5p | 5.0 | 5.9 | 5.4 | 5.3 | 5.0 | 5.2 | 5.5 | 4.9 | 5.1 |
| hsa-miR-6831-3p | 5.2 | 5.7 | 6.0 | 6.4 | 5.8 | 5.8 | 5.6 | 5.0 | 5.5 |
| hsa-miR-0320a | 6.5 | 6.7 | 6.7 | 6.5 | 5.9 | 6.0 | 6.3 | 5.6 | 6.0 |
| hsa-miR-6771-3p | 5.5 | 5.4 | 5.7 | 5.5 | 5.1 | 5.5 | 6.4 | 5.7 | 6.1 |
| hsa-miR-6511a-3p | 5.1 | 5.9 | 6.0 | 5.5 | 5.8 | 5.8 | 5.9 | 5.4 | 5.4 |
| hsa-miR-0374c-3p | 6.4 | 6.6 | 7.1 | 6.2 | 6.0 | 6.0 | 5.2 | 4.0 | 3.8 |
| hsa-miR-8052 | 6.0 | 6.2 | 5.9 | 6.0 | 6.0 | 6.1 | 5.6 | 5.9 | 5.6 |
| hsa-miR-4531 | 2.2 | 2.6 | 3.9 | 2.4 | 3.9 | 3.2 | 5.7 | 6.0 | 6.3 |
| hsa-miR-6790-5p | 5.6 | 6.4 | 5.8 | 6.0 | 5.7 | 6.3 | 5.6 | 6.5 | 6.0 |
| hsa-miR-6883-3p | 4.9 | 5.4 | 5.6 | 5.3 | 5.1 | 5.0 | 5.6 | 5.0 | 5.2 |
| hsa-miR-4655-3p | 6.6 | 6.2 | 5.7 | 6.2 | 5.6 | 4.3 | 5.0 | 5.0 | 5.3 |
| hsa-miR-5189-3p | 5.4 | 5.6 | 5.9 | 5.1 | 4.8 | 5.8 | 5.5 | 5.1 | 5.2 |
| hsa-miR-6753-3p | 5.7 | 5.5 | 5.8 | 5.0 | 4.7 | 5.4 | 5.6 | 5.2 | 5.2 |
| hsa-miR-4455 | 7.0 | 6.5 | 6.1 | 5.1 | 5.1 | 5.2 | 6.1 | 5.4 | 5.5 |
| hsa-miR-3605-3p | 5.6 | 5.7 | 5.5 | 5.3 | 4.9 | 5.0 | 5.4 | 5.1 | 5.1 |
| hsa-miR-4642 | 5.6 | 5.8 | 5.9 | 5.6 | 5.3 | 5.2 | 6.1 | 5.6 | 5.7 |
| hsa-miR-7160-5p | 5.4 | 5.6 | 6.1 | 5.0 | 5.6 | 5.5 | 5.8 | 6.0 | 5.8 |
| hsa-miR-5008-5p | 6.8 | 6.4 | 6.3 | 5.8 | 5.6 | 5.7 | 5.2 | 4.8 | 4.1 |
| hsa-miR-1292-3p | 6.4 | 7.1 | 6.6 | 6.1 | 6.1 | 5.7 | 6.1 | 5.4 | 6.0 |
| hsa-miR-6753-5p | 6.1 | 6.6 | 6.6 | 5.9 | 6.4 | 6.1 | 5.5 | 5.4 | 5.6 |
| hsa-miR-4649-3p | 5.7 | 6.0 | 6.1 | 5.7 | 5.6 | 5.7 | 6.3 | 5.6 | 6.0 |
| hsa-miR-7846-3p | 5.6 | 6.1 | 5.9 | 6.1 | 6.6 | 6.8 | 6.7 | 7.1 | 6.7 |
| hsa-miR-0936 | 7.0 | 6.9 | 6.6 | 6.1 | 6.3 | 5.6 | 5.9 | 5.9 | 5.9 |
| hsa-miR-0504-3p | 5.6 | 6.1 | 5.7 | 5.3 | 5.4 | 6.1 | 5.5 | 5.6 | 5.9 |
| hsa-miR-4746-3p | 6.7 | 6.8 | 6.3 | 6.1 | 6.6 | 6.8 | 5.6 | 6.0 | 6.1 |
| hsa-miR-6833-3p | 5.9 | 5.7 | 5.8 | 5.7 | 5.6 | 5.7 | 5.2 | 5.4 | 5.3 |
| hsa-miR-4279 | 6.1 | 6.3 | 6.1 | 6.1 | 5.9 | 6.4 | 5.7 | 5.4 | 5.9 |
| hsa-miR-6776-5p | 5.3 | 5.3 | 5.1 | 5.2 | 6.0 | 6.3 | 5.6 | 7.1 | 6.1 |
| hsa-miR-6748-3p | 5.3 | 5.7 | 6.0 | 5.4 | 5.3 | 5.5 | 5.6 | 5.2 | 5.3 |
| hsa-miR-4721 | 5.5 | 5.8 | 5.7 | 5.4 | 4.9 | 5.5 | 5.4 | 6.5 | 5.8 |
| hsa-miR-0185-3p | 6.2 | 5.6 | 5.5 | 5.2 | 5.4 | 5.3 | 5.3 | 7.9 | 6.6 |
| hsa-miR-6735-3p | 5.9 | 6.3 | 6.4 | 6.1 | 6.0 | 6.0 | 6.0 | 5.4 | 5.6 |
| hsa-miR-4287 | 6.5 | 6.2 | 7.3 | 6.2 | 5.9 | 6.3 | 5.8 | 5.1 | 5.3 |
| hsa-miR-3173-5p | 4.8 | 5.2 | 5.5 | 4.8 | 4.6 | 4.9 | 5.7 | 5.4 | 5.3 |
| hsa-miR-6782-3p | 5.7 | 6.1 | 6.7 | 5.8 | 5.6 | 5.9 | 6.7 | 5.9 | 6.3 |
| hsa-miR-7112-5p | 6.5 | 6.9 | 6.2 | 5.7 | 5.6 | 6.3 | 4.7 | 5.1 | 5.3 |
| hsa-miR-6794-3p | 6.1 | 6.2 | 6.5 | 5.8 | 5.9 | 5.9 | 5.9 | 5.1 | 5.5 |
| hsa-miR-6757-3p | 5.7 | 6.0 | 6.2 | 5.8 | 5.3 | 5.7 | 6.6 | 5.9 | 6.2 |
| hsa-miR-3622a-3p | 6.1 | 5.8 | 5.9 | 5.4 | 5.3 | 5.2 | 5.0 | 5.4 | 5.1 |
| hsa-miR-6726-3p | 6.2 | 6.5 | 6.3 | 5.9 | 6.1 | 6.0 | 5.5 | 5.5 | 5.1 |
| hsa-miR-0642b-5p | 5.6 | 5.7 | 6.3 | 5.8 | 5.7 | 5.9 | 6.0 | 5.3 | 5.3 |
| hsa-miR-6809-3p | 5.2 | 5.6 | 5.7 | 5.4 | 5.3 | 5.5 | 5.3 | 5.4 | 5.4 |
| hsa-miR-6857-5p | 6.3 | 6.4 | 6.0 | 5.5 | 6.4 | 6.1 | 5.5 | 5.7 | 5.2 |
| hsa-miR-0197-3p | 5.9 | 6.0 | 6.0 | 5.8 | 5.7 | 5.4 | 5.5 | 5.3 | 5.2 |
| hsa-miR-0149-5p | 5.8 | 5.8 | 5.9 | 5.7 | 5.9 | 5.6 | 5.2 | 5.3 | 5.3 |

TABLE 3-continued

| | | | | | | | | | |
|---|---|---|---|---|---|---|---|---|---|
| hsa-miR-4485-5p | 6.1 | 6.2 | 6.2 | 5.8 | 5.8 | 5.9 | 5.5 | 5.5 | 5.4 |
| hsa-miR-0939-3p | 5.9 | 6.4 | 6.4 | 5.9 | 6.1 | 6.0 | 6.1 | 5.5 | 5.7 |
| hsa-miR-6780b-3p | 5.5 | 5.8 | 6.0 | 5.6 | 5.5 | 5.8 | 6.1 | 5.5 | 5.6 |
| hsa-miR-6748-5p | 5.1 | 5.6 | 5.3 | 5.9 | 6.1 | 5.6 | 6.0 | 8.2 | 7.0 |
| hsa-miR-6751-3p | 5.9 | 6.3 | 6.2 | 6.0 | 6.0 | 6.0 | 5.7 | 5.2 | 5.4 |
| hsa-miR-4736 | 6.1 | 5.5 | 6.1 | 5.3 | 6.2 | 6.1 | 5.4 | 5.7 | 6.2 |
| hsa-miR-6778-3p | 5.2 | 5.6 | 6.1 | 5.6 | 5.2 | 5.2 | 5.8 | 5.4 | 5.6 |
| hsa-miR-6827-3p | 5.6 | 5.9 | 6.1 | 5.8 | 5.4 | 5.7 | 6.1 | 5.6 | 5.9 |
| hsa-miR-5698 | 5.6 | 5.9 | 6.2 | 7.1 | 7.0 | 8.1 | 6.8 | 6.9 | 7.4 |
| hsa-miR-0371b-5p | 6.9 | 6.8 | 5.9 | 5.8 | 5.8 | 7.1 | 4.6 | 5.9 | 5.4 |
| hsa-miR-4714-5p | 5.9 | 5.9 | 5.9 | 5.7 | 5.5 | 5.6 | 6.4 | 5.6 | 6.0 |
| hsa-miR-6772-5p | 5.3 | 5.5 | 5.3 | 4.8 | 5.2 | 5.4 | 5.2 | 6.3 | 5.9 |
| hsa-miR-4462 | 6.1 | 6.2 | 6.5 | 7.2 | 6.0 | 7.0 | 5.8 | 5.7 | 5.6 |
| hsa-miR-6793-3p | 5.9 | 6.1 | 6.4 | 5.8 | 5.7 | 5.8 | 6.9 | 6.2 | 6.6 |
| hsa-miR-0328-3p | 6.2 | 6.3 | 6.3 | 6.2 | 5.9 | 6.1 | 5.9 | 5.2 | 5.5 |
| hsa-miR-3202 | 6.2 | 5.4 | 6.3 | 5.5 | 6.9 | 5.6 | 6.3 | 5.8 | 6.0 |
| hsa-miR-6867-5p | 5.8 | 6.1 | 6.7 | 5.9 | 6.0 | 6.0 | 5.7 | 5.2 | 5.4 |
| hsa-miR-0302c-5p | 5.9 | 5.3 | 5.8 | 5.8 | 5.5 | 4.8 | 6.2 | 6.5 | 6.6 |
| hsa-miR-6881-5p | 5.1 | 6.3 | 6.8 | 5.4 | 7.4 | 6.3 | 5.8 | 5.6 | 6.2 |
| hsa-miR-0574-5p | 6.2 | 6.2 | 6.3 | 5.9 | 5.8 | 5.6 | 5.9 | 5.5 | 5.8 |
| hsa-miR-1260b | 6.1 | 6.0 | 6.2 | 5.8 | 5.7 | 5.7 | 5.2 | 5.5 | 5.4 |
| hsa-miR-6834-3p | 5.7 | 6.1 | 6.3 | 5.8 | 5.8 | 5.8 | 6.1 | 5.5 | 5.8 |
| hsa-miR-4763-5p | 6.1 | 6.4 | 6.5 | 6.0 | 6.1 | 5.8 | 5.9 | 5.3 | 5.4 |
| hsa-miR-7110-3p | 5.7 | 6.2 | 6.3 | 5.8 | 5.9 | 6.0 | 5.3 | 5.6 | 5.5 |
| hsa-miR-1825 | 6.1 | 6.3 | 6.1 | 6.1 | 5.7 | 6.1 | 5.8 | 5.4 | 5.5 |
| hsa-miR-3134 | 0.0 | 0.0 | 0.0 | 0.0 | 0.0 | 0.0 | 0.0 | 0.0 | 0.0 |
| hsa-miR-3679-5p | 5.5 | 5.8 | 6.0 | 6.3 | 7.8 | 8.5 | 6.4 | 7.8 | 7.7 |
| hsa-miR-0370-3p | 5.7 | 5.4 | 5.6 | 5.8 | 5.7 | 6.2 | 6.3 | 9.1 | 6.8 |
| hsa-miR-0092a-2-5p | 7.9 | 6.3 | 5.2 | 7.4 | 11.3 | 10.8 | 7.7 | 7.8 | 8.5 |
| hsa-miR-7111-3p | 6.3 | 6.6 | 6.3 | 6.0 | 6.2 | 6.4 | 6.0 | 5.6 | 6.1 |
| hsa-miR-3663-5p | 6.0 | 5.9 | 5.8 | 5.4 | 5.3 | 5.4 | 5.8 | 5.9 | 5.7 |
| hsa-miR-0503-3p | 6.5 | 6.6 | 7.1 | 5.6 | 5.8 | 5.6 | 5.5 | 5.1 | 4.6 |
| hsa-miR-6736-5p | 6.0 | 6.7 | 6.9 | 6.0 | 6.0 | 5.1 | 6.0 | 6.4 | 6.1 |
| hsa-miR-3191-5p | 5.6 | 5.6 | 5.9 | 5.4 | 5.2 | 5.5 | 5.7 | 5.1 | 5.2 |
| hsa-miR-5705 | 6.1 | 6.3 | 6.3 | 5.9 | 6.0 | 6.0 | 5.3 | 5.9 | 5.4 |
| hsa-miR-7977 | 5.8 | 5.9 | 6.0 | 5.4 | 5.7 | 5.7 | 5.9 | 5.6 | 5.5 |
| hsa-miR-6840-5p | 6.3 | 6.4 | 6.8 | 5.7 | 6.0 | 5.5 | 6.5 | 6.3 | 6.4 |
| hsa-miR-6865-3p | 6.1 | 6.3 | 6.2 | 6.0 | 6.0 | 6.0 | 5.8 | 5.3 | 5.4 |
| hsa-miR-6754-3p | 5.8 | 6.0 | 6.2 | 5.4 | 5.5 | 5.7 | 6.1 | 5.7 | 5.7 |
| hsa-miR-6830-5p | 5.7 | 5.5 | 5.8 | 5.4 | 6.4 | 5.7 | 5.9 | 6.7 | 5.8 |
| hsa-miR-6736-3p | 5.4 | 5.9 | 6.4 | 5.9 | 6.0 | 5.7 | 5.9 | 5.7 | 5.7 |
| hsa-miR-6842-5p | 6.2 | 6.2 | 6.7 | 6.3 | 6.8 | 7.3 | 6.4 | 8.3 | 6.6 |
| hsa-miR-6761-3p | 6.2 | 6.0 | 6.2 | 5.6 | 5.3 | 5.6 | 6.0 | 5.5 | 5.7 |
| hsa-miR-1236-3p | 6.0 | 6.4 | 6.4 | 6.0 | 5.9 | 6.3 | 6.6 | 5.8 | 6.2 |
| hsa-miR-5196-3p | 6.3 | 6.2 | 6.4 | 6.2 | 5.8 | 6.0 | 5.6 | 5.5 | 5.5 |
| hsa-miR-1234-3p | 6.3 | 6.7 | 6.5 | 6.2 | 6.0 | 6.2 | 6.4 | 5.7 | 6.0 |
| hsa-miR-3925-5p | 5.5 | 5.4 | 5.8 | 5.5 | 5.9 | 5.6 | 6.2 | 6.4 | 6.5 |
| hsa-miR-6872-5p | 4.7 | 4.3 | 4.7 | 4.6 | 5.6 | 4.7 | 6.6 | 6.1 | 6.9 |
| hsa-miR-4483 | 5.9 | 6.1 | 6.4 | 5.8 | 5.9 | 6.6 | 6.0 | 6.8 | 6.2 |
| hsa-miR-3917 | 5.8 | 6.1 | 5.9 | 6.7 | 6.3 | 8.1 | 8.3 | 10.5 | 9.1 |
| hsa-miR-6877-3p | 6.5 | 6.3 | 6.2 | 6.0 | 6.1 | 6.3 | 5.5 | 5.4 | 5.4 |
| hsa-miR-0520e | 4.7 | 3.7 | 4.5 | 3.8 | 4.4 | 2.4 | 6.3 | 6.3 | 6.5 |
| hsa-miR-4436b-5p | 6.5 | 6.5 | 6.4 | 5.8 | 6.0 | 6.3 | 5.6 | 5.8 | 5.7 |
| hsa-miR-4444 | 4.1 | 4.6 | 3.9 | 4.2 | 4.3 | 3.8 | 8.2 | 6.0 | 7.1 |
| hsa-miR-6759-5p | 5.7 | 6.4 | 6.4 | 4.9 | 5.6 | 5.7 | 5.6 | 6.4 | 5.8 |
| hsa-miR-6511a-5p | 5.9 | 6.3 | 6.4 | 5.8 | 6.0 | 6.1 | 6.4 | 7.2 | 6.6 |
| hsa-miR-4430 | 6.4 | 6.4 | 6.2 | 6.2 | 6.6 | 7.3 | 5.9 | 6.1 | 6.1 |
| hsa-miR-6127 | 5.3 | 5.8 | 5.6 | 5.4 | 5.7 | 6.0 | 6.4 | 8.0 | 6.6 |
| hsa-miR-6740-3p | 5.2 | 5.8 | 6.1 | 5.6 | 5.5 | 5.8 | 6.2 | 5.6 | 5.8 |
| hsa-miR-6747-3p | 5.6 | 6.1 | 6.2 | 5.5 | 5.6 | 5.7 | 5.9 | 5.4 | 5.6 |
| hsa-miR-0133b | 6.2 | 6.1 | 6.3 | 6.0 | 5.6 | 5.5 | 6.5 | 5.9 | 6.2 |
| hsa-miR-4440 | 5.9 | 5.6 | 5.8 | 5.2 | 5.0 | 5.2 | 6.0 | 6.8 | 6.0 |
| hsa-miR-0548q | 6.8 | 7.1 | 6.2 | 6.4 | 6.5 | 6.3 | 5.1 | 5.5 | 5.0 |
| hsa-miR-6741-3p | 5.9 | 6.2 | 6.2 | 6.0 | 5.7 | 6.2 | 5.6 | 5.5 | 5.7 |
| hsa-miR-6779-3p | 6.1 | 6.3 | 6.4 | 5.9 | 5.7 | 5.9 | 5.4 | 5.4 | 5.6 |
| hsa-miR-3622b-5p | 5.5 | 5.6 | 6.1 | 6.0 | 7.0 | 6.9 | 6.1 | 6.2 | 6.8 |
| hsa-miR-6787-3p | 6.0 | 6.2 | 6.2 | 5.7 | 5.5 | 5.6 | 5.3 | 5.3 | 5.4 |
| hsa-miR-6873-3p | 6.1 | 6.2 | 6.2 | 5.8 | 5.6 | 5.5 | 5.7 | 5.2 | 5.1 |
| hsa-miR-4713-5p | 6.3 | 6.4 | 6.4 | 6.2 | 6.1 | 6.0 | 5.8 | 6.0 | 5.9 |
| hsa-miR-6742-3p | 5.8 | 6.5 | 6.9 | 6.1 | 5.8 | 6.0 | 6.7 | 6.2 | 6.4 |
| hsa-miR-0423-5p | 7.1 | 7.0 | 7.4 | 6.7 | 6.7 | 7.3 | 6.2 | 5.6 | 5.7 |
| hsa-miR-0204-3p | 5.4 | 4.9 | 4.7 | 6.1 | 6.3 | 9.3 | 6.2 | 6.6 | 6.9 |
| hsa-miR-6823-3p | 6.0 | 6.2 | 6.4 | 6.2 | 6.2 | 5.9 | 5.7 | 5.8 | 5.7 |
| hsa-miR-6877-5p | 5.8 | 6.2 | 6.4 | 5.8 | 6.7 | 7.0 | 6.4 | 7.0 | 6.1 |
| hsa-miR-4695-3p | 5.7 | 6.0 | 6.3 | 5.5 | 5.4 | 5.7 | 5.8 | 5.7 | 5.7 |
| hsa-miR-0018b-3p | 6.4 | 6.4 | 6.4 | 6.2 | 5.6 | 5.8 | 6.4 | 5.8 | 6.1 |
| hsa-miR-1260a | 6.3 | 6.2 | 6.5 | 6.3 | 6.0 | 5.9 | 6.0 | 5.8 | 5.7 |
| hsa-miR-6803-3p | 6.1 | 6.4 | 6.1 | 6.0 | 5.8 | 6.3 | 5.6 | 5.4 | 5.7 |
| hsa-miR-0211-3p | 7.3 | 6.2 | 6.0 | 7.9 | 7.5 | 7.8 | 6.7 | 7.8 | 7.2 |
| hsa-miR-6875-3p | 6.0 | 5.9 | 6.2 | 5.5 | 5.3 | 5.7 | 6.0 | 5.6 | 5.6 |

TABLE 3-continued

| | | | | | | | | | |
|---|---|---|---|---|---|---|---|---|---|
| hsa-miR-6882-3p | 5.9 | 5.9 | 6.5 | 5.6 | 5.7 | 5.8 | 6.5 | 5.8 | 5.8 |
| hsa-miR-8085 | 5.4 | 6.0 | 5.9 | 6.7 | 6.3 | 6.5 | 6.0 | 5.9 | 6.2 |
| hsa-miR-6750-3p | 5.5 | 6.2 | 6.5 | 5.8 | 5.8 | 5.8 | 5.5 | 5.5 | 5.7 |
| hsa-miR-6879-3p | 6.2 | 6.4 | 6.4 | 6.1 | 6.5 | 6.0 | 5.9 | 5.5 | 5.7 |
| hsa-miR-6867-3p | 6.2 | 6.4 | 6.3 | 5.9 | 5.9 | 6.1 | 6.2 | 5.7 | 5.8 |
| hsa-miR-6890-5p | 6.5 | 6.9 | 7.1 | 6.4 | 6.2 | 5.9 | 6.1 | 5.7 | 5.7 |
| hsa-miR-6894-5p | 6.6 | 6.4 | 6.8 | 6.7 | 6.8 | 7.2 | 6.0 | 7.9 | 6.4 |
| hsa-miR-1306-5p | 6.5 | 6.6 | 6.7 | 6.4 | 6.6 | 6.3 | 6.2 | 6.2 | 6.2 |
| hsa-miR-3121-3p | 0.0 | 0.0 | 0.0 | 0.0 | 0.0 | 0.0 | 0.0 | 0.0 | 0.0 |
| hsa-miR-6886-3p | 5.7 | 6.3 | 6.5 | 5.8 | 6.1 | 6.1 | 5.4 | 5.5 | 6.0 |
| hsa-miR-1267 | 5.7 | 6.1 | 6.3 | 5.9 | 5.7 | 5.8 | 6.9 | 6.4 | 6.5 |
| hsa-miR-6862-3p | 6.1 | 6.4 | 6.6 | 5.9 | 6.1 | 6.2 | 6.0 | 5.6 | 5.8 |
| hsa-miR-4701-5p | 6.1 | 6.2 | 6.4 | 6.1 | 5.8 | 5.8 | 6.6 | 5.8 | 6.3 |
| hsa-miR-6792-5p | 6.9 | 6.8 | 6.9 | 6.7 | 6.4 | 6.4 | 6.6 | 6.2 | 5.8 |
| hsa-miR-4698 | 5.8 | 5.9 | 6.3 | 5.9 | 6.1 | 6.6 | 7.4 | 6.3 | 7.1 |
| hsa-miR-4738-3p | 6.6 | 6.6 | 5.7 | 5.9 | 6.2 | 6.3 | 4.9 | 5.0 | 5.1 |
| hsa-miR-4268 | 6.0 | 6.2 | 6.1 | 5.7 | 5.9 | 6.0 | 5.8 | 5.4 | 5.6 |
| hsa-miR-4664-3p | 6.5 | 6.7 | 6.6 | 6.1 | 5.8 | 6.0 | 6.7 | 6.3 | 6.3 |
| hsa-miR-0877-3p | 6.4 | 6.4 | 6.5 | 6.4 | 6.2 | 6.2 | 5.9 | 5.5 | 6.0 |
| hsa-miR-1304-3p | 6.1 | 6.1 | 6.6 | 6.0 | 5.9 | 5.8 | 6.7 | 6.1 | 6.3 |
| hsa-miR-3118 | 0.0 | 0.0 | 0.0 | 0.0 | 0.0 | 0.0 | 0.0 | 0.0 | 0.0 |
| hsa-miR-6870-3p | 6.1 | 6.5 | 6.8 | 5.9 | 5.8 | 6.1 | 6.7 | 6.3 | 6.5 |
| hsa-miR-0574-3p | 6.6 | 6.8 | 6.7 | 6.7 | 6.4 | 6.1 | 6.1 | 5.7 | 5.8 |
| hsa-miR-4646-3p | 6.0 | 6.4 | 6.6 | 6.2 | 6.1 | 6.4 | 6.4 | 5.7 | 6.0 |
| hsa-miR-6884-3p | 6.2 | 6.3 | 6.9 | 6.1 | 6.5 | 6.3 | 6.7 | 6.1 | 6.4 |
| hsa-miR-0658 | 7.4 | 7.4 | 6.2 | 8.0 | 8.1 | 7.4 | 5.7 | 5.4 | 6.9 |
| hsa-miR-3911 | 6.8 | 6.8 | 7.5 | 7.9 | 9.4 | 7.6 | 6.4 | 5.8 | 6.3 |
| hsa-miR-6743-3p | 6.5 | 6.6 | 6.7 | 6.3 | 6.5 | 6.1 | 6.1 | 5.7 | 5.8 |
| hsa-miR-6870-5p | 6.9 | 6.9 | 6.9 | 7.7 | 7.9 | 8.8 | 7.0 | 6.6 | 7.0 |
| hsa-miR-4685-3p | 6.2 | 6.3 | 6.4 | 6.0 | 5.8 | 6.0 | 6.2 | 5.7 | 6.0 |
| hsa-miR-3191-3p | 7.0 | 7.2 | 7.3 | 6.9 | 6.4 | 6.5 | 6.3 | 7.7 | 6.8 |
| hsa-miR-1281 | 6.8 | 6.8 | 6.7 | 6.6 | 6.6 | 6.5 | 6.3 | 5.6 | 5.8 |
| hsa-miR-4747-5p | 6.4 | 6.4 | 6.8 | 6.5 | 7.2 | 6.6 | 6.4 | 6.3 | 6.4 |
| hsa-miR-0887-3p | 7.5 | 7.3 | 6.1 | 6.7 | 7.1 | 6.9 | 5.7 | 6.1 | 6.7 |
| hsa-miR-4700-3p | 6.2 | 6.3 | 6.6 | 6.1 | 5.9 | 5.9 | 6.8 | 6.4 | 6.4 |
| hsa-miR-6727-3p | 6.7 | 7.4 | 6.7 | 6.4 | 6.4 | 6.3 | 5.5 | 5.8 | 5.8 |
| hsa-miR-5699-5p | 6.3 | 6.5 | 6.6 | 6.4 | 5.9 | 6.5 | 7.1 | 6.2 | 6.7 |
| hsa-miR-0498 | 7.1 | 6.9 | 7.2 | 7.2 | 6.8 | 6.1 | 6.4 | 6.0 | 6.5 |
| hsa-miR-0449b-3p | 6.3 | 6.5 | 6.3 | 6.1 | 5.7 | 6.0 | 5.9 | 5.7 | 6.0 |
| hsa-miR-6735-5p | 7.2 | 7.4 | 7.6 | 7.7 | 7.0 | 7.0 | 6.3 | 6.0 | 6.4 |
| hsa-miR-1343-3p | 6.6 | 6.8 | 6.5 | 6.1 | 6.2 | 6.4 | 8.1 | 8.9 | 8.7 |
| hsa-miR-3126-3p | 3.6 | 3.6 | 4.7 | 4.2 | 4.1 | 3.5 | 3.8 | 3.5 | 3.6 |
| hsa-miR-8071 | 5.6 | 5.7 | 5.8 | 6.0 | 6.0 | 6.9 | 7.2 | 7.5 | 7.0 |
| hsa-miR-1587 | 6.2 | 6.4 | 6.2 | 6.4 | 5.8 | 6.3 | 6.4 | 7.5 | 6.3 |
| hsa-miR-3133 | 0.0 | 0.0 | 0.0 | 0.0 | 0.0 | 0.0 | 0.0 | 0.0 | 1.9 |
| hsa-miR-4793-3p | 5.4 | 5.7 | 6.0 | 4.7 | 5.3 | 5.1 | 4.8 | 4.9 | 5.3 |
| hsa-miR-6730-5p | 6.2 | 5.7 | 6.6 | 6.3 | 6.7 | 6.6 | 7.1 | 6.8 | 7.2 |
| hsa-miR-6076 | 5.6 | 5.8 | 5.4 | 5.9 | 6.6 | 7.8 | 6.7 | 9.2 | 7.8 |
| hsa-miR-8089 | 6.8 | 7.0 | 6.6 | 6.8 | 6.5 | 7.1 | 6.3 | 6.8 | 6.7 |
| hsa-miR-6857-3p | 6.1 | 6.0 | 6.5 | 6.3 | 6.1 | 5.9 | 6.8 | 6.5 | 6.7 |
| hsa-miR-6749-3p | 6.6 | 7.0 | 6.8 | 6.6 | 6.4 | 6.6 | 6.5 | 5.9 | 6.4 |
| hsa-miR-6890-3p | 6.3 | 6.7 | 7.1 | 6.4 | 6.3 | 6.2 | 6.9 | 6.3 | 6.4 |
| hsa-miR-4751 | 6.4 | 6.2 | 6.4 | 6.4 | 6.9 | 6.3 | 6.8 | 7.0 | 6.9 |
| hsa-miR-6825-5p | 6.7 | 6.3 | 6.1 | 6.5 | 8.2 | 8.8 | 7.4 | 6.4 | 7.6 |
| hsa-miR-6810-3p | 6.4 | 6.6 | 6.8 | 6.3 | 6.2 | 6.3 | 7.1 | 6.6 | 6.9 |
| hsa-miR-0365a-3p, hsa-miR-365b-3p | 6.5 | 6.6 | 7.0 | 6.5 | 6.5 | 6.3 | 7.2 | 6.4 | 6.7 |
| hsa-miR-3943 | 6.5 | 6.7 | 7.0 | 6.5 | 5.9 | 6.2 | 6.9 | 6.2 | 6.7 |
| hsa-miR-6728-3p | 6.5 | 6.7 | 6.9 | 6.5 | 6.4 | 6.2 | 6.8 | 6.4 | 6.6 |
| hsa-miR-3185 | 6.9 | 6.6 | 6.3 | 6.1 | 7.4 | 6.8 | 6.0 | 7.0 | 6.9 |
| hsa-miR-6894-3p | 5.8 | 6.6 | 6.8 | 5.9 | 6.0 | 6.3 | 5.8 | 6.0 | 6.0 |
| hsa-miR-8485 | 6.5 | 6.8 | 6.8 | 6.7 | 6.4 | 6.5 | 5.9 | 5.9 | 5.8 |
| hsa-miR-6846-5p | 6.5 | 6.6 | 6.2 | 6.6 | 6.2 | 6.9 | 6.3 | 6.8 | 6.4 |
| hsa-miR-4286 | 6.4 | 6.5 | 6.8 | 6.3 | 6.1 | 6.5 | 7.2 | 6.4 | 6.8 |
| hsa-miR-4259 | 6.1 | 6.5 | 7.1 | 6.2 | 6.4 | 5.7 | 6.4 | 6.8 | 6.5 |
| hsa-miR-0208a-5p | 7.1 | 6.2 | 6.9 | 6.1 | 5.7 | 6.0 | 5.9 | 5.3 | 6.1 |
| hsa-miR-6851-3p | 6.4 | 6.7 | 6.8 | 6.4 | 6.2 | 6.0 | 6.8 | 6.2 | 6.5 |
| hsa-miR-4472 | 7.5 | 6.8 | 7.7 | 6.7 | 7.1 | 7.6 | 6.7 | 7.9 | 6.6 |
| hsa-miR-6820-5p | 6.5 | 6.5 | 5.9 | 6.0 | 6.7 | 7.0 | 6.3 | 6.5 | 6.7 |
| hsa-miR-6855-3p | 6.3 | 6.2 | 6.8 | 6.6 | 6.5 | 6.3 | 7.2 | 6.9 | 7.0 |
| hsa-miR-6801-3p | 6.5 | 6.8 | 6.8 | 6.7 | 6.3 | 6.5 | 6.9 | 6.5 | 6.7 |
| hsa-miR-0634 | 6.3 | 6.2 | 6.6 | 6.3 | 6.0 | 5.8 | 6.9 | 6.5 | 6.8 |
| hsa-miR-1229-3p | 6.2 | 6.8 | 6.9 | 6.2 | 6.0 | 6.3 | 6.0 | 6.0 | 5.9 |
| hsa-miR-7109-3p | 6.5 | 6.5 | 6.6 | 5.9 | 6.2 | 6.3 | 6.3 | 5.9 | 6.0 |
| hsa-miR-6804-3p | 6.3 | 6.5 | 6.7 | 6.2 | 6.3 | 6.4 | 6.4 | 5.8 | 5.9 |
| hsa-miR-4723-3p | 6.5 | 6.7 | 7.2 | 6.7 | 6.7 | 6.7 | 6.8 | 6.1 | 6.3 |
| hsa-miR-6742-5p | 6.3 | 7.2 | 6.3 | 6.5 | 6.2 | 6.4 | 6.9 | 7.2 | 7.1 |
| hsa-miR-6511b-3p | 6.3 | 6.6 | 6.7 | 6.2 | 6.3 | 6.4 | 6.5 | 5.8 | 6.2 |
| hsa-miR-6820-3p | 6.6 | 6.5 | 6.9 | 6.4 | 6.0 | 6.3 | 7.1 | 6.5 | 6.8 |
| hsa-miR-2278 | 6.7 | 7.2 | 7.1 | 7.1 | 6.8 | 6.4 | 6.4 | 6.1 | 6.9 |

TABLE 3-continued

| | | | | | | | | | |
|---|---|---|---|---|---|---|---|---|---|
| hsa-miR-3157-3p | 0.0 | 3.6 | 3.1 | 2.4 | 0.0 | 2.8 | 2.7 | 0.0 | 2.3 |
| hsa-miR-6776-3p | 6.3 | 6.4 | 6.8 | 6.4 | 6.2 | 6.0 | 6.7 | 6.3 | 6.5 |
| hsa-miR-6730-3p | 6.3 | 6.5 | 6.8 | 6.4 | 6.2 | 6.3 | 6.8 | 6.2 | 6.5 |
| hsa-miR-6797-3p | 6.7 | 7.0 | 7.4 | 6.7 | 6.6 | 6.6 | 7.3 | 6.4 | 6.9 |
| hsa-miR-0920 | 5.5 | 6.2 | 6.5 | 6.1 | 6.1 | 6.2 | 7.9 | 7.9 | 8.0 |
| hsa-miR-4443 | 7.5 | 7.0 | 6.0 | 6.9 | 6.3 | 7.8 | 7.0 | 6.6 | 6.9 |
| hsa-miR-6732-3p | 6.6 | 6.9 | 6.9 | 6.4 | 6.4 | 6.6 | 6.5 | 6.0 | 6.2 |
| hsa-miR-0365a-5p | 7.0 | 7.0 | 6.7 | 7.2 | 6.2 | 7.4 | 6.8 | 6.8 | 6.5 |
| hsa-miR-6780a-5p | 5.2 | 5.5 | 5.7 | 5.6 | 6.0 | 5.7 | 7.5 | 6.0 | 6.9 |
| hsa-miR-6510-5p | 6.7 | 6.9 | 7.2 | 7.1 | 7.9 | 8.7 | 7.4 | 6.4 | 7.6 |
| hsa-miR-6745 | 5.2 | 4.5 | 4.9 | 5.3 | 6.3 | 5.2 | 7.4 | 6.8 | 7.5 |
| hsa-miR-7114-3p | 6.5 | 6.6 | 7.2 | 6.5 | 6.7 | 6.4 | 7.0 | 6.6 | 6.9 |
| hsa-miR-7113-3p | 7.2 | 7.2 | 7.3 | 6.9 | 7.1 | 6.9 | 6.6 | 6.2 | 6.3 |
| hsa-miR-4276 | 7.5 | 7.5 | 6.6 | 6.6 | 7.0 | 7.2 | 5.8 | 5.0 | 5.5 |
| hsa-miR-6726-5p | 7.1 | 6.6 | 6.1 | 5.7 | 7.0 | 6.8 | 6.9 | 7.9 | 7.3 |
| hsa-miR-0125a-3p | 6.9 | 7.1 | 6.9 | 6.9 | 6.7 | 6.7 | 7.4 | 6.2 | 7.3 |
| hsa-miR-0486-5p | 6.5 | 6.5 | 6.9 | 6.6 | 6.4 | 6.1 | 6.8 | 6.5 | 6.7 |
| hsa-miR-4499 | 5.1 | 5.1 | 5.8 | 5.3 | 6.0 | 5.3 | 6.8 | 6.8 | 7.6 |
| hsa-miR-4697-3p | 6.5 | 6.6 | 6.9 | 6.3 | 6.1 | 6.0 | 7.0 | 6.5 | 6.5 |
| hsa-miR-6507-5p | 4.7 | 5.4 | 6.1 | 5.5 | 6.5 | 6.0 | 7.6 | 7.1 | 8.0 |
| hsa-miR-1976 | 6.8 | 6.9 | 7.0 | 6.5 | 6.5 | 6.5 | 6.3 | 6.1 | 6.2 |
| hsa-miR-3147 | 6.6 | 6.6 | 6.6 | 6.5 | 7.0 | 6.9 | 5.9 | 6.5 | 7.5 |
| hsa-miR-0519e-5p | 6.7 | 5.1 | 6.0 | 6.0 | 7.2 | 5.6 | 6.9 | 5.6 | 7.4 |
| hsa-miR-6815-5p | 5.7 | 5.2 | 4.9 | 5.5 | 6.4 | 6.2 | 7.8 | 7.6 | 8.4 |
| hsa-miR-4750-5p | 6.9 | 7.2 | 6.4 | 7.3 | 6.7 | 7.4 | 6.3 | 7.2 | 7.2 |
| hsa-miR-4687-5p | 7.0 | 7.2 | 7.2 | 6.8 | 7.0 | 6.9 | 6.7 | 6.3 | 6.5 |
| hsa-miR-6806-5p | 7.6 | 7.6 | 7.4 | 7.2 | 6.9 | 6.9 | 6.1 | 6.1 | 6.3 |
| hsa-miR-4783-3p | 7.3 | 7.5 | 7.4 | 7.3 | 6.7 | 7.2 | 6.8 | 8.0 | 6.9 |
| hsa-miR-6754-5p | 6.3 | 6.3 | 7.3 | 6.5 | 6.7 | 6.7 | 7.1 | 6.7 | 7.0 |
| hsa-miR-4419a | 6.5 | 6.6 | 7.0 | 7.4 | 7.4 | 7.6 | 7.6 | 7.4 | 7.6 |
| hsa-miR-6769a-3p | 6.7 | 6.9 | 6.9 | 6.6 | 6.5 | 6.7 | 6.8 | 6.3 | 6.5 |
| hsa-miR-6846-3p | 6.5 | 6.8 | 6.9 | 6.4 | 6.2 | 6.1 | 7.1 | 6.4 | 6.5 |
| hsa-miR-4769-3p | 6.7 | 6.9 | 7.2 | 6.6 | 6.6 | 6.6 | 7.0 | 6.2 | 6.6 |
| hsa-miR-0744-5p | 7.0 | 7.3 | 6.9 | 6.6 | 6.6 | 6.7 | 5.8 | 6.0 | 6.4 |
| hsa-miR-3184-3p | 6.9 | 7.0 | 7.3 | 6.7 | 6.7 | 6.3 | 6.9 | 6.6 | 6.7 |
| hsa-miR-6792-3p | 6.8 | 7.0 | 7.3 | 6.7 | 6.6 | 6.6 | 7.0 | 6.6 | 6.6 |
| hsa-miR-0150-3p | 7.6 | 7.5 | 6.9 | 8.3 | 7.0 | 7.3 | 7.3 | 7.8 | 7.9 |
| hsa-miR-7155-5p | 7.5 | 7.8 | 7.6 | 7.4 | 7.5 | 7.5 | 6.6 | 6.4 | 6.0 |
| hsa-miR-6858-3p | 6.6 | 6.8 | 7.1 | 6.7 | 6.7 | 6.5 | 7.3 | 6.8 | 7.1 |
| hsa-miR-4690-5p | 8.0 | 7.8 | 7.5 | 6.9 | 7.1 | 6.6 | 5.8 | 7.0 | 6.4 |
| hsa-miR-6861-3p | 6.8 | 6.8 | 6.9 | 6.6 | 6.7 | 6.7 | 6.8 | 6.4 | 6.8 |
| hsa-miR-6069 | 6.8 | 7.2 | 7.6 | 6.8 | 6.7 | 6.8 | 7.3 | 6.5 | 6.9 |
| hsa-miR-0766-3p | 6.7 | 6.8 | 6.7 | 6.6 | 6.2 | 6.1 | 6.3 | 6.1 | 6.1 |
| hsa-miR-4478 | 6.4 | 6.8 | 7.2 | 7.3 | 8.7 | 6.8 | 6.6 | 6.4 | 7.3 |
| hsa-miR-6827-5p | 5.9 | 6.0 | 6.5 | 6.2 | 6.6 | 6.4 | 7.2 | 6.6 | 7.1 |
| hsa-miR-4284 | 6.9 | 6.7 | 7.4 | 6.6 | 6.4 | 6.5 | 7.5 | 6.9 | 7.2 |
| hsa-miR-7108-3p | 6.5 | 6.7 | 7.2 | 6.5 | 6.7 | 6.7 | 7.4 | 6.8 | 7.0 |
| hsa-miR-6889-3p | 6.8 | 6.9 | 7.4 | 7.0 | 6.6 | 6.6 | 7.3 | 6.8 | 7.1 |
| hsa-miR-6860 | 7.0 | 7.2 | 7.2 | 6.9 | 6.6 | 7.1 | 6.5 | 6.7 | 6.7 |
| hsa-miR-3928-3p | 7.2 | 7.8 | 6.6 | 7.5 | 7.0 | 7.6 | 8.1 | 10.4 | 9.4 |
| hsa-miR-6760-5p | 6.1 | 5.4 | 6.0 | 6.0 | 7.3 | 5.9 | 8.0 | 8.3 | 8.7 |
| hsa-miR-4667-5p | 7.1 | 7.3 | 7.5 | 6.9 | 6.7 | 6.7 | 7.0 | 6.6 | 6.7 |
| hsa-miR-1247-3p | 7.6 | 7.1 | 6.3 | 7.2 | 6.2 | 7.7 | 6.9 | 6.1 | 6.8 |
| hsa-miR-6845-3p | 7.1 | 7.2 | 7.1 | 7.0 | 6.8 | 7.0 | 7.0 | 6.5 | 6.9 |
| hsa-miR-4486 | 8.0 | 7.9 | 7.1 | 7.5 | 7.3 | 7.7 | 6.5 | 7.9 | 7.2 |
| hsa-miR-5572 | 7.2 | 7.0 | 6.6 | 6.9 | 7.5 | 8.1 | 6.3 | 6.8 | 6.8 |
| hsa-miR-0484 | 7.1 | 7.0 | 7.5 | 7.1 | 6.7 | 6.5 | 7.1 | 6.5 | 6.7 |
| hsa-miR-6760-3p | 6.9 | 7.0 | 7.6 | 6.6 | 6.8 | 6.5 | 7.5 | 7.1 | 7.3 |
| hsa-miR-6885-3p | 6.6 | 6.9 | 7.0 | 6.5 | 6.4 | 6.5 | 7.3 | 6.8 | 7.1 |
| hsa-miR-6892-3p | 6.8 | 6.8 | 7.4 | 6.6 | 6.7 | 6.7 | 7.4 | 6.7 | 7.0 |
| hsa-miR-2355-5p | 6.5 | 6.5 | 6.9 | 7.1 | 6.2 | 6.2 | 7.3 | 6.5 | 7.1 |
| hsa-miR-3158-3p | 3.7 | 4.2 | 4.4 | 4.5 | 3.9 | 4.6 | 4.2 | 3.6 | 4.0 |
| hsa-miR-6759-3p | 6.8 | 7.1 | 7.2 | 6.7 | 6.7 | 6.6 | 7.1 | 6.8 | 6.9 |
| hsa-miR-0210-5p | 7.1 | 7.0 | 7.5 | 7.2 | 7.0 | 6.9 | 7.0 | 6.8 | 6.7 |
| hsa-miR-6778-5p | 6.7 | 6.9 | 6.8 | 6.9 | 7.4 | 7.0 | 6.8 | 7.5 | 7.5 |
| hsa-miR-2110 | 7.3 | 7.3 | 7.3 | 8.2 | 7.5 | 8.0 | 7.1 | 7.7 | 7.9 |
| hsa-miR-3150a-5p | 3.5 | 3.7 | 3.5 | 3.0 | 1.9 | 2.5 | 2.9 | 2.6 | 3.1 |
| hsa-miR-6731-5p | 6.9 | 7.1 | 7.0 | 7.2 | 7.0 | 6.8 | 6.5 | 6.6 | 7.0 |
| hsa-miR-6756-5p | 6.7 | 7.0 | 7.5 | 6.8 | 7.0 | 6.9 | 7.4 | 6.8 | 7.1 |
| hsa-miR-6786-3p | 6.7 | 7.1 | 7.3 | 6.7 | 6.7 | 6.5 | 7.4 | 6.7 | 6.9 |
| hsa-miR-6831-5p | 6.8 | 7.0 | 7.1 | 7.7 | 8.7 | 9.0 | 7.3 | 6.3 | 9.2 |
| hsa-miR-0652-5p | 7.7 | 7.6 | 9.0 | 8.6 | 9.5 | 9.6 | 7.7 | 9.0 | 7.9 |
| hsa-miR-4419b | 6.9 | 6.5 | 8.2 | 6.7 | 7.3 | 6.9 | 7.9 | 9.0 | 7.9 |
| hsa-miR-4685-5p | 7.2 | 7.6 | 7.8 | 8.1 | 7.2 | 6.9 | 7.3 | 7.3 | 7.5 |
| hsa-miR-0939-5p | 7.1 | 7.3 | 6.5 | 6.3 | 7.6 | 8.3 | 7.7 | 9.4 | 8.5 |
| hsa-miR-6819-3p | 6.8 | 6.8 | 6.9 | 6.8 | 6.3 | 6.5 | 7.4 | 6.5 | 6.8 |
| hsa-miR-6826-3p | 6.9 | 7.1 | 7.5 | 6.8 | 6.7 | 6.8 | 7.5 | 6.9 | 7.0 |
| hsa-miR-0030c-2-3p | 6.1 | 5.7 | 7.1 | 5.3 | 6.3 | 4.4 | 8.4 | 8.4 | 8.4 |
| hsa-miR-6132 | 6.5 | 7.0 | 7.5 | 5.8 | 7.0 | 7.6 | 6.6 | 5.7 | 6.1 |
| hsa-miR-6769b-5p | 6.9 | 7.5 | 7.4 | 8.2 | 9.2 | 9.5 | 7.3 | 7.8 | 7.4 |

TABLE 3-continued

| | | | | | | | | | |
|---|---|---|---|---|---|---|---|---|---|
| hsa-miR-6802-3p | 6.7 | 6.8 | 7.2 | 6.7 | 6.6 | 6.7 | 7.4 | 6.9 | 7.1 |
| hsa-miR-3194-5p | 7.4 | 7.5 | 7.7 | 6.8 | 6.9 | 7.1 | 7.1 | 6.5 | 7.0 |
| hsa-miR-0718 | 8.0 | 7.6 | 7.3 | 6.7 | 6.8 | 6.6 | 7.1 | 6.8 | 6.8 |
| hsa-miR-6861-5p | 7.5 | 7.3 | 6.7 | 7.8 | 7.4 | 7.6 | 9.3 | 11.3 | 10.1 |
| hsa-miR-4313 | 7.0 | 7.0 | 7.2 | 6.5 | 6.2 | 6.2 | 7.5 | 6.6 | 6.9 |
| hsa-miR-6777-5p | 6.9 | 6.4 | 6.7 | 6.5 | 7.4 | 6.8 | 7.6 | 9.1 | 8.0 |
| hsa-miR-6813-5p | 7.1 | 6.7 | 7.1 | 6.5 | 6.8 | 7.1 | 6.6 | 6.3 | 5.9 |
| hsa-miR-4707-3p | 7.4 | 7.2 | 7.3 | 7.0 | 6.9 | 7.0 | 7.2 | 6.6 | 6.8 |
| hsa-miR-7110-5p | 7.5 | 7.6 | 6.7 | 7.0 | 8.2 | 9.4 | 7.4 | 8.1 | 7.9 |
| hsa-miR-4258 | 7.8 | 7.2 | 7.3 | 7.7 | 8.0 | 7.6 | 7.4 | 6.6 | 7.2 |
| hsa-miR-4526 | 7.4 | 7.7 | 6.8 | 7.1 | 6.7 | 6.7 | 5.9 | 6.5 | 5.6 |
| hsa-miR-4758-3p | 7.1 | 7.1 | 7.5 | 7.0 | 6.9 | 6.8 | 7.2 | 6.7 | 6.9 |
| hsa-miR-6889-5p | 7.1 | 7.2 | 7.5 | 6.9 | 8.2 | 7.9 | 7.5 | 8.1 | 8.0 |
| hsa-miR-6752-3p | 7.0 | 7.4 | 7.8 | 6.9 | 7.0 | 6.8 | 7.7 | 7.2 | 7.4 |
| hsa-miR-0711 | 7.3 | 7.6 | 7.0 | 7.6 | 7.3 | 7.9 | 7.1 | 7.1 | 7.0 |
| hsa-miR-6879-5p | 6.4 | 7.0 | 7.2 | 7.4 | 7.8 | 9.4 | 8.2 | 10.1 | 8.8 |
| hsa-miR-8087 | 3.9 | 4.3 | 5.8 | 6.0 | 5.3 | 5.2 | 6.4 | 7.3 | 6.9 |
| hsa-miR-0933 | 5.9 | 5.7 | 7.3 | 6.6 | 6.7 | 6.3 | 7.1 | 5.4 | 6.8 |
| hsa-miR-4507 | 7.8 | 7.6 | 7.2 | 7.5 | 7.2 | 7.1 | 6.9 | 8.3 | 6.9 |
| hsa-miR-4756-5p | 7.2 | 7.3 | 8.1 | 6.7 | 6.9 | 6.4 | 7.1 | 7.0 | 7.1 |
| hsa-miR-1249-5p | 7.2 | 8.4 | 8.5 | 7.9 | 8.3 | 8.8 | 7.1 | 6.4 | 6.9 |
| hsa-miR-0197-5p | 7.2 | 7.5 | 7.9 | 7.6 | 7.6 | 8.1 | 7.7 | 8.8 | 7.9 |
| hsa-miR-4323 | 7.5 | 7.4 | 7.4 | 7.2 | 6.8 | 6.9 | 7.7 | 7.0 | 7.5 |
| hsa-miR-0092b-5p | 8.5 | 8.0 | 7.1 | 8.3 | 9.1 | 9.8 | 7.3 | 8.7 | 7.7 |
| hsa-miR-6887-3p | 7.2 | 7.4 | 7.7 | 7.2 | 7.2 | 7.1 | 7.6 | 7.3 | 7.5 |
| hsa-miR-6893-5p | 6.6 | 6.4 | 6.5 | 7.2 | 7.2 | 8.3 | 8.0 | 10.7 | 8.8 |
| hsa-miR-6813-3p | 7.4 | 7.5 | 7.7 | 7.3 | 7.0 | 7.3 | 7.9 | 7.0 | 7.5 |
| hsa-miR-6891-3p | 7.0 | 7.2 | 7.6 | 7.0 | 7.0 | 7.0 | 7.8 | 7.3 | 7.6 |
| hsa-miR-6731-3p | 7.1 | 7.2 | 7.4 | 7.0 | 6.7 | 6.7 | 7.8 | 7.2 | 7.6 |
| hsa-miR-0345-3p | 9.2 | 8.5 | 7.5 | 8.7 | 8.7 | 8.1 | 7.8 | 7.8 | 7.8 |
| hsa-miR-4640-3p | 7.4 | 7.5 | 7.9 | 7.4 | 7.0 | 7.0 | 7.7 | 6.9 | 7.2 |
| hsa-miR-4716-3p | 7.3 | 7.0 | 7.0 | 6.9 | 7.5 | 7.2 | 7.1 | 7.5 | 6.7 |
| hsa-miR-0371b-3p | 7.5 | 7.6 | 7.9 | 7.3 | 7.1 | 7.1 | 7.6 | 7.3 | 7.3 |
| hsa-miR-6812-5p | 7.5 | 8.1 | 8.0 | 9.0 | 8.6 | 8.6 | 7.7 | 7.6 | 7.8 |
| hsa-miR-6784-3p | 7.2 | 7.2 | 7.8 | 7.0 | 7.0 | 6.9 | 7.9 | 7.5 | 7.6 |
| hsa-miR-6716-5p | 8.0 | 8.7 | 8.5 | 8.3 | 8.1 | 8.4 | 7.2 | 6.5 | 6.9 |
| hsa-miR-4513 | 7.6 | 7.6 | 7.9 | 6.8 | 7.8 | 7.7 | 7.7 | 8.1 | 7.5 |
| hsa-miR-6848-3p | 7.5 | 7.8 | 8.1 | 7.2 | 7.4 | 7.2 | 7.8 | 7.3 | 7.5 |
| hsa-miR-1238-5p | 7.3 | 7.4 | 7.5 | 7.4 | 7.2 | 7.9 | 7.9 | 7.8 | 7.9 |
| hsa-miR-4530 | 8.2 | 8.4 | 7.6 | 8.4 | 8.7 | 10.4 | 7.6 | 8.4 | 8.5 |
| hsa-miR-4655-5p | 7.6 | 7.7 | 7.3 | 8.1 | 7.6 | 8.6 | 6.8 | 8.0 | 7.4 |
| hsa-miR-6785-3p | 7.4 | 7.5 | 7.9 | 7.4 | 7.1 | 7.2 | 8.2 | 7.6 | 8.0 |
| hsa-miR-4728-3p | 7.5 | 7.4 | 7.5 | 7.4 | 6.9 | 7.3 | 7.9 | 7.2 | 7.5 |
| hsa-miR-5090 | 8.0 | 8.0 | 6.8 | 7.7 | 7.8 | 7.8 | 7.0 | 7.4 | 7.2 |
| hsa-miR-6824-5p | 7.7 | 7.6 | 8.4 | 8.2 | 8.4 | 8.8 | 7.5 | 7.4 | 8.3 |
| hsa-miR-4667-5p | 7.1 | 7.6 | 7.7 | 7.2 | 7.6 | 7.6 | 7.8 | 8.0 | 7.8 |
| hsa-miR-0874-5p | 7.3 | 7.5 | 7.9 | 7.4 | 7.1 | 7.2 | 7.9 | 7.3 | 7.5 |
| hsa-miR-4749-5p | 8.1 | 8.2 | 7.8 | 8.8 | 8.7 | 9.5 | 7.1 | 7.4 | 7.9 |
| hsa-miR-6086 | 8.1 | 8.1 | 8.0 | 8.3 | 8.5 | 7.9 | 7.7 | 8.3 | 8.2 |
| hsa-miR-4257 | 6.7 | 6.8 | 7.1 | 7.4 | 6.9 | 7.4 | 9.5 | 10.8 | 9.8 |
| hsa-miR-1224-3p | 7.8 | 7.6 | 7.9 | 7.7 | 7.4 | 7.5 | 8.0 | 7.2 | 7.6 |
| hsa-miR-3610 | 8.2 | 8.0 | 8.0 | 7.6 | 8.3 | 7.9 | 8.0 | 9.6 | 9.7 |
| hsa-miR-6880-5p | 7.8 | 8.0 | 8.1 | 7.8 | 9.0 | 9.0 | 7.9 | 7.7 | 7.5 |
| hsa-miR-0663b | 8.2 | 8.5 | 8.2 | 7.1 | 6.9 | 6.7 | 7.8 | 7.4 | 5.6 |
| hsa-miR-1237-3p | 7.3 | 7.7 | 7.7 | 7.3 | 7.2 | 7.3 | 8.1 | 7.4 | 7.8 |
| hsa-miR-1225-3p | 7.8 | 8.0 | 7.9 | 7.6 | 7.2 | 7.5 | 8.2 | 7.3 | 7.8 |
| hsa-miR-6763-5p | 7.3 | 7.5 | 7.5 | 7.0 | 7.6 | 7.7 | 7.7 | 10.1 | 8.2 |
| hsa-miR-4707-5p | 8.2 | 8.9 | 7.6 | 7.8 | 8.5 | 8.7 | 6.9 | 6.9 | 7.2 |
| hsa-miR-3195 | 8.9 | 8.8 | 8.4 | 8.1 | 8.4 | 8.4 | 7.5 | 7.9 | 8.0 |
| hsa-miR-1231 | 8.1 | 8.0 | 7.2 | 6.2 | 6.3 | 6.3 | 6.4 | 6.3 | 5.6 |
| hsa-miR-4695-5p | 8.1 | 8.4 | 7.6 | 7.7 | 8.2 | 8.4 | 7.2 | 7.7 | 7.7 |
| hsa-miR-1225-5p | 8.6 | 8.5 | 8.0 | 8.0 | 7.9 | 8.4 | 6.9 | 7.3 | 6.9 |
| hsa-miR-6891-5p | 7.4 | 7.8 | 8.8 | 8.6 | 9.0 | 9.1 | 9.5 | 9.4 | 9.2 |
| hsa-miR-3188 | 8.8 | 9.1 | 9.5 | 9.5 | 9.0 | 9.1 | 7.3 | 7.2 | 6.9 |
| hsa-miR-1202 | 8.7 | 9.1 | 9.3 | 9.4 | 9.8 | 10.4 | 8.2 | 8.3 | 8.0 |
| hsa-miR-6807-5p | 7.3 | 7.2 | 8.5 | 8.7 | 9.4 | 9.7 | 8.4 | 8.4 | 8.0 |
| hsa-miR-6738-5p | 8.3 | 8.2 | 8.4 | 8.1 | 8.2 | 7.7 | 7.2 | 7.4 | 7.0 |
| hsa-miR-1238-3p | 8.0 | 7.9 | 8.0 | 7.7 | 7.3 | 7.2 | 8.2 | 7.7 | 7.9 |
| hsa-miR-6840-3p | 8.1 | 7.9 | 7.6 | 7.8 | 8.0 | 8.0 | 7.8 | 10.3 | 7.9 |
| hsa-miR-0583 | 7.6 | 6.8 | 6.3 | 6.8 | 7.4 | 6.4 | 8.1 | 7.6 | 8.3 |
| hsa-miR-4640-5p | 7.9 | 8.3 | 7.8 | 7.3 | 7.7 | 8.4 | 7.5 | 7.9 | 7.3 |
| hsa-miR-0518c-5p | 6.9 | 6.7 | 7.2 | 6.9 | 7.2 | 6.0 | 7.3 | 6.7 | 7.3 |
| hsa-miR-7108-5p | 8.9 | 8.6 | 8.0 | 8.6 | 8.8 | 8.8 | 7.8 | 8.0 | 8.1 |
| hsa-miR-4725-3p | 7.5 | 7.3 | 7.8 | 8.7 | 10.3 | 10.6 | 7.9 | 8.7 | 9.5 |
| hsa-miR-4497 | 8.7 | 8.7 | 7.8 | 7.7 | 8.1 | 9.6 | 7.8 | 8.8 | 8.6 |
| hsa-miR-0361-3p | 7.7 | 7.8 | 8.3 | 7.4 | 7.3 | 7.1 | 8.3 | 7.9 | 8.1 |
| hsa-miR-5001-5p | 8.2 | 8.6 | 7.6 | 8.3 | 7.8 | 7.6 | 9.6 | 10.8 | 10.0 |
| hsa-miR-6880-3p | 7.7 | 8.1 | 8.5 | 7.7 | 7.8 | 7.5 | 8.3 | 7.9 | 8.2 |
| hsa-miR-0659-3p | 8.7 | 9.5 | 9.8 | 8.3 | 8.1 | 7.7 | 7.4 | 6.8 | 6.3 |
| hsa-miR-6848-5p | 8.5 | 8.8 | 8.9 | 8.4 | 8.5 | 8.5 | 7.6 | 8.0 | 7.3 |

TABLE 3-continued

| | | | | | | | | | |
|---|---|---|---|---|---|---|---|---|---|
| hsa-miR-6124 | 8.3 | 8.4 | 8.3 | 9.2 | 9.4 | 10.2 | 8.1 | 7.3 | 8.0 |
| hsa-miR-4750-3p | 7.4 | 7.5 | 8.1 | 7.3 | 7.4 | 7.2 | 8.5 | 7.6 | 8.1 |
| hsa-miR-4665-3p | 8.1 | 8.0 | 7.9 | 7.5 | 7.3 | 7.2 | 8.3 | 7.4 | 7.8 |
| hsa-miR-0373-5p | 8.6 | 9.0 | 9.0 | 9.2 | 8.2 | 8.6 | 8.2 | 7.5 | 7.5 |
| hsa-miR-0128-1-5p | 8.9 | 8.3 | 8.4 | 8.3 | 8.5 | 8.3 | 7.2 | 7.5 | 6.9 |
| hsa-miR-4433b-5p | 7.8 | 7.7 | 8.2 | 7.6 | 7.4 | 7.4 | 8.7 | 7.9 | 8.3 |
| hsa-miR-4433a-3p | 8.6 | 8.8 | 8.3 | 9.1 | 8.2 | 8.6 | 7.6 | 9.4 | 8.0 |
| hsa-miR-6808-5p | 8.8 | 8.9 | 8.9 | 8.9 | 8.6 | 8.9 | 8.1 | 9.6 | 7.9 |
| hsa-miR-6835-5p | 8.8 | 9.7 | 10.4 | 7.0 | 8.3 | 7.6 | 8.9 | 9.0 | 7.3 |
| hsa-miR-5196-5p | 7.8 | 7.4 | 7.4 | 7.9 | 9.0 | 7.8 | 8.8 | 9.3 | 9.4 |
| hsa-miR-6075 | 9.0 | 8.4 | 7.2 | 7.0 | 7.2 | 7.6 | 7.0 | 6.8 | 7.1 |
| hsa-miR-6737-5p | 8.6 | 8.7 | 7.8 | 7.3 | 8.0 | 7.9 | 7.1 | 7.3 | 6.5 |
| hsa-miR-6780b-5p | 7.4 | 7.4 | 7.1 | 9.6 | 10.2 | 11.1 | 7.9 | 9.1 | 9.7 |
| hsa-miR-6732-5p | 8.5 | 8.9 | 8.0 | 8.0 | 8.6 | 8.9 | 7.8 | 8.8 | 8.4 |
| hsa-miR-6865-5p | 8.2 | 8.6 | 8.9 | 7.9 | 8.8 | 7.3 | 8.3 | 8.2 | 9.1 |
| hsa-miR-4665-5p | 8.7 | 10.0 | 8.2 | 8.5 | 8.3 | 8.2 | 7.7 | 8.1 | 8.3 |
| hsa-miR-2116-3p | 7.7 | 8.0 | 8.2 | 7.7 | 7.5 | 7.7 | 8.6 | 7.6 | 8.2 |
| hsa-miR-3152-5p | 3.8 | 4.4 | 4.7 | 3.2 | 1.8 | 3.7 | 4.0 | 2.9 | 3.3 |
| hsa-miR-8059 | 9.0 | 10.0 | 7.2 | 10.7 | 8.9 | 9.4 | 6.5 | 7.0 | 7.4 |
| hsa-miR-6851-5p | 8.6 | 8.3 | 9.2 | 8.5 | 8.7 | 8.8 | 8.2 | 7.5 | 7.3 |
| hsa-miR-4788 | 7.6 | 7.8 | 9.2 | 7.9 | 8.2 | 8.2 | 8.7 | 8.2 | 8.5 |
| hsa-miR-4447 | 8.8 | 9.2 | 8.8 | 8.7 | 7.9 | 8.6 | 8.3 | 9.8 | 8.6 |
| hsa-miR-6744-5p | 8.2 | 7.8 | 9.9 | 7.4 | 8.5 | 8.1 | 9.3 | 8.4 | 9.2 |
| hsa-miR-0187-5p | 8.5 | 7.9 | 7.0 | 7.4 | 7.4 | 7.1 | 7.5 | 8.2 | 7.0 |
| hsa-miR-4467 | 9.6 | 8.9 | 8.0 | 8.0 | 8.8 | 9.6 | 7.7 | 7.9 | 8.4 |
| hsa-miR-0671-5p | 8.8 | 8.7 | 10.1 | 10.1 | 10.5 | 11.0 | 9.0 | 8.1 | 7.9 |
| hsa-miR-6799-5p | 8.2 | 8.7 | 9.2 | 10.0 | 10.7 | 11.5 | 8.9 | 7.7 | 8.4 |
| hsa-miR-4298 | 8.6 | 8.6 | 8.7 | 8.8 | 9.3 | 8.4 | 8.3 | 7.3 | 8.5 |
| hsa-miR-6797-5p | 7.9 | 8.4 | 8.8 | 8.2 | 9.1 | 8.4 | 8.6 | 8.3 | 9.2 |
| hsa-miR-6829-5p | 8.1 | 7.7 | 7.9 | 7.7 | 9.2 | 8.0 | 9.2 | 8.5 | 10.2 |
| hsa-miR-1275 | 9.5 | 9.8 | 10.1 | 10.8 | 9.6 | 9.5 | 8.0 | 8.1 | 7.9 |
| hsa-miR-3614-5p | 8.2 | 8.3 | 8.6 | 8.3 | 7.6 | 7.8 | 8.8 | 8.0 | 8.5 |
| hsa-miR-4688 | 8.6 | 8.4 | 7.8 | 7.7 | 7.7 | 8.0 | 7.6 | 7.1 | 6.9 |
| hsa-miR-1207-5p | 8.8 | 8.3 | 8.2 | 8.4 | 8.1 | 8.1 | 8.5 | 8.9 | 8.4 |
| hsa-miR-6794-5p | 8.6 | 9.1 | 8.4 | 9.4 | 8.9 | 9.1 | 8.9 | 9.3 | 9.1 |
| hsa-miR-6721-5p | 9.0 | 9.0 | 8.7 | 8.2 | 8.6 | 8.6 | 7.7 | 7.9 | 6.9 |
| hsa-miR-0665 | 9.4 | 9.5 | 8.5 | 8.1 | 8.2 | 6.7 | 7.8 | 7.8 | 8.2 |
| hsa-miR-7845-5p | 8.0 | 8.7 | 8.6 | 7.8 | 9.4 | 8.5 | 7.9 | 7.6 | 7.9 |
| hsa-miR-7150 | 8.6 | 9.1 | 9.4 | 9.8 | 9.8 | 10.1 | 8.4 | 7.9 | 8.2 |
| hsa-miR-4433b-3p | 8.5 | 9.1 | 8.5 | 9.1 | 8.6 | 9.1 | 8.3 | 9.3 | 8.5 |
| hsa-miR-7114-5p | 9.2 | 8.7 | 9.2 | 8.7 | 9.3 | 9.1 | 9.0 | 11.3 | 9.9 |
| hsa-miR-4716-5p | 8.1 | 8.0 | 8.2 | 8.0 | 7.7 | 7.9 | 9.0 | 8.1 | 8.8 |
| hsa-miR-6795-3p | 8.2 | 8.3 | 8.6 | 8.1 | 7.8 | 7.7 | 9.0 | 8.3 | 8.7 |
| hsa-miR-4433a-5p | 8.2 | 8.3 | 8.4 | 8.0 | 7.7 | 7.9 | 9.0 | 8.2 | 8.8 |
| hsa-miR-6777-3p | 8.2 | 8.5 | 8.7 | 8.2 | 7.9 | 7.9 | 8.9 | 8.2 | 8.6 |
| hsa-miR-0557 | 9.5 | 9.6 | 9.7 | 9.1 | 9.3 | 9.3 | 8.4 | 8.5 | 8.1 |
| hsa-miR-1185-2-3p | 8.1 | 9.0 | 9.9 | 9.9 | 8.7 | 8.7 | 9.6 | 10.0 | 9.9 |
| hsa-miR-4731-3p | 8.5 | 8.2 | 8.6 | 8.1 | 7.8 | 7.7 | 8.9 | 8.2 | 8.6 |
| hsa-miR-4745-5p | 9.3 | 8.8 | 7.9 | 8.0 | 8.2 | 9.4 | 8.2 | 8.9 | 8.8 |
| hsa-miR-6763-3p | 8.1 | 8.2 | 8.5 | 8.1 | 7.8 | 7.9 | 9.0 | 8.3 | 8.8 |
| hsa-miR-3937 | 9.3 | 9.6 | 8.6 | 9.6 | 8.6 | 9.7 | 7.3 | 8.1 | 8.3 |
| hsa-miR-0625-3p | 8.5 | 8.3 | 8.8 | 8.3 | 8.3 | 7.9 | 9.1 | 8.5 | 8.9 |
| hsa-miR-6800-3p | 8.4 | 8.4 | 8.9 | 8.3 | 8.1 | 8.0 | 9.1 | 8.5 | 8.8 |
| hsa-miR-0940 | 8.5 | 8.7 | 8.9 | 8.6 | 8.1 | 8.9 | 9.0 | 8.1 | 8.8 |
| hsa-miR-6758-5p | 8.7 | 8.2 | 7.9 | 8.2 | 8.6 | 8.3 | 6.9 | 8.1 | 7.4 |
| hsa-miR-4274 | 8.6 | 8.5 | 8.7 | 8.5 | 8.0 | 8.1 | 9.1 | 8.1 | 8.7 |
| hsa-miR-4749-3p | 8.2 | 8.6 | 8.9 | 8.3 | 8.1 | 8.1 | 9.1 | 8.4 | 8.7 |
| hsa-miR-3675-3p | 8.4 | 8.4 | 8.9 | 8.3 | 8.2 | 8.0 | 9.2 | 8.8 | 8.9 |
| hsa-miR-0760 | 9.6 | 9.2 | 8.5 | 10.6 | 9.4 | 10.4 | 8.0 | 9.9 | 9.8 |
| hsa-miR-3620-5p | 9.1 | 9.2 | 8.2 | 8.9 | 8.6 | 8.7 | 7.9 | 9.2 | 7.9 |
| hsa-miR-4484 | 9.3 | 9.3 | 9.1 | 9.1 | 9.8 | 10.6 | 9.0 | 9.6 | 9.5 |
| hsa-miR-6774-5p | 8.9 | 9.4 | 8.9 | 9.0 | 9.5 | 10.3 | 8.7 | 8.5 | 9.6 |
| hsa-miR-0675-5p | 9.5 | 9.9 | 10.2 | 9.9 | 9.5 | 10.3 | 8.2 | 7.4 | 7.4 |
| hsa-miR-1229-5p | 9.4 | 10.2 | 10.1 | 11.6 | 10.2 | 11.0 | 8.7 | 8.5 | 8.8 |
| hsa-miR-4459 | 8.6 | 8.4 | 7.8 | 8.3 | 8.7 | 9.8 | 8.7 | 10.3 | 9.6 |
| hsa-miR-6787-5p | 8.9 | 9.6 | 9.4 | 9.9 | 9.1 | 9.4 | 8.3 | 9.5 | 8.4 |
| hsa-miR-4271 | 9.2 | 9.0 | 9.6 | 9.6 | 9.0 | 9.4 | 8.5 | 7.6 | 7.9 |
| hsa-miR-4417 | 9.5 | 9.6 | 9.2 | 8.9 | 9.0 | 9.1 | 8.3 | 9.4 | 8.2 |
| hsa-miR-4505 | 8.5 | 8.2 | 8.2 | 7.4 | 8.4 | 8.7 | 7.8 | 8.0 | 7.5 |
| hsa-miR-6875-5p | 8.7 | 7.0 | 7.8 | 6.9 | 9.3 | 9.6 | 7.9 | 7.5 | 7.5 |
| hsa-miR-4758-5p | 9.1 | 8.5 | 8.6 | 9.1 | 9.4 | 8.9 | 8.7 | 9.5 | 9.3 |
| hsa-miR-6741-5p | 8.3 | 8.0 | 8.6 | 8.9 | 8.8 | 9.1 | 9.7 | 9.2 | 9.8 |
| hsa-miR-0514b-5p | 9.5 | 9.4 | 10.0 | 9.0 | 9.0 | 8.5 | 8.7 | 9.7 | 8.4 |
| hsa-miR-4726-5p | 9.5 | 9.8 | 10.6 | 9.7 | 9.8 | 10.2 | 9.1 | 8.7 | 8.5 |
| hsa-miR-6791-5p | 9.3 | 9.6 | 8.8 | 8.4 | 9.2 | 9.3 | 8.2 | 9.3 | 8.3 |
| hsa-miR-6789-5p | 9.4 | 9.2 | 8.9 | 8.0 | 8.8 | 8.9 | 8.3 | 8.6 | 7.8 |
| hsa-miR-6762-5p | 10.0 | 9.8 | 8.9 | 8.5 | 8.8 | 8.3 | 8.1 | 8.8 | 7.0 |
| hsa-miR-6859-3p | 8.4 | 8.5 | 8.7 | 8.4 | 8.2 | 8.0 | 9.3 | 8.6 | 9.0 |
| hsa-miR-7109-5p | 9.0 | 9.8 | 10.0 | 10.5 | 10.3 | 10.3 | 9.3 | 8.7 | 9.1 |
| hsa-miR-0937-5p | 9.5 | 9.3 | 8.6 | 11.0 | 10.8 | 10.1 | 10.4 | 10.6 | 11.5 |

TABLE 3-continued

| | | | | | | | | | |
|---|---|---|---|---|---|---|---|---|---|
| hsa-miR-4722-5p | 9.4 | 9.4 | 9.4 | 8.7 | 8.5 | 8.9 | 8.2 | 8.1 | 8.2 |
| hsa-miR-6826-5p | 9.9 | 10.8 | 10.7 | 8.8 | 9.4 | 8.8 | 8.9 | 9.8 | 7.8 |
| hsa-miR-1228-3p | 8.9 | 9.0 | 9.0 | 8.7 | 8.4 | 8.5 | 9.6 | 8.7 | 9.2 |
| hsa-miR-6798-3p | 8.7 | 8.9 | 9.5 | 8.8 | 8.8 | 8.8 | 9.9 | 9.1 | 9.5 |
| hsa-miR-1268b | 9.5 | 10.0 | 8.8 | 9.2 | 10.0 | 9.9 | 9.0 | 9.7 | 10.0 |
| hsa-miR-1909-3p | 10.1 | 9.7 | 9.0 | 9.3 | 10.0 | 9.4 | 8.2 | 8.8 | 8.5 |
| hsa-miR-3136-5p | 0.0 | 0.0 | 0.0 | 0.0 | 0.0 | 0.0 | 0.0 | 0.0 | 1.5 |
| hsa-miR-7847-3p | 8.6 | 9.1 | 10.0 | 9.5 | 11.5 | 9.5 | 9.2 | 8.8 | 9.3 |
| hsa-miR-7107-5p | 8.0 | 7.9 | 8.4 | 8.0 | 9.2 | 9.2 | 8.8 | 9.1 | 9.4 |
| hsa-miR-6729-3p | 8.9 | 8.7 | 9.1 | 8.8 | 8.5 | 8.5 | 9.6 | 8.9 | 9.3 |
| hsa-miR-3648 | 10.1 | 9.4 | 8.6 | 9.4 | 11.1 | 13.1 | 10.1 | 9.4 | 9.6 |
| hsa-miR-6746-5p | 7.7 | 7.6 | 8.8 | 8.5 | 9.1 | 9.1 | 9.3 | 9.5 | 10.1 |
| hsa-miR-6821-5p | 9.8 | 10.2 | 9.5 | 10.4 | 9.3 | 10.1 | 8.8 | 9.8 | 9.6 |
| hsa-miR-6768-5p | 10.3 | 10.3 | 9.6 | 10.5 | 10.0 | 10.7 | 9.4 | 10.0 | 9.9 |
| hsa-miR-1185-1-3p | 8.7 | 9.4 | 10.2 | 10.8 | 9.2 | 9.5 | 10.3 | 10.2 | 10.7 |
| hsa-miR-6798-5p | 9.9 | 10.1 | 9.1 | 8.7 | 9.8 | 9.9 | 8.6 | 9.3 | 9.5 |
| hsa-miR-6743-5p | 9.8 | 9.9 | 9.2 | 9.3 | 9.2 | 9.6 | 9.4 | 9.9 | 9.5 |
| hsa-miR-7111-5p | 8.5 | 8.7 | 9.3 | 9.1 | 9.9 | 10.1 | 9.7 | 9.4 | 9.9 |
| hsa-miR-6769a-5p | 8.7 | 8.8 | 10.2 | 9.5 | 10.1 | 10.1 | 9.6 | 10.0 | 9.7 |
| hsa-miR-6845-5p | 10.1 | 9.8 | 9.3 | 9.3 | 10.0 | 10.4 | 8.9 | 9.4 | 8.6 |
| hsa-miR-3184-5p | 9.7 | 9.1 | 11.1 | 9.4 | 9.8 | 10.1 | 9.4 | 7.8 | 8.1 |
| hsa-miR-4656 | 9.3 | 9.0 | 9.8 | 8.8 | 9.5 | 8.9 | 9.6 | 8.6 | 9.3 |
| hsa-miR-4632-5p | 9.9 | 9.9 | 9.5 | 9.7 | 9.9 | 10.9 | 8.5 | 8.3 | 8.1 |
| hsa-miR-0642b-3p | 10.1 | 10.1 | 10.6 | 11.7 | 11.5 | 11.6 | 9.7 | 8.9 | 9.5 |
| hsa-miR-6724-5p | 9.8 | 10.1 | 8.9 | 9.7 | 9.1 | 10.0 | 8.5 | 8.8 | 8.8 |
| hsa-miR-4651 | 9.9 | 9.7 | 7.8 | 9.1 | 10.0 | 10.0 | 8.9 | 9.0 | 9.3 |
| hsa-miR-6805-3p | 9.3 | 9.3 | 9.2 | 9.1 | 8.8 | 9.2 | 9.8 | 8.9 | 9.6 |
| hsa-miR-4763-3p | 9.6 | 9.9 | 9.1 | 9.2 | 9.7 | 9.3 | 9.0 | 9.0 | 9.2 |
| hsa-miR-3619-3p | 8.6 | 8.9 | 9.0 | 9.7 | 9.1 | 9.1 | 9.8 | 10.4 | 9.9 |
| hsa-miR-6126 | 10.9 | 10.7 | 10.2 | 11.8 | 10.1 | 11.8 | 9.2 | 8.7 | 8.9 |
| hsa-miR-4706 | 9.3 | 9.5 | 9.5 | 9.1 | 9.5 | 8.9 | 9.1 | 9.8 | 9.6 |
| hsa-miR-4634 | 10.2 | 10.6 | 9.4 | 8.5 | 8.6 | 8.5 | 8.5 | 8.4 | 7.7 |
| hsa-miR-6722-3p | 10.3 | 10.3 | 9.5 | 9.7 | 9.6 | 9.6 | 8.8 | 9.2 | 8.4 |
| hsa-miR-6796-3p | 8.8 | 8.8 | 9.4 | 8.7 | 9.0 | 8.5 | 9.8 | 9.2 | 9.6 |
| hsa-miR-6165 | 8.8 | 8.7 | 9.0 | 8.7 | 8.2 | 7.8 | 9.4 | 9.0 | 9.5 |
| hsa-miR-4327 | 9.4 | 9.4 | 9.2 | 9.4 | 9.1 | 9.5 | 9.4 | 9.3 | 9.1 |
| hsa-miR-6781-5p | 9.9 | 10.0 | 9.4 | 9.5 | 10.4 | 10.6 | 9.1 | 9.6 | 9.2 |
| hsa-miR-1913 | 9.4 | 9.3 | 9.7 | 9.4 | 8.9 | 8.8 | 10.1 | 9.2 | 9.9 |
| hsa-miR-3142 | 0.0 | 0.0 | 0.0 | 0.0 | 0.0 | 0.0 | 0.0 | 0.0 | 0.0 |
| hsa-miR-0642a-3p | 9.7 | 9.4 | 11.1 | 11.4 | 12.0 | 12.1 | 10.5 | 8.9 | 9.5 |
| hsa-miR-6756-5p | 9.9 | 10.1 | 9.9 | 10.6 | 10.1 | 9.7 | 10.3 | 11.5 | 11.2 |
| hsa-miR-4731-5p | 9.9 | 9.9 | 10.6 | 9.9 | 9.4 | 9.8 | 10.2 | 9.1 | 9.5 |
| hsa-miR-5739 | 9.5 | 9.6 | 9.6 | 9.5 | 9.1 | 9.3 | 10.4 | 9.9 | 10.2 |
| hsa-miR-6766-3p | 9.1 | 9.3 | 10.0 | 9.2 | 9.2 | 9.1 | 10.3 | 9.6 | 10.0 |
| hsa-miR-4741 | 10.7 | 10.0 | 8.5 | 9.9 | 11.0 | 10.8 | 9.5 | 9.1 | 9.8 |
| hsa-miR-8063 | 11.3 | 11.2 | 10.7 | 10.2 | 10.5 | 9.3 | 9.2 | 10.6 | 8.1 |
| hsa-miR-1249-3p | 9.6 | 9.6 | 10.0 | 9.4 | 9.3 | 9.1 | 10.3 | 9.4 | 10.1 |
| hsa-miR-1914-3p | 10.2 | 10.2 | 9.8 | 9.6 | 10.1 | 9.4 | 10.3 | 9.7 | 10.2 |
| hsa-miR-3143 | 0.0 | 0.0 | 0.0 | 0.0 | 0.0 | 0.0 | 0.0 | 0.0 | 0.0 |
| hsa-miR-6858-5p | 10.4 | 10.0 | 10.9 | 10.6 | 10.7 | 11.2 | 9.7 | 9.7 | 10.6 |
| hsa-miR-3679-3p | 9.4 | 9.4 | 9.9 | 9.3 | 9.2 | 9.1 | 10.4 | 9.6 | 10.1 |
| hsa-miR-1227-5p | 10.5 | 10.4 | 9.7 | 10.2 | 10.5 | 10.6 | 10.9 | 10.6 | 11.1 |
| hsa-miR-6779-5p | 10.1 | 10.4 | 11.5 | 10.5 | 10.6 | 11.3 | 10.9 | 10.0 | 10.2 |
| hsa-miR-6836-3p | 10.8 | 10.3 | 9.7 | 8.7 | 8.6 | 8.5 | 9.6 | 9.0 | 9.1 |
| hsa-miR-5195-3p | 11.0 | 10.9 | 12.1 | 10.7 | 9.8 | 9.7 | 11.4 | 10.1 | 10.5 |
| hsa-miR-3180-3p | 10.9 | 10.5 | 10.1 | 10.3 | 9.9 | 9.6 | 9.0 | 9.5 | 8.7 |
| hsa-miR-4446-3p | 10.8 | 10.3 | 9.9 | 8.3 | 8.3 | 7.9 | 9.0 | 8.9 | 6.8 |
| hsa-miR-1915-3p | 11.0 | 10.5 | 10.1 | 9.6 | 10.6 | 10.1 | 9.3 | 9.4 | 9.3 |
| hsa-miR-3144-5p | 8.0 | 7.4 | 9.0 | 8.1 | 7.9 | 7.6 | 8.0 | 7.4 | 7.6 |
| hsa-miR-1908-5p | 11.2 | 11.0 | 10.1 | 11.7 | 11.5 | 12.2 | 9.6 | 10.1 | 10.2 |
| hsa-miR-3136-3p | 0.0 | 0.0 | 0.0 | 0.0 | 0.0 | 0.0 | 0.0 | 0.0 | 0.0 |
| hsa-miR-6800-5p | 11.2 | 11.1 | 10.8 | 11.0 | 10.6 | 10.0 | 9.3 | 9.8 | 8.6 |
| hsa-miR-0486-3p | 11.3 | 10.9 | 10.0 | 8.8 | 8.6 | 8.0 | 8.1 | 9.2 | 9.1 | 7.4 |
| hsa-miR-4294 | 10.3 | 10.2 | 10.7 | 11.6 | 12.0 | 12.1 | 11.0 | 9.8 | 11.0 |
| hsa-miR-4697-5p | 11.1 | 11.2 | 11.5 | 11.1 | 10.1 | 10.3 | 10.9 | 9.8 | 9.9 |
| hsa-miR-6515-3p | 10.0 | 10.0 | 10.4 | 9.9 | 9.8 | 9.8 | 11.1 | 10.4 | 10.8 |
| hsa-miR-3197 | 10.9 | 10.5 | 10.5 | 10.1 | 12.0 | 11.9 | 10.3 | 10.2 | 10.0 |
| hsa-miR-3180 | 10.7 | 11.2 | 10.8 | 10.6 | 10.4 | 10.0 | 9.3 | 9.5 | 8.7 |
| hsa-miR-6795-5p | 9.1 | 9.1 | 9.8 | 10.5 | 9.4 | 9.5 | 10.8 | 10.7 | 10.9 |
| hsa-miR-6819-5p | 10.8 | 11.5 | 12.2 | 11.2 | 11.4 | 11.9 | 11.1 | 10.5 | 10.3 |
| hsa-miR-1469 | 11.5 | 11.9 | 10.5 | 11.9 | 11.4 | 11.7 | 10.1 | 9.5 | 10.0 |
| hsa-miR-3128 | 0.0 | 0.0 | 0.0 | 0.0 | 0.0 | 0.0 | 0.0 | 0.0 | 0.0 |
| hsa-miR-7106-5p | 8.4 | 7.7 | 8.6 | 8.2 | 9.0 | 8.7 | 10.5 | 10.6 | 11.3 |
| hsa-miR-4728-5p | 10.3 | 10.5 | 10.4 | 10.6 | 10.0 | 9.6 | 11.3 | 10.2 | 11.3 |
| hsa-miR-6802-5p | 11.2 | 11.4 | 12.0 | 11.7 | 10.8 | 11.5 | 10.9 | 10.6 | 9.2 |
| hsa-miR-6749-5p | 10.0 | 10.3 | 11.3 | 11.3 | 11.5 | 11.1 | 11.8 | 11.3 | 12.0 |
| hsa-miR-0371a-5p | 11.2 | 11.0 | 11.8 | 11.4 | 10.7 | 11.0 | 11.0 | 10.4 | 10.2 |
| hsa-miR-4675 | 11.6 | 11.7 | 12.0 | 11.0 | 10.5 | 10.5 | 10.7 | 9.7 | 9.6 |
| hsa-miR-1343-5p | 11.1 | 11.7 | 10.4 | 10.6 | 11.2 | 11.8 | 9.9 | 11.1 | 10.3 |
| hsa-miR-3126-5p | 4.3 | 3.9 | 4.3 | 3.6 | 3.8 | 4.5 | 4.0 | 4.5 | 4.0 |

TABLE 3-continued

| | | | | | | | | | |
|---|---|---|---|---|---|---|---|---|---|
| hsa-miR-0149-3p | 11.1 | 11.6 | 10.8 | 11.2 | 10.6 | 10.4 | 10.6 | 10.7 | 10.3 |
| hsa-miR-1233-5p | 10.1 | 10.4 | 12.0 | 10.1 | 10.9 | 10.9 | 11.6 | 11.2 | 11.2 |
| hsa-miR-6125 | 11.8 | 11.7 | 10.9 | 10.1 | 11.7 | 11.8 | 10.9 | 11.2 | 10.9 |
| hsa-miR-6887-5p | 9.4 | 10.0 | 10.4 | 11.0 | 10.1 | 9.8 | 11.2 | 11.8 | 11.4 |
| hsa-miR-6775-5p | 10.0 | 10.5 | 11.1 | 10.7 | 10.8 | 11.2 | 12.3 | 11.2 | 11.6 |
| hsa-miR-6850-5p | 12.1 | 11.4 | 10.7 | 10.1 | 10.9 | 10.4 | 10.4 | 10.4 | 10.0 |
| hsa-miR-4534 | 11.6 | 10.7 | 11.4 | 11.2 | 12.2 | 11.9 | 10.9 | 10.4 | 12.0 |
| hsa-miR-0296-5p | 11.0 | 11.2 | 11.7 | 11.1 | 10.9 | 10.7 | 11.8 | 10.9 | 11.3 |
| hsa-miR-6803-5p | 11.6 | 11.9 | 12.4 | 12.2 | 11.8 | 12.2 | 11.4 | 11.4 | 11.0 |
| hsa-miR-0663a | 12.1 | 12.2 | 11.2 | 12.6 | 12.1 | 12.4 | 10.7 | 10.0 | 11.1 |
| hsa-miR-6752-5p | 11.9 | 12.1 | 11.6 | 11.9 | 11.9 | 11.5 | 10.6 | 11.3 | 10.9 |
| hsa-miR-4492 | 11.8 | 11.7 | 11.6 | 10.1 | 10.8 | 11.0 | 10.0 | 9.1 | 8.7 |
| hsa-miR-4270 | 11.8 | 12.7 | 12.6 | 11.6 | 11.1 | 11.1 | 11.1 | 10.0 | 9.9 |
| hsa-miR-6816-5p | 12.1 | 12.1 | 11.5 | 11.7 | 11.6 | 11.1 | 10.3 | 10.7 | 9.7 |
| hsa-miR-4687-3p | 11.8 | 12.2 | 13.4 | 12.9 | 12.0 | 12.1 | 12.1 | 11.0 | 11.0 |
| hsa-miR-6771-5p | 11.8 | 12.2 | 12.6 | 11.3 | 11.2 | 11.5 | 10.7 | 10.0 | 9.5 |
| hsa-miR-3656 | 12.3 | 12.3 | 11.6 | 11.9 | 12.0 | 11.6 | 10.9 | 11.4 | 11.1 |
| hsa-miR-4730 | 12.2 | 11.8 | 11.3 | 11.9 | 11.3 | 9.7 | 10.2 | 10.2 | 10.4 |
| hsa-miR-4463 | 12.6 | 12.3 | 12.1 | 12.5 | 12.9 | 12.3 | 11.9 | 12.2 | 12.0 |
| hsa-miR-6805-5p | 12.5 | 13.2 | 12.6 | 11.9 | 12.1 | 12.5 | 11.0 | 11.6 | 10.5 |
| hsa-miR-1268a | 12.2 | 12.7 | 11.8 | 11.8 | 11.9 | 11.8 | 10.9 | 11.1 | 10.7 |
| hsa-miR-8072 | 12.5 | 12.5 | 11.2 | 11.9 | 12.3 | 13.2 | 11.4 | 10.8 | 11.3 |
| hsa-miR-6757-5p | 10.8 | 11.0 | 13.1 | 11.0 | 11.8 | 11.6 | 12.6 | 11.7 | 12.0 |
| hsa-miR-4281 | 12.4 | 11.8 | 13.3 | 12.4 | 12.2 | 12.4 | 11.8 | 10.5 | 11.0 |
| hsa-miR-3663-3p | 13.6 | 12.8 | 12.4 | 12.2 | 12.3 | 11.2 | 11.4 | 11.2 | 11.0 |
| hsa-miR-6786-5p | 12.7 | 12.6 | 12.7 | 12.3 | 13.0 | 13.5 | 12.0 | 11.6 | 11.9 |
| hsa-miR-6765-5p | 12.6 | 12.7 | 12.5 | 12.5 | 12.3 | 11.9 | 11.2 | 11.3 | 10.7 |
| hsa-miR-6729-5p | 12.9 | 12.6 | 11.8 | 11.3 | 12.3 | 12.4 | 11.3 | 11.3 | 10.8 |
| hsa-miR-6087 | 13.4 | 13.1 | 13.1 | 13.2 | 13.1 | 13.5 | 12.0 | 11.8 | 11.2 |
| hsa-miR-6088 | 13.5 | 13.6 | 13.8 | 12.9 | 12.9 | 12.9 | 11.9 | 11.7 | 10.8 |
| hsa-miR-0638 | 13.0 | 12.8 | 11.9 | 11.5 | 12.5 | 12.7 | 11.5 | 11.6 | 11.0 |
| hsa-miR-4674 | 13.4 | 12.8 | 12.1 | 10.7 | 10.6 | 10.5 | 11.0 | 10.7 | 8.9 |
| hsa-miR-4734 | 12.6 | 12.4 | 12.0 | 10.7 | 11.4 | 11.2 | 11.6 | 11.2 | 10.5 |
| hsa-miR-4689 | 12.5 | 12.8 | 13.8 | 13.0 | 12.5 | 12.8 | 13.1 | 12.0 | 12.3 |
| hsa-miR-6784-5p | 13.5 | 13.0 | 12.8 | 12.5 | 13.0 | 12.8 | 11.9 | 12.2 | 11.0 |
| hsa-miR-6785-5p | 13.2 | 13.6 | 13.9 | 12.4 | 12.2 | 11.8 | 11.6 | 11.4 | 10.2 |
| hsa-miR-3621 | 13.8 | 13.6 | 12.8 | 12.1 | 12.3 | 11.3 | 11.6 | 12.5 | 10.9 |
| hsa-miR-0328-5p | 13.4 | 13.5 | 13.6 | 13.6 | 13.3 | 13.9 | 12.4 | 11.5 | 11.8 |
| hsa-miR-4739 | 13.1 | 13.4 | 14.4 | 13.8 | 13.9 | 13.9 | 12.9 | 11.2 | 11.6 |
| hsa-miR-6085 | 11.7 | 12.3 | 13.2 | 13.1 | 13.5 | 13.3 | 13.5 | 12.5 | 13.5 |
| hsa-miR-4442 | 13.8 | 14.5 | 14.7 | 13.4 | 12.6 | 12.8 | 12.4 | 11.6 | 10.6 |
| hsa-miR-4649-5p | 13.5 | 13.7 | 13.3 | 12.3 | 12.6 | 11.3 | 11.7 | 11.7 | 9.8 |
| hsa-miR-3196 | 13.9 | 13.6 | 13.0 | 12.6 | 12.8 | 13.2 | 11.8 | 11.3 | 10.9 |
| hsa-miR-4466 | 13.8 | 13.6 | 12.9 | 12.4 | 12.4 | 12.6 | 12.0 | 11.7 | 11.5 |
| hsa-miR-4508 | 13.5 | 13.3 | 13.1 | 12.1 | 13.2 | 12.9 | 11.9 | 11.6 | 11.5 |
| hsa-miR-1237-5p | 13.7 | 13.9 | 13.1 | 13.3 | 13.3 | 13.1 | 12.1 | 12.6 | 12.1 |
| hsa-miR-4532 | 13.5 | 12.6 | 12.9 | 10.1 | 12.5 | 11.9 | 12.3 | 12.1 | 9.8 |
| hsa-miR-6090 | 13.8 | 13.9 | 13.2 | 13.2 | 13.3 | 13.1 | 12.4 | 12.4 | 12.2 |
| hsa-miR-2861 | 14.0 | 14.0 | 14.4 | 14.2 | 14.0 | 13.9 | 12.9 | 12.4 | 12.1 |
| hsa-miR-3163 | 0.0 | 0.0 | 0.0 | 0.0 | 0.0 | 1.6 | 0.0 | 0.0 | 2.2 |
| hsa-miR-4723-5p | 12.3 | 12.5 | 13.8 | 13.5 | 14.0 | 13.0 | 14.0 | 13.2 | 14.2 |
| hsa-miR-3178 | 14.5 | 14.3 | 13.1 | 12.8 | 13.0 | 13.1 | 12.2 | 11.7 | 11.3 |
| hsa-miR-0128-2-5p | 14.0 | 14.1 | 14.5 | 13.5 | 13.4 | 12.9 | 12.3 | 12.3 | 11.9 |
| hsa-miR-1228-5p | 13.8 | 14.2 | 13.6 | 13.4 | 13.2 | 13.4 | 12.4 | 12.0 | 11.5 |
| hsa-miR-0762 | 14.4 | 14.4 | 13.5 | 13.2 | 13.6 | 13.3 | 12.9 | 13.1 | 11.9 |
| hsa-miR-4488 | 14.4 | 14.7 | 14.1 | 13.9 | 13.9 | 13.3 | 13.0 | 12.9 | 12.4 |
| hsa-miR-8069 | 14.4 | 14.8 | 13.6 | 13.2 | 12.9 | 13.3 | 12.6 | 12.8 | 11.9 |
| hsa-miR-3940-5p | 14.3 | 14.4 | 13.8 | 13.9 | 13.9 | 13.4 | 12.6 | 13.1 | 11.8 |
| hsa-miR-6869-5p | 14.5 | 14.2 | 13.8 | 12.7 | 14.3 | 13.3 | 12.7 | 12.3 | 12.5 |
| hsa-miR-6089 | 14.6 | 14.2 | 14.0 | 13.6 | 14.0 | 13.5 | 13.2 | 13.1 | 12.8 |
| hsa-miR-6727-5p | 14.9 | 14.9 | 14.1 | 13.2 | 13.1 | 13.0 | 12.9 | 12.6 | 11.1 |
| hsa-miR-6885-5p | 14.5 | 14.8 | 15.1 | 13.8 | 13.9 | 13.4 | 13.6 | 12.7 | 12.1 |
| hsa-miR-5787 | 14.7 | 14.8 | 14.0 | 13.6 | 14.2 | 13.9 | 13.2 | 12.8 | 12.7 |
| hsa-miR-4787-5p | 15.1 | 15.1 | 14.3 | 13.5 | 13.8 | 13.9 | 13.2 | 12.6 | 12.1 |
| hsa-miR-7704 | 15.4 | 15.1 | 14.6 | 13.5 | 13.8 | 13.8 | 13.4 | 13.1 | 11.9 |
| hsa-miR-4516 | 16.0 | 15.1 | 14.6 | 14.2 | 14.4 | 13.9 | 14.1 | 14.2 | 12.8 |
| hsa-miR-3665 | 15.9 | 15.1 | 14.7 | 14.1 | 13.8 | 13.9 | 14.0 | 13.9 | 12.5 |
| hsa-miR-3960 | 16.0 | 15.1 | 15.7 | 14.8 | 15.6 | 13.9 | 15.1 | 14.4 | 13.8 |

The invention claimed is:

1. A method, comprising:
   (a) providing a urine or a urine extract obtained from a human subject, wherein the human subject is suspected of having a risk of lung cancer;
   (b) enriching for miR-16-1-3p from the urine or the urine extract obtained from the human subject using a nanowire;
   (c) determining an amount of the miR-16-1-3p in the urine or the urine extract obtained from the human subject;
   (d) diagnosing the human subject as having the risk of the lung cancer when the amount of the miR-16-1-3p is greater relative to an amount of the miR-16-1-3p in a urine or a urine extract obtained from a control human subject that does not exhibit the lung cancer.

2. The method of claim 1, wherein (c) further comprises determining an amount of at least one second miRNA comprising miR-378a-Sp, miR-520c-3p or miR-526b-3p in the urine or the urine extract obtained from the human subject using the nanowire.

3. The method of claim 2, further comprising enriching for the at least one second miRNA from the urine or the urinary extract obtained from the human subject using the nanowire.

4. The method of claim 3, wherein the enriching comprises contacting the urine or the urinary extract obtained from the human subject with the nanowire.

5. The method of claim 4, wherein the enriching comprises collecting extracellular vesicles comprising the at least one second miRNA from the urine or urine extract obtained from the human subject on the nanowire.

6. The method of claim 5, further comprising extracting the at least one second miRNA from the extracellular vesicles collected on the nanowire.

7. The method of claim 1, wherein the nanowire comprises ZnO, SiO2, Li2O, MgO, Al2O3, CaO, TiO2, Mn2O3, Fe2O3, CoO, NiO, CuO, Ga2O3, SrO, In2O3, SnO2, Sm2O3, or EuO.

8. The method of claim 7, wherein the nanowire comprises the ZnO or the Al2O3.

9. The method of claim 8, wherein a core of the nanowire comprises the ZnO and a shell of the nanowire comprises the Al2O3.

10. The method of claim 1, further comprising collecting extracellular vesicles comprising the miR-16-1-3p from the urine or the urine extract obtained from the human subject on the nanowire.

11. The method of claim 10, wherein the extracellular vesicles comprise exosomes, microvesicles, or a combination thereof.

12. The method of claim 10, further comprising extracting the miR-16-1-3p from the extracellular vesicles collected on the nanowire.

13. The method of claim 1, wherein the nanowire is coupled to a substrate.

14. The method of claim 13, wherein the substrate is part of a microfluidic device.

15. The method of claim 14, wherein the nanowire is embedded in the substrate.

16. The method of claim 13, wherein the substrate comprises polydimethylsiloxane (PDMS), silicon (Si), polyethylene, polypropylene, polyvinyl chloride, polyvinylidene chloride, polystyrene, polyvinyl acetate, polytetrafluoroethylene, ABS (acrylonitrile butadiene styrene) resin, acrylonitrile styrene (AS) resin, thermoplastic resin, acrylic resin (PMMA), phenolic resin, epoxy resin, melamine resin, urea resin, unsaturated polyester resin, alkyd resin, polyurethane, polyimide, silicone rubber, polymethylmethacrylate (PMMA), or polycarbonate (PC).

17. The method of claim 1, wherein the control human subject is healthy.

18. The method of claim 1, further comprising in (b): enriching for at least one additional nucleic acid comprising miR-3163, miR-424-3p, miR-558, miR-3127-5p, or miR-4521 from the urine or the urine extract obtained from the human subject using the nanowire.

19. The method of claim 18, further comprising in (c): determining an amount of the at least one additional nucleic acid in the urine or the urine extract.

* * * * *